(12) United States Patent
Barbero Calzado et al.

(10) Patent No.: US 12,102,673 B2
(45) Date of Patent: Oct. 1, 2024

(54) ZIKA VIRUS VACCINE

(71) Applicant: Valneva Austria GmbH, Vienna (AT)

(72) Inventors: Jana Barbero Calzado, Vienna (AT); Mario Nebenführ, Vienna (AT); Robert Schlegl, Siegenfeld (AT); Michael Weber, Vienna (AT); Jürgen Heindl-Wruss, Vienna (AT)

(73) Assignee: Valneva Austria GMBH, Vienna (AT)

( * ) Notice: Subject to any disclaimer, the term of this patent is extended or adjusted under 35 U.S.C. 154(b) by 0 days.

(21) Appl. No.: 18/334,497

(22) Filed: Jun. 14, 2023

(65) Prior Publication Data

US 2024/0108712 A1    Apr. 4, 2024

Related U.S. Application Data

(63) Continuation of application No. 17/548,721, filed on Dec. 13, 2021, now Pat. No. 12,005,111, which is a continuation of application No. 16/813,862, filed on Mar. 10, 2020, now Pat. No. 11,219,681, which is a continuation of application No. 16/063,007, filed as application No. PCT/EP2016/082664 on Dec. 23, 2016, now Pat. No. 10,639,365.

(30) Foreign Application Priority Data

| Dec. 23, 2015 | (EP) | 15202585 |
| Mar. 18, 2016 | (EP) | 16161068 |
| Jun. 23, 2016 | (EP) | 16176025 |
| Jun. 23, 2016 | (EP) | 16176049 |
| Aug. 4, 2016 | (EP) | 16182845 |

(51) Int. Cl.

| A61K 39/12 | (2006.01) |
| A61K 9/00 | (2006.01) |
| A61K 39/00 | (2006.01) |
| A61K 39/39 | (2006.01) |
| A61P 31/14 | (2006.01) |
| C07K 14/18 | (2006.01) |
| C12N 7/00 | (2006.01) |
| C12N 7/02 | (2006.01) |
| C12N 7/06 | (2006.01) |

(52) U.S. Cl.
CPC .............. *A61K 39/12* (2013.01); *A61K 39/39* (2013.01); *A61P 31/14* (2018.01); *C07K 14/18* (2013.01); *C07K 14/1825* (2013.01); *C12N 7/00* (2013.01); *C12N 7/02* (2013.01); *C12N 7/06* (2013.01); *A61K 2039/5252* (2013.01); *A61K 2039/5254* (2013.01); *A61K 2039/5258* (2013.01); *A61K 2039/55505* (2013.01); *C12N 2770/24134* (2013.01); *C12N 2770/24151* (2013.01); *C12N 2770/24163* (2013.01); *Y02A 50/30* (2018.01)

(58) Field of Classification Search
CPC .... A61K 2039/5252; A61K 2039/5254; A61K 2039/5258; A61K 2039/55505; A61K 39/12
See application file for complete search history.

(56) References Cited

U.S. PATENT DOCUMENTS

| 6,309,650 | B1 | 10/2001 | Kim et al. |
| 8,765,148 | B2 | 7/2014 | Wizel et al. |
| 10,086,061 | B2 | 10/2018 | Thomas et al. |
| 10,537,630 | B2 | 1/2020 | Barbero Calzado et al. |
| 10,639,365 | B2 | 5/2020 | Barbero Calzado et al. |
| 10,744,194 | B2 | 8/2020 | Barbero Calzado et al. |
| 11,219,681 | B2 | 1/2022 | Barbero Calzado et al. |
| 11,331,382 | B2 | 5/2022 | Barbero Calzado et al. |
| 11,524,064 | B2 | 12/2022 | Barbero Calzado et al. |
| 2013/0280295 | A1 | 10/2013 | Schlegl et al. |
| 2018/0362936 | A1 | 12/2018 | Barbero Calzado et al. |
| 2018/0362937 | A1 | 12/2018 | Barbero Calzado et al. |
| 2018/0369359 | A1 | 12/2018 | Barbero Calzado et al. |
| 2018/0371027 | A1 | 12/2018 | Barbero Calzado et al. |
| 2019/0008945 | A1 | 1/2019 | Barbero Calzado et al. |
| 2020/0017555 | A9 | 1/2020 | Barbero Calzado et al. |
| 2020/0384099 | A1 | 12/2020 | Barbero Calzado et al. |
| 2021/0093707 | A1 | 4/2021 | Barbero Calzado et al. |
| 2022/0273786 | A1 | 9/2022 | Barbero Calzado et al. |
| 2023/0226165 | A1 | 7/2023 | Barbero Calzado et al. |

FOREIGN PATENT DOCUMENTS

| CN | 105749268 A | 7/2016 |
| WO | WO 1999/011762 A1 | 3/1999 |
| WO | WO 2001/092552 A2 | 12/2001 |
| WO | WO 2004/084938 A1 | 10/2004 |
| WO | WO 2013/083726 A1 | 6/2013 |
| WO | WO 2016/145149 A1 | 9/2016 |
| WO | WO 2017/009873 A1 | 1/2017 |
| WO | WO 2017/109225 A1 | 6/2017 |

OTHER PUBLICATIONS

Notice of Opposition for Patent No. EP3393510, submitted by Maiwald GmbH, Nov. 21, 2023. 57 pages.
Consolidated List of Cited Opposition Documents for Patent No. EP3393510, submitted Nov. 21, 2023. 2 pages.
[No Author Listed], Centers for Disease Control and Prevention Ingredients of vaccines fact sheet. Retrieved from https://www.cdc.gov/vaccines/vac-gen/additives.htm.
[No Author Listed], Centers for Disease Control and Prevention. 2016. Japanese Encephalitis Vaccine. Retrieved from https://www.cdc.gov/japaneseencephalitis/vaccine/ on Jun. 16, 2016.

(Continued)

*Primary Examiner* — Barry A Chestnut
(74) *Attorney, Agent, or Firm* — Banner & Witcoff, Ltd.

(57) ABSTRACT

Described herein are Zika virus vaccines and compositions and methods of producing and administering said vaccines to subjects in need thereof.

32 Claims, 23 Drawing Sheets

Specification includes a Sequence Listing.

(56) References Cited

OTHER PUBLICATIONS

[No Author Listed], Genbank Accession No. ABI54475. polyprotein [Zika virus]. Dec. 24, 2009. 4 pages.
[No Author Listed], Genbank Accession No. AY632535. Zika virus strain MR 766, complete genome. Nov. 23, 2010. 4 pages.
[No Author Listed], Genbank Accession No. KJ776791.2. Zika virus strain H/PF/2013, complete genome. Aug. 31, 2016. 5 pages.
[No Author Listed], Media centre. Zika virus. World Health Organization, 2016. Zika Virus Fact Sheet. Downloaded Mar. 11, 2016 from http://www.who.int/en/news-room/fact-sheets/detail/zika-virus.
[No Author Listed], Pan-American Health Organization. 2015. Number of Reported Cases of Chikungunya Fever in the Americas, by Country or Territory 2013-2014, Cumulative Cases (Updated Oct. 23, 2015).
[No Author Listed], Valneva Announces Successful Generation of a Highly-purified Zika Vaccine Candidate Using its FDA-EMA Approved Japanese Encephalitis Platform. Press release Jul. 7, 2016.
[No Author Listed], Wikimedia Foundation, Inc., 2015. https://en.wikipedia.org/wiki/Protamine_sulfate; updated Sep. 30, 2015; downloaded Nov. 26, 2015.
[No Author Listed], World Health Organization, 2016. Zika Situation Report Feb. 5, 2016.
[No Author Listed], Zika virus, strain H/PF/2013. Nov. 28, 2013. European Virus Archive retrieved on Dec. 22, 2016 from http://www.who.int/mediacentre/factsheets/zika/en.
Abbink et al, Durability and correlates of vaccine protection against Zika virus in rhesus monkeys. Sci. Transl. Med. 2017;9:eaao4163.
Altschul et al., Basic Local Alignment Search Tool. J. Mol. Biol. 1990;215:403-410.
Altschul et al., Gapped BLAST and PSI-BLAST: a new generation of protein database search programs. Nuc. Acids Res. 1997;25:3389-3402.
Athmaram et al., A two step purification strategy for Chikungunya virions purification using sucrose buoyant density gradient separation. J Virology Res. 2013;2(1):18-21.
Aubry et al., Inactivation of Zika virus in plasma with amotosalen and ultraviolet A illumination. Transfusion. Jan. 2016;56(1):33-40. doi: 10.1111/trf.13271. Epub Aug. 18, 2015.
Baronti et al., Complete Coding Sequence of Zika Virus from a French Polynesia Outbreak in 2013. Genome Announc. May-Jun. 2014; 2(3):e00500-14. Abstract.
Bender et al., Zika Virus Vaccine Candidate VLA1601: Cooperation Valneva & Emergent, Presentation at World Vaccine Congress Apr. 4, 2018.
Cohen, Infectious Disease. The race for a Zika vaccine is on. Science. Feb. 5, 2016;351(6273):543-4. doi: 10.1126/science.351.6273.543.
Cox et al., Predicting Zika virus structural biology: Challenges and opportunities for intervention. Antivir Chem Chemother. Aug. 2015;24(3-4):118-26. doi: 10.1177/2040206616653873. Epub Jun. 13, 2016.
Dowall et al., A susceptible mouse model for Zika virus infection. PLOS Neglected Tropical Diseases; DOI:10.1371/journal.pntd.0004658. May 5, 2016.
Fritsche et al., Vaccine hypersensitivity—update and overview. Swiss Med Wkly. 2010;140(17-18):238-246.
Gardner et al., Deliberate Attenuation of Chikungunya Virus by Adaptation to Heparan Sulfate-Dependent Infectivity: A Model of Rational Arboviral Vaccine Design. PLOS Neglected Tropical Diseases. 2014;8(2):e2719.
Geradin et al., Chikungunya virus-associated encephalitis: A cohort study on La Réunion Island, 2005-2009. Neurology. 2016;86(1):94-102.
Haddow et al., Genetic Characterization of Zika Virus Strains: Geographic Expansion of the Asian Lineage. PLoS Negl Trop Dis. 2012;6(2): e1477. doi:10.1371/journal.pntd.0001477.
Hallengärd et al., Prime-Boost Immunization Strategies against Chikungunya Virus. J Virology. 2014;88(22):13333-13343.

Hallengärd et al., Novel Attenuated Chikungunya Vaccine Candidates Elicit Protective Immunity in C57BL/6 mice. J Virology. 2014;88(5):2858-2866.
Hombach et al., Report on a WHO consultation on immunological endpoints for evaluation of new Japanese encephalitis vaccines, WHO, Geneva, Sep. 2-3, 2004. Vaccine. 2005;23(45):5205-5211.
Hutornojs et al., Comparison of ultracentrifugation methods for concentration of recombinant alphaviruses: sucrose and iodixanol cushions, Environmental and Experimental Biology. 2012;10:117-123.
Katoh et al., Recent developments in the MAFFT multiple sequence alignment program. Briefings in Bioinformatics. 2008;9(4):286-298.
Kofler et al., Capsid protein C of tick-borne encephalitis virus tolerates large internal deletions and is a favorable target for attenuation of virulence. J Virol. Apr. 2002;76(7):3534-43.
Konishi et al., Studies on structural proteins of Chikungunya Virus. I. Separation of three species of proteins and their preliminary characterization. Microbiol Immunol. 1980;24(5):419-28. doi: 10.1111/j.1348-0421.1980.tb02846.x.
Kuno et al., Full-length sequencing and genomic characterization of Bagaza, Kedougou, and Zika viruses. Arch Virol. 2007;152(4):687-696. doi:10.1007/s00705-006-0903-z.
Larkin et al., Clustal W and Clustal X version 2.0. Bioinformatics. 2007;23(21):2947-2948.
Larocca et al., Vaccine protection against Zika virus from Brazil. Nature. 2016;536:474-478. doi:10.1038/nature18952. Methods.
Malone et al., Zika Virus: Medical Countermeasure Development Challenges. PLoS Negl Trop Dis. 2016;10(3):e0004530. doi:10.1371/journal.pntd.0004530.
Modjarrad et al., Preliminary aggregate safety and immunogenicity results from three trials of a purified inactivated Zika virus vaccine candidate: phase 1, randomised, double-blind, placebo-controlled clinical trials. www.thelancet.com Published online Dec. 4, 2017 http://dx.doi.org/10.1016/S0140-6736(17)33106-9.
Needleman et al., A general method applicable to the search for similarities in the amino acid sequence of two proteins. J. Mol. Biol. 1970;48(3):443-453.
Pearson et al., Improved tools for biological sequence comparison. Proc. Natl. Acad. Sci. USA. 1988;85(8):2444-8.
Pellerin, Walter Reed Scientists Test Zika Vaccine Candidate, U.S. Department of Defense News. Jun. 9, 2016.
Pinto et al., A Temporal Role Of Type I Interferon Signaling in CD8+ T Cell Maturation during Acute West Nile Virus Infection. PLoS Pathog. 2011;7(12): e1002407. https://doi.org/10.1371/journal.ppat.1002407.
Plevka et al., Maturation of flaviviruses starts from one or more icosahedrally independent nucleation centres EMBO reports. 2011;12(6):602-606.
Putnak et al., Development of a purified, inactivated, dengue-2 virus vaccine prototype in Vero cells: immunogenicity and protection in mice and rhesus monkeys. J Infect Dis. Dec. 1996;174(6):1176-84.
Reed et al., A simple method of estimating fifty percent endpoints. American J Hygiene. 1938;27:493-497.
Rocha et al., Microcephaly: normality parameters and its determinants in northeastern Brazil: a multicentre prospective cohort study. Bull World Health Organ, E-pub: Feb. 8, 2016. doi:http://dx.doi.org/10.2471/BLT.16.171215.
Schlegl, Influence of elemental impurities in aluminum hydroxide adjuvant on the stability of inactivated Japanese Encephalitis vaccine, IXIARO®. Vaccine. 2015;33(44):5989-5996.
Smith et al., Comparison of Biosequences. Adv. Appl. Math. 1981;2:482-489.
Srivastava et al., A purified inactivated Japanese encephalitis virus vaccine made in Vero cells. Vaccine. 2001;19:4557-4565.
Third Party Observations filed in Opposition to EP 16828746.4, filed on Oct. 13, 2021. 6 pages.
Tiwari et al., Assessment of immunogenic potential of Vero adapted formalin inactivated vaccine derived from novel ECSA genotype of Chikungunya virus. Vaccine. Apr. 21, 2009;27(18):2513-22. doi: 10.1016/j.vaccine.2009.02.062. Epub Feb. 27, 2009.

(56) References Cited

OTHER PUBLICATIONS

Vega-Rua et al., Chikungunya Virus Transmission Potential by Local Aedes Mosquitoes in the Americas and Europe. PLOS Neglected Tropical Diseases. 2015;9(5): e0003780.
Waterhouse et al., Jalview Version 2—a multiple sequence alignment editor and analysis workbench. Bioinformatics. 2009;25(9):1189-1191.
Way et al., Comparative studies of some African arboviruses in cell culture and in mice. J Gen Virol. Jan. 1976;30(1):123-30.
Weaver, Arrival of Chikungunya Virus in the New World: Prospects for Spread and Impact on Public Health. PLoS Negl Trop Dis. 2014;8(6):e2921. doi:10.1371/journal.pntd.0002921.
Petition for Inter Partes Review of U.S. Pat. No. 11,219,681. *Takeda Vaccines, Inc.* vs *Valneva Austria GMBH*. 96 pages. Paper No. 2, submitted in PTAB Case No. IPR2023-00354, Dec. 27, 2022.
Petitioner's Updated Exhibit List in Inter Partes Review of U.S. Pat. No. 11,219,681. *Takeda Vaccines, Inc.* vs *Valneva Austria GmbH*. 19 pages. Paper No. 5, submitted in PTAB Case No. IPR2023-00354, Apr. 20, 2023.
Order Denying Authorization of Motion in Inter Partes Review of U.S. Pat. No. 11,219,681. *Takeda Vaccines, Inc.* vs *Valneva Austria GMBH*. 5 pages. Paper No. 6, issued in PTAB Case No. IPR2023-00354, Jun. 6, 2023.
Decision for Inter Partes Review of U.S. Pat. No. 11,219,681. *Takeda Vaccines, Inc.* vs *Valneva Austria GmbH*. 6 pages. Paper No. 7, issued in PTAB Case No. IPR2023-00354, Jun. 9, 2023.
Declaration of Dan H. Barouch, M.D., Ph.D., submitted to United States Patent and Trademark Office Patent Trial and Appeal Board (PTAB); Case No. IPR2023-00354, U.S. Pat. No. 11,219,681. Dec. 15, 2022. 223 pages. Ex. 1002 submitted in PTAB Case No. IPR2023-00354, Dec. 27, 2022.
Curriculum Vitae for Dan H. Barouch. Dec. 14, 2022. 133 pages. Ex. 1003 submitted in PTAB Case No. IPR2023-00354, Dec. 27, 2022.
United States Patent and Trademark Office File History for U.S. Pat. No. 11,219,681. 1023 pages. Ex. 1004, submitted in PTAB Case No. IPR2023-00354, Dec. 27, 2022.
Yoshii et al., A conserved region in the prM protein is a critical determinant in the assembly of flavivirus particles. J Gen Virol. Jan. 2012;93(Pt 1):27-38. doi: 10.1099/vir.0.035964-0. Epub Sep. 28, 2011. Ex. 1005 submitted in PTAB Case No. IPR2023-00354, Dec. 27, 2022.
Larocca et al., Vaccine protection against Zika virus from Brazil. Nature. Aug. 25, 2016;536(7617):474-8. doi: 10.1038/nature18952. Epub Jun. 28, 2016. Ex. 1006 submitted in PTAB Case No. IPR2023-00354, Dec. 27, 2022.
Holloway, Wrair Technology helps create Japanese Encephalitis Vaccine. The United States Army. Retrieved from The Wayback Machine—www.army.mil on Sep. 27, 2022. 2 pages. Ex. 1007 submitted in PTAB Case No. IPR2023-00354, Dec. 27, 2022.
[No Author Listed], Blast Global Alignment results for RID-UNWF87RP114. Retrieved on Dec. 27, 2022. 11 pages. Ex. 1009 submitted in PTAB Case No. IPR2023-00354, Dec. 27, 2022.
[No Author Listed], Certified priority document for Application No. EP15202585.4, filed Dec. 23, 2015. 37 pages. Ex. 1014 submitted in PTAB Case No. IPR2023-00354, Dec. 27, 2022.
[No Author Listed], Certified priority document for Application No. EP 16161068.8, filed Mar. 18, 2016. 79 pages. Ex. 1015 submitted in PTAB Case No. IPR2023-00354, Dec. 27, 2022.
[No Author Listed], Certified priority document for Application No. EP 16176025.1, filed Jun. 23, 2016. 134 pages. Ex. 1016 submitted in PTAB Case No. IPR2023-00354, Dec. 27, 2022.
[No Author Listed], Certified priority document for Application No. EP 16176049.1, filed Jun. 23, 2016. 92 pages. Ex. 1017 submitted in PTAB Case No. IPR2023-00354, Dec. 27, 2022.
[No Author Listed], Certified priority document for Application No. EP 16182845.4, filed Aug. 4, 2016. 137 pages. Ex. 1018 submitted in PTAB Case No. IPR2023-00354, Dec. 27, 2022.
[No Author Listed], Zika virus strain H/PF/2013 polyprotein gene, complete cds. GenBank Acc. No. KJ776791.1. Jun. 13, 2014. Retrieved on Sep. 16, 2022. 5 pages. Ex. 1019 submitted in PTAB Case No. IPR2023-00354, Dec. 27, 2022.
[No Author Listed], Blast Global Alignment results for RID-PKE92BN8114. Retrieved on Nov. 7, 2022. 18 pages. Ex. 1020 submitted in PTAB Case No. IPR2023-00354, Dec. 27, 2022.
Watanaveeradej et al., Safety and immunogenicity of a rederived, live-attenuated dengue virus vaccine in healthy adults living in Thailand: a randomized trial. Am J Trop Med Hyg. Jul. 2014;91(1):119-28. doi: 10.4269/ajtmh.13-0452. Epub May 27, 2014. Ex. 1021 submitted in PTAB Case No. IPR2023-00354, Dec. 27, 2022.
Orenstein et al., Global vaccination recommendations and thimerosal. Pediatrics. Jan. 2013;131(1):149-51. doi: 10.1542/peds.2012-1760. Epub Dec. 17, 2012. Ex. 1022 submitted in PTAB Case No. IPR2023-00354, Dec. 27, 2022.
Eckels et al., Japanese encephalitis virus live-attenuated vaccine, Chinese strain SA14-14-2; adaptation to primary canine kidney cell cultures and preparation of a vaccine for human use. Vaccine. Dec. 1988;6(6):513-8. doi: 10.1016/0264-410x(88)90103-x. Ex. 1023 submitted in PTAB Case No. IPR2023-00354, Dec. 27, 2022.
Martinez et al., Safety and Immunogenicity of a Dengue Virus Serotype-1 Purified-Inactivated Vaccine: Results of a Phase 1 Clinical Trial. Am J Trop Med Hyg. Sep. 2015;93(3):454-460. doi: 10.4269/ajtmh. 14-0819. Epub Jul. 6, 2015. Ex. 1024 submitted in PTAB Case No. IPR2023-00354, Dec. 27, 2022.
World Health Organization, Who Director-General summarizes the outcome of the Emergency Committee regarding clusters of microcephaly and Guillain-Barré syndrome. WHO Media Centre. Retrieved from The Wayback Machine—http://www.who.int on Sep. 22, 2022. 2 pages. Ex. 1025 submitted in PTAB Case No. IPR2023-00354, Dec. 27, 2022.
Li et al., Complete genome sequence of a chikungunya virus isolated in Guangdong, China. J Virol. Aug. 2012;86(16):8904-5. doi: 10.1128/JVI.01289-12. Ex. 1027 submitted in PTAB Case No. IPR2023-00354, Dec. 27, 2022.
Putnak et al., Development of a purified, inactivated, dengue-2 virus vaccine prototype in Vero cells: immunogenicity and protection in mice and rhesus monkeys. J Infect Dis. Dec. 1996;174(6):1176-84. doi: 10.1093/infdis/174.6.1176. Ex. 1028 submitted in PTAB Case No. IPR2023-00354, Dec. 27, 2022.
Musso et al., Potential sexual transmission of Zika virus. Emerg Infect Dis. Feb. 2015;21(2):359-61. doi: 10.3201/eid2102.141363. Erratum in: Emerg Infect Dis. Mar. 2015;21(3):552. Ex. 1029 submitted in PTAB Case No. IPR2023-00354, Dec. 27, 2022.
Cox et al., Predicting Zika virus structural biology: Challenges and opportunities for intervention. Antivir Chem Chemother. Aug. 2015;24(3-4):118-26. doi: 10.1177/2040206616653873. Epub Jun. 13, 2016. Ex. 1030 submitted in PTAB Case No. IPR2023-00354, Dec. 27, 2022.
Duffy et al., Zika virus outbreak on Yap Island, Federated States of Micronesia. N Engl J Med. Jun. 11, 2009;360(24):2536-43. doi: 10.1056/NEJMoa0805715. Ex. 1031 submitted in PTAB Case No. IPR2023-00354, Dec. 27, 2022.
Cao-Lormeau et al., Emerging arboviruses in the Pacific. Lancet. Nov. 1, 2014;384(9954):1571-2. doi: 10.1016/S0140-6736(14)61977-2. Epub Oct. 31, 2014. Ex. 1032 submitted in PTAB Case No. IPR2023-00354, Dec. 27, 2022.
World Health Organization, Zika Virus Microcephaly and Guillain-Barre Syndrome. Situation Report. Mar. 17, 2016. 13 pages. Ex. 1033 submitted in PTAB Case No. IPR2023-00354, Dec. 27, 2022.
Maurice, Who reveals its shopping list for weapons against Zika. Lancet. Feb. 20, 2016;387(10020):733. doi: 10.1016/s0140-6736(16)00390-1. Ex. 1034 submitted in PTAB Case No. IPR2023-00354, Dec. 27, 2022.
Besnard et al., Evidence of perinatal transmission of Zika virus, French Polynesia, Dec. 2013 and Feb. 2014. Euro Surveill. Apr. 3, 2014;19(13):20751. Ex. 1035 submitted in PTAB Case No. IPR2023-00354, Dec. 27, 2022.
Monath et al., Inactivated yellow fever 17D vaccine: development and nonclinical safety, immunogenicity and protective activity. Vaccine. May 14, 2010;28(22):3827-40. doi: 10.1016/j.vaccine. 2010.03.023. Epub Mar. 26, 2010. Ex. 1036 submitted in PTAB Case No. IPR2023-00354, Dec. 27, 2022.

(56) References Cited

OTHER PUBLICATIONS

Rasmussen et al., Vaccines and pregnancy: past, present, and future. Semin Fetal Neonatal Med. Jun. 2014;19(3):161-9. doi: 10.1016/j.siny.2013.11.014. Epub Dec. 17, 2013. Ex. 1037 submitted in PTAB Case No. IPR2023-00354, Dec. 27, 2022.

Plotkin et al., The development of vaccines: how the past led to the future. Nat Rev Microbiol. Oct. 3, 2011;9(12):889-93. doi: 10.1038/nrmicro2668. Ex. 1038 submitted in PTAB Case No. IPR2023-00354, Dec. 27, 2022.

Heinz et al., Flaviviruses and flavivirus vaccines. Vaccine. Jun. 19, 2012;30(29):4301-6. doi: 10.1016/j.vaccine.2011.09.114. Ex. 1039 submitted in PTAB Case No. IPR2023-00354, Dec. 27, 2022.

Shan et al., Zika Virus: Diagnosis, Therapeutics, and Vaccine. ACS Infect Dis. Mar. 11, 2016;2(3):170-2. doi: 10.1021/acsinfecdis.6b00030. Epub Mar. 3, 2016. Ex. 1040 submitted in PTAB Case No. IPR2023-00354, Dec. 27, 2022.

Ishikawa et al., A review of successful flavivirus vaccines and the problems with those flaviviruses for which vaccines are not yet available. Vaccine. Mar. 10, 2014;32(12):1326-37. doi: 10.1016/j.vaccine.2014.01.040. Epub Jan. 29, 2014. Ex. 1041 submitted in PTAB Case No. IPR2023-00354, Dec. 27, 2022.

Burton, Antibodies, viruses and vaccines. Nat Rev Immunol. Sep. 2002;2(9):706-13. doi: 10.1038/nri891. Ex. 1042 submitted in PTAB Case No. IPR2023-00354, Dec. 27, 2022.

Roehrig et al., Guidelines for Plaque-Reduction Neutralization Testing of Human Antibodies to Dengue Viruses. Viral Immunol. Jun. 2008;21(2):123-32. doi: 10.1089/vim.2008.0007. Ex. 1043 submitted in PTAB Case No. IPR2023-00354, Dec. 27, 2022.

Laurie et al., International Laboratory Comparison of Influenza Microneutralization Assays for A(H1N1)pdm09, A(H3N2), and A(H5N1) Influenza Viruses by Consise. Clin Vaccine Immunol. Aug. 2015;22(8):957-64. doi: 10.1128/CVI.00278-15. Epub Jun. 24, 2015. Ex. 1044 submitted in PTAB Case No. IPR2023-00354, Dec. 27, 2022.

Klasse, Neutralization of Virus Infectivity by Antibodies: Old Problems in New Perspectives. Adv Biol. 2014;2014:157895. doi: 10.1155/2014/157895. Epub Sep. 9, 2014. Ex. 1045 submitted in PTAB Case No. IPR2023-00354, Dec. 27, 2022.

Bauer et al., A Phase II, Randomized, Safety and Immunogenicity Trial of a Re-Derived, Live-Attenuated Dengue Virus Vaccine in Healthy Children and Adults Living in Puerto Rico. Am J Trop Med Hyg. Sep. 2015;93(3):441-453. doi: 10.4269/ajtmh.14-0625. Epub Jul. 14, 2015. Ex. 1046 submitted in PTAB Case No. IPR2023-00354, Dec. 27, 2022.

Hombach et al., Report on a WHO consultation on immunological endpoints for evaluation of new Japanese encephalitis vaccines, WHO, Geneva, Sep. 2-3, 2004. Vaccine. Nov. 1, 2005;23(45):5205-11. doi: 10.1016/j.vaccine.2005.07.002. Epub Jul. 18, 2005. Ex. 1047 submitted in PTAB Case No. IPR2023-00354, Dec. 27, 2022.

Lindenbach et al., Molecular biology of flaviviruses. Adv Virus Res. 2003;59:23-61. doi: 10.1016/s0065-3527(03)59002-9. Ex. 1048 submitted in PTAB Case No. IPR2023-00354, Dec. 27, 2022.

Tauber et al., Safety and immunogenicity of a Vero-cell-derived, inactivated Japanese encephalitis vaccine: a non-inferiority, phase III, randomised controlled trial. Lancet. Dec. 1, 2007;370(9602):1847-53. doi: 10.1016/S0140-6736(07)61780-2. Ex. 1049 submitted in PTAB Case No. IPR2023-00354, Dec. 27, 2022.

Brinton et al., Functions of the 3' and 5' genome RNA regions of members of the genus Flavivirus. Virus Res. Aug. 3, 2015;206:108-19. doi: 10.1016/j.virusres.2015.02.006. Epub Feb. 13, 2015. Ex. 1050 submitted in PTAB Case No. IPR2023-00354, Dec. 27, 2022.

Okada et al., Safety and immunogenicity of a freeze-dried, cell culture-derived Japanese encephalitis vaccine (Inactivated) (JEBIK(®)V) in children. Vaccine. Sep. 7, 2012;30(41):5967-72. doi: 10.1016/j.vaccine.2012.07.034. Epub Jul. 25, 2012. Ex. 1051 submitted in PTAB Case No. IPR2023-00354, Dec. 27, 2022.

Cohen, Infectious Disease. The race for a Zika vaccine is on. Science. Feb. 5, 2016;351(6273):543-4. doi: 10.1126/science.351.6273.543. Ex. 1052 submitted in PTAB Case No. IPR2023-00354, Dec. 27, 2022.

[No Author Listed], Zika virus strain MR 766, complete genome. GenBank Acc. No. AY632535.2. Nov. 23, 2010. Retrieved on Sep. 24, 2022. 5 pages. Ex. 1053 submitted in PTAB Case No. IPR2023-00354, Dec. 27, 2022.

[No Author Listed], Zika virus strain PRVABC59, complete genome. GenBank Acc. No. KU501215.1. Feb. 1, 2016. Retrieved on Sep. 24, 2022. 4 pages. Ex. 1054 submitted in PTAB Case No. IPR2023-00354, Dec. 27, 2022.

[No Author Listed], Zika virus isolate Brazil-ZKV2015, complete genome. GenBank Acc. No. KU497555.1. Feb. 18, 2016. Retrieved on Sep. 24, 2022. 5 pages. Ex. 1055 submitted in PTAB Case No. IPR2023-00354, Dec. 27, 2022.

Zhang et al., Genetic and biochemical characterizations of Zika virus NS2A protein. Emerg Microbes Infect. 2019;8(1):585-602. doi: 10.1080/22221751.2019.1598291. Ex. 1056 submitted in PTAB Case No. IPR2023-00354, Dec. 27, 2022.

[No Author Listed], Sample GenBank Record. GenBank. Public nucleic acid sequence repository. Accessible at https://www.ncbi.nlm.nih.gov/genbank/samplerecord/#ModificationDateB. Retrieved on Oct. 2, 2022. 15 pages. Ex. 1057 submitted in PTAB Case No. IPR2023-00354, Dec. 27, 2022.

Musso, Zika Virus Transmission from French Polynesia to Brazil. Emerg Infect Dis. Oct. 2015;21(10):1887. doi: 10.3201/eid2110.151125. Ex. 1058 submitted in PTAB Case No. IPR2023-00354, Dec. 27, 2022.

Schuller et al., Comparison of a single, high-dose vaccination regimen to the standard regimen for the investigational Japanese encephalitis vaccine, IC51: a randomized, observer-blind, controlled Phase 3 study. Vaccine. Mar. 26, 2009;27(15):2188-93. doi: 10.1016/j.vaccine.2008.12.062. Epub Feb. 4, 2009. Ex. 1059 submitted in PTAB Case No. IPR2023-00354, Dec. 27, 2022.

Schuller et al., Long-term immunogenicity of the new Vero cell-derived, inactivated Japanese encephalitis virus vaccine IC51 Six and 12 month results of a multicenter follow-up phase 3 study. Vaccine. Aug. 12, 2008;26(34):4382-6. doi: 10.1016/j.vaccine.2008.05.081. Epub Jun. 17, 2008. Ex. 1060 submitted in PTAB Case No. IPR2023-00354, Dec. 27, 2022.

European Medicines Agency, Assessment Report for Ixiaro. 2009. 50 pages. Ex. 1061 submitted in PTAB Case No. IPR2023-00354, Dec. 27, 2022.

Abbink et al., Protective efficacy of multiple vaccine platforms against Zika virus challenge in rhesus monkeys. Science. Sep. 9, 2016;353(6304):1129-32. doi: 10.1126/science.aah6157. Epub Aug. 4, 2016. Ex. 1062 submitted in PTAB Case No. IPR2023-00354, Dec. 27, 2022.

Schlegl et al., Influence of elemental impurities in aluminum hydroxide adjuvant on the stability of inactivated Japanese Encephalitis vaccine, IXIARO®. Vaccine. Nov. 4, 2015;33(44):5989-96. doi: 10.1016/j.vaccine.2015.05.103. Epub Jun. 19, 2015. Ex. 1063 submitted in PTAB Case No. IPR2023-00354, Dec. 27, 2022.

[No Author Listed], Ixiaro—Summary Basis for Regulatory Action. Vaccines, Blood & Biologics. Retrieved from The Wayback Machine—http://www.fda on Sep. 27, 2022. 17 pages. Ex. 1064 submitted in PTAB Case No. IPR2023-00354, Dec. 27, 2022.

Duggan et al., Japanese encephalitis vaccine (inactivated, adsorbed) [Ixiaro]. Drugs. 2009;69(1):115-22. doi: 10.2165/00003495-200969010-00008. Ex. 1065 submitted in PTAB Case No. IPR2023-00354, Dec. 27, 2022.

Schellack et al., IC31, a novel adjuvant signaling via TLR9, induces potent cellular and humoral immune responses. Vaccine. Jun. 29, 2006;24(26):5461-72. doi: 10.1016/j.vaccine.2006.03.071. Epub Apr. 7, 2006. Ex. 1066 submitted in PTAB Case No. IPR2023-00354, Dec. 27, 2022.

Annunziato et al., The 3 major types of innate and adaptive cell-mediated effector immunity. J Allergy Clin Immunol. Mar. 2015;135(3):626-35. doi: 10.1016/j.jaci.2014.11.001. Epub Dec. 18, 2014. Ex. 1067 submitted in PTAB Case No. IPR2023-00354, Dec. 27, 2022.

Smith et al., Zika virus and Guillain-Barre syndrome: another viral cause to add to the list. Lancet. Apr. 9, 2016;387(10027):1486-1488. doi: 10.1016/S0140-6736(16)00564-X. Epub Mar. 2, 2016. Ex. 1068 submitted in PTAB Case No. IPR2023-00354, Dec. 27, 2022.

(56) References Cited

OTHER PUBLICATIONS

Benson et al., GenBank. Nucleic Acids Res. Jan. 2013;41(Database issue):D36-42. doi: 10.1093/nar/gks1195. Epub Nov. 27, 2012. Ex. 1069 submitted in PTAB Case No. IPR2023-00354, Dec. 27, 2022.

Samarasekera et al., Concern over Zika virus grips the world. Lancet. Feb. 6, 2016;387(10018):521-524. doi: 10.1016/S0140-6736(16)00257-9. Ex. 1070 submitted in PTAB Case No. IPR2023-00354, Dec. 27, 2022.

[No Author Listed], Blast Global Alignment results for RID-PKEBSNWN114. Retrieved on Nov. 7, 2022. 12 pages. Ex. 1071 submitted in PTAB Case No. IPR2023-00354, Dec. 27, 2022.

Fox, Could We Have a Zika Vaccine Soon? NBC News. Retrieved from The Wayback Machine—http://www.nbcnews.com/story1 on Oct. 1, 2022. 5 pages. Ex. 1072 submitted in PTAB Case No. IPR2023-00354, Dec. 27, 2022.

Fauci et al., Zika Virus in the Americas—Yet Another Arbovirus Threat. N Engl J Med. Feb. 18, 2016;374(7):601-4. doi: 10.1056/NEJMp1600297. Epub Jan. 13, 2016. Ex. 1073 submitted in PTAB Case No. IPR2023-00354, Dec. 27, 2022.

Dyer, Zika vaccine could be in production by year's end, says maker. BMJ. Feb. 1, 2016;352:i630. doi: 10.1136/bmj.i630. Ex. 1074 submitted in PTAB Case No. IPR2023-00354, Dec. 27, 2022.

[No Author Listed], Blast Global Alignment results for RID-PKEFKXBV114. Retrieved on Nov. 7, 2022. 18 pages. Ex. 1075 submitted in PTAB Case No. IPR2023-00354, Dec. 27, 2022.

[No Author Listed], Blast Global Alignment results for RID-PKEJEXRF114. Retrieved on Nov. 7, 2022. 12 pages. Ex. 1076 submitted in PTAB Case No. IPR2023-00354, Dec. 27, 2022.

Kumar et al., Metal ion leachates and the physico-chemical stability of biotherapeutic drug products. Curr Pharm Des. 2014;20(8):1173-81. doi: 10.2174/13816128113199990063. Ex. 1077 submitted in PTAB Case No. IPR2023-00354, Dec. 27, 2022.

Declaration of Scott Bailey, Ph.D., submitted to United States Patent and Trademark Office Patent Trial and Appeal Board; Case No. IPR2023-00354, U.S. Pat. No. 11,219,681. Dec. 14, 2022. 39 pages. Ex. 1078 submitted Dec. 27, 2022.

Curriculum Vitae for Scott Bailey. Nov. 1, 2022. 12 pages. Ex. 1079 submitted in PTAB Case No. IPR2023-00354, Dec. 27, 2022.

Luca et al., Crystal structure of the Japanese encephalitis virus envelope protein. J Virol. Feb. 2012;86(4):2337-46. doi: 10.1128/JVI.06072-11. Epub Dec. 7, 2011. Ex. 1080 submitted in PTAB Case No. IPR2023-00354, Dec. 27, 2022.

Klema et al., Dengue Virus Nonstructural Protein 5 (NS5) Assembles into a Dimer with a Unique Methyltransferase and Polymerase Interface. PLoS Pathog. Feb. 19, 2016;12(2):e1005451. doi: 10.1371/journal.ppat.1005451. Ex. 1081 submitted in PTAB Case No. IPR2023-00354, Dec. 27, 2022.

Mukhopadhyay et al., A structural perspective of the flavivirus life cycle. Nat Rev Microbiol. Jan. 2005;3(1):13-22. doi: 10.1038/nrmicro1067. Ex. 1082 submitted in PTAB Case No. IPR2023-00354, Dec. 27, 2022.

[No Author Listed], Zika virus strain H/PF/2013, complete genome. GenBank Acc. No. KJ776791.2. Aug. 31, 2016. Retrieved on Oct. 8, 2022. 5 pages. Ex. 1084 submitted in PTAB Case No. IPR2023-00354, Dec. 27, 2022.

Ledgerwood et al., A West Nile virus DNA vaccine utilizing a modified promoter induces neutralizing antibody in younger and older healthy adults in a phase I clinical trial. J Infect Dis. May 15, 2011;203(10):1396-404. doi: 10.1093/infdis/jir054. Epub Mar. 11, 2011. Ex. 1085 submitted in PTAB Case No. IPR2023-00354, Dec. 27, 2022.

International Preliminary Report on Patentability for International Application No. PCT/EP2016/082664, mailed Jul. 5, 2018. 15 pages. Ex. 1086 submitted in PTAB Case No. IPR2023-00354, Dec. 27, 2022.

Delrue et al., Inactivated virus vaccines from chemistry to prophylaxis: merits, risks and challenges. Expert Rev Vaccines. Jun. 2012;11(6):695-719. doi: 10.1586/erv.12.38. Ex. 1087 submitted in PTAB Case No. IPR2023-00354, Dec. 27, 2022.

Stephenson et al., Safety and immunogenicity of a Zika purified inactivated virus vaccine given via standard, accelerated, or shortened schedules: a single-centre, double-blind, sequential-group, randomised, placebo-controlled, phase 1 trial. Lancet Infect Dis. Sep. 2020;20(9):1061-1070. doi: 10.1016/S1473-3099(20)30085-2. Epub May 6, 2020. Ex. 1088 submitted in PTAB Case No. IPR2023-00354, Dec. 27, 2022.

Collette et al., Single Amino Acid Mutations Affect Zika Virus Replication In Vitro and Virulence In Vivo. Viruses. Nov. 12, 2020;12(11):1295. doi: 10.3390/v12111295. Ex. 1089 submitted in PTAB Case No. IPR2023-00354, Dec. 27, 2022.

Dinunno et al., Identification of a pocket factor that is critical to Zika virus assembly. Nat Commun. Oct. 2, 2020;11(1):4953. doi: 10.1038/s41467-020-18747-4. Ex. 1091 submitted in PTAB Case No. IPR2023-00354, Dec. 27, 2022.

Barnard et al., Molecular Determinants of Flavivirus Virion Assembly. Trends Biochem Sci. May 2021;46(5):378-390. doi: 10.1016/j.tibs.2020.12.007. Epub Jan. 7, 2021. Ex. 1092 submitted in PTAB Case No. IPR2023-00354, Dec. 27, 2022.

Tan et al., Capsid protein structure in Zika virus reveals the flavivirus assembly process. Nat Commun. Feb. 14, 2020;11(1):895. doi: 10.1038/s41467-020-14647-9. Ex. 1093 submitted in PTAB Case No. IPR2023-00354, Dec. 27, 2022.

Ma et al., Identification and characterization of key residues in Zika virus envelope protein for virus assembly and entry. Emerg Microbes Infect. Dec. 2022;11(1):1604-1620. doi: 10.1080/22221751.2022.2082888. 18 pages. Ex. 1094 submitted in PTAB Case No. IPR2023-00354, Dec. 27, 2022.
Pierson et al., Degrees of maturity: the complex structure and biology of flaviviruses. Curr Opin Virol. Apr. 2012;2(2):168-75. doi: 10.1016/j.coviro.2012.02.011. Epub Mar. 23, 2012. Ex. 1095 submitted in PTAB Case No. IPR2023-00354, Dec. 27, 2022.
Barzon et al., Zika virus: from pathogenesis to disease control. FEMS Microbiol Lett. Sep. 2016;363(18):fnw202. doi: 10.1093/femsle/fnw202. Epub Aug. 21, 2016. Ex. 1096 submitted in PTAB Case No. IPR2023-00354, Dec. 27, 2022.
Declaration of Ingrid Hsieh-Yee, Ph.D. in Support of Petition for Inter Partes Review of U.S. Pat. No. 11,219,681, submitted under United States Patent and Trademark Office Patent Trial and Appeal Board; Case No. IPR2023-00354, U.S. Pat. No. 11,219,681. Dec. 19, 2022. 65 pages. Ex. 1097 submitted in PTAB Case No. IPR2023-00354, Dec. 27, 2022.
[No Author Listed], Blast Global Alignment results for RID-U7BP1US5114. Retrieved on Dec. 21, 2022. 17 pages. Ex. 1098 submitted in PTAB Case No. IPR2023-00354, Dec. 27, 2022.
Poland et al., Zika Vaccine Development: Current Status. Mayo Clin Proc. Dec. 2019;94(12):2572-2586. doi: 10.1016/j.mayocp.2019.05.016. Ex. 1099 submitted in PTAB Case No. IPR2023-00354, Dec. 27, 2022.
Aubry et al., Flavivirus reverse genetic systems, construction techniques and applications: a historical perspective. Antiviral Res. Feb. 2015;114:67-85. doi: 10.1016/j.antiviral.2014.12.007. Epub Dec. 12, 2014. Ex. 1100 submitted in PTAB Case No. IPR2023-00354, Dec. 27, 2022.
Shan et al., An Infectious cDNA Clone of Zika Virus to Study Viral Virulence, Mosquito Transmission, and Antiviral Inhibitors. Cell Host Microbe. Jun. 8, 2016;19(6):891-900. doi: 10.1016/j.chom.2016.05.004. Epub May 16, 2016. 11 pages. Ex. 1101 submitted in PTAB Case No. IPR2023-00354, Dec. 27, 2022.
Singh et al., orfipy: a fast and flexible tool for extracting ORFs. Bioinformatics. Sep. 29, 2021;37(18):3019-3020. doi: 10.1093/bioinformatics/btab090. Ex. 1102 submitted in PTAB Case No. IPR2023-00354, Dec. 27, 2022.
Bennett, How Many Particles Are in the Observable Universe? Popular Mechanics. Jul. 11, 2017. Retrieved from https://www.popularmechanics.com/space/a27259/how-many-particles-are-in-the-entire-universe/ on Dec. 14, 2022. 4 pages. Ex. 1103 submitted in PTAB Case No. IPR2023-00354, Dec. 27, 2022.
[No Author Listed], File History for U.S. Appl. No. 16/063,007, filed Jun. 15, 2018. 1449 pages. Ex. 1104 submitted in PTAB Case No. IPR2023-00354, Dec. 27, 2022.

(56) References Cited

OTHER PUBLICATIONS

[No Author Listed], Blast Global Alignment results for RID-PKD4DBPR114. Retrieved on Nov. 7, 2022. 18 pages. Ex. 1105 submitted in PTAB Case No. IPR2023-00354, Dec. 27, 2022.

[No Author Listed], Blast Global Alignment results for RID-PKD84V7U114. Retrieved on Nov. 7, 2022. 18 pages. Ex. 1106 submitted in PTAB Case No. IPR2023-00354, Dec. 27, 2022.

[No Author Listed], Blast Global Alignment results for RID-PKDA0FNF114. Retrieved on Nov. 7, 2022. 18 pages. Ex. 1107 submitted in PTAB Case No. IPR2023-00354, Dec. 27, 2022.

[No Author Listed], Blast Global Alignment results for RID-PKDBBE56114. Retrieved on Nov. 7, 2022. 18 pages. Ex. 1108 submitted in PTAB Case No. IPR2023-00354, Dec. 27, 2022.

[No Author Listed], Blast Global Alignment results for RID-PKDCZZDV114. Retrieved on Nov. 7, 2022. 18 pages. Ex. 1109 submitted in PTAB Case No. IPR2023-00354, Dec. 27, 2022.

[No Author Listed], Blast Global Alignment results for RID-PCDE772T114. Retrieved on Nov. 7, 2022. 18 pages. Ex. 1110 submitted in PTAB Case No. IPR2023-00354, Dec. 27, 2022.

[No Author Listed], Blast Global Alignment results for RID-PKDFM82R114. Retrieved on Nov. 7, 2022. 18 pages. Ex. 1111 submitted in PTAB Case No. IPR2023-00354, Dec. 27, 2022.

[No Author Listed], Blast Global Alignment results for RID-PKDHCCHB114. Retrieved on Nov. 7, 2022. 18 pages. Ex. 1112 submitted in PTAB Case No. IPR2023-00354, Dec. 27, 2022.

[No Author Listed], Blast Global Alignment results for RID-PKDMJ7XV114. Retrieved on Nov. 7, 2022. 18 pages. Ex. 1113 submitted in PTAB Case No. IPR2023-00354, Dec. 27, 2022.

[No Author Listed], Blast Global Alignment results for RID-PKDNW6MB114. Retrieved on Nov. 7, 2022. 18 pages. Ex. 1114 submitted in PTAB Case No. IPR2023-00354, Dec. 27, 2022.

[No Author Listed], Blast Global Alignment results for RID-PKDRIEU6114. Retrieved on Nov. 7, 2022. 18 pages. Ex. 1115 submitted in PTAB Case No. IPR2023-00354, Dec. 27, 2022.

[No Author Listed], Blast Global Alignment results for RID-PKDSNN5B114. Retrieved on Nov. 7, 2022. 18 pages. Ex. 1116 submitted in PTAB Case No. IPR2023-00354, Dec. 27, 2022.

[No Author Listed], Blast Global Alignment results for RID-PKDUZMG3114. Retrieved on Nov. 7, 2022. 18 pages. Ex. 1117 submitted in PTAB Case No. IPR2023-00354, Dec. 27, 2022.

Nema et al., Excipients and their role in approved injectable products: current usage and future directions. PDA J Pharm Sci Technol. May-Jun. 2011;65(3):287-332. doi: 10.5731/pdajpst.2011.00634. Downloaded on Mar. 23, 2022. Ex. 1118 submitted in PTAB Case No. IPR2023-00354, Dec. 27, 2022.

Chen et al., Dengue—quo tu et quo vadis? Viruses. Sep. 2011;3(9):1562-608. doi: 10.3390/v3091562. Epub Sep. 1, 2011. Ex. 1119 submitted in PTAB Case No. IPR2023-00354, Dec. 27, 2022.

Manikandan, Measures of central tendency: The mean. J Pharmacol Pharmacother. Apr. 2011;2(2):140-2. doi: 10.4103/0976-500X.81920. Ex. 1120 submitted in PTAB Case No. IPR2023-00354, Dec. 27, 2022.

Miller, Jr. College Physics. Harcourt Brace Jovanovich, Inc. 4$^{th}$ Ed. 1977:790. 4 pages. Ex. 1121 submitted in PTAB Case No. IPR2023-00354, Dec. 27, 2022.

Bayat, Science, medicine, and the future: Bioinformatics. BMJ. Apr. 27, 2002;324(7344):1018- 22. doi: 10.1136/bmj.324.7344.1018. Ex. 1122 submitted in PTAB Case No. IPR2023-00354, Dec. 27, 2022.

Ekmekci et al., An Introduction to Programming for Bioscientists: A Python-Based Primer. PLoS Comput Biol. Jun. 7, 2016;12(6):e1004867. doi: 10.1371/journal.pcbi.1004867. Ex. 1123 submitted in PTAB Case No. IPR2023-00354, Dec. 27, 2022.

Sauter et al., New Python-based methods for data processing. Acta Crystallogr D Biol Crystallogr. Jul. 2013;69(Pt 7):1274-82. doi: 10.1107/S0907444913000863. Epub Jun. 18, 2013. Ex. 1124 submitted in PTAB Case No. IPR2023-00354, Dec. 27, 2022.

Venners, The Making of Python: A Conversation with Guido van Rossum, Part I. Jan. 13, 2003. 3 pages. Accessible at https://www.artima.com/articles/the-making-of-python. Retrieved on Nov. 10, 2022. 3 pages. Ex. 1125 submitted in PTAB Case No. IPR2023-00354, Dec. 27, 2022.

Adams et al., Phenix: a comprehensive Python-based system for macromolecular structure solution. Acta Crystallogr D Biol Crystallogr. Feb. 2010;66(Pt 2):213-21. doi: 10.1107/S0907444909052925. Epub Jan. 22, 2010. Ex. 1126 submitted in PTAB Case No. IPR2023-00354, Dec. 27, 2022.

Hayes et al., Structural basis for promiscuous PAM recognition in type I-E Cascade from E. coli. Nature. Feb. 25, 2016;530(7591):499-503. doi: 10.1038/nature16995. Epub Feb. 10, 2016. Author Manuscript. 23 pages. Ex. 1127 submitted in PTAB Case No. IPR2023-00354, Dec. 27, 2022.

[No Author Listed], BLAST+ 2.13.0 is here! BLAST® Basic Local Alignment Search Tool. Mar. 17, 2022. Retrieved on Nov. 10, 2022. 10 pages. Ex. 1128 submitted in PTAB Case No. IPR2023-00354, Dec. 27, 2022.

Mount, Using the Basic Local Alignment Search Tool (BLAST). CSH Protoc. Jul. 1, 2007;2007:pdb.top17. doi: 10.1101/pdb.top17. 6 pages. Ex. 1129 submitted in PTAB Case No. IPR2023-00354, Dec. 27, 2022.

Chen et al., Cut site selection by the two nuclease domains of the Cas9 RNA-guided endonuclease. J Biol Chem. May 9, 2014;289(19):13284-94. doi: 10.1074/jbc.M113.539726. Epub Mar. 14, 2014. Ex. 1130 submitted in PTAB Case No. IPR2023-00354, Dec. 27, 2022.

Mann, Introductory Statistics. 7$^{th}$ Ed. John Wiley & Sons, Inc. 2010. 750 pages. Ex. 1131 submitted in PTAB Case No. IPR2023-00354, Dec. 27, 2022.

[No Author Listed], Summation Notation. Retrieved from www.columbia.edu/itc/sipa/math/summation.html on Nov. 10, 2022. 4 pages. Ex. 1132 submitted in PTAB Case No. IPR2023-00354, Dec. 27, 2022.

Harvey et al., How many stars are in the universe? Space. Feb. 11, 2022. Retrieved from https://www.space.com/26078-how-many-stars-are-there.html on Nov. 10, 2022. 18 pages. Ex. 1133 submitted in PTAB Case No. IPR2023-00354, Dec. 27, 2022.

Lopez et al., Biochemistry, Essential Amino Acids. Mar. 18, 2022. In: StatPearls [Internet]. Treasure Island (FL): StatPearls Publishing; Jan. 2022—Retrieved from https://www.ncbi.nlm.nih.gov/books/NBK557845/?report=printable on Nov. 10, 2022. 5 pages. Ex. 1134 submitted in PTAB Case No. IPR2023-00354, Dec. 27, 2022.

Shchelochkov, Open Reading Frame. Updated Dec. 8, 2022. Retrieved from https://www.genome.gov/genetics-glossary/open-reading-frame on Dec. 14, 2022. 4 pages. Ex. 1135 submitted in PTAB Case No. IPR2023-00354, Dec. 27, 2022.

[No Author Listed], Read. Definition. NHS Health Education England. Retrieved from https://www.genomicseducation.hee.nhs.uk/glossary/read/ on Nov. 10, 2022. 4 pages. Ex. 1136 submitted in PTAB Case No. IPR2023-00354, Dec. 27, 2022.

Kurnaz et al., A statistical analysis of the robustness of alternate genetic coding tables. Int J Mol Sci. May 2008;9(5):679-697. doi: 10.3390/ijms9050679. Epub May 2, 2008. 20 pages. Ex. 1137 submitted in PTAB Case No. IPR2023-00354, Dec. 27, 2022.

Enfissi et al., Zika virus genome from the Americas. Lancet. Jan. 16, 2016;387(10015):227-8. doi: 10.1016/S0140-6736(16)00003-9. Epub Jan. 8, 2016. Ex. 1138 submitted in PTAB Case No. IPR2023-00354, Dec. 27, 2022.

Baronti et al., Complete coding sequence of zika virus from a French polynesia outbreak in 2013. Genome Announc. Jun. 5, 2014;2(3):e00500-14. doi: 10.1128/genomeA.00500-14. Ex. 1139 submitted in PTAB Case No. IPR2023-00354, Dec. 27, 2022.

[No Author Listed], The Wayback Machine page for http://www.who.int/entity/csr/research-and-developmen. 1 page. Ex. 1140 submitted in PTAB Case No. IPR2023-00354, Dec. 27, 2022.

[No Author Listed], Table of Contents. Genome Announcements. American Society for Microbiology. May/Jun. 2014. Retrieved from The Wayback Machine—http://genomea.asm.org:80/content/2/3.toc on Nov. 11, 2022. 16 pages. Ex. 1141 submitted in PTAB Case No. IPR2023-00354, Dec. 27, 2022.

(56) References Cited

OTHER PUBLICATIONS

[No Author Listed], Complete coding sequence of zika virus from a French Polynesia outbreak in 2013. Google Scholar Search Results. 2 pages. Ex. 1142 submitted in PTAB Case No. IPR2023-00354, Dec. 27, 2022.

[No Author Listed], Current Zika Product Pipeline. World Health Organization. Retrieved from The Wayback Machine—http://www.who.int/csr/research-and-dev on Nov. 10, 2022. 18 pages. Ex. 1143 submitted in PTAB Case No. IPR2023-00354, Dec. 27, 2022.

[No Author Listed], WHO and experts prioritize vaccines, diagnostics and innovative vector control tools for Zika R&D. World Health Organization. Mar. 9, 2016. Retrieved from The Wayback Machine—http://www.who.int/mediacentre/news/notes/2016/research-development-zika/en/ on Dec. 5, 2022. 4 pages. Ex. 1144 submitted in PTAB Case No. IPR2023-00354, Dec. 27, 2022.

Sifferlin, U.S. Launches 'Full-court Press' for a Zika Vaccine. Time—Health. Jan. 21, 2016. Retrieved from The Wayback Machine—http://time.com/4188973/zika-virus-vaccine-nih/ on Dec. 5, 2022. 3 pages. Ex. 1145. submitted in PTAB Case No. IPR2023-00354, Dec. 27, 2022.

Srivastava et al., A purified inactivated Japanese encephalitis virus vaccine made in Vero cells. Vaccine. Aug. 14, 2001;19(31):4557-65. doi: 10.1016/s0264-410x(01)00208-0. 13 pages. Ex. 1146 submitted in PTAB Case No. IPR2023-00354, Dec. 27, 2022.

[No Author Listed], Vaccine. UW-Madison Libraries Catalog Search Results. Retrieved from https://search.library.wisc.edu/catalog/999552122802121 on Nov. 11, 2022. 6 pages. Ex. 1147 submitted in PTAB Case No. IPR2023-00354, Dec. 27, 2022.

Srivastava et al., A purified inactivated Japanese encephalitis virus vaccine made in Vero cells. Vaccine. Aug. 14, 2001;19(31):4557-65. doi: 10.1016/s0264-410x(01)00208-0. Abstract only. 3 pages. Ex. 1148 submitted in PTAB Case No. IPR2023-00354, Dec. 27, 2022.

[No Author Listed], Vaccine. Elsevier Science. 1999-2002. Cover page. Retrieved from The Wayback Machine—http://www.elsevier.com/locate/vaccine on Nov. 26, 2022. 2 pages. Ex. 1149 submitted in PTAB Case No. IPR2023-00354, Dec. 27, 2022.

[No Author Listed], A purified inactivated Japanese encephalitis virus vaccine made in Vero cells. Google Scholar Search Results. 2 pages. Ex. 1150 submitted in PTAB Case No. IPR2023-00354, Dec. 27, 2022.

Thomas et al., A phase II, randomized, safety and immunogenicity study of a re-derived, live-attenuated dengue virus vaccine in healthy adults. Am J Trop Med Hyg. Jan. 2013;88(1):73-88. doi: 10.4269/ajtmh.2012.12-0361. Epub Dec. 3, 2012. 20 pages. Ex. 1151 submitted in PTAB Case No. IPR2023-00354, Dec. 27, 2022.

[No Author Listed], The American journal of tropical medicine and hygiene. PubMed Central Journal Page Search Results. https://catalog.nlm.nih.gov/permalink/01NLM_INST/101phhn/alma991179293406676. Retrieved on Nov. 15, 2022. 9 pages. Ex. 1152 submitted in PTAB Case No. IPR2023-00354, Dec. 27, 2022.

Thomas et al., A phase II, randomized, safety and immunogenicity study of a re-derived, live-attenuated dengue virus vaccine in healthy adults. Am J Trop Med Hyg. Jan. 2013;88(1):73-88. doi: 10.4269/ajtmh.2012.12-0361. Epub Dec. 3, 2012. Abstract only. 4 pages. Ex. 1153 submitted in PTAB Case No. IPR2023-00354, Dec. 27, 2022.

[No Author Listed], A phase II, randomized, safety and immunogenicity study of a re-derived, live-attenuated . . . Google Scholar Search Results. 2 pages. Ex. 1154 submitted in PTAB Case No. IPR2023-00354, Dec. 27, 2022.

Baronti et al., Complete coding sequence of Zika virus from a French polynesia outbreak in 2013. Genome Announc. Jun. 5, 2014;2(3):e00500-14. doi: 10.1128/genomeA.00500-14. Ex. 1160 submitted in PTAB Case No. IPR2023-00354, Dec. 27, 2022.

[No Author Listed] World Health Organization: Current Zika Product Pipeline. Mar. 3, 2016. 16 pages. Ex. 1161 submitted in PTAB Case No. IPR2023-00354, Dec. 27, 2022.

Sifferlin, U.S. Launches 'Full-Court Press' for a Zika Vaccine. Time. Jan. 21, 2016, Retrieved from https://time.com/4188973/zika-virus-vaccine-nih/ on Nov. 11, 2022. 2 pages. Ex. 1162 submitted in PTAB Case No. IPR2023-00354, Dec. 27, 2022.

Srivastava et al., A purified inactivated Japanese encephalitis virus vaccine made in Vero cells. Vaccine. Aug. 14, 2001;19(31):4557-65. doi: 10.1016/s0264-410x(01)00208-0. Ex. 1163 submitted in PTAB Case No. IPR2023-00354, Dec. 27, 2022.

Thomas et al., A phase II, randomized, safety and immunogenicity study of a re-derived, live-attenuated dengue virus vaccine in healthy adults. Am J Trop Med Hyg. Jan. 2013;88(1):73-88. doi: 10.4269/ajtmh.2012.12-0361. Epub Dec. 3, 2012. Ex.1164 submitted in PTAB Case No. IPR2023-00354, Dec. 27, 2022.

Declaration of Nathaniel E. Frank-White, Nov. 16, 2022, archive.org, 42 pages. Ex. 1166 submitted in PTAB Case No. IPR2023-00354, Dec. 27, 2022.

Hsieh-Yee, Curriculum Vitae, 21 pages. Ex. 1167 submitted in PTAB Case No. IPR2023-00354, Dec. 27, 2022.

[No Author Listed] Part Vii: A Summary of Commonly Used MARC 21 Fields. MARC 21 Reference Materials. Retrieved from https://www.loc.gov/marc/umb/um07to10.html on Dec. 5, 2022. 17 pages. Ex. 1168 submitted in PTAB Case No. IPR2023-00354, Dec. 27, 2022.

[No Author Listed] Stop Codon. ScienceDirect Topics. Retrieved from https://www.sciencedirect.com/topics/neuroscience/stop-codon#:~:text=Premature stop codons are those, as truncated) protein is formed on Dec. 6, 2022. 10 pages. Ex. 1169 submitted in PTAB Case No. IPR2023-00354, Dec. 27, 2022.

Shiver, et al. Scientific Notation and Order of Magnitude, Visionlearning, 2016. Retrieved from https://www.visionlearning.com/en/library/Math-in-Science/62/Scientific-Notation-and-Order-of-Magnitude/250#top on Dec. 6, 2022. 16 pages. Ex. 1170 submitted in PTAB Case No. IPR2023-00354, Dec. 27, 2022.

[No Author Listed] Python Code as RAN. Sequence Length 5, Identity 60. 1 page. Ex. 1171 submitted in PTAB Case No. IPR2023-00354, Dec. 27, 2022.

[No Author Listed] Python Code as RAN. Sequence Length 500, Identity 95. 1 page. Ex. 1172 submitted in PTAB Case No. IPR2023-00354, Dec. 27, 2022.

[No Author Listed] Python (Calculate Number of AA Sequences). Sequence Length 500, Identity 95. 1 page. Ex. 1173 submitted in PTAB Case No. IPR2023-00354, Dec. 27, 2022.

[No Author Listed] Python (Calculate Number of DNA Sequences). Sequence Length 10272, Identity 99.99. 1 page. Ex. 1174 submitted in PTAB Case No. IPR2023-00354, Dec. 27, 2022.

[No Author Listed] Python (Calculate Number of Protein Sequences without Internal Stops). 3 pages. Ex. 1175 submitted in PTAB Case No. IPR2023-00354, Dec. 27, 2022.

Ramachandran et al., Processing and integration of functionally oriented prespacers in the *Escherichia coli* CRISPR system depends on bacterial host exonucleases. J Biol Chem. Mar. 13, 2020;295(11):3403-3414. doi: 10.1074/jbc.RA119.012196. Epub Dec. 30, 2019. Ex. 1176 submitted in PTAB Case No. IPR2023-00354, Dec. 27, 2022.

Plevka et al., Maturation of flaviviruses starts from one or more icosahedrally independent nucleation centres. EMBO Rep. Jun. 2011;12(6):602-6. doi: 10.1038/embor.2011.75. Epub May 13, 2011. Ex. 1177 submitted in PTAB Case No. IPR2023-00354, Dec. 27, 2022.

Rodrigues et al., Viral vaccines and their manufacturing cell substrates: New trends and designs in modern vaccinology. Biotechnol J. Sep. 2015;10(9):1329-44. doi: 10.1002/biot.201400387. Epub Jul. 24, 2015. Ex. 1178 submitted in PTAB Case No. IPR2023-00354, Dec. 27, 2022.

Souza et al., Production of yellow fever virus in microcarrier-based Vero cell cultures. Vaccine. Oct. 30, 2009;27(46):6420-3. doi: 10.1016/j.vaccine.2009.06.023. Epub Jun. 24, 2009. Ex. 1179 submitted in PTAB Case No. IPR2023-00354, Dec. 27, 2022.

Pereira et al., An inactivated yellow fever 17DD vaccine cultivated in Vero cell cultures. Vaccine. Aug. 20, 2015;33(35):4261-8. doi: 10.1016/j.vaccine.2015.03.077. Epub Apr. 7, 2015. Ex. 1180 submitted in PTAB Case No. IPR2023-00354, Dec. 27, 2022.

[No Author Listed], Amended Articles of Incorporation of OCLC, Inc. Revised Jun. 23, 2017. 2 pages. Ex. 1181 submitted in PTAB Case No. IPR2023-00354, Dec. 27, 2022.

(56) References Cited

OTHER PUBLICATIONS

[No Author Listed], Discussion Paper No. 2020-DP16. Marc Standards. Retrieved from https://www.loc.gov/marc/mac/2020/2020-dp16.html on Dec. 13, 2022. 12 pages. Ex. 1183 submitted in PTAB Case No. IPR2023-00354, Dec. 27, 2022.
Baronti et al., Complete Coding Sequence of Zika Virus from a French Polynesia Outbreak in 2013. ASM Journals. Genome Announcements. Jun. 5, 2014;2(3). Partial abstract only. 1 page. Ex. 1185 submitted in PTAB Case No. IPR2023-00354, Dec. 27, 2022.
[No Author Listed], Trending Articles. PubMed records with recent increases in activity. 2 pages. Ex. 1186 submitted in PTAB Case No. IPR2023-00354, Dec. 27, 2022.
[No Author Listed], Early Citations to Baronti from 2015. 1 page. Ex. 1187 submitted in PTAB Case No. IPR2023-00354, Dec. 27, 2022.
[No Author Listed], Current Zika Product Pipeline. World Health Organization. Mar. 3, 2016. Retrieved from who.int/publications/m/item/current-zika-product-pipeline. 1 page. Ex. 1188 submitted in PTAB Case No. IPR2023-00354, Dec. 27, 2022.
[No Author Listed], Library Search Page. WorldCat.Org. Retrieved from https://www.worldcat.org on Dec. 13, 2022. 5 pages. Ex. 1189 submitted in PTAB Case No. IPR2023-00354, Dec. 27, 2022.
[No Author Listed], Blast Global Alignment results for RID-THJEH558114. Retrieved on Dec. 13, 2022. 17 pages. Ex. 1190 submitted in PTAB Case No. IPR2023-00354, Dec. 27, 2022.
[No Author Listed], Blast Global Alignment results for RID-THT9HZ7G114. Retrieved on Dec. 13, 2022. 17 pages. Ex. 1191 submitted in PTAB Case No. IPR2023-00354, Dec. 27, 2022.
[No Author Listed], Blast Global Alignment results for RID-THTJHT47114. Retrieved on Dec. 13, 2022. 11 pages. Ex. 1192 submitted in PTAB Case No. IPR2023-00354, Dec. 27, 2022.
[No Author Listed], Python Code as RAN. 6 pages. Ex. 1193 submitted in PTAB Case No. IPR2023-00354, Dec. 27, 2022.
Srivastava et al., A purified inactivated Japanese encephalitis virus vaccine made in Vero cells. Vaccine. Aug. 14, 2001;19(31):4557-65. doi: 10.1016/s0264-410x(01)00208-0. Journal Article Home Page. Retrieved from sciencedirect.com/science/article/pii/S0264410X01002080?via%3Dihub. 1 page. Ex. 1195 submitted in PTAB Case No. IPR2023-00354, Dec. 27, 2022.
[No Author Listed], ScienceDirect Webpage. Elsevier. 2022. Retrieved from https://www.elsevier.com/. 9 pages. Ex. 1197 submitted in PTAB Case No. IPR2023-00354, Dec. 27, 2022.
[No Author Listed], Vaccine. WorldCat.org. Retrieved from https://worldcat.org/title/10399916 on Dec. 13, 2022. 5 pages. Ex. 1198 submitted in PTAB Case No. IPR2023-00354, Dec. 27, 2022.
[No Author Listed], Vaccine Journal Home Page. ScienceDirect. Retrieved from https://www.sciencedirect.com/journal/vaccine on Dec. 13, 2022. 9 pages. Ex. 1199 submitted in PTAB Case No. IPR2023-00354, Dec. 27, 2022.
[No Author Listed], Directory of OCLC Members: gzm. Retrieved from https://www.oclc.org/en/contacts/libraries.html on Dec. 13, 2022. 2 pages. Ex. 1200 submitted in PTAB Case No. IPR2023-00354, Dec. 27, 2022.
[No Author Listed], W: General Medicine. Health Professions. NIH National Library Classification 2022 Summer Edition. Retrieved from https://classification.nlm.nih.gov/schedules/w on Dec. 13, 2022. 9 pages. Ex. 1202 submitted in PTAB Case No. IPR2023-00354, Dec. 27, 2022.
Thomas et al., A phase II, randomized, safety and immunogenicity study of a re-derived, live-attenuated dengue virus vaccine in healthy adults. Am J Trop Med Hyg. Jan. 2013;88(1):73-88. doi: 10.4269/ajtmh.2012.12-0361. Epub Dec. 3, 2012. Introduction. Retrieved from ajtmh.org/view/journals/tpmd/88/1/article-p73.xml. 25 pages. Ex. 1204 submitted in PTAB Case No. IPR2023-00354, Dec. 27, 2022.
[No Author Listed], The American Journal of Tropical Medicine and Hygiene. WorldCat.org Search Page. Retrieved from https://worldcat.org/title/1724826 on Dec. 13, 2022. 5 pages. Ex. 1205 submitted in PTAB Case No. IPR2023-00354, Dec. 27, 2022.
[No Author Listed], Dnlm Search Results from MARC Code List for Organizations. Retrieved from https://www.loc.gov/marc/organizations/org-search.php on Dec. 13, 2022. 1 page. Ex. 1206 submitted in PTAB Case No. IPR2023-00354, Dec. 27, 2022.
[No Author Listed], Medline/PubMed Data Element (Field) Descriptions. PubMed Resources. Retrieved from https://www.nlm.nih.gov/bsd/mms/medlineelements.html on Dec. 13, 2022. 35 pages. Ex. 1207 submitted in PTAB Case No. IPR2023-00354, Dec. 27, 2022.
[No Author Listed], Early Citations to Thomas from Jun. 2013-Mar. 2014. 1 page. Ex. 1208 submitted in PTAB Case No. IPR2023-00354, Dec. 27, 2022.
[No Author Listed], Early Citations to Srivastava from 2002-2003. 1 page. Ex. 1209 submitted in PTAB Case No. IPR2023-00354, Dec. 27, 2022.
Telephonic Conference Transcript of Conference Taking Place Apr. 19, 2023 in Inter Partes Review of U.S. Pat. No. 11,219,681. *Takeda Vaccines, Inc.* vs *Valneva Austria GmbH*. 38 pages. Ex. 1210 submitted in PTAB Case No. IPR2023-00354, Apr. 20, 2023.
Email Regarding Statutory Disclaimer Filing in U.S. Pat. No. 11,219,681. Submitted in Inter Partes Review of *Takeda Vaccines, Inc.* vs *Valneva Austria GmbH*. 1 page. Ex. 3001 in PTAB Case No. IPR2023-00354, Mar. 22, 2023.
Statutory Disclaimer, Form PTO-SB-43 submitted in U.S. Pat. No. 11,219,681. Submitted in Inter Partes Review of *Takeda Vaccines, Inc.* vs *Valneva Austria GmbH*. 1 page. Ex. 3002 in PTAB Case No. IPR2023-00354, Mar. 21, 2023.
Petitioner's Email Response to Email Regarding Statutory Disclaimer Filing in U.S. Pat. No. 11,219,681. Submitted in Inter Partes Review of *Takeda Vaccines, Inc.* vs *Valneva Austria GmbH*. 2 pages. Ex. 3003 in PTAB Case No. IPR2023-00354, Mar. 24, 2023.
Confirmation Email from The PTAB Confirming Understanding of Parties Positions on Statutory Disclaimer in U.S. Pat. No. 11,219,681. Submitted in Inter Partes Review of *Takeda Vaccines, Inc.* vs *Valneva Austria GmbH*. 4 pages. Ex. 3004 in PTAB Case No. IPR2023-00354, Mar. 28, 2023.
Cox et al., Predicting Zika virus structural biology: Challenges and opportunities for intervention. Antivir Chem Chemother. Aug. 2015;24(3-4):118-26. doi: 10.1177/2040206616653873. Epub Jun. 13, 2016. D1 on Consolidated list of cited opposition documents for Patent No. EP3393510, submitted Nov. 21, 2023.
Srivastava et al., A purified inactivated Japanese encephalitis virus vaccine made in Vero cells. Vaccine. Aug. 14, 2001;19(31):4557-65. doi: 10.1016/s0264-410x(01)00208-0. D2 on Consolidated list of cited opposition documents for Patent No. EP3393510, submitted Nov. 21, 2023.
[No Author Listed], Highlights of prescribing information for IXIARO. Intercell AG. Last revised: Sep. 2010. 13 pages. D2a on Consolidated list of cited opposition documents for Patent No. EP3393510, submitted Nov. 21, 2023.
[No Author Listed], Certified priority document for Application No. PCT/IN2016/050241, filed Jul. 16, 2015. 14 pages. D5a on Consolidated list of cited opposition documents for Patent No. EP3393510, submitted Nov. 21, 2023.
Larocca et al., Vaccine protection against Zika virus from Brazil. Nature. Aug. 25, 2016;536(7617):474-8. doi: 10.1038/nature18952. Epub Jun. 28, 2016. D7 on Consolidated list of cited opposition documents for Patent No. EP3393510, submitted Nov. 21, 2023.
Abbink et al., Protective efficacy of multiple vaccine platforms against Zika virus challenge in rhesus monkeys. Science. Sep. 9, 2016;353(6304):1129-32. doi: 10.1126/science.aah6157. D8 on Consolidated list of cited opposition documents for Patent No. EP3393510, submitted Nov. 21, 2023.
Abbink et al., Supplementary Materials for Protective efficacy of multiple vaccine platforms against Zika virus challenge in rhesus monkeys. Science. 2016. 20 pages. D8a on Consolidated list of cited opposition documents for Patent No. EP3393510, submitted Nov. 21, 2023.
Cohen, Infectious Disease. The race for a Zika vaccine is on. Science. Feb. 5, 2016;351(6273):543-4. doi: 10.1126/science.351.6273.543. D9 on Consolidated list of cited opposition documents for Patent No. EP3393510, submitted Nov. 21, 2023.
Putnak et al., Development of a purified, inactivated, dengue-2 virus vaccine prototype in Vero cells: immunogenicity and protection in

(56) References Cited

OTHER PUBLICATIONS mice and rhesus monkeys. J Infect Dis. Dec. 1996;174(6):1176-84. doi: 10.1093/infdis/174.6.1176. D10 on Consolidated list of cited opposition documents for Patent No. EP3393510, submitted Nov. 21, 2023.

Baronti et al., Complete Coding Sequence of Zika Virus from a French Polynesia Outbreak in 2013. Genome Announc. May-Jun. 2014;2(3):e00500-14. Abstract. D11 on Consolidated list of cited opposition documents for Patent No. EP3393510, submitted Nov. 21, 2023.

[No Author Listed], Zika virus strain H/PF/2013 polyprotein gene, complete cds. GenBank Acc. No. KJ776791.1. Jun. 13, 2014. Retrieved on Sep. 16, 2022. 5 pages. D11a on Consolidated list of cited opposition documents for Patent No. EP3393510, submitted Nov. 21, 2023.

[No Author Listed], Blast Global Alignment results for RID-PKE92BN8114. Retrieved on Nov. 7, 2022. 18 pages. D11b on Consolidated list of cited opposition documents for Patent No. EP3393510, submitted Nov. 21, 2023.

[No Author Listed], Blast Global Alignment results for RID-PKEBSNWN114. Retrieved on Nov. 7, 2022. 12 pages. D11c on Consolidated list of cited opposition documents for Patent No. EP3393510, submitted Nov. 21, 2023.

World Health Organization, Zika Virus Microcephaly and Guillain-Barre Syndrome. Situation Report. Mar. 17, 2016. 13 pages. D12 on Consolidated list of cited opposition documents for Patent No. EP3393510, submitted Nov. 21, 2023.

Musso, Zika Virus Transmission from French Polynesia to Brazil. Emerg Infect Dis. Oct. 2015;21(10):1887. doi: 10.3201/eid2110. 151125. D13 on Consolidated list of cited opposition documents for Patent No. EP3393510, submitted Nov. 21, 2023.

Enfissi et al., Zika virus genome from the Americas. Lancet. Jan. 16, 2016;387(10015):227-8. doi: 10.1016/S0140-6736(16)00003-9. Epub Jan. 8, 2016. D14 on Consolidated list of cited opposition documents for Patent No. EP3393510, submitted Nov. 21, 2023.

[No Author Listed], Decision in the Inter Partes Review IPR2023-00354 of the corresponding U.S. Pat. No. 11,219,681 (*Takeda Vaccines, Inc.* v. *Valneva Austria GMBH*), entered Jun. 9, 2023. D16 on Consolidated list of cited opposition documents for Patent No. EP3393510, submitted Nov. 21, 2023.

Schlegl et al., Influence of elemental impurities in aluminum hydroxide adjuvant on the stability of inactivated Japanese Encephalitis vaccine, IXIARO®. Vaccine. Nov. 4, 2015;33(44):5989-96. doi: 10.1016/j.vaccine.2015.05.103. Epub Jun. 19, 2015. D17 on Consolidated list of cited opposition documents for Patent No. EP3393510, submitted Nov. 21, 2023.

World Health Organization, World Health Organization: Current Zika Product Pipeline. Mar. 3, 2016. 16 pages. D20 on Consolidated list of cited opposition documents for Patent No. EP3393510, submitted Nov. 21, 2023.

Petersen et al., Zika Virus. N Engl J Med. Apr. 21, 2016;374(16):1552-63. doi: 10.1056/NEJMra1602113. Epub Mar. 30, 2016. D21 on Consolidated list of cited opposition documents for Patent No. EP3393510, submitted Nov. 21, 2023.

Sanders et al., Introduction to Vaccines Based on Inactivated Viruses. Chapter 2.1 in: Vaccine Analysis: Strategies, Principles, and Control. Springer-Verlag Berlin Heidelberg, eds. 2015; 45-49. DOI 10.1007 /978-3-662-45024-6_2. D22 on Consolidated list of cited opposition documents for Patent No. EP3393510, submitted Nov. 21, 2023.

Lawrence et al., Purification of viruses by centrifugation. Manual of Aquatic Viral Ecology, ASLO. 2010; 166-181. DOI 10.4319/mave.2010.978-0-9845591-0-7.166. D23 on Consolidated list of cited opposition documents for Patent No. EP3393510, submitted Nov. 21, 2023.

Hombach et al., Report on a WHO consultation on immunological endpoints for evaluation of new Japanese encephalitis vaccines, WHO, Geneva, Sep. 2-3, 2004. Vaccine. Nov. 1, 2005;23(45):5205-11. doi: 10.1016/j.vaccine.2005.07.002. Epub Jul. 1, 20058. D24 on Consolidated list of cited opposition documents for Patent No. EP3393510, submitted Nov. 21, 2023.

[No Author Listed], Text intended for grant for Application No. PCT/EP2016/082664 as of Aug. 30, 2022. 444 pages. D25 on Consolidated list of cited opposition documents for Patent No. EP3393510, submitted Nov. 21, 2023.

Response to Communication pursuant to Article 94(3) EPC by R. Dempster (on behalf of Script IP Limited) dated Aug. 13, 2020, for Application No. EP16828746.4. 8 pages. D26 on Consolidated list of cited opposition documents for Patent No. EP3393510, submitted Nov. 21, 2023.

Response to Communication pursuant to Article 94(3) EPC by R. Dempster (on behalf of Script IP Limited) dated Jun. 22, 2021, for Application No. EP16828746.4. 4 pages. D27 on Consolidated list of cited opposition documents for Patent No. EP3393510, submitted Nov. 21, 2023.

[No Author Listed], Third-party observations for Application No. EP16828746.4, submitted on Oct. 13, 2021. D28 on Consolidated list of cited opposition documents for Patent No. EP3393510, submitted Nov. 21, 2023.

[No Author Listed], Communication pursuant to Article 94(3) EPC for Application No. EP16828746.4, dated Feb. 3, 2022. D29 on Consolidated list of cited opposition documents for Patent No. EP3393510, submitted Nov. 21, 2023.

Response to Communication pursuant to Article 94(3) EPC by R. Dempster (on behalf of Script IP Limited) dated May 4, 2022, for Application No. EP16828746.4. 28 pages. D30 on Consolidated list of cited opposition documents for Patent No. EP3393510, submitted Nov. 21, 2023.

[No Author Listed], Communication pursuant to Article 94(3) EPC for Application No. EP16828746.4, dated Feb. 18, 2021. D31 on Consolidated list of cited opposition documents for Patent No. EP3393510, submitted Nov. 21, 2023.

Declaration of Scott Bailey, Ph.D, executed Dec. 14, 2022. 39 pages. D32 on Consolidated list of cited opposition documents for Patent No. EP3393510, submitted Nov. 21, 2023.

Exhibit submitted with Declaration of Scott Bailey, Ph.D. 1489 pages. D32a on Consolidated list of cited opposition documents for Patent No. EP3393510, submitted Nov. 21, 2023.

Zhang et al., Genetic and biochemical characterizations of Zika virus NS2A protein. Emerg Microbes Infect. 2019;8(1):585-602. doi: 10.1080/22221751.2019.1598291. D33 on Consolidated list of cited opposition documents for Patent No. EP3393510, submitted Nov. 21, 2023.

Malik et al. "Zika Virus—An Imminent Risk to the World" Journal of Immunology and Immunopathology; vol. 17, No. 2, Jul.-Dec. 2015: 57-59, DOI: 10.5958/0973-9149.2015.00019.2.

Hong et al. "Preparation of a purified, inactivated Japanese encephalitis (JE) virus vaccine in Vero cells" Biotechnology Letters 23: 1565-1573, 2001.

ZIKA VIRUS VACCINE

RELATED APPLICATIONS

This application is a continuation of U.S. application Ser. No. 17/548,721, filed Dec. 13, 2021, which is a continuation of U.S. application Ser. No. 16/813,862, now U.S. Pat. No. 11,219,681, filed Mar. 10, 2020, which is a continuation of U.S. application Ser. No. 16/063,007, now U.S. Pat. No. 10,639,365, filed Jun. 15, 2018, which is a national stage filing under 35 U.S.C. § 371 of International Patent Application Serial No. PCT/EP2016/082664, filed Dec. 23, 2016, the contents of each of which is herein incorporated by reference in its entirety.

REFERENCE TO AN ELECTRONIC SEQUENCE LISTING

The contents of the electronic sequence listing (I042270125US04-SEQ-JRV.xml; Size: 292,493 bytes; and Date of Creation: Jun. 7, 2023) is herein incorporated by reference in its entirety.

FIELD OF INVENTION

The disclosure relates to methods for the purification of Zika viruses for use in vaccines and in particular relates to an improved sucrose gradient process step allowing the separation of impurities such as protamine sulphate. The disclosure also relates to Zika virus vaccines and compositions and methods for producing said vaccines and administering the vaccines to subjects for the generation of an anti-Zika virus immune response.

BACKGROUND OF THE INVENTION

Adverse responses to protamine sulfate have been known for many years. Previous exposure to protamine can induce a humoral immune response and predispose susceptible individuals to the development of untoward reactions from the subsequent use of this drug. Patients exposed to protamine through the use of protamine-containing insulin or during heparin neutralization may experience life-threatening reactions and fatal anaphylaxis upon receiving large doses of protamine intravenously. Severe reactions to intravenous protamine can occur in the absence of local or systemic allergic reactions to subcutaneous injection of protamine-containing insulin. Although there is no clear evidence for hypersensitivity reactions of protamine sulphate linked to vaccination, vaccines containing protamine impurities have a precaution and contraindication warning in their labels stating that a serious allergic reaction after a previous dose of such a protamine containing vaccine (e.g. IXIARO®, see CDC site www.cdc.gov/japaneseencephalitis/vaccine/) is a contraindication to further doses. Thus elimination of said impurity is a medical request for an improved safety profile. On the other hand protamine sulphate is an excellent tool (and often better than other tools such as benzonase) to purify crude harvests of viruses grown on cell substrates.

In 2007, Zika virus was detected for the first time outside of the endemic regions of Asia and Africa since its discovery in a Rhesus monkey in Uganda in 1947. Since then, the virus has caused a large epidemic in French Polynesia, spreading through islands in the Pacific and into South and Central America by 2015 (WHO "Zika Situation Report" Feb. 5, 2016). Evidence suggests that in addition to being transmitted by *Aedes* species mosquitos, other vectors may exist, and the virus may be transmitted by blood transfusion, transplacentally, and through sexual transmission (WHO Zika Virus Fact Sheet, February 2016). Though the symptoms of Zika virus infection include mild fever, rash, and conjunctivitis, there is a likely correlation between infection and neurological disorders, including Guillain-Barré syndrome and microcephaly in fetuses/neonates subsequent to infection during pregnancy. There is currently no specific treatment or vaccine for Zika virus and the only preventative measures involve control of the mosquito vector. Zika virus presents a substantial public health threat due to the wide circulation of the *Aedes* mosquito, multiple routes of transmission, and potentially severe neurological effects of infection.

A preventative vaccine against Zika virus is a pressing medical need in endemic areas and in geographical areas where the vector is spreading. Furthermore, as Zika infection has dire consequences on embryonic and fetal development, a safe and effective vaccine for women of child-bearing potential or pregnant women is needed. Vaccines administered during pregnancy must be very safe for both the mother and the developing fetus. While live attenuated viral vaccines are highly effective, they are often not considered safe enough for administration to pregnant women. In this regard, inactivated viral vaccines, which lack the ability to propagate in the vaccinated subject, are considered much safer. Development of an inactivated Zika virus vaccine for administration to at-risk patients would fill this need.

SUMMARY OF THE INVENTION

During the course of virus purification, it was observed that addition of protamine sulfate to a virus harvest produced on a cell substrate removed not only contaminating DNA derived from host cells, as expected, but surprisingly also virtually eliminated immature and otherwise non-infectious virus particles from the preparation. This finding provided a streamlined, gentle, reproducible and broadly-applicable process for obtaining highly-purified infectious virus particles for applications such as vaccine preparation. In addition, it was surprisingly found that said protamine sulfate can be very efficiently separated from the virus fraction allowing for a safer vaccine produced at high yields.

Disclosed herein are virus vaccines and compositions comprising an inactivated Zika virus, and related methods of producing said vaccines and compositions. Also provided are methods of administering said Zika virus vaccines for the prevention of Zika virus infection and/or for the production of an anti-virus immune response in subjects, for example subjects at risk of being exposed to Zika virus. In particular, the invention is directed to a virus vaccine comprising an optimally inactivated Zika virus particle, wherein the Zika virus particle in an appropriate dose is able to seroconvert a subject that is administered the virus vaccine with at least a 70% probability, preferably an 80% probability. Another advantage of the invention is that related methods of producing said vaccines and compositions are very efficient and provide pure compositions largely devoid of impurities, in particular protamine sulphate, allowing for high volume production of vaccines. Detail experimental examples to the above are provided for Zika virus.

The herein disclosed in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was unexpectedly higher than the recently reported inactivated Zika virus vaccine candidate (Larocca, et. al, 2016, Nature doi:10.1038/nature18952.). Inactivated viruses are among the safest vaccines and especially preferred for delivery to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing, alignments were performed with the multi alignment package Jalview (Waterhouse et al., 2009, Bioinformatics 25 (9) 1189-1191). In the drawings:

Figure 1:
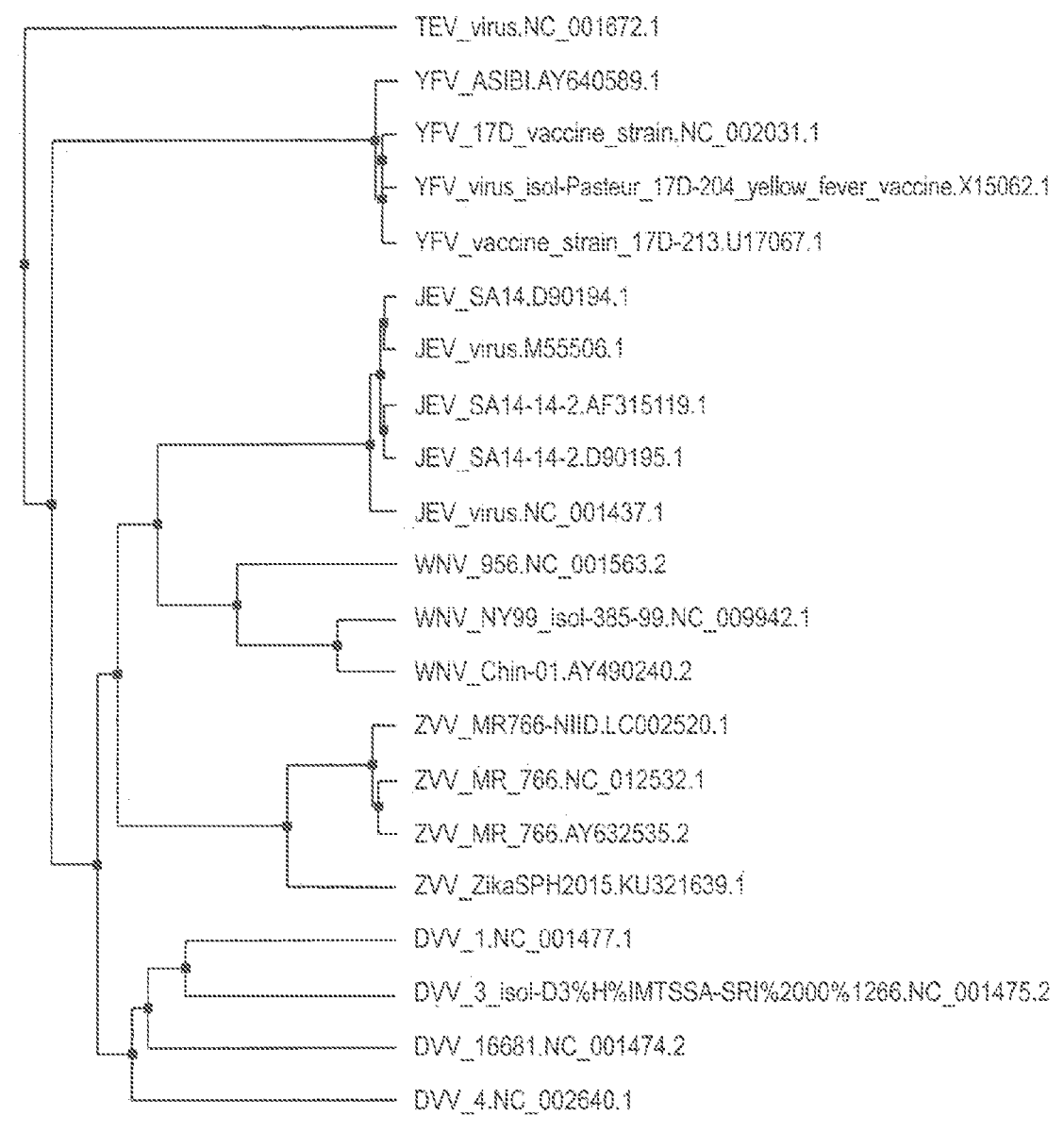

FIG. 1: Average distance tree (by % identity, nt), complete genomes.

Figure 4:
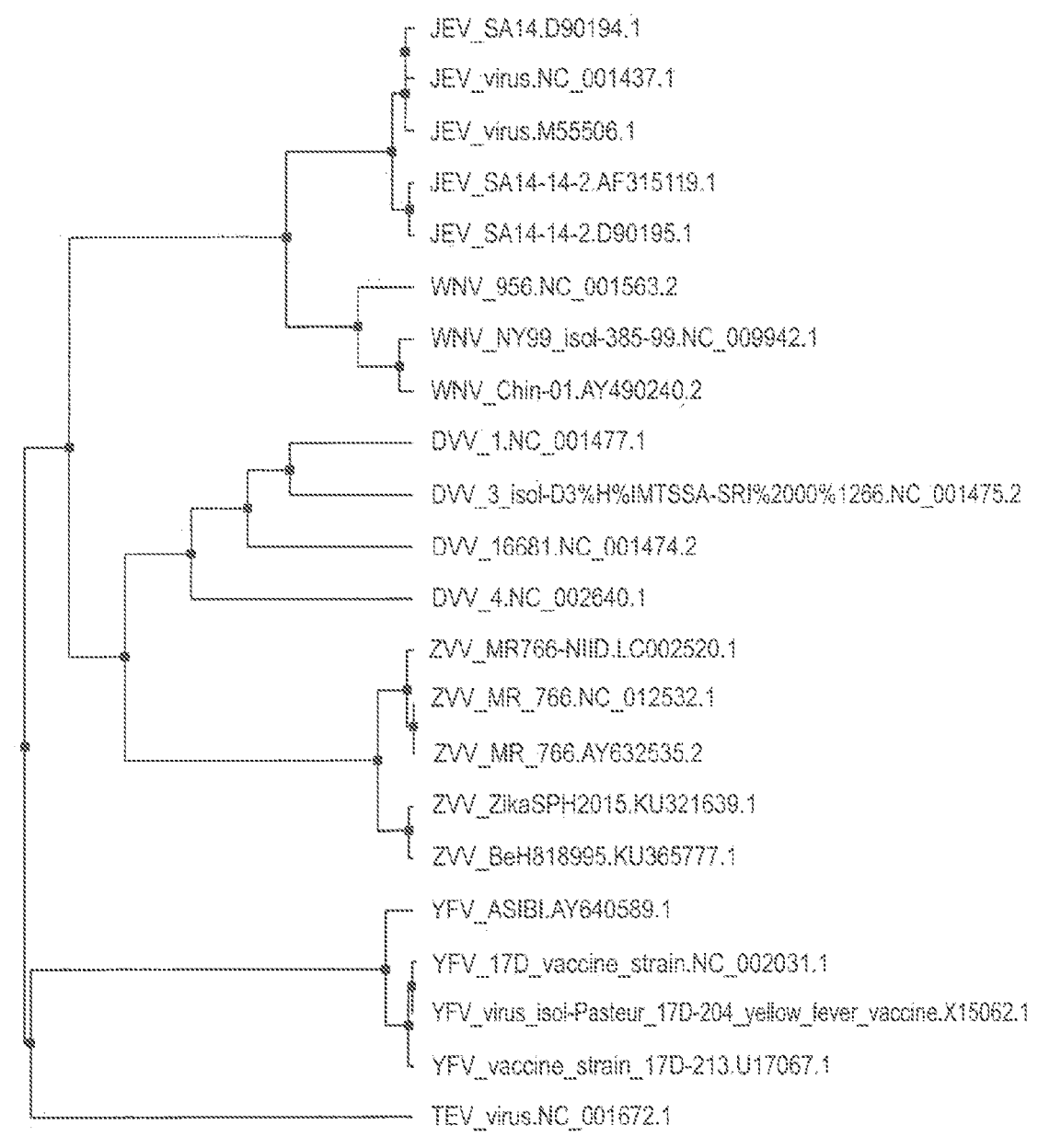

FIG. 4: Average distance tree (by % identity, aa), E-protein.

Figure 6:
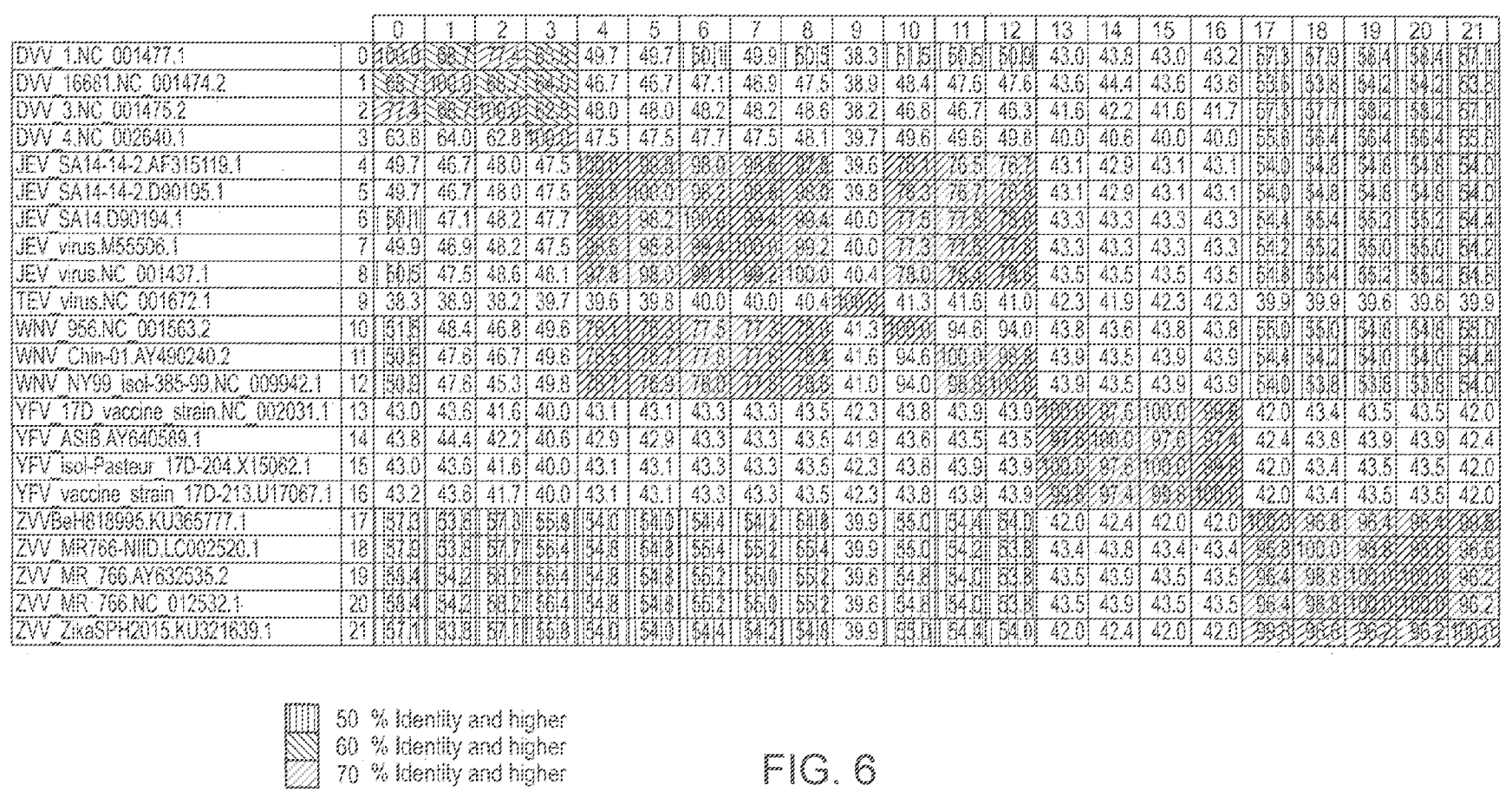

FIG. 6: Pairwise alignment-Jalview (% identity, aa), E-protein.

Figure 7C:
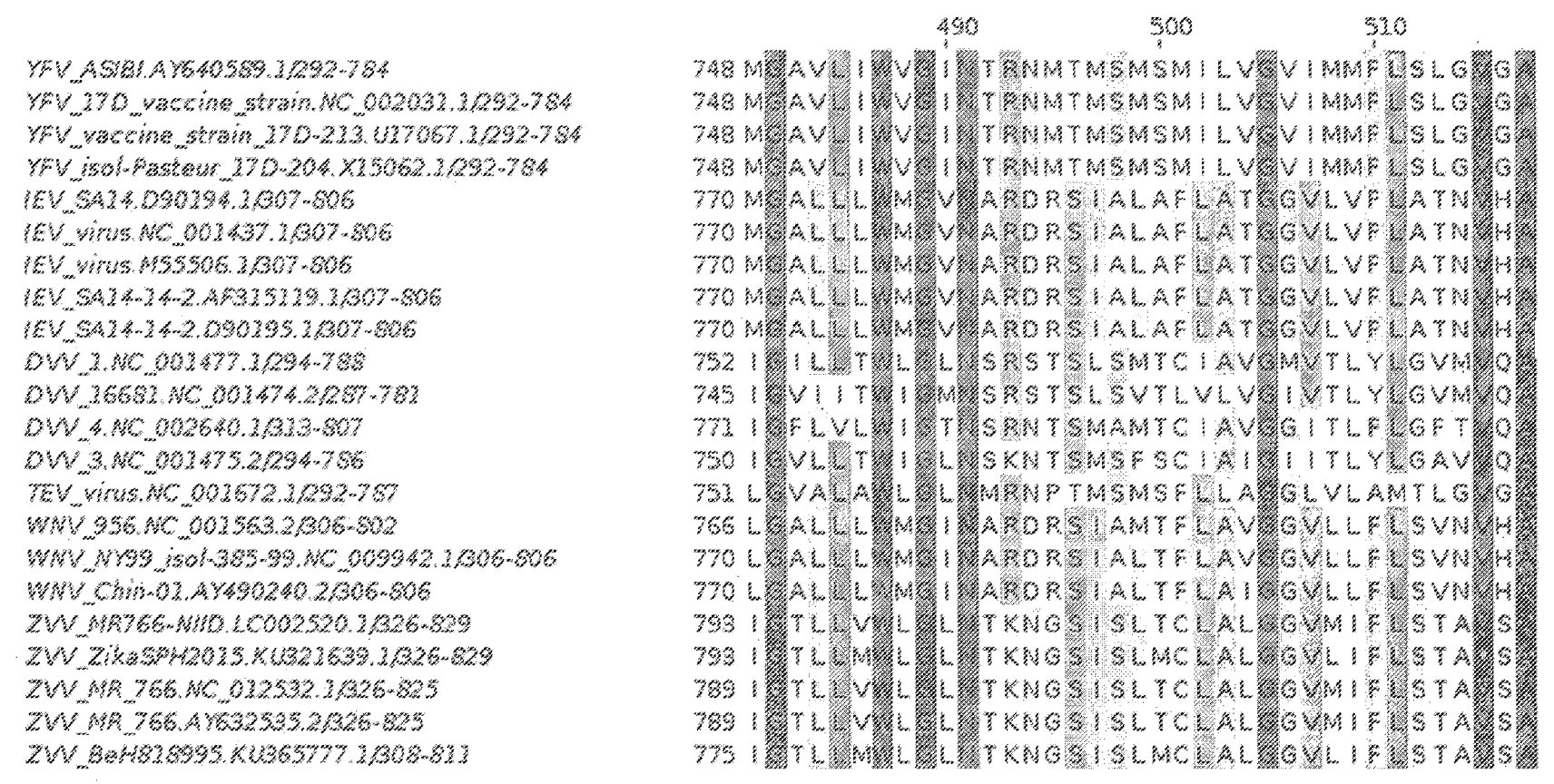

FIGS. 7A-7C: Alignment (shading: % identity, aa), E-protein.

DETAILED DESCRIPTION OF THE INVENTION

Figure 2:
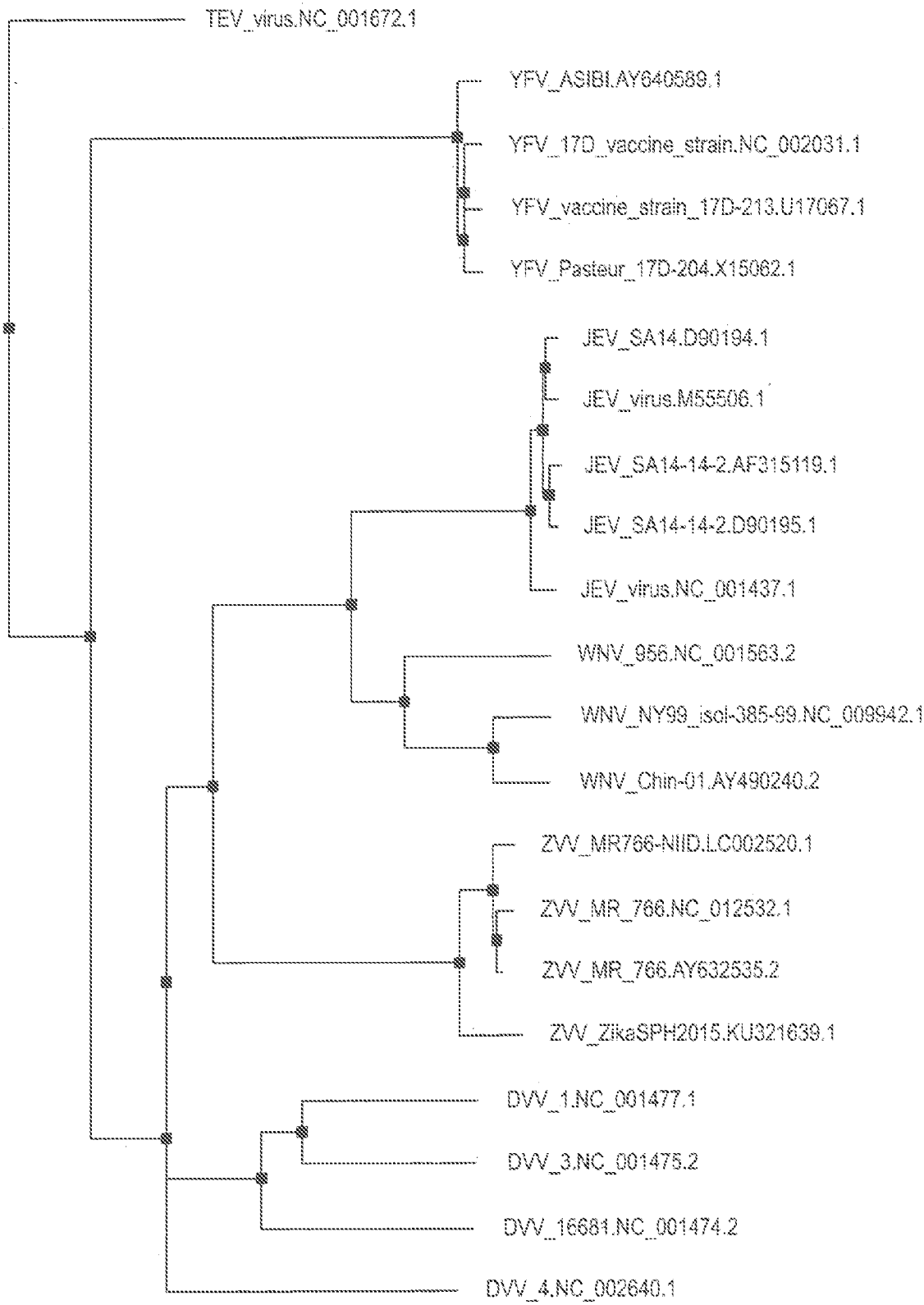
FIG. 2: Neighbor joining tree (by % identity, nt), complete genomes.
Figure 3:
FIG. 3: Pairwise alignment-Jalview (% identity, nt), complete genomes.
Figure 5:
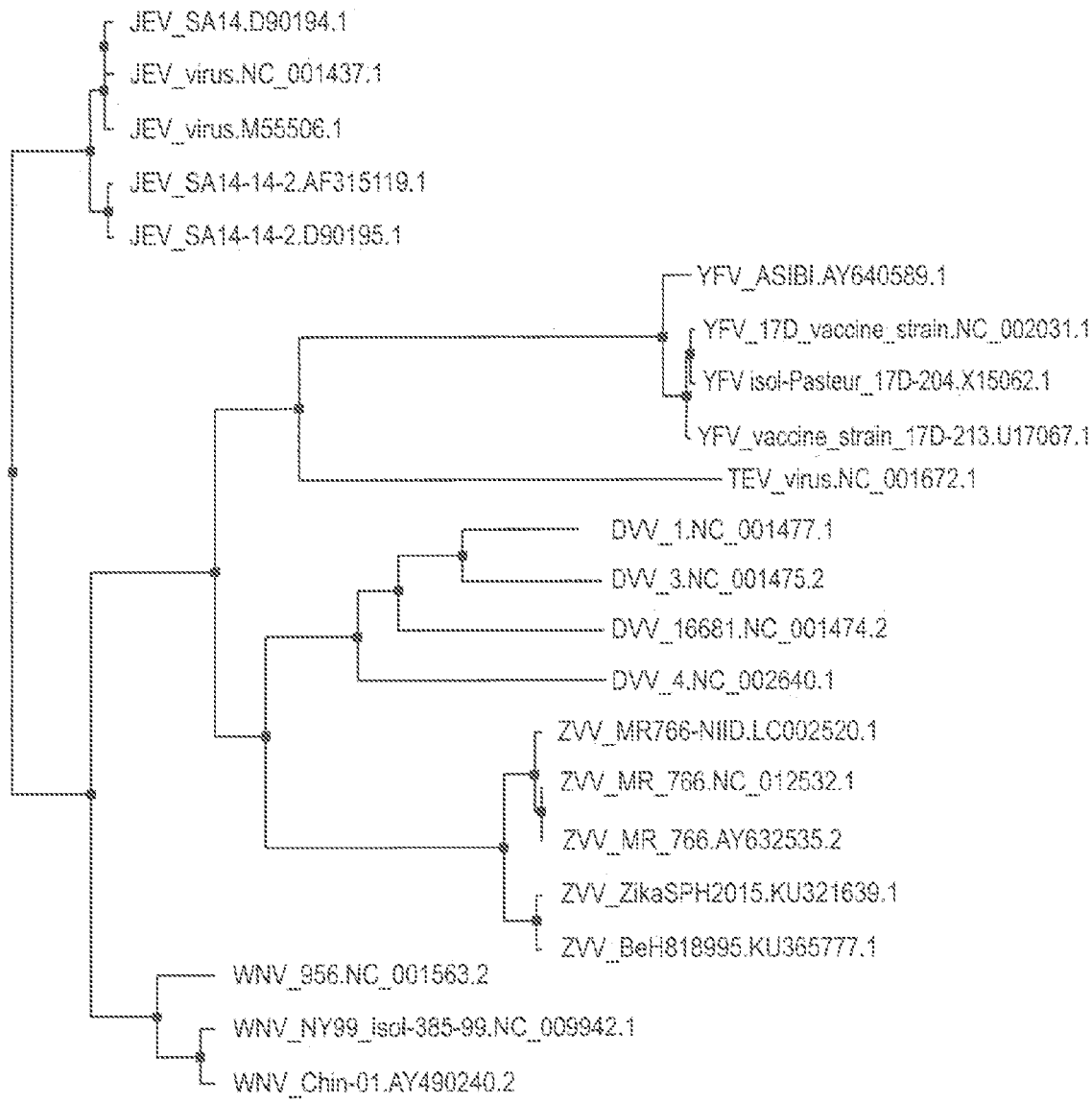
FIG. 5: Neighbor joining tree (by % identity. aa), E-protein.
Figure 7A:
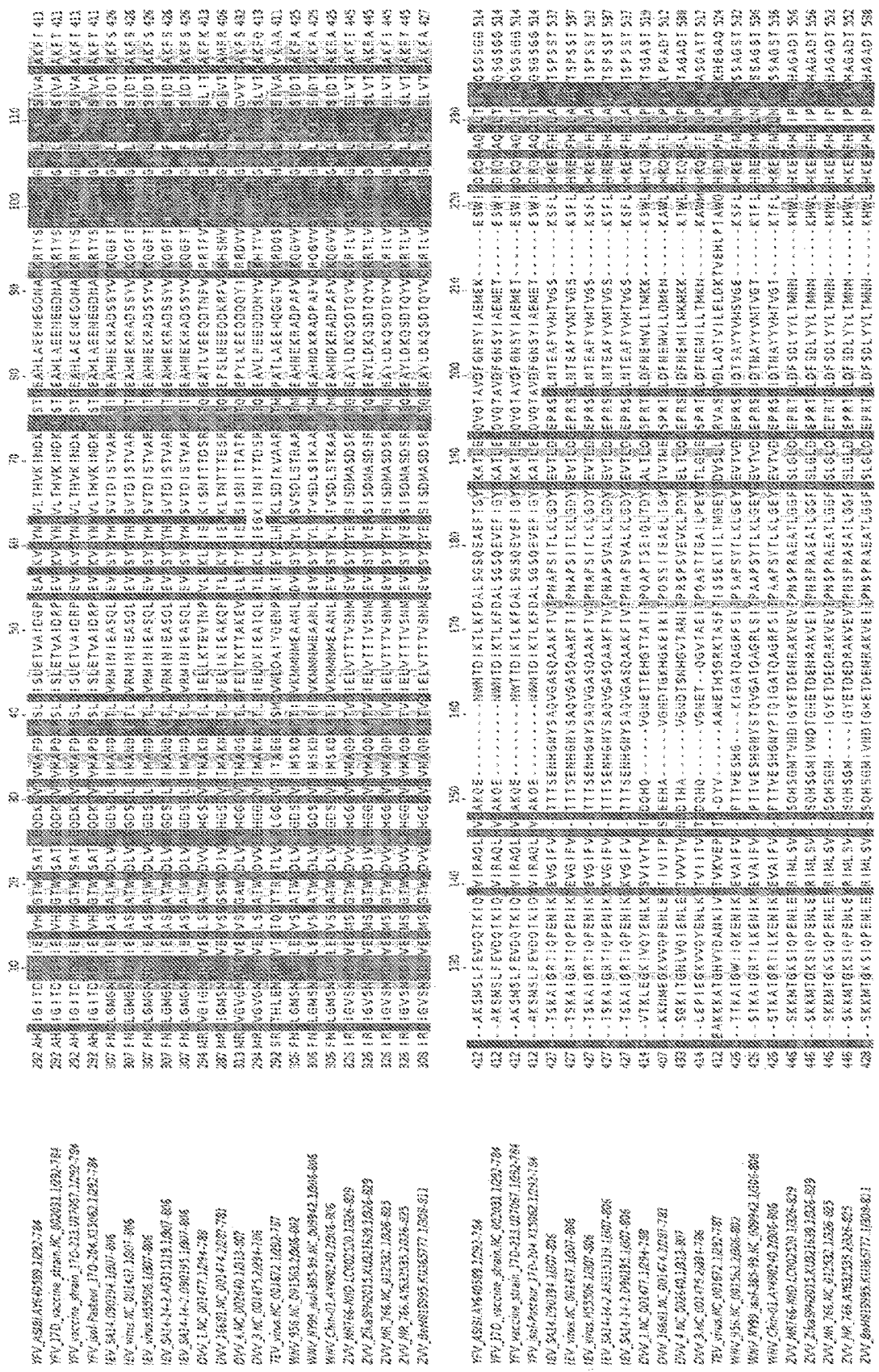
Figure 7B:
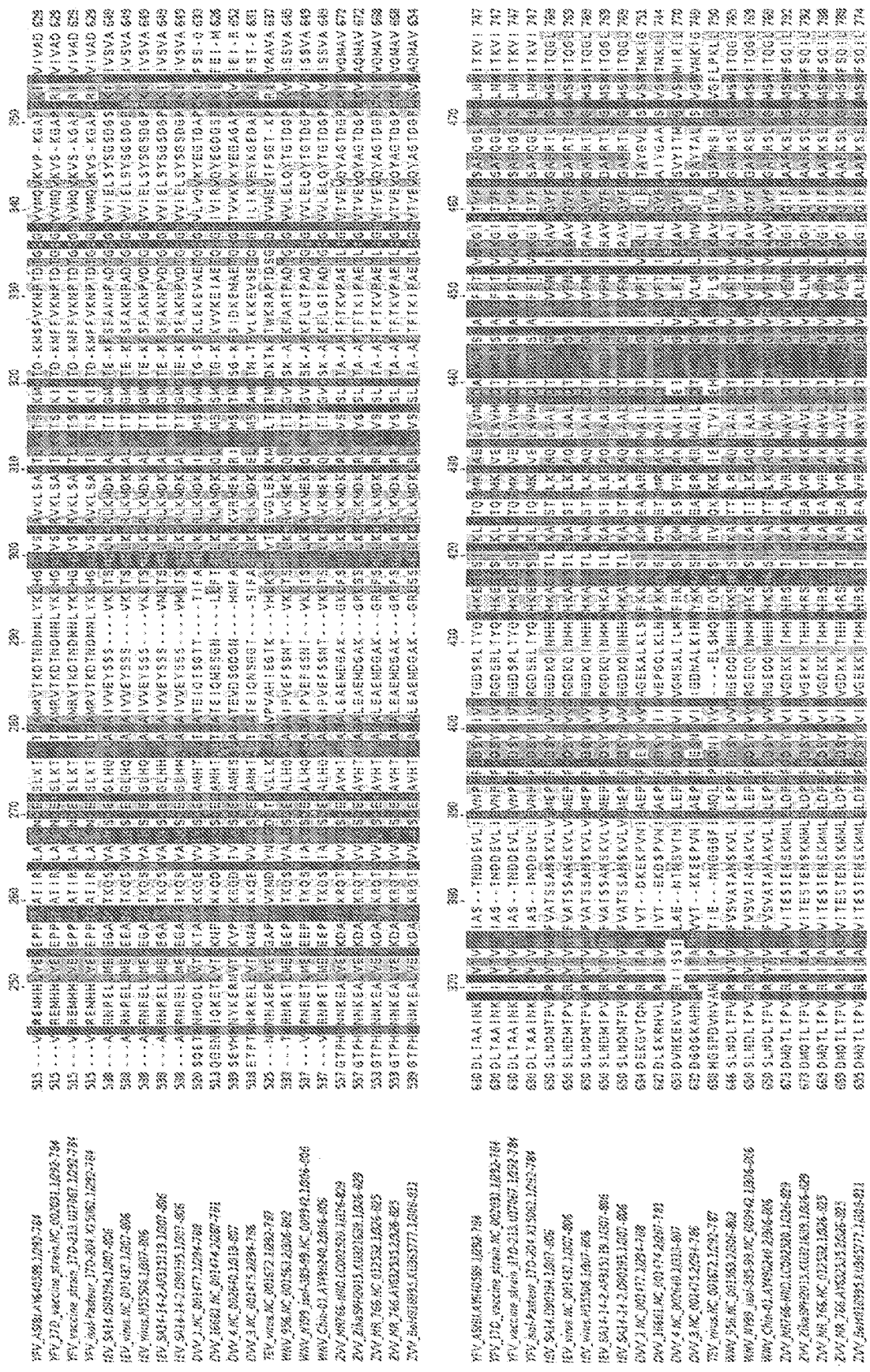
Figure 8:
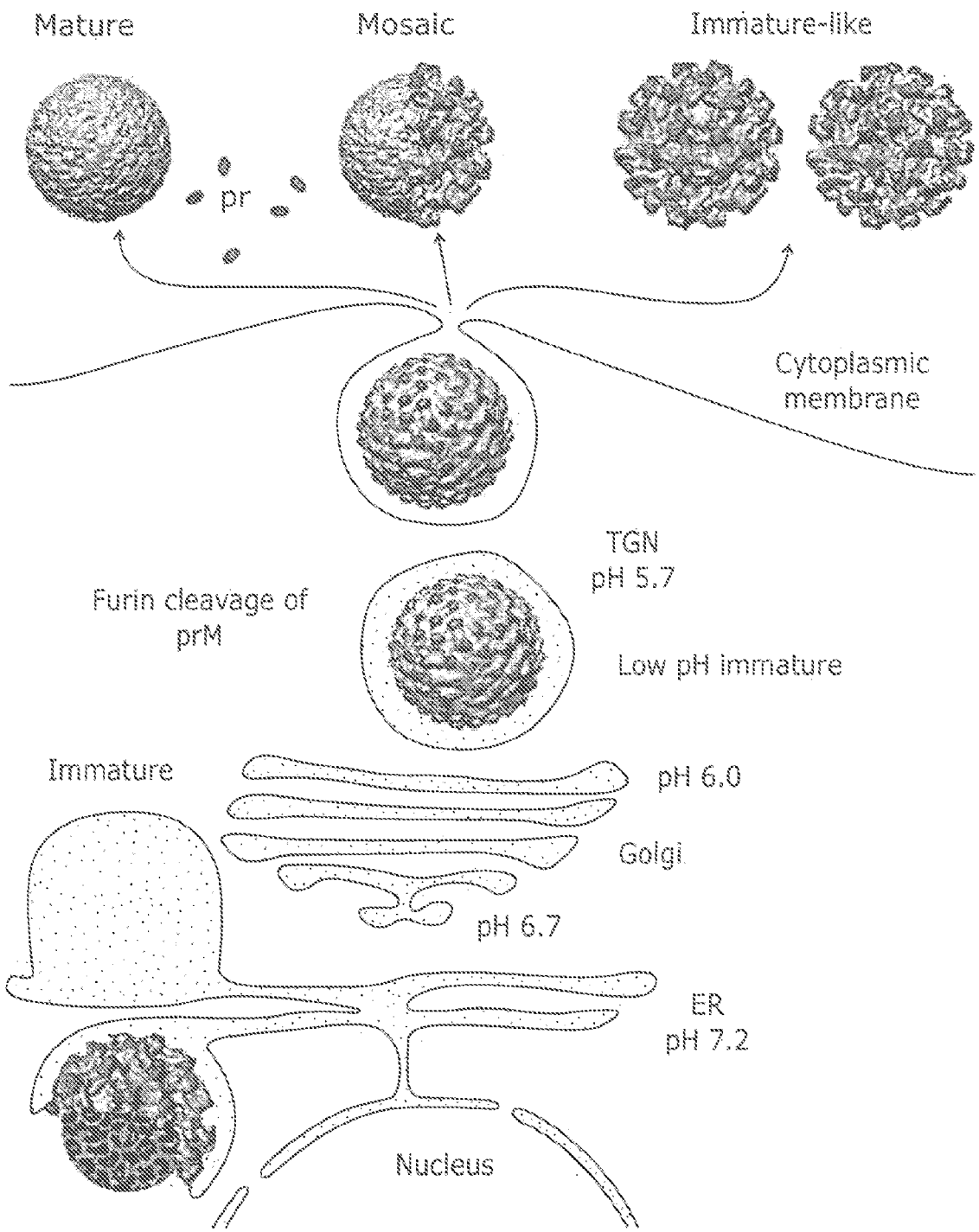
FIG. 8: An example of virus particle maturation in the host cell. As observed in flaviviruses, full maturation of the particles requires proteolytic cleavage of the precursor membrane glycoprotein (prM) by the host protease furin. Not all prM molecules are cleaved, resulting in the release of mature, mosaic or immature-like conformations from the cells. Mosaic and immature forms are generally not infectious-only mature virions are infective and have hemagglutinin (HA)/TCID50 activity. (Figure adapted from Plevka, et al., Maturation of flaviviruses starts from one or more icosahedrally independent nucleation centres, EMBO reports (2011) 12, 602-606).

Disclosed herein are Zika virus vaccines and compositions comprising an inactivated Zika virus, and related methods of producing said vaccines and compositions. Also provided are methods of administering said virus vaccines for the prevention of virus infection and/or for the production of an anti-virus immune response in subjects, for example subjects at risk of being exposed to virus. In particular, the invention is directed to a virus vaccine comprising an optimally inactivated virus particle, wherein the virus particle in an appropriate dose is able to seroconvert a subject that is administered the virus vaccine with at least a 70% probability, preferably an 80% probability. Another advantage of the invention is that related methods of producing said vaccines and compositions are very efficient and provide pure compositions largely devoid of impurities, in particular protamine sulphate, allowing for high volume production of vaccines. Examples to the above are provided for Zika virus.

Disclosed herein are downstream processes for purifying Zika virus particles from a crude preparation. The downstream process can be applied to either a virus which has not adapted for propagation on a particular cell substrate or for a partially/fully cell substrate adapted Zika virus particle.

Aspects of the invention provide processes for the purification of infectious Zika virus particles comprising the steps of (a) providing a crude harvest (a) comprising virus particles and impurities, wherein the impurities are generated from growing said virus particles on a cell substrate; (b) reducing impurities from the crude harvest (a) by precipitation with an agent comprising a protamine salt, preferably a protamine sulphate, to obtain a virus preparation (b); and further purifying the virus preparation (b) by an optimized sucrose density gradient centrifugation to obtain a virus preparation (c) comprising the infectious virus particles.

In some embodiments, the concentration of protamine sulphate in step (b) is about 1 to 10 mg/ml, more preferably about 1 to 5 mg/ml, more preferably about 1 to 2 mg/ml. In one embodiment, the concentration of protamine sulphate in step (b) is about 2 mg/mL. In one embodiment, the concentration of protamine sulphate is 1.2 to 1.8 mg/ml, more preferably 1.4 to 1.6 mg/ml. In a preferred embodiment, the concentration of protamine sulphate in step (b) is about 2 mg/ml.

In some embodiments, the residual host cell DNA of the virus preparation (c) is less than 1 µg/mL, especially less than 900, 800, 700, 600, 500, 400, 300 or 200 ng/mL, preferably less than 100 ng/mL.

In a preferred embodiment, the residual host cell DNA of the virus preparation (c) is less than 10 ng/mL. In some embodiments, the residual host cell protein of the final virus preparation (c) is less than 10 µg/mL, especially less than 9, 8, 7, 6, 5, 4, 3 or 2 µg/mL, preferably less than 1 µg/mL. In a preferred embodiment, the residual host cell protein of the virus preparation (c) is less than 100 ng/mL. In some embodiments, the residual non-infectious virus particles of the final virus preparation (c) is less than 10 µg/mL, especially less than 9, 8, 7, 6, 5, 4, 3 or 2 µg/mL, preferably less than 1 µg/mL. In a preferred embodiment, the content of residual non-infectious virus particles of the virus preparation (c) is less than 100 ng/mL.

In some embodiments, the residual protamine is less than 1 µg/mL, especially less than 900, 800, 700, 600, 500, 400, 300 or 200 ng/mL, preferably less than 100 ng/mL, more preferably is below the detection limit of HPLC, in particular below the detection limit in the final drug substance. In some embodiments, the PS content is tested by HPLC or size exclusion chromatography (SEC). For example, HPLC is validated for PS determination in JEV sucrose gradient pool samples as a routine release assay and is very sensitive (i.e., LOQ 3 µg/mL; LOD 1 µg/mL). In the current invention, PS content in in Zika virus DS samples was <LOD. In one embodiment, the HPLC assessment of PS content can be performed on a Superdex Peptide 10/300GL column (GE: 17-5176-01) using 30% Acetonitrile, 0.1% Trifluoroacetic acid as solvent with a flow rate of 0.6 ml/min at 25° C. and detection at 214 nm. A more sensitive method of measurement for residual protamine in a purified virus preparation is mass spectrometry (MS). In some embodiments, the residual PS levels in a Zika virus preparation are tested by MS or other such highly sensitive method, e.g. nuclear magnetic resonance (NMR). With this method, residual PS, as well as fragments and/or break-down products of PS, can be detected at trace amounts, such as levels as low as, for example, $10^6$, $10^7$ or $10^8$ molecules per typical sample load. In some embodiments, the PS levels are tested in the sucrose gradient pool. In some embodiments, the PS levels are tested in the drug product. In some embodiments, the PS levels are tested in the drug substance.

In some embodiments, the crude harvest (a) comprising the virus particles and impurities is subjected to one or more pre-purification step(s) prior to step (b). In some embodiments, the one or more pre-purification step(s) comprises digesting host cell genomic DNA in the crude harvest (a) comprising the virus particles and impurities by enzymatic treatment. In some embodiments, the one or more pre-purification step(s) comprises filtration, ultrafiltration, concentration, buffer exchange and/or diafiltration. In some embodiments, the one or more pre-purification steps is filtration using a filter having a pore size equal to or less than 1 µm. In some embodiments, the filter has a pore size equal to or less than 0.2 µm. In a preferred embodiment, the filter has a pore size of 0.2 µm. In some embodiments, the concentration and/or ultra/diafiltration and/or buffer exchange is performed by tangential flow filtration (TFF). In some embodiments, ultra/diafiltration of the crude harvest (a) comprising the virus particles and impurities is performed using a hollow fiber membrane having a cut-off of equal to or less than 300 kDa. In a preferred embodiment, the hollow fiber membrane has a cut-off of about 100 kDa.

The process according to the current invention may also comprise the use of a sucrose gradient, preferably an optimized sucrose gradient. The sucrose gradient is preferably optimized for the removal of protamine sulfate, also for the removal of immature viral particles or other viral particles which are non-infectious or host cell proteins or nucleic acids (DNA, RNA, mRNA, etc) or other host cell debris. In the current invention the optimized sucrose gradient comprises at least two, at least three, at least four layers of sucrose solutions with different densities. In one embodiment, the virus preparation to be purified is provided in a sucrose solution which has a density of about 8%, about 9%, about 10%, about 11%, about 12% sucrose (w/w), preferably about 10%. In one embodiment, one sucrose solution in the gradient has a density of about 45%, about 46%, about 47%, about 48%, about 49%, about 50%, about 51%, about 52%, about 53%, about 54%, about 55% sucrose (w/w), preferably about 50%. In one embodiment, one sucrose solution in the gradient has a density of about 30%, about 31%, about 32%, about 33%, about 34%, about 35%, about 36%, about 37%, about 38%, about 39%, about 40% sucrose (w/w), preferably about 35%. In one embodiment, one sucrose solution in the gradient has a density of about 10%, about 11%, about 12%, about 13%, about 14%, about 15%, about 16%, about 17%, about 18%, about 19%, about 20% sucrose (w/w), preferably about 15% sucrose. In a preferred embodiment, the sucrose gradient comprises three layers of sucrose solutions of about 50%, about 35% and about 15% (w/w) sucrose and the virus composition to be purified is contained in about 10% (w/w) sucrose. Because the invention provided for means to not only test for host cell DNA but also immature viral particles, the skilled person in the art is able to more precisely optimize the sucrose gradient for most efficient purification and include additional tools such as PRNT assay to monitor purification success.

In some embodiments, the virus particle is a live virus, a chimeric virus, an attenuated live virus, a modified live virus, or a recombinant live virus. In a further step, the virus particles of the invention may be optionally inactivated. In some embodiments, the virus particle is an attenuated form of the virus particle. For example, the virus may have reduced infectivity, virulence, and/or replication in a host, as compared to a wild-type virus. In some embodiments, the virus is a mutated or modified virus, for example the nucleic acid of the virus may contain at least one mutation relative to the wild-type virus. In some embodiments, the virus is a recombinant live virus, meaning a virus that is generated recombinantly and may contain nucleic acid from different sources.

In some embodiments, the Zika virus particle is a live virus, an attenuated live virus, a modified live virus, or a recombinant live virus. In preferred embodiments, the Zika virus is a Zika virus from the Asian lineage.

In some embodiments, the relative reduction of impurity of the final virus preparation relative to the liquid medium (a) comprising the virus particles and impurities is in a range from 60 to 95%. In some embodiments, the residual impurity of the final virus preparation is less than 1%.

In some embodiments, the Zika virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line. In some embodiments, said cell line is a duck cell line. In some embodiments, said cell line is a diploid avian cell line. In some embodiments, said cell line is an EB66 cell line. In a preferred embodiment, said cell line is a Vero cell line.

Aspects of the invention provide a use of any of the processes described herein for manufacturing a composition for immunization against a viral infection. In a preferred embodiment, the composition or vaccine is directed against Zika virus such as e.g. a Zika virus of the Asian lineage.

Other aspects provide compositions comprising the Zika virus particles obtainable by any of the processes described herein for treating and/or preventing (i.e. protecting from) a viral infection. In a preferred embodiment, the viral infection is caused by Zika virus such as e.g. a Zika virus of the Asian lineage.

Furthermore, disclosed herein are Zika virus vaccines and compositions comprising an inactivated Zika virus, and related methods of producing said vaccines and compositions. Also provided are methods of administering the Zika virus vaccines for the prevention of Zika virus infection and/or for the production of an anti-Zika virus immune response in subjects, for example subjects at risk of being exposed to Zika virus.

Zika virus is a flavivirus closely related to Dengue virus and is similarly transmitted by the *Aedes* species mosquito, although other arthropod vectors for Zika virus are possible. Since it was first isolated from a Rhesus monkey in the Zika forest of Uganda in 1947, there were very few reported incidents of human infection, especially outside of the endemic regions of Africa and Asia until a large outbreak in French Polynesia in 2007 (Haddow et al. *PLoS Neglected Tropical Diseases* (2012) 6(2), Malone et al. *PLoS Neglected Tropical Diseases* (2016) 10(3),). The virus has since spread through islands of the Pacific, including Oceania, and into South and Central America (WHO "Zika Situation Report" Feb. 5, 2016).

In addition to being spread by the bite of an infected mosquito, evidence also suggests transmission may occur between individuals, such as from the blood of an infected individual, in utero/transplacental transmission from an infected mother to the fetus, sexual transmission between sexual partners, and possibly by other local transmission routes. There is a possible association between Zika virus infection during pregnancy and microcephaly in the fetus/neonate. Microcephaly is a rare condition in which a baby's head circumference is significantly less than expected based on the average for their age, sex, and ethnicity. This is a result of the brain failing to undergo proper embryonic development, and in 90% of cases is associated with mental retardation (Rocha et al. (2016) *Bull World Health Organ* 8 Feb. 2016).

There is a probable association between individuals having had a prior Zika virus infection and the incidence of Guillain-Barré syndrome, a neurological disorder in which the individual's immune system destroys the myelin sheath surrounding axons of the peripheral nervous system (WHO "Zika Situation Report" Feb. 5, 2016).

No specific treatments or vaccines for Zika virus currently exist, and the only measures at this time to prevent infection are through vector control and avoiding travel to regions experiencing outbreaks.

Described herein are Zika virus vaccines and compositions comprising inactivated Zika virus that provide a safe method for generating an immune response to Zika virus, including virus-neutralizing antibodies, that may help prevent against Zika virus infection.

Any strain of Zika virus may be used in the methods and compositions described herein. In some embodiments, the Zika virus is an isolate from an infected subject during a Zika virus outbreak. In some embodiments, the Zika virus is a strain isolated from Africa or from the African virus lineage. In some embodiments, the Zika virus is a strain isolated from Asia or from the Asian lineage (includes also strains from French Polynesia). In some embodiments, the Zika virus is a strain isolated from the Americas (South America, Central America, or North America), such as a Suriname Zika virus strain. In some embodiments, the Zika virus has an RNA genome corresponding (but not limited) to the DNA sequence provided by GenBank Accession No. AY632535.2, KU321639.1, KU497555.1, KU501215.1, KU509998.1, KU527068.1, KU681081.3, KU681082.3, KU707826.1, KU744693.1, or LC002520.1 or RNA genome disclosed partially or fully herein (SEQ ID NO: 2 to 69).

In some embodiments, the process of the invention results in an enrichment of infectious Zika virus particles from the crude harvest comprising infectious Zika virus particles and non-infectious virus particles and other virus products such that the enrichment of the infectious virus particles is at least 50%, at least 60%, at least 70%, at least 80%, at least 90%, at least 95%, preferably at least 80%, especially at least 85% relative to the total virus particle content of the crude harvest (a) comprising the virus particles and impurities.

In some embodiments, the residual impurity of the final virus preparation with respect to all impurities in the crude harvest is less than 10%, 9%, 8%, 7%, 6%, 5%, 4%, 3%, 2%, 1%, preferably less than 5% as determined by SEC-HPLC (Size Exclusion Chromatography—HPLC).

A unique aspect of the current invention is the realization that know-how related to the vaccine design and purification approach used for the Japanese Encephalitis Vaccine (JEV) IXIARO® (see Srivastava A. K. et al., 2001, Vaccine 19, 4557-4565, WO99/11762) may be employed and improved upon in order to expedite the development of a Zika virus vaccine and provide it to the subjects in need as soon as possible. The industrial process as disclosed for IXIARO®, providing a very effective vaccine against JEV, was complemented by further significant improvements disclosed herein in order to provide a more efficient (higher yield) and safer (less or no protamine sulphate with its allergic potential) Zika vaccine compared to the available JEV vaccine. A particular innovation of the herein disclosed vaccines is their greatly reduced protamine salt (SEQ ID NO: 1) content in the final drug substance facilitated by the development of an improved sucrose gradient. Said sucrose gradient not only allowed the separation of protamine sulphate but also allowed for a very effective inactivation by formaldehyde and resulted in the case of Zika with over 90% yield with the improved process disclosed herein vs about 35% yield with the published JEV process, see experimental part for comparison).

Aspects of the disclosure relate to methods of producing a virus in Vero tissue culture cells. Vero cells are a commonly used tissue culture cell line derived from the kidney of an African green monkey. The Vero cells used in the methods described herein are the Vero (WHO) cell line, obtained from the Health Protection Agency general cell collection under catalogue number 88020401.

Vero cells can be grown to confluent monolayers, for example in tissue culture flasks; in suspension (on microcarriers), for example in roller bottles; or in any other cell culture system for viral production. In some embodiments, the Vero cells are grown in a bioreactor for viral production. For plaque assays or the plaque reduction neutralization test (PRNT), Vero cells are grown in monolayers in tissue culture flasks, dishes, or wells of a plate. To infect the Vero cells with the virus, the culture medium is inoculated with virus and the cells are incubated with the virus for a period of time. The cells may be washed after inoculation to remove any virus that did not adsorb to the cells in a given amount of time.

The methods provided herein involve passaging the virus in Vero cells. As used herein, the terms "passage" or "passaging" refer to infecting a population of Vero cells with virus and subsequently inoculating a second population of Vero cells with virus produced by infection of the first Vero cell population. In some embodiments, a portion of the culture medium from the infected Vero cells (containing virus that was released from the infected cells) is used to inoculate a second population of Vero cells. This is referred to as one passage or one round of passaging. The passaging may be performed serially, for example, a portion of the culture medium from the infected second population of Vero cells is used to inoculate a third population of Vero cells, and so on. In some embodiments, virus obtained from a single plaque is used to inoculate another population of cells.

In some embodiments, the virus is passaged in Vero cells several times, such as at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 times. In some embodiments, the virus is passaged in Vero cells at least 4 times or 5 times. In some embodiments, the virus is passaged in Vero cells at least 30 times. It is important that the virus population, i.e. the virus sequences, stays as much as possible constant over said passaging. If adaption of the virus occurs (i.e. appearance of mutated viruses in the original virus population), it is preferred that said passages are not used in the context of manufacturing of said virus, e.g. for Zika it was found that up to passage 3 and culturing to day 7 can be used without major shifts in virus population, i.e. introduction of virus population with mutations. However this observation needs to be done for each virus strain and may be different.

In some embodiments, the Vero cells are incubated for at least 2 days after inoculation with the virus at e.g. a typical 0.01 MOI (multiplicity of infection) to allow for viral production prior to passaging. In some embodiments, the Vero cells are incubated for at least 3, 4, 5, 6, 7, 8, 9, 10 or more than 10 days e.g. at least 7 days after inoculation with the virus prior to passaging. The number of days the Vero cells are incubated after viral inoculation may depend on factors such as the multiplicity of infection used to inoculate the cells and the viral titer desired in the culture medium. Serial passaging of the virus in Vero cells may result in generation of a Vero cell adapted virus strain.

The culture medium from the infected Vero cells may be harvested (collected) to obtain the virus. In some embodiments, the culture medium is harvested from infected Vero cells and is replaced with fresh culture medium, which is then harvested after another period of time. In some embodiments, the culture medium harvested from infected Vero cells is pooled from independent Vero cell cultures and/or from independent days. Harvesting can be repeated up to 4 times by 7 or 9 days post infection, for example, and result in a high yield of virus per unit cell culture. In order to minimize the adaption of Zika virus strain to Vero cells, it was found that Vero cells could be incubated for at least 7 days, more preferably 5 days, prior to passaging and subsequently supernatants could be harvested at days 2, 3, 5 and 7 or 2, 3, and 5 (see also experimental part). The harvested culture medium can be stored at +4° C. prior to purification of the virus from the culture medium up to 2 weeks.

In some embodiments, debris from infected and lysed Vero cells may be removed from the harvested culture medium, referred to as a "clarification" of the culture medium. The harvested culture medium may be clarified by common methods known in the art, such as low-speed centrifugation, for example, at 1500 g for 10 min, and/or by filtration through a filter of pore size of 0.45 μm. The harvested culture medium can be stored at +4° C. prior to concentration.

To concentrate the titer of the Zika virus in the harvested culture medium, it may be subjected to concentration by any method known in the art. For example, the harvested culture medium may be concentrated by methods including, without limitation, ultrafiltration, ultracentrifugation, centrifugal concentrator, vacuum centrifugation, and lyophilization. In some embodiments, the harvested culture medium is concentrated by ultrafiltration and the retentate containing the Zika virus is collected. In some embodiments, the harvested culture medium is concentrated by precipitation in which polyethylene glycol (PEG) 8000 is dissolved in the culture medium (up to 10%) and the precipitate is dissolved in a buffer, for example phosphate-buffered saline (PBS, pH 7.0).

The harvested culture medium may be precipitated to produce a virus supernatant. In some embodiments, the harvested culture medium is precipitated to remove Vero cell DNA and other undesired material, such as Vero cell debris, from the harvested culture medium. In some embodiments, the harvested culture medium is concentrated prior to precipitation. In some embodiments, the harvested culture medium is precipitated by adding protamine sulfate (e.g. SEQ ID NO: 1) to the harvested culture medium and incubating the mixture, for example at +4° C. or on ice. In some embodiments, the harvested culture medium is treated with benzonase to remove Vero cell DNA and other undesired material, such as Vero cell debris, from the harvested culture medium. However, it was found that the treatment with protamine sulfate is preferred (see experimental part). In some embodiments, the precipitated culture medium is centrifuged to collect precipitated material and the supernatant containing the virus, referred to as a "virus supernatant", is collected.

The virus supernatant may be further purified after precipitation, for example density gradient ultracentrifugation. In some embodiments, the virus supernatant is further purified by sucrose gradient. Fractions may be collected from the sucrose gradients and assayed for presence of the virus. Methods for assaying for virus positive fractions include plaque assay, hemagglutination assay, polyacrylamide gel electrophoresis, and antigen assays such as Western blotting and ELISA. The fractions containing virus may be pooled based on titer of the virus and level of other impurities. The level or amount of impurities present in the virus supernatant can be estimated by testing for Vero cell DNA, virus aggregates and/or Vero cell protein (see experimental part). A particular embodiment of the invention is the improved sucrose gradient that allows for an efficient protamine separation as shown in the experimental part. It was surprisingly found that the addition of a virus-containing fraction with 10% (w/w) sucrose to a simple three layer sucrose density gradient (e.g. a gradient comprising a 15% (w/w) sucrose solution, a 35% (w/w) sucrose solution, and a 50% (w/w) sucrose solution) resulted in efficient separation of protamine sulphate without much loss of virus. Thus a particularly preferred embodiment of the invention is the use of a sucrose density gradient that is able to efficiently separate protamine sulphate, wherein said sucrose density gradient is used in the purification of virus such as the viruses described herein, i.e. a Zika virus.

To achieve a safe vaccine or composition for the administration to subjects, the virus supernatant may be inactivated (see experimental part for Zika virus). As used herein, the terms "inactivated" and "optimally inactivated" may be used interchangeably and refer to a process (or its result) by which the virus is rendered unable to infect a host cell (non-infectious), but that does not affect or substantially affect the antigenicity of the virus, for example, the immunogenic antigens exposed on the surface of the virus are able to stimulate an immune response in a subject (e.g., antigen-specific antibodies). By "does not affect or substantially affect the antigenicity of the virus" is meant that the inactivated virus retains at least 50%, at least 55%, at least 60%, at least 65%, at least 70%, at least 75%, at least 80%, at least 85%, at least 90%, at least 95%, at least 96%, at least 97%, at least 98%, at least 99%, or even essentially 100% of the antigenicity of a virus that is not subjected to inactivation.

A variety of methods are known in the art for inactivating viruses. In some embodiments, the virus is inactivated by chemical inactivation, thermal inactivation, pH inactivation, or UV inactivation.

In some embodiments, the inactivating is by chemical inactivation and involves contacting the virus with one or more chemical inactivation agents for a period of time under conditions such that the virus is inactivated but the antigenic epitopes are substantially intact. In some embodiments, the virus is inactivated for a period of time that is longer than is required to completely inactivate the virus. In some embodiments, the virus supernatant is inactivated for the number of days required to inactivate the virus plus at least one additional day. Samples of the virus supernatant may be taken at one or more times throughout the inactivation process and assessed for viral viability (infectivity) by any method known in the art, such as by infecting a monolayer of host cells (i.e., plaque assay). Using such a procedure, the period of time that is required to completely inactivate the virus can be determined, and a longer period of time is selected to ensure complete inactivation.

In some embodiments, the virus is contacted with a chemical inactivation agent for between 1 day and 50 days, between 2 days and 40 days, between 2 days and 30 days, between 2 days and 20 days, between 2 days and 10 days, between 3 days and 9 days, between 4 days and 8 days, between 5 days and 7 days, between 2 days and 5 days, or between 5 and 10 days. In some embodiments, the virus is contacted with one or more chemical inactivation agents for at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, or at least 50 days.

In some embodiments, the chemical inactivation is performed at about +5° C., +10° C., +15° C., +20° C., +25° C., +30° C., +35° C., +40° C., or about +45° C. In some embodiments, the chemical inactivation is performed at about +4° C. In some embodiments, the chemical inactivation is performed at about +22° C.

Any chemical inactivation agent known in the art may be suitable for inactivating the virus in the methods described herein. It will be appreciated by one of skill in the art that factors such as the chemical inactivation agent and the temperature at which inactivation is performed may affect the length of time (number of days) required to completely inactivate the virus. Examples of chemical inactivation agents include, without limitation, formaldehyde, enzymes, β-propiolactone, ethanol, trifluroacetic acid, acetonitrile, bleach, urea, guanidine hydrochloride, tri-n-butyl phosphate, ethylene-imine or a derivatives thereof, and organic solvents such as Tween, Triton, sodium deoxycholate, and sulphobetaine. A preferred inactivation is inactivation with formaldehyde at 22° C.+/−2° C. for about 10 days.

In some embodiments, the inactivating agent is neutralized after chemical inactivation of the virus. In some embodiments, the inactivating agent is formaldehyde and is neutralized after chemical inactivation using sodium thiosulphate or sodium metabisulfite.

In some embodiments, the virus is inactivated by thermal inactivation. In some embodiments, the thermal inactivation involves exposing the virus to heat, such as dry heat or vapor heat, for a period of time. In some embodiments, the thermal inactivation involves exposing the virus to temperatures of about +40° C., +45° C., +50° C., +55° C., +60° C., +65° C., +70° C., +75° C., +80° C., +85° C., +90° C., +95° C., or about +100° C. In some embodiments, the virus is exposed to heat for at least 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, about 96 hours, or longer. A preferred thermal inactivation involves exposing the virus to temperatures of about +56° C. for 60 minutes.

In some embodiments, the virus is inactivated by exposing the virus to acidic or alkaline conditions for a period of time such that the virus is completely inactivated. The pH of a virus preparation may be adjusted to a desired pH, for example by the addition of an acid, a base, or a buffer with a particular pH to the virus preparation. In some embodiments, the virus is inactivated at an acidic pH of about 2, 2.5, 3, 3.5, 4, 4.5, 5 or about 5.5. In other embodiments, the virus is inactivated at an alkaline pH of about 8, 8.5, 9, 9.5, 10, or about 10.5.

In some embodiments, the virus is inactivated using UV inactivation. UV inactivation involves exposing the virus to energy-rich radiation, such as UV-A, UV-B, or UV-C light for a period of time. It will be appreciated that any two or more methods of inactivation may be combined and performed concurrently or serially.

The inactivated virus may be subsequently dialyzed to remove any undesired material, including the inactivating agent and any neutralizing agent, and/or to replace the buffer with a buffer that is pharmaceutically acceptable for administration to subjects. In some embodiments, the inactivated virus is dialyzed with PBS. In addition or alternatively, the inactivated virus may be filtered, such as sterile filtered, through a 0.22 μm filter.

Any of the methods or uses described herein may be for the prevention of a Zika virus infection in a subject. As used herein, the terms "prevent," "preventing" and "protection from" include the administration of a virus vaccine or composition to a subject to reduce, or delay the onset of the manifestation of clinical or subclinical symptoms, complications, pathologies or biochemical indicia of a disease or infection, or to reduce or inhibit the spread/transmission of the Zika virus. As used herein, antigen(s), such as an inactivated Zika virus, that is administered to a subject prophylactically (e.g., prior to infection) may be referred to as a vaccine.

Zika Vaccine

As described herein Zika virus may cause any of a variety of symptoms upon infection of a subject, and is generally characterized by mild fever; rash (exanthema) on face, neck, trunk, upper arms; headache; sensitivity to light; non-inflammatory joint pain; conjunctivitis; lack of appetite; diarrhea; abdominal pain; and/or dizziness. Zika virus infection during pregnancy is associated with microcephaly in the fetus/neonate. There is also a probable association between the onset of Guillain-Barré syndrome or symptoms thereof. Diagnosis of Zika virus infection in subjects exposed to Zika virus or suspected of being exposed to Zika virus involves detecting the presence of virus-specific antibodies and/or molecular testing, such as PCR or real-time PCR detection of Zika virus.

Provided herein are methods for administering a dose of a therapeutically effective amount of a Zika virus vaccine to a subject in need thereof. In some embodiments, the subject is a mammalian subject, such as a human, non-human primate, rodent, rabbit, sheep, dog, cat, horse, or cow. In some embodiments, the subject is a mouse. In some embodiments, the subject is a human subject, such as a child, an adult, or an elderly adult. In some embodiments, the subject is a female subject. In some embodiments, the subject is pregnant or planning on becoming pregnant. In some embodiments, the subject is at risk of being exposed to Zika virus. In some embodiments, the subject is living in or traveling to an area where Zika virus is present or is thought to be present. In some embodiments, the subject has been previously infected with or vaccinated against Dengue virus; i.e., at risk for antibody-dependent enhancement of disease. In some embodiments, the subject is living in or traveling to an area that is experiencing a Zika virus infection outbreak. In some embodiments, the subject is living in or traveling to an area where an arthropod vector capable of transmitting the Zika virus vector is present or is thought to be present.

Any of the Zika virus vaccines or compositions described herein may be administered to a subject in a therapeutically effective amount or a dose of a therapeutically effective amount. As used herein, a "therapeutically effective amount" of vaccine is any amount that results in a desired response or outcome in a subject, such as those described herein, including but not limited to prevention of infection, an immune response or an enhanced immune response to Zika virus, or prevention or reduction of symptoms associated with Zika disease.

In some embodiments, the therapeutically effective amount of a Zika virus vaccine or composition described herein is an amount sufficient to generate antigen-specific antibodies (e.g., anti-Zika virus antibodies). In some embodiments, the therapeutically effective amount is sufficient to provide seroprotection in a subject; i.e., to generate sufficient antigen-specific antibodies to prevent/protect from infection. In some embodiments, seroprotection is conferred on at least 75%, 80%, 90%, 95%, 96%, 97%, 98%, or at least 99% of vaccinated subjects. In some embodiments, seroprotection is defined by a reduction in the number of Zika virus plaques by 50% or more in a plaque reduction neutralization test (PRNT) by a 1:10 or higher dilution of sera from a vaccinated subject. In some embodiments, an effective amount of the Zika vaccine is sufficient to seroconvert a subject with at least 70% probability. In some embodiments, the therapeutically effective amount is sufficient to seroconvert a subject with at least 75%, 80%, 85% 90%, 95%, 96%, 97%, 98%, or at least 99% probability. Whether a subject has been seroconverted can be assessed by any method known in the art, such as obtaining a serum sample from the subject and performing an assay to detect anti-Zika virus antibodies. In some embodiments, a subject is seroconverted if a serum sample from the subject contains an amount of anti-Zika virus antibodies that surpasses a threshold or predetermined baseline. A subject is generally considered seroconverted if there is at least a 4-fold increase in anti-Zika virus antibodies (i.e., anti-Zika E protein IgG antibodies) in a serum sample from the subject as compared to a serum sample previously taken from the same subject.

In some embodiments, seroconversion of a subject is assessed by performing a plaque reduction neutralization test (PRNT). Briefly, PRNT is used to determine the serum titer required to reduce the number of Zika virus plaques by 50% (PRNT50) as compared to a control serum/antibody. The PRNT50 may be carried out using monolayers of Vero cells or any other cell type/line that can be infected with Zika virus. Sera from subjects are diluted and incubated with live, non-inactivated Zika virus. The serum/virus mixture may be applied to the Vero cells and incubated for a period of time. Plaques formed on the Vero cell monolayers are counted and compared to the number of plaques formed by the Zika virus in the absence of serum or a control antibody. A threshold of neutralizing antibodies of 1:10 dilution of serum in a PRNT50 is generally accepted as evidence of protection (Hombach et. al. Vaccine (2005) 23:5205-5211).

In some embodiments, the Zika virus may be formulated for administration in a composition, such as a pharmaceutical composition. The term "pharmaceutical composition" as used herein means a product that results from the mixing or combining of at least one active ingredient, such as an inactivated Zika virus, and one or more inactive ingredients, which may include one or more pharmaceutically acceptable excipient.

Pharmaceutical compositions of the invention, including vaccines, can be prepared in accordance with methods well known and routinely practiced in the art (see e.g., Remington: The Science and Practice of Pharmacy, Mack Publishing Co. 20th ed. 2000; and Ingredients of Vaccines—Fact Sheet from the Centers for Disease Control and Prevention, e.g., adjuvants and enhancers such as alum to help the vaccine improve its work, preservatives and stabilizers to help the vaccine remain unchanged (e.g., albumin, phenols, glycine)). Pharmaceutical compositions are preferably manufactured under GMP conditions. Typically a therapeutically effective dose of the inactivated Zika virus preparation is employed in the pharmaceutical composition of the invention. The inactivated Zika virus is formulated into pharmaceutically acceptable dosage forms by conventional methods known to those of skill in the art. Dosage regimens are adjusted to provide the optimum desired response (e.g., the prophylactic response).

Dosages of the active ingredients in the pharmaceutical compositions of the present invention can be varied so as to obtain an amount of the active ingredient which is effective to achieve the desired pharmaceutical response for a particular subject, composition, and mode of administration, without being toxic to the subject. The selected dosage level depends upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the inactivated Zika virus vaccine employed in the pharmaceutical composition at levels lower than that required to achieve the desired therapeutic effect and gradually increase the dosage until the desired effect (e.g., production of anti-Zika virus antibodies) is achieved. In general, effective doses of the compositions of the present invention, for the prophylactic treatment of groups of people as described herein vary depending upon many different factors, including means of administration, target site, physiological state of the patient, whether the patient is human or an animal, other medications administered, and the titer of anti-Zika virus antibodies desired. Dosages need to be titrated to optimize safety and efficacy. In some embodiments, the dosing regimen entails subcutaneous or intramuscular administration of a dose of inactivated Zika virus twice, once at day 0 and once at about day 7. In some embodiments, the dosing regimen entails subcutaneous administration of a dose of inactivated Zika virus twice, once at day 0 and once at about day 14. In some embodiments, the dosing regimen entails subcutaneous administration of a dose of inactivated Zika virus twice, once at day 0 and once at about day 28. In some embodiments, the inactivated Zika virus is administered to the subject once.

Any of the Zika virus vaccines or compositions described herein may be administered to a subject with, prior to, or after administration of one or more adjuvants. An adjuvant is a molecule that enhances a response in a subject, such as an immune response, to an antigen or other molecule. In some embodiments, an adjuvant may stabilize an antigen or other molecule. Determining whether a Zika virus vaccine or compositions thereof are administered with an adjuvant depends on various factors (e.g., type and extent of response desired) and will be evident to one of skill in the art. In some embodiments, administering any of the Zika virus vaccines or compositions described herein with, prior to, or after administration of an adjuvant may enhance the production of virus neutralizing (anti-Zika virus) antibodies. In some embodiments, a subject that is administered any of the Zika virus vaccines or compositions described herein with, prior to, or after administration of an adjuvant may only require a single administration of the Zika virus vaccine or composition to be seroconverted (produce a level of anti-Zika virus antibodies). Examples of adjuvants may include, without limitation, aluminium salt (aluminium hydroxide or aluminium phosphate), calcium phosphate hydroxide, paraffin oil, killed bacteria, bacterial toxins, toxoids, subunits of bacteria, squalene, thimerosal, detergents, IL-1, IL-2, IL-12, 2-component adjuvants, such as 2-component adjuvants containing an antibacterial peptide and a TLR9 agonist (e.g., IC31®), and combinations such as Freund's complete adjuvant and Freund's incomplete adjuvant. In some embodiments, the Zika virus vaccines or compositions is administered with aluminium hydroxide. In some embodiments, the inactivated Zika virus vaccine or composition is administered with aluminium phosphate salt. A preferred aluminium salt is the aluminium hydroxide with reduced Cu content, e.g. lower than 1.25 ppb based on the weight of the Zika composition, an adjuvant described in detail in WO 2013/083726 or Schlegl et al., Vaccine 33 (2015) 5989-5996.

In some embodiments, the adjuvant is comprised of two components. In some embodiments, the 2-component adjuvant comprises an antibacterial peptide and a TLR9 agonist. In some embodiments, the antibacterial peptide is provided by the amino acid sequence KLKL$_5$KLK (SEQ ID NO: 71). In some embodiments, the TLR9 agonist is a deoxyinosine-containing immunostimulatory oligodeoxynucleic acid molecule (I-ODN). In some embodiments, the I-ODN comprises the nucleic acid sequence (dIdC)$_{13}$ (SEQ ID NO: 70). In some embodiments, the adjuvant is IC31®. In some embodiments, the adjuvant is in nanoparticle form (See, e.g., U.S. Pat. No. 8,765,148 B2, incorporated by reference in its entirety). In some embodiments, the adjuvant is IC31®, i.e. KLKL$_5$KLK (SEQ ID NO: 71) and the nucleic acid sequence (dIdC)$_{13}$ (SEQ ID NO: 70), in combination with an aluminium salt such as aluminium hydroxide.

The Zika virus vaccines or compositions described herein may be administered to a subject concomitantly with one or more vaccines to another infectious agent, such as another infectious agent is that present or thought to be present in the same geographic area as Zika virus. In some embodiments, the other infectious agent is one that the subject is also at risk of being in contact with. In some embodiments, the other infectious agent is transmitted by the same arthropod vector as Zika virus. In some embodiments, the other infectious agent is Japanese Encephalitis virus, Yellow Fever virus, Dengue virus and/or Chikungunya virus.

Also within the scope of the present disclosure are kits for use in prophylactically administering to a subject, for example to prevent or reduce the severity of Zika virus infection. Such kits can include one or more containers comprising a composition containing inactivated Zika virus, such as an inactivated Zika virus vaccine. In some embodiments, the kit may further include one or more additional containing comprising a second composition, such as a second vaccine. In some embodiments, the second vaccine is a vaccine for another arbovirus. In some embodiments, the second vaccine is a Dengue virus vaccine and/or a Chikungunya virus vaccine.

In some embodiments, the kit can comprise instructions for use in accordance with any of the methods described herein. The included instructions can comprise a description of administration of the composition containing inactivated Zika virus to prevent, delay the onset, or reduce the severity of Zika virus infection. The kit may further comprise a description of selecting a subject suitable for administration based on identifying whether that subject is at risk for exposure to Zika virus or contracting a Zika virus infection. In still other embodiments, the instructions comprise a description of administering a composition containing inactivated Zika virus to a subject at risk of exposure to Zika virus or contracting Zika virus infection.

The instructions relating to the use of the composition containing inactivated Zika virus generally include information as to the dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine readable instructions are also acceptable.

The kits of the present disclosure are in suitable packaging. Suitable packaging includes, but is not limited to, vials, bottles, jars, flexible packaging, and the like. Also contemplated are packages for use in combination with a specific device, such as a syringe or an infusion device. The container may have a sterile access port, for example the container may be a vial having a stopper pierceable by a hypodermic injection needle. At least one active agent in the composition is an inactivated Zika virus, as described herein.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having,", "containing", "involving", and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

TABLE 1

Overview of process buffers and stock solutions.

| Buffer | Composition | Final pH | Final conductivity [mS/cm] |
|---|---|---|---|
| A | 0.5M NaOH | | n.a. |
| B | 0.1M NaOH | | n.a. |
| C | 25 mM Tris, 150 mM NaCl | 7.4 ± 0.2 | 16.5 |
| D | 1M Tris | 7.4 ± 0.2 | n.a. |
| E | 4.5M NaCl | n.a. | n.a. |
| F | 1M NaCl | n.a. | n.a. |
| G | 1% SDS | n.a. | n.a. |
| H | 50% (w/w) Sucrose in 25 mM Tris, 150 mM NaCl | 7.4 ± 0.2 | n.a. |
| I | 35% (w/w) Sucrose in 25 mM Tris, 150 mM NaCl | 7.4 ± 0.2 | n.a. |
| J | 15% (w/w) Sucrose in 25 mM Tris, 150 mM NaCl | 7.4 ± 0.2 | n.a. |
| K | 10× PBS | 7.4 ± 0.2 | n.a. |
| L | 50 mg/mL Protamine sulphate | 7.4 ± 0.2 | n.a. |

TABLE 1-continued

Overview of process buffers and stock solutions.

| Buffer | Composition | Final pH | Final conductivity [mS/cm] |
|---|---|---|---|
| M | Drug substance formulation buffer (10 mM Tris(hydroxymethyl)-aminomethan, 5% Sucrose, 1% (10 mg/mL) rHSA) | 7.4 ± 0.2 | 1.3 |

TABLE 2

Abbreviations.

| | |
|---|---|
| ° Bx | Degrees Brix = sugar content (w/w) of an aqueous solution* |
| BSA | Bovine serum albumin |
| CC700 | Capto ™ Core 700 |
| CPE | Cytopathic effect |
| EtOH | Ethanol |
| EU | Endotoxin units |
| DS | Drug Substance |
| DP | Drug Product |
| DSP | Downstream Process |
| HCP | Host cell protein |
| hcDNA | Host cell DNA |
| hpi | Hours post infection |
| HPLC | High Performance Liquid Chromatography |
| ID | Inner diameter |
| JEV | Japanese Encephalitis virus |
| LAL | Limulus amebocyte lysate |
| LDS buffer | Lithium dodecyl sulfate sample loading buffer |
| LOD | Limit of detection |
| LOQ | Limit of quantitation |
| MALLS | Multiangle light scattering |
| mAU | Milli absorbance units |
| MS | Mass spectroscopy |
| NIV | Neutralized inactivated virus |
| PBS | Phosphate buffered saline |
| PD | Process development |
| PFU | Plaque forming units |
| p.i. | Post-infection |
| PS | Protamine sulphate or protamine sulfate |
| rcf | Relative centrifugal force |
| rHSA | Recombinant human serum albumin |
| Rms radius | Root mean square radius |
| rMSB | Research master seed bank |
| RSD | Relative standard deviation |
| SEC | Size exclusion chromatography |
| SGC | Sucrose gradient centrifugation |
| SGP | Sucrose gradient purified |
| SDS | Sodium dodecyl sulphate |
| TBS | Tris buffered saline |
| TFF | Tangential flow filtration |
| TCID50 | Tissue culture infectious dose 50% |
| UF/DF | Ultrafiltration/diafiltration |
| WFI | Water for injection |
| ZikaV | Zika virus |

*Degrees Brix (° Bx) is the sugar content of an aqueous solution. One degree Brix is 1 gram of sucrose in 100 grams of solution and represents the strength of the solution as percentage by mass. ° Bx corresponds to the sucrose content in percent (w/w), e.g., 45° Bx equals 45% (w/w) sucrose.

TABLE A

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 1 | 9320_Zika_PF_1F | SEQ ID NO: 74 ttaggatccGTTGTTGATCTGTGTGAAT | 69.9 | 74.6 | 707 |
|  | 9321_Zika_PF_1R | SEQ ID NO: 75 taactcgagCGTACACAACCCAAGTT | 69.3 | 75.6 |  |
| 2 | 9322_Zika_PF_2F | SEQ ID NO: 76 ttaggatccTCACTAGACGTGGGAGTG | 70 | 73.9 | 704 |
|  | 9323_Zika_PF_2R | SEQ ID NO: 77 taactcgagAAGCCATGTCYGATATTGAT | 69.8 | 73.7 |  |
| 3 | 9324_Zika_PF_3F | SEQ ID NO: 78 ttaggatccGCATACAGCATCAGGTG | 72.3 | 74.5 | 712 |
|  | 9325_Zika_PF_3R | SEQ ID NO: 79 taactcgagTGTGGAGTTCCGGTGTCT | 72 | 76.4 |  |
| 4 | 9326_Zika_PF_4F | SEQ ID NO: 80 ttaggatccGAATAGAGCGAARGTTGAGATA | 70.9 | 74 | 712 |
|  | 9327_Zika_PF_4R | SEQ ID NO: 81 taactcgAGTGGTGGGTGATCTTCTTCT | 70.5 | 73.7 |  |
| 5 | 9328_Zika_PF_5F | SEQ ID NO: 82 ttaggatcCAGTCACAGTGGAGGTACAGTAC | 70.3 | 75 | 704 |
|  | 9329_Zika_PF_5R | SEQ ID NO: 83 taactcgagCRCAGATACCATCTTCCC | 71.5 | 77.3 |  |
| 6 | 9330_Zika_PF_6F | SEQ ID NO: 84 ttaggatCCCTTATGTGCTTGGCCTTAG | 70.7 | 72.7 | 698 |
|  | 9331_Zika_PF_6R | SEQ ID NO: 85 taactcgagTCTTCAGCCTCCATGTG | 70.4 | 76.9 |  |
| 7 | 9332_Zika_PF_7F | SEQ ID NO: 86 ttaggatccAATGCCCACTCAAACATAGA | 71.9 | 75 | 716 |
|  | 9333_Zika_PF_7R | SEQ ID NO: 87 taactcgagTCATTCTCTTCTTCAGCCCTT | 71 | 74 |  |
| 8 | 9334_Zika_PF_8F | SEQ ID NO: 88 ttaggatccAAGGGTGATCGAGGAAT | 70.9 | 75.2 | 703 |
|  | 9335_Zika_PF_8R | SEQ ID NO: 89 taactcgagTTCCCTTCAGAGAGAGGAGC | 71.9 | 73.4 |  |
| 9 | 9336_Zika_PF_9F | SEQ ID NO: 90 ttaggatccTCTTTTGCAAACTGCGATC | 71.9 | 75 | 699 |
|  | 9337_Zika_PF_9R | SEQ ID NO: 91 taactcgagTCCAGCTGCAAAGGGTAT | 71 | 74.9 |  |
| 10 | 9338_Zika_PF_10F | SEQ ID NO: 92 ttaggatccGTGTGGACATGTACATTGA | 71.4 | 75.8 | 706 |
|  | 9339_Zika_PF_10R | SEQ ID NO: 93 taactcgagCCCATTGCCATAAAGTC | 70.4 | 75.8 |  |
| 11 | 9340_Zika_PF_11F | SEQ ID NO: 94 ttaggatccTCATACTGTGGTCCATGGA | 71.6 | 78.1 | 692 |
|  | 9341_Zika_PF_11R | SEQ ID NO: 95 taactcgagGCCCATCTCAACCCTTG | 74 | 78 |  |
| 12 | 9342_Zika_PF_12F | SEQ ID NO: 96 ttaggatccTAGAGGGCTTCCAGTGC | 70.9 | 74 | 707 |

TABLE A-continued

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
|  | 9343_Zika_PF_12R | SEQ ID NO: 97<br>taactcgAGATACTCATCTCCAGGTTTGTTG | 70.2 | 72.2 |  |
| 13 | 9344_Zika_PF_13F | SEQ ID NO: 98<br>ttaggatccGAAAACAAAACATCAAGAGTG | 70.6 | 75.4 | 726 |
|  | 9345_Zika_PF_13R | SEQ ID NO: 99<br>taactcgagGAATCTCTCTGTCATGTGTCCT | 71.9 | 75.6 |  |
| 14 | 9346_Zika_PF_14F | SEQ ID NO: 100<br>ttaggatccTTGATGGCACGACCAAC | 73.1 | 75.6 | 715 |
|  | 9347_Zika_PF_14R | SEQ ID NO: 101<br>ttaggatccGTTGTTGATCTGTGTGAAT | 70.8 | 77.9 |  |
| 15 | 9348_Zika_PF_15F | SEQ ID NO: 102<br>taactcgagCAGGTCAATGTCCATTG | 71.9 | 75.4 | 719 |
|  | 9349_Zika_PF_15R | SEQ ID NO: 103<br>ttaggatccTGTTGTGTTCCTATTGCTGGT | 73.9 | 77.2 |  |
| 16 | 9350_Zika_PF_16F | SEQ ID NO: 104<br>taactcgaGTGATCAGRGCCCCAGC | 72.3 | 75.4 | 703 |
|  | 9351_Zika_PF_16R | SEQ ID NO: 105<br>ttaggatccTGCTGCCCAGAAGAGAA | 72 | 76.3 |  |
| 17 | 9352_Zika_PF_17F | SEQ ID NO: 106<br>taactcgaGCACCAACAYGGGTTCTT | 73.6 | 76 | 705 |
|  | 9353_Zika_PF_17R | SEQ ID NO: 107<br>ttaggatcCTCAAGGACGGTGTGGC | 72 | 75.5 |  |
| 18 | 9354_Zika_PF_18F | SEQ ID NO: 108<br>taactcgagCAATGATCTTCATGTTGGG | 71.7 | 75.8 | 699 |
|  | 9355_Zika_PF_18R | SEQ ID NO: 109<br>ttaggatccTATGGGGGAGGACTGGT | 71 | 74.1 |  |
| 19 | 9356_Zika_PF_19F | SEQ ID NO: 110<br>taactcGAGCCCAGAACCTTGGATC | 73.3 | 75.5 | 711 |
|  | 9357_Zika_PF_19R | SEQ ID NO: 111<br>ttaggatcCAGACCCCCAAGAAGGC | 71.3 | 76.9 |  |
| 20 | 9358_Zika_PF_20F | SEQ ID NO: 112<br>taactcgagCCCCTTTGGTCTTGTCT | 71.7 | 75 | 706 |
|  | 9359_Zika_PF_20R | SEQ ID NO: 113<br>ttaggatccAGGAAGGATGTATGCAGATG | 71.9 | 73.9 |  |
| 21 | 9360_Zika_PF_21F | SEQ ID NO: 114<br>taactcgagACATTTGCGCATATGATTTTG | 70.4 | 75.7 | 709 |
|  | 9361_Zika_PF_21R | SEQ ID NO: 115<br>ttaggatccAGGAAGGACACACAAGAGT | 71.8 | 75 |  |
| 22 | 9362_Zika_PF_22F | SEQ ID NO: 116<br>taactcgagACAGGCTGCACAGCTTT | 70 | 79.1 | 581 |
|  | 9363_Zika_PF_22R | SEQ ID NO: 117<br>ttaggatccTCTCTCATAGGGCACAGAC | 74.8 | 81.1 |  |

A typical form of protamine

SEQ ID NO: 1

PRRRRSSSRP VRRRRRPRVS RRRRRRGGRR RR

Provided below are examples of nucleic acid sequences of the genomes of Zika viruses that may be used in the methods, compositions, and/or vaccines described herein.

KU321639.1 Zika virus strain ZikaSPH2015, Brazil, complete genome

SEQ ID NO: 2

GTTGTTACTGTTGCTGACTCAGACTGCGACAGTTCGAGTTTGAAGCGAAAGCTAGCAACAGTATCAACAGGTTTTATTTGG

ATTTGGAAACGAGAGTTTCTGGTCATGAAAAACCCAAAAAAGAAATCCGGAGGATTCCGGATTGTCAATATGCTAAAACG

CGGAGTAGCCCGTGTGAGCCCCTTTGGGGGCTTGAAGAGGCTGCCAGCCGGACTTCTGCTGGGTCATGGGCCCATCAGG

ATGGTCTTGGCAATTCTAGCCTTTTTGAGATTCACGGCAATCAAGCCATCACTGGGTCTCATCAATAGATGGGGTTCAGTG

GGGAAAAAGAGGCTATGGAAATAATAAAGAAGTTCAAGAAAGATCTGGCTGCCATGCTGAGAATAATCAATGCTAGGA

AGGAGAAGAAGAGACGGGGCGCAGATACTAGTGTCGGAATTGTTGGCCTCCTGCTGACCACAGCTATGGCAGCGGAGG

TCACTAGACGTGGGAGTGCATACTATATGTACTTGGACAGAAACGATGCTGGGGAGGCCATATCTTTTCCAACCACATTG

GGGATGAATAAGTGTTATATACAGATCATGGATCTTGGACACATGTGTGATGCCACCATGAGCTATGAATGCCCTATGCT

GGATGAGGGGTGGAACCAGATGACGTCGATTGTTGGTGCAACACGACGTCAACTTGGGTTGTGTACGGAACCTGCCAT

CACAAAAAGGTGAAGCACGGAGATCTAGAAGAGCTGTGACGCTCCCCTCCCATTCCACTAGGAAGCTGCAAACGCGGT

CGCAAACCTGGTTGGAATCAAGAGAATACACAAAGCACTTGATTAGAGTCGAAAATTGGATATTCAGGAACCCTGGCTTC

GCGTTAGCAGCAGCTGCCATCGCTTGGCTTTTGGGAAGCTCAACGAGCCAAAAAGTCATATACTTGGTCATGATACTGCT

GATTGCCCCGGCATACAGCATCAGGTGCATAGGAGTCAGCAATAGGGACTTTGTGGAAGGTATGTCAGGTGGGACTTGG

GTTGATATTGTCTTGGAACATGGAGGTTGTGTCACCGTAATGGCACAGGACAAACCGACTGTCGACATAGAGCTGGTTAC

AACAACAGTCAGCAACATGGCGGAGGTAAGATCCTACTGCTATGAGGCATCAATATCAGACATGGCTTCGGACAGCCGCT

GCCCAACACAAGGTGAAGCCTACCTTGACAAGCAATCAGACACTCAATATGTCTGCAAAAGAACGTTAGTGGACAGAGGC

TGGGGAAATGGATGTGGACTTTTTGGCAAAGGGAGTCTGGTGACATGCGCTAAGTTTGCATGCTCCAAGAAAATGACCG

GGAAGAGCATCCAGCCAGAGAATCTGGAGTACCGGATAATGCTGTCAGTTCATGGCTCCCAGCACAGTGGGATGATCGT

TAATGACACAGGACATGAAACTGATGAGAATAGAGCGAAGGTTGAGATAACGCCCAATTCACCAAGAGCCGAAGCCACC

CTGGGGGGTTTTGGAAGCCTAGGACTTGATTGTGAACCGAGGACAGGCCTTGACTTTTCAGATTTGTATTACTTGACTATG

AATAACAAGCACTGGTTGGTTCACAAGGAGTGGTTCCACGACATTCCATTACCTTGGCACGCTGGGGCAGACACCGGAAC

TCCACACTGGAACAACAAAGAAGCACTGGTAGAGTTCAAGGACGCACATGCCAAAAGGCAAACTGTCGTGGTTCTAGGG

AGTCAAGAAGGAGCAGTTCACACGGCCCTTGCTGGAGCTCTGGAGGCTGAGATGGATGGTGCAAAGGGAAGGCTGTCCT

CTGGCCACTTGAAATGTCGCCTGAAAATGGATAAACTTAGATTGAAGGGCGTGTCATACTCCTTGTGTACCGCAGCGTTCA

CATTCACCAAGATCCCGGCTGAAACACTGCACGGGACAGTCACAGTGGAGGTACAGTACGCAGGGACAGATGGACCTTG

CAAGGTTCCAGCTCAGATGGCGGTGGACATGCAAACTCTGACCCCAGTTGGGAGGTTGATAACCGCTAACCCCGTAATCA

CTGAAAGCACTGAGAACTCTAAGATGATGCTGGAACTTGATCCACCATTTGGGGACTCTTACATTGTCATAGGAGTCGGG

GAGAAGAAGATCACCCACCACTGGCACAGGAGTGGCAGCACCATTGGAAAAGCATTTGAAGCCACTGTGAGAGGTGCCA

AGAGAATGGCAGTCTTGGGAGACACAGCCTGGGACTTTGGATCAGTTGGAGGCGCTCTCAACTCATTGGGCAAGGGCAT

CCATCAAATTTTTGGAGCAGCTTTCAAATCATTGTTTGGAGGAATGTCCTGGTTCTCACAAATTCTCATTGGAACGTTGCTG

ATGTGGTTGGGTCTGAACACAAAGAATGGATCTATTTCCCTTATGTGCTTGGCCTTAGGGGGAGTGTTGATCTTCTTATCC

ACAGCCGTCTCTGCTGATGTGGGGTGCTCGGTGGACTTCTCAAAGAAGGAGACGAGATGCGGTACAGGGGTGTTCGTCT

ATAACGACGTTGAAGCCTGGAGGGACAGGTACAAGTACCATCCTGACTCCCCCCGTAGATTGGCAGCAGCAGTCAAGCA

AGCCTGGGAAGATGGTATCTGCGGGATCTCCTCTGTTTCAAGAATGGAAAACATCATGTGGAGATCAGTAGAAGGGGAG

CTCAACGCAATCCTGGAAGAGAATGGAGTTCAACTGACGGTCGTTGTGGGATCTGTAAAAAACCCCATGTGGAGAGGTC

CACAGAGATTGCCCGTGCCTGTGAACGAGCTGCCCCACGGCTGGAAGGCTTGGGGGAAATCGCACTTCGTCAGAGCAGC

-continued

```
AAAGACAAATAACAGCTTTGTCGTGGATGGTGACACACTGAAGGAATGCCCACTCAAACATAGAGCATGGAACAGCTTTC
TTGTGGAGGATCATGGGTTCGGGGTATTTCACACTAGTGTCTGGCTCAAGGTTAGAGAAGATTATTCATTAGAGTGTGAT
CCAGCCGTTATTGGAACAGCTGTTAAGGGAAAGGAGGCTGTACACAGTGATCTAGGCTACTGGATTGAGAGTGAGAAGA
ATGACACATGGAGGCTGAAGAGGGCCCATCTGATCGAGATGAAAACATGTGAATGGCCAAAGTCCCACACATTGTGGAC
AGATGGAATAGAAGAGAGTGATCTGATCATACCCAAGTCTTTAGCTGGGCCACTCAGCCATCACAATACCAGAGAGGCT
ACAGGACCCAAATGAAAGGGCCATGGCACAGTGAAGAGCTTGAAATTCGGTTTGAGGAATGCCCAGGCACTAAGGTCCA
CGTGGAGGAAACATGTGGAACAAGAGGACCATCTCTGAGATCAACCACTGCAAGCGGAAGGGTGATCGAGGAATGGTG
CTGCAGGGAGTGCACAATGCCCCCACTGTCGTTCCGGGCTAAAGATGGCTGTTGGTATGGAATGGAGATAAGGCCCAGG
AAAGAACCAGAAAGCAACTTAGTAAGGTCAATGGTGACTGCAGGATCAACTGATCACATGGATCACTTCTCCCTTGGAGT
GCTTGTGATTCTGCTCATGGTGCAGGAAGGGCTGAAGAAGAGAATGACCACAAAGATCATCATAAGCACATCAATGGCA
GTGCTGGTAGCTATGATCCTGGGAGGATTTTCAATGAGTGACCTGGCTAAGCTTGCAATTTTGATGGGTGCCACCTTCGC
GGAAATGAACACTGGAGGAGATGTAGCTCATCTGGCGCTGATAGCGGCATTCAAAGTCAGACCAGCGTTGCTGGTATCTT
TCATCTTCAGAGCTAATTGGACACCCCGTGAAAGCATGCTGCTGGCCTTGGCCTCGTGTCTTTTGCAAACTGCGATCTCCG
CCTTGGAAGGCGACCTGATGGTTCTCATCAATGGTTTTGCTTTGGCCTGGTTGGCAATACGAGCGATGGTTGTTCCACGCA
CTGATAACATCACCTTGGCAATCCTGGCTGCTCTGACACCACTGGCCCGGGGCACACTGCTTGTGGCGTGGAGAGCAGGC
CTTGCTACTTGCGGGGGGTTTATGCTCCTCTCTCTGAAGGGAAAAGGCAGTGTGAAGAAGAACTTACCATTTGTCATGGC
CCTGGGACTAACCGCTGTGAGGCTGGTCGACCCCATCAACGTGGTGGGGCTGCTGTTGCTCACAAGGAGTGGGAAGCGG
AGCTGGCCCCCTAGCGAAGTACTCACAGCTGTTGGCCTGATATGCGCATTGGCTGGAGGGTTCGCCAAGGCAGATATAGA
GATGGCTGGGCCCATGGCCGCGGTCGGTCTGCTAATTGTCAGTTACGTGGTCTCAGGAAAGAGTGTGGACATGTACATTG
AAAGAGCAGGTGACATCACATGGGAAAAAGATGCGGAAGTCACTGGAAACAGTCCCCGGCTCGATGTGGCGCTAGATG
AGAGTGGTGATTTCTCCCTGGTGGAGGATGACGGTCCCCCCATGAGAGAGATCATACTCAAGGTGGTCCTGATGACCATC
TGTGGCATGAACCCAATAGCCATACCCTTTGCAGCTGGAGCGTGGTACGTATACGTGAAGACTGGAAAAAGGAGTGGTG
CTCTATGGGATGTGCCTGCTCCCAAGGAAGTAAAAAAGGGGGAGACCACAGATGGAGTGTACAGAGTAATGACTCGTAG
ACTGCTAGGTTCAACACAAGTTGGAGTGGGAGTTATGCAAGAGGGGGTCTTTCACACTATGTGGCACGTCACAAAAGGA
TCCGCGCTGAGAAGCGGTGAAGGGAGACTTGATCCATACTGGGGAGATGTCAAGCAGGATCTGGTGTCATACTGTGGTC
CATGGAAGCTAGATGCCGCCTGGGACGGGCACAGCGAGGTGCAGCTCTTGGCCGTGCCCCCCGGAGAGAGAGCGAGGA
ACATCCAGACTCTGCCCGGAATATTTAAGACAAAGGATGGGGACATTGGAGCGGTTGCGCTGGATTACCCAGCAGGAAC
TTCAGGATCTCCAATCCTAGACAAGTGTGGGAGAGTGATAGGACTTTATGGCAATGGGGTCGTGATCAAAAATGGGAGT
TATGTTAGTGCCATCACCCAAGGGAGGAGGGAGGAAGAGACTCCTGTTGAGTGCTTCGAGCCTTCGATGCTGAAGAAGA
AGCAGCTAACTGTCTTAGACTTGCATCCTGGAGCTGGGAAAACCAGGAGAGTTCTTCCTGAAATAGTCCGTGAAGCCATA
AAAACAAGACTCCGTACTGTGATCTTAGCTCCAACCAGGGTTGTCGCTGCTGAAATGGAGGAAGCCCTTAGAGGGCTTCC
AGTGCGTTATATGACAACAGCAGTCAATGTCACCCACTCTGGAACAGAAATCGTCGACTTAATGTGCCATGCCACCTTCAC
TTCACGTCTACTACAGCCAATCAGAGTCCCCAACTATAATCTGTATATTATGGATGAGGCCCACTTCACAGATCCCTCAAGT
ATAGCAGCAAGAGGATACATTTCAACAAGGGTTGAGATGGGCGAGGCGGCTGCCATCTTCATGACCGCCACGCCACCAG
GAACCCGTGACGCATTTCCGGACTCCAACTCACCAATTATGGACACCGAAGTGGAAGTCCCAGAGAGAGCCTGGAGCTCA
GGCTTTGATTGGGTGACGGATTATTCTGGAAAAACAGTTTGGTTTGTTCCAAGCGTGAGGAACGGCAATGAGATCGCAGC
TTGTCTGACAAAGGCTGGAAAACGGGTCATACAGCTCAGCAGAAAGACTTTTGAGACAGAGTTCAGAAAACAAAACATC
AAGAGTGGGACTTTGTCGTGACAACTGACATTTCAGAGATGGGCGCCAACTTTAAAGCTGACCGTGTCATAGATTCCAGG
AGATGCCTAAAGCCGGTCATACTTGATGGCGAGAGAGTCATTCTGGCTGGACCCATGCCTGTCACACATGCCAGCGCTGC
CCAGAGGAGGGGCGCATAGGCAGGAATCCCAACAAACCTGGAGATGAGTATCTGTATGGAGGTGGGTGCGCAGAGAC
TGACGAAGACCATGCACACTGGCTTGAAGCAAGAATGCTCCTTGACAATATTTACCTCCAAGATGGCCTCATAGCCTCGCT
```

```
CTATCGACCTGAGGCCGACAAAGTAGCAGCCATTGAGGGAGAGTTCAAGCTTAGGACGGAGCAAAGGAAGACCTTTGTG

GAACTCATGAAAAGAGGAGATCTTCCTGTTTGGCTGGCCTATCAGGTTGCATCTGCCGGAATAACCTACACAGATAGAAG

ATGGTGCTTTGATGGCACGACCAACAACACCATAATGGAAGACAGTGTGCCGGCAGAGGTGTGGACCAGACACGGAGA

GAAAAGAGTGCTCAAACCGAGGTGGATGGACGCCAGAGTTTGTTCAGATCATGCGGCCCTGAAGTCATTCAAGGAGTTT

GCCGCTGGGAAAAGAGGAGCGGCTTTTGGAGTGATGGAAGCCCTGGGAACACTGCCAGGACACATGACAGAGAGATTC

CAGGAAGCCATTGACAACCTCGCTGTGCTCATGCGGGCAGAGACTGGAAGCAGGCCTTACAAAGCCGCGGCGGCCCAAT

TGCCGGAGACCCTAGAGACCATTATGCTTTTGGGGTTGCTGGGAACAGTCTCGCTGGGAATCTTTTTCGTCTTGATGAGG

AACAAGGGCATAGGGAAGATGGGCTTTGGAATGGTGACTCTTGGGGCCAGCGCATGGCTCATGTGGCTCTCGGAAATTG

AGCCAGCCAGAATTGCATGTGTCCTCATTGTTGTGTTCCTATTGCTGGTGGTGCTCATACCTGAGCCAGAAAAGCAAGAT

CTCCCCAGGACAACCAAATGGCAATCATCATCATGGTAGCAGTAGGTCTTCTGGGCTTGATTACCGCCAATGAACTCGGAT

GGTTGGAGAGAACAAAGAGTGACCTAAGCCATCTAATGGGAAGGAGAGAGGAGGGGGCAACCATGGGATTCTCAATGG

ACATTGACCTGCGGCCAGCCTCAGCTTGGGCCATCTATGCTGCCTTGACAACTTTCATTACCCCAGCCGTCCAACATGCAGT

GACCACTTCATACAACAACTACTCCTTAATGGCGATGGCCACGCAAGCTGGAGTGTTGTTTGGTATGGGCAAAGGGATGC

CATTCTACGCATGGGACTTTGGAGTCCCGCTGCTAATGATAGGTTGCTACTCACAATTAACGCCCCTGACCCTAATAGTGG

CCATCATTTTGCTCGTGGCGCACTACATGTACTTGATCCCAGGGCTGCAGGCAGCAGCTGCGCGTGCTGCCCAGAAGAGA

ACGGCAGCTGGCATCATGAAGAACCCTGTTGTGGATGGAATAGTGGTGACTGACATTGACACAATGACAATTGACCCCCA

AGTGGAGAAAAAGATGGGACAGGTGCTACTCATGGCAGTAGCCGTCTCCAGCGCCATACTGTCGCGGACCGCCTGGGGG

TGGGGGGAGGCTGGGGCCCTGATCACAGCCGCAACTTCCACTTTGTGGGAAGGCTCTCCGAACAAGTACTGGAACTCCTC

TACAGCCACTTCACTGTGTAACATTTTTAGGGGAAGTTACTTGGCTGGAGCTTCTCTAATCTACACAGTAACAAGAAACGC

TGGCTTGGTCAAGAGACGTGGGGGTGGAACAGGAGAGACCCTGGGAGAGAAATGGAAGGCCCGCTTGAACCAGATGTC

GGCCCTGGAGTTCTACTCCTACAAAAAGTCAGGCATCACCGAGGTGTGCAGAGAAGAGGCCCGCCGCGCCCTCAAGGAC

GGTGTGGCAACGGGAGGCCATGCTGTGTCCCGAGGAAGTGCAAAGCTGAGATGGTTGGTGGAGCGGGGATACCTGCAG

CCCTATGGAAAGGTCATTGATCTTGGATGTGGCAGAGGGGGCTGGAGTTACTACGCCGCCACCATCCGCAAAGTTCAAGA

AGTGAAAGGATACACAAAAGGAGGCCCTGGTCATGAAGAACCCGTGTTGGTGCAAAGCTATGGGTGGAACATAGTCCGT

CTTAAGAGTGGGGTGGACGTCTTTCATATGGCGGCTGAGCCGTGTGACACGTTGCTGTGTGACATAGGTGAGTCATCATC

TAGTCCTGAAGTGGAAGAAGCACGGACGCTCAGAGTCCTCTCCATGGTGGGGATTGGCTTGAAAAAAGACCAGGAGCC

TTTTGTATAAAAGTGTTGTGCCCATACACCAGCACTATGATGGAAACCCTGGAGCGACTGCAGCGTAGGTATGGGGGAG

GACTGGTCAGAGTGCCACTCTCCCGCAACTCTACACATGAGATGTACTGGGTCTCTGGAGCGAAAAGCAACACCATAAAA

AGTGTGTCCACCACGAGCCAGCTCCTCTTGGGCGCATGGACGGGCCTAGGAGGCCAGTGAAATATGAGGAGGATGTGA

ATCTCGGCTCTGGCACGCGGGCTGTGGTAAGCTGCGCTGAAGCTCCCAACATGAAGATCATTGGTAACCGCATTGAAAGG

ATCCGCAGTGAGCACGCGGAAACGTGGTTCTTTGACGAGAACCACCCATATAGGACATGGGCTTACCATGGAAGCTATGA

GGCCCCCACACAAGGGTCAGCGTCCTCTCTAATAAACGGGGTTGTCAGGCTCCTGTCAAAACCCTGGGATGTGGTGACTG

GAGTCACAGGAATAGCCATGACCGACACCACACCGTATGGTCAGCAAAGAGTTTTCAAGGAAAAAGTGGACACTAGGGT

GCCAGACCCCCAAGAAGGTACTCGTCAGGTTATGAGCATGGTCTCTTCCTGGTTGTGGAAAGAGCTAGGCAAACACAAAC

GGCCACGAGTCTGTACCAAAGAAGAGTTCATCAACAAGGTTCGTAGCAATGCAGCATTAGGGGCAATATTTGAAGAGGA

AAAAGAGTGGAAGACTGCAGTGGAAGCTGTGAACGATCCAAGGTTCTGGGCTCTAGTGGACAAGGAAAGAGAGCACCA

CCTGAGAGGAGAGTGCCAGAGTTGTGTGTACAACATGATGGGAAAAAGAGAAAAGAAACAAGGGGAATTTGGAAAGGC

CAAGGGCAGCCGCGCCATCTGGTATATGTGGCTAGGGGCTAGATTTCTAGAGTTCGAAGCCCTTGGATTCTTGAACGAGG

ATCACTGGATGGGGAGAGAACTCAGGAGGTGGTGTTGAAGGGCTGGGATTACAAAGACTCGGATATGTCCTAGAAG

AGATGAGTCGCATACCAGGAGGAAGGATGTATGCAGATGACACTGCTGGCTGGGACACCCGCATCAGCAGGTTTGATCT
```

-continued

```
GGAGAATGAAGCTCTAATCACCAACCAAATGGAGAAAGGGCACAGGGCCTTGGCATTGGCCATAATCAAGTACACATAC

CAAAACAAAGTGGTAAAGGTCCTTAGACCAGCTGAAAAAGGGAAAACAGTTATGGACATTATTTCGAGACAAGACCAAA

GGGGGAGCGGACAAGTTGTCACTTACGCTCTTAACACATTTACCAACCTAGTGGTGCAACTCATTCGGAATATGGAGGCT

GAGGAAGTCCTAGAGATGCAAGACTTGTGGCTGCTGCGGAGGTCAGAGAAAGTGACCAACTGGTTGCAGAGCAACGGA

TGGGATAGGCTCAAACGAATGGCAGTCAGTGGAGATGATTGCGTTGTGAAGCCAATTGATGATAGGTTTGCACATGCCCT

CAGGTTCTTGAATGATATGGGAAAAGTTAGGAAGGACACACAAGAGTGGAAACCCTCAACTGGATGGGACAACTGGGAA

GAAGTTCCGTTTTGCTCCCACCACTTCAACAAGCTCCATCTCAAGGACGGGAGGTCCATTGTGGTTCCCTGCCGCCACCAA

GATGAACTGATTGGCCGGGCCCGCGTCTCTCCAGGGGCGGGATGGAGCATCCGGGAGACTGCTTGCCTAGCAAAATCAT

ATGCGCAAATGTGGCAGCTCCTTTATTTCCACAGAAGGGACCTCCGACTGATGGCCAATGCCATTTGTTCATCTGTGCCAG

TTGACTGGGTTCCAACTGGGAGAACTACCTGGTCAATCCATGGAAAGGGAGAATGGATGACCACTGAAGACATGCTTGT

GGTGTGGAACAGAGTGTGGATTGAGGAGAACGACCACATGGAAGACAAGACCCCAGTTACGAAATGGACAGACATTCCC

TATTTGGGAAAAAGGGAAGACTTGTGGTGTGGATCTCTCATAGGGCACAGACCGCGCACCACCTGGGCTGAGAACATTA

AAAACACAGTCAACATGGTGCGCAGGATCATAGGTGATGAAGAAAAGTACATGGACTACCTATCCACCCAAGTTCGCTAC

TTGGGTGAAGAAGGGTCTACACCTGGAGTGCTGTAAGCACCAATCTTAATGTTGTCAGGCCTGCTAGTCAGCCACAGCTT

GGGGAAAGCTGTGCAGCCTGTGACCCCCCCAGGAGAAGCTGGGAAACCAAGCCTATAGTCAGGCCGAGAACGCCATGG

CACGGAAGAAGCCATGCTGCCTGTGAGCCCCTCAGAGGACACTGAGTCAAAAACCCCACGCGCTTGGAGGCGCAGGAT

GGGAAAAGAAGGTGGCGACCTTCCCCACCCTTCAATCTGGGGCCTGAACTGGAGATCAGCTGTGGATCTCCAGAAGAGG

GACTAGTGGTTAGAGGAGA
```

KU497555.1 Zika virus isolate Brazil-ZKV2015, Brazil, complete genome

SEQ ID NO: 3

```
CCAATCTGTGAATCAGACTGCGACAGTTCGAGTTTGAAGCGAAAGCTAGCAACAGTATCAACAGGTTTTATTTTGGATTTG

GAAACGAGAGTTTCTGGTCATGAAAAACCCAAAAAAGAAATCCGGAGGATTCCGGATTGTCAATATGCTAAAACGCGGA

GTAGCCCGTGTGAGCCCCTTTGGGGGCTTGAAGAGGCTGCCAGCCGGACTTCTGCTGGGTCATGGGCCCATCAGGATGG

TCTTGGCGATTCTAGCCTTTTTGAGATTCACGGCAATCAAGCCATCACTGGGTCTCATCAATAGATGGGGTTCAGTGGGA

AAAAAGAGGCTATGGAAATAATAAAGAAGTTCAAGAAAGATCTGGCTGCCATGCTGAGAATAATCAATGCCAGGAAGGA

GAAGAAGAGACGAGGCGCAGATACTAGTGTCGGAATCGTTGGCCTCCTGCTGACCACAGCTATGGCAGCGGAGGTCACT

AGACGTGGGAGTGCATACTATATGTACTTGGACAGAAACGATGCTGGGGAGGCCATATCTTTTCCAACCACATTGGGGAT

GAATAAGTGTTATATACAGATCATGGATCTTGGACACATGTGTGATGCCACCATGAGCTATGAATGCCCTATGCTGGATG

AGGGGGTGGAACCAGATGACGTCGATTGTTGGTGCAACACGACGTCAACTTGGGTTGTGTACGGAACCTGCCATCACAA

AAAAGGTGAAGCACGGAGATCTAGAAGAGCTGTGACGCTCCCCTCCCATTCCACTAGGAAGCTGCAAACGCGGTCGCAA

ACCTGGTTGGAATCAAGAGAATACACAAAGCACTTGATTAGAGTCGAAAATTGGATATTCAGGAACCCTGGCTTCGCGTT

AGCAGCAGCTGCCATCGCTTGGCTTTTGGGAAGCTCAACGAGCCAAAAAGTCATATACTTGGTCATGATACTGCTGATTGC

CCCGGCATACAGCATCAGGTGCATAGGAGTCAGCAATAGGGACTTTGTGGAAGGTATGTCAGGTGGGACTTGGGTTGAT

GTTGTCTTGGAACATGGGGGTTGTGTCACCGTAATGGCACAGGACAAACCGACTGTCGACATAGAGCTGGTTACAACAAC

AGTCAGCAACATGGCGGAGGTAAGATCCTACTGCTATGAGGCATCAATATCAGACATGGCTTCGGACAGCCGCTGCCCAA

CACAAGGTGAAGCCTACCTTGACAAGCAATCAGACACTCAATATGTCTGCAAAAGAACGTTAGTGGACAGAGGCTGGGG

AAATGGATGTGGACTTTTTGGCAAAGGGAGCCTGGTGACATGCGCTAAGTTTGCATGCTCCAAGAAAATGACCGGGAAG

AGCATCCAGCCAGAGAATCTGGAGTACCGGATAATGCTGTCAGTTCATGGCTCCCAGCACAGTGGGATGATCGTTAATGA

CACAGGACATGAAACTGATGAGAATAGAGCGAAGGTTGAGATAACGCCCAATTCACCAAGAGCCGAAGCCACCCTGGGG

GGTTTTGGAAGCTTAGGACTTGATTGTGAACCGAGGACAGGCCTTGACTTTTCAGATTTGTATTACTTGACTATGAATAAC

AAGCACTGGTTGGTTCACAAGGAGTGGTTCCACGACATTCCATTACCTTGGCACGCTGGGGCAGACACCGGAACTCCACA

CTGGAACAACAAAGAAGCACTGGTAGAGTTCAAGGACGCACATGCCAAAAGGCAAACTGTCGTGGTTCTAGGGACTCAA
```

-continued

```
GAAGGAGCAGTTCACACGGCCCTTGCTGGAGCTCTGGAGGCTGAGATGGATGGTGCAAAGGGAAGGCTGTCCTCTGGCC

ACTTGAAATGTCGCCTGAAAATGGATAAACTTAGATTGAAGGGCGTGTCATACTCCTTGTGTACCGCAGCGTTCACATTCA

CCAAGATCCCGGCTGAAACACTGCACGGGACAGTCACAGTGGAGGTACAGTACGCAGGGACAGATGGACCTTGCAAGGT

TCCAGCTCAGATGGCGGTGGACATGCAAACTCTGACCCCAGTTGGGAGGTTGATAACCGCTAACCCCGTAATCACTGAAA

GCACTGAGAACTCTAAGATGATGCTGGAACTTGATCCACCATTTGGGGACTCTTACATTGTCATAGGAGTCGGGGAGAAG

AAGATCACCCACCACTGGCACAGGAGTGGCAGCACCATTGGAAAAGCATTTGAAGCCACTGTGAGAGGTGCCAAGAGAA

TGGCAGTCTTGGGAGACACAGCCTGGGACTTTGGATCAGTTGGAGGCGCTCTCAACTCATTGGGCAAGGGCATCCATCAA

ATTTTTGGAGCAGCTTTCAAATCATTGTTTGGAGGAATGTCCTGGTTCTCACAAATTCTCATTGGAACGTTGCTGATGTGGT

TGGGTCTGAACACAAAGAATGGATCTATTTCCCTTATGTGCTTGGCCTTAGGGGAGTGTTGATCTTCTTATCCACAGCCG

TCTCTGCTGATGTGGGGTGCTCGGTGGACTTCTCAAAGAAGGAGACGAGATGTGGTACAGGGGTGTTCGTCTATAACGA

CGTTGAAGCCTGGAGGGACAGGTACAAGTACCATCCTGACTCTCCCCGTAGATTGGCAGCAGCAGTCAAGCAAGCCTGG

GAAGATGGTATCTGCGGGATCTCCTCTGTTTCAAGAATGGAAAACATCATGTGGAGATCAGTAGAAGGGGAGCTTAACG

CAATCCTGGAAGAGAATGGAGTTCAACTGACGGTCGTTGTGGGATCTGTAAAAAACCCCATGTGGAGAGGTCCACAGAG

ATTGCCCGTGCCTGTGAACGAGCTGCCCCACGGCTGGAAGGCTTGGGGGAAATCGTACTTCGTCAGAGCAGCAAAGACA

AATAACAGCTTTGTCGTGGATGGTGACACACTGAAGGAATGCCCACTCAAACATAGAGCATGGAACAGCTTTCTTGTGGA

GGATCATGGGTTCGGGGTATTTCACACTAGTGTCTGGCTCAAGGTTAGAGAAGATTATTCATTAGAGTGTGATCCAGCCG

TTATTGGAACAGCTGTTAAGGGAAAGGAGGCTGTACACAGTGATCTAGGCTACTGGATTGAGAGTGAGAAGAATGACAC

ATGGAGGCTGAAGAGGGCCCATCTGATCGAGATGAAAACATGTGAATGGCCAAAGTCCCACACATTGTGGACAGATGGA

ATAGAAGAGAGTGATCTGATCATACCCAAGTCTTTAGCTGGGCCACTCAGCCATCACAATACCAGAGAGGGCTACAGGAC

CCAAATGAAAGGGCCATGGCACAGTGAAGAGCTTGAAATTCGGTTTGAGGAATGCCCAGGCACTAAGGTCCACGTGGAG

GAAACATGTGGAACAAGAGGACCATCTCTGAGATCAACCACTGCAAGCGGAAGGGTGATCGAGGAATGGTGCTGCAGG

GAGTGCACAATGCCCCCACTGTCGTTCCGGGCTAAAGATGGCTGTTGGTATGGAATGGAGATAAGGCCCAGGAAAGAAC

CAGAAAGCAACTTAGTAAGGTCAATGGTGACTGCAGGATCAACTGATCACATGGATCACTTCTCCCTTGGAGTGCTTGTG

ATTCTGCTCATGGTGCAGGAAGGGCTGAAGAAGAGAATGACCACAAAGATCATCATAAGCACATCAATGGCAGTGCTGG

TAGCTATGATCCTGGGAGGATTTTCAATGAGTGACCTGGCTAAGCTTGCAATTTTGATGGGTGCCACCTTCGCGGAAATG

AACACTGGAGGAGATGTAGCTCATCTGGCGCTGATAGCGGCATTCAAAGTCAGACCAGCGTTGCTGGTATCTTTCATCTTC

AGAGCTAATTGGACACCCCGTGAAAGCATGCTGCTGGCCTTGGCCTCGTGTTTTTTGCAAACTGCGATCTCCGCCTTGGAA

GGCGACCTGATGGTTCTCATCAATGGTTTTGCTTTGGCCTGGTTGGCAATACGAGCGATGGTTGTTCCACGCACTGACAAC

ATCACCTTGGCAATCCTGGCTGCTCTGACACCACTGGCCCGGGGCACACTGCTTGTGGCGTGGAGAGCAGGCCTTGCTAC

TTGCGGGGGTTTATGCTCCTCTCTCTGAAGGGAAAAGGCAGTGTGAAGAAGAACTTACCATTTGTCATGGCCCTGGGAC

TAACCGCTGTGAGGCTGGTCGACCCCATCAACGTGGTGGGACTGCTGTTGCTCACAAGGAGTGGGAAGCGGAGCTGGCC

CCCTAGCGAAGTACTCACAGCTGTTGGCCTGATATGCGCATTGGCTGGAGGGTTCGCCAAGGCAGATATAGAGATGGCT

GGGCCCATGGCCGCGGTCGGTCTGCTAATTGTCAGTTACGTGGTCTCAGGAAAGAGTGTGGACATGTACATTGAAAGAG

CAGGTGACATCACATGGGAAAAGATGCGGAAGTCACTGGAAACAGTCCCCGGCTCGATGTGGCGCTAGATGAGAGTG

GTGACTTCTCCCTGGTGGAGGATGACGGTCCCCCCATGAGAGAGATCATACTCAAGGTGGTCCTGATGACCATCTGTGGC

ATGAACCCAATAGCCATACCCTTTGCAGCTGGAGCGTGGTACGTATACGTGAAGACTGGAAAAAGGAGTGGTGCTCTATG

GGATGTGCCTGCTCCCAAGGAAGTAAAAAAGGGGGAGACCACAGATGGAGTGTACAGAGTAATGACTCGTAGACTGCTA

GGTTCAACACAAGTTGGAGTGGGAGTTATGCAAGAGGGGGTCTTTCACACTATGTGGCACGTCACAAAAGGATCCGCGC

TGAGAAGCGGTGAAGGGAGACTTGATCCATACTGGGGAGATGTCAAGCAGGATCTGGTGTCATACTGTGGTCCATGAA

GCTAGATGCCGCCTGGGACGGGCACAGCGAGGTGCAGCTCTTGGCCGTGCCCCCCGGAGAGAGAGCGAGGAACATCCA
```

-continued

```
GACTCTGCCCGGAATATTTAAGACAAAGGATGGGGACATTGGAGCGGTTGCGCTGGATTACCCAGCAGGAACTTCAGGA

TCTCCAATCCTAGACAAGTGTGGGAGAGTGATAGGACTTTATGGCAATGGGGTCGTGATAAAAAATGGGAGTTATGTTA

GTGCCATCACCCAAGGGAGGAGGGAGGAAGAGACTCCTGTTGAGTGCTTCGAGCCTTCGATGCTGAAGAAGAAGCAGCT

AACTGTCTTAGACTTGCATCCTGGAGCTGGGAAAACCAGGAGAGTTCTTCCTGAAATAGTCCGTGAAGCCATAAAAACAA

GACTCCGTACTGTGATCTTAGCTCCAACCAGGGTTGTCGCTGCTGAAATGGAGGAAGCCCTTAGAGGGCTTCCAGTGCGT

TATATGACAACAGCAGTCAATGTCACCCACTCTGGAACAGAAATCGTCGACTTAATGTGCCATGCCACCTTCACTTCACGT

CTACTACAGCCAATCAGAGTCCCCAACTATAATCTGTATATTATGGATGAGGCCCACTTCACAGATCCCTCAAGCATAGCA

GCAAGAGGATACATTTCAACAAGGGTTGAGATGGGCGAGGCGGCTGCCATCTTCATGACCGCCACGCCACCAGGAACCC

GTGACGCATTTCCGGACTCCAACTCACCAATTATGGACACCGAAGTGGAAGTCCCAGAGAGAGCCTGGAGCTCAGGCTTT

GATTGGGTGACGGATCATTCTGGAAAAACAGTTTGGTTTGTTCCAAGCGTGAGGAACGGCAATGAGATCGCAGCTTGTCT

GACAAAGGCTGGAAAACGGGTCATACAGCTCAGCAGAAAGACTTTTGAGACAGAGTTCCAGAAAACAAACATCAAGAG

TGGGACTTTGTCGTGACAACTGACATTTCAGAGATGGGCGCCAACTTTAAAGCTGACCGTGTCATAGATTCCAGGAGATG

CCTAAAGCCGGTCATACTTGATGGCGAGAGAGTCATTCTGGCTGGACCCATGCCTGTCACACATGCCAGCGCTGCCCAGA

GGAGGGGCGCATAGGCAGGAATCCCAACAAACCTGGAGATGAGTACCTGTATGGAGGTGGGTGCGCAGAGACTGACG

AAGACCATGCACACTGGCTTGAAGCAAGAATGCTCCTTGACAATATTTACCTCCAAGATGGCCTCATAGCCTCGCTCTATC

GACCTGAGGCCGACAAAGTAGCAGCCATTGAGGGAGAGTTCAAGCTTAGGACGGAGCAAAGGAAGACCTTTGTGGAAC

TCATGAAAGAGGAGATCTTCCTGTTTGGCTGGCCTATCAGGTTGCATCTGCCGAATAACCTACACAGATAGAAGATGG

TGCTTTGATGGCACGACCAACAACACCATAATGGAAGACAGTGTGCCGGCAGAGGTGTGGACCAGACACGGAGAGAAA

AGAGTGCTCAAACCGAGGTGGATGGACGCCAGAGTTTGTTCAGATCATGCGGCCCTGAAGTCATTCAAGGAGTTTGCCGC

TGGGAAAAGAGGAGCGGCTTTTGGAGTGATGGAAGCCCTGGGAACACTGCCAGGACACATGACAGAGAGATTCCAGGA

AGCCATTGACAACCTCGCTGTGCTCATGCGGGCAGAGACTGGAAGCAGGCCTTACAAAGCCGCGGCGGCCCAATTGCCG

GAGACCCTAGAGACCATTATGCTTTTGGGGTTGCTGGGAACAGTCTCGCTGGGAATCTTTTTCGTCTTGATGAGGAACAA

GGGCATAGGGAAGATGGGCTTTGGAATGGTGACTCTTGGGGCCAGCGCATGGCTCATGTGGCTCTCGGAAATTGAGCCA

GCCAGAATTGCATGTGTCCTCATTGTTGTGTTCCTATTGCTGGTGGTGCTCATACCTGAGCCAGAAAAGCAAAGATCTCCC

CAGGACAACCAAATGGCAATCATCATCATGGTAGCAGTAGGTCTTCTGGGCTTGATTACCGCCAATGAACTCGGATGGTT

GGAGAGAACAAAGAGTGACCTAAGCCATCTAATGGGAAGGAGAGAGGAGGGGGCAACCATAGGATTCTCAATGGACAT

TGACCTGCGGCCAGCCTCAGCTTGGGCCATCTATGCTGCCTTGACAACTTTCATTACCCCAGCCGTCCAACATGCAGTGAC

CACTTCATACAACAACTACTCCTTAATGGCGATGGCCACGCAAGCTGGAGTGTTGTTTGGTATGGGCAAAGGGATGCCAT

TCTACGCATGGGACTTTGGAGTCCCGCTGCTAATGATAGGTTGCTACTCACAATTAACACCCCTGACCCTAATAGTGGCCA

TCATTTTGCTCGTGGCGCACTACATGTACTTGATCCCAGGGCTGCAGGCAGCAGCTGCGCGTGCTGCCCAGAAGAGAACG

GCAGCTGGCATCATGAAGAACCCTGTTGTGGATGGAATAGTGGTGACTGACATTGACACAATGACAATTGACCCCCAAGT

GGAGAAAAGATGGGACAGGTGCTACTCATAGCAGTAGCCGTCTCCAGCGCCATACTGTCGCGGACCGCCTGGGGGTGG

GGGGAGGCTGGGGCCCTGATCACAGCCGCAACTTCCACTTTGTGGGAAGGCTCTCCGAACAAGTACTGGAACTCCTCTAC

AGCCACTTCACTGTGTAACATTTTTAGGGGAAGTTACTTGGCTGGAGCTTCTCTAATCTACACAGTAACAAGAAACGCTGG

CTTGGTCAAGAGACGTGGGGGTGGAACAGGAGAGACCCTGGGAGAGAAATGGAAGGCCCGCTTGAACCAGATGTCGGC

CCTGGAGTTCTACTCCTACAAAAAGTCAGGCATCACCGAGGTGTGCAGAGAAGAGGCCCGCCGCGCCCTCAAGGACGGT

GTGGCAACGGGAGGCCATGCTGTGTCCCGAGGAAGTGCAAAGCTGAGATGGTTGGTGGAGCGGGGATACCTGCAGCCC

TATGGAAAGGTCATTGATCTTGGATGTGGCAGAGGGGGCTGGAGTTACTACGCCGCCACCATCCGCAAAGTTCAAGAAG

TGAAAGGATACACAAAAGGAGGCCCTGGTCATGAAGAACCCGTGTTGGTGCAAAGCTATGGGTGGAACATAGTCCGTCT

TAAGAGTGGGGTGGACGTCTTTCATATGGCGGCTGAGCCGTGTGACACGTTGCTGTGTGACATAGGTGAGTCATCATCTA

GTCCTGAAGTGGAAGAAGCACGGACGCTCAGAGTCCTCTCCATGGTGGGGGATTGGCTTGAAAAAAGACCAGGAGCCTT
```

-continued

```
TTGCATAAAAGTGTTGTGCCCATACACCAGCACTATGATGGAAACCCTGGAGCGACTGCAGCGTAGGTATGGGGAGGA
CTGGTCAGAGTGCCACTCTCCCGCAACTCTACACATGAGATGTACTGGGTCTCTGGAGCGAAAAGCAACACCATAAAAG
TGTGTCCACCACGAGCCAGCTCCTCTTGGGGCGCATGGACGGGCCTAGGAGGCCAGTGAAATATGAGGAGGATGTGAAT
CTCGGCTCTGGCACGCGGGCTGTGGTAAGCTGCGCTGAAGCTCCCAACATGAAGATCATTGGTAACCGCATTGAAAGGAT
CCGCAGTGAGCACGCGGAAACGTGGTTCTTTGACGAAAACCACCCATATAGGACATGGGCTTACCATGGAAGCTATGTG
GCCCCCACACAAGGGTCAGCGTCCTCTCTAATAAACGGGGTTGTCAGGCTCCTGTCAAACCCTGGGATGTGGTGACTGG
AGTCACAGGAATAGCCATGACCGACACCACACCGTATGGTCAGCAAAGAGTTTTCAAGGAAAAGTGGACACTAGGGTG
CCAGACCCCCAAGAAGGCACTCGTCAGGTTATGAGCATGGTCTCTTCCTGGTTGTGGAAAGAGCTAGGCAAACACAAACG
ACCACGAGTCTGTACCAAAGAAGAGTTCATCAACAAGGTTCGTAGCAATGCAGCATTAGGGGCAATATTTGAAGAGGAA
AAAGAGTGGAAGACTGCAGTGGAAGCTGTGAACGATCCAAGGTTCTGGGCTCTAGTGGACAAGGAAAGAGAGCACCAC
CTGAGAGGAGAGTGCCAGAGTTGTGTGTACAACATGATGGGAAAAAGAGAAAAGAAACAAGGGGAATTTGGAAAGGCC
AAGGGCAGCCGCGCCATCTGGTATATGTGGCTAGGGGCTAGATTTCTAGAGTTCGAAGCCCTTGGATTCTTGAACGAGGA
TCACTGGATGGGAGAGAGAACTCAGGAGGTGGTGTTGAAGGGCTGGGATTACAAAGACTCGGATATGTCCTAGAAGA
GATGAGTCGCATACCAGGAGGAAGGATGTATGCAGATGACACTGCTGGCTGGGACACCCGCATCAGCAGGTTTGATCTG
GAGAATGAAGCTCTAATCACCAACCAAATGGAGAAAGGGCACAGGGCCTTGGCATTGGCCATAATCAAGTACACATACC
AAAACAAAGTGGTAAAGGTCCTTAGACCAGCTGAAAAAGGGAAAACAGTTATGGACATTATTTCGAGACAAGACCAAAG
GGGGAGCGGACAAGTTGTCACTTACGCTCTTAACACATTTACCAACCTAGTGGTGCAACTCATTCGGAATATGGAGGCTG
AGGAAGTTCTAGAGATGCAAGACTTGTGGCTGCTGCGGAGGTCAGAGAAAGTGACCAACTGGTTGCAGAGCAACGGAT
GGGATAGGCTCAAACGAATGGCAGTCAGTGGAGATGATTGCGTTGTGAAGCCAATTGATGATAGGTTTGCACATGCCCTC
AGGTTCTTGAATGATATGGGAAAAGTTAGGAAGGACACACAAGAGTGGAAACCCTCAACTGGATGGGACAACTGGGAA
GAAGTTCCGTTTTGCTCCCACCACTTCAACAAGCTCCATCTCAAGGACGGGAGGTCCATTGTGGTTCCCTGCCGCCACCAA
GATGAACTGATTGGCCGGGCCCGCGTCTCTCCAGGGGCGGGATGGAGCATCCGGGAGACTGCTTGCCTAGCAAAATCAT
ATGCGCAAATGTGGCAGCTCCTTTATTTCCACAGAAGGGACCTCCGACTGATGGCCAATGCCATTTGTTCATCTGTGCCAG
TTGACTGGGTTCCAACTGGGAGAACTACCTGGTCAATCCATGGAAAGGGAGAATGGATGACCACTGAAGACATGCTTGT
GGTGTGGAACAGAGTGTGGATTGAGGAGAACGACCACATGGAAGACAAGACCCCAGTTACGAAATGGACAGACATTCCC
TATTTGGGAAAAAGGGGAAGACTTGTGGTGTGGATCTCTCATAGGGCACAGACCGCGCACCACCTGGGCTGAGAACATTA
AAAATACAGTCAACATGGTGCGCAGGATCATAGGTGATGAAGAAAAGTACATGGACTACCTATCCACCCAAGTTCGCTAC
TTGGGTGAAGAAGGGTCTACACCTGGAGTGCTGTGAGCACCAATCTTAATGTTGTCAGGCCTGCTAGTCAGCCACAGCTT
GGGGAAAGCTGTGCAGCCTGTGACCCCTCCAGGAGAAGCTGGGTAACCAAGCCTATAGTCAGGCCGAGAACGCCATGGC
ACGGAAGAAGCCATGCTGCCTGTGAGCCCCTCAGAGGACACTGAGTCAAAAAACCCCACGCGCTTGGAGGCGCAGGATG
GGAAAAGAAGGTGGCGACCTTCCCCACCCTTCAATCTGGGGCCTGAACTGGAGATCAGCTGTGGATCTCCAGAAGAGGG
ACTAGTGGTTAGAGGAGACCCCCCGGAAAACGCAAAACAGCATATTGACGCTGGGAAAGACCAGAGACTCCATGAGTTT
CCACCACGCTGGCCGCCAGGCACAGATCGCCGAATAGCGGCGGCCGGTGTGGGGAAATCCA
```

KU501215.1 Zika virus strain PRVABC59, Puerto Rico, complete genome
SEQ ID NO: 4

```
GTTGTTGATCTGTGTGAATCAGACTGCGACAGTTCGAGTTTGAAGCGAAAGCTAGCAACAGTATCAACAGGTTTTATTTTG
GATTTGGAAACGAGAGTTTCTGGTCATGAAAAACCCAAAAAAGAAATCCGGAGGATTCCGGATTGTCAATATGCTAAAAC
GCGGAGTAGCCCGTGTGAGCCCCTTTGGGGGCTTGAAGAGGCTGCCAGCCGGACTTCTGCTGGGTCATGGGCCCATCAG
GATGGTCTTGGCGATTCTAGCCTTTTTGAGATTCACGGCAATCAAGCCATCACTGGGTCTCATCAATAGATGGGGTTCAGT
GGGGAAAAAGAGGCTATGAAACAATAAAGAAGTTCAAGAAAGATCTGGCTGCCATGCTGAGAATAATCAATGCTAGG
AAGGAGAAGAAGAGACGAGGCGCAGATACTAGTGTCGGAATTGTTGGCCTCCTGCTGACCACAGCTATGGCAGCGGAG
```

-continued

```
GTCACTAGACGTGGGAGTGCATACTATATGTACTTGGACAGAAACGATGCTGGGGAGGCCATATCTTTTCCAACCACATT

GGGGATGAATAAGTGTTATATACAGATCATGGATCTTGGACACATGTGTGATGCCACCATGAGCTATGAATGCCCTATGC

TGGATGAGGGGGTGGAACCAGATGACGTCGATTGTTGGTGCAACACGACGTCAACTTGGGTTGTGTACGGAACCTGCCA

TCACAAAAAAGGTGAAGCACGGAGATCTAGAAGAGCTGTGACGCTCCCCTCCCATTCCACCAGGAAGCTGCAAACGCGG

TCGCAAACCTGGTTGGAATCAAGAGAATACACAAAGCACTTGATTAGAGTCGAAAATTGGATATTCAGGAACCCTGGCTT

CGCGTTAGCAGCAGCTGCCATCGCTTGGCTTTTGGGAAGCTCAACGAGCCAAAAAGTCATATACTTGGTCATGATACTGCT

GATTGCCCCGGCATACAGCATCAGGTGCATAGGAGTCAGCAATAGGGACTTTGTGGAAGGTATGTCAGGTGGGACTTGG

GTTGATGTTGTCTTGGAACATGGAGGTTGTGTCACCGTAATGGCACAGGACAAACCGACTGTCGACATAGAGCTGGTTAC

AACAACAGTCAGCAACATGGCGGAGGTAAGATCCTACTGCTATGAGGCATCAATATCAGACATGGCTTCTGACAGCCGCT

GCCCAACACAAGGTGAAGCCTACCTTGACAAGCAATCAGACACTCAATATGTCTGCAAAAGAACGTTAGTGGACAGAGGC

TGGGGAAATGGATGTGGACTTTTTGGCAAAGGGAGCCTGGTGACATGCGCTAAGTTTGCATGCTCCAAGAAAATGACCG

GGAAGAGCATCCAGCCAGAGAATCTGGAGTACCGGATAATGCTGTCAGTTCATGGCTCCCAGCACAGTGGGATGATCGT

TAATGACACAGGACATGAAACTGATGAGAATAGAGCGAAAGTTGAGATAACGCCCAATTCACCGAGAGCCGAAGCCACC

CTGGGGGGTTTTGGAAGCCTAGGACTTGATTGTGAACCGAGGACAGGCCTTGACTTTTCAGATTTGTATTACTTGACTATG

AATAACAAGCACTGGTTGGTTCACAAGGAGTGGTTCCACGACATTCCATTACCTTGGCACGCTGGGGCAGACACCGGAAC

TCCACACTGGAACAACAAAGAAGCACTGGTAGAGTTCAAGGACGCACATGCCAAAAGGCAAACTGTCGTGGTTCTAGGG

AGTCAAGAAGGAGCAGTTCACACGGCCCTTGCTGGAGCTCTGGAGGCTGAGATGGATGGTGCAAAGGGAAGGCTGTCCT

CTGGCCACTTGAAATGTCGCCTGAAAATGGATAAACTTAGATTGAAGGGCGTGTCATACTCCTTGTGTACTGCAGCGTTCA

CATTCACCAAGATCCCGGCTGAAACACTGCACGGGACAGTCACAGTGGAGGTACAGTACGCAGGGACAGATGGACCTTG

CAAGGTTCCAGCTCAGATGGCGGTGGACATGCAAACTCTGACCCCAGTTGGGAGGTTGATAACCGCTAACCCCGTAATCA

CTGAAAGCACTGAGAACTCTAAGATGATGCTGGAACTTGATCCACCATTTGGGGACTCTTACATTGTCATAGGAGTCGGG

GAGAAGAAGATCACCCACCACTGGCACAGGAGTGGCAGCACCATTGGAAAAGCATTTGAAGCCACTGTGAGAGGTGCCA

AGAGAATGGCAGTCTTGGGAGACACAGCCTGGGACTTTGGATCAGTTGGAGGCGCTCTCAACTCATTGGGCAAGGGCAT

CCATCAAATTTTTGGAGCAGCTTTCAAATCATTGTTTGGAGGAATGTCCTGGTTCTCACAAATTCTCATTGGAACGTTGCTG

ATGTGGTTGGGTCTGAACACAAAGAATGGATCTATTTCCCTTATGTGCTTGGCCTTAGGGGAGTGTTGATCTTCTTATCC

ACAGCCGTCTCTGCTGATGTGGGGTGCTCGGTGGACTTCTCAAAGAAGGAGACGAGATGCGGTACAGGGGTGTTCGTCT

ATAACGACGTTGAAGCCTGGAGGGACAGGTACAAGTACCATCCTGACTCCCCCCGTAGATTGGCAGCAGCAGTCAAGCA

AGCCTGGGAAGATGGTATCTGCGGGATCTCCTCTGTTTCAAGAATGGAAAACATCATGTGGAGATCAGTAGAAGGGGAG

CTCAACGCAATCCTGGAAGAGAATGGAGTTCAACTGACGGTCGTTGTGGGATCTGTAAAAAACCCCATGTGGAGAGGTC

CACAGAGATTGCCCGTGCCTGTGAACGAGCTGCCCCACGGCTGGAAGGCTTGGGGGAAATCGTATTTCGTCAGAGCAGC

AAAGACAAATAACAGCTTTGTCGTGGATGGTGACACACTGAAGGAATGCCCACTCAAACATAGAGCATGGAACAGCTTTC

TTGTGGAGGATCATGGGTTCGGGGTATTTCACACTAGTGTCTGGCTCAAGGTTAGAGAAGATTATTCATTAGAGTGTGAT

CCAGCCGTTATTGGAACAGCTGTTAAGGGAAAGGAGGCTGTACACAGTGATCTAGGCTACTGGATTGAGAGTGAGAAGA

ATGACACATGGAGGCTGAAGAGGGCCCATCTGATCGAGATGAAAACATGTGAATGCCAAAGTCCCACACATTGTGGAC

AGATGGAATAGAAGAGAGTGATCTGATCATACCCAAGTCTTTAGCTGGGCCACTCAGCCATCACAATACCAGAGAGGGCT

ACAGGACCCAAATGAAAGGGCCATGGCACAGTGAAGAGCTTGAAATTCGGTTTGAGGAATGCCCAGGCACTAAGGTCCA

CGTGGAGGAAACATGTGGAACAAGAGGACCATCTCTGAGATCAACCACTGCAAGCGGAAGGGTGATCGAGGAATGGTG

CTGCAGGGAGTGCACAATGCCCCCACTGTCGTTCCGGGCTAAAGATGGCTGTTGGTATGGAATGGAGATAAGGCCCAGG

AAAGAACCAGAAAGCAACTTAGTAAGGTCAATGGTGACTGCAGGATCAACTGATCACATGGACCACTTCTCCCTTGGAGT

GCTTGTGATCCTGCTCATGGTGCAGGAAGGGCTGAAGAAGAGAATGACCACAAAGATCATCATAAGCACATCAATGGCA

GTGCTGGTAGCTATGATCCTGGGAGGATTTTCAATGAGTGACCTGGCTAAGCTTGCAATTTTGATGGGTGCCACCTTCGC
```

-continued

```
GGAAATGAACACTGGAGGAGATGTAGCTCATCTGGCGCTGATAGCGGCATTCAAAGTCAGACCAGCGTTGCTGGTATCTT
TCATCTTCAGAGCTAATTGGACACCCCGTGAAAGCATGCTGCTGGCCTTGGCCTCGTGTCTTTTGCAAACTGCGATCTCCG
CCTTGGAAGGCGACCTGATGGTTCTCATCAATGGTTTTGCTTTGGCCTGGTTGGCAATACGAGCGATGGTTGTTCCACGCA
CTGATAACATCACCTTGGCAATCCTGGCTGCTCTGACACCACTGGCCCGGGGCACACTGCTTGTGGCGTGGAGAGCAGGC
CTTGCTACTTGCGGGGGGTTTATGCTCCTCTCTCTGAAGGGAAAAGGCAGTGTGAAGAAGAACTTACCATTTGTCATGGC
CCTGGGACTAACCGCTGTGAGGCTGGTCGACCCCATCAACGTGGTGGGACTGCTGTTGCTCACAAGGAGTGGGAAGCGG
AGCTGGCCCCCTAGCGAAGTACTCACAGCTGTTGGCCTGATATGCGCATTGGCTGGAGGGTTCGCCAAGGCAGATATAGA
GATGGCTGGGCCCATGGCCGCGGTCGGTCTGCTAATTGTCAGTTACGTGGTCTCAGGAAAGAGTGTGGACATGTACATTG
AAAGAGCAGGTGACATCACATGGGAAAAGATGCGGAAGTCACTGGAAACAGTCCCCGGCTCGATGTGGCGCTAGATG
AGAGTGGTGATTTCTCCCTGGTGGAGGATGACGGTCCCCCCATGAGAGAGATCATACTCAAGGTGGTCCTGATGACCATC
TGTGGCATGAACCCAATAGCCATACCCTTTGCAGCTGGAGCGTGGTACGTATACGTGAAGACTGGAAAAAGGAGTGGTG
CTCTATGGGATGTGCCTGCTCCCAAGGAAGTAAAAAAGGGGGAGACCACAGATGGAGTGTACAGAGTAATGACTCGTAG
ACTGCTAGGTTCAACACAAGTTGGAGTGGGAGTTATGCAAGAGGGGGTCTTTCACACTATGTGGCACGTCACAAAAGGA
TCCGCGCTGAGAAGCGGTGAAGGGAGACTTGATCCATACTGGGGAGATGTCAAGCAGGATCTGGTGTCATACTGTGGTC
CATGGAAGCTAGATGCCGCCTGGGATGGGCACAGCGAGGTGCAGCTCTTGGCCGTGCCCCCCGGAGAGAGAGCGAGGA
ACATCCAGACTCTGCCCGGAATATTTAAGACAAAGGATGGGGACATTGGAGCGGTTGCGCTGGATTACCCAGCAGGAAC
TTCAGGATCTCCAATCCTAGACAAGTGTGGGAGAGTGATAGGACTTTATGGCAATGGGGTCGTGATCAAAAACGGGAGT
TATGTTAGTGCCATCACCCAAGGGAGGAGGGAGGAAGAGACTCCTGTTGAGTGCTTCGAGCCCTCGATGCTGAAGAAGA
AGCAGCTAACTGTCTTAGACTTGCATCCTGGAGCTGGGAAAACCAGGAGAGTTCTTCCTGAAATAGTCCGTGAAGCCATA
AAAACAAGACTCCGTACTGTGATCTTAGCTCCAACCAGGGTTGTCGCTGCTGAAATGGAGGAGGCCCTTAGAGGGCTTCC
AGTGCGTTATATGACAACAGCAGTCAATGTCACCCACTCTGGAACAGAAATCGTCGACTTAATGTGCCATGCCACCTTCAC
TTCACGTCTACTACAGCCAATCAGAGTCCCCAACTATAATCTGTATATTATGGATGAGGCCCACTTCACAGATCCCTCAAGT
ATAGCAGCAAGAGGATACATTTCAACAAGGGTTGAGATGGGCGAGGCGGCTGCCATCTTCATGACCGCCACGCCACCAG
GAACCCGTGACGCATTTCCGGACTCCAACTCACCAATTATGGACACCGAAGTGGAAGTCCCAGAGAGAGCCTGGAGCTCA
GGCTTTGATTGGGTGACGGATCATTCTGGAAAAACAGTTTGGTTTGTTCCAAGCGTGAGGAACGGCAATGAGATCGCAGC
TTGTCTGACAAAGGCTGGAAAACGGGTCATACAGCTCAGCAGAAAGACTTTTGAGACAGAGTTCCAGAAAACAAAACATC
AAGAGTGGGACTTTGTCGTGACAACTGACATTTCAGAGATGGGCGCCAACTTTAAAGCTGACCGTGTCATAGATTCCAGG
AGATGCCTAAAGCCGGTCATACTTGATGGCGAGAGAGTCATTCTGGCTGGACCCATGCCTGTCACACATGCCAGCGCTGC
CCAGAGGAGGGGCGCATAGGCAGGAATCCCAACAAACCTGGAGATGAGTATCTGTATGGAGGTGGGTGCGCAGAGAC
TGACGAAGACCATGCACACTGGCTTGAAGCAAGAATGCTCCTTGACAATATTTACCTCCAAGATGGCCTCATAGCCTCGCT
CTATCGACCTGAGGCCGACAAAGTAGCAGCCATTGAGGGAGAGTTCAAGCTTAGGACGGAGCAAAGGAAGACCTTTGTG
GAACTCATGAAAAGAGGAGATCTTCCTGTTTGGCTGGCCTATCAGGTTGCATCTGCCGGAATAACCTACACAGATAGAAG
ATGGTGCTTTGATGGCACGACCAACAACACCATAATGGAAGACAGTGTGCCGGCAGAGGTGTGGACCAGACACGGAGA
GAAAAGAGTGCTCAAACCGAGGTGGATGGACGCCAGAGTTTGTTCAGATCATGCGGCCCTGAAGTCATTCAAGGAGTTT
GCCGCTGGGAAAAGAGGAGCGGCTTTTGGAGTGATGGAAGCCCTGGGAACACTGCCAGGACACATGACAGAGAGATTC
CAGGAAGCCATTGACAACCTCGCTGTGCTCATGCGGGCAGAGACTGGAAGCAGGCCTTACAAAGCCGCGGCGGCCCAAT
TGCCGGAGACCCTAGAGACCATAATGCTTTTGGGGTTGCTGGGAACAGTCTCGCTGGGAATCTTCTTCGTCTTGATGAGG
AACAAGGGCATAGGGAAGATGGGCTTTGGAATGGTGACTCTTGGGGCCAGCGCATGGCTCATGTGGCTCTCGGAAATTG
AGCCAGCCAGAATTGCATGTGTCCTCATTGTTGTGTTCCTATTGCTGGTGGTGCTCATACCTGAGCCAGAAAAGCAAAGAT
CTCCCCAGGACAACCAAATGGCAATCATCATCATGGTAGCAGTAGGTCTTCTGGGCTTGATTACCGCCAATGAACTCGGAT
```

-continued

```
GGTTGGAGAGAACAAAGAGTGACCTAAGCCATCTAATGGGAAGGAGAGAGGAGGGGGCAACCATAGGATTCTCAATGG
ACATTGACCTGCGGCCAGCCTCAGCTTGGGCCATCTATGCTGCCTTGACAACTTTCATTACCCCAGCCGTCCAACATGCAGT
GACCACCTCATACAACAACTACTCCTTAATGGCGATGGCCACGCAAGCTGGAGTGTTGTTTGGCATGGGCAAAGGGATGC
CATTCTACGCATGGGACTTTGGAGTCCCGCTGCTAATGATAGGTTGCTACTCACAATTAACACCCCTGACCCTAATAGTGG
CCATCATTTTGCTCGTGGCGCACTACATGTACTTGATCCCAGGGCTGCAGGCAGCAGCTGCGCGTGCTGCCCAGAAGAGA
ACGGCAGCTGGCATCATGAAGAACCCTGTTGTGGATGGAATAGTGGTGACTGACATTGACACAATGACAATTGACCCCCA
AGTGGAGAAAAAGATGGGACAGGTGCTACTCATAGCAGTAGCCGTCTCCAGCGCCATACTGTCGCGGACCGCCTGGGGG
TGGGGGGAGGCTGGGGCTCTGATCACAGCCGCAACTTCCACTTTGTGGGAAGGCTCTCCGAACAAGTACTGGAACTCCTC
TACAGCCACTTCACTGTGTAACATTTTTAGGGGAAGTTACTTGGCTGGAGCTTCTCTAATCTACACAGTAACAAGAAACGC
TGGCTTGGTCAAGAGACGTGGGGGTGGAACAGGAGAGACCCTGGGAGAGAAATGGAAGGCCCGCTTGAACCAGATGTC
GGCCCTGGAGTTCTACTCCTACAAAAAGTCAGGCATCACCGAGGTGTGCAGAGAAGAGGCCCGCCGCGCCCTCAAGGAC
GGTGTGGCAACGGGAGGCCATGCTGTGTCCCGAGGAAGTGCAAAGCTGAGATGGTTGGTGGAGCGGGATACCTGCAG
CCCTATGGAAAGGTCATTGATCTTGGATGTGGCAGAGGGGCTGGAGTTACTACGTCGCCACCATCCGCAAAGTTCAAGA
AGTGAAAGGATACACAAAAGGAGGCCCTGGTCATGAAGAACCCGTGTTGGTGCAAAGCTATGGGTGGAACATAGTCCGT
CTTAAGAGTGGGGTGGACGTCTTTCATATGGCGGCTGAGCCGTGTGACACGTTGCTGTGTGACATAGGTGAGTCATCATC
TAGTCCTGAAGTGGAAGAAGCACGGACGCTCAGAGTCCTCTCCATGGTGGGGATTGGCTTGAAAAAAGACCAGGAGCC
TTTTGTATAAAAGTGTTGTGCCCATACACCAGCACTATGATGGAAACCCTGGAGCGACTGCAGCGTAGGTATGGGGGAG
GACTGGTCAGAGTGCCACTCTCCCGCAACTCTACACATGAGATGTACTGGGTCTCTGGAGCGAAAAGCAACACCATAAAA
AGTGTGTCCACCACGAGCCAGCTCCTCTTGGGGCGCATGGACGGGCCTAGGAGGCCAGTGAAATATGAGGAGGATGTGA
ATCTCGGCTCTGGCACGCGGGCTGTGGTAAGCTGCGCTGAAGCTCCCAACATGAAGATCATTGGTAACCGCATTGAAAGG
ATCCGCAGTGAGCACGCGGAAACGTGGTTCTTTGACGAGAACCACCCATATAGGACATGGGCTTACCATGGAAGCTATGA
GGCCCCCACACAAGGGTCAGCGTCCTCTCTAATAAACGGGGTTGTCAGGCTCCTGTCAAAACCCTGGGATGTGGTGACTG
GAGTCACAGGAATAGCCATGACCGACACCACACCGTATGGTCAGCAAAGAGTTTTCAAGGAAAAAGTGGACACTAGGGT
GCCAGACCCCCAAGAAGGCACTCGTCAGGTTATGAGCATGGTCTCTTCCTGGTTGTGGAAAGAGCTAGGCAAACACAAAC
GGCCACGAGTCTGCACCAAAGAAGAGTTCATCAACAAGGTTCGTAGCAATGCAGCATTAGGGGCAATATTTGAAGAGGA
AAAAGAGTGGAAGACTGCAGTGGAAGCTGTGAACGATCCAAGGTTCTGGGCTCTAGTGGACAAGGAAAGAGAGCACCA
CCTGAGAGGAGAGTGCCAGAGCTGTGTGTACAACATGATGGGAAAAAGAGAAAAGAAACAAGGGGAATTTGGAAAGGC
CAAGGGCAGCCGCGCCATCTGGTATATGTGGCTAGGGCTAGATTTCTAGAGTTCGAAGCCCTTGGATTCTTGAACGAGG
ATCACTGGATGGGAGAGAGAACTCAGGAGGTGGTGTTGAAGGGCTGGGATTACAAAGACTCGGATATGTCCTAGAAG
AGATGAGTCGTATACCAGGAGGAAGGATGTATGCAGATGACACTGCTGGCTGGGACACCCGCATTAGCAGGTTTGATCT
GGAGAATGAAGCTCTAATCACCAACCAAATGGAGAAAGGGCACAGGGCCTTGGCATTGGCCATAATCAAGTACACATAC
CAAAACAAAGTGGTAAAGGTCCTTAGACCAGCTGAAAAAGGGAAAACAGTTATGGACATTATTTCGAGACAAGACCAAA
GGGGGAGCGGACAAGTTGTCACTTACGCTCTTAACACATTTACCAACCTAGTGGTGCAACTCATTCGGAATATGGAGGCT
GAGGAAGTTCTAGAGATGCAAGACTTGTGGCTGCTGCGGAGGTCAGAGAAAGTGACCAACTGGTTGCAGAGCAACGGA
TGGGATAGGCTCAAACGAATGGCAGTCAGTGGAGATGATTGCGTTGTGAAGCCAATTGATGATAGGTTTGCACATGCCCT
CAGGTTCTTGAATGATATGGGAAAAGTTAGGAAGGACACACAAGAGTGGAAACCCTCAACTGGATGGACAACTGGGAA
GAAGTTCCGTTTTGCTCCCACCACTTCAACAAGCTCCATCTCAAGGACGGGAGGTCCATTGTGGTTCCCTGCCGCCACCAA
GATGAACTGATTGGCCGGGCCCGCGTCTCTCCAGGGGCGGGATGGAGCATCCGGGAGACTGCTTGCCTAGCAAAATCAT
ATGCGCAAATGTGGCAGCTCCTTTATTTCCACAGAAGGGACCTCCGACTGATGGCCAATGCCATTTGTTCATCTGTGCCAG
TTGACTGGGTTCCAACTGGGAGAACTACCTGGTCAATCCATGGAAAGGGAGAATGGATGACCACTGAAGACATGCTTGT
GGTGTGGAACAGAGTGTGGATTGAGGAGAACGACCACATGGAAGACAAGACCCCAGTTACGAAATGGACAGACATTCCC
```

-continued

TATTTGGGAAAAAGGGAAGACTTGTGGTGTGGATCTCTCATAGGGCACAGACCGCGCACCACCTGGGCTGAGAACATTA

AAAACACAGTCAACATGGTGCGCAGGATCATAGGTGATGAAGAAAAGTACATGGACTACCTATCCACCCAAGTTCGCTAC

TTGGGTGAAGAAGGGTCTACACCTGGAGTGCTGTAAGCACCAATCTTAATGTTGTCAGGCCTGCTAGTCAGCCACAGCTT

GGGGAAAGCTGTGCAGCCTGTGACCCCCCCAGGAGAAGCTGGGAAACCAAGCCTATAGTCAGGCCGAGAACGCCATGG

CACGGAAGAAGCCATGCTGCCTGTGAGCCCCTCAGAGGACACTGAGTCAAAAAACCCCACGCGCTTGGAGGCGCAGGAT

GGGAAAAGAAGGTGGCGACCTTCCCCACCCTTCAATCTGGGGCCTGAACTGGAGATCAGCTGTGGATCTCCAGAAGAGG

GACTAGTGGTTAGAGGA

KU509998.1 Zika virus strain Haiti/1225/2014, Haiti, complete genome

SEQ ID NO: 5

GTTGTTACTGTTGCTGACTCAGACTGCGACAGTTCGAGTTTGAAGCGAAAGCTAGCAACAGTATCAACAGGTTTTATTTGG

ATTTGGAAACGAGAGTTTCTGGTCATGAAAAACCCAAAAAAGAAATCCGGAGGATTCCGGATTGTCAATATGCTAAAACG

CGGAGTAGCCCGTGTGAGCCCCTTTGGGGGCTTGAAGAGGCTGCCAGCCGGACTTCTGCTGGGTCATGGGCCCATCAGG

ATGGTCTTGGCAATTCTAGCCTTTTTGAGATTCACGGCAATCAAGCCATCACTGGGTCTCATCAATAGATGGGGTTCAGTG

GGGAAAAAAGAGGCTATGGAAATAATAAAGAAGTTCAAGAAAGATCTGGCTGCCATGCTGAGAATAATCAATGCTAGGA

AGGAGAAGAAGAGACGAGGCGCAGATACTAGTGTCGGAATTGTTGGCCTCCTGCTGACCACAGCTATGGCAGCGGAGG

TCACTAGACGTGGGAGTGCATACTATATGTACTTGGACAGAAACGATGCTGGGGAGGCCATATCTTTTCCAACCACATTG

GGGATGAATAAGTGTTATATACAGATCATGGATCTTGGACACATGTGTGATGCCACCATGAGCTATGAATGCCCTATGCT

GGATGAGGGGGTGGAACCAGATGACGTCGATTGTTGGTGCAACACGACGTCAACTTGGGTTGTGTACGGAACCTGCCAT

CACAAAAAAGGTGAAGCACGGAGATCTAGAAGAGCTGTGACGCTCCCCTCCCATTCCACTAGGAAGCTGCAAACGCGGT

CGCAAACCTGGTTGGAATCAAGAGAATACACAAAGCACTTGATTAGAGTCGAAAATTGGATATTCAGGAACCCTGGCTTC

GCGTTAGCAGCAGCTGCCATCGCTTGGCTTTTGGGAAGCTCAACGAGCCAAAAAGTCATATACTTGGTCATGATACTGCT

GATTGCCCCGGCATACAGCATCAGGTGCATAGGAGTCAGCAATAGGGACTTTGTGGAAGGTATGTCAGGTGGGACTTGG

GTTGATGTTGTCTTGGAACATGGAGGTTGTGTCACCGTAATGGCACAGGACAAACCGACTGTCGACATAGAGCTGGTTAC

AACAACAGTCAGCAACATGGCGGAGGTAAGATCCTACTGCTATGAGGCATCAATATCAGACATGGCTTCGGACAGCCGCT

GCCCAACACAAGGTGAAGCCTACCTTGACAAGCAATCAGACACTCAATATGTCTGCAAAAGAACGTTAGTGGACAGAGGC

TGGGGAAATGGATGTGGACTTTTTGGCAAAGGGAGTCTGGTGACATGCGCTAAGTTTGCATGCTCCAAGAAAATGACCG

GGAAGAGCATCCAGCCAGAGAATCTGGAGTACCGGATAATGCTGTCAGTTCATGGCTCCCAGCACAGTGGGATGATCGT

TAATGACACAGGACATGAAACTGATGAGAATAGAGCGAAGGTTGAGATAACGCCCAATTCACCAAGAGCCGAAGCCACC

CTGGGGGGTTTTGGAAGCCTAGGACTTGATTGTGAACCGAGGACAGGCCTTGACTTTTCAGATTTGTATTACTTGACTATG

AATAACAAGCACTGGTTGGTTCACAAGGAGTGGTTCCACGACATTCCATTACCTTGGCACGCTGGGGCAGACACCGGAAC

TCCACACTGGAACAACAAAGAAGCACTGGTAGAGTTCAAGGACGCACATGCCAAAAGGCAAACTGTCGTGGTTCTAGGG

AGTCAAGAAGGAGCAGTTCACACGGCCCTTGCTGGAGCTCTGGAGGCTGAGATGGATGGTGCAAAGGGAAGGCTGTCCT

CTGGCCACTTGAAATGTCGCCTGAAAATGGATAAACTTAGATTGAAGGGCGTGTCATACTCCTTGTGTACCGCAGCGTTCA

CATTCACCAAGATCCCGGCTGAAACACTGCACGGGACAGTCACAGTGGAGGTACAGTACGCAGGGACAGATGGACCTTG

CAAGGTTCCAGCTCAGATGGCGGTGGACATGCAAACTCTGACCCCAGTTGGGAGGTTGATAACCGCTAACCCCGTAATCA

CTGAAAGCACTGAGAACTCTAAGATGATGCTGGAACTTGATCCACCATTTGGGGACTCTTACATTGTCATAGGAGTCGGG

GAGAAGAAGATCACCCACCACTGGCACAGGAGTGGCAGCACCATTGGAAAAGCATTTGAAGCCACTGTGAGAGGTGCCA

AGAGAATGGCAGTCTTGGGAGACACAGCCTGGGACTTTGGATCAGTTGGAGGCGCTCTCAACTCATTGGGCAAGGGCAT

CCATCAAATTTTTGGAGCAGCTTTCAAATCATTGTTTGGAGGAATGTCCTGGTTCTCACAAATTCTCATTGGAACGTTGCTG

ATGTGGTTGGGTCTGAACACAAAGAATGGATCTATTTCCCTTATGTGCTTGGCCTTAGGGGGAGTGTTGATCTTCTTATCC

ACAGCCGTCTCTGCTGATGTGGGGTGCTCGGTGGACTTCTCAAAGAAGGAGACGAGATGCGGTACAGGGGTGTTCGTCT

-continued

```
ATAACGACGTTGAAGCCTGGAGGGACAGGTACAAGTACCATCCTGACTCCCCCCGTAGATTGGCAGCAGCAGTCAAGCA
AGCCTGGGAAGATGGTATCTGCGGGATCTCCTCTGTTTCAAGAATGGAAAACATCATGTGGAGATCAGTAGAAGGGGAG
CTCAACGCAATCCTGGAAGAGAATGGAGTTCAACTGACGGTCGTTGTGGGATCTGTAAAAAACCCCATGTGGAGAGGTC
CACAGAGATTGCCCGTGCCTGTGAACGAGCTGCCCCACGGCTGGAAGGCTTGGGGGAAATCGCACTTCGTCAGAGCAGC
AAAGACAAATAACAGCTTTGTCGTGGATGGTGACACACTGAAGGAATGCCCACTCAAACATAGAGCATGGAACAGCTTTC
TTGTGGAGGATCATGGGTTCGGGGTATTTCACACTAGTGTCTGGCTCAAGGTTAGAGAAGATTATTCATTAGAGTGTGAT
CCAGCCGTTATTGGAACAGCTGTTAAGGGAAAGGAGGCTGTACACAGTGATCTAGGCTACTGGATTGAGAGTGAGAAGA
ATGACACATGGAGGCTGAAGAGGGCCCATCTGATCGAGATGAAAACATGTGAATGGCCAAAGTCCCACACATTGTGGAC
AGATGGAATAGAAGAGAGTGATCTGATCATACCCAAGTCTTTAGCTGGGCCACTCAGCCATCACAATACCAGAGAGGGCT
ACAGGACCCAAATGAAAGGGCCATGGCACAGTGAAGAGCTTGAAATTCGGTTTGAGGAATGCCCAGGCACTAAGGTCCA
CGTGGAGGAAACATGTGGAACAAGAGGACCATCTCTGAGATCAACCACTGCAAGCGGAAGGGTGATCGAGGAATGGTG
CTGCAGGGAGTGCACAATGCCCCCACTGTCGTTCCGGGCTAAAGATGGCTGTTGGTATGGAATGGAGATAAGGCCCAGG
AAAGAACCAGAAAGCAACTTAGTAAGGTCAATGGTGACTGCAGGATCAACTGATCACATGGATCACTTCTCCCTTGGAGT
GCTTGTGATTCTGCTCATGGTGCAGGAAGGGCTGAAGAAGAGAATGACCACAAAGATCATCATAAGCACATCAATGGCA
GTGCTGGTAGCTATGATCCTGGGAGGATTTTCAATGAGTGACCTGGCTAAGCTTGCAATTTTGATGGGTGCCACCTTCGC
GGAAATGAACACTGGAGGAGATGTAGCTCATCTGGCGCTGATAGCGGCATTCAAAGTCAGACCAGCGTTGCTGGTATCTT
TCATCTTCAGAGCTAATTGGACACCCCGTGAAAGCATGCTGCTGGCCTTGGCCTCGTGTCTTTTGCAAACTGCGATCTCCG
CCTTGGAAGGCGACCTGATGGTTCTCATCAATGGTTTTGCTTTGGCCTGGTTGGCAATACGAGCGATGGTTGTTCCACGCA
CTGATAACATCACCTTGGCAATCCTGGCTGCTCTGACACCACTGGCCCGGGGCACACTGCTTGTGGCGTGGAGAGCAGGC
CTTGCTACTTGCGGGGGGTTTATGCTCCTCTCTCTGAAGGGAAAAGGCAGTGTGAAGAAGAACTTACCATTTGTCATGGC
CCTGGGACTAACCGCTGTGAGGCTGGTCGACCCCATCAACGTGGTGGGGCTGCTGTTGCTCACAAGGAGTGGGAAGCGG
AGCTGGCCCCCTAGCGAAGTACTCACAGCTGTTGGCCTGATATGCGCATTGGCTGGAGGGTTCGCCAAGGCAGATATAGA
GATGGCTGGGCCCATGGCCGCGGTCGGTCGCTAATTGTCAGTTACGTGGTCTCAGGAAAGAGTGTGGACATGTACATTG
AAAGAGCAGGTGACATCACATGGGAAAAAGATGCGGAAGTCACTGGAAACAGTCCCCGGCTCGATGTGGCGCTAGATG
AGAGTGGTGATTTCTCCCTGGTGGAGGATGACGGTCCCCCCATGAGAGAGATCATACTCAAGGTGGTCCTGATGACCATC
TGTGGCATGAACCCAATAGCCATACCCTTTGCAGCTGGAGCGTGGTACGTATACGTGAAGACTGGAAAAAGGAGTGGTG
CTCTATGGGATGTGCCTGCTCCCAAGGAAGTAAAAAAGGGGGAGACCACAGATGGAGTGTACAGAGTAATGACTCGTAG
ACTGCTAGGTTCAACACAAGTTGGAGTGGGAGTTATGCAAGAGGGGTCTTTCACACTATGTGGCACGTCACAAAAGGA
TCCGCGCTGAGAAGCGGTGAAGGGAGACTTGATCCATACTGGGGAGATGTCAAGCAGGATCTGGTGTCATACTGTGGTC
CATGGAAGCTAGATGCCGCCTGGGACGGGCACAGCGAGGTGCAGCTCTTGGCCGTGCCCCCCGGAGAGAGAGCGAGGA
ACATCCAGACTCTGCCCGGAATATTTAAGACAAAGGATGGGGACATTGGAGCGGTTGCGCTGGATTACCCAGCAGGAAC
TTCAGGATCTCCAATCCTAGACAAGTGTGGGAGAGTGATAGGACTTTATGGCAATGGGGTCGTGATCAAAAATGGGAGT
TATGTTAGTGCCATCACCCAAGGGAGGAGGGAGGAAGAGACTCCTGTTGAGTGCTTCAGCCTTCGATGCTGAAGAAGA
AGCAGCTAACTGTCTTAGACTTGCATCCTGGAGCTGGGAAAACCAGGAGAGTTCTTCCTGAAATAGTCCGTGAAGCCATA
AAAACAAGACTCCGTACTGTGATCTTAGCTCCAACCAGGGTTGTCGCTGCTGAAATGGAGGAAGCCCTTAGAGGGCTTCC
AGTGCGTTATATGACAACAGCAGTCAATGTCACCCACTCTGGAACAGAAATCGTCGACTTAATGTGCCATGCCACCTTCAC
TTCACGTCTACTACAGCCAATCAGAGTCCCCAACTATAATCTGTATATTATGGATGAGGCCCACTTCACAGATCCCTCAAGT
ATAGCAGCAAGAGGATACATTTCAACAAGGGTTGAGATGGGCGAGGCGGCTGCCATCTTCATGACCGCCACGCCACCAG
GAACCCGTGACGCATTTCCGGACTCCAACTCACCAATTATGGACACCGAAGTGGAAGTCCCAGAGAGAGCCTGGAGCTCA
GGCTTTGATTGGGTGACGGATTATTCTGGAAAAACAGTTTGGTTTGTTCCAAGCGTGAGGAACGGCAATGAGATCGCAGC
TTGTCTGACAAAGGCTGGAAAACGGGTCATACAGCTCAGCAGAAAGACTTTTGAGACAGAGTTCCAGAAAACAAAACATC
```

-continued

```
AAGAGTGGGACTTTGTCGTGACAACTGACATTTCAGAGATGGGCGCCAACTTTAAAGCTGACCGTGTCATAGATTCCAGG
AGATGCCTAAAGCCGGTCATACTTGATGGCGAGAGAGTCATTCTGGCTGGACCCATGCCTGTCACACATGCCAGCGCTGC
CCAGAGGAGGGGGCGCATAGGCAGGAATCCCAACAAACCTGGAGATGAGTATCTGTATGGAGGTGGGTGCGCAGAGAC
TGACGAAGACCATGCACACTGGCTTGAAGCAAGAATGCTCCTTGACAATATTTACCTCCAAGATGGCCTCATAGCCTCGCT
CTATCGACCTGAGGCCGACAAAGTAGCAGCCATTGAGGGAGAGTTCAAGCTTAGGACGGAGCAAAGGAAGACCTTTGTG
GAACTCATGAAAAGAGGAGATCTTCCTGTTTGGCTGGCCTATCAGGTTGCATCTGCCGGAATAACCTACACAGATAGAAG
ATGGTGCTTTGATGGCACGACCAACAACACCATAATGGAAGACAGTGTGCCGGCAGAGGTGTGGACCAGACACGGAGA
GAAAAGAGTGCTCAAACCGAGGTGGATGGACGCCAGAGTTTGTTCAGATCATGCGGCCCTGAAGTCATTCAAGGAGTTT
GCCGCTGGGAAAAGAGGAGCGGCTTTTGGAGTGATGGAAGCCCTGGGAACACTGCCAGGACACATGACAGAGAGATTC
CAGGAAGCCATTGACAACCTCGCTGTGCTCATGCGGGCAGAGACTGGAAGCAGGCCTTACAAAGCCGCGGCGGCCCAAT
TGCCGGAGACCCTAGAGACCATTATGCTTTTGGGGTTGCTGGGAACAGTCTCGCTGGGAATCTTTTTCGTCTTGATGAGG
AACAAGGGCATAGGGAAGATGGGCTTTGGAATGGTGACTCTTGGGGCCAGCGCATGGCTCATGTGGCTCTCGGAAATTG
AGCCAGCCAGAATTGCATGTGTCCTCATTGTTGTGTTCCTATTGCTGGTGGTGCTCATACCTGAGCCAGAAAAGCAAAGAT
CTCCCCAGGACAACCAAATGGCAATCATCATCATGGTAGCAGTAGGTCTTCTGGGCTTGATTACCGCCAATGAACTCGGAT
GGTTGGAGAGAACAAAGAGTGACCTAAGCCATCTAATGGGAAGGAGAGAGGAGGGGGCAACCATGGGATTCTCAATGG
ACATTGACCTGCGGCCAGCCTCAGCTTGGGCCATCTATGCTGCCTTGACAACTTTCATTACCCCAGCCGTCCAACATGCAGT
GACCACTTCATACAACAACTACTCCTTAATGGCGATGGCCACGCAAGCTGGAGTGTTGTTTGGTATGGGCAAAGGGATGC
CATTCTACGCATGGGACTTTGGAGTCCCGCTGCTAATGATAGGTTGCTACTCACAATTAACGCCCCTGACCCTAATAGTGG
CCATCATTTTGCTCGTGGCGCACTACATGTACTTGATCCCAGGGCTGCAGGCAGCAGCTGCGCGTGCTGCCCAGAAGAGA
ACGGCAGCTGGCATCATGAAGAACCCTGTTGTGGATGGAATAGTGGTGACTGACATTGACACAATGACAATTGACCCCCA
AGTGGAGAAAAAGATGGGACAGGTGCTACTCATGGCAGTAGCCGTCTCCAGCGCCATACTGTCGCGGACCGCCTGGGGG
TGGGGGGAGGCTGGGGCCCTGATCACAGCCGCAACTTCCACTTTGTGGGAAGGCTCTCCGAACAAGTACTGGAACTCCTC
TACAGCCACTTCACTGTGTAACATTTTTAGGGGAAGTTACTTGGCTGGAGCTTCTCTAATCTACACAGTAACAAGAAACGC
TGGCTTGGTCAAGAGACGTGGGGGTGGAACAGGAGAGACCCTGGGAGAGAAATGGAAGGCCCGCTTGAACCAGATGTC
GGCCCTGGAGTTCTACTCCTACAAAAAGTCAGGCATCACCGAGGTGTGCAGAGAAGAGGCCCGCCGCGCCCTCAAGGAC
GGTGTGGCAACGGGAGGCCATGCTGTGTCCCGAGGAAGTGCAAAGCTGAGATGGTTGGTGGAGCGGGGATACCTGCAG
CCCTATGGAAAGGTCATTGATCTTGGATGTGGCAGAGGGGCTGGAGTTACTACGCCGCCACCATCCGCAAAGTTCAAGA
AGTGAAAGGATACACAAAAGGAGGCCCTGGTCATGAAGAACCCGTGTTGGTGCAAAGCTATGGGTGGAACATAGTCCGT
CTTAAGAGTGGGGTGGACGTCTTTCATATGGCGGCTGAGCCGTGTGACACGTTGCTGTGTGACATAGGTGAGTCATCATC
TAGTCCTGAAGTGGAAGAAGCACGGACGCTCAGAGTCCTCTCCATGGTGGGGATTGGCTTGAAAAAAGACCAGGAGCC
TTTTGTATAAAAGTGTTGTGCCCATACACCAGCACTATGATGGAAACCCTGGAGCGACTGCAGCGTAGGTATGGGGGAG
GACTGGTCAGAGTGCCACTCTCCCGCAACTCTACACATGAGATGTACTGGGTCTCTGGAGCGAAAAGCAACACCATAAAA
AGTGTGTCCACCACGAGCCAGCTCCTCTTGGGGCGCATGGACGGGCCTAGGAGGCCAGTGAAATATGAGGAGGATGTGA
ATCTCGGCTCTGGCACGCGGGCTGTGGTAAGCTGCGCTGAAGCTCCCAACATGAAGATCATTGGTAACCGCATTGAAAGG
ATCCGCAGTGAGCACGCGGAAACGTGGTTCTTTGACGAGAACCACCCATATAGGACATGGGCTTACCATGGAAGCTATGA
GGCCCCCACACAAGGGTCAGCGTCCTCTCTAATAAACGGGGTTGTCAGGCTCCTGTCAAAACCCTGGGATGTGGTGACTG
GAGTCACAGGAATAGCCATGACCGACACCACACCGTATGGTCAGCAAAGAGTTTTCAAGGAAAAAGTGGACACTAGGGT
GCCAGACCCCCAAGAAGGCACTCGTCAGGTTATGAGCATGGTCTCTTCCTGGTTGTGGAAAGAGCTAGGCAAACACAAAC
GGCCACGAGTCTGTACCAAAGAAGAGTTCATCAACAAGGTTCGTAGCAATGCAGCATTAGGGGCAATATTTGAAGAGGA
AAAAGAGTGGAAGACTGCAGTGGAAGCTGTGAACGATCCAAGGTTCTGGGCTCTAGTGGACAAGGAAAGAGAGCACCA
```

-continued

```
CCTGAGAGGAGAGTGCCAGAGTTGTGTGTACAACATGATGGGAAAAAGAGAAAAGAAACAAGGGGAATTTGGAAAGGC
CAAGGGCAGCCGCGCCATCTGGTATATGTGGCTAGGGGCTAGATTTCTAGAGTTCGAAGCCCTTGGATTCTTGAACGAGG
ATCACTGGATGGGGAGAGAGAACTCAGGAGGTGGTGTTGAAGGGCTGGGATTACAAAGACTCGGATATGTCCTAGAAG
AGATGAGTCGCATACCAGGAGGAAGGATGTATGCAGATGACACTGCTGGCTGGGACACCCGCATCAGCAGGTTTGATCT
GGAGAATGAAGCTCTAATCACCAACCAAATGGAGAAAGGGCACAGGGCCTTGGCATTGGCCATAATCAAGTACACATAC
CAAAACAAAGTGGTAAAGGTCCTTAGACCAGCTGAAAAAGGGAAGACAGTTATGGACATTATTTCGAGACAAGACCAAA
GGGGGAGCGGACAAGTTGTCACTTACGCTCTTAACACATTTACCAACCTAGTGGTGCAACTCATTCGGAATATGGAGGCT
GAGGAAGTTCTAGAGATGCAAGACTTGTGGCTGCTGCGGAGGTCAGAGAAAGTGACCAACTGGTTGCAGAGCAACGGA
TGGGATAGGCTCAAACGAATGGCAGTCAGTGGAGATGATTGCGTTGTGAAGCCAATTGATGATAGGTTTGCACATGCCCT
CAGGTTCTTGAATGATATGGGAAAAGTTAGGAAGGACACACAAGAGTGGAAACCCTCAACTGGATGGGACAACTGGGAA
GAAGTTCCGTTTTGCTCCCACCACTTCAACAAGCTCCATCTCAAGGACGGGAGGTCCATTGTGGTTCCCTGCCGCCACCAA
GATGAACTGATTGGCCGGGCCCGCGTCTCTCCAGGGGCGGGATGGAGCATCCGGGAGACTGCTTGCCTAGCAAAATCAT
ATGCGCAAATGTGGCAGCTCCTTTATTTCCACAGAAGGGACCTCCGACTGATGGCCAATGCCATTTGTTCATCTGTGCCAG
TTGACTGGGTTCCAACTGGGAGAACTACCTGGTCAATCCATGGAAAGGGAGAATGGATGACCACTGAAGACATGCTTGT
GGTGTGGAACAGAGTGTGGATTGAGGAGAACGACCACATGGAAGACAAGACCCCAGTTACGAAATGGACAGACATTCCC
TATTTGGGAAAAAGGGAAGACTTGTGGTGTGGATCTCTCATAGGGCACAGACCGCGCACCACCTGGGCTGAGAACATTA
AAAACACAGTCAACATGGTGCGCAGGATCATAGGTGATGAAGAAAAGTACATGGACTACCTATCCACCCAAGTTCGCTAC
TTGGGTGAAGAAGGGTCTACACCTGGAGTGCTGTAAGCACCAATCTTAATGTTGTCAGGCCTGCTAGTCAGCCACAGCTT
GGGGAAAGCTGTGCAGCCTGTGACCCCCCCAGGAGAAGCTGGGAAACCAAGCCTATAGTCAGGCCGAGAACGCCATGG
CACGGAAGAAGCCATGCTGCCTGTGAGCCCCTCAGAGGACACTGAGTCAAAAAACCCCACGCGCTTGGAGGCGCAGGAT
GGGAAAAGAAGGTGGCGACCTTCCCCACCCTTCAATCTGGGGCCTGAACTGGAGATCAGCTGTGGATCTCCAGAAGAGG
GACTAGTGGTTAGAGGAGA

KU527068.1 Zika virus strain Natal RGN, Brazil: Rio Grande do Norte, Natal,
complete genome
                                                                SEQ ID NO: 6
AGTTGTTGATCTGTGTGAATCAGACTGCGACAGTTCGAGTTTGAAGCGAAAGCTAGCAACAGTATCAACAGGTTTTATTTT
GGATTTGGAAACGAGAGTTTCTGGTCATGAAAAACCCAAAAAAGAAATCCGGAGGATTCCGGATTGTCAATATGCTAAAA
CGCGGAGTAGCCCCGTGTGAGCCCCTTTGGGGGCTTGAAGAGGCTGCCAGCCGGACTTCTGCTGGGTCATGGGCCCATCA
GGATGGTCTTGGCAATTCTAGCCTTTTTGAGATTCACGGCAATCAAGCCATCACTGGGTCTCATCAATAGATGGGGTTCAG
TGGGGAAAAAAGAGGCTATGGAAATAATAAAGAAGTTCAAGAAAGATCTGGCTGCCATGCTGAGAATAATCAATGCTAG
GAAGGAGAAGAAGAGACGAGGCGCAGATACTAGTGTCGGAATTGTTGGCCTCCTGCTGACCACAGCTATGGCAGCGGA
GGTCACTAGACGTGGGAGTGCATACTATATGTACTTGGACAGAAACGATGCTGGGGAGGCCATATCTTTTCCAACCACAT
TGGGGATGAATAAGTGTTATATACAGATCATGGATCTTGGACACATGTGTGATGCCACCATGAGCTATGAATGCCCTATG
CTGGATGAGGGGGTGGAACCAGATGACGTCGATTGTTGGTGCAACACGACGTCAACTTGGGTTGTGTACGGAACCTGCC
ATCACAAAAAAGGTGAAGCACGGAGATCTAGAAGAGCTGTGACGCTCCCCTCCCATTCCACTAGGAAGCTGCAAACGCG
GTCGCAAACCTGGTTGGAATCAAGAGAATACACAAAGCACTTGATTAGAGTCGAAAATTGGATATTCAGGAACCCTGGCT
TCGCGTTAGCAGCAGCTGCCATCGCTTGGCTTTTGGGAAGCTCAACGAGCCAAAAAGTCATATACTTGGTCATGATACTGC
TGATTGCCCCGGCATACAGCATCAGGTGCATAGGAGTCAGCAATAGGGACTTTGTGGAAGGTATGTCAGGTGGGACTTG
GGTTGATGTTGTCTTGGAACATGGAGGTTGTGTCACCGTAATGGCACAGGACAAACCGACTGTCGACATAGAGCTGGTTA
CAACAACAGTCAGCAACATGGCGGAGGTAAGATCCTACTGCTATGAGGCATCAATATCAGACATGGCTTCGGACAGCCGC
TGCCCAACACAAGGTGAAGCCTACCTTGACAAGCAATCAGACACTCAATATGTCTGCAAAAGAACGTTAGTGGACAGAGG
CTGGGGAAATGGATGTGGACTTTTTGGCAAAGGGAGCCTGGTGACATGCGCTAAGTTTGCATGCTCCAAGAAAATGACC
```

-continued

GGGAAGAGCATCCAGCCAGAGAATCTGGAGTACCGGATAATGCTGTCAGTTCATGGCTCCCAGCACAGTGGGATGATCG
TTAATGACACAGGACATGAAACTGATGAGAATAGAGCGAAGGTTGAGATAACGCCCAATTCACCAAGAGCCGAAGCCAC
CCTGGGGGGTTTTGGAAGCCTAGGACTTGATTGTGAACCGAGGACAGGCCTTGACTTTTCAGATTTGTATTACTTGACTAT
GAATAACAAGCACTGGTTGGTCCACAAGGAGTGGTTCCACGACATTCCATTACCTTGGCACGCTGGGGCAGACACCGGAA
CTCCACACTGGAACAACAAAGAAGCACTGGTAGAGTTCAAGGACGCACATGCCAAAAGGCAAACTGTCGTGGTTCTAGG
GAGTCAAGAAGGAGCAGTTCACACGGCCCTTGCTGGAGCTCTGGAGGCTGAGATGGATGGTGCAAAGGGAAGGCTGTC
CTCTGGCCACTTGAAATGTCGCCTGAAAATGGATAAACTTAGATTGAAGGGCGTGTCATACTCCTTGTGTACCGCAGCGTT
CACATTCACCAAGATCCCGGCTGAAACACTGCACGGGACAGTCACAGTGGAGGTACAGTACGCAGGGACAGATGGACCT
TGCAAGGTTCCAGCTCAGATGGCGGTGGACATGCAAACTCTGACCCCAGTTGGGAGGTTGATAACCGCTAACCCCGTAAT
CACTGAAAGCACTGAGAACTCTAAGATGATGCTGGAACTTGATCCACCATTTGGGGACTCTTACATTGTCATAGGAGTCG
GGGAGAAGAAGATCACCCACCACTGGCACAGGAGTGGCAGCACCATTGGAAAAGCATTTGAAGCCACTGTGAGAGGTG
CCAAGAGAATGGCAGTCTTGGGAGACACAGCCTGGGACTTTGGATCAGTTGGAGGCGCTCTCAACTCATTGGGCAAGGG
CATCCATCAAATTTTTGGAGCAGCTTTCAAATCATTGTTTGGAGGAATGTCCTGGTTCTCACAAATCCTCATTGGAACGTTG
CTGATGTGGTTGGGTCTGAACACAAAGAATGGATCTATTTCCCTTATGTGCTTGGCCTTAGGGGAGTGTTGATCTTCTTA
TCCACAGCCGTCTCTGCTGATGTGGGGTGCTCGGTGGACTTCTCAAAGAAGGAGACGAGATGCGGTACAGGGGTGTTCG
TCTATAACGACGTTGAAGCCTGGAGGGACAGGTACAAGTACCATCCTGACTCCCCCCGTAGATTGGCAGCAGCAGTCAAG
CAAGCCTGGGAAGATGGTATCTGCGGGATCTCCTCTGTTTCAAGAATGGAGAACATCATGTGGAGATCAGTAGAAGGGG
AGCTCAACGCAATCTTGGAAGAGAATGGAGTTCAACTGACGGTCGTTGTGGGATCTGTAAAAAACCCCATGTGGAGAGG
TCCACAGAGATTGCCCGTGCCTGTGAACGAGCTGCCCCACGGCTGGAAGGCTTGGGGGAAATCGTACTTCGTCAGAGCA
GCAAAGACAAATAACAGCTTTGTCGTGGATGGTGACACACTGAAGGAATGCCCACTCGAACATAGAGCATGGAACAGCT
TTCTTGTGGAGGATCATGGGTTCGGGGTATTTCACACTAGTGTCTGGCTCAAGGTTAGAGAAGATTATTCATTAGAGTGT
GATCCAGCCGTTATTGGAACAGCTGTTAAGGGGAAGGAGGCTGTACACAGTGATCTAGGCTACTGGATTGAGAGTGAGA
AGAATGACACATGGAGGCTGAAGAGGGCCCATCTAATCGAGATGAAAACATGTGAATGGCCAAAGTCCCACACATTGTG
GGCAGATGGAATAGAAGAGAGTGATCTGATCATTCCCAAGTCTTTAGCTGGGCCACTCAGCCATCACAATACCAGAGAGG
GCTACAGGACCCAAATGAAAGGGCCATGGCACAGTGAAGAGCTTGAAATTCGGTTTGAGGAATGCCCGGGCACTAAGGT
CCACGTGGAGGAAACATGTGGAACAAGAGGACCATCTCTGAGATCAACCACTGCAAGCGGAAGGGTGATCGAGGAATG
GTGCTGCAGGGAGTGCACAATGCCCCCACTGTCGTTCCGGGCTAAAGATGGCTGTTGGTATGGAATGGAGATAAGGCCC
AGGAAAGAACCAGAAAGCAACTTAGTAAGGTCAGTGGTGACTGCAGGATCAACTGATCACATGGATCACTTCTCCCTTGG
AGTGCTTGTGATTCTGCTCATGGTGCAGGAAGGGCTGAAGAAGAGAATGACCACAAAGATCATCATAAGCACATCAATG
GCAGTGCTGGTAGCTATGATCCTGGGAGGATTTTCAATGAGTGACCTGGCTAAGCTTGCAATTTTGATGGGCGCCACCTT
CGCGGAAATGAACACTGGAGGAGATGTAGCTCATCTGGCGCTGATAGCGGCATTCAAAGTCAGACCAGCGTTGCTGGTA
TCTTTCATCTTCAGAGCTAATTGGACACCCCGTGAAAGCATGCTGCTGGCCTTGGCCTCGTGTCTTTTGCAAACTGCGATCT
CCGCCTTGGAAGGCGACCTGATGGTTCTCATCAATGGTTTTGCTTTGGCCTGGTTGGCAATACGAGCGATGGTTGTTCCAC
GCACTGATAACATCACCTTGGCAATCCTGGCTGCTCTGACACCACTGGCCCGGGGCACACTGCTTGTGGCGTGGAGAGCA
GGCCTTGCTACTTGCGGGGGGTTTATGCTCCTCTCTCTGAAGGGAAAAGGCAGTGTGAAGAAGAACTTACCATTTGTCAT
GGCCCTGGGACTAACCGCTGTGAGGCTGGTCGACCCCATCAACGTGGTGGGACTGCTGTTGCTCACAAGGAGTGGGAAG
CGGAGCTGGCCCCCTAGCGAAGTACTCACAGCTGTTGGCCTGATATGCGCATTGGCTGGAGGGTTCGCCAAGGCAGATAT
AGAGATGGCTGGGCCCATGGCCGCGGTCGGTCTGCTAATTGTCAGTTACGTGGTCTCAGGAAAGAGTGTGGACATGTAC
ATTGAAAGAGCAGGTGACATCACATGGGAAAAAGATGCGGAAGTCACTGGAAACAGTCCCCGGCTCGATGTGGCGCTAG
ATGAGAGTGGTGATTTCTCCCTGGTGGAGGATGACGGTCCCCCCATGAGAGAGATCATACTCAAGGTGGTCCTGATGACC
ATCTGTGGCATGAACCCAATAGCCATACCCTTTGCAGCTGGAGCGTGGTACGTATACGTGAAGACTGGAAAAAGGAGTG

-continued

```
GTGCTCTATGGGATGTGCCTGCTCCCAAGGAAGTAAAAAAGGGGGAGACCACAGATGGAGTGTACAGAGTAATGACTCG

TAGACTGCTAGGTTCAACACAAGTTGGAGTGGGAGTTATGCAAGAGGGGGTCTTTCACACTATGTGGCACGTCACAAAA

GGATCCGCGCTGAGAAGCGGTGAAGGGAGACTTGATCCATACTGGGGAGATGTCAAGCAGGATCGGTGTCATACTGTG

GTCCATGGAAGCTAGATGCCGCCTGGGACGGGCACAGCGAGGTGCAGCTCTTGGCCGTGCCCCCCGGAGAGAGAGCGA

GGAACATCCAGACTCTGCCCGGAATATTTAAGACAAAGGATGGGGACATTGGAGCGGTTGCGCTGGATTACCCAGCAGG

AACTTCAGGATCTCCAATCCTAGACAAGTGTGGGAGAGTGATAGGACTTTATGGCAATGGGGTCGTGATCAAAAATGGG

AGTTATGTTAGTGCCATCACCCAAGGGAGGAGGGAGGAAGAGACTCCTGTTGAGTGCTTCGAGCCTTCGATGCTGAAGA

AGAAGCAGCTAACTGTCTTAGACTTGCATCCTGGAGCTGGGAAAACCAGGAGAGTTCTTCCTGAAATAGTCCGTGAAGCC

ATAAAAACAAGACTCCGTACTGTGATCTTAGCTCCAACCAGGGTTGTCGCTGCTGAAATGGAGGAAGCCCTTAGAGGGCT

TCCAGTGCGTTATATGACAACAGCAGTCAATGTCACCCACTCTGGAACAGAAATCGTCGACTTAATGTGCCATGCCACCTT

CACTTCACGTCTACTACAGCCAATCAGAGTCCCCAACTATAATCTGTATATTATGGATGAGGCCCACTTCACAGATCCCTCA

AGTATAGCAGCAAGAGGATACATTTCAACAAGGGTTGAGATGGGCGAGGCGGCTGCCATCTTCATGACCGCCACGCCAC

CAGGAACCCGTGACGCATTTCCGGACTCCAACTCACCAATTATGGACACCGAAGTGGAAGTCCCAGAGAGAGCCTGGAG

CTCAGGCTTTGATTGGGTGACGGATCATTCTGGAAAAACAGTTTGGTTTGTTCCAAGCGTGAGGAACGGCAATGAGATCG

CAGCTTGTCTGACAAAGGCTGGAAAACGGGTCATACAGCTCAGCAGAAAGACTTTTGAGACAGAGTTCCAGAAAACAAA

ACATCAAGAGTGGGACTTTGTCGTGACAACTGACATTTCAGAGATGGGCGCCAACTTTAAAGCTGACCGTGTCATAGATT

CCAGGAGATGCCTAAAGCCGGTCATACTTGATGGCGAGAGAGTCATTTTGGCTGGACCCATGCCTGTCACACATGCCAGC

GCTGCCCAGAGGAGGGGCGCATAGGCAGGAATCCCAACAAACCTGGAGATGAGTATCTGTATGGAGGTGGGTGCGCA

GAGACTGACGAAGACCATGCACACTGGCTTGAAGCAAGAATGCTCCTTGACAATATTTACCTCCAAGATGGCCTCATAGC

CTCGCTCTATCGACCTGAGGCCGACAAAGTAGCAGCCATTGAGGGAGAGTTCAAGCTTAGGACGGAGCAAAGGAAGACC

TTTGTGGAACTCATGAAAAGAGGAGATCTTCCTGTTTGGCTGGCCTATCAGGTTGCATCTGCCGGAATAACCTACACAGAT

AGAAGATGGTGCTTTGATGGCACGACCAACAACACCATAATGGAAGACAGTGTGCCGGCAGAGGTGTGGACCAGACAC

GGAGAGAAAAGAGTGCTCAAACCGAGGTGGATGGACGCCAGAGTTTGTTCAGATCATGCGGCCCTGAAGTCATTCAAGG

AGTTTGCCGCTGGGAAAAGAGGAGCGGCTTTTGGAGTGATGGAAGCCCTGGGAACACTGCCAGGACACATGACAGAGA

GATTCCAGGAAGCCATTGACAACCTCGCTGTGCTCATGCGGGCAGAGACTGGAAGCAGGCCTTACAAAGCCGCGGCGGC

CCAATTGCCGGAGACCCTAGAGACCATTATGCTTTTGGGGTTGCTGGGAACAGTCTCGCTGGGAATCTTTTTCGTCTTGAT

GAGGAACAAGGGCATAGGGAAGATGGGCTTTGGAATGGTGACTCTTGGGGCCAGCGCATGGCTCATGTGGCTCTCGGA

AATTGAGCCAGCCAGAATTGCATGTGTCCTCATTGTTGTGTTCCTATTGCTGGTGGTGCTCATACCTGAGCCAGAAAAGCA

AAGATCTCCCCAGGACAACCAAATGGCAATCATCATCATGGTAGCAGTAGGTCTTCTGGGCTTGATTACCGCCAATGAACT

CGGATGGTTGGAGAGAACAAAGAGTGACCTAAGCCATCTAATGGGAAGGAGAGAGGAGGGAGCAACCATAGGATTCTC

AATGGACATTGACCTGCGGCCAGCCTCAGCTTGGGCCATCTATGCTGCCTTGACAACTTTCATTACCCCAGCCGTCCAACA

TGCAGTGACCACTTCATACAACAACTACTCCTTAATGGCGATGGCCACGCAAGCTGGAGTGTTGTTTGGTATGGGCAAAG

GGATGCCATTCTACGCATGGGACTTTGGAGTCCCGCTGCTAATGATAGGTTGCTACTCACAATTAACACCCCTGACCCTAA

TAGTGGCCATCATTTTGCTCGTGGCGCACTACATGTACTTGATCCCAGGGCTGCAGGCAGCAGCTGCGCGTGCTGCCCAG

AAGAGAACGGCAGCTGGCATCATGAAGAACCCTGTTGTGGATGGAATAGTGGTGACTGACATTGACACAATGACAATTG

ACCCCCAAGTGGAGAAAAAGATGGGACAGGTGCTACTCATAGCAGTAGCAGTCTCCAGCGCCATACTGTCGCGGACCGC

CTGGGGGTGGGGGGAGGCTGGGGCCCTGATCACAGCCGCAACTTCCACTTTGTGGGAAGGCTCTCCGAACAAGTACTGG

AACTCCTCTACAGCCACTTCACTGTGTAACATTTTTAGGGGAAGTTACTTGGCTGGAGCTTCTCTAATCTACATAGTAACAA

GAAACGCTGGCTTGGTCAAGAGACGTGGGGGTGGAACAGGAGAGACCCTGGGAGAGAAATGGAAGGCCCGCTTGAAC

CAGATGTCGGCCCTGGAGTTCTACTCCTACAAAAAGTCAGGCATCACCGAGGTGTGCAGAGAAGAGGCCCGCCGCGCCC
```

-continued

```
TCAAGGATGGTGTGGCAACGGGAGGCCATGCTGTGTCCCGAGGAAGTGCAAAGCTGAGATGGTTGGTGGAGCGGGAT
ACCTGCAGCCCTATGGAAAGGTCATTGATCTTGGATGTGGCAGAGGGGGCTGGAGTTACTACGCCGCCACCATCCGCAAA
GTTCAAGAAGTGAAAGGATACACAAAAGGAGGCCCTGGTCATGAAGAACCCGTGTTGGTGCAAAGCTATGGGTGGAAC
ATAGTCCGTCTTAAGAGTGGGGTGGACGTCTTTCATATGGCGGCTGAGCCGTGTGACACGTTGCTGTGTGACATAGGTGA
GTCATCATCTAGTCCTGAAGTGGAAGAAGCACGGACGCTCAGAGTCCTCTCCATGGTGGGGGATTGGCTTGAAAAAAGA
CCAGGAGCCTTTTGTATAAAAGTGTTGTGCCCATACACCAGCACTATGATGGAAACCCTGGAGCGACTGCAGCGTAGGTA
TGGGGGAGGACTGGTCAGAGTGCCACTCTCCCGCAACTCTACACATGAGATGTACTGGGTCTCTGGAGCGAAAAGCAAC
ACCATAAAAAGTGTGTCCACCACGAGCCAGCTCCTCTTGGGGCGCATGGACGGGCCTAGGAGGCCAGTGAAATATGAGG
AGGATGTGAATCTCGGCTCTGGCACGCGGGCTGTGGTAAGCTGCGCTGAAGCTCCCAACATGAAGATCATTGGTAACCGC
ATTGAAAGGATCCGCAGTGAGCACGCGGAAACGTGGTTCTTTGACGAGAACCACCCATATAGGACATGGGCTTACCATG
GAAGCTATGAGGCCCCCACACAAGGGTCAGCGTCCTCTCTAATAAACGGGGTTGTCAGGCTCCTGTCAAAACCCTGGGAT
GTGGTGACTGGAGTCACAGGAATAGCCATGACCGACACCACACCGTATGGTCAGCAAAGAGTTTTCAAGGAAAAAGTGG
ACACTAGGGTGCCAGACCCCCAAGAAGGCACTCGTCAGGTTATGAGCATGGTCTCTTCCTGGTTGTGGAAAGAGCTAGGC
AAACACAAACGGCCACGAGTCTGTACCAAAGAAGAGTTCATCAACAAGGTTCGTAGCAATGCAGCATTAGGGGCAATATT
TGAAGAGGAAAAAGAGTGGAAGACTGCAGTGGAAGCTGTGAACGATCCAAGGTTCTGGGCTCTAGTGGACAAGGAAAG
AGAGCACCACCTGAGAGGAGAGTGCCAGAGTTGTGTGTACAACATGATGGGAAAAAGAGAAAAGAAACAAGGGGAATT
TGGAAAGGCCAAGGGCAGCCGCGCCATCTGGTATATGTGGCTAGGGGCTAGATTTCTAGAGTTCGAAGCCCTTGGATTCT
TGAACGAGGATCACTGGATGGGGAGAGAGAACTCAGGAGGTGGTGTTGAAGGGCTGGGATTACAAAGACTCGGATATG
TCCTAGAAGAGATGAGTCGCATACCAGGAGGAAGGATGTATGCAGATGACACTGCTGGCTGGGACACCCGCATCAGCAG
GTTCGATCTGGAGAATGAAGCTCTAATCACCAACCAAATGGAGAAAGGGCATAGGGCCTTGGCATTGGCCATAATCAAGT
ACACATACCAAAACAAAGTGGTAAAGGTCCTTAGACCAGCTGAAAAAGGGAAAACAGTTATGGACATTATTTCGAGACAA
GACCAAAGGGGGAGCGGACAAGTTGTCACTTACGCTCTTAACACATTTACCAACCTAGTGGTGCAACTCATTCGGAATAT
GGAGGCTGAGGAAGTTCTAGAGATGCAAGACTTGTGGCTGCTGCGGAGGTCAGAGAAAGTGACCAACTGGTTGCAGAG
CAACGGATGGGATAGGCTCAAACGAATGGCAGTCAGTGGAGATGATTGCGTTGTGAAGCCAATTGATGATAGGTTTGCA
CATGCCCTCAGGTTCTTGAATGATATGGGAAAAGTTAGGAAGGACACACAAGAGTGGAAACCCTCAACTGGATGGGACA
ACTGGGAAGAAGTTCCGTTTTGCTCCCACCACTTCAACAAGCTCCATCTCAAGGACGGGAGGTCCATTGTGGTTCCCTGCC
GCCACCAAGATGAACTGATTGGCCGGGCCCGCGTCTCTCCAGGGGCGGGATGGAGCATCCGGGAGACTGCTTGCCTAGC
AAAATCATATGCGCAAATGTGGCAGCTCCTTTATTTCCACAGAAGGGACCTCCGACTGATGGCCAATGCCATTTGTTCATC
TGTGCCAGTTGACTGGGTTCCAACTGGGAGAACTACCTGGTCAATCCATGGAAAGGGAGAATGGATGACCACTGAAGAC
ATGCTTGTGGTGTGGAACAGAGTGTGGATTGAGGAGAACGACCACATGGAAGACAAGACCCCAGTTACGAAATGGACA
GACATTCCCTATTTGGGAAAAAGGGAAGACTTGTGGTGTGGATCTCTCATAGGGCACAGACCGCGCACCACCTGGGCTGA
GAACATTAAAAACACAGTCAACATGGTGCGCAGGATCATAGGTGATGAAGAAAGTACATGGACTACCTATCCACCCAAG
TTCGCTACTTGGGTGAAGAAGGGTCTACACCTGGAGTGCTGTAAGCACCAATCTTAATGTTGTCAGGCCTGCTAGTCAGC
CACAGCTTGGGGAAAGCTGTGCAGCCTGTGACCCCCCAGGAGAAGCTGGGAAACCAAGCCTATAGTCAGGCCGAGAAC
GCCATGGCACGGAAGAAGCCATGCTGCCTGTGAGCCCCTCAGAGGACACTGAGTCAAAAAACCCCATGCGCTTGGAGGC
GCAGGATGGGAAAAGAAGGTGGCGACCTTCCCCACCCTTCAATCTGGGGCCTGAACTGGAGATCAGCTGTGGATCTCCA
GAAGAGGGACTAGTGGTTAGAGGAGACCCCCCGGAAAACGCAAAACAGCATATTGACGCTGGGAAAGACCAGAGACTC
CATGAGTTTCCACCACGCTGGCCGCCAGGCACAGATCGCCGAATAGCGGCGGCCGGTGTGGGGAAATCCATGGGTCTT
```

KU681081.3 Zika virus isolate Zika virus/*H.sapiens*-tc/THA/2014/SV0127-14, Thailand, complete genome

SEQ ID NO: 7

AGTTGTTGATCTGTGTGAATCAGACTGCGACAGTTCGAGTTTGAAGCGAAAGCTAGCAACAGTATCAACAGGTTTTATTTT

GGATTTGGAAACGAGAGTTTCTGGTCATGAAAAACCCAAAAAAGAAATCCGGAGGATTCCGGATTGTCAATATGCTAAAA

CGCGGAGTAGCCCGTGTGAGCCCCTTTGGGGGCTTGAAGAGGCTGCCAGCCGGACTTCTGCTGGGTCATGGGCCCATCA

GGATGGTCTTGGCGATTCTAGCCTTTTTGAGATTCACGGCAATCAAGCCATCACTGGGTCTCATCAATAGATGGGGTTCAG

TGGGAAAAAAAGAGGCTATGGAAATAATAAAGAAGTTCAAGAAAGATCTGGCTGCCATGCTGAGAATAATCAATGCTAG

GAAGGAGAAGAAGAGACGAGGCACAGATACTAGTGTCGGAATTGTTGGCCTCCTGCTGACCACAGCTATGGCAGCGGA

GGTCACTAGACGTGGGAGTGCATACTATATGTACTTGGACAGAAGCGATGCTGGGGAGGCCATATCTTTTCCAACCACAC

TGGGGATGAATAAGTGTTATATACAGATCATGGATCTTGGACACATGTGTGATGCCACCATGAGCTATGAATGCCCTATG

CTGGATGAGGGGGTAGAACCAGATGACGTCGATTGTTGGTGCAACACGACGTCAACTTGGGTTGTGTACGGAACCTGCC

ATCACAAAAAAGGTGAAGCACGGAGATCCAGAAGAGCTGTGACGCTCCCCTCCCATTCCACTAGGAAGCTGCAAACGCG

GTCGCAGACCTGGTTGGAATCAAGAGAATACACAAAGCACTTGATTAGAGTCGAAAATTGGATATTCAGGAACCCTGGCT

TCGCGTTAGCAGCAGCTGCCATCGCTTGGCTTTTGGGAAGCTCAACGAGCCAAAAAGTCATATACTTGGTCATGATACTGC

TGATTGCCCCGGCATACAGCATCAGGTGCATAGGAGTCAGTAATAGGGACTTTGTGGAAGGTATGTCAGGTGGGACTTG

GGTTGATGTTGTCTTGGAACATGGAGGTTGTGTCACCGTAATGGCACAGGACAAACCGACTGTCGACATAGAGCTGGTTA

CAACAACAGTCAGCAACATGGCGGAGGTAAGATCCTACTGCTATGAGGCATCAATATCGGACATGGCTTCGGACAGCCG

CTGCCCAACACAAGGTGAAGCCTACCTTGACAAGCAATCAGACACTCAATATGTCTGCAAAAGAACGTTAGTGGACAGAG

GCTGGGGAAATGGATGTGGACTTTTTGGCAAAGGGAGCCTGGTGACATGCGCTAAGTTTGCATGCTCCAAGAAAATGAC

CGGGAAGAGCATCCAGCCAGAGAATCTGGAGTACCGGATAATGCTGTCAGTTCATGGCTCCCAGCACAGTGGGATGATC

GTTAATGACACAGGACATGAAACTGATGAGAATAGAGCGAAGGTTGAGATAACGCCCAATTCACCAAGAGCCGAAGCCA

CCCTGGGGGGTTTTGGAAGCCTAGGACTTGATTGTGAACCGAGGACAGGCCTTGACTTTTCAGATTTGTATTACTTGACTA

TGAACAACAAGCACTGGTTGGTTCACAAGGAGTGGTTCCACGACATTCCATTACCTTGGCACACTGGGGCAGACACCGGA

ACTCCACACTGGAACAACAAAGAAGCACTGGTAGAGTTCAAGGACGCACATGCCAAAAGGCAAACTGTCGTGGTTCTAG

GGAGTCAAGAAGGAGCAGTTCACACGGCCCTTGCTGGAGCTCTGGAGGCTGAGATGGATGGTGCAAAGGGAAGGCTGT

CCTCTGGCCACTTGAAATGTCGCCTGAAAATGGATAAACTTAGATTGAAGGGCGTGTCATACTCCTTGTGTACCGCAGCGT

TCACATTCACCAAGATCCCGGCTGAAACACTGCACGGGACAGTCACAGTGGAGGTACAGTACGCAGGGACAGATGGACC

TTGCAAGGTTCCAGCTCAGATGGCGGTGGACATGCAAACTCTGACCCCAGTTGGGAGGTTGATAACCGCTAACCCCGTAA

TCACTGAAGGCACTGAGAACTCTAAGATGATGCTGGAACTTGATCCACCATTTGGGGACTCTTACATTGTCATAGGAGTCG

GGGAGAAGAAGATCACCCACCACTGGCACAGGAGTGGCAGCACCATTGGAAAAGCATTTGAAGCCACTGTGAGAGGTG

CCAAGAGAATGGCAGTCTTGGGAGACACAGCCTGGGACTTTGGATCAGTTGGAGGCGTTCTTAACTCATTGGGCAAGGG

CATCCATCAAATTTTTGGAGCAGCTTTCAAATCATTGTTTGGAGGAATGTCCTGGTTCTCACAAATTCTCATTGGAACGTTG

CTGATGTGGTTGGGTCTGAATACAAAGAATGGATCTATTTCCCTTATGTGCTTGGCCTTAGGGGGAGTGTTGATCTTCTTA

TCCACAGCCGTCTCCGCTGATGTGGGGTGCTCGGTGGACTTCTCAAAGAAGGAAACGAGATGCGGTACAGGGGTGTTCG

TCTATAACGACGTTGAAGCCTGGAGGGACAGGTACAAGTACCATCCTGACTCCCCTCGTAGATTGGCAGCAGTAGTCAAG

CAAGCCTGGGAAGATGGTATCTGTGGGATCTCCTCTGTTTCAAGAATGGAAAACATCATGTGGAGATCAGTAGAAGGGG

AGCTCAACGCAATCCTGGAAGAGAATGGAGTTCAACTGACGGTCGTTGTGGGATCTGTAAAAAACCCCATGTGGAGAGG

TCCACAGAGATTGCCCGTGCCTGTGAACGAGCTGCCCCACGGCTGGAAGGCTTGGGGGAAATCGTACTTCGTCAGAGCA

GCAAAGACAAATAACAGCTTTGTCGTGGATGGTGACACACTGAAGGAATGCCCACTCAAACATAGAGCATGGAACAGCTT

TCTTGTGGAGGATCATGGGTTCGGGGTATTTCACACTAGTGTCTGGCTCAAGGTTAGAGAAGATTATTCACTAGAGTGTG

ATCCAGCCGTCATTGGAACAGCTGTTAAGGGAAAGGAGGCTGTACACAGTGATCTAGGCTACTGGATTGAGAGTGAGAA

```
GAACGACACATGGAGGCTGAGGAGGGCCCACCTGATCGAGATGAAAACATGTGAATGGCCAAAGTCCCACACATTGTGG

ACAGATGGAATAGAAGAGAGTGATCTGATCATACCCAAGTCTTTAGCTGGGCCACTCAGCCATCACAACACCAGAGAGG

GCTACAGGACCCAAATGAAAGGGCCATGGCACAGTGAAGAGCTTGAAATTCGGTTTGAGGAATGCCCAGGCACTAAGGT

CCACGTGGAGGAAACATGTGGAACAAGAGGACCATCTCTGAGATCAACCACTGCAAGCGGAAGGGTGATCGAGGAATG

GTGCTGCAGGGAGTGCACAATGCCCCCACTGTCGTTCCGGGCTAAAGATGGCTGTTGGTATGGAATGGAGATAAGGCCC

AGGAAAGAACCAGAAAGTAACTTAGTAAGGTCAATGGTGACTGCAGGATCAACTGATCACATGGATCACTTTTCCCTTGG

AGTGCTTGTGATTCTGCTCATGGTGCAGGAAGGGCTGAAGAAGAGAATGACCACAAAGATCATCATAAGCACATCAATG

GCAGTGCTGGTAGCTATGATCCTGGGAGGATTTTCAATGAGTGATCTGGCTAAGCTTGCAATTTTGATGGGTGCCACCTTT

GCGGAAATGAACACTGGAGGAGATGTAGCTCATCTGGCGCTGGTAGCGGCATTCAAAGTCAGACCAGCGTTGCTGGTAT

CTTTCATCTTCAGAGCTAATTGGACACCCCGTGAAAGCATGCTGCTGGCCTTGGCCTCGTGTCTTTTGCAAACTGCGATCTC

CGCCTTGGAAGGCGACCTGATGGTTCTCATCAATGGTTTTGCTTTGGCCTGGTTGGCAATACGAGCGATGGTTGTTCCACG

CACTGACAATATCACCTTGGCAATCCTGGCTGCTCTGACACCACTGGCCCGGGGCACACTGCTTGTGGCGTGGAGAGCAG

GCCTTGCTACTTGCGGGGGGTTCATGCTCCTCTCTCTGAAGGGGAAAGGCAGTGTGAAGAAGAACTTACCATTTGTCATG

GCCCTGGGACTAACCGCTGTGAGGCTGGTCGACCCCATCAACGTGGTGGGACTGCTGTTGCTCACAAGGAGTGGGAAGC

GGAGCTGGCCCCCTAGCGAAGTACTCACAGCTGTTGGCCTGATATGCGCATTGGCTGGAGGGTTCGCCAAGGCAGATAT

AGAGATGGCTGGGCCCATGGCCGCGGTCGGTCTGCTAATTGTCAGTTACGTGGTCTCAGGAAAGAGTGTGGACATGTAC

ATTGAAAGAGCAGGTGACATCACATGGGAAAAAGATGCGGAAGTTACTGGAAACAGTCCCCGGCTCGATGTGGCACTAG

ATGAGAGTGGTGATTTCTCCCTGGTGGAGGATGACGGTCCCCCCATGAGAGAGATCATACTCAAAGTGGTCCTGATGACC

ATCTGTGGCATGAACCCAATAGCCATACCCTTTGCAGCTGGAGCGTGGTACGTATACGTGAAAACTGGAAAAAGGAGTG

GTGCTCTATGGGATGTGCCTGCTCCCAAGGAAGTAAAAAAGGGGGAGACCACAGATGGAGTGTACAGAGTAATGACTCG

TAGACTGCTAGGTTCAACACAAGTTGGAGTGGGAGTTATGCAAGAGGGGTCTTTCACACTATGTGGCATGTCACAAAAG

GATCCGCGCTGAGAAGCGGTGAAGGGAGACTTGATCCATACTGGGGAGATGTCAAGCAGGATCTGGTGTCATACTGTGG

TCCATGGAAGCTAGATGCCGCTGGGACGGGCACAGCGAGGTGCAGCTCTTGGCCGTGCCCCCCGGAGAGAGAGCGAG

GAACATCCAGACTCTGCCCGGAATATTTAAGACAAAGGATGGGGACATTGGAGCGGTTGCGCTGGACTATCCAGCAGGA

ACTTCAGGATCTCCAATCCTAGACAAGTGTGGGAGAGTGATAGGACTCTATGGCAATGGGGTCGTGATCAAGAATGGGA

GTTATGTCAGTGCCATCACCCAAGGGAGGAGGGAGGAAGAGACTCCTGTTGAGTGCTTCGAGCCTTCGATGCTGAAGAA

GAAGCAGCTAACTGTCTTAGACTTGCATCCTGGAGCTGGGAAAACCAGGAGAGTTCTTCCTGAAATAGTCCGTGAAGCCA

TAAAAACGAGACTCCGTACTGTGATCTTAGCTCCAACCAGGGTTGTCGCTGCTGAAATGGAGGAAGCCCTTAGAGGGCTT

CCAGTGCGTTATATGACAACAGCAGTCAATGTCACCCATTCTGGGACAGAAATCGTTGACTTAATGTGCCATGCCACCTTC

ACTTCACGTCTACTACAGCCAATCAGAGTCCCCAACTATAATCTGTATATTATGGATGAGGCCCACTTCACAGATCCCTCAA

GTATAGCAGCAAGAGGATACATTTCAACAAGGGTTGAGATGGGCGAGGCAGCTGCCATCTTCATGACCGCCACGCCACC

AGGAACCCGTGACGCATTCCCGGACTCCAACTCACCAATTATGGACACCGAAGTGGAAGTCCCAGAGAGAGCCTGGAGC

TCAGGCTTTGATTGGGTGACGGATCATTCTGGAAAAACAGTTTGGTTTGTCCCAAGCGTGAGGAACGGCAATGAGATCGC

AGCTTGTCTGACAAAGGCTGGAAAACGGGTCATACAGCTCAGCAGAAAGACTTTTGAGACAGAGTTCCAGAAAACAAAA

CATCAAGAGTGGGACTTCGTCGTGACAACTGACATTTCAGAGATGGGCGCCAACTTTAAAGCTGACCGTGTCATAGATTC

CAGGAGATGCCTAAAGCCGGTCATACTTGATGGCGAGAGAGTCATTCTGGCTGGACCCATGCCTGTCACACATGCCAGCG

CTGCCCAGAGGAGGGGGCGCATAGGCAGGAATCCCAACAAACCTGGAGATGAGTATCTGTATGGAGGTGGGTGCGCAG

AGACTGATGAAGACCATGCACACTGGCTTGAAGCAAGAATGCTCCTTGACAATATTTACCTCCAAGATGGCCTCATAGCCT

CGCTCTATCGACCTGAGGCCGACAAAGTAGCAGCCATTGAGGGAGAGTTCAAGCTTAGGACGGAGCAAAGGAAGACCTT

TGTGGAACTCATGAAAAGAGGAGATCTTCCTGTTTGGCTGGCCTATCAGGTTGCATCTGCCGGAATAACCTACACAGATA
```

-continued

GAAGATGGTGCTTTGATGGCATGACCAACAACACCATAATGGAAGACAGTGTGCCGGCAGAGGTGTGGACCAGACACG
GAGAGAAAAGAGTGCTCAAACCGAGGTGGATGGACGCCAGAGTTTGTTCAGATCATGCGGCCCTGAAGTCATTCAAGGA
GTTTGCCGCTGGGAAAAGAGGAGCGGCTTTTGGAGTGATGGAAGCCCTGGGAACACTGCCAGGACACATGACGGAGAG
ATTCCAGGAAGCCATTGACAACCTCGCTGTGCTCATGCGGGCAGAGACTGGAAGCAGGCCTTACAAAGCCGCGGCGGCC
CAATTGCCGGAGACCCTAGAGACCATTATGCTTTTGGGGTTGCTGGGAACAGTCTCGCTGGGAATCTTTTTCGTCTTGATG
CGGAACAAGGGCATAGGGAAGATGGGCTTTGGAATGGTGACTCTTGGGGCCAGCGCATGGCTCATGTGGCTCTCGGAAA
TTGAGCCAGCCAGAATTGCATGCGTCCTCATTGTTGTGTTCCTATTGCTGGTGGTGCTCATACCTGAGCCAGAAAAGCAAA
GATCCCCCCAGGACAACCAAATGGCAATCATCATCATGGTAGCAGTAGGTCTTCTGGGCTTGATTACCGCCAATGAACTCG
GATGGTTGGAGAGAACAAAGAGTGACCTAAGCCATCTAATGGGAAGGAGAGAGGAGGGGGCAACCATAGGATTCTCAA
TGGACATTGACCTGCGGCCAGCCTCGGCCTGGGCCATCTATGCTGCCCTGACAACTTTCATTACCCCAGCCGTCCAACATG
CAGTGACCACTTCATACAACAACTACTCCTTAATGGCGATGGCCACGCAAGCTGGAGTGTTGTTTGGTATGGGCAAAGGG
ATGCCATTCTACGCATGGGACTTTGGAGTCCCGCTGCTAATGATAGGTTGCTACTCACAATTAACACCCCTGACCCTAATA
GTGGCTATCATTTTGCTCGTGGCGCACTACATGTACTTGATCCCAGGGCTGCAGGCAGCAGCTGCGCGTGCTGCCCAGAA
GAGAACGGCAGCTGGCATCATGAAGAACCCTGTTGTGGATGGAATAGTGGTGACTGACATTGACACAATGACTATTGAC
CCCCAAGTGGAGAAAAAGATGGGACAGGTGCTACTCATAGCAGTAGCCGTCTCCAGCGCCATACTGTCGCGGACCGCCT
GGGGGTGGGGGGAAGCTGGGGCCCTGATCACAGCTGCAACTTCCACTTTGTGGGAAGGCTCTCCGAACAAGTACTGGAA
CTCCTCTACAGCCACTTCACTGTGCAACATTTTTAGGGGAAGTTACTTGGCTGGAGCTTCTCTAATCTACACAGTAACAAGA
AACGCTGGCTTGGTCAAGAGACGTGGGGGTGGAACAGGAGAGACCCTGGGAGAGAAATGGAAGGCCCGCTTGAACCA
GATGTCGGCCCTGGAGTTCTACTCCTACAAAAAGTCAGGCATCACCGAGGTGTGCAGAGAAGAGGCCCGCCGCGCCCTC
AAGGACGGTGTGGCAACGGGAGGCCATGCTGTGTCCCGAGGAAGTGCAAAGCTGAGATGGTTGGTGGAGCGGGGATAC
CTGCAGCCCTATGGAAAGGTCATTGATCTTGGATGTGGCAGAGGGGGCTGGAGTTACTACGCCGCCACCATCCGCAAAGT
TCAAGAAGTGAAAGGATACACAAAAGGAGGCCCTGGTCATGAAGAACCCATGTTGGTGCAAAGCTATGGGTGGAACATA
GTCCGTCTTAAGAGTGGGGTGGACGTCTTTCATATGGCGGCTGAGCCGTGTGACACGTTGCTGTGTGACATAGGTGAGTC
ATCATCTAGTCCTGAAGTGGAAGAAGCACGGACGCTCAGAGTCCTCTCCATGGTGGGGGATTGGCTTGAAAAAAGACCA
GGAGCCTTTTGTGTAAAAGTGTTGTGCCCATACACCAGCACTATGATGGAAACCCTGGAGCGACTGCAGCGTAGGTATGG
GGGAGGACTGGTCAGAGTGCCACTCTCCCGCAACTCTACACATGAGATGTACTGGGTCTCTGGAGCGAAAAGCAACACC
ATAAAAAGTGTGTCCACCACGAGCCAGCTCCTCTTGGGGCGCATGGACGGGCCCAGGAGGCCAGTGAAATATGAGGAG
GATGTGAATCTCGGCTCTGGCACGCGGGCTGTGGTAAGCTGCGCTGAAGCTCCCAACATGAAGATCATTGGTAACCGCAT
TGAAAGGATCCGCAGTGAGCACGCGGAAACGTGGTTCTTTGACGAGAACCACCCATATAGGACATGGGCTTACCATGGA
AGCTATGAGGCCCCTACACAAGGGTCAGCGTCCTCTCTAATAAACGGGGTTGTCAGGCTCCTGTCAAAACCCTGGGATGT
GGTGACTGGAGTCACAGGAATAGCCATGACCGACACCACACCGTATGGTCAGCAAAGAGTTTTCAAGGAAAAAGTGGAC
ACCAGGGTGCCAGACCCCCAAGAAGGCACTCGTCAGGTTATGAGCATGGTCTCTTCCTGGTTGTGGAAAGAGCTAGGCA
AACACAAACGGCCACGAGTCTGTACCAAAGAAGAGTTCATCAACAAGGTTCGTAGCAATGCAGCATTAGGGGCAATATTT
GAAGAGGAAAAGAGTGGAAGACCGCAGTGGAAGCTGTGAACGATCCAAGGTTCTGGGCTCTAGTGGACAAGGAAAGA
GAGCACCACCTGAGAGGAGAGTGCCAGAGCTGTGTGTACAACATGATGGGAAAAAGAGAAAAGAAACAAGGGGAATTT
GGAAAGGCCAAGGGCAGCCGCGCCATCTGGTATATGTGGCTAGGGGCTAGATTTCTAGAGTTCGAAGCCCTTGGATTCTT
AAATGAGGATCACTGGATGGGGAGAGAGAACTCAGGAGGTGGTGTTGAAGGGCTGGGATTACAAAGACTCGGATATGT
CCTAGAAGAGATGAGTCGCATACCAGGAGGAAGGATGTATGCAGATGACACTGCTGGCTGGGACACCCGCATCAGCAG
GTTTGATCTGGAGAATGAAGCTTTAATCACCAACCAAATGGAGAAAGGGCACAGGGCCTTAGCATTGGCCATAATCAAGT
ACACATACCAAAACAAAGTGGTAAAGGTCCTTAGACCAGCTGAAAAAGGGAAGACAGTTATGGACATTATTTCAAGACAA
GACCAAAGGGGAGCGGACAAGTTGTCACTTACGCTCTTAACACATTTACCAACCTAGTGGTGCAACTCATTCGGAATAT

-continued

```
GGAGGCTGAGGAAGTTCTAGAGATGCAAGACTTGTGGCTGCTGCGGAGGTCAGAGAAAGTGACCAACTGGTTGCAGAG

CAACGGATGGGATAGGCTCAAACGAATGGCAGTCAGTGGAGATGATTGCGTTGTGAAGCCAATTGATGATAGGTTTGCA

CATGCCCTCAGGTTCTTGAATGATATGGGAAAAGTTAGGAAGGACACACAAGAGTGGAAACCCTCAACTGGATGGGACA

ACTGGGAAGAAGTTCCGTTTTGTTCCCACCACTTCAACAAGCTCCATCTCAAGGACGGGAGGTCCATTGTGGTTCCCTGCC

GCCACCAAGATGAACTGATTGGCCGGGCCCGTGTCTCTCCAGGGGCGGGATGGAGCATCCGGGAGACTGCTTGCCTAGC

AAAGTCATATGCGCAAATGTGGCAGCTCCTTTATTTCCACAGAAGGGACCTCCGACTGATGGCCAATGCCATCTGTTCATC

TGTGCCAGTTGACTGGGTTCCAACTGGGAGAACTACCTGGTCAATCCATGGAAAGGGAGAATGGATGACCACTGAAGAC

ATGCTTGTGGTGTGGAACAGAGTGTGGATTGAGGAGAACGACCACATGGAAGACAAGACCCCAGTTACGAAATGGACA

GACATTCCCTATCTGGGAAAAAGGGAAGACTTGTGGTGTGGATCTCTCATAGGGCACAGACCGCGCACCACCTGGGCTG

AGAACATTAAAAACACAGTCAACATGGTGCGCAGGATCATAGGTGATGAAGAAAGTACATGGACTACCTATCCACCCAA

GTTCGCTACTTGGGTGAAGAAGGGTCTACACCTGGAGTGCTATAAGCACCAATCTTAGTGTTGTCAGGCCTGCTAGTCAG

CCACAGCTTGGGGAAAGCTGTGCAGCCTGTGACCCCCCCAGGAGAGGCTGGGAAACCAAGCCCATAGTCAGGCCGAGAA

CGCCATGGCACGGAAGAAGCCATGCTGCCTGTGAGCCCCTCAGAGGACACTGAGTCAAAAAACCCCACGCGCTTGGAGG

CGCAGGATGGGAAAAGAAGGTGGCGACCTTCCCCACCCTTCAATCTGGGGCCTGAACTGGAGATCAGCTGTGGATCTCC

AGAAGAGGGACTAGTGGTTAGAGGAGACCCCCCGGAAAACGCAAAACAGCATATTGACGCTGGGAAAGACCAGAGACT

CCATGAGTTTCCACCACGCTGGCCGCCAGGCACAGATCGCCGAATAGCGGCGGCCGGTGTGGGGAAATCCATGGGTCT
```

KU681082.3 Zika virus isolate Zika virus/H. sapiens-tc/PHL/2012/CPC-0740, Philippines, complete genome

SEQ ID NO: 8

```
AGTTGTTGATCTGTGTGAATCAGACTGCGACAGTTCGAGTTTGAAGCGAAAGCTAGCAACAGTATCAACAGGTTTTATTTT

GGATTTGGAAACGAGAGTTTCTGGTCATGAAAAACCCAAAAAAGAAATCCGGAGGATTCCGGATTGTCAATATGCTAAAA

CGCGGAGTAGCCCGTGTGAGCCCCTTTGGGGGCTTGAAGAGGCTGCCAGCCGGACTTCTGCTGGGCATGGGCCCATCA

GGATGGTCTTGGCGATACTAGCCTTTTTGAGATTCACGGCAATCAAGCCATCACTGGGTCTCATCAATAGATGGGGTTCA

GTGGGGAAAAAGAGGCTATGGAAATAATAAAGAAGTTCAAGAAAGATCTGGCTGCCATGCTGAGAATAATCAATGCTA

GGAAGGAGAAGAAGAGACGAGGCGCAGATACTAGCGTCGGAATTGTTGGCCTCCTCCTGACCACAGCCATGGCAGTAG

AGGTCACTAGACGTGGGAGTGCATACTATATGTACTTGGACAGAAGCGATGCTGGGGAGGCCATATCTTTTCCAACCACA

CTGGGGATGAATAAGTGTTACATACAAATCATGGATCTTGGACACATGTGTGATGCCACCATGAGCTATGAATGCCCTAT

GTTGGATGAGGGGGTAGAACCAGATGACGTCGATTGCTGGTGCAACACGACATCAACTTGGGTTGTGTATGGAACCTGC

CACCACAAAAAAGGTGAAGCACGGAGATCTAGAAGAGCTGTGACGCTCCCCTCCCATTCCACTAGGAAGCTGCAAACGC

GGTCGCAGACCTGGTTGGAATCAAGAGAATACACAAAGCACCTGATTAGAGTTGAAAATTGGATATTCAGGAACCCTGG

CTTCGCGTTAGCAGCAGCTGTCATCGCTTGGCTTTTGGGAAGTTCAACGAGCCAAAAAGTCATATATCTGGTCATGATACT

GCTGATTGCCCCGGCATACAGCATCAGGTGCATAGGAGTCAGCAATAGGGACTTTGTGGAAGGTATGTCAGGTGGGACT

TGGGTTGATGTTGTCTTGGAACATGGAGGTTGTGTTACCGTAATGGCACAGGACAAACCGACTGTCGACATAGAGCTGGT

TACAACAACAGTCAGCAACATGGCGGAGGTAAGATCCTACTGCTATGAGGCATCAATATCGGATATGGCTTCGGACAGCC

GCTGCCCAACACAAGGTGAGGCCTACCTTGACAAGCAGTCAGACACTCAATATGTCTGCAAAAGAACGTTAGTGGACAGA

GGCTGGGGAAATGGATGTGGACTTTTTGGCAAAGGGAGCCTGGTGACATGCGCTAAGTTTGCATGCTCCAAGAAAATGA

CCGGGAAGAGCATCCAGCCAGAGAATCTGGAGTACCGGATAATGCTGTCAGTTCATGGCTCCCAGCACAGTGGGATGAT

CGTTAATGACACAGGACATGAAACTGATGAGAATAGAGCGAAGGTTGAGATAACGCCCAATTCACCAAGAGCCGAAGCC

ACCCTGGGGGGTTTTGGGAGCCTAGGACTTGATTGTGAACCGAGGACAGGCCTTGACTTTTCAGATTTGTATTACCTGACT

ATGAATAACAAGCACTGGTTGGTTCACAAGGAGTGGTTCCACGACATTCCATTACCTTGGCATGCTGGGGCAGACACTGG

AACTCCACATTGGAACAACAAAGAAGCACTGGTAGAGTTCAAGGACGCACATGCAAAAAGGCAAACTGTCGTGGTTCTA

GGGAGTCAAGAAGGAGCAGTTCACACGGCCCTTGCTGGAGCTCTGGAGGCTGAGATGGATGGAGCCAAGGGAAGGCTG
```

-continued

```
TCCTCTGGCCACTTGAAATGTCGCCTGAAAATGGATAAACTTAGATTGAAGGGCGTGTCATACTCCTTGTGCACTGCAGCG

TTCACATTCACCAAGATCCCGGCTGAAACACTGCACGGGACAGTCACAGTGGAGGTACAGTACGCAGGGACAGATGGAC

CTTGCAAGGTTCCAGCTCAGATGGCGGTGGATATGCAAACTCTGACCCCAGTTGGGAGGTTGATAACCGCTAACCCTGTA

ATCACTGAAAGCACCGAGAACTCTAAGATGATGCTGGAACTTGATCCACCATTTGGGACTCTTACATTGTCATAGGAGTC

GGGGAGAAGAAGATCACCCATCACTGGCACAGGAGTGGCAGCACCATTGGAAAAGCATTTGAAGCCACTGTGAGAGGT

GCCAAGAGAATGGCAGTCTTGGGAGACACAGCCTGGGACTTTGGATCAGTTGGGGGTGCTCTCAACTCATTGGGCAAGG

GCATCCATCAAATTTTTGGAGCAGCTTTCAAATCATTGTTCGGAGGAATGTCCTGGTTCTCACAAATTCTCATTGGAACGTT

GCTGGTGTGGTTGGGTCTGAATACAAAGAATGGATCTATTTCCCTTACGTGCTTGGCCTTAGGGGGAGTGTTGATCTTCTT

ATCCACAGCCGTTTCTGCTGATGTGGGGTGCTCGGTGGACTTCTCAAAGAAGGAAACGAGATGCGGTACAGGGGTGTTC

GTCTATAACGACGTTGAAGCCTGGAGGGACAGGTACAAGTACCATCCTGACTCCCCTCGTAGATTGGCAGCAGCAGTCAA

GCAAGCCTGGGAAGATGGGATCTGTGGGATCTCCTCTGTCTCAAGAATGGAAAACATCATGTGGAGATCAGTAGAAGGG

GAGCTCAACGCAATCCTGGAAGAGAATGGAGTTCAACTGACGGTCGTTGTGGGATCTGTAAAAAACCCCATGTGGAGAG

GTCCACAGAGATTGCCCGTGCCTGTGAACGAGCTGCCCCACGGCTGGAAGGCTTGGGGGAAATCGTACTTCGTCAGAGC

AGCAAAGACAAATAACAGCTTTGTCGTGGATGGTGACACACTGAAGGAATGCCCACTCAAACATAGAGCATGGAACAGC

TTTCTTGTGGAGGATCATGGGTTTGGGGTATTTCACACTAGTGTCTGGCTCAAGGTTAGAGAAGATTATTCATTAGAGTGT

GATCCAGCCGTCATTGGAACAGCTGCTAAGGGAAAGGAGGCTGTGCACAGCGATCTAGGCTACTGGATTGAGAGTGAGA

AGAACGACACATGGAGGCTGAAGAGGGCCCACCTGATCGAGATGAAAACATGTGAATGGCCAAAGTCCCACACATTGTG

GACAGATGGAGTAGAAGAAAGTGATCTGATCATACCCAAGTCTTTAGCTGGGCCACTCAGCCATCACAACACCAGAGAG

GGCTACAGGACTCAAATGAAAGGGCCATGGCACAGTGAAGAGCTTGAAATTCGGTTTGAGGAATGCCCAGGCACTAAGG

TCCACGTGGAGGAAACATGTGGGACAAGAGGACCATCCCTGAGATCAACCACTGCAAGCGGAAGGGTGATCGAGGAAT

GGTGCTGCAGGGAATGCACAATGCCCCCACTGTCGTTCCGAGCTAAAGATGGCTGTTGGTATGGAATGGAGATAAGGCC

CAGGAAAGAACCAGAAAGTAACTTAGTAAGGTCAATGGTGACTGCAGGATCAACTGATCACATGGATCACTTCTCTCTTG

GAGTGCTTGTGATTTTGCTCATGGTGCAGGAAGGGCTGAAGAAGAGAATGACCACAAAGATCATCATAAGCACATCAAT

GGCAGTGCTGGTAGCCATGATCCTGGGAGGATTTTCAATGAGTGACCTGGCTAAGCTTGCAATTTTGATGGGTGCCACCT

TCGCGGAAATGAACACTGGAGGAGATGTAGCTCATTTGGCGCTGATAGCGGCATTCAAAGTCAGACCTGCGTTGCTGGTA

TCTTTCATCTTCAGAGCTAATTGGACACCCCGTGAGAGCATGCTGCTGGCCTTGGCCTCGTGTCTTCTGCAAACTGCGATCT

CCGCCTTGGAAGGCGACCTGATGGTTCTCATCAATGGTTTTGCTTTGGCCTGGTTGGCAATACGAGCGATGGTTGTTCCAC

GCACTGACAACATCACCTTGGCAATCCTGGCTGCTCTGACACCACTGGCCCGGGGCACACTGCTTGTGGCGTGGAGAGCA

GGCCTTGCTACTTGCGGGGGGTTCATGCTCCTCTCTCTGAAGGGGAAAGGCAGTGTGAAGAAGAACCTACCATTTGTCAT

GGCCTTGGGACTAACTGCTGTGAGGCTGGTCGACCCCATCAACGTGGTGGGACTGCTGTTGCTCACAAGGAGTGGGAAG

CGGAGCTGGCCCCCTAGTGAAGTACTCACAGCTGTTGGCCTGATATGCGCATTGGCTGGAGGGTTCGCCAAGGCGGATA

TAGAGATGGCTGGGCCCATGGCCGCGGTCGGTCTGCTAATTGTCAGTTACGTGGTCTCAGGAAAGAGTGTGGACATGTA

CATTGAAAGAGCAGGTGACATCACATGGGAAAAAGATGCGGAAATCACTGGAAACAGTCCCCGGCTCGATGTGGCACTA

GATGAGAGTGGTGATTTCTCCCTAGTGGAGGATGATGGTCCACCCATGAGAGAGATCATACTCAAAGTGGTCCTGATGAC

CATCTGCGGCATGAACCCAATAGCCATACCCTTTGCAGCTGGAGCGTGGTACGTGTATGTGAAGACTGGAAAAAGGAGT

GGTGCTCTATGGGATGTGCCTGCTCCCAAGGAAGTAAAAAAGGGGGAGACCACAGATGGAGTGTACAGAGTAATGACTC

GTAGACTGCTTGGTTCAACACAAGTTGGAGTGGGAGTCATGCAAGAGGGGGTCTTCCACACTATGTGGCACGTCACAAA

AGGATCCGCGCTGAGAAGCGGTGAAGGGAGACTTGATCCATACTGGGGAGATGTCAAGCAGGATCTGGTGTCATACTGT

GGTCCGTGGAAGCTAGACGCCGCCTGGGACGGGCACAGCGAGGTGCAGCTCTTGGCCGTGCCCCCCGGAGAGAGAGCG

AGGAACATCCAGACTCTGCCCGGAACATTTAAGACAAAGGATGGGGACATTGGAGCAGTTGCGCTGGACTACCCAGCAG
```

-continued
```
GAACTTCAGGATCTCCAATCCTAGACAAGTGTGGGAGAGTGATAGGACTCTATGGTAATGGGGTCGTGATAAAAAATGG

GAGTTATGTTAGTGCCATCACCCAAGGGAGGAGGGAGGAAGAGACTCCTGTTGAGTGCTTCGAGCCTTCGATGCTGAAG

AAGAAGCAGCTAACTGTCTTAGACCTGCATCCTGGAGCCGGGAAAACCAGGAGAGTTCTTCCTGAAATAGTCCGTGAAGC

CATAAAAACAAGACTCCGTACTGTGATCTTAGCTCCAACCAGGGTCGTCGCTGCTGAAATGGAGGAAGCCCTTAGAGGGC

TTCCAGTTCGTTATATGACAACAGCAGTCAATGTCACCCATTCTGGGACAGAAATCGTTGACTTAATGTGCCATGCTACCTT

CACTTCACGCCTACTACAACCAATCAGAGTCCCCAACTATAATTTGTATATTATGGATGAGGCCCACTTCACAGATCCCTCA

AGTATAGCAGCAAGAGGATACATTTCAACAAGGGTTGAGATGGGCGAGGCGGCTGCCATCTTCATGACCGCCACGCCAC

CAGGAACCCGTGACGCATTCCCGGACTCCAACTCACCAATTATGGACACCGAGGTGGAAGTCCCAGAGAGAGCCTGGAG

CACAGGCTTTGATTGGGTGACGGATCATTCTGGGAAAACAGTCTGGTTTGTTCCAAGCGTGAGGAACGGCAATGAGATC

GCAGCTTGTCTGACAAAGGCTGGAAAACGGGTCATACAGCTCAGCAGAAAGACTTTTGAGACAGAGTTCCAGAAAACGA

AAAATCAAGAGTGGGACTTCGTCGTGACAACCGACATTTCAGAGATGGGCGCCAACTTTAAAGCTGACCGTGTCATAGAT

TCCAGGAGATGCTTAAAGCCGGTCATACTTGATGGCGAGAGAGTCATTTGGCTGGACCCATGCCTGTCACACATGCCAG

CGCTGCTCAGAGGAGGGGCGCATAGGCAGGAATCCCAACAAACCTGGAGATGAGTATCTGTATGGAGGTGGGTGCGC

AGAGACTGATGAAGATCACGCACACTGGCTTGAAGCAAGAATGCTTCTTGACAACATTTACCTCCAAGATGGCCTCATAG

CTTCGCTCTATCGACCTGAGGCCGACAAAGTAGCAGCTATTGAGGGAGAGTTCAAGCTTAGGACGGAGCAAAGGAAGAC

CTTTGTGGAACTCATGAAAAGAGGAGATCTTCCGGTTTGGTTGGCCTATCAGGTTGCATCTGCCGGAATAACCTACACAG

ATAGAAGATGGTGCTTTGATGGCATGACCAACAACACCATAATGGAAGACAGTGTGCCGGCAGAGGTGTGGACCAGATA

CGGAGAGAAAAGAGTGCTCAAACCGAGGTGGATGGACGCCAGAGTTTGTTCAGATCATGCGGCCCTGAAGTCATTCAAA

GAGTTTGCCGCTGGGAAAAGAGGAGCGGCCTTTGGAGTGATAGAAGCCCTGGGAACACTGCCAGGACACATGACAGAG

AGATTCCAGGAAGCCATTGACAACCTCGCTGTGCTCATGCGGGCAGAGACTGGAAGCAGGCCTTACAAAGCCGCGGCGG

CCCAATTGCCGGAGACCCTAGAGACCATTATGCTTTTGGGGTTGCTGGGAACAGTCTCGCTGGGAATCTTTTTCGTCTTGA

TGCGGAACAAGGGCATGGGAAGATGGGCTTTGGAATGGTGACTCTTGGGGCCAGCGCATGGCTTATGTGGCTCTCGGA

AATTGAGCCAGCCAGAATTGCATGTGTCCTCATTGTCGTGTTCCTATTGCTGGTGGTGCTCATACCTGAGCCAGAAAAGCA

AAGATCTCCTCAGGACAACCAAATGGCAATCATCATCATGGTAGCAGTGGGTCTTCTGGGCTTGATTACCGCCAATGAACT

CGGATGGTTGGAGAGAACAAAAAGTGACCTAAGCCATCTAATGGGAAGGAGAGAGGAGGGGGCAACCACAGGATTCTC

AATGGACATTGACCTGCGGCCAGCCTCAGCTTGGGCTATCTATGCTGCTCTGACAACTTTCATCACCCCAGCCGTCCAACA

TGCGGTGACCACTTCATACAACAACTACTCCTTAATGGCGATGGCCACGCAAGCTGGGGTGTTGTTTGGTATGGGCAAAG

GGATGCCATTCTACGCATGGGACTTTGGAGTCCCGCTGCTAATGATGGGTTGCTACTCACAATTAACACCTCTGACCCTAA

TAGTGGCCATCATTTTGCTCGTGGCGCACTACATGTACTTGATCCCAGGGCTGCAGGCAGCAGCTGCGCGGGCTGCCCAG

AAGAGAACGGCAGCTGGCATCATGAAGAACCCTGTTGTGGATGGAATAGTGGTGACTGACATTGACACAATGACAATTG

ACCCCCAAGTGGAAAAAAGATGGGGCAGGTGCTACTCATAGCAGTAGCCGTCTCCAGCGCCATACTGTCGCGGACCGC

CTGGGGGTGGGGGAGGCTGGGGCCCTGATCACAGCTGCAACTTCCACCTTGTGGGAAGGCTCTCCGAACAAGTACTGG

AACTCCTCCACAGCCACTTCACTGTGTAACATTTTTAGGGGAAGTTACTTGGCTGGAGCTTCTCTAATCTACACAGTAACAA

GAAACGCTGGCTTGGTCAAGAGACGTGGGGGTGGAACGGGAGAGACCCTGGGAGAGAAATGGAAGGCCCGCCTGAAC

CAGATGTCGGCCCTGGAGTTCTACTCCTACAAAAAGTCAGGCATCACCGAGGTGTGCAGAGAAGAGGCCCGCCGTGCCCT

CAAGGACGGTGTGGCAACAGGAGGCCATGCTGTGTCCCGAGGAAGTGCAAAGCTTAGATGGCTGGTGGAGAGAGGATA

CCTGCAGCCCTATGGAAAGGTCATTGATCTTGGATGTGGCAGAGGGGGCTGGAGTTACTATGCCGCCACCATCCGCAAAG

TTCAGGAAGTGAAAGGATACACAAAAGGAGGCCCTGGTCATGAAGAACCCATGTTGGTGCAAAGCTATGGGTGGAACAT

AGTCCGTCTTAAGAGTGGGGTGGACGTCTTTCACATGGCGGCTGAGCCGTGTGACACTTTGCTGTGTGATATAGGTGAGT

CATCATCTAGTCCTGAAGTGGAAGAAGCACGGACGCTCAGAGTCCTCTCCATGGTGGGGATTGGCTTGAAAAAAGACC

AGGAGCCTTTTGTATAAAAGTGTTGTGCCCATACACCAGCACTATGATGGAAACCCTGGAGCGACTGCAGCGTAGGTATG
```

-continued

```
GGGGAGGACTGGTCAGGGTGCCACTCTCCCGCAACTCTACACATGAGATGTACTGGGTCTCTGGAGCGAAAAGCAACAC
CATAAAAAGTGTGTCCACCACGAGCCAGCTCCTCTTGGGGCGCATGGACGGGCCCAGGAGGCCAGTGAAATATGAGGAG
GATGTGAATCTCGGCTCTGGCACGCGGGCTGTGGTAAGCTGCGCTGAAGCTCCCAACATGAAGATCATTGGTAACCGCAT
TGAGAGGATCCGCAGTGAGCACGCGGAAACGTGGTTCTTTGACGAGAACCACCCATATAGGACATGGGCTTACCATGGA
AGCTATGAGGCCCCTACACAAGGGTCAGCGTCCTCTCTAATAAACGGGGTTGTCAGGCTCCTGTCAAAACCCTGGGATGT
GGTGACTGGAGTCACAGGAATAGCCATGACTGACACCACACCGTATGGTCAGCAAAGAGTTTTCAAGGAAAAAGTGGAC
ACTAGGGTGCCAGACCCCCAAGAAGGCACTCGTCAGGTTATGAGCATGGTCTCTTCCTGGTTATGGAAGGAGCTAGGCAA
ACACAAACGGCCACGAGTCTGTACCAAAGAAGAGTTCATCAACAAGGTTCGTAGCAATGCAGCATTAGGGGCAATATTTG
AAGAGGAAAAAGAGTGGAAGACTGCAGTGGAAGCTGTGAATGATCCAAGGTTCTGGGCTCTAGTGGACAAGGAAAGAG
AGCATCACCTGAGAGGAGAGTGTCAGAGCTGTGTGTACAACATGATGGGAAAAAGAGAAAAGAAACAAGGGGAATTTG
GAAAGGCCAAGGGCAGCCGCGCCATCTGGTATATGTGGCTAGGGGCTAGATTCCTAGAGTTCGAAGCCCTTGGATTCTTG
AATGAGGATCATTGGATGGGGAGAGAGAATTCAGGAGGTGGTGTTGAAGGACTGGGATTACAAAGACTCGGATATGTC
CTAGAAGAGATGAGTCGCATACCAGGAGGAAGGATGTATGCAGATGATACTGCTGGCTGGGACACCCGCATCAGCAGGT
TTGATCTGGAGAATGAAGCTCTAATCACCAACCAAATGGAGAAAGGGCACAGGGCCTTGGCATTGGCCATAATCAAGTAC
ACATACCAAAACAAAGTGGTAAAGGTCCTTAGACCAGCTGAAAAAGGGAAGACAGTTATGGACATTATTTCAAGACAAG
ACCAAAGGGGAGCGGACAAGTTGTCACTTACGCTCTTAATACATTCACCAACCTGGTGGTGCAGCTCATTCGGAATATG
GAGGCTGAGGAAGTTCTAGAGATGCAAGACTTGTGGCTGCTGCGGAGGCCAGAGAAAGTGACCAACTGGTTGCAAAGC
AACGGATGGGATAGGCTCAAAAGAATGGCAGTCAGTGGAGATGATTGCGTTGTGAAACCAATTGATGATAGGTTTGCAC
ATGCCCTCAGGTTCTTGAATGATATGGGAAAAGTTAGGAAGGACACACAAGAGTGGAAACCCTCAACTGGATGGGACAA
CTGGGAAGAAGTTCCGTTTTGCTCCCACCACTTCAACAAACTCCATCTTAAGGACGGGAGGTCCATTGTGGTTCCCTGCCG
CCACCAAGATGAACTGATTGGCCGAGCCCGCGTATCACCAGGGGCGGGATGGAGCATCCGGGAGACTGCTTGCCTAGCA
AAATCATATGCGCAAATGTGGCAGCTCCTTTATTTCCACAGAAGGGACCTCCGACTGATGGCCAATGCCATTTGTTCATCT
GTGCCAGTTGATTGGGTTCCAACTGGGAGAACTACCTGGTCAATCCATGGAAAGGGAGAATGGATGACCACTGAAGACA
TGCTTGTGGTATGGAACAGAGTGTGGATTGAGGAAAACGACCACATGGAAGACAAGACCCCCAGTTACAAAATGGACAGA
CATTCCCTATTTGGGAAAAAGAGAAGACTTGTGGTGTGGATCTCTCATAGGGCACAGACCGCGTACTACCTGGGCTGAGA
ACATCAAAAATACAGTCAACATGATGCGCAGGATCATAGGTGATGAAGAAAAGTACATGGACTACCTATCCACCCAGGTT
CGCTACTTGGGTGAAGAAGGGTCCACACCTGGAGTGCTGTAAGCACCAATCTTAGTGTTGTCAGGCCTGCTAGTCAGCCA
CAGCTTGGGGAAAGCTGTGCAGCCTGTGACCCCCCCAGGAGAAGCTGGGAAACCAAGCCTATAGTCAGGCCGAGAACGC
CATGGCACGGAAGAAGCCATGCTGCCTGTGAGCCCCTCAGAGGACACTGAGTCAAAAACCCCACGCGCTTGGAGGCGC
AGGATGGGAAAAGAAGGTGGCGACCTTCCCCACCCTTCAATCTGGGGCCTGAACTGGAGATCAGCTGTGGATCTCCAGA
AGAGGGACTAGTGGTTAGAGGAGACCCCCCGGAAAACGCAAAACAGCATATTGACGCTGGGAAAGACCAGAGACTCCA
TGAGTTTCCACCACGCTGGCCGCCAGGCACAGATCGCCGAATAGCGGCGGCCGGTGTGGGGAAATCCATGGGTCT
```

KU707826.1 Zika virus isolate SSABR1, Brazil, complete genome

SEQ ID NO: 9
```
GACAGTTCGAGTTTGAAGCGAAAGCTAGCAACAGTATCAACAGGTTTTATTTGGATTTGGAAACGAGAGTTTCTGGTCAT
GAAAAACCCAAAAAAGAAATCCGGAGGATTCCGGATTGTCAATATGCTAAAACGCGGAGTAGCCCGTGTGAGCCCCTTT
GGGGGCTTGAAGAGGCTGCCAGCCGGACTTCTGCTGGGTCATGGGCCCATCAGGATGGTCTTGGCGATTCTAGCCTTTTT
GAGATTCACGGCAATCAAGCCATCACTGGGTCTCATCAATAGATGGGGTTCAGTGGGAAAAAAGAGGCTATGGAAATA
ATAAAGAAGTTCAAGAAAGATCTGGCTGCCATGCTGAGAATAATCAATGCTAGGAAGGAGAAGAAGAGACGAGGCGCA
GATACTAGTGTCGGAATTGTTGGCCTCCTGCTGACCACAGCTATGGCAGCGGAGGTCACTAGACGTGGGAGTGCATACTA
TATGTACTTGGACAGAAACGATGCTGGGGAGGCCATATCTTTTCCAACCACATTGGGGATGAATAAGTGTTATATACAGA
```

-continued

```
TCATGGATCTTGGACACATGTGTGATGCCACCATGAGCTATGAATGCCCTATGCTGGATGAGGGGTGGAACCAGATGAC
GTCGATTGTTGGTGCAACACGACGTCAACTTGGGTTGTGTACGGAACCTGCCATCACAAAAAAGGTGAAGCACGGAGAT
CTAGAAGAGCTGTGACGCTCCCCTCCCATTCCACTAGGAAGCTGCAAACGCGGTCGCAAACCTGGTTGGAATCAAGAGAA
TACACAAAGCACTTGATTAGAGTCGAAAATTGGATATTCAGGAACCCTGGCTTCGCGTTAGCAGCAGCTGCCATCGCTTG
GCTTTTGGGAAGCTCAACGAGCCAAAAAGTCATATACTTGGTCATGATACTGCTGATTGCCCCGGCATACAGCATCAGGT
GCATAGGAGTCAGCAATAGGGACTTTGTGGAAGGTATGTCAGGTGGGACCTGGGTTGATGTTGTCTTGGAACATGGAGG
TTGTGTCACCGTAATGGCACAGGACAAACCGACTGTCGACATAGAGCTGGTTACAACAACAGTCAGCAACATGGCGGAG
GTAAGATCCTACTGCTATGAGGCATCAATATCAGACATGGCTTCGGACAGCCGCTGCCCAACACAAGGTGAAGCCTACCT
TGACAAGCAATCAGACACTCAATATGTCTGCAAAAGAACGTTAGTGGACAGAGGCTGGGGAAATGGATGTGGACTTTTT
GGCAAAGGGAGCCTGGTGACATGCGCTAAGTTTGCATGCTCCAAGAAAATGACCGGGAAGAGCATCCAGCCAGAGAATC
TGGAGTACCGGATAATGCTGTCAGTTCATGGCTCCCAGCACAGTGGGATGATTGTTAATGACACAGGACATGAAACTGAT
GAGAATAGAGCGAAAGTTGAGATAACGCCCAATTCACCAAGAGCCGAAGCCACCCTGGGGGGTTTTGGAAGCCTAGGAC
TTGATTGTGAACCGAGGACAGGCCTTGACTTTTCAGATTTGTATTACTTGACTATGAATAACAAGCACTGGTTGGTTCACA
AGGAGTGGTTCCACGACATTCCATTACCTTGGCACGCTGGGGCAGACACCGGAACTCCACACTGGAACAACAAAGAAGC
ACTGGTAGAGTTCAAGGACGCACATGCCAAAAGGCAAACTGTCGTGGTTCTAGGGAGTCAAGAAGGAGCAGTTCACACG
GCCCTTGCTGGAGCTCTGGAGGCTGAGATGGATGGTGCAAAGGGAAGGCTGTCCTCTGGCCACTTGAAATGTCGCCTGA
AAATGGATAAACTTAGATTGAAGGGCGTGTCATACTCCTTGTGTACTGCAGCGTTCACATTCACCAAGATCCCGGCTGAAA
CACTGCACGGGACAGTCACAGTGGAGGTACAGTACGCAGGGACAGATGGACCTTGCAAGGTTCCAGCTCAGATGGCGGT
GGACATGCAAACTCTGACCCCAGTTGGGAGGTTGATAACCGCTAACCCCGTAATCACTGAAAGCACTGAGAACTCTAAGA
TGATGCTGGAACTTGATCCACCATTTGGGGACTCTTACATTGTCATAGGAGTCGGGGAGAAGAAGATCACCCACCACTGG
CACAGGAGTGGCAGCACCATTGGAAAAGCATTTGAAGCCACTGTGAGAGGTGCCAAGAGAATGGCAGTCTTGGGAGAC
ACAGCCTGGGACTTTGGATCAGTTGGAGGCGCTCTCAACTCATTGGGCAAGGGCATCCATCAAATTTTTGGAGCAGCTTT
CAAATCATTGTTTGGAGGAATGTCCTGGTTCTCACAAATTCTCATTGGAACGTTGCTGATGTGGTTGGGTCTGAACACAAA
GAATGGATCTATTTCCCTTATGTGCTTGGCCTTAGGGGGAGTGTTGATCTTCTTATCCACAGCCGTCTCTGCTGATGTGGG
GTGCTCGGTGGACTTCTCAAAGAAGGAGACGAGATGCGGTACAGGGGTGTTCGTCTATAACGACGTTGAAGCCTGGAGG
GACAGGTACAAGTACCATCCTGACTCCCCCCGTAGATTGGCAGCAGCAGTCAAGCAAGCCTGGGAAGATGGTATCTGCG
GGATCTCCTCTGTTTCAAGAATGGAAAACATCATGTGGAGATCAGTAGAAGGGGAGCTCAACGCAATCCTGGAAGAGAA
TGGAGTTCAACTGACGGTCGTTGTGGGATCTGTAAAAAACCCCATGTGGAGAGGTCCACAGAGATTGCCCGTGCCTGTGA
ACGAGCTGCCCCACGGCTGGAAGGCTTGGGGGAAATCGTACTTCGTCAGAGCAGCAAAGACAAATAACAGCTTTGTCGT
GGATGGTGACACACTGAAGGAATGCCCACTCAAACATAGAGCATGGAACAGCTTTCTTGTGGAGGATCATGGGTTCGGG
GTATTTCACACTAGTGTCTGGCTCAAGGTTAGAGAAGATTATTCATTAGAGTGTGATCCAGCCGTTATTGGAACAGCTGTT
AAGGGAAAGGAGGCTGTACACAGTGATCTAGGCTACTGGATTGAGAGTGAGAAGAATGACACATGGAGGCTGAAGAGG
GCCCATCTGATCGAGATGAAAACATGTGAATGGCCAAAGTCCCACACATTGTGGACAGATGGAATAGAAGAGAGTGATC
TGATCATACCCAAGTCTTTAGCTGGGCCACTCAGCCATCACAATACCAGAGAGGGCTACAGGACCCAAATGAAAGGGCCA
TGGCACAGTGAAGAGCTTGAAATTCGGTTTGAGGAATGCCCAGGCACTAAGGTCCACGTGGAGGAAACATGTGGAACAA
GAGGACCATCTCTGAGATCAACCACTGCAAGCGGAAGGGTGATCGAGGAATGGTGCTGCAGGGAGTGCACAATGCCCCC
ACTGTCGTTCCGGGCTAAAGATGGCTGTTGGTATGGAATGGAGATAAGGCCCAGGAAAGAACCAGAAAGCAACTTAGTA
AGGTCAATGGTGACTGCAGGATCAACTGATCACATGGACCACTTCTCCCTTGGAGTGCTTGTGATTCTGCTCATGGTGCAG
GAAGGGCTGAAGAAGAGAATGACCACAAAGATCATCATAAGCACATCAATGGCAGTGCTGGTAGCTATGATCCTGGGAG
GATTTTCAATGAGTGACCTGGCTAAGCTTGCAATTTTGATGGGTGCCACCTTCGCGGAAATGAACACTGGAGGAGATGTA
GCTCATCTGGCGCTGATAGCGGCATTCAAAGTCAGACCAGCGTTGCTGGTATCTTTCATCTTCAGAGCTAATTGGACACCC
```

-continued

```
CGTGAAAGCATGCTGCTGGCCTTGGCCTCGTGTCTTTTGCAAACTGCGATCTCCGCCTTGGAAGGCGACCTGATGGTTCTC
ATCAATGGTTTTGCTTTGGCCTGGTTGGCAATACGAGCGATGGTTGTTCCACGCACTGATAACATCACCTTGGCAATCCTG
GCTGCTCTGACACCACTGGCCCGGGGCACACTGCTTGTGGCGTGGAGAGCAGGCCTTGCTACTTGCGGGGGGTTTATGCT
CCTCTCTCTGAAGGGAAAAGGCAGTGTGAAGAAGAACTTACCATTTGTCATGGCCCTGGGACTAACCGCTGTGAGGCTGG
TCGACCCCATCAACGTGGTGGGACTGCTGTTGCTCACAAGGAGTGGGAAGCGGAGCTGGCCCCCTAGCGAAGTACTCAC
AGCTGTTGGCCTGATATGCGCATTGGCTGGAGGGTTCGCCAAGGCAGATATAGAGATGGCTGGGCCCATGGCCGCGGTC
GGTCTGCTAATTGTCAGTTACGTGGTCTCAGGAAAGAGTGTGGACATGTACATTGAAAGAGCAGGTGACATCACATGGG
AAAAAGATGCGGAAGTCACTGGAAACAGTCCCCGGCTCGATGTGGCGCTAGATGAGAGTGGTGATTTCTCCCTGGTGGA
GGATGACGGTCCCCCCATGAGAGAGATCATACTCAAGGTGGTCCTGATGACCATCTGTGGCATGAACCCAATAGCCATAC
CCTTTGCAGCTGGAGCGTGGTACGTATACGTGAAGACTGGAAAAAGGAGTGGTGCTCTATGGGATGCCTGCTCCCAA
GGAAGTAAAAAAGGGGGAGACCACAGATGGAGTGTACAGAGTAATGACTCGTAGACTGCTAGGTTCAACACAAGTTGG
AGTGGGAGTTATGCAAGAGGGGGTCTTTCACACTATGTGGCACGTCACAAAAGGATCCGCGCTGAGAAGCGGTGAAGG
GAGACTTGATCCATACTGGGGAGATGTCAAGCAGGATCTGGTGTCATACTGTGGTCCATGGAAGCTAGATGCCGCCTGG
GACGGGCACAGCGAGGTGCAGCTCTTGGCCGTGCCCCCCGGAGAGAGAGCGAGGAACATCCAGACTCTGCCCGGAATAT
TTAAGACAAAGGATGGGGACATTGGAGCGGTTGCGCTGGATTACCCAGCAGGAACTTCAGGATCTCCAATCCTAGACAA
GTGTGGGAGAGTGATAGGACTTTATGGCAATGGGGTCGTGATCAAAAATGGGAGTTATGTTAGTGCCATCACCCAAGGG
AGGAGGGAGGAAGAGACTCCTGTTGAGTGCTTCGAGCCTTCGATGCTGAAGAAGAAGCAGCTAACTGTCTTAGACTTGC
ATCCTGGAGCTGGGAAAACCAGGAGAGTTCTTCCTGAAATAGTCCGTGAAGCCATAAAAACAAGACTCCGTACTGTGATC
TTAGCTCCAACCAGGGTTGTCGCTGCTGAAATGGAGGAGGCCCTTAGAGGGCTTCCAGTGCGTTATATGACAACAGCAGT
CAATGTCACCCACTCTGGAACAGAAATCGTCGACTTAATGTGCCATGCCACCTTCACTTCACGTCTACTACAGCCAATCAGA
GTCCCCAACTATAATCTGTATATTATGGATGAGGCCCACTTCACAGATCCCTCAAGTATAGCAGCAAGAGGATACATTTCA
ACAAGGGTTGAGATGGGCGAGGCGGCTGCCATCTTCATGACCGCCACGCCACCAGGAACCCGTGACGCATTTCCGGACT
CCAACTCACCAATTATGGACACCGAAGTGGAAGTCCCAGAGAGAGCCTGGAGCTCAGGCTTTGATTGGGTGACGGATCA
TTCTGGAAAAACAGTTTGGTTTGTTCCAAGCGTGAGGAACGGCAATGAGATCGCAGCTTGTCTGACAAAGGCTGGAAAAC
GGGTCATACAGCTCAGCAGAAAGACTTTTGAGACAGAGTTCCAGAAAACAAAACATCAAGAGTGGGACTTTGTCGTGAC
AACTGACATTTCAGAGATGGGCGCCAACTTTAAAGCTGACCGTGTCATAGATTCCAGGAGATGCCTAAAGCCGGTCATAC
TTGATGGCGAGAGAGTCATTCTGGCTGGACCCATGCCTGTCACACATGCCAGCGCTGCCCAGAGGAGGGGCGCATAGG
CAGGAATCCCAACAAACCTGGAGATGAGTATCTGTATGGAGGTGGGTGCGCAGAGACTGACGAAGACCATGCACACTGG
CTTGAAGCAAGAATGCTCCTTGACAATATTTACCTCCAAGATGGCCTCATAGCCTCGCTCTATCGACCTGAGGCCGACAAA
GTAGCAGCCATTGAGGGAGAGTTCAAGCTTAGGACGGAGCAAAGGAAGACCTTTGTGGAACTCATGAAAAGAGGAGAT
CTTCCTGTTTGGCTGGCCTATCAGGTTGCATCTGCCGGAATAACCTACACAGATAGAAGATGGTGCTTTGATGGCACGACC
AACAACACCATAATGGAAGACAGTGTGCCGGCAGAGGTGTGGACCAGACACGGAGAGAAAAGAGTGCTCAAACCGAGG
TGGATGGACGCCAGAGTTTGTTCAGATCATGCGGCCCTGAAGTCATTCAAGGAGTTTGCCGCTGGGAAAAGAGGAGCGG
CTTTTGGAGTGATGGAAGCCCTGGGAACACTGCCAGGACACATGACAGAGAGATTCCAGGAAGCCATTGACAACCTCGC
TGTGCTCATGCGGGCAGAGACTGGAAGCAGGCCTTACAAAGCCGCGGCGGCCCAATTGCCGGAGACCCTAGAGACCATT
ATGCTTTTGGGGTTGCTGGGAACAGTCTCGCTGGGAATCTTCTTCGTCTTGATGAGGAACAAGGGCATAGGGAAGATGG
GCTTTGGAATGGTGACTCTTGGGGCCAGCGCATGGCTCATGTGGCTCTCGGAAATTGAGCCAGCCAGAATTGCATGTGTC
CTCATTGTTGTGTTTCTATTGCTGGTGGTGCTCATACCTGAGCCAGAAAAGCAAAGATCTCCCCAGGACAACCAAATGGCA
ATCATCATCATGGTAGCAGTAGGTCTTCTGGGCTTGATTACCGCCAATGAACTCGGATGGTTGGAGAGAACAAAGAGTGA
CCTAAGCCATCTAATGGGAAGGAGAGAGGAGGGGGCAACCATAGGATTCTCAATGGACATTGACCTGCGGCCAGCCTCA
```

-continued

```
GCTTGGGCCATCTATGCTGCCTTGACAACTTTCATTACCCCAGCCGTCCAACATGCAGTGACCACTTCATACAACAACTACT
CCTTAATGGCGATGGCCACGCAAGCTGGAGTGTTGTTTGGTATGGGCAAAGGGATGCCATTCTACGCATGGGACTTTGGA
GTCCCGCTGCTAATGATAGGTTGCTACTCACAATTAACACCCCTGACCCTAATAGTGGCCATCATTTTGCTCGTGGCGCACT
ACATGTACTTGATCCCAGGGCTGCAGGCAGCAGCTGCGCGTGCTGCCCAGAAGAGAACGGCAGCTGGCATCATGAAGAA
CCCTGTTGTGGATGGAATAGTGGTGACTGACATTGACACAATGACAATTGACCCCCAAGTGGAGAAAAAGATGGGACAG
GTGCTACTCATAGCAGTAGCCGTCTCCAGCGCCATACTGTCGCGGACCGCCTGGGGGTGGGGGGAGGCTGGGGCCCTGA
TCACAGCCGCAACTTCCACTTTGTGGGAAGGCTCTCCGAACAAGTACTGGAACTCCTCTACAGCCACTTCACTGTGTAACA
TTTTTAGGGGAAGTTACTTGGCTGGAGCTTCTCTAATCTACACAGTAACAAGAAACGCTGGCTTGGTCAAGAGACGTGGG
GGTGGAACAGGAGAGACCCTGGGAGAGAAATGGAAGGCCCGCTTGAACCAGATGTCGGCCCTGGAGTTCTACTCCTACA
AAAAGTCAGGCATCACCGAGGTGTGCAGAGAAGAGGCCCGCCGCGCCCTCAAGGACGGTGTGGCAACGGGAGGCCATG
CTGTGTCCCGAGGAAGTGCAAAGCTGAGATGGTTGGTGGAGCGGGATACCTGCAGCCCTATGGAAAGGTCATTGATCT
TGGATGTGGCAGAGGGGGCTGGAGTTACTACGCCGCCACCATCCGCAAAGTTCAAGAAGTGAAAGGATACACAAAAGG
AGGCCCTGGTCATGAAGAACCCGTGTTGGTGCAAAGCTATGGGTGGAACATAGTCCGTCTTAAGAGTGGGGTGGACGTC
TTTCATATGGCGGCTGAGCCGTGTGACACGTTGCTGTGTGACATAGGTGAGTCATCATCTAGTCCTGAAGTGGAAGAAGC
ACGGACGCTCAGAGTCCTCTCCATGGTGGGGGATTGGCTTGAAAAAAGACCAGGAGCCTTTTGTATAAAGGTGTTGTGCC
CATACACCAGCACTATGATGGAAACCCTGGAGCGACTGCAGCGTAGGTATGGGGAGGACTGGTCAGAGTGCCACTCTC
CCGCAACTCTACACATGAGATGTATTGGGTCTCTGGAGCGAAAAGCAACACCATAAAAAGTGTGTCCACCACGAGCCAGC
TCCTCTTGGGGCGCATGGACGGGCCTAGGAGGCCAGTGAAATATGAGGAGGATGTGAATCTCGGCTCTGGCACGCGGGC
TGTGGTAAGCTGCGCTGAAGCTCCCAACATGAAGATCATTGGTAACCGCATTGAAAGGATCCGCAGTGAGCACGCGGAA
ACGTGGTTCTTTGACGAGAACCACCCATATAGGACATGGGCTTACCATGGAAGCTATGAGGCCCCCACACAAGGGTCAGC
GTCCTCTCTAATAAACGGGGTTGTCAGGCTCCTGTCAAAACCCTGGGATGTGGTGACTGGAGTCACAGGAATAGCCATGA
CCGACACCACACCGTATGGTCAGCAAAGAGTTTTCAAGGAAAAAGTGGACACTAGGGTGCCAGACCCCCAAGAAGGCAC
TCGTCAGGTTATGAGCATGGTCTCTTCCTGGTTGTGGAAAGAGCTAGGCAAACACAAACGGCCACGAGTCTGTACCAAAG
AAGAGTTCATCAACAAGGTTCGTAGCAATGCAGCATTAGGGGCAATATTTGAAGAGGAAAAAGAGTGGAAGACTGCAGT
GGAAGCTGTGAACGATCCAAGGTTCTGGGCTCTAGTGGATAAGGAAAGAGAGCACCACCTGAGAGGAGAGTGCCAGAG
TTGTGTGTACAACATGATGGGAAAAAGAGAAAAGAAACAAGGGGAATTTGGAAAGGCCAAGGGCAGCCGCGCCATCTG
GTATATGTGGCTAGGGGCTAGATTTCTAGAGTTCGAAGCCCTTGGATTCTTGAACGAGGATCACTGGATGGGGAGAGAG
AACTCAGGAGGTGGTGTTGAAGGGCTGGGATTACAAAGACTCGGATATGTCCTAGAAGAGATGAGTCGTATACCAGGAG
GAAGGATGTATGCAGATGACACTGCTGGCTGGGACACCCGCATCAGCAGGTTTGATCTGGAGAATGAAGCTCTAATCACC
AACCAAATGGAAAAGGGCACAGGGCCTTGGCATTGGCCATAATCAAGTACACATACCAAAACAAAGTGGTAAAGGTCC
TTAGACCAGCTGAAAAAGGGAAAACAGTTATGGACATTATTTCGAGACAAGACCAAAGGGGGAGCGGACAAGTTGTCAC
TTACGCTCTTAACACATTTACCAACCTAGTGGTGCAACTCATTCGGAATATGGAGGCTGAGGAAGTTCTAGAGATGCAAG
ACTTGTGGCTGCTGCGGAGGTCAGAGAAAGTGACCAACTGGTTGCAGAGCAACGGATGGGATAGGCTCAAACGAATGG
CAGTCAGTGGAGATGATTGCGTTGTGAAGCCAATTGATGATAGGTTTGCACATGCCCTCAGGTTCTTGAATGATATGGGA
AAAGTTAGGAAGGACACACAAGAGTGGAAACCCTCAACTGGATGGGACAACTGGGAAGAAGTTCCGTTTTGCTCCCACC
ACTTCAACAAGCTCCATCTCAAGGACGGGAGGTCCATTGTGGTTCCCTGCCGCCACCAAGATGAACTGATTGGCCGGGCC
CGCGTCTCTCCAGGGGCGGATGGAGCATCCGGGAGACTGCTTGCCTAGCAAAATCATATGCGCAAATGTGGCAGCTCCT
TTATTTCCACAGAAGGGACCTCCGACTGATGGCCAATGCCATTTGTTCATCTGTGCCAGTTGACTGGGTTCCAACTGGGAG
AACTACCTGGTCAATCCATGGAAAGGGAGAATGGATGACCACTGAAGACATGCTTGTGGTGTGGAACAGAGTGTGGATT
GAGGAGAACGACCACATGGAAGACAAGACCCCAGTTACGAAATGGACAGACATCCCCTATTTGGGAAAAAGGGAAGACT
TGTGGTGTGGATCTCTCATAGGGCACAGACCGCGCACCACCTGGGCTGAGAACATTAAAAACACAGTCAACATGGTGCGC
```

-continued

AGGATCATAGGTGATGAAGAAAAGTACATGGACTACCTATCCACCCAAGTTCGCTACTTGGGTGAAGAAGGGTCTACACC

TGGAGTGCTGTAAGCACCAGTCTTAATGTTGTCAGGCCTGCTAGTCAGCCACAGCTTGGGGAAAGCTGTGCAGCCTGTGA

CCCCCCCAGGAGAAGCTGGGAAACCAAGCCTATAGTCAGGCCGAGAACGCCATGGCACGGAAGAAGCCATGCTGCCTGT

GAGCCCCTCAGAGGACACTGAGTCAAAAAACCCCACGCGCTTGGAGGCGCAGGATGGGAAAAGAAGGTGGCGACCTTC

CCCACCCTTCAATCTGGGGCCTGAACTGGAGATCAGCTGTGGATCTCCAGAAGAGGGACTAGTGGTTAGAGGAG

KU744693.1 Zika virus isolate VE_Ganxian, China, complete genome

SEQ ID NO: 10

GTTGTTACTGTTGCTGACTCAGACTGCGACAGTTCGAGTTTGAAGCGAAAGCTAGCAACAGTATCAACAGGTTTTATTTGG

ATTTGGAAACGAGAGTTTCTGGTCATGAAAAACCCAAAAAAGAAATCCGGAGGATTCCGGATTGTCAATATGCTAAAACG

CGGAGTAGCCCGTGTGAGCCCCTTTGGGGGCTTGAAGAGGCTGCCAGCCGGACTTCTGCTGGGTCATGGGCCCATCAGG

ATGGTCTTGGCAATTCTAGCCTTTTTGAGATTCACGGCAATCAAGCCATCACTGGGTCTCATCAATAGATGGGGTTCAGTG

GGGAAAAAAGATGCTATGGAAATAATAAAGAAGTTCAAGAAAGATCTGGCTGCCATGCTGAGAATAATCAATGCTAGGA

AGGAGAAGAAGAGACGAGGCGCAGATACTAGTGTCGGAATTGTTGGCCTCCTGCTGACCACAGCTATGGCAGCGGAGG

TCACTAGACGTGGGAGTGCATACTATATGTACTTGGACAGAAACGATGCTGGGGAGGCCATATCTTTTCCAACCACATTG

GGGATGAATAAGTGTTATATACAGATCATGGATCTTGGACACATGTGTGATGCCACCATGAGCTATGAATGCCCTATGCT

GGATGAGGGGGTGGAACCAGATGACGTCGATTGTTGGTGCAACACGACGTCAACTTGGGTTGTGTACGGAACCTGCCAT

CACAAAAAAGGTGAAGCACGGAGATCTAGAAGAGCTGTGACGCTCCCTTCCCATTCCACTAGGAAGCTGCAAACGCGGT

CGCAAACCTGGTTGGAATCAAGAGAATACACAAAGCACTTGATTAGAGTCGAAAATTGGATATTCAGGAACCCTGGCTTC

GCGTTAGCAGCAGCTGCCATCGCTTGGCTTTTGGGAAGCTCAACGAGCCAAAAAGTCATATACTTGGTCATGATACTGCT

GATTGCCCCGGCATACAGCATCAGGTGCATAGGAGTCAGCAATAGGGACTTTGTGGAAGGTATGTCAGGTGGGACTTGG

GTTGATGTTGTCTTGGAACATGGAGGTTGTGTCACCGCAATGGCACAGGACAAACCGACTGTCGACATAGAGCTGGTTAC

AACAACAGTCAGCAACATGGCGGAGGTAAGATCCTACTGCTATGAGGCATCAATATCAGACATGGCTTCGGACAGCCGCT

GCCCAACACAAGGTGAAGCCTACCTTGACAAGCAATCAGACACTCAATATGTTTGCAAAAGAACGTTAGTGGACAGAGGC

TGGGGAAATGGATGTGGACTTTTTGGCAAAGGGAGTCTGGTGACATGCGCTAAGTTTGCATGCTCCAAGAAAATGACCG

GGAAGAGCATCCAGCCAGAGAATCTGGAGTACCGGATAATGCTGTCAGTTCATGGCTCCCAGCACAGTGGGATGCTCGTT

AATGACACAGGACATGAAACTGATGAGAATAGAGCGAAGGTTGAGATAACGCCCAATTCACCAAGAGCCGAAGCCACCC

TGGGGGGTTTTGGAAGCCTAGGACTTGATTGTGAACCGAGGACAGGCCTTGACTTTTCAGATTTGTATTACTTGACTATGA

ATAACAAGCACTGGTTGGCTCACAAGGAGTGGTTCCACGACATTCCATTACCTTGGCACGCTGGGGCAGCCACCGGAACT

CCACACTGGAACAACAAAGAAGCACTGGTAGAGTTCAAGGACGCACATGCCAAAAGGCAAACTGTCGTGGTTCTAGGGA

GTCAAGAAGGAGCAGTTCACACGGCCCTTGCTGGAGCTCTGGAGGCTGAGATGGATGGTGCAAAGGGAAGGCTGTCCTC

TGGCCACTTGAAATGTCGCCTGAAAATGGATAAACTTAGATTGAAGGGCGTGTCATACTCCTTGTGTACCGCAGCGTTCAC

ATTCACCAAGATCCCGGCTGAAACAGTGGACGGGACAGTCACAGTGGAGGGACAGTACGGAGGGACAGATGGACCTTG

CAAGGTTCCAGCTCAGATGGCGGTGGACATGCAGACTCTGACCCCAGTTGGGAGGTTGATAACCGCTAACCCCGTAATCA

CTGAAAGCACTGAGAACTCTAAGATGATGCTGGAACTTGATCCACCATTTGGGGACTCTTACATTGTCATAGGAGTCGGG

GAGAAGAAGATCACCCACCACTGGCACAGGAGTGGCAGCACCATTGGAAAAGCATTTGAAGCCACTGTGAGAGGTGCCA

AGAGAATGGCAGTCTTGGGAGACACAGCCTGGGACTTTGGATCAGTTGGAGGCGCTCTCAACTCATTGGGCAAGGGCAT

CCATCAAATTATTGGAGCAGCTTTCAAATCATTGTTTGGAGGAATGTCCTGGTTCTCACAAATTCTCATTGGGACGTTGCTG

ATGTGGTTGGGTCTGAACACAAAGAATGGATCTATTTCCCTTATGTGCTTGGCCTTAGGGGAGTGTTGATCTTCTTATCC

ACAGCCGTCTCAGGTGGTGTGGGGTGCTCGGTGGACTTCTCAAAGAAGGAGACGAGATGCGGTACAGGGGTGTTCGTCT

ATAACGATGTTGAAGCTGGAGGGACAGGTACAAGTACCATCCTGACTCCCCCCGTAGATTGGCAGCAGCAGTCAAGCA

AGCCTGGGAAGATGGTATCTGCGGGATCTCCTCTGTTTCAAGAATGGAAAACATCATGTGGAGATCAGTAGAAGGGGAG

-continued

```
CTCAACGCAATCCTGGAAGAGAATGGAGTTCAACTGACGGTCGTTGTGGGATCTGTAAAAAACCCCATGTGGAGAGGTC
CACAGAGATTGCCCGTGCCTGTGAACGAGCTGCCCCACGGCTGGAAGGCTTGGGGGAAATCGTACTTCGTCAGAGCAGC
AAAGACAAATAACAGCTTTGTCGTGGATGGTGACACACTGAAGGAATGCCCACTCAAACATAGAGCATGGAACAGCTTTC
TTGTGGAGGATCATGGGTTCGGGGTATTTCACACTAGTGTCTGGCTCAAGGTTAGAGAAGACTATTGGTTAGAGTGTGAT
CCAGCCGTTATTGGAACAGCTGTTAAGGGAAAGGAGGCTGTACACAGTGATCTAGGCTACTGGATTGAGAGTGAGAAGA
ATGACACATGGTGGCTGAAGAGGGCCCATCTGATCGAGATGAAAACATGTGAATGGCCAAAGTCCCACACATTGTGGAC
AGATGGAATAGAAGAGAGTGATCTGATCATACCCAAGTCTTTAGCTGGGCCACTCAGCCATCACAATGCCAGAGAGGGCT
ACAGGACCCAAATGAAAGGGCCATGGCACAGTGAAGAGCTTGAAATTCGGTTTGAGGAATGCCCAGGCACTAAGGTCCA
CGTGGAGGAAACATGTGGAACAAGAGGACCATCTCTGAGATCAACCACTGCAAGCGGAAGGGTGATCGAGGAATGGTG
CTCCAGGGAGTGCACAATGCCCCCACTGTCCTTCCAGGCTAAAGATGGCTGTTGGTATGGAATGGAGATAAGGCCCAGG
AAAGAACCAGAAAGCAACTTAGTAAGGTCAATGGTGACTGCAGGATCAACTGATCACATGGATCACTTCTCCCTTGGAGT
GCTTGTGATTCTGCTCATGGTGCAGGAAGGGCTGAAGAAGAGAATGACCACAAAGATCATCATAAGCACATCAATGGCA
GTGCTGGTAGCTATGATCCTGGGAGGATTTTCAATGAGTGACCTGGCTAAGCTTGCAATTTTGATGGGTGCCACCTTCGC
GGAAATGAACACTGGAGGAGATGTAGCTCATCTGGCGCTGATAGCGGCATTCAAAGTCAGACCAGCGTTGCTGGTATCTT
TCATCTTCAGAGCTAATTGGACACCCCGTGAAAGCATGCTGCTGGCCTTGGCCTCGTGTCTTTTGCAAACTGCGATCTCCG
CCTTGGAAGGCGACCTGATGGTTCTCATCAATGGTTTTGCTTTGGCTGGTTGGCAATACGAGCGATGGTTGTTCCACGCA
CTGATAACATCACCTTAGCAATCCTGGCTGCTCTGACACCACTGGCCCGGGGCACACTGCTTGTGGCGTGGAGAGCAGGC
CTTGCTACTTGCGGGGGGTTTATGCTCCTCTCTCTGAAGGGAAAAGGCAGTGTGAAGAAGAACTTACCATTTGTCATGGC
CCTGGGACTAACCGCTGTGAGGCTGGTCGACCCCATCAACGTGGTGGGACTGCTGTTGCTCACAAGGAGTGGGAAGCGG
AGCTGGCCCCCTAGCGAAGTACTCACAGCTGTTGGCCTGATATGCGCATTGGCTGGAGGGTTCGCCAAGGCAGATATAGA
GATGGCTGGGCCCATGGCCGCGGTCGGTCTGCTAATTGTCAGTTACGTGGTCTCAGGAAAGAGTGTGGACATGTACATTG
AAAGAGCAGGTGACATCACATGGGAAAAAGATGCGGAAGTCACTGGAAACAGTCCCCGGCTCGATGTGGCGCTAGATG
AGAGTGGTGATTTCTCCCTGGTGGAGGATGACGGTCCCCCCATGAGAGAGATCATACTCAAGGTGGTCCTGATGACCATC
TGTGGCATGAACCCAATAGCCATACCCTTTGCAGCTGGAGCGTGGTACGTATACGTGAAGACTGGAAAAAGGAGTGGTG
CTCTATGGGATGTGCCTGCTCCCAAGGAAGTAAAAAAGGGGGAGACCACAGATGGAGTGTACAGAGTAATGACTCGCAG
ACTGCTAGGTTCAACACAAGTTGGAGTGGGAGTTATGCAAGAGGGGGTCTTTCACACTATGTGGCACGTCACAAAAGGA
TCCGCGCTGAGAAGCGGTGAAGGGAGACTTGATCCATACTGGGGAGATGTCAAGCAGGATCTGGTGTCATACTGTGGTC
CATGGAAGCTAGATGCCGCCTGGGACGGGCACAGCGAGGTGCAGCTCTTGGCCGTGCCCCCCGGAGAGAGAGCGAGGA
ACATCCAGACTCTGCCCGGAATATTTAAGACAAAGGATGGGGACATTGGAGCGGTTGCACTGGATTACCCAGCAGGAAC
TTCAGGATCTCCAATCCTAGACAAGTGTGGGAGAGTGATAGGACTTTATGGCAATGGGGTCGTGATCAAAAATGGGAGT
TATGTTAGTGCCATCACCCAAGGGAGGAGGGAGGAAGAGACTCCTGTTGAGTGCTTCGAGCCTTCGATGCTGAAGAAGA
AGCAGCTAACTGTCTTAGACTTGCATCCTGGAGCTGGGAAAACCAGGAGAGTTCTTCCTGAAATAGTCCGTGAAGCCATA
AAAACAAGACTCCGTACTGTGATCTTGGCTCCAACCAGGGTTGTCGCTGCTGAAATGGAGGAGGCCCTTAGAGGGCTTCC
AGTGCGTTATATGACAACAGCAGTCAATGTCACCCACTCTGGAACAGAAATCGTCGACTTAATGTGCCATGCCACCTTCAC
TTCACGTCTACTACAGCCAATTAGAGTCCCCAACTATAATCTGTATATTATGGATGAGGCCCACTTCACAGATCCCTCAAGT
ATAGCAGCAAGAGGATACATTTCAACAAGGGTTGAGATGGGCGAGGCGGCTGCCATCTTCATGACCGCCACGCCACCAG
GAACCCGTGACGCATTTCCGGACTCCAACTCACCAATTATGGACACCGAAGTGGAAGTCCCAGAGAGAGCCTGGAGCTCA
GGCTTTGATTGGGTGACGGAGTATTCTGGAAAAACAGTTTGGTTTGTTCCACGCGTGAGGAACGGCAATGAGATCGCAG
CTTGTCTGACAAAGGCTGGAAAACGGGTCATACAGCTCAGCAGAAAGACTTTTGAGACAGAGTTCCAGAAAACAAAACAT
CAAGAGTGGGACTTTGTCGTGACAACTGACATTTCAGAGATGGGCGCAACTTTAAAGCTGACCGTGTCATAGATTCCAG
GAGATGCCTAAAGCCGGTCATACTTGGTGGCGAGAGAGTCATTCTGGCTGGACCCATGCCTGTCACACATGCCAGCGCTG
```

-continued

```
CCCAGAGGAGGGGGCGCATAGGCAGGAATCCCAACAAACCTGGAGATGAGTATCTGTATGGAGGTGGGTGCGCAGAGA
CTGACGAAGACCATGCACACTGGCTTGAAGCAAGAATGCTCCTTGACAATATTTACCTCCAAGATGGCCTCATAGCCTCGC
TCTATCGACCTGAGGCCGACAAAGTAGCAGCCATTGAGGGAGAGTTCAAGCTTAGGACGGAGCAAAGGAAGACCTTTGT
GGAACTCATGAAAAGAGGAGATCTTCCTGTTTGGCTGGCCTATCAGGTTGCATCTGCCGAATAACCTACACAGATAGAA
GATGGTGCTTTGATGGCACGACCAACAACACCATAATGGAAGACAGTGTGCCGGCAGAGGTGTGGACCAGACACGGAG
AGAAAAGAGTGCTCAAACCGAGGTGGATGGACGCCAGAGTTTGTTCAGATCATGCGGCCCTGAAGTCATTCAAGGAGTT
TGCCGCTGGGAAAAGAGGAGCGGCTTTTGGAGTGATGGAAGCCCTGGGAACACTGCCAGGACACATGACAGAGAGATT
CCAGGAAGCCATTGACAACCTCGCTGTGCTCATGCGGGCAGAGACTGGAAGCAGGCCTTACAAAGCCGCGGCGGCCCAA
TTGCCGGAGACCCTAGAGACCATTATGCTTTTGGGGTTGCTGGGAACAGTCTCGCTGGGAATCTTTTTCGTCTTGATGAGG
AACAAGGGCATAGGGAAGATGGGCTTTGGAATGGTGACTCTTGGGGCCAGCGCATGGCTCATGTGGCTCTCGGAAATTG
AGCCAGCCAGAATTGCATGTGTCCTCATTGTTGTGTTCCTATTGCTGGTGGTGCTCATACCTGAGCCAGAAAAGCAAAGAT
CTCCCCAGGACAACCAAATGGCCATCATCATCATGGTAGCAGTAGGTCTTCTGGGCTTGATTACCGCCAATGAACTCGGAT
GGTTGGAGAGAACAAAGAGTGACCTAAGCCATCTAATGGGAAGGAGAGAGGAGGGGGCAACCATGGGATTCTCAATGG
ACATTGACCTGCGGCCAGCCTCAGCTTGGGCCATCTATCCTGCCTTGACATCTTTCATTACCCCAGCCGTCCAACATGCAGT
GACCACTTCATACAACAACTACTCCTTAATGGCGATGGCCACGCAAGCTGGAGTGTTGTTTGGTATGGGCAAAGGGATGC
CATTCTACGCATGGGACTTTGGAGTCCCGCTGCTAATGATAGGTTGCTACTCACAATTAACGCCCCTGACCCTAATAGTGG
CCATCATTTTGCTCGTGGCGCACTACATGTACTTGATCCCAGGGCTGCAGGCAGCAGCTGCGCGTGCTGCCCAGAAGAGA
ACGGCAGCTGGCATCATGAAGAACCCTGTTGTGGAGGGAATAGTGGTGACTGACATTGACACAATGACAATTGACCCCC
AAGTGGAGAAAAAGATGGGACAGGTGCTACTCATGGCAGTAGCCGTCTCCAGCGCCATACTGTCGAGGACCGCCTGGGG
GTGGGGGAGGCTGGGGCCCTGATCACAGCCGCAACTTCCACTTTGTGGGAAGGCTCTCCGAACAAGTACTGGAACTCC
TCTACAGCCACCTCACTGTGTAACATTTTTAGGGGAAGTTACTTGGCTGGAGCTTCTCTAATCTACACAGTAACAAGAAAC
GCTGGCTTGGTCAAGAGACGTGGGGGTGGAACAGGAGAGACCCTGGGAGAGAAATGGAAGGCCCGCTTGAACCAGAT
GTCGGCCCTGGAGTTCTACTCCTACAAAAAGTCAGGCATCACCGAGGTGTGCAGAGAAGAGGCCCGCCGCGCCCTCAAG
GACGGTGTGGCAACGGGAGGCCATGCTGTGTCCCGAGGAAGTGCAAAGCTGAGATGGTTGGTGGAGCGGGGATACCTG
CAGCCCTATGGAAAGGTCATTGATCTTGGATGTGGCAGAGGGGCTGGAGTTACTACGCCGCCACCATCCGCAAAGTTCA
AGAAGTGAAAGGATACACAAAAGGAGGCCCTGGTCATGAAGAACCCGTGTTGGTGCAAAGCTATGGGTGGAACATAGT
CCGTCTTAAGAGTGGGGTGGACGTCTTTCATATGGCGGCTGAGCCGTGTGACACGTTGCTGTGTGACATAGGTGAGTCAT
CATCTAGTCCTGAAGTGGAAGAAGCACGGACGCTCAGAGTCCTCTCCATGGTGGGGATTGGCTTGAAAAAGACCAGG
AGCCTTTTGTATAAAAGTGTTGTGCCCATACACCAGCACTATGATGGAAACCCTGGAGCGACTGCAGCGTAGGTATGGGG
GAGGACTGGTCAGAGTGCCACTCTCCCGCAACTCTACACATGAGATGTACTGGGTCTCTGGAGCGAAAAGCAACACCATA
AAAAGTGTGTCCACCACGAGCCAGCTCCTCTTGGGGCGCATGGACGGGCCTAGGAGGCCAGTGAAATATGAGGAGGAT
GTGAATCTCGGCTCTGGCACGCGGGCTGTGGTAAGCTGCGCTGAAGCTCCCAACATGAAGATCATTGGTAACCGCATTGA
AAGGATCCGCGCTGAGAAAGCGGAAACGTGGTTCTTTGACGAGAACCACCCATATAGGACATGGGCTTACCATGGAAGC
TATGATGCCGCCACACAAGGGTCAGCGTCCTCTCTAATAAACGGGGTTGTCAGGCTCCTGTCAAAACCCTGGGATGTGGT
GACTGGAGTCACAGGAATAGCCATGACCGACACCACACCGTATGGTCAGCAAAGAGTTTTCAAGGAAAAAGTGGACACT
AGGGTGCCAGACCCCCAAGAAGGCACTCGTCAGGTTATGAGCATGGTCTCTTCCTGGTTGTGGAAAGAGCTAGGCAAAC
ACAAACGGCCACGAGTCTGTACCAAAGAAGAGTTCATCAACAAGGTTCGTAGCAATGCAGCATTAGGGGCAATATTTGAA
GAGGAAAAAGAGTGGAAGACTGCAGTGGAAGCTGTGAACGATCCAAGGTTCTGGGCTCTAGTGGACAAGGAAAGAGAG
CACCACCTGAGAGGAGAGTGCCAGAGTTGTGTGTACATCACAATGGGAAAAAGAGAAAAGAAACAAGGGGAATTTGGA
AAGGCCAAGGGCAGCCGCGCCATCTGGTATATGTGGCTAGGGGCTAGATTTCTAGAGTTCGAAGCCCTTGGATTCTTGAA
```

-continued

```
CGAGGATCACTGGATGGGGAGAGAGAACTCAGGAGGTGGTGTTGAAGGGCTGGGATTACAAAGACTCGGATATGTCCT
AGAAGAGATGAGTCGCATACCAGGAGGAAGGATGTATGCAGATGACACTGCTGGCTGGGACACCCGCATCAGCAGGTTT
GATCTGGAGAATGAAGCTCTAATCACCAACCAAATGGAGAAAGGGCACAGGGCCTTGGCATTGGCCATAATCAAGTACA
CATACCAAAACAAAGTGGTAAAGGTCCTTAGACCAGCTGAAAAAGGGAAGACAGTTATGGACATTATTTCGAGACAAGA
CCAAAGGGGGAGCGGACAAGTTGTCACTTACGCTCTCAACACATTTACCAACCTAGTGGTGCAACTCATTCGGAATATGG
AGGCTGAGGAAGTTCTAGAGATGCAAGACTTGTGGCTGCTGCGGAGGTCAGAGAAAGTGACCAACTGGTTGCAGAGCA
ACGGATGGGATAGGCTCAAACGAATGGCGGTCAGTGGAGATGATTGCGTTGTGAAACCAATTGATGATAGGTTTGCACA
TGCCCTCAGGTTCTTGAATGATATGGGAAAAGTTAGGAAGGACACACAAGAGTGGAAACCCTCAACTGGATGGGACAAC
TGGGAAGAAGTTCCCTTCTGCTCCCACCACTTCAACAAGCTCCATCTCAAGGACGGGAGGTCCATTGTGGTTCCCTGCCGC
CACCAAGATGAACTGATTGGCCGGGCCCGCGTCTCTCCAGGGGCGGGATGGAGCATCCGGGAGACTGCTTGCCTAGCAA
AATCATATGCGCAAATGTGGCAGCTCCTTTATTTCCACAGAAGGGACCTCCGACTGATGGCCAATGCCATTTGTTCATCTG
TGCCAGTTGACTGGGTTCCAACTGGGAGAACTACCTGGTCAATCCATGGAAAGGGAGAATGGATGACCACTGAAGACAT
GCTTGTGGCGTGGAACAGAGTGTGGATTGAGGAGAACGACCACATGGAAGACAAGACCCCAGTCACGAAATGGACAGA
CATTCCCTATTTGGGAAAAAGGGAAGACTTGTGGTGTGGATCTCTCATAGGGCACAGACCGCGCACCACCTGGGCTGAGA
ACATTAAAAACACAGTCAACATGGTGCGCAGGATCATAGGTGATGAAGAAAAGTACATGGACTACCTATCCACCCAAGTT
CGCTACTTGGGTGAAGAAGGGTCTACACCTGGAGTGCTGTAAGCACCAATCTTAATGTTGTCAGGCCTGCTAGTCAGCCA
CAGCTTGGGGAAAGCTGTGCAGCCTGTGACCCCCCCAGGAGAAGCTGGGAAACCAAGCCTATAGTCAGGCCGAGAACGC
CATGGCACGGAAGAAGCCATGCTGCCTGTGAGCCCCTCAGAGGACACTGAGTCAAAAAACCCCACGCGCTTGGAGGCGC
AGGATGGGAAAAGAAGGTGGCGACCTTCCCCACCCTTCAATCTGGGGCCTGAACTGGAGATCAGCTGTGGATCTCCAGA
AGAGGGACTAGTGGTTAGAGGAGA
```

LC002520.1 Zika virus genomic RNA, strain: MR766-NIID, Uganda, complete genome
SEQ ID NO: 11

```
AGTTGTTGATCTGTGTGAGTCAGACTGCGACAGTTCGAGTCTGAAGCGAGAGCTAACAACAGTATCAACAGGTTTAATTT
GGATTTGGAAACGAGAGTTTCTGGTCATGAAAAACCCAAAGAAGAAATCCGGAGGATTCCGGATTGTCAATATGCTAAA
ACGCGGAGTAGCCCGTGTAAACCCCTTGGGAGGTTTGAAGAGGTTGCCAGCCGGACTTCTGCTGGGTCATGGACCCATCA
GAATGGTTTTGGCGATACTAGCCTTTTTGAGATTTACAGCAATCAAGCCATCACTGGGCCTTATCAACAGATGGGGTTCCG
TGGGGAAAAAAGAGGCTATGGAAATAATAAAGAAGTTCAAGAAAGATCTTGCTGCCATGTTGAGAATAATCAATGCTAG
GAAAGAGAGGAAGAGACGTGGCGCAGACACCAGCATCGGAATCATTGGCCTCCTGCTGACTACAGCCATGGCAGCAGA
GATCACTAGACGCGGGAGTGCATACTACATGTACTTGGATAGGAGCGATGCCGGGAAGGCCATTTCGTTTGCTACCACAT
TGGGAGTGAACAAGTGCCACGTACAGATCATGGACCTCGGGCACATGTGTGACGCCACCATGAGTTATGAGTGCCCTATG
CTGGATGAGGGAGTGGAACCAGATGATGTCGATTGCTGGTGCAACACGACATCAACTTGGGTTGTGTACGGAACCTGTC
ATCACAAAAAAGGTGAGGCACGGCGATCTAGAAGAGCCGTGACGCTCCCTTCTCACTCTACAAGGAAGTTGCAAACGCG
GTCGCAGACCTGGTTAGAATCAAGAGAATACACGAAGCACTTGATCAAGGTTGAAAACTGGATATTCAGGAACCCCGGG
TTTGCGCTAGTGGCCGTTGCCATTGCCTGGCTTTTGGGAAGCTCGACGAGCCAAAAAGTCATATACTTGGTCATGATACTG
CTGATTGCCCCGGCATACAGTATCAGGTGCATTGGAGTCAGCAATAGAGACTTCGTGGAGGGCATGTCAGGTGGGACCT
GGGTTGATGTTGTCTTGGAACATGGAGGCTGCGTTACCGTGATGGCACAGGACAAGCCAACAGTTGACATAGAGTTGGT
CACGACGACGGTTAGTAACATGGCCGAGGTAAGATCCTATTGCTACGAGGCATCGATATCGGACATGGCTTCGGACAGTC
GTTGCCCAACACAAGGTGAAGCCTACCTTGACAAGCAATCAGACACTCAATATGTCTGCAAAAGAACATTAGTGGACAGA
GGTTGGGGAAACGGTTGTGGACTTTTTGGCAAAGGGAGCTTGGTGACATGTGCCAAGTTTACGTGTTCTAAGAAGATGA
CCGGGAAGAGCATTCAACCGGAAAATCTGGAGTATCGGATAATGCTATCAGTGCATGGCTCCCAGCATAGCGGGATGAC
TGTCAATGATATAGGATATGAAACTGACGAAAATAGAGCGAAAGTCGAGGTTACGCCTAATTCACCAAGAGCGGAAGCA
ACCTTGGGAGGCTTTGGAAGCTTAGGACTTGACTGTGAACCAAGGACAGGCCTTGACTTTTCAGATCTGTATTACCTGACC
```

-continued

```
ATGAACAATAAGCATTGGTTGGTGCACAAAGAGTGGTTTCATGACATCCCATTGCCTTGGCATGCTGGGGCAGACACTGG

AACTCCACACTGGAACAACAAAGAGGCATTGGTAGAATTCAAGGATGCCCACGCCAAGAGGCAAACCGTCGTCGTTCTG

GGGAGCCAGGAAGGAGCCGTTCACACGGCTCTCGCTGGAGCTCTAGAGGCTGAGATGGATGGTGCAAAGGGAAAGCTG

TTCTCTGGCCATTTGAAATGCCGCCTAAAAATGGACAAGCTTAGATTGAAGGGCGTGTCATATTCCTTGTGCACTGCGGCA

TTCACATTCACCAAGGTCCCAGCTGAAACACTGCATGGAACAGTCACAGTGGAGGTGCAGTATGCAGGGACAGATGGAC

CCTGCAAGATCCCAGTCCAGATGGCGGTGGACATGCAGACCCTGACCCCAGTTGGAAGGCTGATAACCGCCAACCCCGTG

ATTACTGAAAGCACTGAGAACTCAAAGATGATGTTGGAGCTTGACCCACCATTTGGGGATTCTTACATTGTCATAGGAGTT

GGGGACAAGAAAATCACCCACCACTGGCATAGGAGTGGTAGCACCATCGGAAAGGCATTTGAGGCCACTGTGAGAGGC

GCCAAGAGAATGGCAGTCCTGGGGATACAGCCTGGGACTTCGGATCAGTCGGGGGTGTGTTCAACTCACTGGGTAAGG

GCATTCACCAGATTTTTGGAGCAGCCTTCAAATCACTGTTTGGAGGAATGTCCTGGTTCTCACAGATCCTCATAGGCACGC

TGCTAGTGTGGTTAGGTTTGAACACAAAGAATGGATCTATCTCCCTCACATGCTTGGCCCTGGGGGAGTGATGATCTTCC

TCTCCACGGCTGTTTCTGCTGACGTGGGGTGCTCAGTGGACTTCTCAAAAAAGGAAACGAGATGTGGCACGGGGTATTC

ATCTATAATGATGTTGAAGCCTGGAGGGACCGGTACAAGTACCATCCTGACTCCCCCCGCAGATTGGCAGCAGCAGTCAA

GCAGGCCTGGGAAGAGGGGATCTGTGGGATCTCATCCGTTTCAAGAATGGAAAACATCATGTGGAAATCAGTAGAAGGG

GAGCTCAATGCTATCCTAGAGGAGAATGGAGTTCAACTGACAGTTGTTGTGGGATCTGTAAAAAACCCCATGTGGAGAG

GTCCACAAAGATTGCCAGTGCCTGTGAATGAGCTGCCCCATGGCTGGAAAGCCTGGGGGAAATCGTATTTTGTTAGGGCG

GCAAAGACCAACAACAGTTTTGTTGTCGACGGTGACACACTGAAGGAATGTCCGCTTGAGCACAGAGCATGGAATAGTTT

TCTTGTGGAGGATCACGGGTTTGGAGTCTTCCACACCAGTGTCTGGCTTAAGGTCAGAGAAGATTACTCATTAGAATGTG

ACCCAGCCGTCATAGGAACAGCTGTTAAGGGAAGGGAGGCCGCGCACAGTGATCTGGGCTATTGGATTGAAAGTGAAAA

GAATGACACATGGAGGCTGAAGAGGGCCCACCTGATTGAGATGAAAACATGTGAATGGCCAAAGTCTCACACATTGTGG

ACAGATGGAGTAGAAGAAAGTGATCTTATCATACCCAAGTCTTTAGCTGGTCCACTCAGCCACCACAACACCAGAGAGGG

TTACAGAACCCAAGTGAAAGGGCCATGGCACAGTGAAGAGCTTGAAATCCGGTTTGAGGAATGTCCAGGCACCAAGGTT

TACGTGGAGGAGACATGCGGAACTAGAGGACCATCTCTGAGATCAACTACTGCAAGTGGAAGGGTCATTGAGGAATGGT

GCTGTAGGGAATGCACAATGCCCCCACTATCGTTTCGAGCAAAAGACGGCTGCTGGTATGGAATGGAGATAAGGCCCAG

GAAAGAACCAGAGAGCAACTTAGTGAGGTCAATGGTGACAGCGGGGTCAACCGATCATATGGACCACTTCTCTCTTGGA

GTGCTTGTGATTCTACTCATGGTGCAGGAGGGGTTGAAGAAGAGAATGACCACAAAGATCATCATGAGCACATCAATGG

CAGTGCTGGTAGTCATGATCTTGGGAGGATTTTCAATGAGTGACCTGGCCAAGCTTGTGATCCTGATGGGTGCTACTTTCG

CAGAAATGAACACTGGAGGAGATGTAGCTCACTTGGCATTGGTAGCGGCATTTAAAGTCAGACCAGCCTTGCTGGTCTCC

TTCATTTTCAGAGCCAATTGGACACCCCGTGAGAGCATGCTGCTAGCCCTGGCTTCGTGTCTTCTGCAAACTGCGATCTCT

GCTCTTGAAGGTGACTTGATGGTCCTCATTAATGGATTTGCTTTGGCCTGGTTGGCAATTCGAGCAATGGCCGTGCCACGC

ACTGACAACATCGCTCTACCAATCTTGGCTGCTCTAACACCACTAGCTCGAGGCACACTGCTCGTGGCATGGAGAGCGGG

CCTGGCTACTTGTGGAGGGATCATGCTCCTCTCCCTGAAAGGGAAAGGTAGTGTGAAGAAGAACCTGCCATTTGTCATGG

CCCTGGGATTGACAGCTGTGAGGGTAGTAGACCCTATTAATGTGGTAGGACTACTGTTACTCACAAGGAGTGGGAAGCG

GAGCTGGCCCCTAGTGAAGTTCTCACAGCCGTTGGCCTGATATGTGCACTGGCCGGAGGGTTTGCCAAGGCAGACATTG

AGATGGCTGGACCCATGGCTGCAGTAGGCTTGCTAATTGTCAGCTATGTGGTCTCGGGAAAGAGTGTGGACATGTACATT

GAAAGAGCAGGTGACATCACATGGGAAAGGACGCGGAAGTCACTGGAAACAGTCCTCGGCTTGACGTGGCACTGGAT

GAGAGTGGTGATTTCTCCTTGGTAGAGGAAGATGGTCCACCCATGAGAGAGATCATACTTAAGGTGGTCCTGATGGCCAT

CTGTGGCATGAACCCAATAGCTATACCTTTTGCTGCAGGAGCGTGGTATGTGTATGTGAAGACTGGGAAAAGGAGTGGC

GCCCTCTGGGACGTGCCTGCTCCCAAAGAAGTGAAGAAAGGAGAGACCACAGATGGAGTGTACAGAGTGATGACTCGCA

GACTGCTAGGTTCAACACAGGTTGGAGTGGGAGTCATGCAAGAGGGAGTCTTCCACACCATGTGGCACGTTACAAAAGG
```

-continued

```
AGCCGCACTGAGGAGCGGTGAGGGAAGACTTGATCCATACTGGGGGGATGTCAAGCAGGACTTGGTGTCATACTGTGG
GCCTTGGAAGTTGGATGCAGCTTGGGATGGACTCAGCGAGGTACAGCTTTTGGCCGTACCTCCCGGAGAGAGGGCCAGA
AACATTCAGACCCTGCCTGGAATATTCAAGACAAAGGACGGGGACATCGGAGCAGTTGCTCTGGACTACCCTGCAGGGA
CCTCAGGATCTCCGATCCTAGACAAATGTGGAAGAGTGATAGGACTCTATGGCAATGGGGTTGTGATCAAGAATGGAAG
CTATGTTAGTGCTATAACCCAGGGAAAGAGGGAGGAGGAGACTCCGGTTGAATGTTTCGAACCCTCGATGCTGAAGAAG
AAGCAGCTAACTGTCTTGGATCTGCATCCAGGAGCCGGAAAAACCAGGAGAGTTCTTCCTGAAATAGTCCGTGAAGCCAT
AAAAAAGAGACTCCGGACAGTGATCTTGGCACCAACTAGGGTTGTCGCTGCTGAGATGGAGGAGGCCTTGAGAGGACTT
CCGGTGCGTTACATGACAACAGCAGTCAACGTCACCCATTCTGGGACAGAAATCGTTGATTTGATGTGCCATGCCACTTTC
ACTTCACGCTTACTACAACCCATCAGAGTCCCTAATTACAATCTCTACATCATGGATGAAGCCCACTTCACAGACCCCTCAA
GTATAGCTGCAAGAGGATATATATCAACAAGGGTTGAAATGGGCGAGGCGGCTGCCATTTTTATGACTGCCACACCACCA
GGAACCCGTGATGCGTTTCCTGACTCTAACTCACCAATCATGGACACAGAAGTGGAAGTCCCAGAGAGAGCCTGGAGCTC
AGGCTTTGATTGGGTGACAGACCATTCTGGGAAAACAGTTTGGTTCGTTCCAAGCGTGAGAAACGGAAATGAAATCGCA
GCCTGTCTGACAAAGGCTGGAAAGCGGGTCATACAGCTCAGCAGGAAGACTTTTGAGACAGAATTTCAGAAAACAAAAA
ATCAAGAGTGGGACTTTGTCATAACAACTGACATCTCAGAGATGGGCGCCAACTTCAAGGCTGACCGGGTCATAGACTCT
AGGAGATGCCTAAAACCAGTCATACTTGATGGTGAGAGAGTCATCTTGGCTGGGCCCATGCCTGTCACGCATGCTAGTGC
TGCTCAGAGGAGAGGACGTATAGGCAGGAACCCTAACAAACCTGGAGATGAGTACATGTATGGAGGTGGGTGTGCAGA
GACTGATGAAGGCCATGCACACTGGCTTGAAGCAAGAATGCTTCTTGACAACATCTACCTCCAGGATGGCCTCATAGCCTC
GCTCTATCGGCCTGAGGCCGATAAGGTAGCCGCCATTGAGGGAGAGTTTAAGCTGAGGACAGAGCAAAGGAAGACCTTC
GTGGAACTCATGAAGAGAGGAGACCTTCCCGTCTGGCTAGCCTATCAGGTTGCATCTGCCGGAATAACTTACACAGACAG
AAGATGGTGCTTTGATGGCACAACCAACAACACCATAATGGAAGACAGCGTACCAGCAGAGGTGTGGACAAAGTATGGA
GAGAAGAGAGTGCTCAAACCGAGATGGATGGATGCTAGGGTCTGTTCAGACCATGCGGCCCTGAAGTCGTTCAAAGAAT
TCGCCGCTGGAAAAAGAGGAGCGGCTTTGGGAGTAATGGAGGCCCTGGGAACACTGCCAGGACACATGACAGAGAGGT
TTCAGGAAGCCATTGACAACCTCGCCGTGCTCATGCGAGCAGAGACTGGAAGCAGGCCTTATAAGGCAGCGGCAGCCCA
ACTGCCGGAGACCCTAGAGACCATTATGCTCTTAGGTTTGCTGGGAACAGTTTCACTGGGGATCTTCTTCGTCTTGATGCG
GAATAAGGGCATCGGGAAGATGGGCTTTGAATGGTAACCCTTGGGGCCAGTGCATGGCTCATGTGGCTTTCGGAAATT
GAACCAGCCAGAATTGCATGTGTCCTCATTGTTGTGTTTTTATTACTGGTGGTGCTCATACCCGAGCCAGAGAAGCAAAGA
TCTCCCCAAGATAACCAGATGGCAATTATCATCATGGTGGCAGTGGGCCTTCTAGGTTTGATAACTGCAAACGAACTTGGA
TGGCTGGAAAGAACAAAAAATGACATAGCTCATCTAATGGGAAGGAGAGAAGAAGGAGCAACCATGGGATTCTCAATG
GACATTGATCTGCGGCCAGCCTCCGCCTGGGCTATCTATGCCGCATTGACAACTCTCATCACCCCAGCTGTCCAACATGCG
GTAACCACTTCATACAACAACTACTCCTTAATGGCGATGGCCACACAAGCTGGAGTGCTGTTTGGCATGGGCAAAGGGAT
GCCATTTTATGCATGGGACCTTGGAGTCCCGCTGCTAATGATGGGTTGCTATTCACAATTAACACCCCTGACTCTGATAGT
AGCTATCATTCTGCTTGTGGCGCACTACATGTACTTGATCCCAGGCCTACAAGCGGCAGCAGCGCGTGCTGCCCAGAAAA
GGACAGCAGCTGGCATCATGAAGAATCCCGTTGTGGATGGAATAGTGGTAACTGACATTGACACAATGACAATAGACCC
CCAGGTGGAGAAGAAGATGGGACAAGTGTTACTCATAGCAGTAGCCATCTCCAGTGCTGTGCTGCTGCGGACCGCCTGG
GGATGGGGGGAGGCTGGAGCTCTGATCACAGCAGCGACCTCCACCTTGTGGGAAGGCTCTCCAAACAAATACTGGAACT
CCTCTACAGCCACCTCACTGTGCAACATCTTCAGAGGAAGCTATCTGGCAGGAGCTTCCCTTATCTATACAGTGACGAGAA
ACGCTGGCCTGGTTAAGAGACGTGGAGGTGGGACGGGAGAGACTCTGGGAGAGAAGTGGAAAGCTCGTCTGAATCAGA
TGTCGGCCCTGGAGTTCTACTCTTATAAAAAGTCAGGTATCACTGAAGTGTGTAGAGAGGAGGCTCGCCGTGCCCTCAAG
GATGGAGTGGCCACAGGAGGACATGCCGTATCCCGGGGAAGTGCAAAGCTCAGATGGTTGGTGGAGAGAGGATATCTG
CAGCCCTATGGGAAGGTTGTTGACCTCGGATGTGGCAGAGGGGGCTGGAGCTATTATGCCGCCACCATCCGCAAAGTGC
AGGAGGTGAGAGGATACACAAAGGGAGGTCCCGGTCATGAAGAACCCATGCTGGTGCAAAGCTATGGGTGGAACATAG
```

-continued

```
TTCGTCTCAAGAGTGGAGTGGACGTCTTCCACATGGCGGCTGAGCCGTGTGACACTCTGCTGTGTGACATAGGTGAGTCA

TCATCTAGTCCTGAAGTGGAAGAGACACGAACACTCAGAGTGCTCTCTATGGTGGGGGACTGGCTTGAAAAAAGACCAG

GGGCCTTCTGTATAAAGGTGCTGTGCCCATACACCAGCACTATGATGGAAACCATGGAGCGACTGCAACGTAGGCATGG

GGGAGGATTAGTCAGAGTGCCATTGTCTCGCAACTCCACACATGAGATGTACTGGGTCTCTGGGGCAAAGAGCAACATCA

TAAAAAGTGTGTCCACCACAAGTCAGCTCCTCCTGGGACGCATGGATGGCCCCAGGAGGCCAGTGAAATATGAGGAGGA

TGTGAACCTCGGCTCGGGTACACGAGCTGTGGCAAGCTGTGCTGAGGCTCCTAACATGAAAATCATCGGCAGGCGCATTG

AGAGAATCCGCAATGAACATGCAGAAACATGGTTTCTTGATGAAAACCACCCATACAGGACATGGGCCTACCATGGGAGC

TACGAAGCCCCCACGCAAGGATCAGCGTCTTCCCTCGTGAACGGGGTTGTTAGACTCCTGTCAAAGCCTTGGGACGTGGT

GACTGGAGTTACAGGAATAGCCATGACTGACACCACACCATACGGCCAACAAAGAGTCTTCAAAGAAAAAGTGGACACC

AGGGTGCCAGATCCCCAAGAAGGCACTCGCCAGGTAATGAACATAGTCTCTTCCTGGCTGTGGAAGGAGCTGGGGAAAC

GCAAGCGGCCACGCGTCTGCACCAAAGAAGAGTTTATCAACAAGGTGCGCAGCAATGCAGCACTGGGAGCAATATTTGA

AGAGGAAAAGAATGGAAGACGGCTGTGGAAGCTGTGAATGATCCAAGGTTTTGGGCCCTAGTGGATAGGGAGAGAGA

ACACCACCTGAGAGGAGAGTGTCACAGCTGTGTGTACAACATGATGGGAAAAAGAGAAAAGAAGCAAGGAGAGTTCGG

GAAAGCAAAAGGTAGCCGCGCCATCTGGTACATGTGGTTGGGAGCCAGATTCTTGGAGTTTGAAGCCCTTGGATTCTTGA

ACGAGGACCATTGGATGGGAAGAGAAAACTCAGGAGGTGGAGTCGAAGGGTTAGGATTGCAAAGACTTGGATACATTC

TAGAAGAAATGAATCGGGCACCAGGAGGAAAGATGTACGCAGATGACACTGCTGGCTGGGACACCCGCATTAGTAAGTT

TGATCTGGAGAATGAAGCTCTGATTACCAACCAAATGGAGGAAGGGCACAGAACTCTGGCGTTGGCCGTGATTAAATAC

ACATACCAAAACAAAGTGGTGAAGGTTCTCAGACCAGCTGAAGGAGGAAAAACAGTTATGGACATCATTTCAAGACAAG

ACCAGAGAGGGAGTGGACAAGTTGTCACTTATGCTCTCAACACATTCACCAACTTGGTGGTGCAGCTTATCCGGAACATG

GAAGCTGAGGAAGTGTTAGAGATGCAAGACTTATGGTTGTTGAGGAAGCCAGAGAAAGTGACCAGATGGTTGCAGAGC

AATGGATGGGATAGACTCAAACGAATGGCGGTCAGTGGAGATGACTGCGTTGTGAAGCCAATCGATGATAGGTTTGCAC

ATGCCCTCAGGTTCTTGAATGACATGGGAAAAGTTAGGAAAGACACACAGGAGTGGAAACCCTCGACTGGATGGAGCAA

TTGGGAAGAAGTCCCGTTCTGCTCCCACCACTTCAACAAGCTGTACCTCAAGGATGGGAGATCCATTGTGGTCCCTTGCCG

CCACCAAGATGAACTGATTGGCCGAGCTCGCGTCTCACCAGGGGCAGGATGGAGCATCCGGGAGACTGCCTGTCTTGCA

AAATCATATGCGCAGATGTGGCAGCTCCTTTATTTCCACAGAAGAGACCTTCGACTGATGGCTAATGCCATTTGCTCGGCT

GTGCCAGTTGACTGGGTACCAACTGGGAGAACCACCTGGTCAATCCATGGAAAGGGAGAATGGATGACCACTGAGGACA

TGCTCATGGTGTGGAATAGAGTGTGGATTGAGGAGAACGACCATATGGAGGACAAGACTCCTGTAACAAAATGGACAGA

CATTCCCTATCTAGGAAAAAGGGAGGACTTATGGTGTGGATCCCTTATAGGGCACAGACCCCGCACCACTTGGGCTGAAA

ACATCAAAGACACAGTCAACATGGTGCGCAGGATCATAGGTGATGAAGAAAGTACATGGACTATCTATCCACCCAAGTC

CGCTACTTGGGTGAGGAAGGGTCCACACCCGGAGTGTTGTAAGCACCAATTTTAGTGTTGTCAGGCCTGCTAGTCAGCCA

CAGTTTGGGAAAGCTGTGCAGCCTGTAACCCCCCCAGGAGAAGCTGGGAAACCAAGCTCATAGTCAGGCCGAGAACGC

CATGGCACGGAAGAAGCCATGCTGCCTGTGAGCCCCTCAGAGGACACTGAGTCAAAAAACCCCACGCGCTTGGAAGCGC

AGGATGGGAAAAGAAGGTGGCGACCTTCCCCACCCTTCAATCTGGGGCCTGAACTGGAGACTAGCTGTGAATCTCCAGC

AGAGGGACTAGTGGTTAGAGGAGACCCCCCGGAAAACGCAAAACAGCATATTGACGCTGGGAAAGACCAGAGACTCCA

TGAGTTTCCACCACGCTGGCCGCCAGGCACAGATCGCCGAACAGCGGCGGCCGGTGTGGGGAAATCCATGGTTTCT
```

AY632535.2 NC_012532.1 Zika virus strain MR 766, Uganda, complete genome

SEQ ID NO: 12

```
AGTTGTTGATCTGTGTGAGTCAGACTGCGACAGTTCGAGTCTGAAGCGAGAGCTAACAACAGTATCAACAGGTTTAATTT

GGATTTGGAAACGAGAGTTTCTGGTCATGAAAAACCCCAAAGAAGAAATCCGGAGGATCCGGATTGTCAATATGCTAAA

ACGCGGAGTAGCCCGTGTAAACCCCTTGGGAGGTTTGAAGAGGTTGCCAGCCGGACTTCTGCTGGGTCATGGACCCATCA

GAATGGTTTTGGCGATACTAGCCTTTTTGAGATTTACAGCAATCAAGCCATCACTGGGCCTTATCAACAGATGGGGTTCCG
```

-continued

```
TGGGGAAAAAAGAGGCTATGGAAATAATAAAGAAGTTCAAGAAAGATCTTGCTGCCATGTTGAGAATAATCAATGCTAG

GAAAGAGAGGAAGAGACGTGGCGCAGACACCAGCATCGGAATCATTGGCCTCCTGCTGACTACAGCCATGGCAGCAGA

GATCACTAGACGCGGGAGTGCATACTACATGTACTTGGATAGGAGCGATGCCGGGAAGGCCATTTCGTTTGCTACCACAT

TGGGAGTGAACAAGTGCCACGTACAGATCATGGACCTCGGGCACATGTGTGACGCCACCATGAGTTATGAGTGCCCTATG

CTGGATGAGGGAGTGGAACCAGATGATGTCGATTGCTGGTGCAACACGACATCAACTTGGGTTGTGTACGGAACCTGTC

ATCACAAAAAAGGTGAGGCACGGCGATCTAGAAGAGCCGTGACGCTCCCTTCTCACTCTACAAGGAAGTTGCAAACGCG

GTCGCAGACCTGGTTAGAATCAAGAGAATACACGAAGCACTTGATCAAGGTTGAAAACTGGATATTCAGGAACCCCGGG

TTTGCGCTAGTGGCCGTTGCCATTGCCTGGCTTTTGGGAAGCTCGACGAGCCAAAAAGTCATATACTTGGTCATGATACTG

CTGATTGCCCCGGCATACAGTATCAGGTGCATTGGAGTCAGCAATAGAGACTTCGTGGAGGGCATGTCAGGTGGGACCT

GGGTTGATGTTGTCTTGGAACATGGAGGCTGCGTTACCGTGATGGCACAGGACAAGCCAACAGTCGACATAGAGTTGGT

CACGACGACGGTTAGTAACATGGCCGAGGTAAGATCCTATTGCTACGAGGCATCGATATCGGACATGGCTTCGGACAGTC

GTTGCCCAACACAAGGTGAAGCCTACCTTGACAAGCAATCAGACACTCAATATGTCTGCAAAAGAACATTAGTGGACAGA

GGTTGGGGAAACGGTTGTGGACTTTTTGGCAAAGGGAGCTTGGTGACATGTGCCAAGTTTACGTGTTCTAAGAAGATGA

CCGGGAAGAGCATTCAACCGGAAAATCTGGAGTATCGGATAATGCTATCAGTGCATGGCTCCCAGCATAGCGGGATGAT

TGGATATGAAACTGACGAAGATAGAGCGAAAGTCGAGGTTACGCCTAATTCACCAAGAGCGGAAGCAACCTTGGGAGGC

TTTGGAAGCTTAGGACTTGACTGTGAACCAAGGACAGGCCTTGACTTTTCAGATCTGTATTACCTGACCATGAACAATAAG

CATTGGTTGGTGCACAAAGAGTGGTTTCATGACATCCCATTGCCTTGGCATGCTGGGGCAGACACCGGAACTCCACACTG

GAACAACAAAGAGGCATTGGTAGAATTCAAGGATGCCCACGCCAAGAGGCAAACCGTCGTCGTTCTGGGGAGCCAGGAA

GGAGCCGTTCACACGGCTCTCGCTGGAGCTCTAGAGGCTGAGATGGATGGTGCAAAGGGAAGGCTGTTCTCTGGCCATT

TGAAATGCCGCCTAAAAATGGACAAGCTTAGATTGAAGGGCGTGTCATATTCCTTGTGCACTGCGGCATTCACATTCACCA

AGGTCCCAGCTGAAACACTGCATGGAACAGTCACAGTGGAGGTGCAGTATGCAGGGACAGATGGACCCTGCAAGATCCC

AGTCCAGATGGCGGTGGACATGCAGACCCTGACCCCAGTTGGAAGGCTGATAACCGCCAACCCCGTGATTACTGAAAGC

ACTGAGAACTCAAAGATGATGTTGGAGCTTGACCCACCATTTGGGGATTCTTACATTGTCATAGGAGTTGGGGACAAGAA

AATCACCCACCACTGGCATAGGAGTGGTAGCACCATCGGAAAGGCATTTGAGGCCACTGTGAGAGGCGCCAAGAGAATG

GCAGTCCTGGGGGATACAGCCTGGGACTTCGGATCAGTCGGGGGTGTGTTCAACTCACTGGGTAAGGGCATTCACCAGA

TTTTTGGAGCAGCCTTCAAATCACTGTTTGGAGGAATGTCCTGGTTCTCACAGATCCTCATAGGCACGCTGCTAGTGTGGT

TAGGTTTGAACACAAAGAATGGATCTATCTCCCTCACATGCTTGGCCCTGGGGGGAGTGATGATCTTCCTCTCCACGGCTG

TTTCTGCTGACGTGGGGTGCTCAGTGGACTTCTCAAAAAAGGAAACGAGATGTGGCACGGGGTATTCATCTATAATGAT

GTTGAAGCCTGGAGGGACCGGTACAAGTACCATCCTGACTCCCCCCGCAGATTGGCAGCAGCAGTCAAGCAGGCCTGGG

AAGAGGGGATCTGTGGGATCTCATCCGTTTCAAGAATGGAAAACATCATGTGGAAATCAGTAGAAGGGGAGCTCAATGC

TATCCTAGAGGAGAATGGAGTTCAACTGACAGTTGTTGTGGGATCTGTAAAAAACCCCATGTGGAGAGGTCCACAAAGAT

TGCCAGTGCCTGTGAATGAGCTGCCCCATGGCTGGAAAGCCTGGGGGAAATCGTATTTTGTTAGGGCGGCAAAGACCAA

CAACAGTTTTGTTGTCGACGGTGACACACTGAAGGAATGTCCGCTTGAGCACAGAGCATGGAATAGTTTTCTTGTGGAGG

ATCACGGGTTTGGAGTCTTCCACACCAGTGTCTGGCTTAAGGTCAGAGAAGATTACTCATTAGAATGTGACCCAGCCGTCA

TAGGAACAGCTGTTAAGGGAAGGGAGGCCGCGCACAGTGATCTGGGCTATTGGATTGAAAGTGAAAAGAATGACACAT

GGAGGCTGAAGAGGGCCCACCTGATTGAGATGAAAACATGTGAATGGCCAAAGTCTCACACATTGTGGACAGATGGAGT

AGAAGAAAGTGATCTTATCATACCCAAGTCTTTAGCTGGTCCACTCAGCCACCACAACACCAGAGAGGGTTACAGAACCC

AAGTGAAAGGGCCATGGCACAGTGAAGAGCTTGAAATCCGGTTTGAGGAATGTCCAGGCACCAAGGTTTACGTGGAGG

AGACATGCGGAACTAGAGGACCATCTCTGAGATCAACTACTGCAAGTGGAAGGGTCATTGAGGAATGGTGCTGTAGGGA

ATGCACAATGCCCCCACTATCGTTTCGAGCAAAAGACGGCTGCTGGTATGGAATGGAGATAAGGCCCAGGAAAGAACCA

GAGAGCAACTTAGTGAGGTCAATGGTGACAGCGGGGTCAACCGATCATATGGACCACTTCTCTCTTGGAGTGCTTGTGAT
```

-continued

```
TCTACTCATGGTGCAGGAGGGGTTGAAGAAGAGAATGACCACAAAGATCATCATGAGCACATCAATGGCAGTGCTGGTA
GTCATGATCTTGGGAGGATTTTCAATGAGTGACCTGGCCAAGCTTGTGATCCTGATGGGTGCTACTTTCGCAGAAATGAA
CACTGGAGGAGATGTAGCTCACTTGGCATTGGTAGCGGCATTTAAAGTCAGACCAGCCTTGCTGGTCTCCTTCATTTTCAG
AGCCAATTGGACACCCCGTGAGAGCATGCTGCTAGCCCTGGCTTCGTGTCTTCTGCAAACTGCGATCTCTGCTCTTGAAGG
TGACTTGATGGTCCTCATTAATGGATTTGCTTTGGCCTGGTTGGCAATTCGAGCAATGGCCGTGCCACGCACTGACAACAT
CGCTCTACCAATCTTGGCTGCTCTAACACCACTAGCTCGAGGCACACTGCTCGTGGCATGGAGAGCGGGCCTGGCTACTT
GTGGAGGGATCATGCTCCTCTCCCTGAAAGGGAAAGGTAGTGTGAAGAAGAACCTGCCATTTGTCATGGCCCTGGGATT
GACAGCTGTGAGGGTAGTAGACCCTATTAATGTGGTAGGACTACTGTTACTCACAAGGAGTGGGAAGCGGAGCTGGCCC
CCTAGTGAAGTTCTCACAGCCGTTGGCCTGATATGTGCACTGGCCGGAGGGTTTGCCAAGGCAGACATTGAGATGGCTG
GACCCATGGCTGCAGTAGGCTTGCTAATTGTCAGCTATGTGGTCTCGGGAAAGAGTGTGGACATGTACATTGAAAGAGCA
GGTGACATCACATGGGAAAAGGACGCGGAAGTCACTGGAAACAGTCCTCGGCTTGACGTGGCACTGGATGAGAGTGGT
GACTTCTCCTTGGTAGAGGAAGATGGTCCACCCATGAGAGATCATACTCAAGGTGGTCCTGATGGCCATCTGTGGCAT
GAACCCAATAGCTATACCTTTTGCTGCAGGAGCGTGGTATGTGTATGTGAAGACTGGGAAAAGGAGTGGCGCCCTCTGG
GACGTGCCTGCTCCCAAAGAAGTGAAGAAAGGAGAGACCACAGATGGAGTGTACAGAGTGATGACTCGCAGACTGCTA
GGTTCAACACAGGTTGGAGTGGGAGTCATGCAAGAGGGAGTCTTCCACACCATGTGGCACGTTACAAAAGGAGCCGCAC
TGAGGAGCGGTGAGGGAAGACTTGATCCATACTGGGGGGATGTCAAGCAGGACTTGGTGTCATACTGTGGGCCTTGGAA
GTTGGATGCAGCTTGGGATGGACTCAGCGAGGTACAGCTTTTGGCCGTACCTCCCGGAGAGAGGGCCAGAAACATTCAG
ACCCTGCCTGGAATATTCAAGACAAAGGACGGGGACATCGGAGCAGTTGCTCTGGACTACCCTGCAGGGACCTCAGGAT
CTCCGATCCTAGACAAATGTGGAAGAGTGATAGGACTCTATGGCAATGGGGTTGTGATCAAGAATGGAAGCTATGTTAGT
GCTATAACCCAGGGAAAGAGGGAGGAGGAGACTCCGGTTGAATGTTTCGAACCCTCGATGCTGAAGAAGAAGCAGCTA
ACTGTCTTGGATCTGCATCCAGGAGCCGGAAAAACCAGGAGAGTTCTTCCTGAAATAGTCCGTGAAGCCATAAAAAAGAG
ACTCCGGACAGTGATCTTGGCACCAACTAGGGTTGTCGCTGCTGAGATGGAGGAGGCCTTGAGAGGACTTCCGGTGCGT
TACATGACAACAGCAGTCAACGTCACCCATTCTGGGACAGAAATCGTTGATTTGATGTGCCATGCCACTTTCACTTCACGC
TTACTACAACCCATCAGAGTCCCTAATTACAATCTCAACATCATGGATGAAGCCCACTTCACAGACCCCTCAAGTATAGCTG
CAAGAGGATACATATCAACAAGGGTTGAAATGGGCGAGGCGGCTGCCATTTTTATGACTGCCACACCACCAGGAACCCGT
GATGCGTTTCCTGACTCTAACTCACCAATCATGGACACAGAAGTGGAAGTCCCAGAGAGAGCCTGGAGCTCAGGCTTTGA
TTGGGTGACAGACCATTCTGGGAAAACAGTTTGGTTCGTTCCAAGCGTGAGAAACGGAAATGAAATCGCAGCCTGTCTGA
CAAAGGCTGGAAAGCGGGTCATACAGCTCAGCAGGAAGACTTTTGAGACAGAATTTCAGAAAACAAAAAATCAAGAGTG
GGACTTTGTCATAACAACTGACATCTCAGAGATGGGCGCCAACTTCAAGGCTGACCGGGTCATAGACTCTAGGAGATGCC
TAAAACCAGTCATACTTGATGGTGAGAGAGTCATCTTGGCTGGGCCCATGCCTGTCACGCATGCTAGTGCTGCTCAGAGG
AGAGGACGTATAGGCAGGAACCCTAACAAACCTGGAGATGAGTACATGTATGGAGGTGGGTGTGCAGAGACTGATGAA
GGCCATGCACACTGGCTTGAAGCAAGAATGCTTCTTGACAACATCTACCTCCAGGATGGCCTCATAGCCTCGCTCTATCGG
CCTGAGGCCGATAAGGTAGCCGCCATTGAGGGAGAGTTTAAGCTGAGGACAGAGCAAAGGAAGACCTTCGTGGAACTC
ATGAAGAGAGGAGACCTTCCCGTCTGGCTAGCCTATCAGGTTGCATCTGCCGGAATAACTTACACAGACAGAAGATGGTG
CTTTGATGGCACAACCAACAACACCATAATGGAAGACAGTGTACCAGCAGAGGTTTGGACAAAGTATGGAGAGAAGAGA
GTGCTCAAACCGAGATGGATGGATGCTAGGGTCTGTTCAGACCATGCGGCCCTGAAGTCGTTCAAAGAATTCGCCGCTGG
AAAAAGAGGAGCGGCTTTGGGAGTAATGGAGGCCCTGGGAACACTGCCAGGACACATGACAGAGAGGTTTCAGGAAGC
CATTGACAACCTCGCCGTGCTCATGCGAGCAGAGACTGGAAGCAGGCCTTATAAGGCAGCGGCAGCCCAACTGCCGGAG
ACCCTAGAGACCATTATGCTCTTAGGTTTGCTGGGAACAGTTTCACTGGGGATCTTCTTCGTCTTGATGCGGAATAAGGGC
ATCGGGAAGATGGGCTTTGGAATGGTAACCCTTGGGGCCAGTGCATGGCTCATGTGGCTTTCGGAAATTGAACCAGCCA
```

-continued

```
GAATTGCATGTGTCCTCATTGTTGTGTTTTTATTACTGGTGGTGCTCATACCCGAGCCAGAGAAGCAAAGATCTCCCCAAG

ATAACCAGATGGCAATTATCATCATGGTGGCAGTGGGCCTTCTAGGTTTGATAACTGCAAACGAACTTGGATGGCTGGAA

AGAACAAAAAATGACATAGCTCATCTAATGGGAAGGAGAGAAGAAGGAGCAACCATGGGATTCTCAATGGACATTGATC

TGCGGCCAGCCTCCGCCTGGGCTATCTATGCCGCATTGACAACTCTCATCACCCCAGCTGTCCAACATGCGGTAACCACTT

CATACAACAACTACTCCTTAATGGCGATGGCCACACAAGCTGGAGTGCTGTTTGGCATGGGCAAAGGGATGCCATTTATG

CATGGGGACCTTGGAGTCCCGCTGCTAATGATGGGTTGCTATTCACAATTAACACCCCTGACTCTGATAGTAGCTATCATT

CTGCTTGTGGCGCACTACATGTACTTGATCCCAGGCCTACAAGCGGCAGCAGCGCGTGCTGCCCAGAAAAGGACAGCAG

CTGGCATCATGAAGAATCCCGTTGTGGATGGAATAGTGGTAACTGACATTGACACAATGACAATAGACCCCCAGGTGGA

GAAGAAGATGGGACAAGTGTTACTCATAGCAGTAGCCATCTCCAGTGCTGTGCTGCTGCGGACCGCCTGGGGATGGGGG

GAGGCTGGAGCTCTGATCACAGCAGCGACCTCCACCTTGTGGGAAGGCTCTCCAAACAAATACTGGAACTCCTCTACAGC

CACCTCACTGTGCAACATCTTCAGAGGAAGCTATCTGGCAGGAGCTTCCCTTATCTATACAGTGACGAGAAACGCTGGCCT

GGTTAAGAGACGTGGAGGTGGGACGGGAGAGACTCTGGGAGAGAAGTGGAAAGCTCGTCTGAATCAGATGTCGGCCCT

GGAGTTCTACTCTTATAAAAAGTCAGGTATCACTGAAGTGTGTAGAGAGGAGGCTCGCCGTGCCCTCAAGGATGGAGTG

GCCACAGGAGGACATGCCGTATCCCGGGGAAGTGCAAAGATCAGATGGTTGGAGGAGAGAGGATATCTGCAGCCCTAT

GGGAAGGTTGTTGACCTCGGATGTGGCAGAGGGGGCTGGAGCTATTATGCCGCCACCATCCGCAAAGTGCAGGAGGTG

AGAGGATACACAAAGGGAGGTCCCGGTCATGAAGAACCCATGCTGGTGCAAAGCTATGGGTGGAACATAGTTCGTCTCA

AGAGTGGAGTGGACGTCTTCCACATGGCGGCTGAGCCGTGTGACACTCTGCTGTGTGACATAGGTGAGTCATCATCTAGT

CCTGAAGTGGAAGAGACACGAACACTCAGAGTGCTCTCTATGGTGGGGACTGGCTTGAAAAAGACCAGGGGCCTTCT

GTATAAAGGTGCTGTGCCCATACACCAGCACTATGATGGAAACCATGGAGCGACTGCAACGTAGGCATGGGGAGGATT

AGTCAGAGTGCCATTGTGTCGCAACTCCACACATGAGATGTACTGGGTCTCTGGGGCAAAGAGCAACATCATAAAAAGTG

TGTCCACCACAAGTCAGCTCCTCCTGGGACGCATGGATGGCCCCAGGAGGCCAGTGAAATATGAGGAGGATGTGAACCT

CGGCTCGGGTACACGAGCTGTGGCAAGCTGTGCTGAGGCTCCTAACATGAAAATCATCGGCAGGCGCATTGAGAGAATC

CGCAATGAACATGCAGAAACATGGTTTCTTGATGAAAACCACCCATACAGGACATGGGCCTACCATGGGAGCTACGAAGC

CCCCACGCAAGGATCAGCGTCTTCCCTCGTGAACGGGGTTGTTAGACTCCTGTCAAAGCCTTGGGACGTGGTGACTGGAG

TTACAGGAATAGCCATGACTGACACCACACCATACGGCCAACAAAGAGTCTTCAAAGAAAAAGTGGACACCAGGGTGCC

AGATCCCCAAGAAGGCACTCGCCAGGTAATGAACATAGTCTCTTCCTGGCTGTGGAAGGAGCTGGGGAAACGCAAGCGG

CCACGCGTCTGCACCAAAGAAGAGTTTATCAACAAGGTGCGCAGCAATGCAGCACTGGGAGCAATATTTGAAGAGGAAA

AAGAATGGAAGACGGCTGTGGAAGCTGTGAATGATCCAAGGTTTTGGGCCCTAGTGGATAGGGAGAGAGAACACCACC

TGAGAGGAGAGTGTCACAGCTGTGTGTACAACATGATGGGAAAAAGAGAAAAGAAGCAAGGAGAGTTCGGGAAAGCA

AAAGGTAGCCGCGCCATCTGGTACATGTGGTTGGGAGCCAGATTCTTGGAGTTTGAAGCCCTTGGATTCTTGAACGAGGA

CCATTGGATGGAAGAGAAAACTCAGGAGGTGGAGTCGAAGGGTTAGGATTGCAAAGACTTGGATACATTCTAGAAGA

AATGAATCGGGCACCAGGAGGAAAGATGTACGCAGATGACACTGCTGGCTGGGACACCCGCATTAGTAAGTTTGATCTG

GAGAATGAAGCTCTGATTACCAACCAAATGGAGGAAGGGCACAGAACTCTGGCGTTGGCCGTGATTAAATACACATACC

AAAACAAAGTGGTGAAGGTTCTCAGACCAGCTGAAGGAGGAAAAACAGTTATGGACATCATTTCAAGACAAGACCAGAG

AGGGAGTGGACAAGTTGTCACTTATGCTCTCAACACATTCACCAACTTGGTGGTGCAGCTTATCCGGAACATGGAAGCTG

AGGAAGTGTTAGAGATGCAAGACTTATGGTTGTTGAGGAAGCCAGAGAAAGTGACCAGATGGTTGCAGAGCAATGGAT

GGGATAGACTCAAACGAATGGCGGTCAGTGGAGATGACTGCGTTGTGAAGCCAATCGATGATAGGTTTGCACATGCCCT

CAGGTTCTTGAATGACATGGGAAAAGTTAGGAAAGACACACAGGAGTGGAAACCCTCGACTGGATGGAGCAATTGGGA

AGAAGTCCCGTTCTGCTCCCACCACTTCAACAAGCTGTACCTCAAGGATGGGAGATCCATTGTGGTCCCTTGCCGCCACCA

AGATGAACTGATTGGCCGAGCTCGCGTCTCACCAGGGGCAGGATGGAGCATCCGGGAGACTGCCTGTCTTGCAAAATCA

TATGCGCAGATGTGGCAGCTCCTTTATTTCCACAGAAGAGACCTTCGACTGATGGCTAATGCCATTTGCTCGGCTGTGCCA
```

-continued

```
GTTGACTGGGTACCAACTGGGAGAACCACCTGGTCAATCCATGGAAAGGGAGAATGGATGACCACTGAGGACATGCTCA
TGGTGTGGAATAGAGTGTGGATTGAGGAGAACGACCCATATGGAGGACAAGACTCCTGTAACAAAATGGACAGACATTCC
CTATCTAGGAAAAAGGGAGGACTTATGGTGTGGATCCCTTATAGGGCACAGACCCCGCACCACTTGGGCTGAAAACATCA
AAGACACAGTCAACATGGTGCGCAGGATCATAGGTGATGAAGAAAAGTACATGGACTATCTATCCACCCAAGTCCGCTAC
TTGGGTGAGGAAGGGTCCACACCCGGAGTGTTGTAAGCACCAATTTTAGTGTTGTCAGGCCTGCTAGTCAGCCACAGTTT
GGGGAAAGCTGTGCAGCCTGTAACCCCCCAGGAGAAGCTGGGAAACCAAGCTCATAGTCAGGCCGAGAACGCCATGG
CACGGAAGAAGCCATGCTGCCTGTGAGCCCCTCAGAGGACACTGAGTCAAAAACCCCACGCGCTTGGAAGCGCAGGAT
GGGAAAAGAAGGTGGCGACCTTCCCCACCCTTCAATCTGGGGCCTGAACTGGAGACTAGCTGTGAATCTCCAGCAGAGG
GACTAGTGGTTAGAGGAGACCCCCCGGAAAACGCAAAACAGCATATTGACGTGGGAAAGACCAGAGACTCCATGAGTTT
CCACCACGCTGGCCGCCAGGCACAGATCGCCGAACTTCGGCGGCCGGTGTGGGGAAATCCATGGTTTCT
```

KJ776791.1, Zika virus strain H/PF/2013 polyprotein gene, complete cds
SEQ ID NO: 13

```
AGTATCAACAGGTTTTATTTTGGATTTGGAAACGAGAGTTTCTGGTCATGAAAAACCCAAAAAGAAATCCGGAGGATTC
CGGATTGTCAATATGCTAAAACGCGGAGTAGCCCGTGTGAGCCCCTTTGGGGGCTTGAAGAGGCTGCCAGCCGGACTTCT
GCTGGGTCATGGGCCCATCAGGATGGTCTTGGCGATTCTAGCCTTTTTGAGATTCACGGCAATCAAGCCATCACTGGGTCT
CATCAATAGATGGGGTTCAGTGGGAAAAAAGAGGCTATGGAAATAATAAAGAAGTTCAAGAAAGATCTGGCTGCCATG
CTGAGAATAATCAATGCTAGGAAGGAGAAGAAGAGACGAGGCGCAGATACTAGTGTCGGAATTGTTGGCCTCCTGCTGA
CCACAGCTATGGCAGCGGAGGTCACTAGACGTGGGAGTGCATACTATATGTACTTGGACAGAAACGACGCTGGGGAGGC
CATATCTTTTCCAACCACATTGGGGATGAATAAGTGTTATATACAGATCATGGATCTTGACACATGTGTGATGCCACCAT
GAGCTATGAATGCCCTATGCTGGATGAGGGGGTGGAACCAGATGACGTCGATTGTTGGTGCAACACGACGTCAACTTGG
GTTGTGTACGGAACCTGCCATCACAAAAAAGGTGAAGCACGGAGATCTAGAAGAGCTGTGACGCTCCCCTCCCATTCCAC
TAGGAAGCTGCAAACGCGGTCGCAAACCTGGTTGGAATCAAGAGAATACACAAAGCACTTGATTAGAGTCGAAAATTGG
ATATTCAGGAACCCTGGCTTCGCGTTAGCAGCAGCTGCCATCGCTTGGCTTTTGGGAAGCTCAACGAGCCAAAAAGTCAT
ATACTTGGTCATGATACTGCTGATTGCCCCGGCATACAGCATCAGGTGCATAGGAGTCAGCAATAGGGACTTTGTGGAAG
GTATGTCAGGTGGGACTTGGGTTGATGTTGTCTTGGAACATGGAGGTTGTGTCACCGTAATGGCACAGGACAAACCGACT
GTCGACATAGAGCTGGTTACAACAACAGTCAGCAACATGGCGGAGGTAAGATCCTACTGCTATGAGGCATCAATATCGG
ACATGGCTTCGGACAGCCGCTGCCCAACACAAGGTGAAGCCTACCTTGACAAGCAATCAGACACTCAATATGTCTGCAAA
AGAACGTTAGTGGACAGAGGCTGGGGAAATGGATGTGGACTTTTTGGCAAAGGGAGCCTGGTGACATGCGCTAAGTTTG
CATGCTCCAAGAAAATGACCGGGAAGAGCATCCAGCCAGAGAATCTGGAGTACCGGATAATGCTGTCAGTTCATGGCTCC
CAGCACAGTGGGATGATCGTTAATGACACAGGACATGAAACTGATGAGAATAGAGCGAAGGTTGAGATAACGCCCAATT
CACCAAGAGCCGAAGCCACCCTGGGGGGTTTTGGAAGCCTAGGACTTGATTGTGAACCGAGGACAGGCCTTGACTTTTCA
GATTTGTATTACTTGACTATGAATAACAAGCACTGGTTGGTTCACAAGGAGTGGTTCCACGACATTCCATTACCTTGGCAC
GCTGGGGCAGACACCGGAACTCCACACTGGAACAACAAAGAAGCACTGGTAGAGTTCAAGGACGCACATGCCAAAGG
CAAACTGTCGTGGTTCTAGGGAGTCAAGAAGGAGCAGTTCACACGGCCCTTGCTGGAGCTCTGGAGGCTGAGATGGATG
GTGCAAAGGGAAGGCTGTCCTCTGGCCACTTGAAATGTCGCCTGAAAATGGATAAACTTAGATTGAAGGGCGTGTCATAC
TCCTTGTGTACCGCAGCGTTCACATTCACCAAGATCCCGGCTGAAACACTGCACGGGACAGTCACAGTGGAGGTACAGTA
CGCAGGGACAGATGGACCTTGCAAGGTTCCAGCTCAGATGGCGGTGGACATGCAAACTCTGACCCCAGTTGGGAGGTTG
ATAACCGCTAACCCCGTAATCACTGAAAGCACTGAGAACTCTAAGATGATGCTGGAACTTGATCCACCATTTGGGGACTCT
TACATTGTCATAGGAGTCGGGGAGAAGAAGATCACCCACCACTGGCACAGGAGTGGCAGCACCATTGGAAAAGCATTTG
AAGCCACTGTGAGAGGTGCCAAGAGAATGGCAGTCTTGGGAGACACAGCCTGGGACTTTGGATCAGTTGGAGGCGCTCT
CAACTCATTGGGCAAGGGCATCCATCAAATTTTTGGAGCAGCTTTCAAATCATTGTTTGGAGGAATGTCCTGGTTCTCACA
```

-continued

```
AATTCTCATTGGAACGTTGCTGATGTGGTTGGGTCTGAACACAAAGAATGGATCTATTTCCCTTATGTGCTTGGCCTTAGG
GGGAGTGTTGATCTTCTTATCCACAGCTGTCTCTGCTGATGTGGGGTGCTCGGTGGACTTCTCAAAGAAGGAGACGAGAT
GCGGTACAGGGGTGTTCGTCTATAACGACGTTGAAGCCTGGAGGGACAGGTACAAGTACCATCCTGACTCCCCCCGTAGA
TTGGCAGCAGCAGTCAAGCAAGCCTGGGAAGATGGTATCTGTGGGATCTCCTCTGTTTCAAGAATGGAAAACATCATGTG
GAGATCAGTAGAAGGGGAGCTCAACGCAATCCTGGAAGAGAATGGAGTTCAACTGACGGTCGTTGTGGGATCTGTAAAA
AACCCCATGTGGAGAGGTCCACAGAGATTGCCCGTGCCTGTGAACGAGCTGCCCCACGGCTGGAAGGCTTGGGGGAAAT
CGTACTTCGTCAGAGCAGCAAAGACAAATAACAGCTTTGTCGTGGATGGTGACACACTGAAGGAATGCCCACTCAAACAT
AGAGCATGGAACAGCTTTCTTGTGGAGGATCATGGGTTCGGGGTATTTCACACTAGTGTCTGGCTCAAGGTTAGAGAAGA
TTATTCATTAGAGTGTGATCCAGCCGTTATTGGAACAGCTGTTAAGGGAAAGGAGGCTGTACACAGTGATCTAGGCTACT
GGATTGAGAGTGAGAAGAATGACACATGGAGGCTGAAGAGGGCCCATCTGATCGAGATGAAAACATGTGAATGGCCAA
AGTCCCACACATTGTGGACAGATGGAATAGAAGAGAGTGATCTGATCATACCCAAGTCTTTAGCTGGGCCACTCAGCCAT
CACAATACCAGAGAGGGCTACAGGACCCAAATGAAAGGGCCATGGCACAGTGAAGAGCTTGAAATTCGGTTTGAGGAAT
GCCCAGGCACTAAGGTCCACGTGGAGGAAACATGTGGAACAAGAGGACCATCTCTGAGATCAACCACTGCAAGCGGAAG
GGTGATCGAGGAATGGTGCTGCAGGGAGTGCACAATGCCCCCACTGTCGTTCCGGGCTAAAGATGGCTGTTGGTATGGA
ATGGAGATAAGGCCCAGGAAAGAACCAGAAAGTAACTTAGTAAGGTCAATGGTGACTGCAGGATCAACTGATCACATGG
ATCACTTCTCCCTTGGAGTGCTTGTGATTCTGCTCATGGTGCAGGAAGGGCTGAAGAAGAGAATGACCACAAAGATCATC
ATAAGCACATCGATGGCAGTGCTGGTAGCTATGATCCTGGGAGGATTTTCAATGAGTGACCTGGCTAAGCTTGCAATTTT
GATGGGTGCCACCTTCGCGGAAATGAACACTGGAGGAGATGTAGCTCATCTGGCGCTGATAGCGGCATTCAAAGTCAGA
CCAGCGTTGCTGGTATCTTTCATCTTCAGAGCTAATTGGACACCCCGTGAAAGCATGCTGCTGGCCTTGGCCTCGTGTCTTT
TGCAAACTGCGATCTCCGCCTTGGAAGGCGACCTGATGGTTCTCATCAATGGTTTTGCTTTGGCCTGGTTGGCAATACGAG
CGATGGTTGTTCCACGCACTGATAACATCACCTTGGCAATCCTGGCTGCTCTGACACCACTGGCCCGGGGCACACTGCTTG
TGGCGTGGAGAGCAGGCCTTGCTACTTGCGGGGGGTTTATGCTCCTCTCTCTGAAGGGAAAAGGCAGTGTGAAGAAGAA
CTTACCATTTGTCATGGCCCTGGGACTAACCGCTGTGAGGCTGGTCGACCCCATCAACGTGGTGGGACTGCTGTTGCTCAC
AAGGAGTGGGAAGCGGAGCTGGCCCCCTAGCGAAGTACTCACAGCTGTTGGCCTGATATGCGCATTGGCTGGAGGGTTC
GCCAAGGCAGATATAGAGATGGCTGGGCCCATGGCCGCGGTCGGTCTGCTAATTGTCAGTTACGTGGTCTCAGGAAAGA
GTGTGGACATGTACATTGAAAGAGCAGGTGACATCACATGGGAAAAAGATGCGGAAGTCACTGGAAACAGTCCCCGGCT
CGATGTGGCGCTAGATGAGAGTGGTGATTTCTCCCTGGTGGAGGATGACGGTCCCCCCATGAGAGAGATCATACTCAAG
GTGGTCCTGATGACCATCTGTGGCATGAACCCAATAGCCATACCCTTTGCAGCTGGAGCGTGGTACGTATACGTGAAGAC
TGGAAAAAGGAGTGGTGCTCTATGGGATGTGCCTGCTCCCAAGGAAGTAAAAAAGGGGGAGACCACAGATGGAGTGTA
CAGAGTAATGACTCGTAGACTGCTAGGTTCAACACAAGTTGGAGTGGGAGTTATGCAAGAGGGGTCTTTCACACTATGT
GGCACGTCACAAAAGGATCCGCGCTGAGAAGCGGTGAAGGGAGACTTGATCCATACTGGGGAGATGTCAAGCAGGATC
TGGTGTCATACTGTGGTCCATGGAAGCTAGATGCCGCCTGGGACGGGCACAGCGAGGTGCAGCTCTTGGCCGTGCCCCC
CGGAGAGAGAGCGAGGAACATCCAGACTCTGCCCGGAATATTTAAGACAAAGGATGGGGACATTGGAGCGGTTGCGCT
GGATTACCCAGCAGGAACTTCAGGATCTCCAATCCTAGACAAGTGTGGGAGAGTGATAGGACTTTATGGCAATGGGTC
GTGATCAAAAATGGGAGTTATGTTAGTGCCATCACCCAAGGGAGGAGGGAGGAAGAGACTCCTGTTGAGTGCTTCGAGC
CTTCGATGCTGAAGAAGAAGCAGCTAACTGTCTTAGACTTGCATCCTGGAGCTGGGAAAACCAGGAGAGTTCTTCCTGAA
ATAGTCCGTGAAGCCATAAAAACAAGACTCCGTACTGTGATCTTAGCTCCAACCAGGGTTGTCGCTGCTGAAATGGAGGA
AGCCCTTAGAGGGCTTCCAGTGCGTTATATGACAACAGCAGTCAATGTCACCCACTCTGGAACAGAAATCGTCGACTTAAT
GTGCCATGCCCACCTTCACTTCACGTCTACTACAGCCAATCAGAGTCCCCAACTATAATCTGTATATTATGGATGAGGCCCAC
TTCACAGATCCCTCAAGTATAGCAGCAAGAGGATACATTTCAACAAGGGTTGAGATGGGCGAGGCGGCTGCCATCTTCAT
GACCGCCACGCCACCAGGAACCCGTGACGCATTTCCGGACTCCAACTCACCAATTATGGACACCGAAGTGGAAGTCCCAG
```

-continued

```
AGAGAGCCTGGAGCTCAGGCTTTGATTGGGTGACGGATCATTCTGGAAAAACAGTTTGGTTTGTTCCAAGCGTGAGGAAC
GGCAATGAGATCGCAGCTTGTCTGACAAAGGCTGGAAAACGGGTCATACAGCTCAGCAGAAAGACTTTTGAGACAGAGT
TCCAGAAAACAAAACATCAAGAGTGGGACTTTGTCGTGACAACTGACATTTCAGAGATGGGCGCCAACTTTAAAGCTGAC
CGTGTCATAGATTCCAGGAGATGCCTAAAGCCGGTCATACTTGATGGCGAGAGAGTCATTCTGGCTGGACCCATGCCTGT
CACACATGCCAGCGCTGCCCAGAGGAGGGGGCGCATAGGCAGGAATCCCAACAAACCTGGAGATGAGTATCTGTATGGA
GGTGGGTGCGCAGAGACTGACGAAGACCATGCACACTGGCTTGAAGCAAGAATGCTCCTTGACAATATTTACCTCCAAGA
TGGCCTCATAGCCTCGCTCTATCGACCTGAGGCCGACAAAGTAGCAGCCATTGAGGGAGAGTTCAAGCTTAGGACGGAG
CAAAGGAAGACCTTTGTGGAACTCATGAAAAGAGGAGATCTTCCTGTTTGGCTGGCCTATCAGGTTGCATCTGCCGGAAT
AACCTACACAGATAGAAGATGGTGCTTTGATGGCACGACCAACAACACCATAATGGAAGACAGTGTGCCGGCAGAGGTG
TGGACCAGACACGGAGAGAAAAGAGTGCTCAAACCGAGGTGGATGGACGCCAGAGTTTGTTCAGATCATGCGGCCCTGA
AGTCATTCAAGGAGTTTGCCGCTGGGAAAAGAGGAGCGGCTTTTGGAGTGATGGAAGCCCTGGGAACACTGCCAGGACA
CATGACAGAGAGATTCCAGGAAGCCATTGACAACCTCGCTGTGCTCATGCGGGCAGAGACTGGAAGCAGGCCTTACAAA
GCCGCGGCGGCCCAATTGCCGGAGACCCTAGAGACCATTATGCTTTTGGGGTTGCTGGGAACAGTCTCGCTGGGAATCTT
TTTCGTCTTGATGAGGAACAAGGGCATAGGGAAGATGGGCTTTGGAATGGTGACTCTTGGGGCCAGCGCATGGCTCATG
TGGCTCTCGGAAATTGAGCCAGCCAGAATTGCATGTGTCCTCATTGTTGTGTTCCTATTGCTGGTGGTGCTCATACCTGAG
CCAGAAAAGCAAAGATCTCCCCAGGACAACCAAATGGCAATCATCATCATGGTAGCAGTAGGTCTTCTGGGCTTGATTAC
CGCCAATGAACTCGGATGGTTGGAGAGAACAAAGAGTGACCTAAGCCATCTAATGGGAAGGAGAGAGGAGGGGCAAC
CATAGGATTCTCAATGGACATTGACCTGCGGCCAGCCTCAGCTTGGGCCATCTATGCTGCCTTGACAACTTTCATTACCCCA
GCCGTCCAACATGCAGTGACCACTTCATACAACAACTACTCCTTAATGGCGATGGCCACGCAAGCTGGAGTGTTGTTTGGT
ATGGGCAAAGGGATGCCATTCTACGCATGGGACTTTGGAGTCCCGCTGCTAATGATAGGTTGCTACTCACAATTAACACC
CCTGACCCTAATAGTGGCCATCATTTTGCTCGTGGCGCACTACATGTACTTGATCCCAGGGCTGCAGGCAGCAGCTGCGC
GTGCTGCCCAGAAGAGAACGGCAGCTGGCATCATGAAGAACCCTGTTGTGGATGGAATAGTGGTGACTGACATTGACAC
AATGACAATTGACCCCCAAGTGGAGAAAAAGATGGGACAGGTGCTACTCATAGCAGTAGCCGTCTCCAGCGCCATACTGT
CGCGGACCGCCTGGGGGTGGGGGGAGGCTGGGGCCCTGATCACAGCGGCAACTTCCACTTTGTGGGAAGGCTCTCCGA
ACAAGTACTGGAACTCCTCTACAGCCACTTCACTGTGTAACATTTTTAGGGGAAGTTACTTGGCTGGAGCTTCTCTAATCTA
CACAGTAACAAGAAACGCTGGCTTGGTCAAGAGACGTGGGGGTGGAACAGGAGAGACCCTGGGAGAGAAATGGAAGG
CCCGCTTGAACCAGATGTCGGCCCTGGAGTTCTACTCCTACAAAAAGTCAGGCATCACCGAGGTGTGCAGAGAAGAGGCC
CGCCGCGCCCTCAAGGACGGTGTGGCAACGGGAGGCCATGCTGTGTCCCGAGGAAGTGCAAAGCTGAGATGGTTGGTG
GAGCGGGATACCTGCAGCCCTATGGAAAGGTCATTGATCTTGGATGTGGCAGAGGGGCTGGAGTTACTACGCCGCCA
CCATCCGCAAAGTTCAAGAAGTGAAAGGATACACAAAAGGAGGCCCTGGTCATGAAGAACCCATGTTGGTGCAAAGCTA
TGGGTGGAACATAGTCCGTCTTAAGAGTGGGGTGGACGTCTTTCATATGGCGGCTGAGCCGTGTGACACGTTGCTGTGTG
ACATAGGTGAGTCATCATCTAGTCCTGAAGTGGAAGAAGCACGGACGCTCAGAGTCCTCTCCATGGTGGGGATTGGCTT
GAAAAAAGACCAGGAGCCTTTTGTATAAAAGTGTTGTGCCCATACACCAGCACTATGATGGAAACCCTGGAGCGACTGCA
GCGTAGGTATGGGGAGGACTGGTCAGAGTGCCACTCTCCCGCAACTCTACACATGAGATGTACTGGGTCTCTGGAGCG
AAAAGCAACACCATAAAAAGTGTGTCCACCACGAGCCAGCTCCTCTTGGGGCGCATGGACGGGCCCAGGAGGCCAGTGA
AATATGAGGAGGATGTGAATCTCGGCTCTGGCACGCGGGCTGTGGTAAGCTGCGCTGAAGCTCCCAACATGAAGATCAT
TGGTAACCGCATTGAAAGGATCCGCAGTGAGCACGCGGAAACGTGGTTCTTTGACGAGAACCACCCATATAGGACATGG
GCTTACCATGGAAGCTATGAGGCCCCCACACAAGGGTCAGCGTCCTCTCTAATAAACGGGGTTGTCAGGCTCCTGTCAAA
ACCCTGGGATGTGGTGACTGGAGTCACAGGAATAGCCATGACCGACACCACACCGTATGGTCAGCAAAGAGTTTTCAAG
GAAAAAGTGGACACTAGGGTGCCAGACCCCCAAGAAGGCACTCGTCAGGTTATGAGCATGGTCTCTTCCTGGTTGTGGA
```

-continued

```
AAGAGCTAGGCAAACACAAACGGCCACGAGTCTGTACCAAAGAAGAGTTCATCAACAAGGTTCGTAGCAATGCAGCATT

AGGGGCAATATTTGAAGAGGAAAAAGAGTGGAAGACTGCAGTGGAAGCTGTGAACGATCCAAGGTTCTGGGCTCTAGT

GGACAAGGAAAGAGAGCACCACCTGAGAGGAGAGTGCCAGAGTTGTGTGTACAACATGATGGGAAAAAGAGAAAAGA

AACAAGGGGAATTTGGAAAGGCCAAGGGCAGCCGCGCCATCTGGTATATGTGGCTAGGGGCTAGATTTCTAGAGTTCGA

AGCCCTTGGATTCTTGAACGAGGATCACTGGATGGGGAGAGAGAACTCAGGAGGTGGTGTTGAAGGGCTGGGATTACA

AAGACTCGGATATGTCCTAGAAGAGATGAGTCGCATACCAGGAGGAAGGATGTATGCAGATGACACTGCTGGCTGGGAC

ACCCGCATCAGCAGGTTTGATCTGGAGAATGAAGCTCTAATCACCAACCAAATGGAGAAAGGGCACAGGGCCTTGGCAT

TGGCCATAATCAAGTACACATACCAAAACAAAGTGGTAAAGGTCCTTAGACCAGCTGAAAAAGGGAAGACAGTTATGGA

CATTATTTCGAGACAAGACCAAAGGGGGAGCGGACAAGTTGTCACTTACGCTCTTAACACATTTACCAACCTAGTGGTGC

AACTCATTCGGAATATGGAGGCTGAGGAAGTTCTAGAGATGCAAGACTTGTGGCTGCTGCGGAGGTCAGAGAAAGTGAC

CAACTGGTTGCAGAGCAACGGATGGGATAGGCTCAAACGAATGGCAGTCAGTGGAGATGATTGCGTTGTGAAGCCAATT

GATGATAGGTTTGCACATGCCCTCAGGTTCTTGAATGATATGGGAAAAGTTAGGAAGGACACACAAGAGTGGAAACCCT

CAACTGGATGGGACAACTGGGAAGAAGTTCCGTTTTGCTCCCACCACTTCAACAAGCTCCATCTCAAGGACGGGAGGTCC

ATTGTGGTTCCCTGCCGCCACCAAGATGAACTGATTGGCCGGGCCCGCGTCTCTCCAGGGGCGGGATGGAGCATCCGGG

AGACTGCTTGCCTAGCAAAATCATATGCGCAAATGTGGCAGCTCCTTTATTTCCACAGAAGGGACCTCCGACTGATGGCCA

ATGCCATTTGTTCATCTGTGCCAGTTGACTGGGTTCCAACTGGGAGAACTACCTGGTCAATCCATGGAAAGGGAGAATGG

ATGACCACTGAAGCATGCTTGTGGTGTGGAACAGAGTGTGGATTGAGGAGAACGACCACATGGAAGACAAGACCCCA

GTTACGAAATGGACAGACATTCCCTATTTGGGAAAAAGGGAAGACTTGTGGTGTGGATCTCTCATAGGGCACAGACCGC

GCACCACCTGGGCTGAGAACATTAAAAACACAGTCAACATGGTGCGCAGGATCATAGGTGATGAAGAAAAGTACATGGA

CTACCTATCCACCCAAGTTCGCTACTTGGGTGAAGAAGGGTCTACACCTGGAGTGCTGTAAGCACCAATCTTAGTGTTGTC

AGGCCTGCTAGTCAGCCACAGCTTGGGGAAAGCTGTGCAGCCTGTGACCCCCCAGGAGAAGCTGGGAAACCAAGCCTA

TAGTCAGGCCGAGAACGCCATGGCACGGAAGAAGCCATGCTGCCTGTGAGCCCCTCAGAGGACACTGAGTCAAAAAACC

CCACGCGCTTGGAGGCGCAGGATGGGAAAAGAAGGTGGCGACCTTCCCCACCCTTCAATCTGGGGCCTGAACTGGAGAT

CAGCTGTGGATCTCCAGAAGAGGGACTAGTGGTTAGAGGAG
```

In some embodiments, the Zika virus has a RNA genome corresponding to the DNA sequence provided by the nucleic acid sequence of any one of SEQ ID NOs: 2-13 or 72. In some embodiments, the Zika virus has a variant genome that is at least 80%, 81%, 82%, 83%, 84%, 85%, 86%, 87%, 88%, 89%, 90%, 91%, 92%. 93%, 94%, 95%, 96%, 97%, 98%, 99%, 99.5%, 99.6%, 99.7%, 99.8% or 99.9% identical to any one of SEQ ID NOs: 2-13 or 72.

Provided below are amino acid sequences of the E-proteins of Zika strains that may be used in the methods, compositions, and/or vaccines described herein.

```
isol-ARB15076.AHF49784.1.Central_African_Republic/291-788
Flavivirus envelope glycoprotein E.
                                                          SEQ ID NO: 14
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDE

NRAKVEVTPNSPRAEATLGGFGSLGLDCEPRTGLDFSDLYYLTMNNKHWLVHKEWFHDIPLPWHAGADTGTPHWNNKE

ALVEFKDAHAKRQTVVVLGSQEGAVHTALAGALEAEMDGAKGRLFSGHLKCRLKMDKLRLKGVSYSLCTAAFTFTKVP

AETLHGTVTVEVQYAGTDGPCKVPAQMAVDMQTLTPVGRLITANPVITESTENSKMMLELDPPFGDSYIVIGVGDKKI

THHWHRSGSTIGKAFEATVRGAKRMAVLGDTAWDFGSVGGVFNSLGKGIHQIFGAAFKSLFGGMSWFSQILIGTLLVW

LGLNTKNGSISLTCLALGGVMIFLSTAVSA
``` isol-IbH_30656.AEN75265.1.Nigeria/291-788 Flavivirus envelope
glycoprotein E.
SEQ ID NO: 15

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDE

NRAKVEVTPNSPRAEATLGGFGSLGLDCEPRTGLDFSDLYYLTMNNKHWLVHKEWFHDIPLPWHSGADTETPHWNNKE

ALVEFKDAHAKRQTVVVLGSQEGAVHTALAGALEAEMDGAKGRLSSGHLKCRLKMDKLRLKGVSYSLCTAAFTFTKVP

AETLHGTVTVEVQYAGRDGPCKVPAQMAVDMQTLTPVGRLITANPVITESTENSKMMLELDPPFGDSYIVIGVGDKKI

THHWHRSGSIIGKAFEATVRGAKRMAVLGDTAWDFGSVGGVFNSLGKGIHQIFGAAFKSLFGGMSWFSQILIGTLLVW

LGLNTKNGSISLTCLALGGVMIFLSTAVSA

ArB1362.AHL43500.1.-/291-794 Flavivirus envelope glycoprotein E.
SEQ ID NO: 16

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDX

XXXXXXNRAEVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAAF

TFTKVPAETLHGTVTVEVQYAGTDGPCKVPAQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA

ArD128000.AHL43502.1.-/291-794 Flavivirus envelope glycoprotein E.
SEQ ID NO: 17

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMXXXXX

GHETDENRAKVEVTPNSPRAEATLGGFGSLGLDCEPRTGLDFSDLYYLTMNNKHRLVRKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAAF

TFTKVPAETLHGTVTVEVQYAGTDGPCKVPAQMAVDMQTLTPVGRLITANPVITESTENSKMMLELDPPFGDSYIVIG

VGDKKITHHWLKKGSSIGKAFEATVRGAKRMAVLGDTAWDFGSVGGVFNSLGKGVHQIFGAAFKSLFGGMSWFSQILI

GTLLVWLGLNTKNGSISLTCLALGGVMIFLSTAVSA

ArD158095.AHL43505.1.-/291-794 Flavivirus envelope glycoprotein E.
SEQ ID NO: 18

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDI

GHETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAAF

TFTKVPAETLHGTVTVEVQYAGTDGPCKVPAQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA

ArD158084.AHL43504.1.-/291-794 Flavivirus envelope glycoprotein E.
SEQ ID NO: 19

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDI

GHETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAAF

TFTKVPAETLHGTVTVEVQYAGTDGPCKVPAQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA

-continued isol-ARB13565.AHF49783.1.Central_African_Republic/291-794 Flavivirus
envelope glycoprotein E.
SEQ ID NO: 20
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDI

GHETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAAF

TFTKVPAETLHGTVTVEVQYAGTDGPCKVPAQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGVHQIFGAAFKSLFGGMSWFSQILI

GTLLVWLGLNTKNGSISLTCLALGGVMIFLSTAVSA isol-ARB7701.AHF49785.1.Central_African_Republic/291-794 Flavivirus
envelope glycoprotein E.
SEQ ID NO: 21
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDI

GHETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAAF

TFTKVPAETLHGTVTVEVQYAGTDGPCKVPAQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGVHQIFGAAFKSLFGGMSWFSQILI

GTLLVWLGLNTKNGSISLTCLALGGVMIFLSTAVSA isol-ArD_41519.AEN75266.1.Senegal/291-794 Flavivirus envelope
glycoprotein E.
SEQ ID NO: 22
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDT

GHETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAAF

TFTKVPAETLHGTVTVEVQYAGTDGPCKVPAQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA

MR766-NIID.BAP47441.1.Uganda/291-794 Flavivirus envelope
glycoprotein E.
SEQ ID NO: 23
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMTVNDI

GYETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGKLFSGHLKCRLKMDKLRLKGVSYSLCTAAF

TFTKVPAETLHGTVTVEVQYAGTDGPCKIPVQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA

LC002520.1/326-829 Zika virus genomic RNA, strain: MR766-NIID, Uganda,
Flavivirus envelope glycoprotein E.
SEQ ID NO: 24
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMTVNDI

GYETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGKLFSGHLKCRLKMDKLRLKGVSYSLCTAAF

TFTKVPAETLHGTVTVEVQYAGTDGPCKIPVQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA isol-MR_766.AEN75263.1.Uganda/291-794 Flavivirus envelope
glycoprotein E.
SEQ ID NO: 25

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDT

GYETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGKLFSGHLKCRLKMDKLRLKGVSYSLCTAAF

TFTKVPAETLHGTVTVEVQYAGTDGPCKIPVQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA

ArD7117.AHL43501.1.-/291-794 Flavivirus envelope
glycoprotein E.
SEQ ID NO: 26

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIVNDI

GHETDENRAKVEVTPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLFSGHLKCRLKMDKLRLKGVSYSLCTAVC

TAAKVPAETLHGTVTVEVQYAGTDGPCKVPAQMAVDMQTLTPVGRLITANPVITESTENSKMMLELDPPFGDSYIVIG

VGDKKITHHWHRSGSTIGKAFEATVRGAKRMAVLGDTAWDFGSVGGVFNSLGKGIHQIFGAAFKSLFGGMSWFSQILI

GTLLVWLGLNTKNGSISLTCLALGGVMIFLSTAVSA

AY632535.2/326-825 NC_012532.1 Zika virus strain MR 766, Uganda,
Flavivirus envelope glycoprotein E.
SEQ ID NO: 27

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIGYET

DEDRAKVEVTPNSPRAEATLGGFGSLGLDCEPRTGLDFSDLYYLTMNNKHWLVHKEWFHDIPLPWHAGADTGTPHWNN

KEALVEFKDAHAKRQTVVVLGSQEGAVHTALAGALEAEMDGAKGRLFSGHLKCRLKMDKLRLKGVSYSLCTAAFTFTK

VPAETLHGTVTVEVQYAGTDGPCKIPVQMAVDMQTLTPVGRLITANPVITESTENSKMMLELDPPFGDSYIVIGVGDK

KITHHWHRSGSTIGKAFEATVRGAKRMAVLGDTAWDFGSVGGVFNSLGKGIHQIFGAAFKSLFGGMSWFSQILIGTLL

VWLGLNTKNGSISLTCLALGGVMIFLSTAVSA

MR_766.AAV34151.1.Uganda/291-790 Flavivirus envelope
glycoprotein E.|Q32ZE1|Q32ZE1_9FL
SEQ ID NO: 28

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIGYET

DEDRAKVEVTPNSPRAEATLGGFGSLGLDCEPRTGLDFSDLYYLTMNNKHWLVHKEWFHDIPLPWHAGADTGTPHWNN

KEALVEFKDAHAKRQTVVVLGSQEGAVHTALAGALEAEMDGAKGRLFSGHLKCRLKMDKLRLKGVSYSLCTAAFTFTK

VPAETLHGTVTVEVQYAGTDGPCKIPVQMAVDMQTLTPVGRLITANPVITESTENSKMMLELDPPFGDSYIVIGVGDK

KITHHWHRSGSTIGKAFEATVRGAKRMAVLGDTAWDFGSVGGVFNSLGKGIHQIFGAAFKSLFGGMSWFSQILIGTLL

VWLGLNTKNGSISLTCLALGGVMIFLSTAVSA

MR_766.YP_009227198.1.Uganda/1-500 envelope protein E [Zika virus]
SEQ ID NO: 29

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFTCSKKMTGKSIQPENLEYRIMLSVHGSQHSGMIGYET

DEDRAKVEVTPNSPRAEATLGGFGSLGLDCEPRTGLDFSDLYYLTMNNKHWLVHKEWFHDIPLPWHAGADTGTPHWNN

-continued

```
KEALVEFKDAHAKRQTVVVLGSQEGAVHTALAGALEAEMDGAKGRLFSGHLKCRLKMDKLRLKGVSYSLCTAAFTFTK

VPAETLHGTVTVEVQYAGTDGPCKIPVQMAVDMQTLTPVGRLITANPVITESTENSKMMLELDPPFGDSYIVIGVGDK

KITHHWHRSGSTIGKAFEATVRGAKRMAVLGDTAWDFGSVGGVFNSLGKGIHQIFGAAFKSLFGGMSWFSQILIGTLL

VWLGLNTKNGSISLTCLALGGVMIFLSTAVSA
```

KU681081.3/308-811 Zika virus isolate Zika virus/*H.sapiens*-tc/THA/2014/
SV0127- 14, Thailand, Flavivirus envelope glycoprotein E.
SEQ ID NO: 30

```
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHTGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITEGTENSKMMLELDPPFGDSYIVIG

VGEKKITHHWHRSGSTIGKAFEATVRGAKRMAVLGDTAWDFGSVGGVLNSLGKGIHQIFGAAFKSLFGGMSWFSQILI

GTLLMWLGLNTKNGSISLMCLALGGVLIFLSTAVSA
``` isol-Zika_virus%*H.sapiens*-tc%THA%2014%SV0127-_14.AMD61710.1.Thailand/
291-794 Flavivirus envelope glycoprotein E.
SEQ ID NO: 31

```
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHTGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITEGTENSKMMLELDPPFGDSYIVIG

VGEKKITHHWHRSGSTIGKAFEATVRGAKRMAVLGDTAWDFGSVGGVLNSLGKGIHQIFGAAFKSLFGGMSWFSQILI

GTLLMWLGLNTKNGSISLMCLALGGVLIFLSTAVSA
```

CK-ISL_2014.AIC06934.1.Cook_Islands/1-504 Flavivirus envelope glycoprotein
E. (Fragment) OS = Zika virus GN = E PE = 4 SV = 1
SEQ ID NO: 32

```
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA
```

Natal_RGN.AMB18850.1.Brazil:_Rio_Grande_do_Norte,_Natal/291-794
Flavivirus envelope glycoprotein E.]
SEQ ID NO: 33

```
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA
``` isol-Si323.AMC37200.1.Colombia/1-504 Flavivirus envelope glycoprotein E.
SEQ ID NO: 34

```
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT
```

```
GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA
```

KU707826.1/317-820 Zika virus isolate SSABR1, Brazil, Flavivirus envelope
glycoprotein E.

SEQ ID NO: 35
```
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA
```

KU509998.1/326-829 Zika virus strain Haiti/1225/2014, Haiti, Flavivirus
envelope glycoprotein E.

SEQ ID NO: 36
```
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA
``` isol-GDZ16001.AML82110.1.China/291-794 Flavivirus envelope
glycoprotein E.

SEQ ID NO: 37
```
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA
```

BeH819015.AMA12085.1.Brazil/291-794 Flavivirus envelope
glycoprotein E.]

SEQ ID NO: 38
```
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA
```

-continued

MRS_OPY_Martinique_PaRi_2015.AMC33116.1.Martinique/291-794
Flavivirus envelope glycoprotein E.
SEQ ID NO: 39

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

KU501215.1/308-811 Zika virus strain PRVABC59, Puerto Rico,
Flavivirus envelope glycoprotein E.
SEQ ID NO: 40

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

Haiti%1225%2014.AMB37295.1.Haiti/291-794 Flavivirus envelope
glycoprotein E.
SEQ ID NO: 41

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

KU527068.1/308-811 Zika virus strain Natal RGN, Brazil: Rio Grande do Norte,
Natal, Flavivirus envelope glycoprotein E.
SEQ ID NO: 42

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA isol-Z1106027.ALX35662.1.Suriname/5-508 Flavivirus envelope glycoprotein E.
SEQ ID NO: 43

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

-continued

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA isol-FLR.AMM39804.1.Colombia:_Barranquilla/291-794 Flavivirus
envelope glycoprotein E.

SEQ ID NO: 44

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

PLCal_ZV_isol-From_Vero_E6_cells.AHL37808.1.Canada/254-757 Flavivirus
envelope glycoprotein E.

SEQ ID NO: 45

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

BeH818995.AMA12084.1.Brazil/291-794 Flavivirus envelope glycoprotein
E. [Zika virus].

SEQ ID NO: 46

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

H/PF/2013.AHZ13508.1.French_Polynesia/291-794 Flavivirus envelope
glycoprotein E.

SEQ ID NO: 47

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

PRVABC59.AMC13911.1.Puerto_Rico/291-794 Flavivirus envelope glycoprotein E.

SEQ ID NO: 48

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

-continued

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

KU321639.1/326-829 Zika virus strain ZikaSPH2015, Brazil, Flavivirus envelope glycoprotein E.

SEQ ID NO: 49

IRCIGVSNRDFVEGMSGGTWVDIVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

ZikaSPH2015.ALU33341.1.Brazil/291-794 Flavivirus envelope glycoprotein E.

SEQ ID NO: 50

IRCIGVSNRDFVEGMSGGTWVDIVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

103344.AMC13912.1.Guatemala/291-794 polyprotein [Zika virus].
103344.AMC13912.1.Guatemala Flavivirus envelope glycoprotein E.

SEQ ID NO: 51

IRCIGVSNRDFVEGMSGGTWVDVVLEHGGCVTVMAQDKPTVDIELVTTTVSNMAEIRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA isol-Brazil-ZKV2015.AMD16557.1.Brazil/291-794 Flavivirus envelope glycoprotein E.

SEQ ID NO: 52

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGTQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

KU497555.1/308-811 Zika virus isolate Brazil-ZKV2015, Flavivirus envelope glycoprotein E.

SEQ ID NO: 53

IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

```
GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGTQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA isol-ZJ03.AMM39806.1.China/291-794 Flavivirus envelope glycoprotein E.
                                                               SEQ ID NO: 54
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGARRMAVLGDTAWDFGSVGGALNSLGKGIHQIFGAAFKSLFGGMSWFSQILI

GTLLMWLGLNTKNGSISLMCLALGGVLIFLSTAVSA isol-FSS13025.AFD30972.1.Cambodia/291-794 Flavivirus envelope glycoprotein E.
                                                               SEQ ID NO: 55
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLVWLGLNTKNGSISLMCLALGGVLIFLSTAVSA isol-Z1106032.ALX35660.1.Suriname/291-794 Flavivirus envelope
glycoprotein E. [Zika virus]
                                                               SEQ ID NO: 56
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNAKNGSISLMCLALGGVLIFLSTAVSA isol-Z1106033.ALX35659.1.Suriname/291-794 Flavivirus envelope
glycoprotein E. [Zika virus]
                                                               SEQ ID NO: 57
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNAKNGSISLMCLALGGVLIFLSTAVSA isol-BeH828305.AMK49165.1.Brazil/291-794 Flavivirus envelope glycoprotein E.
                                                               SEQ ID NO: 58
IRCIGVSNRDFVEGMSGGTWVDVVLEHGGCVTVMAQDKPTVDIELVTTTVSNMAEVRSYCYEASISDMASDSRCPTQG EAYLDKQSDTQYVCKRTLVDRGWGNGCGLFGKGSLVTCAKFACSKKMTGKSIQPENLEYRIMLSVHGSQHSGMIVNDT
```

```
GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDTQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA isol-GD01.AMK79468.1.China/291-794 Flavivirus envelope glycoprotein E.
                                                                SEQ ID NO: 59
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNGT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA isol-Z1106031.ALX35661.1.Suriname/291-794 Flavivirus envelope glycoprotein E.
                                                                SEQ ID NO: 60
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVLAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA

ACD75819.1.Micronesia/291-794 Flavivirus envelope glycoprotein E.
                                                                SEQ ID NO: 61
IRCIGVSNRDFVEGMSGGTWVDVVLEHGGCVTVMAQDKPAVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLVWLGLNTKNGSISLTCLALGGVLIFLSTAVSA

KU681082.3/308-811 Zika virus isolate Zika virus/H.sapiens-tc/PHL/2012/
CPC-0740, Philippines, Flavivirus envelope glycoprotein E.
                                                                SEQ ID NO: 62
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLVWLGLNTKNGSISLTCLALGGVLIFLSTAVSA
```

-continued isol-Zika_virus%*H.sapiens*-tc%PHL%2012%CPC-0740.AMD61711.1.Philippines/
291-794 Flavivirus envelope glycoprotein E.
SEQ ID NO: 63
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLVWLGLNTKNGSISLTCLALGGVLIFLSTAVSA isol-BeH823339.AMK49164.2.Brazil/291-794 Flavivirus envelope glycoprotein E.
SEQ ID NO: 64
IRCIGVSNRDFVEGMSGGTWVDVVLEHGGCVTVMAQDKPTVDIELVSTTVSNMAEVRSYCYEATISDIASDSRCPTQG

EAYLDKQSDTQYVCKRTLVDRGWGNGCGLFGKGSLVTCAKFACSKKMTGKSIQPENLEYRIMLSVHGSQHSGMIVNDT

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTAVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIFGAAFKSLFGGMSWFSQILI

GTLLMWLGLNTKNGSISLMCLALGGVLIFLSTAVSA isol-P6-740.AEN75264.1.Malaysia/291-794 Flavivirus envelope glycoprotein E.
SEQ ID NO: 65
IRCIGVSNRDFVEGMSGGTWVDVVLEHGGCVTVMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMIVNDX

GHETDENRAKVEITPNSPRAEATLGGFGSLGLDCEPRTGLDFSDLYYLTMNNKHWLVHKEWFHDIPLPWHAGADTGTP

HWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIG

VGDKKITHHWXRSGSTIGKAFEATVRGAKRMAVLGDTAWDFGSVGGALNSLGKGIHQIFGAAFKSLFGGMSWFSQILI

GTLLVWLGLNTKNGSISLTCLALGGVLIFLSTAVSA

KU744693.1/326-829 Zika virus isolate VE_Ganxian, China, Flavivirus
envelope glycoprotein E.
SEQ ID NO: 66
IRCIGVSNRDFVEGMSGGTWVDVVLEHGGCVTAMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMLVNDT

GHETDENRAKVEITPNSPRAEATLGGFGSLGLDCEPRTGLDFSDLYYLTMNNKHWLAHKEWFHDIPLPWHAGAATGTP

HWNNKEALVEFKDAHAKRQTVVVLGSQEGAVHTALAGALEAEMDGAKGRLSSGHLKCRLKMDKLRLKGVSYSLCTAAF

TFTKIPAETVDGTVTVEGQYGGTDGPCKVPAQMAVDMQTLTPVGRLITANPVITESTENSKMMLELDPPFGDSYIVIG

VGEKKITHHWHRSGSTIGKAFEATVRGAKRMAVLGDTAWDFGSVGGALNSLGKGIHQIIGAAFKSLFGGMSWFSQILI

GTLLMWLGLNTKNGSISLMCLALGGVLIFLSTAVSG isol-VE_Ganxian.AMK79469.1.China/291-794 Flavivirus envelope glycoprotein E.
SEQ ID NO: 67
IRCIGVSNRDFVEGMSGGTWVDVVLEHGGCVTAMAQDKPTVDIELVTTTVSNMAEVRSYCYEASISDMASDSRCPTQG

EAYLDKQSDTQYVCKRTLVDRGWGNGCGLFGKGSLVTCAKFACSKKMTGKSIQPENLEYRIMLSVHGSQHSGMLVNDT

GHETDENRAKVEITPNSPRAEATLGGFGSLGLDCEPRTGLDFSDLYYLTMNNKHWLAHKEWFHDIPLPWHAGAATGTP

HWNNKEALVEFKDAHAKRQTVVVLGSQEGAVHTALAGALEAEMDGAKGRLSSGHLKCRLKMDKLRLKGVSYSLCTAAF

TFTKIPAETVDGTVTVEGQYGGTDGPCKVPAQMAVDMQTLTPVGRLITANPVITESTENSKMMLELDPPFGDSYIVIG

-continued

VGEKKITHHWHRSGSTIGKAFEATVRGAKRMAVLGDTAWDFGSVGGALNSLGKGIHQIIGAAFKSLFGGMSWFSQILI
GTLLMWLGLNTKNGSISLMCLALGGVLIFLSTAVSG

ArD157995.AHL43503.1.-/291-794 Flavivirus envelope glycoprotein E.
SEQ ID NO: 68
ISCIGVSNRDLVEGMSGGTWVDVVLEHGGCVTEMAQDKPTVDIELVTMTVSNMAEVRSYCYEASLSDMASASRCPTQG
EPSLDKQSDTQSVCKRTLGDRGWGNGCGIFGKGSLVTCSKFTCCKKMPGKSIQPENLEYRIMLPVHGSQHSGMIVNDI
GHETDENRAKVEVTPNSPRAEATLGGFGSLGLDCEPRTGLDFSDLYYLTMNNKHWLVHKEWFHDIPLPWHAGADTGTP
HWNNKEALVEFKDAHAKRQTVVVLGSQEGAVHTALAGALEAEMDGAKGRLFSGHLKCRLKMDKLRLKGVSYSLCTAAF
TFTKVPAETLHGTVTVEVQSAGTDGPCKVPAQMAVDMQTLTPVGRLITANPVITESTENSKMMLELDPPFGDSYIVIG
VGDKKITHHWHRSGSTIGKAFEATVRGAKRMAVLGDTAWDFGSVGGVFNSLGKGIHQIFGAAFKSLFGGMSWFSQILI
GTLLVWLGLNTKNGSISLTCLALGGVMIFLSTAVSA MR_766.ABI54475.1.Uganda/291-788 Flavivirus envelope glycoprotein E.
SEQ ID NO: 69
IRCIGVSNRDFVEGMSGGTWVDVVLEHGGCVTVMAQDKPTVDIELVTTTVSNMAEVRSYCYEASISDMASDSRCPTQG
EAYLDKQSDTQYVCKRTLVDRGWGNGCGLFGKGSLVTCAKFTCSKKMTGKSIQPENLEYRIMLSVHGSQHSGMIVNDE
NRAKVEVTPNSPRAEATLGGFGSLGLDCEPRTGLDFSDLYYLTMNNKHWLVHKEWFHDIPLPWHAGADTGTPHWNNKE
ALVEFKDAHAKRQTVVVLGSQEGAVHTALAGALEAEMDGAKGRLFSGHLKCRLKMDKLRLKGVSYSLCTAAFTFTKVP
AETLHGTVTVEVQYAGTDGPCKVPAQMAVDMQTLTPVGRLITANPVITESTENSKMMLELDPPFGDSYIVIGVGDKKI
THHWHRSGSTIGKAFEATVRGAKRMAVLGDTAWDFGSVGGVFNSLGKGIHQIFGAAFKSLFGGMSWFSQILIGTLLVW
LGLNTKNGSISLTCLALGGVMIFLSTAVSA 5'-(dIdC)$_{13}$-3'
SEQ ID NO: 70
dIdC dIdC dIdC dIdC dIdC dIdC dIdC dIdC dIdC dIdC dIdC dIdC dIdC KLK peptide
SEQ ID NO: 71
KLKLLLLLKLK ZIKV Sequence H/PF/2013 as sequenced
SEQ ID NO: 72
CAGACTGCGACAGTTCGAGTTTGAAGCGAAAGCTAGCAACAGTATCAACAGGTTTTATTTTGGATTTGGAAACGAGAG
TTTCTGGTCATGAAAAACCCAAAAAAGAAATCCGGAGGATTCCGGATTGTCAATATGCTAAAACGCGGAGTAGCCCGT
GTGAGCCCCTTTGGGGGCTTGAAGAGGCTGCCAGCCGGACTTCTGCTGGGTCATGGGCCCATCAGGATGGTCTTGGCG
ATTCTAGCCTTTTTTGAGATTCACGGCAATCAAGCCATCACTGGGTCTCATCAATAGATGGGGTTCAGTGGGAAAAAA
GAGGCTATGGAAATAATAAAGAAGTTCAAGAAAGATCTGGCTGCCATGCTGAGAATAATCAATGCTAGGAAGGAGAAG
AAGAGACGAGGCGCAGATACTAGTGTCGGAATTGTTGGCCTCCTGCTGACCACAGCTATGGCAGCGGAGGTCACTAGA
CGTGGGAGTGCATACTATATGTACTTGGACAGAAACGACGCTGGGGAGGCCATATCTTTTCCAACCACATTGGGGATG
AATAAGTGTTATATACAGATCATGGATCTTGGACACATGTGTGATGCCACCATGAGCTATGAATGCCCTATGCTGGAT
GAGGGGGTGGAACCAGATGACGTCGATTGTTGGTGCAACACGACGTCAACTTGGGTTGTGTACGGAACCTGCCATCAC
AAAAAAGGTGAAGCACGAGATCTAGAAGAGCTGTGACGCTCCCCTCCCATTCCACTAGGAAGCTGCAAACGCGGTCG
CAAACCTGGTTGGAATCAAGAGAATACACAAAGCACTTGATTAGAGTCGAAAATTGGATATTCAGGAACCCTGGCTTC
GCGTTAGCAGCAGCTGCCATCGCTTGGCTTTTGGGAAGCTCAACGAGCCAAAAAGTCATATACTTGGTCATGATACTG
CTGATTGCCCCGGCATACAGCATCAGGTGCATAGGAGTCAGCAATAGGGACTTTGTGGAAGGTATGTCAGGTGGGACT
TGGGTTGATGTTGTCTTGGAACATGGAGGTTGTGTCACCGTAATGGCACAGGACAAACCGACTGTCGACATAGAGCTG
GTTACAACAACAGTCAGCAACATGGCGGAGGTAAGATCCTACTGCTATGAGGCATCAATATCGGACATGGCTTCGGAC
AGCCGCTGCCCAACACAAGGTGAAGCCTACCTTGACAAGCAATCAGACACTCAATATGTCTGCAAAAGAACGTTAGTG
GACAGAGGCTGGGGAAATGGATGTGGACTTTTTGGCAAAGGGAGCCTGGTGACATGCGCTAAGTTTGCATGCTCCAAG -continued

```
AAAATGACCGGGAAGAGCATCCAGCCAGAGAATCTGGAGTACCGGATAATGCTGTCAGTTCATGGCTCCCAGCACAGT

GGGATGATCGTTAATGACACAGGACATGAAACTGATGAGAATAGAGCGAAGGTTGAGATAACGCCCAATTCACCAAGA

GCCGAAGCCACCCTGGGGGGTTTTGGAAGCCTAGGACTTGATTGTGAACCGAGGACAGGCCTTGACTTTTCAGATTTG

TATTACTTGACTATGAATAACAAGCACTGGTTGGTTCACAAGGAGTGGTTCCACGACATTCCATTACCTTGGCACGCT

GGGGCAGACACCGGAACTCCACACTGGAACAACAAAGAAGCACTGGTAGAGTTCAAGGACGCACATGCCAAAAGGCAA

ACTGTCGTGGTTCTAGGGAGTCAAGAAGGAGCAGTTCACACGGCCCTTGCTGGAGCTCTGGAGGCTGAGATGGATGGT

GCAAAGGGAAGGCTGTCCTCTGGCCACTTGAAATGTCGCCTGAAATGGATAAACTTAGATTGAAGGGCGTGTCATAC

TCCTTGTGTACCGCAGCGTTCACATTCACCAAGATCCCGGCTGAAACACTGCACGGGACAGTCACAGTGGAGGTACAG

TACGCAGGGACAGATGGACCTTGCAAGGTTCCAGCTCAGATGGCGGTGGACATGCAAACTCTGACCCCAGTTGGGAGG

TTGATAACCGCTAACCCCGTAATCACTGAAAGCACTGAGAACTCTAAGATGATGCTGGAACTTGATCCACCATTTGGG

GACTCTTACATTGTCATAGGAGTCGGGGAGAAGAAGATCACCCACCACTGGCACAGGAGTGGCAGCACCATTGGAAAA

GCATTTGAAGCCACTGTGAGAGGTGCCAAGAGAATGGCAGTCTTGGGAGACACAGCCTGGGACTTTGGATCAGTTGGA

GGCGCTCTCAACTCATTGGGCAAGGGCATCCATCAAATTTTTGGAGCAGCTTTCAAATCATTGTTTGGAGGAATGTCC

TGGTTCTCACAAATTCTCATTGGAACGTTGCTGATGTGGTTGGGTCTGAACACAAAGAATGGATCTATTTCCCTTATG

TGCTTGGCCTTAGGGGGAGTGTTGATCTTCTTATCCACAGCTGTCTCTGCTGATGTGGGGTGCTCGGTGGACTTCTCA

AAGAAGGAGACGAGATGCGGTACAGGGGTGTTCGTCTATAACGACGTTGAAGCCTGGAGGGACAGGTACAAGTACCAT

CCTGACTCCCCCCGTAGATTGGCAGCAGCAGTCAAGCAAGCCTGGGAAGATGGTATCTGTGGGATCTCCTCTGTTTCA

AGAATGGAAAACATCATGTGGAGATCAGTAGAAGGGGAGCTCAACGCAATCCTGGAAGAGAATGGAGTTCAACTGACG

GTCGTTGTGGGATCTGTAAAAAACCCCATGTGGAGAGGTCCACAGAGATTGCCCGTGCCTGTGAACGAGCTGCCCCAC

GGCTGGAAGGCTTGGGGGAAATCGTACTTCGTCAGAGCAGCAAAGACAAATAACAGCTTTGTCGTGGATGGTGACACA

CTGAAGGAATGCCCACTCAAACATAGAGCATGGAACAGCTTTCTTGTGGAGGATCATGGGTTCGGGGTATTTCACACT

AGTGTCTGGCTCAAGGTTAGAGAAGATTATTCATTAGAGTGTGATCCAGCCGTTATTGGAACAGCTGTTAAGGGAAAG

GAGGCTGTACACAGTGATCTAGGCTACTGGATTGAGAGTGAGAAGAATGACACATGGAGGCTGAAGAGGGCCCATCTG

ATCGAGATGAAAACATGTGAATGGCCAAAGTCCCACACATTGTGGACAGATGGAATAGAAGAGTGATCTGATCATA

CCCAAGTCTTTAGCTGGGCCACTCAGCCATCACAATACCAGAGAGGGCTACAGGACCCAAATGAAAGGGCCATGGCAC

AGTGAAGAGCTTGAAATTCGGTTTGAGGAATGCCCAGGCACTAAGGTCCACGTGGAGGAAACATGTGGAACAAGAGGA

CCATCTCTGAGATCAACCACTGCAAGCGGAAGGGTGATCGAGGAATGGTGCTGCAGGGAGTGCACAATGCCCCACTG

TCGTTCCGGGCTAAAGATGGCTGTTGGTATGGAATGGAGATAAGGCCCAGGAAGAACCAGAAAGTAACTTAGTAAGG

TCAATGGTGACTGCAGGATCAACTGATCACATGGATCACTTCTCCCTTGGAGTGCTTGTGATTCTGCTCATGGTGCAG

GAAGGGCTGAAGAAGAGAATGACCACAAAGATCATCATAAGCACATCGATGGCAGTGCTGGTAGCTATGATCCTGGGA

GGATTTTCAATGAGTGACCTGGCTAAGCTTGCAATTTTGATGGGTGCCACCTTCGCGGAAATGAACACTGGAGGAGAT

GTAGCTCATCTGGCGCTGATAGCGGCATTCAAAGTCAGACCAGCGTTGCTGGTATCTTTCATCTTCAGAGCTAATTGG

ACACCCCGTGAAAGCATGCTGCTGGCCTTGGCCTCGTGTCTTTTGCAAACTGCGATCTCCGCCTTGGAAGGCGACCTG

ATGGTTCTCATCAATGGTTTTGCTTTGGCCTGGTTGGCAATACGAGCGATGGTTGTTCCACGCACTGATAACATCACC

TTGGCAATCCTGGCTGCTCTGACACCACTGGCCCGGGGCACACTGCTTGTGGCGTGGAGAGCAGGCCTTGCTACTTGC

GGGGGGTTTATGCTCCTCTCTCTGAAGGGAAAAGGCAGTGTGAAGAAGAACTTACCATTTGTCATGGCCCTGGGACTA

ACCGCTGTGAGGCTGGTCGACCCCATCAACGTGGTGGGACTGCTGTTGCTCACAAGGAGTGGGAAGCGGAGCTGGCCC

CCTAGCGAAGTACTCACAGCTGTTGGCCTGATATGCGCATTGGCTGGAGGGTTCGCCAAGGCAGATATAGAGATGGCT

GGGCCCATGGCCGCGGTCGGTCTGCTAATTGTCAGTTACGTGGTCTCAGGAAAGAGTGTGGACATGTACATTGAAAGA

GCAGGTGACATCACATGGGAAAAGATGCGGAAGTCACTGGAAACAGTCCCCGGCTCGATGTGGCGCTAGATGAGAGT

GGTGATTTCTCCCTGGTGGAGGATGACGGTCCCCCCATGAGAGAGATCATACTCAAGGTGGTCCTGATGACCATCTGT
```

-continued

```
GGCATGAACCCAATAGCCATACCCTTTGCAGCTGGAGCGTGGTACGTATACGTGAAGACTGGAAAAAGGAGTGGTGCT

CTATGGGATGTGCCTGCTCCCAAGGAAGTAAAAAAGGGGGAGACCACAGATGGAGTGTACAGAGTAATGACTCGTAGA

CTGCTAGGTTCAACACAAGTTGGAGTGGGAGTTATGCAAGAGGGGGTCTTTCACACTATGTGGCACGTCACAAAAGGA

TCCGCGCTGAGAAGCGGTGAAGGGAGACTTGATCCATACTGGGGAGATGTCAAGCAGGATCTGGTGTCATACTGTGGT

CCATGGAAGCTAGATGCCGCCTGGGACGGGCACAGCGAGGTGCAGCTCTTGGCCGTGCCCCCCGGAGAGAGAGCGAGG

AACATCCAGACTCTGCCCGGAATATTTAAGACAAAGGATGGGGACATTGGAGCGGTTGCGCTGGATTACCCAGCAGGA

ACTTCAGGATCTCCAATCCTAGACAAGTGTGGGAGAGTGATAGGACTTTATGGCAATGGGGTCGTGATCAAAAATGGG

AGTTATGTTAGTGCCATCACCCAAGGGAGGAGGGAGGAAGAGACTCCTGTTGAGTGCTTCGAGCCTTCGATGCTGAAG

AAGAAGCAGCTAACTGTCTTAGACTTGCATCCTGGAGCTGGGAAAACCAGGAGAGTTCTTCCTGAAATAGTCCGTGAA

GCCATAAAAACAAGACTCCGTACTGTGATCTTAGCTCCAACCAGGGTTGTCGCTGCTGAAATGGAGGAAGCCCTTAGA

GGGCTTCCAGTGCGTTATATGACAACAGCAGTCAATGTCACCCACTCTGGAACAGAAATCGTCGACTTAATGTGCCAT

GCCACCTTCACTTCACGTCTACTACAGCCAATCAGAGTCCCCAACTATAATCTGTATATTATGGATGAGGCCCACTTC

ACAGATCCCTCAAGTATAGCAGCAAGAGGATACATTTCAACAAGGGTTGAGATGGGCGAGGCGGCTGCCATCTTCATG

ACCGCCACGCCACCAGGAACCCGTGACGCATTTCCGGACTCCAACTCACCAATTATGGACACCGAAGTGGAAGTCCCA

GAGAGAGCCTGGAGCTCAGGCTTTGATTGGGTGACGGATCATTCTGGAAAAACAGTTTGGTTTGTTCCAAGCGTGAGG

AACGGCAATGAGATCGCAGCTTGTCTGACAAAGGCTGGAAAACGGGTCATACAGCTCAGCAGAAAGACTTTTGAGACA

GAGTTCCAGAAAACAAAACATCAAGAGTGGGACTTTGTCGTGACAACTGACATTTCAGAGATGGGCGCCAACTTTAAA

GCTGACCGTGTCATAGATTCCAGGAGATGCCTAAAGCCGGTCATACTTGATGGCGAGAGAGTCATTCTGGCTGGACCC

ATGCCTGTCACACATGCCAGCGCTGCCCAGAGGAGGGGCGCATAGGCAGGAATCCCAACAAACCTGGAGATGAGTAT

CTGTATGGAGGTGGGTGCGCAGAGACTGACGAAGACCATGCACACTGGCTTGAAGCAAGAATGCTCCTTGACAATATT

TACCTCCAAGATGGCCTCATAGCCTCGCTCTATCGACCTGAGGCCGACAAAGTAGCAGCCATTGAGGGAGAGTTCAAG

CTTAGGACGGAGCAAAGGAAGACCTTTGTGGAACTCATGAAAAGAGGAGATCTTCCTGTTTGGCTGGCCTATCAGGTT

GCATCTGCCGGAATAACCTACACAGATAGAAGATGGTGCTTTGATGGCACGACCAACAACACCATAATGGAAGACAGT

GTGCCGGCAGAGGTGTGGACCAGACACGGAGAGAAAAGAGTGCTCAAACCGAGGTGGATGGACGCCAGAGTTTGTTCA

GATCATGCGGCCCTGAAGTCATTCAAGGAGTTTGCCGCTGGGAAAAGAGGAGCGGCTTTTGGAGTGATGGAAGCCCTG

GGAACACTGCCAGGACACATGACAGAGAGATTCCAGGAAGCCATTGACAACCTCGCTGTGCTCATGCGGGCAGAGACT

GGAAGCAGGCCTTACAAAGCCGCGGCGGCCCAATTGCCGGAGACCCTAGAGACCATTATGCTTTTGGGGTTGCTGGGA

ACAGTCTCGCTGGGAATCTTTTTCGTCTTGATGAGGAACAAGGGCATAGGGAAGATGGGCTTTGGAATGGTGACTCTT

GGGGCCAGCGCATGGCTCATGTGGCTCTCGGAAATTGAGCCAGCCAGAATTGCATGTGTCCTCATTGTTGTGTTCCTA

TTGCTGGTGGTGCTCATACCTGAGCCAGAAAAGCAAAGATCTCCCCAGGACAACCAAATGGCAATCATCATCATGGTA

GCAGTAGGTCTTCTGGGCTTGATTACCGCCAATGAACTCGGATGGTTGGAGAGAACAAAGAGTGACCTAAGCCATCTA

ATGGGAAGGAGAGAGGAGGGGGCAACCATAGGATTCTCAATGGACATTGACCTGCGGCCAGCCTCAGCTTGGGCCATC

TATGCTGCCTTGACAACTTTCATTACCCCAGCCGTCCAACATGCAGTGACCACTTCATCAACAACTACTCCTTAATG

GCGATGGCCACGCAAGCTGGAGTGTTGTTTGGTATGGGCAAAGGGATGCCATTCTACGCATGGGACTTTGGAGTCCCG

CTGCTAATGATAGGTTGCTACTCACAATTAACACCCCTGACCCTAATAGTGGCCATCATTTTGCTCGTGGCGCACTAC

ATGTACTTGATCCCAGGGCTGCAGGCAGCAGCTGCGCGTGCTGCCCAGAAGAGAACGGCAGCTGGCATCATGAAGAAC

CCTGTTGTGGATGGAATAGTGGTGACTGACATTGACACAATGACAATTGACCCCCAAGTGGAGAAAAAGATGGGACAG

GTGCTACTCATAGCAGTAGCCGTCTCCAGCGCCATACTGTCGCGGACCGCCTGGGGGTGGGGGAGGCTGGGGCCCTG

ATCACAGCGGCAACTTCCACTTTGTGGGAAGGCTCTCCGAACAAGTACTGGAACTCCTCTACAGCCACTTCACTGTGT

AACATTTTTAGGGGAAGTTACTTGGCTGGAGCTTCTCTAATCTACACAGTAACAAGAAACGCTGGCTTGGTCAAGAGA
```

-continued

```
CGTGGGGGTGGAACAGGAGAGACCCTGGGAGAGAAATGGAAGGCCCGCTTGAACCAGATGTCGGCCCTGGAGTTCTAC

TCCTACAAAAAGTCAGGCATCACCGAGGTGTGCAGAGAAGAGGCCCGCCGCGCCCTCAAGGACGGTGTGGCAACGGGA

GGCCATGCTGTGTCCCGAGGAAGTGCAAAGCTGAGATGGTTGGTGGAGCGGGGATACCTGCAGCCCTATGGAAAGGTC

ATTGATCTTGGATGTGGCAGAGGGGGCTGGAGTTACTACGCCGCCACCATCCGCAAAGTTCAAGAAGTGAAAGGATAC

ACAAAAGGAGGCCCTGGTCATGAAGAACCCATGTTGGTGCAAAGCTATGGGTGGAACATAGTCCGTCTTAAGAGTGGG

GTGGACGTCTTTCATATGGCGGCTGAGCCGTGTGACACGTTGCTGTGTGACATAGGTGAGTCATCATCTAGTCCTGAA

GTGGAAGAAGCACGGACGCTCAGAGTCCTCTCCATGGTGGGGGATTGGCTTGAAAAAAGACCAGGAGCCTTTTGTATA

AAAGTGTTGTGCCCATACACCAGCACTATGATGGAAACCCTGGAGCGACTGCAGCGTAGGTATGGGGGAGGACTGGTC

AGAGTGCCACTCTCCCGCAACTCTACACATGAGATGTACTGGGTCTCTGGAGCGAAAAGCAACACCATAAAAGTGTG

TCCACCACGAGCCAGCTCCTCTTGGGGCGCATGGACGGGCCCAGGAGGCCAGTGAAATATGAGGAGGATGTGAATCTC

GGCTCTGGCACGCGGGCTGTGGTAAGCTGCGCTGAAGCTCCCAACATGAAGATCATTGGTAACCGCATTGAAAGGATC

CGCAGTGAGCACGCGGAAACGTGGTTCTTTGACGAGAACCACCCATATAGGACATGGGCTTACCATGGAAGCTATGAG

GCCCCCACACAAGGGTCAGCGTCCTCTCTAATAAACGGGGTTGTCAGGCTCCTGTCAAAACCCTGGGATGTGGTGACT

GGAGTCACAGGAATAGCCATGACCGACACCACACCGTATGGTCAGCAAAGAGTTTTCAAGGAAAAAGTGGACACTAGG

GTGCCAGACCCCCAAGAAGGCACTCGTCAGGTTATGAGCATGGTCTCTTCCTGGTTGTGAAAGAGCTAGGCAAACAC

AAACGGCCACGAGTCTGTACCAAAGAAGAGTTCATCAACAAGGTTCGTAGCAATGCAGCATTAGGGGCAATATTTGAA

GAGGAAAAAGAGTGGAAGACTGCAGTGGAAGCTGTGAACGATCCAAGGTTCTGGGCTCTAGTGGACAAGGAAAGAGAG

CACCACCTGAGAGGAGAGTGCCAGAGTTGTGTGTACAACATGATGGGAAAAAGAGAAAAGAAACAAGGGGAATTTGGA

AAGGCCAAGGGCAGCCGCGCCATCTGGTATATGTGGCTAGGGGCTAGATTTCTAGAGTTCGAAGCCCTTGGATTCTTG

AACGAGGATCACTGGATGGGGAGAGAGAACTCAGGAGGTGGTGTTGAAGGGCTGGGATTACAAAGACTCGGATATGTC

CTAGAAGAGATGAGTCGCATACCAGGAGGAAGGATGTATGCAGATGACACTGCTGGCTGGGACACCCGCATCAGCAGG

TTTGATCTGGAGAATGAAGCTCTAATCACCAACCAAATGGAGAAAGGGCACAGGGCCTTGGCATTGGCCATAATCAAG

TACACATACCAAAACAAAGTGGTAAAGGTCCTTAGACCAGCTGAAAAAGGGAAGACAGTTATGGACATTATTTCGAGA

CAAGACCAAAGGGGGAGCGGACAAGTTGTCACTTACGCTCTTAACACATTTACCAACCTAGTGGTGCAACTCATTCGG

AATATGGAGGCTGAGGAAGTTCTAGAGATGCAAGACTTGTGGCTGCTGCGGAGGTCAGAGAAAGTGACCAACTGGTTG

CAGAGCAACGGATGGGATAGGCTCAAACGAATGGCAGTCAGTGGAGATGATTGCGTTGTGAAGCCAATTGATGATAGG

TTTGCACATGCCCTCAGGTTCTTGAATGATATGGGAAAAGTTAGGAAGGACACACAAGAGTGGAAACCCTCAACTGGA

TGGGACAACTGGGAAGAAGTTCCGTTTTGCTCCCACCACTTCAACAAGCTCCATCTCAAGGACGGGAGGTCCATTGTG

GTTCCCTGCCGCCACCAAGATGAACTGATTGGCCGGGCCCGCGTCTCTCCAGGGCGGGATGGAGCATCCGGGAGACT

GCTTGCCTAGCAAAATCATATGCGCAAATGTGGCAGCTCCTTTATTTCCACAGAAGGGACCTCCGACTGATGGCCAAT

GCCATTTGTTCATCTGTGCCAGTTGACTGGGTTCCAACTGGGAGAACTACCTGGTCAATCCATGGAAAGGGAGAATGG

ATGACCACTGAAGACATGCTTGTGGTGTGGAACAGAGTGTGGATTGAGGAGAACGACCACATGGAAGACAAGACCCCA

GTTACGAAATGGACAGACATTCCCTATTTGGGAAAAAGGGAAGACTTGTGGTGTGGATCTCTCATAGGGCACAGACCG

CGCACCACCTGGGCTGAGAACATTAAAAACACAGTCAACATGGTGCGCAGGATCATAGGTGATGAAGAAAGTACATG

GACTACCTATCCACCCAAGTTCGCTACTTGGGTGAAGAAGGGTCTACACCTGGAGTGCTGTAAGCACCAATCTTAGTG

TTGTCAGGCCTGCTAGTCAGCCACAGCTTGGGGAAAGCTGTGCAGCCTGTGACCCCCCAGGAGAAGCTGGGAAACCA

AGCCTATAGTCAGGCCGAGAACGCCATGGCACGGAAGAAGCCATGCTGCCTGTGAGCCCCTCAGAGGACACTGAGTCA

AAAAACCCCACGCGCTTGGAGGCGCAGGATGGGAAAAGAAGGTGGCGACCTTCCCCACCCTTCAATCTGGGGCCTGAA

CTGGAGATCAGCTGTGGATCTCCAGAAGAGGGACTAGTGGTTAGAGGAGACCCCCCGGAAAACGCAAAACAGCATATT

GACGCTGGGAAAGACCAGAGACTCCATGAGTTTCCACCACGCTGGCCGCCAGGCACAGATCGCCGAATAGCGGCGGCC

GGTGTGGGG
```

-continued

AHZ13508.1, Zika virus polyprotein from Polynesian outbreak (H/PF/2013)
SEQ ID NO: 73

MKNPKKKSGGFRIVNMLKRGVARVSPFGGLKRLPAGLLLGHGPIRMVLAILAFLRFTAIKPSLGLINRWGSVGKKEAM

EIIKKFKKDLAAMLRIINARKEKKRRGADTSVGIVGLLLTTAMAAEVTRRGSAYYMYLDRNDAGEAISFPTTLGMNKC

YIQIMDLGHMCDATMSYECPMLDEGVEPDDVDCWCNTTSTWVVYGTCHHKKGEARRSRRAVTLPSHSTRKLQTRSQTW

LESREYTKHLIRVENWIFRNPGFALAAAAIAWLLGSSTSQKVIYLVMILLIAPAYSIRCIGVSNRDFVEGMSGGTWVD

VVLEHGGCVTVMAQDKPTVDIELVTTTVSNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSGMIVNDTGHETDENRAKVEITPNSPRAEA

TLGGFGSLGLDCEPRTGLDFSDLYYLTMNNKHWLVHKEWFHDIPLPWHAGADTGTPHWNNKEALVEFKDAHAKRQTVV

VLGSQEGAVHTALAGALEAEMDGAKGRLSSGHLKCRLKMDKLRLKGVSYSLCTAAFTFTKIPAETLHGTVTVEVQYAG

TDGPCKVPAQMAVDMQTLTPVGRLITANPVITESTENSKMMLELDPPFGDSYIVIGVGEKKITHHWHRSGSTIGKAFE

ATVRGAKRMAVLGDTAWDFGSVGGALNSLGKG1HQ1FGAAFKSLFGGMSWFSQILIGTLLMWLGLNTKNGSISLMCLA

LGGVLIFLSTAVSADVGCSVDFSKKETRCGTGVFVYNDVEAWRDRYKYHPDSPRRLAAAVKQAWEDGICGISSVSRME

NIMWRSVEGELNAILEENGVQLTVVVGSVKNPMWRGPQRLPVPVNELPHGWKAWGKSYFVRAAKTNNSFVVDGDTLKE

CPLKHRAWNSFLVEDHGFGVFHTSVWLKVREDYSLECDPAVIGTAVKGKEAVHSDLGYWIESEKNDTWRLKRAHLIEM

KTCEWPKSHTLWTDGIEESDLIIPKSLAGPLSHHNTREGYRTQMKGPWHSEELEIRFEECPGTKVHVEETCGTRGPSL

RSTTASGRVIEEWCCRECTMPPLSFRAKDGCWYGMElRPRKEPESNLVRSMVTAGSTDHMDHFSLGVLVILLMVQEGL

KKRMTTKIIISTSMAVLVAMILGGFSMSDLAKLAILMGATFAEMNTGGDVAHLALIAAFKVRPALLVSFIFRANWTPR

ESMLLALASCLLQTAISALEGDLMVLINGFALAWLAIRAMVVPRTDNITLAILAALTPLARGTLLVAWRAGLATCGGF

MLLSLKGKGSVKKNLPFVMALGLTAVRLVDPINVVGLLLLTRSGKRSWPPSEVLTAVGLICALAGGFAKADIEMAGPM

AAVGLLIVSYVVSGKSVDMYIERAGDITWEKDAEVTGNSPRLDVALDESGDFSLVEDDGPPMREIILKVVLMTICGMN

PIAIPFAAGAWYVYVKTGKRSGALWDVPAPKEVKKGETTDGVYRVMTRRLLGSTQVGVGVMQEGVFHTMWHVTKGSAL

RSGEGRLDPYWGDVKQDLVSYCGPWKLDAAWDGHSEVQLLAVPPGERARNIQTLPGIFKTKDGDIGAVALDYPAGTSG

SPILDKCGRVIGLYGNGVVIKNGSYVSAITQGRREEETPVECFEPSMLKKKQLTVLDLHPGAGKTRRVLPEIVREAIK

TRLRTVILAPTRVVAAEMEEALRGLPVRYMTTAVNVTHSGTEIVDLMCHATFTSRLLQPIRVPNYNLYIMDEANFTDP

SSIAARGYISTRVEMGEAAAIFMTATPPGTRDAFPDSNSPIMDTEVEVPERAWSSGFDWVTDHSGKTVWFVPSVRNGN

EIAACLTKAGKRVIQLSRKTFETEFQKTKHQEWDFVVTTDISEMGANFKADRVIDSRRCLKPVILDGERVILAGPMPV

THASAAQRRGRIGRNPNKPGDEYLYGGGCAETDEDHAHWLEARMLLDNIYLQDGLIASLYRPEADKVAAIEGEFKLRT

EQRKTFVELMKRGDLPVWLAYQVASAGITYTDRRWCFDGTTNNTIMEDSVPAEVWTRHGEKRVLKPRWMDARVCSDHA

ALKSFKEFAAGKRGAAFGVMEALGTLPGHMTERFQEAIDNLAVLMRAETGSRPYKAAAAQLPETLETIMLLGLLGTVS

LGIFFVLMRNKGIGKMGFGMVTLGASAWLMWLSEIEPARIACVLIVVFLLLVVLIPEPEKQRSPQDNQMAIIIMVAVG

LLGLITANELGWLERTKSDLSHLMGRREEGATIGFSMDIDLRPASAWAIYAALTTFITPAVQHAVTTSYNNYSLMAMA

TQAGVLFGMGKGMPFYAWDFGVPLLMIGCYSQLTPLTLIVAIILLVAHYMYLIPGLQAAAARAAQKRTAAGIMKNPVV

DGIVVTDIDTMTIDPQVEKKMGQVLLIAVAVSSAILSRTAWGWGEAGALITAATSTLWEGSPNKYWNSSTATSLCNIF

RGSYLAGASLIYTVTRNAGLVKRRGGGTGETLGEKWKARLNQMSALEFYSYKKSGITEVCREEARRALKDGVATGGHA

VSRGSAKLRWLVERGYLQPYGKVIDLGCGRGGWSYYAATIRKVQEVKGYTKGGPGHEEPMLVQSYGWNIVRLKSGVDV

FHMAAEPCDTLLCDIGESSSSPEVEEARTLRVLSMVGDWLEKRPGAFCIKVLCPYTSTMMETLERLQRRYGGGLVRVP

LSRNSTHEMYWVSGAKSNTIKSVSTTSQLLLGRMDGPRRPVKYEEDVNLGSGTRAVVSCAEAPNMKIIGNRIERIRSE

HAETWFFDENHPYRTWAYHGSYEAPTQGSASSLINGVVRLLSKPWDVVTGVTGIAMTDTTPYGQQRVFKEKVDTRVPD

PQEGTRQVMSMVSSWLWKELGKHKRPRVCTKEEFINKVRSNAALGAIFEEEKEWKTAVEAVNDPRFWALVDKEREHHL

RGECQSCVYNMMGKREKKQGEFGKAKGSRAIWYMWLGARFLEFEALGFLNEDHWMGRENSGGGVEGLGLQRLGYVLEE

-continued

MSRIPGGRMYADDTAGWDTRISRFDLENEALITNQMEKGHRALALAIIKYTYQNKVVKVLRPAEKGKTVMDIISRQDQ
RGSGQVVTYALNTFTNLVVQLIRNMEAEEVLEMQDLWLLRRSEKVTNWLQSNGWDRLKRMAVSGDDCVVKPIDDRFAH
ALRFLNDMGKVRKDTQEWKPSTGWDNWEEVPFCSHHFNKLHLKDGRSIVVPCRHQDELIGRARVSPGAGWSIRETACL
AKSYAQMWQLLYFHRRDLRLMANAICSSVPVDWVPTGRTTWSIHGKGEWMTTEDMLVVWNRVWIEENDHMEDKTPVTK
WTDIPYLGKREDLWCGSLIGHRPRTTWAENIKNTVNMVRRIIGDEEKYMDYLSTQVRYLGEEGSTPGVL

9320_Zika_PF_1F  SEQ ID NO: 74
ttaggatccGTTGTTGATCTGTGTGAAT

9321_Zika_PF_1R  SEQ ID NO: 75
taactcgagCGTACACAACCCAAGTT

9322_Zika_PF_2F  SEQ ID NO: 76
ttaggatccTCACTAGACGTGGGAGTG

9323_Zika_PF_2R  SEQ ID NO: 77
taactcgagAAGCCATGTCYGATATTGAT

9324_Zika_PF_3F  SEQ ID NO: 78
ttaggatccGCATACAGCATCAGGTG

9325_Zika_PF_3R  SEQ ID NO: 79
taactcgagTGTGGAGTTCCGGTGTCT

9326_Zika_PF_4F  SEQ ID NO: 80
ttaggatccGAATAGAGCGAARGTTGAGATA

9327_Zika_PF_4R  SEQ ID NO: 81
taactcgAGTGGTGGGTGATCTTCTTCT

9328_Zika_PF_5F  SEQ ID NO: 82
ttaggatcCAGTCACAGTGGAGGTACAGTAC

9329_Zika_PF_5R  SEQ ID NO: 83
taactcgagCRCAGATACCATCTTCCC

9330_Zika_PF_6F  SEQ ID NO: 84
ttaggatCCCTTATGTGCTTGGCCTTAG

9331_Zika_PF_6R  SEQ ID NO: 85
taactcgagTCTTCAGCCTCCATGTG

9332_Zika_PF_7F  SEQ ID NO: 86
ttaggatccAATGCCCACTCAAACATAGA

9333_Zika_PF_7R  SEQ ID NO: 87
taactcgagTCATTCTCTTCTTCAGCCCTT

9334_Zika_PF_8F  SEQ ID NO: 88
ttaggatccAAGGGTGATCGAGGAAT

9335_Zika_PF_8R  SEQ ID NO: 89
taactcgagTTCCCTTCAGAGAGAGGAGC

9336_Zika_PF_9F  SEQ ID NO: 90
ttaggatccTCTTTTGCAAACTGCGATC

-continued

| | |
|---|---|
| 9337_Zika_PF_9R<br>taactcgagTCCAGCTGCAAAGGGTAT | SEQ ID NO: 91 |
| 9338_Zika_PF_10F<br>ttaggatccGTGTGGACATGTACATTGA | SEQ ID NO: 92 |
| 9339_Zika_PF_10R<br>taactcgagCCCATTGCCATAAAGTC | SEQ ID NO: 93 |
| 9340_Zika_PF_11F<br>ttaggatccTCATACTGTGGTCCATGGA | SEQ ID NO: 94 |
| 9341_Zika_PF_11R<br>taactcgagGCCCATCTCAACCCTTG | SEQ ID NO: 95 |
| 9342_Zika_PF_12F<br>ttaggatccTAGAGGGCTTCCAGTGC | SEQ ID NO: 96 |
| 9343_Zika_PF_12R<br>taactcgAGATACTCATCTCCAGGTTTGTTG | SEQ ID NO: 97 |
| 9344_Zika_PF_13F<br>ttaggatccGAAAACAAAACATCAAGAGTG | SEQ ID NO: 98 |
| 9345_Zika_PF_13R<br>taactcgagGAATCTCTCTGTCATGTGTCCT | SEQ ID NO: 99 |
| 9346_Zika_PF_14F<br>ttaggatccTTGATGGCACGACCAAC | SEQ ID NO: 100 |
| 9347_Zika_PF_14R<br>ttaggatccGTTGTTGATCTGTGTGAAT | SEQ ID NO: 101 |
| 9348_Zika_PF_15F<br>taactcgagCAGGTCAATGTCCATTG | SEQ ID NO: 102 |
| 9349_Zika_PF_15R<br>ttaggatccTGTTGTGTTCCTATTGCTGGT | SEQ ID NO: 103 |
| 9350_Zika_PF_16F<br>taactcgaGTGATCAGRGCCCCAGC | SEQ ID NO: 104 |
| 9351_Zika_PF_16R<br>ttaggatccTGCTGCCCAGAAGAGAA | SEQ ID NO: 105 |
| 9352_Zika_PF_17F<br>taactcgaGCACCAACAYGGGTTCTT | SEQ ID NO: 106 |
| 9353_Zika_PF_17R<br>ttaggatcCTCAAGGACGGTGTGGC | SEQ ID NO: 107 |
| 9354_Zika_PF_18F<br>taactcgagCAATGATCTTCATGTTGGG | SEQ ID NO: 108 |
| 9355_Zika_PF_18R<br>ttaggatccTATGGGGAGGACTGGT | SEQ ID NO: 109 |
| 9356_Zika_PF_19F<br>taactcGAGCCCAGAACCTTGGATC | SEQ ID NO: 110 |

```
9357_Zika_PF_19R
                                                          SEQ ID NO: 111
ttaggatcCAGACCCCCAAGAAGGC 9358_Zika_PF_20F
                                                          SEQ ID NO: 112
taactcgagCCCCTTTGGTCTTGTCT 9359_Zika_PF_20R
                                                          SEQ ID NO: 113
ttaggatccAGGAAGGATGTATGCAGATG 9360_Zika_PF_21F
                                                          SEQ ID NO: 114
taactcgagACATTTGCGCATATGATTTTG 9361_Zika_PF_21R
                                                          SEQ ID NO: 115
ttaggatccAGGAAGGACACACAAGAGT 9362_Zika_PF_22F
                                                          SEQ ID NO: 116
taactcgagACAGGCTGCACAGCTTT 9363_Zika_PF_22R
                                                          SEQ ID NO: 117
ttaggatccTCTCTCATAGGGCACAGAC
```

In some embodiments, the Zika virus has polyprotein, including an envelope (E) protein, with an amino acid sequence provided by any one of SEQ ID NOs: 14-69 or 72. In some embodiments, the polyprotein or E protein sequence is at least 80%, 81%, 82%, 83%, 84%, 85%, 86%, 87%, 88%, 89%, 90%, 91%, 92%. 93%, 94%, 95%, 96%, 97%, 98%, 99%, 99.5%, 99.6%, 99.7%, 99.8% or 99.9% identical to any one of SEQ ID NOs: 2-69 or 72.

The terms "identical" or percent "identity" in the context of two or more nucleic acids or amino acid sequences refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, or 99% identity) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length. In some embodiments, the identity exists over the length of a protein, such as the E protein.

For sequence comparison, typically one sequence acts as a reference sequence, to which test sequences are compared. Methods of alignment of sequences for comparison are well known in the art. See, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman. Proc. Natl. Acad. Sci. USA 85:2444, 1988, by computerized implementations of these algorithms (GAP, BESTFIT, FASTA, Jalview and TFASTA in the Wisconsin Genetics Software Package, Genetics Computer Group. 575 Science Dr., Madison. WI), by multi sequence alignment implementation using e.g. CLUSTALW (Larkin et al., (2007). Bioinformatics, 23, 2947-2948.) or MAFFT (Katoh & Toh 2008 Briefings in Bioinformatics 9:286-298), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977 and Altschul et al., J. Mol. Biol. 215:403-410, 1990, respectively.

EXAMPLES

Figure 9A:
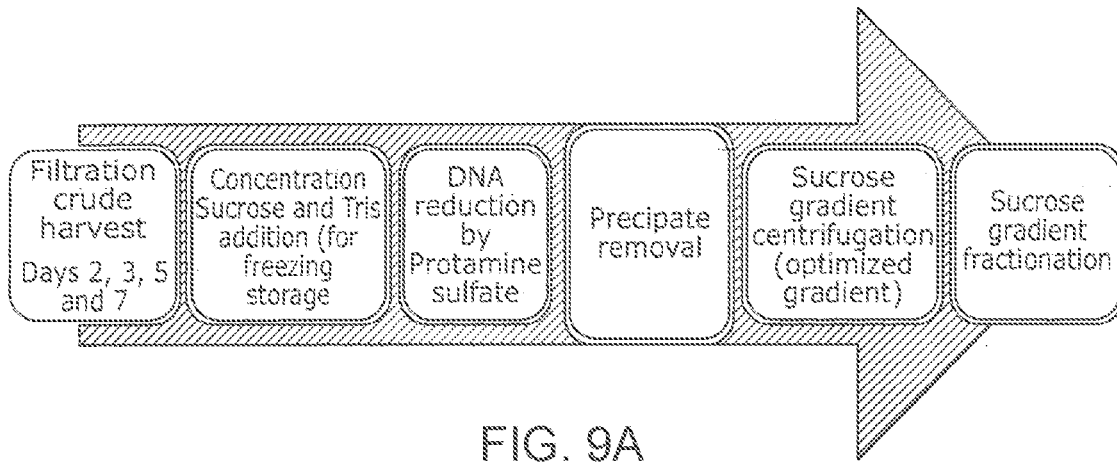
FIGS. 9A-9B: An exemplary downstream virus purification process from the crude harvest to formulation of the drug substance (vaccine), a preferred embodiment of the process of the invention (FIG. 9A). A flow-chart of an exemplary virus inactivation process is shown in (FIG. 9B).
Figure 9B:
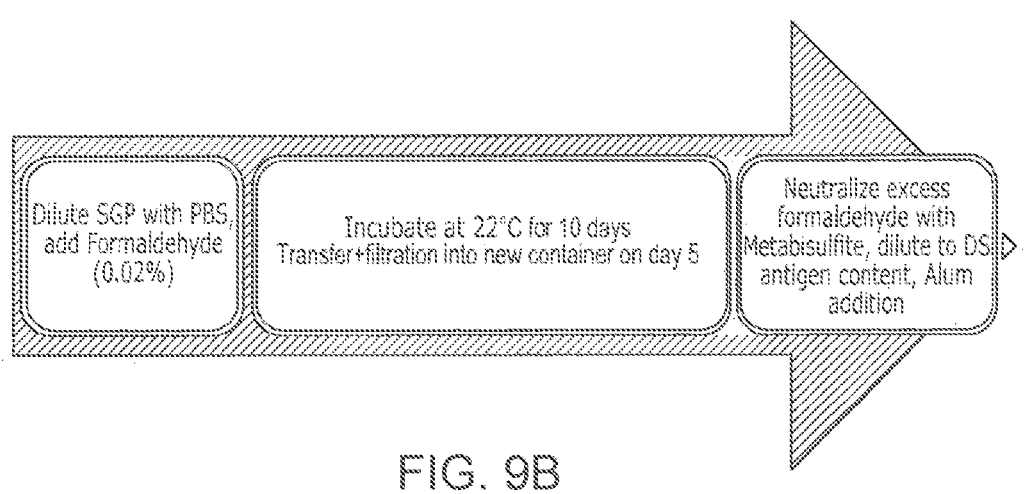
Figure 10:
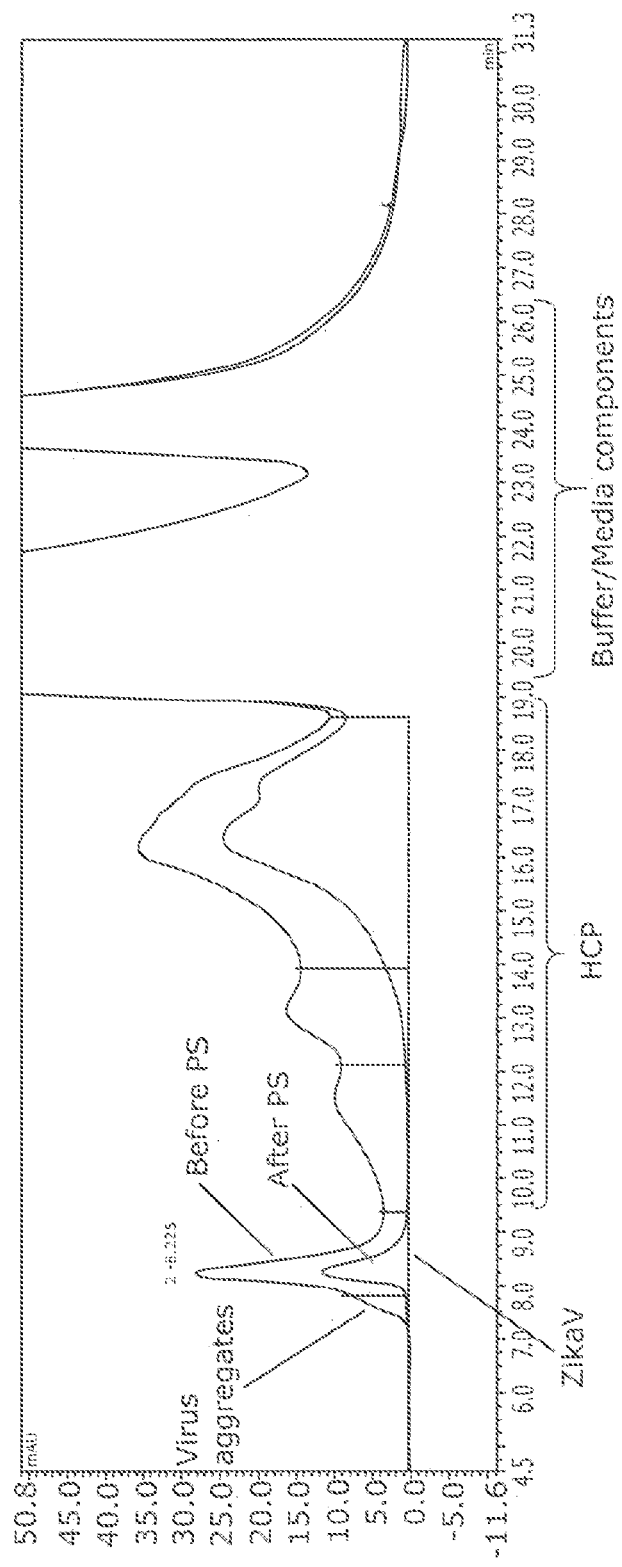
FIG. 10: PS treatment results in selective removal of Zika virus aggregates and Vero HCP and LMW impurities (SEC-HPLC of 30× concentrated Zika Virus harvest day 5).

Example 1: Production of a Zika Drug Substance Suitable for Application as a Vaccine in Humans and Animals Materials and Methods For the production of ZikaV the JEV process platform (Srivastava et al., Vaccine 19 (2001) 4557-4565; U.S. Pat. No. 6,309,650B1) was used as a basis. Small changes of certain process steps were adapted to ZikaV properties and to improve purity. A short summary of the process steps is outlined below (see also FIGS. 9A and B). Briefly, the unexpected and novel purification properties of protamine sulphate (PS) were evaluated in purification processes for Zika Virus. As shown in FIG. 10, non-infectious virus particle aggregates, HCP and other LMW impurities were removed by PS precipitation as shown by removal of aggregate shoulder in SEC-HPLC and no loss of infectious virus titer by PS treatment. Further optimization of the Zika purification protocol is provided below.

Figure 21:
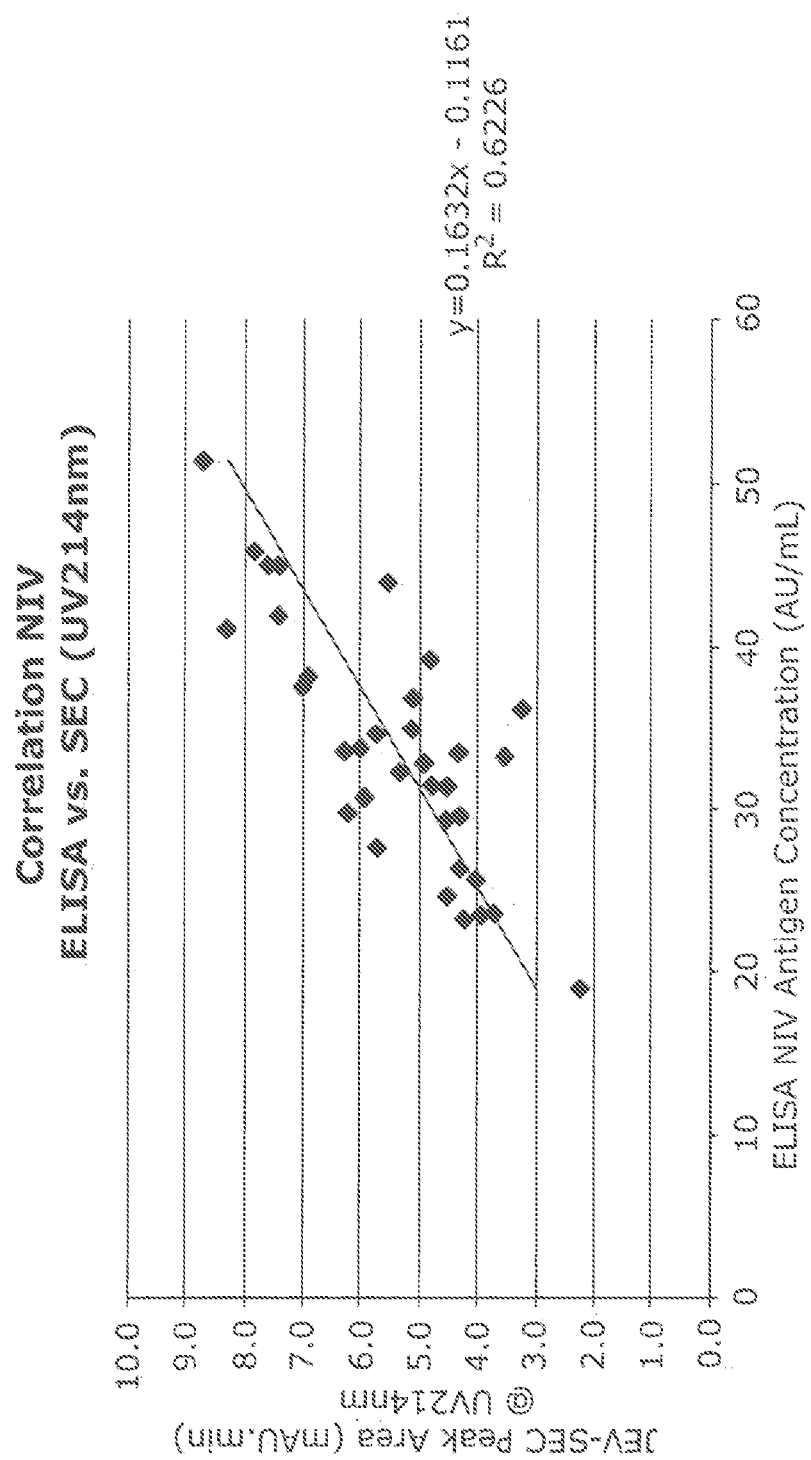
FIG. 21: Correlation between JEV antigen content in neutralized inactivated virus (NIV) analysed by ELISA and SEC-HPLC (Dionex Ultimate 3000, Superose 6 column).

Upstream:
  Roller Bottle based Vero cell expansion (25×850 cm2 CellBind):
  5% $CO_2$, 35° C., MEM+2 mM L-Glutamine+10% FBS
  Infection with ZikaV research Master Seed Bank (rMSB) at MOI 0.01
  Virus Production without serum
  5% $CO_2$, 35° C., MEM+2 mM L-Glutamine
  Multiple harvests (days 2, 3, 5 and 7) with re-feed
  Sterile filtration of harvests and storage at 2-8° C. until further processing Downstream:
  Pooling of harvests and concentration by ultrafiltration (100 kDa)
  Stabilization of concentrated harvest (Tris/10% sucrose) for storage if required (−80° C.)
- Removal of hcDNA by Protamine Sulphate (2 mg/mL)
- Sucrose Gradient Purification (optimized three layered gradient)
- Formaldehyde Inactivation (0.02%, 22° C., 10 days), neutralization with Na-metabisulfite
- Dilution to DS antigen target content and formulation with Aluminium hydroxide (0.5 mg Al/mL)

Zika Virus Strain H/PF/2013 was originally isolated from a 51-year-old woman (accession number KJ776791.1, also SEQ ID NO: 13 herein) from French Polynesia. A sample was obtained from the European Virus Archive (EVAg; Ref-SKU: 001v-EVA1545). Based on this material, a research master seed bank (rMSB) was prepared on Vero cells as the cell substrate and the genomic sequence was checked by sequencing. Because the genomic sequence at the 5' and 3'flanking sequences of Zika virus strain H/PF/2013 was unknown, primers for sequencing were designed in those regions based on other Zika virus strains whereas the internal primers were designed from the published sequence (SEQ ID NOs: 74 to 117, see also Table A). The sequence obtained from the rMSB by use of these primers is provided by SEQ ID NO: 72. There was 100% overlap of the sequence with the published sequence of Zika Virus Strain H/PF/2013 (SEQ ID NO: 13). However, we sequenced additional regions 5' (an additional 40 bp) and 3' (an additional 160 bp) represented in SEQ ID NO: 72. In a preferred embodiment, the Zika virus of the invention comprises SEQ ID NO: 72. The genomic RNA is somewhat longer than the sequence according to SEQ ID NO: 72 (perhaps an additional 200 bp). Additionally, a Zika virus adapted to a host cell such as e.g. Vero cells may be expected to contain one or more mutations. For these reasons, the Zika virus of the current invention comprises the sequence of SEQ ID NO: 72 or, preferably, a sequence with at least 95%, 96%, 97%, 98%, or at least 99% sequence identity to the sequence provided by SEQ ID NO: 72. Furthermore, because the viral genome is likely to contain even further flanking regions to SEQ ID NO: 72; in one embodiment, the Zika virus of the invention contains the sequence of SEQ ID NO: 72 and optionally further comprises extensions at the 5' and/or 3' ends of at least 10, at least 20, at least 30, at least 40, at least 50, at least 60, at least 70, at least 80, at least 90, at least 100, at least 110, at least 120 or at least 130 nucleotides. In a preferred embodiment, the Zika virus comprises at least the coding sequence for the entire polyprotein of Zika Virus Strain H/PF/2013 of the invention i.e. the amino acid sequence of SEQ ID NO: 73 or a polyprotein with at least 95%, 96%, 97%, 98%, or at least 99% sequence identity to the sequence provided by SEQ ID NO: 73. Furthermore, the Zika virus comprises at least the coding sequence for the E-protein of Zika Virus Strain H/PF/2013 of the invention SEQ ID NO: 47 or an E-protein thereof with at least 95%, 96%, 97%, 98%, or at least 99% sequence identity to the sequence provided by SEQ ID NO: 47.

Virus Growth on Vero Cells

Vero cells were grown in Eagle's minimal essential medium (EMEM) containing 10% fetal bovine serum (FBS). Roller bottle cultures of Vero cell monolayers were infected with Zika Virus Strain H/PF/2013 at a multiplicity of infection (moi) of 0.01 plaque forming units (pfu) per cell. After 2 hours of virus adsorption, the cultures were washed 3 times with PBS and fed with EMEM without FBS and incubated at +35° C. with 5% $CO_2$. Infected Vero cell cultures were incubated until the virus titer reaches a desired level.

The culture medium was harvested at days 2, 3, 5 and 7 and were pooled from those harvest days and then centrifuged in a standard centrifuge. The supernatants were then filtered. Virus culture supernatants were concentrated by TFF ultrafiltration to remove cell culture media components and to reduce batch volume.

Evaluation of Harvest Procedure

The current JEV harvest process has scheduled harvests on days 3, 5, 7 and 9 post infection. To mimic the JEV process roller bottles were infected with ZIKV bank P4-FBS at an MOI of 0.01 in infection medium (MEM with 2% FBS+2 mM L-glutamine) for 2 hours. After removing the inoculum the cells were washed twice with PBS and 200 mL production medium (MEM+2 mM L-glutamine) was added.

After taking a sample on day 2 the first virus harvest was conducted on day 3 after infection. At this point significantly higher CPE could be observed compared to cells where virus was removed on day 2. Plaque assay analysis showed that the viral titers on day 2 were in the same range as for the standard harvesting schedule. However, starting with the day 3 harvest, the observed titers were significantly lower correlating with the increased CPE observed compared to the standard harvest schedule. On day 5 post infection no more living cells could be observed at all and the experiment was terminated with a final day 5 harvest.

TABLE 3

The calculated titers per plaque assay are summarized in the list below.

| | Log 10 PFU/mL |
|---|---|
| sample day 2 | 7.02 |
| harvest day 3 | 6.66 |
| harvest day 5 | 6.26 |

This finding led to an optimized harvest schedule to better control of CPE and allow additional harvest day 5 and 7, see FIG. 15. For both harvest days the optimized ZikaV protocol yield significant higher virus titers compared to the modified protocol showing that the time of the first harvest is crucial for production yields. Additionally first harvesting at day 3 results in maximum 2 harvest points whereas first harvesting at day 2 allows for 4 harvest points further increasing the yield gain.

Downstream Purification of Zika Virus

The purification process was carried out at room temperature (18-22° C.) unless stated otherwise. Virus purification started with concentration of filtered combined harvest using 100 kDa cut-off TFF ultrafiltration modules to remove cell culture media components and reduce batch volume. After concentration, the pooled filtered harvest material was adjusted to a final concentration of 25 mM Tris pH 7.5 and 10% sucrose (w/w) using stock solution of both components (see FIG. 11 for SEC-HPLC of different harvests prior to PS treatment). This allowed for freezing the concentrated harvest at <−65° C. if required.

Host cell DNA and protein reduction as well reduction of non-infectious virus aggregates in the concentrated material was achieved by precipitation with protamine sulphate (2 mg/mL) followed by sucrose density centrifugation (2-8° C.) as final polishing step (see FIG. 20 for SEC-HPLC of different harvests post PS treatment). The purification process was designed to be completed within 2 working days with SGC starting on end of day 1 followed by fractionation and SDS-PAGE analysis on day 2. The sucrose gradient fractions were stored at 2-8° C. during the SDS-PAGE analysis (Silver staining) to identify the pure fractions containing ZikaV (see FIG. 21). After pooling the relevant fractions, the pool was diluted and inactivated by Formalin. After pooling the relevant fractions of sucrose gradient centrifugation, the pool was diluted 1:3 in PBS and inactivated by Formalin (0.02% v/v, 200 ppm). Fractions were subjected to analysis by SDS-PAGE.

Effect of PS Treatment on Virus Recovery

Figure 11:
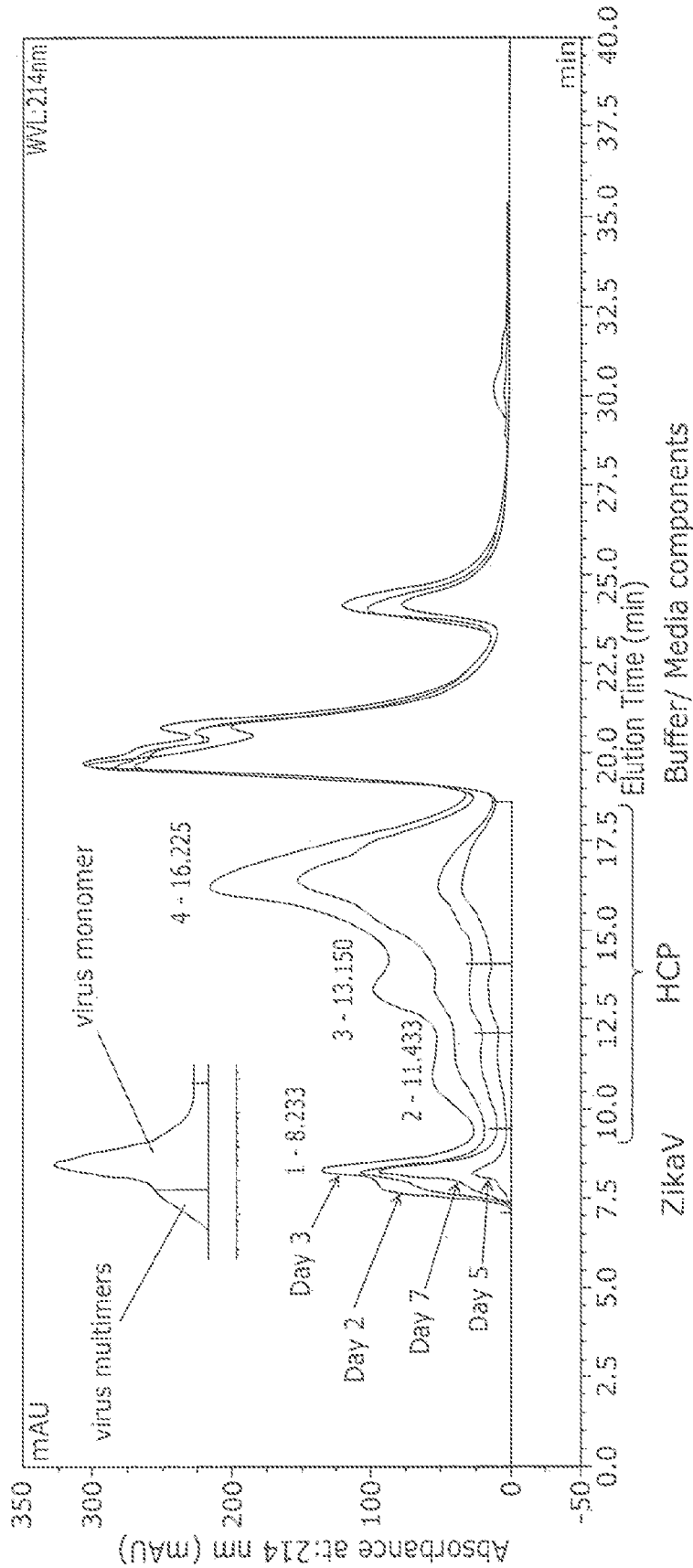
FIG. 11: SEC-HPLC of individual 30× concentrated Zika harvest prior to PS treatment at different time points.
Figure 12:
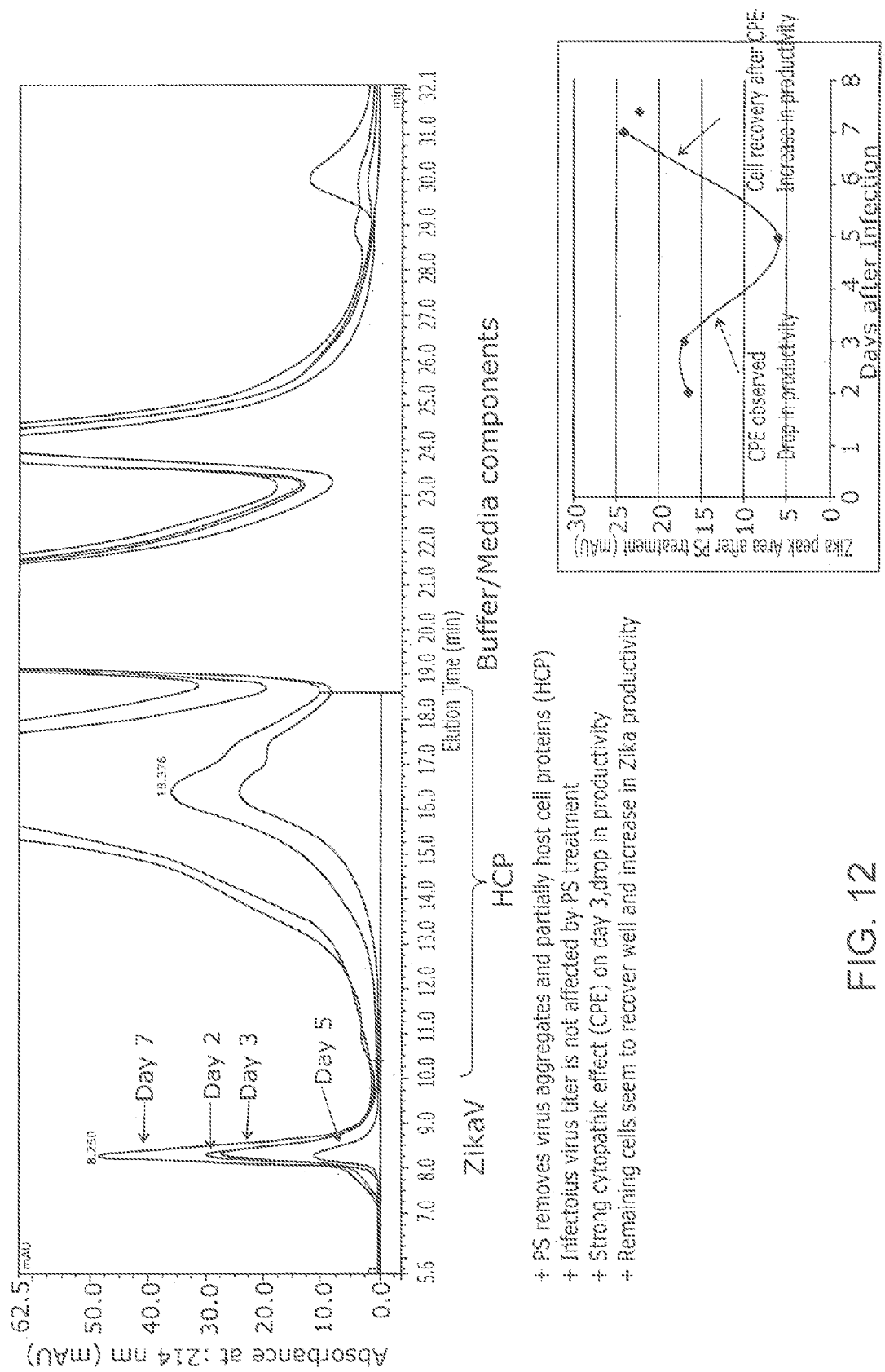
FIG. 12: SEC-HPLC of individual 30× concentrated Zika harvest post PS treatment at different time points. The smaller graph indicates the observed cytopathic effect (CPE) over time.
Figure 13:
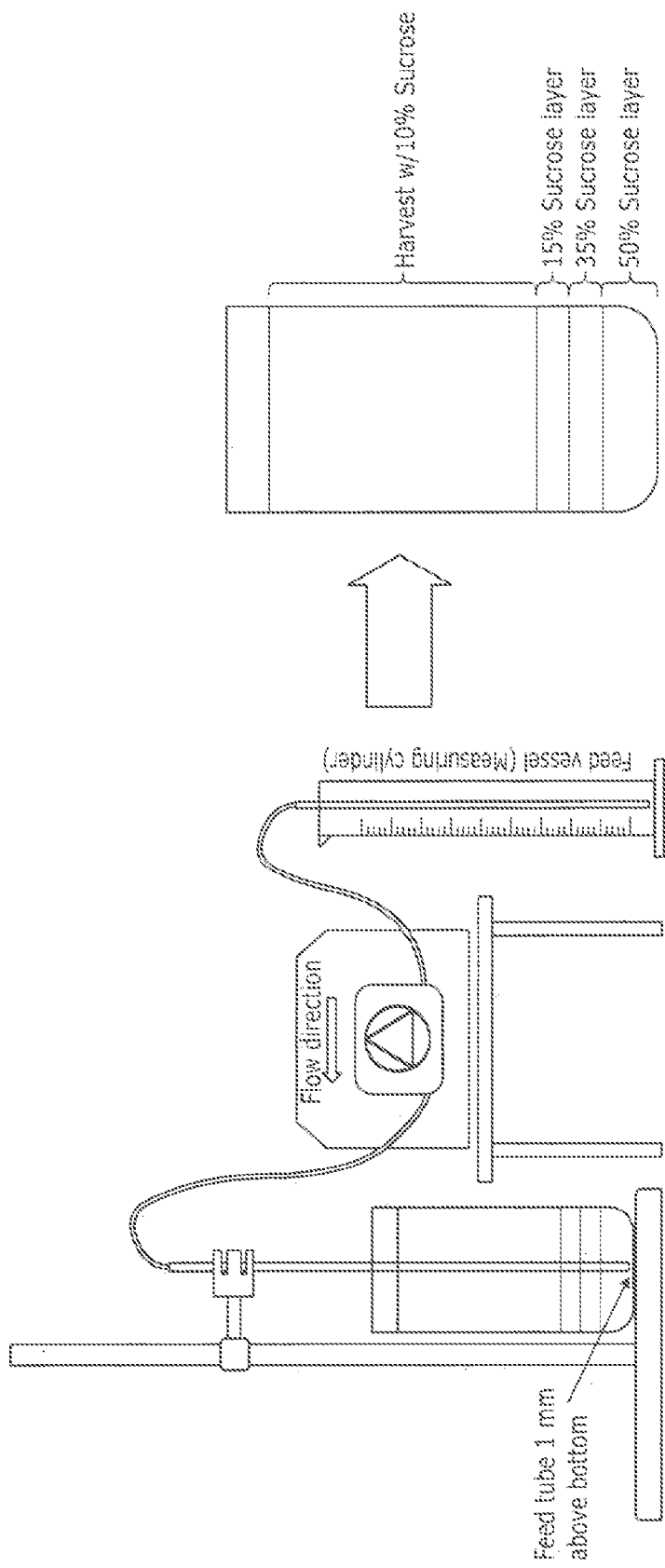
FIG. 13: Preparation of the sucrose gradient.
Figure 14:
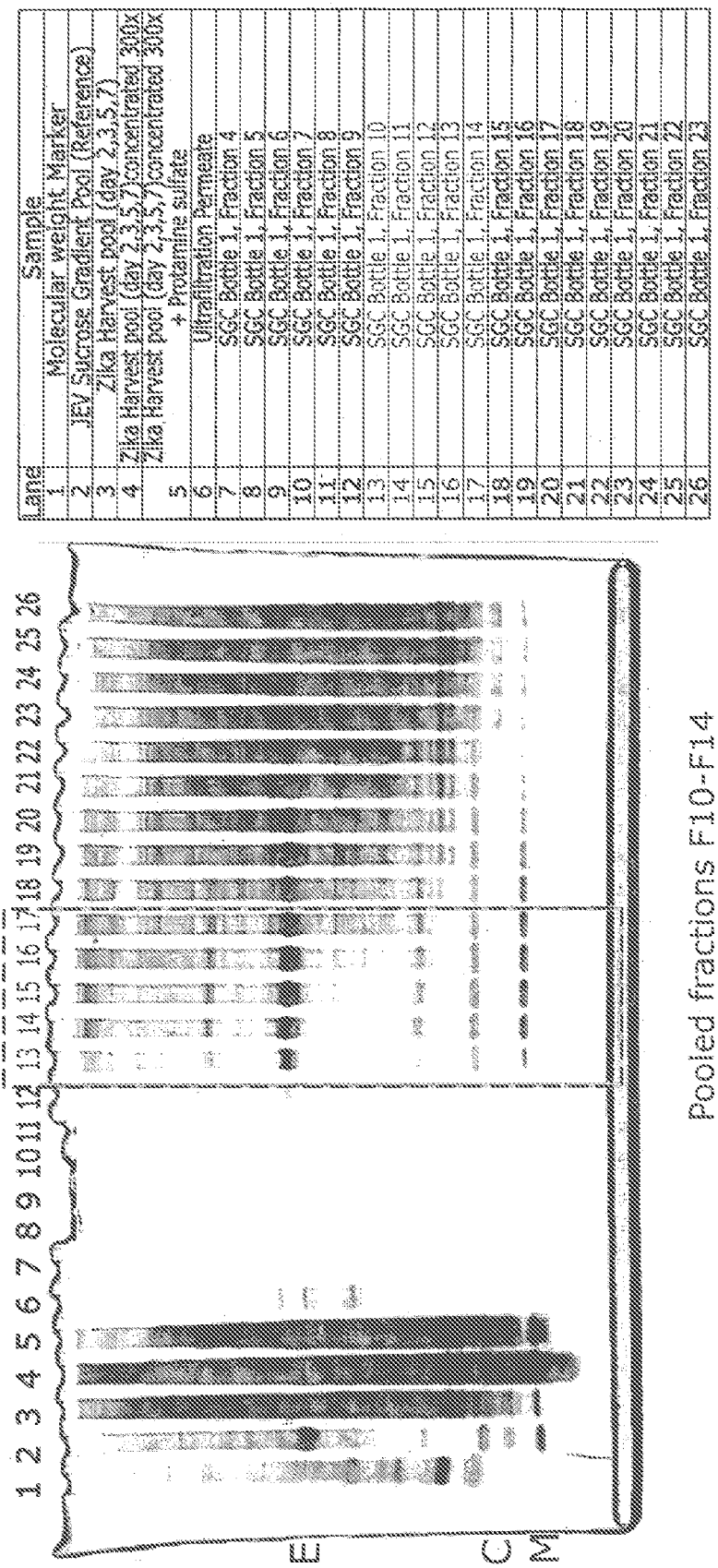
FIG. 14: Representative SDS-PAGE from the sucrose gradient harvest of a Zika purification is shown.
Figure 15:
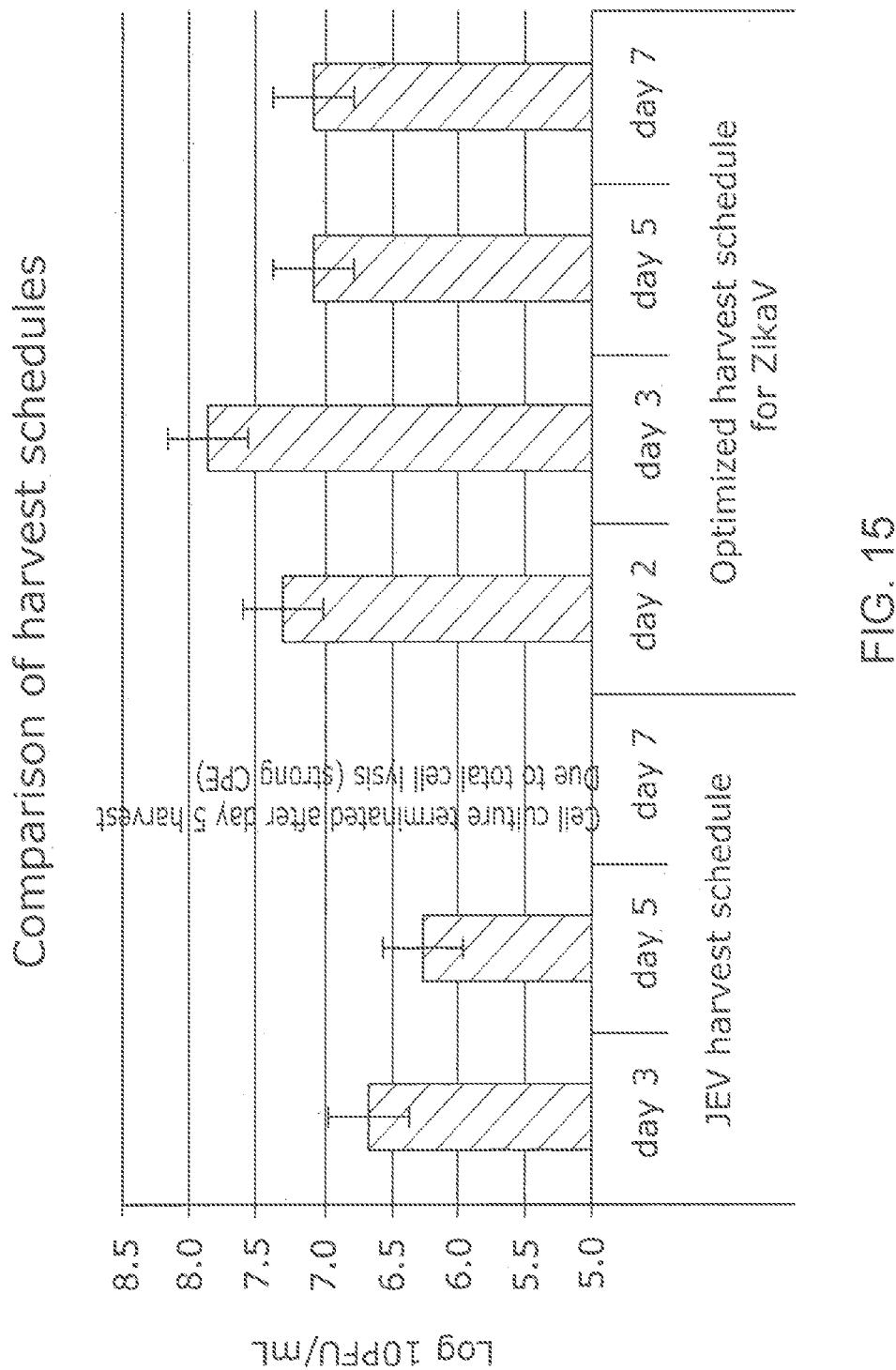
FIG. 15: Comparison of JEV and ZikaV harvest schedules/yields.
Figure 16:
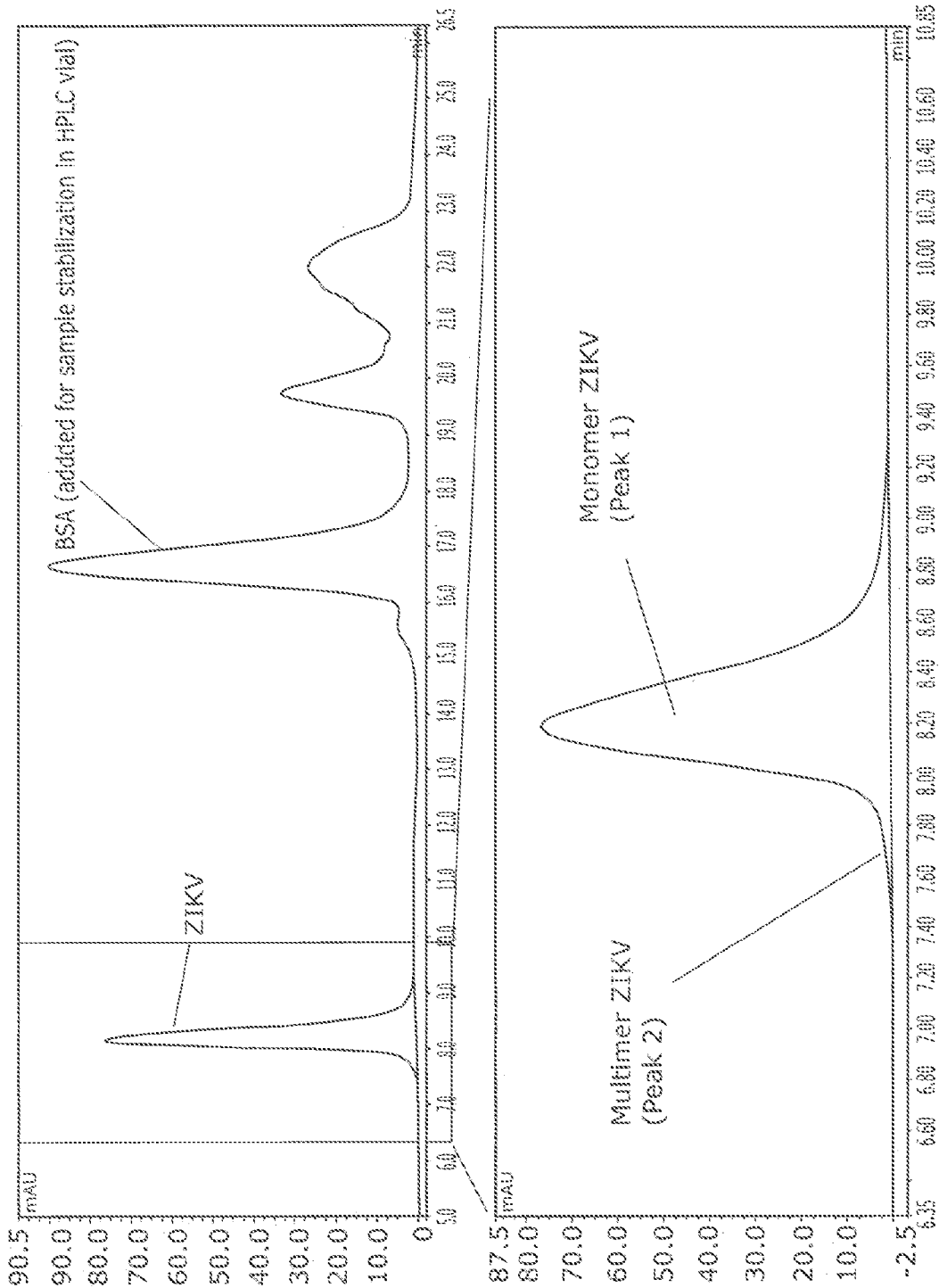
FIG. 16: SEC-HPLC elution profile of ZikaV NIV. Data were processed on Dionex Ultimate 3000/Superose 6 Increase column. Both panels are from the same chromatogram. The upper graph is the complete elution profile; the lower graph is an enlargement of the ZIKAV elution peak.
Figure 17:
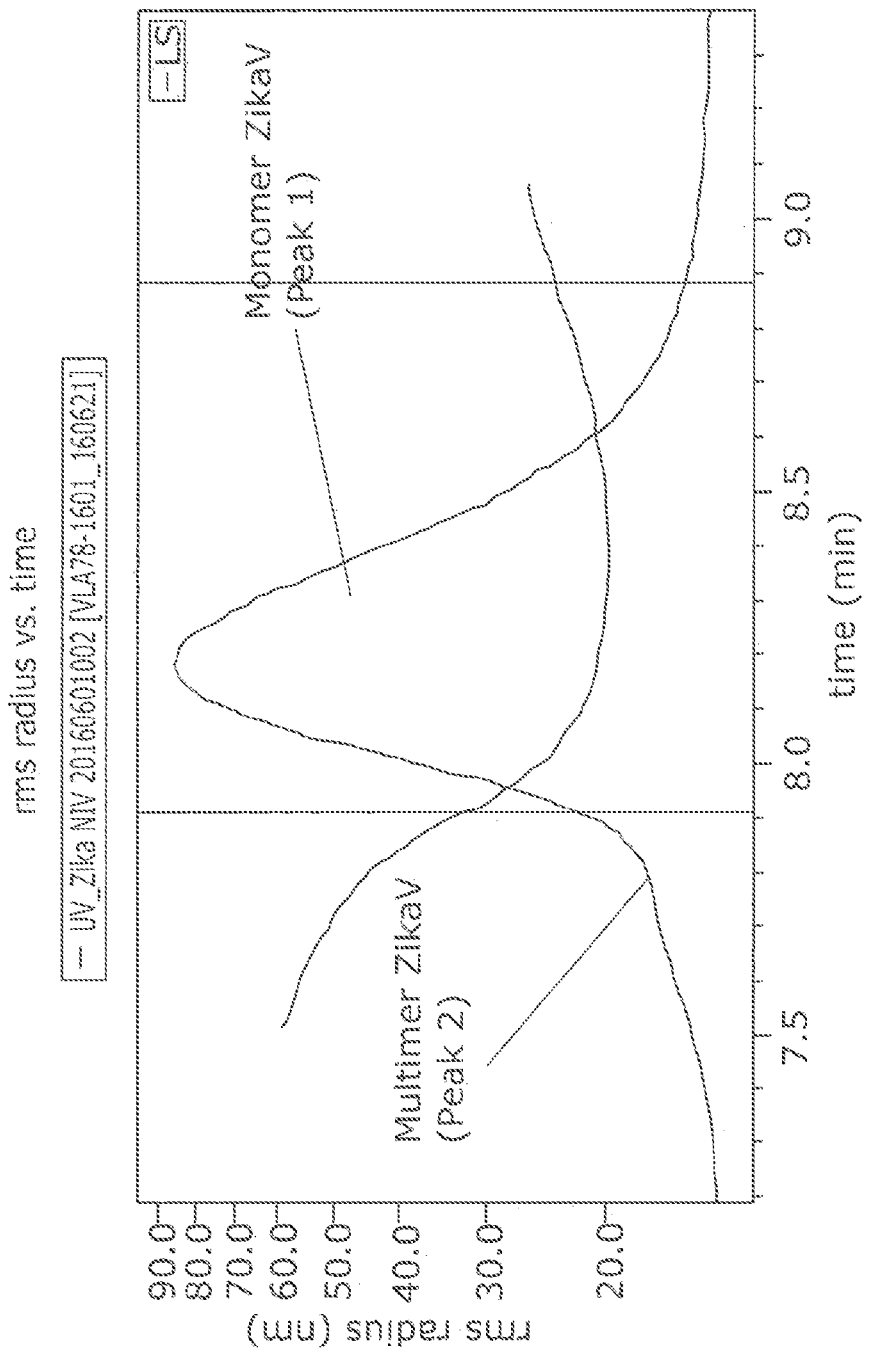
FIG. 17: SEC-MALLS analysis of inactivated ZikaV.
Figure 18:
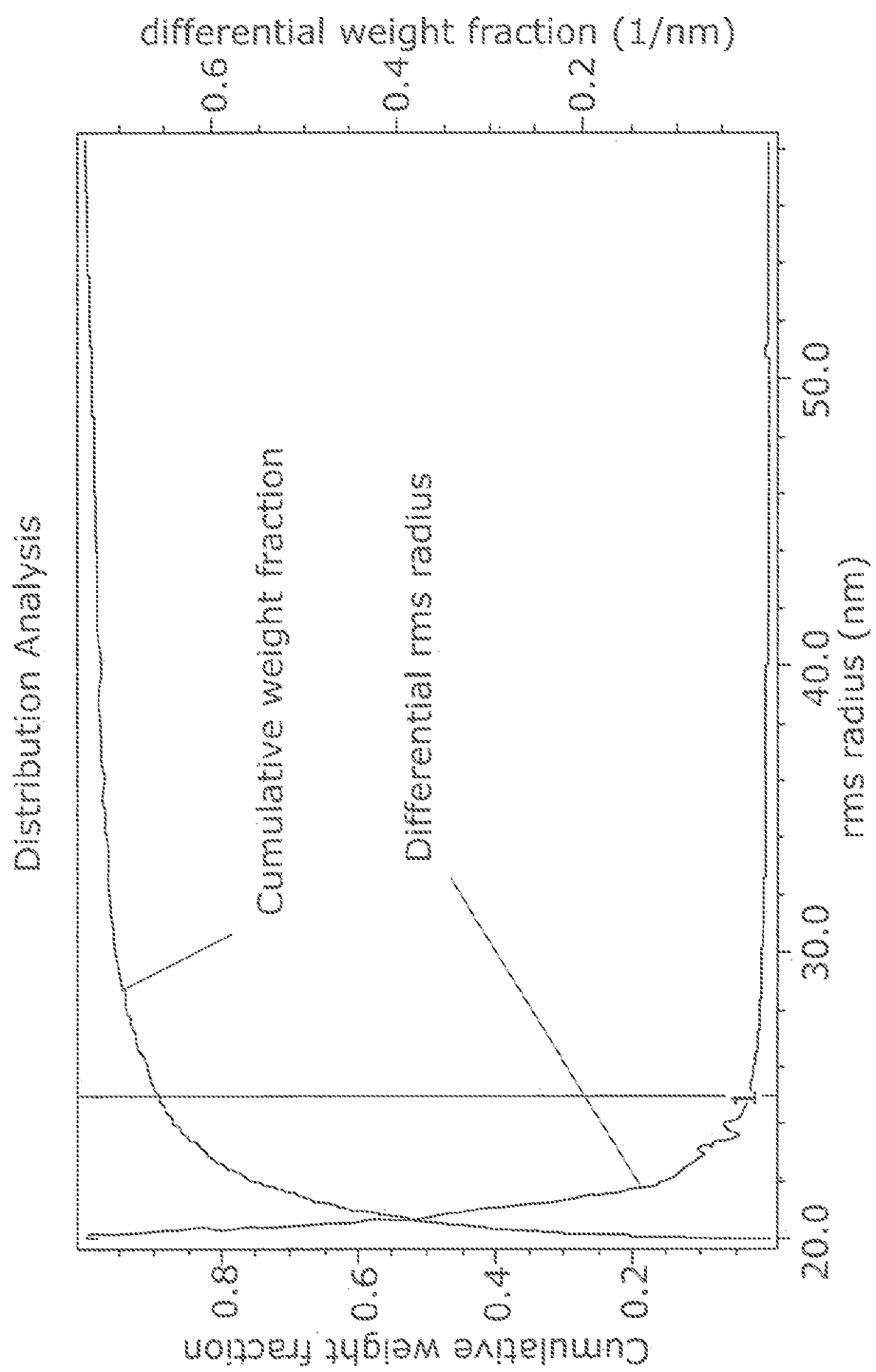
FIG. 18: Cumulative particle size distribution of Zika NIV.

Samples of individual 30× concentrated harvests days 2, 3, 5 and 7 were analysed before (FIG. 11) and after PS (FIG. 12) treatment by SEC-HPLC and plaque assay. SEC-HPLC was used for determination of relative total ZikaV content (active+inactive) expressed as peak area, whereas the rel. ZikaV peak purity is given as relative content of virus monomer population to total virus peak. Plaque assay states the content of total active virus particles in each sample. Experimental results are summarized in Table 4. The virus peak recovery by SEC-HPLC was only between 12 to 36% with peak purity after PS treatment in the range of >90% (no virus aggregates detected). The recovery of active virus particles by plaque assay was all >100% (130-700%, range within the variability of the assay) showing that no active virus particles were lost during PS treatment. These results show that during PS treatment only non-infective (immature and/or aggregated virus) particles were removed.

TABLE 4

ZikaV recovery by SEC-HPLC and plaque assay before and after PS treatment.

SEC-HPLC

| | Peak area mAU * min | | | rel. virus monomer |
|---|---|---|---|---|
| Harvest day | 30× conc | 30× + PS | SEC Recovery (%) | content after PS (%) |
| Day 2 | 101.36 | 18.63 | 18 | 89% |
| Day 3 | 144.51 | 17.48 | 12 | 90% |
| Day 5 | 19.97 | 5.92 | 30 | 96% |
| Day 7 | 68.80 | 24.43 | 36 | 99% |

Plaque Assay

| | PFU/mL | | Plaque Recovery |
|---|---|---|---|
| Harvest day | 30× conc | 30× + PS | (%) |
| Day 2 | 3E+08 | 5E+08 | 179 |
| Day 3 | 2E+08 | 4E+08 | 193 |
| Day 5 | 1E+08 | 9E+08 | 700 |
| Day 7 | 3E+08 | 4E+08 | 132 |

Sucrose Gradient Centrifugation

The PS treated harvest was split in two parts and loaded on two centrifuge bottles. Sucrose density gradient centrifugation (SGC) was used for final concentration and polishing of the ZikaV material. The ZikaV PS treated concentrated harvest was loaded on top of a solution consisting of three layers of sucrose with different densities. The three sucrose layers were selected based on a preliminary study which showed the formation of a linear sucrose gradient and complete separation of the virus particles from residual contaminants as demonstrated for ChikV (FIG. 15D). The optimal volumes of the sucrose solutions were determined empirically. The volumes of individual layers for a centrifugation in 100 mL bottle scale are shown in Table 5.

TABLE 5

Individual layers/volumes for a centrifugation in bottle.

| Solution | Volume (mL) |
|---|---|
| PS treated harvest in 10% sucrose (L) | 40 |
| 15% sucrose (J) | 15 |
| 35% sucrose (I) | 15 |
| 50% sucrose (H) | 20 |
| Total volume | 90 |

The sucrose gradient bottles were prepared by stratifying the individual sucrose layers. A plastic tube was attached to peristaltic pump tubing. The plastic tube was mounted on a laboratory stand using a clamp and placed into the centrifuge bottle. The nozzle of the plastic tube was touching the bottom of the bottle. Using a peristaltic pump the ZikaV material and the sucrose solutions were pumped into the cylinder. A measuring cylinder was used as feed vessel. The first solution pumped was the ZikaV material as it represented the solution of lowest density (10% sucrose (w/w)). After the ZikaV material the sucrose solutions were pumped in ascending order starting with the 15% (w/w) solution J, followed by 35% sucrose solution I and finishing with the highest density sucrose solution H (50% (w/w)). The described setup is shown in FIG. 14. After all sucrose solutions were transferred the plastic tubing was carefully removed in order not to disturb the layers.

Prior to centrifugation the centrifuge was pre-cooled to 4° C. The prepared SG bottles were carefully transferred into the pre-cooled rotor. (Note: Sudden movement of the bottles during transfer to the rotor must be avoided in order not to disturb the sucrose layers.) The bottles were centrifuged at ~11.000 RCF max at 4° C. for at least 20 hours, no brake/deceleration activated. In case a different centrifuge system with a different rotor is used the necessary speed and centrifugation times need to be calculated based on the k-factor in order to achieve comparable centrifugation efficiency.

Harvesting of the sucrose gradient was done manually using a peristaltic pump. A plastic tube attached to peristaltic pump tubing was used for harvesting the sucrose gradient. The bottle containing the gradient was mounted onto a laboratory stand in a tilted position (~12°) using a clamp. The plastic tubing was then placed into the bottle touching the bottom edge of the bottle and was fastened in position using a clamp. This resulted in a small gap of 1-2 mm between the tubing inlet and the bottom of the bottle (see FIG. 14).

Using a peristaltic pump set to a flow rate of 30 mL per minute the gradient was harvested and manually split into 2 mL fractions. A total number of 32 fractions per bottle were harvested (~64 mL) and the remaining volume was discarded. The fractions were immediately tested by SDS-PAGE/silver stain to identify the virus containing fractions with sufficient high purity. Representative SDS-PAGE is shown in FIG. 14. Fraction 10-14 were pooled and further processed.

The purified viral solution was inactivated by incubation with 0.02% formaldehyde over a period of ten days in a 22° C. controlled-temperature incubator. The formaldehyde is neutralized by addition of sodium metabisulphite on the tenth day.

The sucrose gradient pool (~17 mL after sampling) was further diluted 3-fold with PBS to a final volume of 51 mL in a PETG container. A volume of 1% formaldehyde (10,000 ppm) solution equivalent to 1/50 of the final volume of the pre-formaldehyde pool was added to this pool resulting in an effective concentration of 200 ppm. The formaldehyde-treated solution was mixed on a magnetic stirrer for 10 minutes. After sampling, the formaldehyde-treated viral solution was placed within a cooled incubator at 22° C.±2° C. On Day 5 post addition of formaldehyde, the formaldehyde-treated viral solution was filtered through a 0.2 m filter and then placed in the incubator at 22° C.±2° C. again. On Day 10, after removing the 10-Day inactivation final sample, a volume of 1% (of the weight of the final formaldehyde-treated viral solution) of 200 mM-sodium metabisulphite solution (2 mM final concentration) was aseptically transferred into the PETG container containing the formaldehyde-treated viral solution. After mixing for 5 minutes on a magnetic stirrer, the neutralized inactivated viral solution is held at room temperature (20 to 25° C.) for a minimum of 30 minutes. After sampling, the neutralized inactivated viral solution is stored at 5° C.±3° C. until further processing.

Inactivation by Formaldehyde

Critical parameters for this step are final formalin concentration, temperature, mixing and transfer into a new container. A preliminary acceptance criterion for maximum pfu/mL (determined by plaque assay) has been set on the diluted pool pre formaldehyde treatment. The quality of the neutralized inactivated viral solution was monitored by the following parameters: Plaque assay on Day 10, SEC-HPLC, SDS-PAGE/Western Blot.

Interestingly, SEC-HPLC analysis of samples taken during the inactivation period followed by neutralization with bisulfite showed more or less constant peak area throughout the inactivation period. This is in contrast to JEV where losses of viral particles up to 60% are observed using the process disclosed by Srivastava et al. Vaccine 19 (2001) 4557-4565. In a scale-down model the viral losses were even much higher due to surface/area ratio at smaller scale and high losses due to unspecific adsorption. Differences of the ZikaV inactivation experiment and JEV inactivation were noticed as follows:

A) Much higher purity of ZikaV SGP pool with regard to residual PS (<2 μg/mL) compared to JEV. The 3-fold ZikaV inactivated sample contained therefore <<1 μg/mL of residual PS. Commercial JEV SGP pool contains on average ~120 μg/mL (up to 152 μg/mL possible). The average dilution to inactivation solution of ~14-fold results in a residual PS content up to~11 μg/mL. It may be that higher amount of residual PS could cause virus precipitation due to cross-linking/reaction with formalin.

B) ZikaV inactivation sample contained ~10% sucrose (3-fold dilution of SGP pool containing ~30-35% sucrose). Sucrose might have stabilizing effect of viral ZikaV particles during treatment with formalin.

Dilution to DS and Formulation with Aluminium Hydroxide (DP)

For preparation of ZikaV drug substance used in mouse potency assay an antigen content (expressed as total viral particles or SEC peak area) of 5 times higher compared to Ixiaro was targeted. The basis for determination of antigen content was SEC-HPLC. Briefly, a Superose 6 10/300 Increase column (GE Healthcare) equilibrated with PBS+250 mM NaCl, pH 7.4 at 1 ml/min and 25° C., was used to detect ZikaV at 214 nm detection wavelength in harvest samples and throughout the downstream process. In the current JEV process the antigen content in NIV is determined by a specific ELISA. A good correlation was observed between antigen content determined by ELISA and SEC-HPLC. On average, the antigen content in commercial NIV samples is in the range of 33 AU/mL corresponding to ~5.2 mAU JEV peak area, see FIG. 21.

ZikaV NIV day 10 (Zika peak ~36 mAU, analysed on Waters HPLC/Superose6 Increase column) was diluted with PBS to a target of 6.3 (~5.7× dilution). Aluminium hydroxide was added to a final concentration of 0.5 mg/mL Aluminium (1/20 v/v Alum 2% stock solution added) to prepare ZikaV Drug Product (DP). The DP was gently mixed for 5 min. An aliquot of the DP was removed, Alum sedimented by centrifugation and the clear supernatant analysed by SEC-HPLC. No ZikaV peak was detected in the supernatant indicating complete adsorption (estimated as >95%) of viral particles on the mineral adjuvant. Formulated ZikaV DP was stored at 2-8° C.

The impurity profile of the inactivated Zika virus DS is comparable to the profile of JEV DS with the exception of a lower PS content (Table 6).

TABLE 6

Determination of impurity profile in Zika and JEV DS samples:

| | Specification (JEV DS) | JEV | Zika |
|---|---|---|---|
| HCP (ng/mL) | <100<br>LOQ 12 ng/mL | <LOQ | <LOQ |
| DNA (pg/mL) | <200<br>LOQ 40 pg/mL | <40 | <40 |
| Aggregates by SEC-MALLS (%) | Not specified, part of characterization<br>LOQ 5% | <LOQ | <LOQ |
| PS (μg/mL) | Specification only at SGP pool to demonstrate consistent process performance (19-152 μg/mL),<br>*PS content in DS calculated based on PS content in SGP pool (~100 μg/mL) and average dilution factor (~28×) to DS; LOQ 2 μg/mL | ~4* | <<LOQ |

*Typical PS impurity in a JEV sample produced in accordance with protocol disclosed in Srivastava et al. Vaccine 19 (2001) 4557-4565.

SEC-MALLS Results

A representative SEC-HPLC elution profile of ZikaV NIV at 214 nm detection wave length is shown in FIG. 16. Note that BSA (50 μg/mL) was added to the sample to minimize losses in HPLC glass vial due to unspecific surface adsorption. ZikaV monomer content was estimated as ~98% with a multimer content of ~2%.

SEC-MALLS analysis (FIG. 17) of the sample confirmed the radius Rz of the monomer ZikaV population peak 1 as 21.6 nm and ~49 nm for the multimer peak 2. Cumulative particle size distribution showed that 89% of all viral particles are within a radius range between 18 to 25 nm (FIG. 18).

Results confirm purity and homogeneity of ZikaV NIV.

Viral Titer by Plaque Assay

TABLE 7

Active ZikaV pfus were quantified by plaque assay throughout the process.

| Sample | Pfu/mL |
|---|---|
| Harvest day 2 (filtered) | $6.4 \times 10^7$ |
| Harvest day 3 (filtered) | $1.0 \times 10^8$ |
| Harvest day 5 (filtered) | $1.5 \times 10^8$ |
| Harvest day 7 (filtered) | $1.1 \times 10^8$ |

TABLE 7-continued

Active ZikaV pfus were quantified by
plaque assay throughout the process.

| Sample | Pfu/mL |
| --- | --- |
| PS treated harvest 300× concentrate (=SGP load) | $9.0 \times 10^8$ |
| SGP pool | $8.9 \times 10^8$ |
| Inactivation start (SGP pool 1:3 diluted) | $3.4 \times 10^8$ |
| Inactivation day 5 | <LOD |
| Inactivation day 10 | <LOD |

Comparison of PS and Benzonase on Process Performance

A direct comparison of DNA removal method of concentrated ZikaV harvest pool was done. One aliquot was treated with PS (2 mg/mL, 15 min at room temperature), the other aliquot was treated with Benzonase (50 U/mL, 2 mM MgCl2, 4 h RT, 48 h 2-8° C.). Both samples were further purified by sucrose gradient as described in this report. Interestingly, the Benzonase treated samples did not yield any pure fractions after sucrose gradient centrifugation of the treated ZikaV harvest. In those fractions where the specific virus bands were detected, a high amount of host cell protein was detected throughout the collected fractions. The PS treated material resulted in pure ZikaV containing fractions as expected. This finding may suggest that PS is not only effective for DNA removal by precipitation; in addition it improves the recovery of virus particles in the gradient by disrupting interaction of DNA (fragments) and virus particles. Benzonase treatment does not remove DNA, it only results in its fragmentation. Residual DNA fragments might still interact with virus particles and residual HCPs resulting in cross-contamination and co-purification in the sucrose gradient. Pooled SGP fractions were also analysed by SEC-HPLC. Although a large peak was detected, SDS-PAGE confirmed that this sample was highly contaminated with HCPs. A large peak might be detected at UV214 and 280 nm after SEC-HPLC analysis due to possible interaction of HCPs with large virus particles, changing the UV absorbance.

Immunogenicity of Vero Grown Zika Virus

Immunization of Mice

Prior to immunization, groups of ten 6-week-old female CD1 mice were bled via vena facialis and pre-immune sera were prepared. One intraperitoneal immunizations of 200 μL were administered. A dose titration (12 μg, 3 μg, 1 μg, 0.33 μg, 0.11 μg, 0.037 μg and 0.012 μg, equivalent to the protein amount in IXIARO) of inactivated Zika virus formulated with aluminium hydroxide (Al(OH)3) at a final concentration of 0.7%. Three weeks after immunization, blood was collected and immune sera were prepared. All animal experiments were conducted in accordance with Austrian law (BGB1 Nr. 501/1989) and approved by "Magistratsabteilung 58".

Plaque Reduction Neutralization Test (PRNT)

Twelve well plates were used for PRNT. Each well was seeded with 1 mL medium containing $4 \times 10^5$ Vero cells and incubated 35° C. with 5% $CO_2$ overnight. Pools of heat inactivated sera from each dose group were tested in triplicate. The target viruses (H/PF/2013 (SEQ ID NO: 13) or MR766 (SEQ ID NO: 11)) were diluted to 100 pfu/165 μL. Equal volumes of target virus and serum dilution were incubated at 35° C. with 5% $CO_2$ for 1 hour. The cell culture medium was aspirated from the Vero cells and 330 μL of the mixture target virus/serum dilution were added to each well and the plates were rocked back and forth 5 times before incubating for 2 hours at 35° C. with 5% $CO_2$. To each well 1 mL of a 2% methylcellulose solution containing EMEM and nutrients was added, the plates were then incubated for 5 days at 35° C. with 5% $CO_2$ before staining the cells for 1 hour with crystal violet/5% formaldehyde and subsequently washed 3 times with deionized water. The plates were air dried and the numbers of plaques in each well were manually counted.

Results

Figure 19:
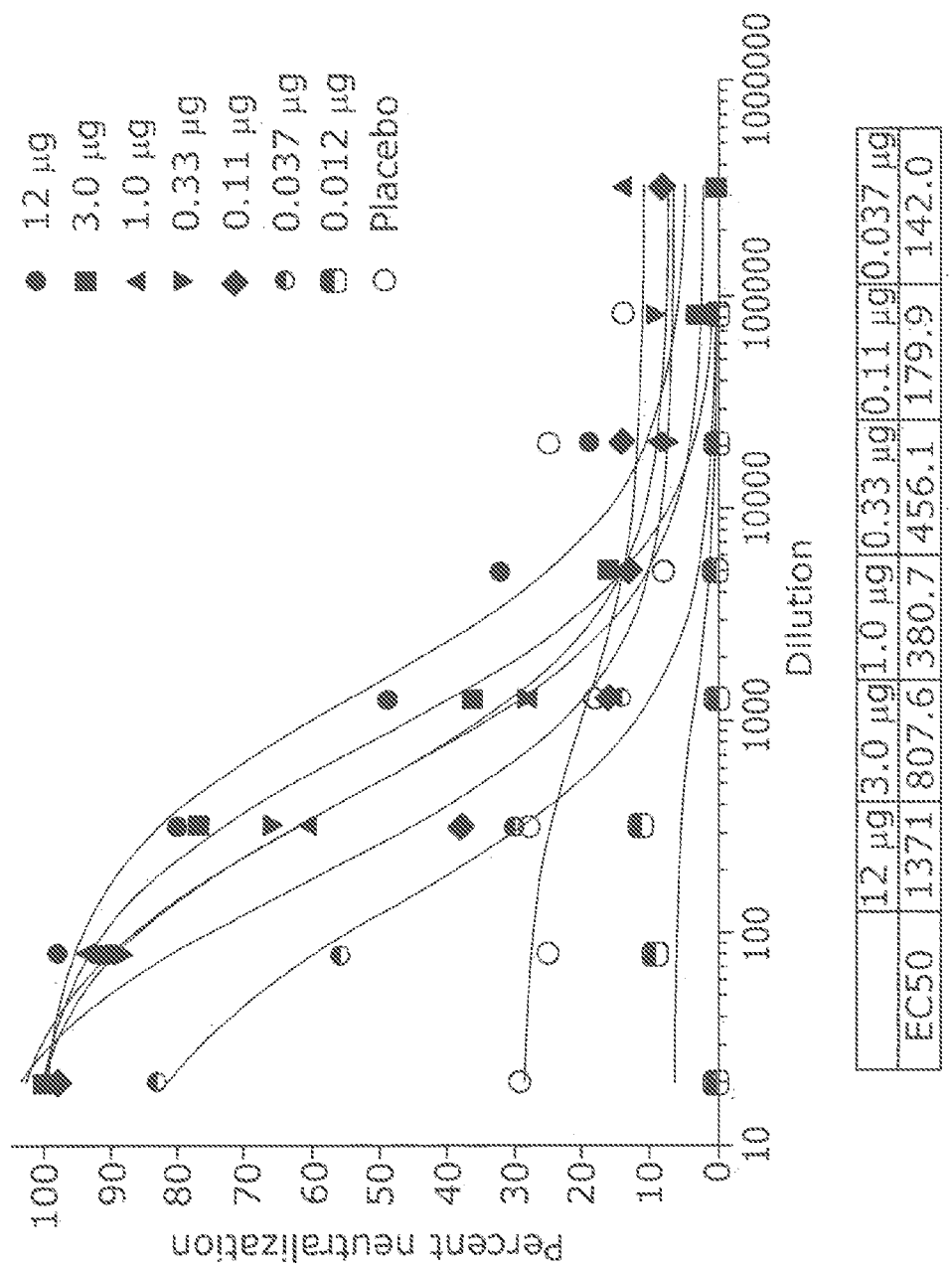
FIG. 19: Graphical representation of the neutralization of the Zika virus H/PF/2013 with pooled mouse sera. The number of plaques without serum was set to 100%. The EC50 was calculated using the 3-parameter method.
Figure 20:
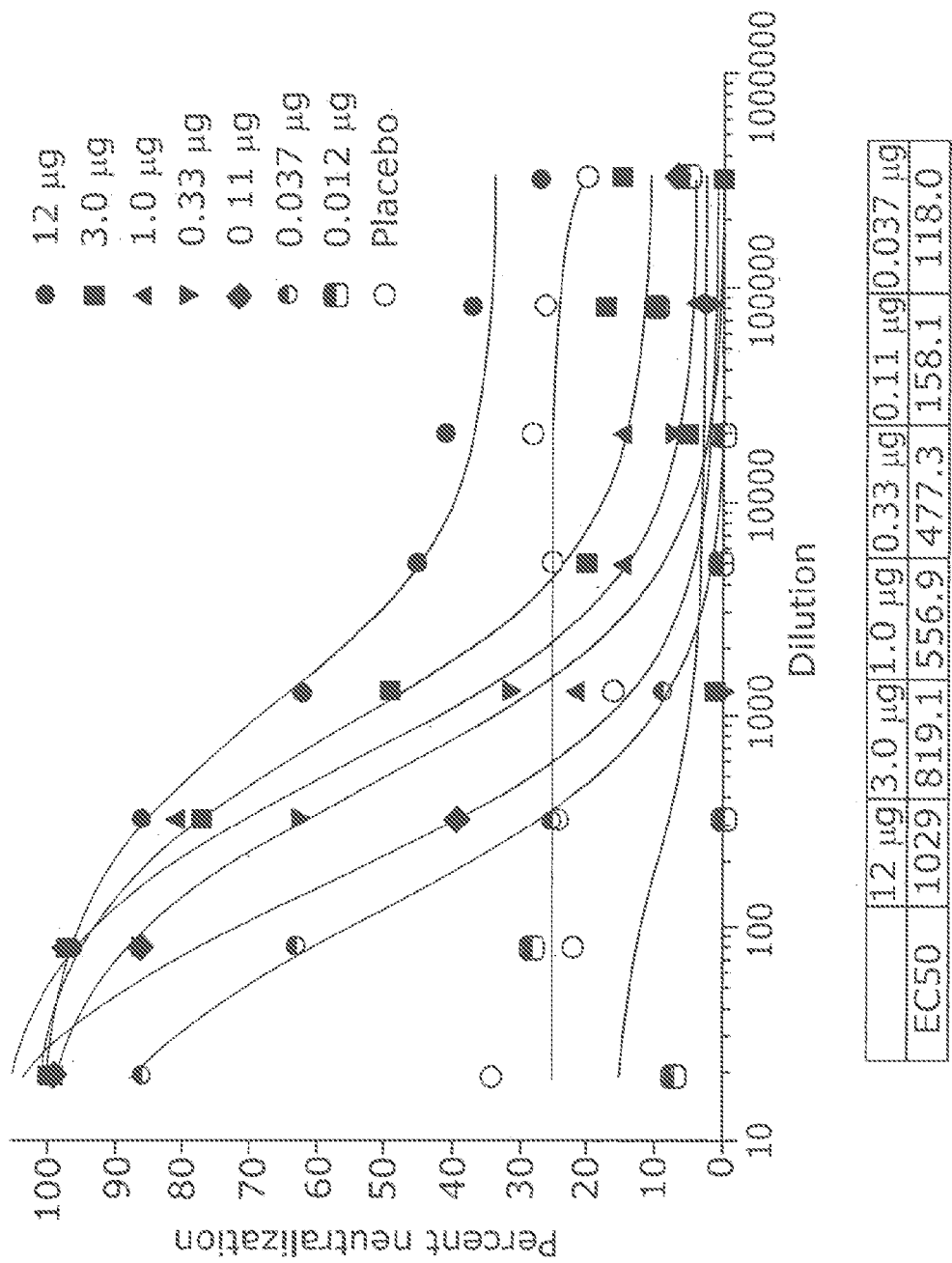
FIG. 20: Graphical representation of the neutralization of the Zika virus MR766 with pooled mouse sera. The number of plaques without serum was set to 100%. The EC50 was calculated using the 3-parameter method.

Neutralization was observed with serum pools from mice immunized with inactivated Zika virus vaccine (H/PF/2013) down to 37 ng (dosing equivalent to the amount protein in IXIARO®) against Zika viruses of both the Asian (H/PF/2013) and African (MR766) lineages (FIGS. 19 and 20, respectively). Complete inhibition was seen at the 1:20 serum dilution with an immunization dose down to 110 ng (dosing equivalent to the amount protein in IXIARO®). The neutralization of both the Asian (H/PF/2013) and African (MR766) lineages of the Zika virus was equivalent, which indicates high cross-neutralization between different Zika virus strains of the inactivated Zika virus vaccine (H/PF/2013).

Another neutralization assay was performed using the microneutralization assay as described by Larocca, et al. (2016, Nature doi:10.1038/nature18952). It was found that the inactivated Zika virus of the current invention had an MN50 (microneutralization) titer of 90 at 1 μg of inactivated purified virus.

Further methods: The immunogenicity of inactivated Zika virus preparations is assessed using a mouse model of Zika infection. Groups of adult mice are immunized subcutaneously (s.c.) with 500, 50, or 5 ng of inactivated Zika virus with adjuvant (e.g. aluminium hydroxide with or without IC31®), or without adjuvant. An additional group of mice receive PBS as a negative control. Each group is administered the indicated inoculum at t=0 and in some cases also at three to four weeks later (t=3/4). Beginning approximately three weeks after administration of the last immunization, serum samples are obtained from each of the mice at regular intervals. The serum samples are tested for the presence of neutralizing antibodies using PRNT.

The in vivo protective efficacy of the inactivated Zika virus preparations is also assessed using a mouse model of Zika infection, i.e. IFN-alpha/beta receptor knock-out mice (A129) (see e.g. Dowall et al., 4. March 2016, dx.doi.org/10.1101/042358) or blocking of the IFN-alpha/beta receptor by administration of anti-IFN-alpha/beta receptor monoclonal antibodies to C57BL/6 or BALB/c mice (see e.g. Pinto et al., 7. Dec. 2011, DOI: 10.1371/journal.ppat.1002407). For protection assays, groups of 10 three- to eight-weeks-old A129, C57BL/6 of BALB/c mice are inoculated subcutaneously in the hindquarters with inactivated Zika virus with adjuvant (aluminium hydroxide) or without adjuvant at t=0. Age-matched controls are inoculated with PBS or non-specific antigens in alum. Mice are optionally boosted with a second administration of the indicated inoculation three to four weeks later. The mice are then challenged subcutaneously at three to eight weeks post immunization by inoculation with a deadly dose of live Zika virus. One day prior to challenge of C57BL/6 and BALB/c mice, they are passively administered (intraperitoneally) anti-IFN-alpha/beta receptor monoclonal antibodies. Challenged mice are monitored daily for morbidity and mortality for up to twenty-one days. Another alternative is to challenge intracranially adult vaccinated/non-vaccinated adult mice and observe protection.

It is expected that the Zika virus produced by the process of the invention will provide very similar functional readouts in in vitro, in vivo and finally human trials as the currently licensed JEV vaccine in the EU and US and elsewhere, IXIARO®. The dosage may alter but due to the very similar impurity profile and almost identical manufacture, a very similar efficacy and safety result will be expected as was determined for the currently licensed JEV vaccine (licensed in the EU and US and elsewhere).

DISCUSSION & CONCLUSION

The existing manufacturing platform for production of inactivated JEV vaccine IXIARO® was used as a basis for a manufacturing feasibility study of inactivated ZikaV vaccine candidate (Asian strain H/PF/2013). The virus was produced on Vero cells cultivated in roller bottles. The virus was purified by PS treatment followed by an optimized sucrose gradient. Inactivation was done by formalin treat (0.02%, 10 days at 22° C.). For exploratory immunization studies in mice, a DP formulated with Alum was prepared with an estimated 5-fold higher virus particle content compared to IXIARO®, the commercial JEV Vaccine. The impurity profile of the DS met all criteria as defined in the specification for IXIARO®, the commercial JEV vaccine. The neutralization of both the Asian (H/PF/2013) and African (MR766) lineages of the Zika virus was equivalent, which indicates high cross-neutralization between different Zika virus strains of the inactivated Zika virus vaccine (H/PF/2013).

The in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was higher than the recently reported inactivated Zika virus vaccine candidate (Larocca, et. al, 2016, supra.). Inactivated viruses are among the safest vaccines and especially preferred for deliver to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

Further More Detailed Aspects of the Invention:

A1. A Zika virus vaccine comprising an inactivated Zika virus particle, wherein the Zika virus particle is able to seroconvert a subject that is administered the Zika virus vaccine with at least a 70% probability.

A2. The Zika virus vaccine of A1, wherein the Zika virus particle is able to seroconvert the subject that is administered the Zika virus vaccine with at least a 80%, 85%, 90%, or 95% probability.

A3. The vaccine of A1 or A2, wherein the Zika virus particle has a RNA genome corresponding to the DNA sequence provided by any one of the nucleic acid sequences of SEQ ID NOs: 2-13 or 72, or a variant nucleic acid sequence that is at least 88% identical to any one of SEQ ID NOs: 2-13 or 72 and able to pack a virulent Zika virus.

A4. The vaccine of any one of A1-A3, wherein the Zika virus particle has an E protein selected from the amino acid sequences provided by any one of SEQ ID NOs: 14-69, or a variant amino acid sequence that is at least 95% identical to any one of SEQ ID NOs: 14-69 and able to pack a virulent Zika virus.

A5. The vaccine of any one of A1-A4, wherein the Zika virus is inactivated by chemical inactivation, thermal inactivation, pH inactivation, or UV inactivation.

A6. The vaccine of A5, wherein the chemical inactivation comprises contacting the Zika virus with a chemical inactivation agent to completely inactivate the Zika virus as measured by plaque assay.

A7. The vaccine of A6, wherein the chemical inactivation comprises contacting the Zika virus with formaldehyde.

A8. The vaccine of A7, wherein the formaldehyde inactivation comprises contacting the Zika virus with formaldehyde for between 2-10 days.

A9. The vaccine of any one of A5-A8, wherein the chemical activation is performed at about +4° C. or about +22° C.

A10. The vaccine of any one of A1-A9, further comprising an adjuvant.

A11. The vaccine of A10, wherein the adjuvant is an aluminum salt adjuvant.

A12. The vaccine of A11, wherein the aluminum salt adjuvant is aluminium hydroxide or aluminium phosphate salt.

A13. The vaccine of any one of A10-A12, wherein the vaccine comprises or further comprises an adjuvant comprising a peptide and a deoxyinosine-containing immunostimulatory oligodeoxynucleic acid molecule (I-ODN).

A14. The vaccine of A13, wherein the peptide comprises the sequence KLKL5KLK (SEQ ID NO: 71) and the I-ODN comprises oligo-d(IC)13 (SEQ ID NO: 70).

A15. The vaccine of any one of A1-A14, further comprising one or more pharmaceutically acceptable excipient.

A16. The vaccine of any one of A1-A15, wherein the vaccine contains protamine sulphate or fragments or breakdown products of PS at amounts too low to detect by HPLC, i.e., below 1 μg/mL, especially below 100 ng/mL.

A17. The vaccine of A16, wherein said protamine sulphate or fragments or break-down products of PS can be detected by mass spectroscopy or another sensitive method.

B1. A kit comprising a Zika virus vaccine of any one of A1-A15.

B2. The kit of B1, further comprising a second vaccine.

B3. The kit of B2, wherein the second vaccine is a West Nile virus vaccine, a Japanese Encephalitis virus vaccine, a Yellow Fever virus vaccine, a Dengue virus vaccine or a Chikungunya virus vaccine.

C1. A method, comprising administering a first dose of a therapeutically effective amount of the Zika virus vaccine of any one of A1-A15 to a subject in need thereof.

C2. The method of C1, further comprising administering a second dose of a therapeutically effective amount of the Zika virus vaccine.

C3. The method of C1 or C2, wherein the second dose of the Zika virus vaccine is administered about 7 days after the first dose of the Zika virus vaccine.

C4. The method of C1 or C2, wherein the second dose of the Zika virus vaccine is administered about 14 days after the first dose of the Zika virus vaccine.

C5. The method of C1 or C2, wherein the second dose of the Zika virus vaccine is administered about 28 days after the first dose of the Zika virus vaccine.

C6. The method of any one of C1-C5, wherein the administering results in production of Zika virus neutralizing antibodies.

D1. A method of producing a Zika virus vaccine, comprising
  (i) passaging a Zika virus on Vero cells, thereby producing a culture supernatant comprising the Zika virus;
  (ii) harvesting the culture medium of (i);
  (iii) precipitating the harvested culture medium of (ii), thereby producing a Zika virus supernatant; and
  (iv) optimally inactivating the Zika virus in the Zika virus supernatant of (iii) thereby producing an inactivated Zika virus.

D2. The method of D1, further comprising concentrating the culture medium of (ii) prior to step (iii).

D3. The method of D1 or D2, wherein the precipitating of (iii) comprises contacting the culture medium of (ii) with protamine sulfate or benzoate.

D4. The method of any one of D1-D3, further comprising (v) dialyzing the inactivated Zika virus of (iv), thereby producing a dialyzed Zika virus.

D5. The method of D4, further comprising (vi) filtering the dialyzed Zika virus of (v).

D6. The method of any one of D1-D5, wherein the inactivating is by chemical inactivation, thermal inactivation, pH inactivation, or UV inactivation.

D7. The method of D6, wherein the chemical inactivation comprises contacting the Zika virus with a chemical inactivation agent for at least 4 days.

D8. The method of D6 or D7, wherein the chemical inactivation agent comprises formaldehyde.

D9. The method of any one of D6-D8, wherein the chemical activation is performed at about +4° C. or about +22° C.

D10. The method of D8 or D9, further comprising neutralizing the formaldehyde.

D11. The method of D10, wherein the neutralizing is performed with sodium metabisulfite.

E1. The use of the optimally inactivated Zika virus vaccine of any one of A1-A15 for the treatment and/or prevention of a Zika virus infection.

E2. The use of E1, wherein the inactivated Zika virus vaccine is administered in a first dose of a therapeutically effective amount to a subject in need thereof.

E3. The use of E2, wherein the inactivated Zika virus vaccine is administered in a second dose of a therapeutically effective amount to the subject.

E4. The use of E3, wherein the second dose of the inactivated Zika virus vaccine is administered about 7 days after the first dose of the Zika virus vaccine.

E5. The use of E3, wherein the second dose of the Zika virus vaccine is administered about 14 days after the first dose of the Zika virus vaccine.

E6. The use of E3, wherein the second dose of the Zika virus vaccine is administered about 28 days after the first dose of the Zika virus vaccine.

E7. The use of any one of E1-E6, wherein the vaccine administration results in production of Zika virus neutralizing antibodies.

F1. A pharmaceutical composition for use in the treatment or prevention of a Zika virus infection, wherein said pharmaceutical composition comprises the optimally inactivated Zika virus vaccine of any one of A1-A15.

F2. The pharmaceutical composition of F1, wherein the inactivated Zika virus vaccine is administered in a first dose of a therapeutically effective amount to a subject in need thereof.

F3. The use of F2, wherein the inactivated Zika virus vaccine is administered in a second dose of a therapeutically effective amount to the subject.

F4. The use of F3, wherein the second dose of the inactivated Zika virus vaccine is administered about 7 days after the first dose of the Zika virus vaccine.

F5. The use of F3, wherein the second dose of the Zika virus vaccine is administered about 14 days after the first dose of the Zika virus vaccine.

F6. The use of F3, wherein the second dose of the Zika virus vaccine is administered about 28 days after the first dose of the Zika virus vaccine.

F7. The use of any one of F1-F6, wherein the vaccine administration results in production of Zika virus neutralizing antibodies.

G1. Use of an optimized sucrose gradient centrifugation for removal of protamine sulphate from purified infectious Zika virus particles.

G2. The use according to G1, wherein said optimized sucrose gradient centrifugation comprises a virus comprising fraction in a 10%+/−1% (w/w) sucrose solution and three further layers of sucrose solutions with different densities, i.e. a first sucrose solution with 15%+/−1% (w/w) sucrose, a second sucrose solution with 35%+/−1% (w/w) sucrose, and a third sucrose solution with a 50%+/−1% (w/w) sucrose.

G3. A process of purification of infectious Zika virus particles, comprising the steps of:
  a) providing a crude harvest (a) comprising virus particles and impurities, wherein the impurities are generated from growing said virus particles on a cell substrate;
  b) reducing impurities from the crude harvest (a) by precipitation with an agent comprising protamine, preferably a protamine salt, more preferably a protamine sulphate, even more preferably a recombinant protamine sulphate, to obtain a virus preparation (b);
  c) further purifying the virus preparation (b) by an optimized sucrose density gradient centrifugation, wherein the optimized sucrose gradient is provided such that the protamine can be completely or almost completely separated from the virus fraction; and wherein the protamine concentration is reduced by this step to the extent that the protamine concentration in the final drug substance is below 1 µg/ml, preferably below 0.5 µg/mL, more preferably below 0.1 µg/mL, most preferably below 0.05 µg/mL.

G4. The process of G3, wherein said optimized sucrose density gradient centrifugation comprises a virus comprising fraction in a 10%+/−1% (w/w) sucrose solution and three layers of sucrose with different densities, i.e. a first sucrose solution with 15%+/−1% (w/w) sucrose, a second sucrose solution with 35%+/−1% (w/w) sucrose, and a third sucrose solution with a 50%+/−1% (w/w) sucrose.

G5. The process of any one of G3 to G4, additionally comprising a further purification step of: (d) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles.

G6. The process of any of G3 to G5, wherein the residual host cell DNA content of the Zika virus preparation (c) is less than 10 ng/mL and the residual host cell protein content of the final virus preparation (c) is less than 100 ng/mL.

G7. The process of any of G3 to G6, wherein said crude harvest (a) comprising Zika virus particles and impurities is subjected to one or more pre-purification step(s) prior to step (b).

G8. The process of G7, wherein the one or more pre-purification step(s) comprises
   a) filtration using a filter having a pore size equal to or less than 0.2 μm; and/or
   b) digestion of host cell genomic DNA by enzymatic treatment; and/or
   c) ultra/diafiltration using a hollow fiber membrane having a pore size equal to or greater than 300 kDa, preferably equal to or greater than 100 kDa.

G9. The process of any one of G3 to G8, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml or 2 mg/ml.

G10. The process of any one of G3 to G9, wherein the enrichment of infectious Zika virus particles in the virus preparation (c) or any final virus preparation relative to total virus products in the crude harvest (a) is in the range from at least 50% to 95%, preferably at least 80%.

G11. The process of any one of G7 to G10, wherein the one or more pre-purification step(s) prior to step (b) of any of G8 to G11 is performed using a filter having a pore size equal to or less than 1 μm, preferably 0.2 μm.

G12. The process of any one of G3 to G11, wherein the residual impurity of the Zika virus preparation (c) is less than 10%.

G13. The process of any one of G3 to G12, wherein the Zika virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

G14. The process of G13, wherein said cell line is a Vero cell line.

G15. The process of any one of G3 to G14, wherein said infectious Zika virus particle is an infectious virus particle that is a live virus, a live attenuated virus, a chimeric virus, a modified live virus, or a recombinant live virus.

G16. The process of any one of G3 to G15, wherein said Zika virus is preferably a strain of the Asian lineage.

G17. The process of any one of G3 to G16, wherein said process resulting in final virus preparation (c) or (d) is followed by an inactivation step, wherein the virus is inactivated preferably by formaldehyde.

G18. Use of the process according to any one of G3 to G17 for manufacturing a composition for immunization against a virus infection.

G19. The use according to G18, wherein said virus infection is an infection caused by a Zika virus.

Q1. A process of purification of infectious Zika virus particles, comprising the steps of:
   (a) providing a crude harvest (a) comprising Zika virus particles and impurities, wherein the impurities are generated from growing said virus particles on a cell substrate;
   (b) reducing impurities from the crude harvest (a) by precipitation with an agent comprising protamine, preferably a protamine salt, more preferably a protamine sulphate, even more preferably a recombinant protamine sulphate, to obtain a virus preparation (b);
   (c) further purifying the virus preparation (b) by an optimized sucrose density gradient centrifugation, wherein the optimized sucrose gradient is provided such that the protamine can be completely or almost completely separated from the virus fraction; and wherein the protamine concentration is reduced by this step to the extent that the protamine concentration in the final drug substance is below 1 μg/ml, preferably below 0.5 μg/mL, more preferably below 0.1 μg/mL, most preferably below 0.05 μg/mL.

Q2. The process of Q2, wherein the virus particles are from Zika virus.

Q3. The process of Q1 or Q2, additionally comprising the step of:
   (d) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles.

Q4. The process of any of Q1 to 3, wherein the residual host cell DNA of the virus preparation (c) is less than 10 ng/mL and the residual host cell protein of the final virus preparation (c) is less than 100 ng/mL.

Q5. The process of any of Q1 to 4, wherein the crude harvest (a) comprising virus particles and impurities is subjected to one or more pre-purification step(s) prior to step (b).

Q6. The process of Q5, wherein the one or more pre-purification step(s) comprises
   (a) filtration using a filter having a pore size equal to or less than 0.2 μm; and/or
   (b) digestion of host cell genomic DNA by enzymatic treatment; and/or
   (c) ultra/diafiltration using a hollow fiber membrane having a pore size equal to or greater than 300 kDa, preferably equal to or greater than 100 kDa.

Q7. The process of any one of Q1 to 6, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml or 2 mg/ml.

Q8. The process of any one of Q1 to 7, wherein the enrichment of infectious virus particles in the virus preparation (c) or any final virus preparation relative to total virus products in the crude harvest (a) is in the range from at least 50% to 95%, preferably at least 80%.

Q9. The process of any one of Q5 to 8, wherein the one or more pre-purification step(s) prior to step (b) of any of Q5 to 8 is performed using a filter having a pore size equal to or less than 1 μm, preferably 0.2 μm.

Q10. The process of any one of Q1 to 9, wherein the residual impurity of the virus preparation (c) is less than 10%.

Q11. The process of any one of Q1 to 10, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

Q12. The process of Q11, wherein said cell line is a Vero cell line.

Q13. The process of any one of Q1 to 12, wherein the infectious virus particles is an infectious Zika virus particle that is a live virus, an attenuated live virus, a chimeric virus, a modified live virus, or a recombinant live virus.

Q14. The process of any one of Q1 to 13, wherein the Zika virus is a Zika virus strain of the Asian lineage or an immunogenic variant thereof.

Q15. The process of any one of Q1 to 14, wherein said process resulting in final virus preparation (c) or (d) is followed by an inactivation step, wherein the virus is inactivated preferably by formaldehyde.

Q16. Use of the process according to any one of Q1 to 15 for manufacturing a composition for immunization against a virus infection.

Q17. The use according to Q16, wherein the composition for immunization against a virus infection is an infection caused by Zika virus.

Q18. A composition comprising the virus particles obtainable or obtained by the process of any one of Q1 to 17 for treating and/or preventing an infection, such as e.g. a Zika virus infection.

Q19. A Zika virus vaccine comprising an inactivated Zika virus particle grown on vero cells, wherein the Zika virus particle is able to seroconvert a subject that is administered the Zika virus vaccine with at least a 70% probability and comprises minor amounts of protamine sulphate, preferably below the detection limit.

Q20. The Zika virus vaccine of Q19, wherein the Zika virus particle is able to seroconvert the subject that is administered the Zika virus vaccine with at least a 80%, 85%, 90%, or 95% probability, preferably a 80% probability.

Q21. The vaccine of Q19 or 20, wherein the Zika virus particle has a RNA genome corresponding to the DNA sequence provided by any one of the nucleic acid sequences of SEQ ID NOs: 2-13, or a variant nucleic acid sequence that is at least 88% identical to any one of SEQ ID NOs: 2-13 and able to pack a virulent Zika virus.

Q22. The vaccine of any one of Q19, 20 and 21, wherein the Zika virus particle has an E protein selected from the amino acid sequences provided by any one of SEQ ID NOs: 14-69 or 72, or a variant amino acid sequence that is at least 95% identical to any one of SEQ ID NOs: 14-69 or 72 and able to pack a virulent Zika virus.

Q23. The vaccine of any one of Q19, 20 to 22, wherein the Zika virus obtained by culturing on Vero cells is purified by protamine sulfate precipitation and sucrose gradient centrifugation.

Q24. The vaccine of Q23, wherein the sucrose gradient centrifugation is an optimized sucrose gradient centrifugation.

Q25. The vaccine of Q24, wherein the optimized sucrose gradient centrifugation comprises a virus comprising fraction in a 10% (w/w) sucrose solution and three layers of sucrose with different densities, i.e. a first sucrose solution with 15% (w/w) sucrose solution, a second sucrose solution with 35% (w/w) sucrose solution, and a third sucrose solution with a 50% (w/w) sucrose solution.

Q26. The vaccine of any one of Q19, 20 to 25, wherein the Zika virus is inactivated by chemical inactivation, thermal inactivation, pH inactivation, or UV inactivation.

Q27. The vaccine of Q26, wherein the chemical inactivation comprises contacting the Zika virus with a chemical inactivation agent for longer than is required to completely inactivate the Zika virus as measured by plaque assay.

Q28. The vaccine of Q27, wherein the chemical inactivation comprises contacting the Zika virus with formaldehyde.

Q29. The vaccine of Q28, wherein the formaldehyde inactivation comprises contacting the Zika virus with formaldehyde for between 2-10 days.

Q30. The vaccine of any one of Q27-29, wherein the chemical activation is performed at about +4° C. or about +22° C.

Q31. The vaccine of any one of Q19 to 30, further comprising an adjuvant.

Q32. The vaccine of Q31, wherein the adjuvant is an aluminum salt adjuvant.

Q33. The vaccine of Q32, wherein the aluminum salt adjuvant is aluminium hydroxide or aluminium phosphate salt.

Q34. The vaccine of Q32, wherein the aluminum salt adjuvant is aluminium hydroxide with less than 1.25 ppb Cu based on the final pharmaceutical composition comprising the Zika virus, preferably the inactivated Zika virus.

Q35. The vaccine of any one of Q19 to 34, further comprising one or more pharmaceutically acceptable excipient.

R1. Use of protamine, preferably a protamine salt, to separate infectious and non-infectious Zika virus particles, host cell proteins and/or undefined low molecular weight materials.

R2. A process of purification of infectious Zika virus particles, comprising the steps of:

(a) providing a crude harvest (a) comprising Zika virus particles and impurities, wherein the impurities are generated from growing said virus particles on a cell substrate;

(b) reducing impurities from the crude harvest (a) by precipitation with an agent comprising protamine, preferably a protamine salt, more preferably a protamine sulphate, even more preferably a recombinant protamine sulphate, to obtain a virus preparation (b), wherein the enrichment of infectious virus particles in the virus preparation (b) relative to total virus products in the crude harvest (a) is in the range from at least 50% to 95%, preferably at least 80%.

R3. The use of R1 or the process of R2, wherein the virus particles are from Zika virus.

R4. A process of purification of infectious Zika virus particles, comprising the steps of:

(a) providing a crude harvest (a) comprising Zika virus particles and impurities, wherein the impurities are generated from growing said virus particles on a cell substrate;

(b) reducing impurities from the crude harvest (a) by precipitation with an agent comprising protamine, preferably a protamine salt, more preferably a protamine sulphate, even more preferably a recombinant protamine sulphate, to obtain a virus preparation (b);

(c) further purifying the virus preparation (b) by one or more size exclusion methods such as (i) a sucrose density gradient centrifugation, (ii) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles, and/or (iii) size exclusion chromatography to obtain a virus preparation (c) comprising the infectious virus particles, wherein the residual host cell DNA of the virus preparation (c) is less than 100 ng/mL and the residual host cell protein and the residual aggregates of infectious virus particles of the final virus preparation (c) is less than 1 μg/mL.

R5. The process of R4, wherein the residual host cell DNA of the virus preparation (c) is less than 10 ng/mL and the residual host cell protein of the final virus preparation (c) is less than 100 ng/mL.

R6. The process of any of R2 to 5, wherein the crude harvest (a) comprising virus particles and impurities is subjected to one or more pre-purification step(s) prior to step (b).

R7. The process of R6, wherein the one or more pre-purification step(s) comprises
(a) filtration using a filter having a pore size equal to or less than 0.2 µm; and/or
(b) digestion of host cell genomic DNA by enzymatic treatment; and/or
(c) ultra/diafiltration using a hollow fiber membrane having a pore size equal to or greater than 300 kDa, preferably equal to or greater than 100 kDa.

R8. The process of any one of R2 to 7, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml.

R9. The process of any one of R2 to 8, wherein the enrichment of infectious virus particles in the virus preparation (c) or any final virus preparation relative to total virus products in the crude harvest (a) is in the range from at least 50% to 95%, preferably at least 80%.

R10. The process of any one of R6 to 9, wherein the one or more pre-purification step(s) prior to step (b) of any of R6 to 9 is performed using a filter having a pore size equal to or less than 1 µm, preferably 0.2 µm.

R11. The process of any one of R2 to 10, wherein the residual impurity of the virus preparation (c) is less than 10%.

R12. The process of any one of R2 to 11, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

R13. The process of R12, wherein said cell line is a Vero cell line.

R14. The process of any one of R2 to 13, wherein the Zika virus is a live virus, an attenuated live virus, a chimeric virus, a modified live virus, or a recombinant live virus.

R15. The process of any one of R2 to 14, wherein the Zika virus is a Zika virus strain of the Asian lineage or an immunogenic variant thereof.

R16. The process of any one of R2 to 15, wherein said process resulting in final virus preparation (c) is followed by an inactivation step, wherein the virus is inactivated preferably by formaldehyde.

R17. Use of the process according to any one of R1 to 16 for manufacturing a composition for immunization against a virus infection.

R18. The use according to R17, wherein the composition for immunization against a virus infection is an infection caused by a Zika virus.

R19. A composition comprising the virus particles obtainable or obtained by the process of any one of R2 to 16 for treating and/or preventing an infection.

What is claimed is:

1. A Zika virus vaccine comprising a Zika virus having an RNA genome, wherein said Zika virus vaccine is capable of stimulating a neutralizing antibody titer greater than 15 in at least 70% of vaccinated subjects, wherein the neutralizing antibody titer is determined using a microneutralization assay (MN50) following a single administration of the Zika virus vaccine to a subject; and wherein the Zika virus comprises an E protein having an amino acid sequence having at least 95% sequence identity to any one of SEQ ID NOs: 14-69 and is able to pack a virulent Zika virus.

2. The Zika virus vaccine of claim 1, wherein the Zika virus comprises an E protein having an amino acid sequence having at least 96%, 97%, 98%, 99% or 99.5% sequence identity to any one of SEQ ID NOs: 14-69 and is able to pack a virulent Zika virus.

3. The Zika virus vaccine of claim 1, wherein the Zika virus comprises an E protein having an amino acid sequence having at least 95% sequence identity to SEQ ID NO: 47 or 48 and is able to pack a virulent Zika virus.

4. The Zika virus vaccine of claim 1, wherein the Zika virus comprises an E protein having an amino acid sequence having at least 96%, 97%, 98%, 99% or 99.5% sequence identity to SEQ ID NO: 47 or 48 and is able to pack a virulent Zika virus.

5. The Zika virus vaccine of claim 1, wherein the RNA genome corresponds to the DNA sequence provided by SEQ ID NO: 4 or a variant nucleic acid having at least 99% identity to SEQ ID NO: 4.

6. The Zika virus vaccine of claim 5, wherein the variant nucleic acid has at least 99.5% identity to SEQ ID NO: 4.

7. The Zika virus vaccine of claim 1, wherein said MN50 is greater than 20.

8. The Zika virus vaccine of claim 1, wherein said MN50 is greater than 30.

9. The Zika virus vaccine of claim 1, wherein said MN50 is greater than 40.

10. The Zika virus vaccine of claim 1, wherein said MN50 is greater than 50.

11. The Zika virus vaccine of claim 1, wherein said MN50 is greater than 60.

12. The Zika virus vaccine of claim 1, wherein said MN50 is greater than 70.

13. The Zika virus vaccine of claim 1, wherein said MN50 is greater than 80.

14. The Zika virus vaccine according to claim 1, wherein said MN50 is greater than or equal to 90.

15. The Zika virus vaccine of claim 1, wherein the Zika virus vaccine is capable of stimulating an MN50 titer greater than 15 in at least 80% of vaccinated subjects.

16. The Zika virus vaccine of claim 1, wherein the Zika virus vaccine is capable of stimulating an MN50 titer greater than 15 in at least 90% of vaccinated subjects.

17. The Zika virus vaccine of claim 1, wherein the Zika virus vaccine is capable of stimulating an MN50 titer greater than 15 in at least 95% of vaccinated subjects.

18. The Zika virus vaccine of claim 1, wherein the Zika virus vaccine is capable of stimulating an MN50 titer greater than 15 in at least 99% of vaccinated subjects.

19. The Zika virus vaccine of claim 1, wherein the Zika virus is inactivated by chemical inactivation, thermal inactivation, pH inactivation, or UV inactivation.

20. The Zika virus vaccine of claim 19, wherein the chemical inactivation comprises contacting the Zika virus with a chemical inactivation agent for longer than is required to completely inactivate the Zika virus as measured by plaque assay.

21. The Zika virus vaccine of claim 19, wherein the chemical inactivation comprises contacting the Zika virus with formaldehyde.

22. The Zika virus vaccine of claim 19, wherein the chemical inactivation comprises contacting the Zika virus with formaldehyde for between 2-10 days.

23. The Zika virus vaccine of claim 21, wherein the chemical activation is performed at about +4° C. or about +22° C.

24. The Zika virus vaccine of claim 1, further comprising an adjuvant.

25. The Zika virus vaccine of claim 24, wherein the adjuvant is an aluminium salt adjuvant.

26. The Zika virus vaccine of claim 25, wherein said aluminium salt adjuvant is aluminium hydroxide with less than 1.25 parts per billion copper based on a final pharmaceutical composition comprising the Zika virus.

27. The Zika virus vaccine of claim 24, wherein the adjuvant comprises a peptide and a deoxyinosine-containing immunostimulatory oligodeoxynucleic acid molecule (I-ODN).

28. The Zika virus vaccine of claim 27, wherein the peptide comprises the sequence KLKL5KLK (SEQ ID NO: 71) and the I-ODN comprises oligo-d(IC)13 (SEQ ID NO: 70).

29. The Zika virus vaccine of claim 1, further comprising one or more pharmaceutically acceptable excipients.

30. The Zika virus vaccine of claim 1, wherein the vaccine comprises protamine sulphate (PS) or fragments or breakdown products of PS at amounts below the limits of detection by high performance liquid chromatography (HPLC).

31. The Zika virus vaccine of claim 30, wherein said PS or fragments or break-down products of PS are detectable by mass spectroscopy.

32. The Zika virus vaccine of claim 1, wherein the vaccine comprises protamine sulphate (PS) or fragments or break-down products of PS at amounts below 1 µg/mL or below 100 ng/mL.

\* \* \* \* \*

SEQUENCE LISTING

```
Sequence total quantity: 117
SEQ ID NO: 1            moltype = AA  length = 32
FEATURE                 Location/Qualifiers
REGION                  1..32
                        note = synthetic peptide
source                  1..32
                        mol_type = protein
                        organism = synthetic construct
SEQUENCE: 1
PRRRRSSSRP VRRRRRPRVS RRRRRRGGRR RR                                 32

SEQ ID NO: 2            moltype = DNA  length = 10676
FEATURE                 Location/Qualifiers
source                  1..10676
                        mol_type = genomic DNA
                        organism = Zika virus
SEQUENCE: 2
gttgttactg ttgctgactc agactgcgac agttcgagtt tgaagcgaaa gctagcaaca   60
gtatcaacag gttttatttg gatttggaaa cgagagtttc tggtcatgaa aaacccaaaa  120
aagaaatccg gaggattccg gattgtcaat atgctaaaac gcggagtagc ccgtgtgagc  180
ccctttgggg gcttgaagag gctgccagcc ggacttctgc tgggtcatgg gcccatcagg  240
atggtcttgg caattctagc cttttttgaga ttcacggcaa tcaagccatc actgggtctc  300
atcaatagat ggggttcagt ggggaaaaaa gaggctatgg aaataataaa gaagttcaag  360
aaagatctgg ctgccatgct gagaataatc aatgctagga aggagaagaa agacgaggc  420
gcagatacta gtgtcggaat tgttggcctc ctgctgacca cagctatggc agcggaggtc  480
actagacgtg ggagtgcata ctatatgtac ttggacagaa acgatgctgg ggaggccata  540
tcttttccaa ccacattggg gatgaataag tgttatatac agatcatgga tcttggacac  600
atgtgtgatg ccaccatgag ctatgaatgc cctatgctgg atgaggggt ggaaccagat  660
gacgtcgatt gttggtgcaa cacgacgtca acttgggttg tgtacggaac ctgccatcac  720
aaaaaaggtg aagcacggag atctagaaga gctgtgacgc tcccctccca ttccactagg  780
aagctgcaaa cgcggtcgca aacctggttg gaatcaagag aatacacaaa gcacttgatt  840
agagtcgaaa attggatatt caggaaccct ggcttcgcgt tagcagcagc tgccatcgct  900
tggcttttgg gaagctcaac gagccaaaaa gtcatatact tggtcatgat actgctgatt  960
gccccggcat acagcatcag gtgcatagga gtcagcaata gggacttgt ggaaggtatg 1020
tcaggtggga ctttgggtttga tattgtcttg gaacatggag gttgtgtcac cgtaatggca 1080
caggacaaac cgactgtcga catagagctg gttacaacaa cagtcagcaa catggcggag 1140
gtaagatcct actgctatga ggcatcaata tcagacatgg cttcggacag ccgctgccca 1200
acacaaggtg aagcctacct tgacaagcaa tcagacactc aatatgtctg caaaagaacg 1260
ttagtggaca gaggctgggg aaatggatgt ggactttttg gcaaagggag tctggtgaca 1320
tgcgctaagt ttgcatgctc caagaaaatg accgggaaga gcatccagcc agagaatctg 1380
gagtaccgga taatgctgtc agttcatggc tcccagcaca gtgggatgat cgttaatgac 1440
```

```
acaggacatg aaactgatga gaatagagcg aaggttgaga taacgcccaa ttcaccaaga   1500
gccgaagcca ccctgggggg ttttggaagc ctaggacttg attgtgaacc gaggacaggc   1560
cttgactttt cagatttgta ttacttgact atgaataaca agcactggtt ggttcacaag   1620
gagtggttcc acgacattcc attaccttgg cacgctgggg cagacaccgg aactccacac   1680
tggaacaaca aagaagcact ggtagagttc aaggacgcac atgccaaaag gcaaactgtc   1740
gtggttctag ggagtcaaga aggagcagtt cacacggccc ttgctggagc tctggaggct   1800
gagatggatg gtgcaaaggg aaggctgtcc tctggccact tgaaatgtcg cctgaaaatg   1860
gataaactta gattgaaggg cgtgtcatac tccttgtgta ccgcagcgtt cacattcacc   1920
aagatcccgg ctgaaacact gcacgggaca gtcacagtgg aggtacagta cgcagggaca   1980
gatggacctt gcaaggttcc agctcagatg gcggtggaca tgcaaactct gaccccagtt   2040
gggaggttga taaccgctaa ccccgtaatc actgaaagca ctgagaactc taagatgatg   2100
ctggaacttg atccaccatt tggggactct tacattgtca taggagtcgg ggagaagaag   2160
atcacccacc actggcacag gagtggcagc accattggaa aagcatttga agccactgtg   2220
agaggtgcca agagaatggc agtcttggga gacacagcct gggactttgg atcagttgga   2280
ggcgctctca actcattggg caagggcatc catcaaattt ttggagcagc tttcaaatca   2340
ttgtttggag gaatgtcctg gttctcacaa attctcattg gaacgttgct gatgtggttg   2400
ggtctgaaca caaagaatgg atctatttcc cttatgtgct tggccttagg gggagtgttg   2460
atcttcttat ccacagccgt cctgctgat gtgggggtgc tgggacttt ctcaaagaag   2520
gagacgagat gcggtacagg ggtgttcgtc tataacgacg ttgaagcctg gaggacagg   2580
tacaagtacc atcctgactc cccccgtaga ttggcagcag cagtcaagca agcctgggaa   2640
gatggtatct gcgggatctc ctctgtttca agaatgaaaa acatcatgtg gagatcagta   2700
gaagggggagc tcaacgcaat cctggaagag aatggagttc aactgacggt cgttgtggga   2760
tctgtaaaaa accccatgtg gagaggtcca cagagattgc ccgtgcctgt gaacgagctg   2820
ccccacggct ggaaggcttg ggggaaatcg cacttcgtca gagcagcaaa gacaaataac   2880
agctttgtcg tggatggtga cactgaag gaatgcccac tcaaacatag agcatggaac   2940
agctttcttg tggaggatca tgggttcggg gtatttcaca ctagtgtctg gctcaaggtt   3000
agagaagatt attcattaga gtgtgatcca gccgttattg gaacagctgt taagggaaag   3060
gaggctgtac acagtgatct aggctactgg attgagagtg agaagaatga cacatggagg   3120
ctgaagaggg cccatctgat cgagatgaaa acatgtgaat ggccaaagtc ccacacattg   3180
tggacagatg gaatagaaga gagtgatctg atcatccca agtcttag tgggccactc   3240
agccatcaca ataccagaga gggctacagg acccaaatga aagggccatg gcacagtgaa   3300
gagcttgaaa ttcggtttga ggaatgccca ggcactaagg tccacgtgga ggaaacatgt   3360
ggaacaagag gaccatctct gagatcaacc actgcaagcg aagggtgat cgaggaatgc   3420
tgctgcaggg agtgcacaat gccccccactg tcgttccggg ctaaagatgg ctgttggtat   3480
ggaatggaaa taaggcccag gaaagaacca gaaagcaact tagtaaggtc aatggtgact   3540
gcaggatcaa ctgatcacat ggatcacttc tcccttggag tgcttgtgat tctgctcatg   3600
gtgcaggaag ggctgaagaa gagaatgacc acaaagatca tcataagcac atcaatggca   3660
gtgctggtag ctatgatcct gggaggattt tcaatgagtg acctggctaa gcttgcaatt   3720
ttgatggctg ccacttgc ggaaatgaac actgggagg atgtagctca tctgcgcgtg   3780
atagcggcat tcaaagtcag accagcgttg ctggtatctt tcatcttcag agctaattgg   3840
acaccccgtg aaagcatgct gctggccttg gcctcgtgtc ttttgcaaac tgcgatctcc   3900
gccttggaag gcgacctgat ggttctcatc aatggtttg ctttgcctg gttggcaata   3960
cgagcgatgg ttgttccacg cactgataac atcaccttgg caatcctggc tgctctgaca   4020
ccactggccc ggggcacact gcttgtggcg tggagagcag gccttgctac ttgcggggg   4080
tttatgctcc tctctctgaa gggaaaaggc agtgtgaaga agaacttacc atttgtcatg   4140
gccctgggac taaccgctgt gaggctggtc gacccccatca acgtggtggg gctgctgttg   4200
ctcacaagga gtgggaagcg gagctggccc cctagcaagg tactcacagc tgttggcctg   4260
atatgcgcat tggctggagg gttcgccaag gcagatatag agatggctgg gcccatggcc   4320
gcggtcggtc tgctaattgt cagttacgtg gtctcaggaa agagtgtgga catgtacatt   4380
gaaagagcag gtgacatcac atgggaaaaa gatgcggaag tcactggaaa cagtcccggg   4440
ctcgatgtgg cgctagatga gagtggtgat ttctcccctg tggaggatga cggtccccc   4500
atgagagaga tcatactcaa ggtggtcctg atgaccatct gtggcatgaa cccaatagcc   4560
ataccctttg cagctggagc gtggtacgta tacgtgaaga ctggaaaag gagtggtgct   4620
ctatgggatg tgcctgctcc caaggaagta aaaaagggg agaccacaga tggagtgtac   4680
agagtaatga ctcgtagact gctaggttca acacaagttg gagtgggaag tatgcaagag   4740
ggggtctttc acactatgtg gcacgtcaca aaaggatccg cgctgagaag cggtgaaggg   4800
agacttgatc catactgggg agatgtcaag caggatctgg tgtcatactg gtccatgg   4860
aagctagatg ccgcctggga cgggcacagc gaggtgcagc tcttggccgt gccccccgga   4920
gagagagcga ggaactcca gactctgccc ggaatattta agacaaagga tggggacatt   4980
ggagcggttg cgctggatta cccagcagga acttcaggat tccaatcct agacaagtgt   5040
gggagagtga taggacttta tggcaatggg gtcgtgatca aaaatgggag ttatgttagt   5100
gccatcaccc aagggaggag gaggaagag actcctgttg agtgcttcga gccttcgatg   5160
ctgaagaaga gcagctaac tgtcttagac ttgcatcctg gagctgggaa aaccaggaga   5220
gttcttcctg aaatagtccg tgaagccata aaaacagctc ccgtactagt gatcttagct   5280
ccaaccaggg ttgtcgctgc tgaaatggag gaagccctta gagggcttcc agtgcgttat   5340
atgcaaacag cagtcaatgt cacccactct ggaacagaaa tcgtcgactt aatgtgccat   5400
gccacccttca cttcacgtct actacagcca atcagagtcc ccaactataa tctgtatatt   5460
atggatgagg cccacttcac agatcccta agtagcaac aagaggata catttcaaca   5520
aggtttgaa tgggcgaggc ggctgccatc ttcatgacg ccacgccacc aggaaccgtg   5580
gacgcatttc cggactccaa ctcaccaatt atggacaccg aagtggaagt cccagagaga   5640
gcctggagct caggctttga ttgggtgacg gattattgcg gaaaaacagt ttggtttgtt   5700
ccaagcgtga ggaacggcaa tgagatcgca gcttgtctga caaaggctgg aaaacgggtc   5760
atacagctca gcagaaagac ttttgagaca gagttccaga aaacaaaca tcaagagtgg   5820
gactttgtg tgacaactga catttcagag atggggggca actttaagc tgaccgtgtc   5880
atagattcca ggagatgcct aaagccggtc atacttgatg cgagagagt cattctggct   5940
ggacccatgc ctgtcacaca tgccagcgct gcccagagga ggggcgcat aggcaggaat   6000
cccaacaaac ctgagatga gtatctgtat ggaggtgggt gcgcagagac tgacgaagac   6060
catgcacact ggcttgaagc aagaatgctc cttgacaata tttacctcca agatggcctc   6120
atagcctcgc tctatcgacc tgaggccgac aaagtagcag ccattgagg agagttcaag   6180
```

```
cttaggacgg agcaaaggaa gacctttgtg gaactcatga aaagaggaga tcttcctgtt  6240
tggctggcct atcaggttgc atctgccgga ataacctaca cagatagaag atggtgcttt  6300
gatggcacga ccaacaacac cataatggaa gacagtgtgc cggcagaggt gtggaccaga  6360
cacggagaga aaagagtgct caaaccgagg tggatgacg ccagagtttg ttcagatcat  6420
gcggccctga agtcattcaa ggagtttgcc gctgggaaaa gaggagcggc ttttggagtg  6480
atggaagccc tgggaacact gccaggacac atgacagaga gattccagga agccattgac  6540
aacctcgctg tgctcatgcg ggcagagact ggaagcaggc cttacaaagc cgcggcggcc  6600
caattgccgg agaccctaga gaccattatg cttttggggt tgctgggaac agtctcgctg  6660
ggaatctttt tcgtcttgat gaggaacaag ggcataggga agatgggctt tggaatggtg  6720
actcttgggg ccagcgcatg gctcatgtgg ctctcggaaa ttgagccagc cagaattgca  6780
tgtgtcctca ttgttgtgtt cctattgctg gtggtgctca tacctgagcc agaaaagcaa  6840
agatctcccc aggacaacca aatggcaatc atcatcatgg tagcagtagg tcttctgggc  6900
ttgattaccg ccaatgaact cggatggttg gagagaacaa agagtgacct aagccatcta  6960
atgggaagga gagaggaggg ggcaaccatg ggattctcaa tggacattga cctgcggcca  7020
gcctcagctt gggccatcta tgctgccttg acaactttca ttacccccagc cgtccaacat  7080
gcagtcgacca cttcatacaa caactactcc ttaatggcga tggccacgca agctggagtg  7140
ttgtttggta tgggcaaagg gatgccattc tacgcatggg actttggagt cccgctgcta  7200
atgataggtt gctactcaca attaacgccc ctgaccctaa tagtggccat cattttgctc  7260
gtggcgcact acatgtactt gatcccaggg ctgcaggcag cagctgcgcg tgctgcccag  7320
aagagaacgg cagctggcat catgaagaac cctgttgtgg atggaatagt ggtgactgac  7380
attgacacaa tgacaattga ccccaagtg gagaaaaaga tgggacaggt gctactcatg  7440
gcagtagccg tctccagcgc catactgtcg cggaccgcct gggggtgggg gaggctggg  7500
gccctgatca cagccgcaac ttccactttg tgggaagct ctccgaacaa gtactgaac  7560
tcctctacag ccacttcact gtgtaacatt tttaggggaa gttacttggc tggagcttct  7620
ctaatctaca cagtaacaag aaacgctggc ttggtcaaga gacgtggggg tggaacagga  7680
gagaccctgg gagagaaatg gaaggcccgc ttgaaccaga tgtcggccct ggagttctac  7740
tcctacaaaa agtcaggcat caccgaggtg tgcagaagaa aggcccgccg cgcctaag  7800
gacggtgtgg caacgggagg ccatgctgtg tcccgaggaa gtgcaaagct gagatgttg  7860
gtggagcgga gatacctgca gcctatggaa aaggtcattg atcttggatg tggcagagggg  7920
ggctggagtt actacgccgc caccatccgc aaagttcaag aagtgaaagg atacacaaaa  7980
ggaggccctg gtcatgaaga acccgtgttg gtgcaaagct atgggtggaa catagtccgt  8040
cttaagagtg gggtggacgt ctttcatatg cgcgctgagc cgtgtgacac gttgctgtgt  8100
gacataggtg agtcatcatc tagtcctgaa gtggaagaag cacggacgct cagagtcctc  8160
tccatggtgg gggattggct tgaaaaaaga ccaggagcct ttttgataaa agtgttgtgc  8220
ccatacacca gcactatgat ggaaaccctg agcgactgc agcgtaggta tgggggagga  8280
ctggtcagag tgccactctc ccgcaactct acacatgaga tgtactgggt ctctggagcg  8340
aaaagcaaca ccataaaaag tgtgtccacc acgagccagc tcctcttggg gcgcatggac  8400
gggcctagga ggccagtgaa atatgaggag gatgtgaatc tcggctctgg cacgcgggct  8460
gtggtaagct gcgctgaagc tcccaacatg aagatcattg gtaaccgcat tgaaaggatc  8520
cgcagtgagc acgcggaaac gtggttcttt gacgagaacc acccatatag gacatggcct  8580
taccatggaa gctatgaggc ccccacacaa gggtcagcgt cctctctaat aaacggggtt  8640
gtcaggctcc tgtcaaaacc ctgggatgtg gtgactggag tcacaggaat agccatgacc  8700
gacaccacc cgtatggtca gcaaagagtt ttcaaggaaa aagtggacac taggtgtcca  8760
gaccccaag aaggtactcg tcaggttatg agcatggtct cttcctggtt gtggaaagaa  8820
ctaggcaaac acaaacggcc acgagtctgt accaaagaag agttcatcaa caaggttcgt  8880
agcaatgcag cattaggggc aatatttgaa gaggaaaaag agtggaagac tgcagtggaa  8940
gctgtgaacg atccaaggtt ctgggctcta gtggacaagg aaagagagca ccacctgaga  9000
ggagagtgcc agagttgtgt gtacaacatg atgggaaaaa gagaaaagaa acaaggggaa  9060
tttgaaaagg ccaagggcag ccgcgccatc tggtatatgt ggctaggggc tagatttcta  9120
gagttcgaag cccttggatt cttgaacgag atcactggga tggggagaga gaactcagga  9180
ggtggtttga accgcctgtt aaggggctggg attacaaaga ctcggatatg tcctagaga gatgagtcga  9240
ataccaggag gaaggatgta tgcagatgac actgctggct gggacacccg catcagcagg  9300
tttgatctgg agaatgaagc tctaatcacc aaccaaatgg agaaaggca cagggccttg  9360
gcattggcca taatcaagta cacataccaa aacaagtgg taaaggtcct tagaccagct  9420
gaaaaaggga aaacagttat ggacattatt tcgagacaag accaaagggg gagcggacaa  9480
gttgtcactt acgctcttaa cacatttacc aacctagtgg tgcaactcat tcggaatatg  9540
gaggctgagg aagtcctaga gatgcaagac ttgtggctgc tgcggaggtc agagaaagtg  9600
accaactggt tgcagagcaa cggatgggat aggctcaaac gaatggcagt cagtggagat  9660
gattgcgttg tgaagccaat tgatgatagg tttgcacatg ccctcagg ctttaatgat  9720
atgggaaaag ttaggaagga cacacagag tggaaccct caactgatg ggacaactgg  9780
gaagaagttc cgttttgctc ccaccacttc aacaagctcc atctcaagga cgggaggtcc  9840
attgtggttc cctgccgcca ccaagatgaa ctgattggcc gggcccgcgt ctctccaggg  9900
gcgggatgga gcatccggga gactgcttgc ctagcaaaat catatgcgca aatgtggcag  9960
ctcctttatt tccacagaag ggacctccga ctgatggcca aggcccattg tcatctgtg  10020
ccagttgact gggttccaac tgggagaact acctggtcaa tccatggaaa gggagaatgg  10080
atgaccactg aagacatgct tgtggtgtgg aacagagtgt ggattgagga gaacgaccac  10140
atggaagaca gaccccagt tacgaaatgg acagacattc cctatttggg aaaaaggaa  10200
gacttgtggt gtggatctct cataggcac agaccgcgca ccacctgggc tgaaactt  10260
aaaacacag tcaacatggt gcgcagatc ataggtgatg aagaaagta catggactac  10320
ctatccaccc aagttcgcta cttggtgaa aagggtctac cctggagtgctgtaagca 10380
ccaatcttaa tgttgtcagg cctgctagtc agccacagct tggggaaagc tgtgcagcct  10440
gtgacccccc caggagaagc tgggaaacca agcctatgt caggccgagaacgccatggc  10500
acggaagaag ccatgctgcc tgtgagcccc tcagaggaca ctgagtcaa aaaccccacg  10560
cgcttgagg cgcaggatgg gaaaagaagg tggccgacct ccccaccctt caatctgggg  10620
cctgaactgg agatcagctg tggatctcca gaagagggac tagtggttag aggaga  10676

SEQ ID NO: 3     moltype = DNA   length = 10793
FEATURE          Location/Qualifiers
source           1..10793
```

-continued

```
                         mol_type = genomic DNA
                         organism = Zika virus
SEQUENCE: 3
ccaatctgtg aatcagactg cgacagttcg agtttgaagc gaaagctagc aacagtatca  60
acaggtttta ttttggattt ggaaacgaga gtttctggtc atgaaaaacc caaaaaagaa  120
atccggagga ttccggattg tcaatatgct aaaacgcgga gtagcccgtg tgagcccctt  180
tgggggcttg aagaggctgc cagccggact tctgctgggt catgggccca tcaggatggt  240
cttggcgatt ctagcctttt tgagattcac ggcaatcaag ccatcactgg gtctcatcaa  300
tagatggggt tcagtgggga aaaaagaggc tatggaaata ataaagaagt tcaagaaaga  360
tctggctgcc atgctgagaa taatcaatgc caggaaggag aagaagagac gaggcgcaga  420
tactagtgtc ggaatcgttg gcctcctgct gaccacagct atggcagcgg aggtcactag  480
acgtgggagt gcatactata tgtacttgga cagaaacgat gctggggagg ccatatcttt  540
tccaaccaca ttggggatga ataagtgtta tatacagatc atggatcttg gacacatgtg  600
tgatgccacc atgagctatg aatgccctat gctggatgag ggggtggaac cagatgacgt  660
cgattgttgg tgcaacacga cgtcaacttg ggttgtgtac ggaacctgcc atcacaaaaa  720
aggtgaagca cggagatcta gaagagctgt gacgctcccc tcccattcca ctaggaagct  780
gcaaacgcgg tcgcaaacct ggttggaatc aagagaatac acaaagcact tgattagagt  840
cgaaaattgg atattcagga accctggctt cgcgttagca gcagctgcca tcgcttggct  900
tttgggaagc tcaacgagcc aaaaagtcat atacttggtc atgatactgc tgattgcccc  960
ggcatacagc atcaggtgca taggagtcag caatagggac tttgtggaag gtatgtcagg  1020
tgggacttgg gttgatgttg tcttggaaca tgggggttgt gtcaccgtaa tggcacagga  1080
caaaccgact gtcgacatag agctggttac aacaacagtc agcaacatgg cggaggtaag  1140
atcctactgc tatgaggcat caatatcaga catggcttcg gacagccgct gcccaacaca  1200
aggtgaagcc taccttgaca agcaatcaga cactcaatat gtctgcaaaa gaacgttagt  1260
ggacagaggc tggggaaatg gatgtggact tttggcaaa gggagcctgg tgacatgcgc  1320
taagtttgca tgctccaaga aaatgaccgg gaagagcatc cagccagaga atctggagta  1380
ccggataatg ctgtcagttc atggctccca gcacagtggg atgatcgtta atgacacagg  1440
acatgaaact gatgagaata gagcgaaggt tgagataacg cccaattcac caagagccga  1500
agccaccctg gggggtttg gaagcttagg acttgattgt gaaccgagga caggccttga  1560
cttttcagat ttgtattact tgactatgaa taacaagcac tggttggttc acaaggagtg  1620
gttccacgac attccattac cttggcacgc tggggcagac accggaactc cacactggaa  1680
caacaaagaa gcactggtag agttcaagga cgcacatgcc aaaaggcaaa ctgtcgtggt  1740
tctagggact caagaaggag cagttcacac ggcccttgct ggagctctgg aggctgagat  1800
ggatggtgca aagggaaggc tgtcctctgg ccacttgaaa tgtcgcctga aaatggataa  1860
acttagattg aagggcgtgt catactcctt gtgtaccgca gcgttcacat tcaccaagat  1920
cccggctgaa acactgcacg ggacagtcac agtggaggta cagtacgcag ggacagatgg  1980
accttgcaag gttccagctc agatggcggt ggacatgcaa actctgaccc cagttgggag  2040
gttgataacc gctaaccccg taatcactga aagcactgag aactctaaga tgatgctgga  2100
acttgatcca ccatttgggg actcttacat tgtcatagga gtcggggaga agaagatcac  2160
ccaccactgg cacaggagtg gcagcaccat tggaaaagca tttgaagcca ctgtgagagg  2220
tgccaagaga atggcagtct tgggagacac agcctgggac tttggatcag ttggaggcgc  2280
tctcaactca ttgggcaagg gcatccatca aattttgga gcagctttca aatcattgtt  2340
tggaggaatg tcctggttct cacaaattct cattggaacg ttgctgatgt ggttgggtct  2400
gaacacaaag aatggatcta tttcccttat gtgcttggcc ttagggggag tgttgatctt  2460
cttatccaca gccgtctctg ctgatgtggg gtgctcggtg gacttctcaa agaaggagac  2520
gagatgtggt acaggggtgt tcgtctataa cgacgttgaa gcctggaggg acaggtacaa  2580
gtaccatcct gactctcccc gtagattggc agcagcagtc aagcaagcct gggaagatgg  2640
tatctgcggg atctcctctg tttcaagaat ggaaaacatc atgtggagat cagtagaagg  2700
ggagcttaac gcaatcctgg aagagaatgg agttcaactg acggtcgttg tgggatctgt  2760
aaaaaacccc atgtggagag gtccacagag attgcccgtg cctgtgaacg agctgcccca  2820
cggctggaag gcttggggga aatcgtactt cgtcagagca gcaaagacaa ataacagctt  2880
tgtcgtggat ggtgacacac tgaaggaatg cccactcaaa catagagcat ggaacagctt  2940
tcttgtggag gatcatgggt tcggggtatt tcacactagt gtctggctca aggttagaga  3000
agattattca ttagagtgtg atccagccgt tattggaaca gctgttaagg gaaaggaggc  3060
tgtacacagt gatctaggct actggattga gagtgagaag aatgacacat ggaggctgaa  3120
gagggcccat ctgatcgaga tgaaaacatg tgaatggcca aagtcccaca cattgtggac  3180
agatggaata gaagagagtg atctgatcat acccaagtct ttagctgggc cactcagcca  3240
tcacaatacc agagagggct acaggaccca aatgaaaggg ccatggcaca gtgaagagct  3300
tgaaattcgg tttgaggaat gcccaggcac taaggtccac gtggaggaaa catgtggaac  3360
aagaggacca tctctgagat caaccactgc aagcggaagg gtgatcgagg aatggtgctg  3420
cagggagtgc acaatgcccc cactgtcgtt ccgggctaaa gatggctgtt ggtatggaat  3480
ggagataagg cccaggaaag aaccagaaag caacttagta aggtcaatgg tgactgcagg  3540
atcaactgat cacatggatc acttctccct tggagtgctt gtgattctgc tcatggtgca  3600
ggaagggctg aagaagagaa tgaccacaaa gatcatcata agcacatcaa tggcagtgct  3660
ggtagctatg atcctgggag gattttcaat gagtgacctg gctaagcttg caattttgat  3720
gggtgccacc ttcgcggaaa tgaacactgg aggagatgta gctcatctgg cgctgatagc  3780
ggcattcaaa gtcagaccag cgttgctggt atctttcatc ttcagagcta attggacacc  3840
ccgtgaaagc atgctgctgg ccttggcctc gtgtttttg caaactgcga tctccgcctt  3900
ggaaggcgac ctgatggttc tcatcaatgg ttttgctttg gcctggttgg caatacgagc  3960
gatggttgtt ccacgcactg acaacatcac cttggcaatc ctggctgctc tgacaccact  4020
ggcccggggc acactgcttg tggcgtggag agcaggcctt gctacttgcg gggggtttat  4080
gctcctctct ctgaagggaa aaggcagtgt gaagaagaac ttaccatttg tcatggccct  4140
gggactaacc gctgtgaggc tggtcgaccc catcaacgtg gtgggactgc tgttgctcac  4200
aaggagtggg aagcggagct ggccccctag cgaagtactc acagctgttg gcctgatatg  4260
cgcattggct ggagggttcg ccaaggcaga tatagagatg gctgggccca tggccgcggt  4320
cggtctgcta attgtcagtt acgtggtctc aggaaagagt gtggacatgt acattgaaag  4380
agcaggtgac atcacatggg aaaaagatgc ggaagtcact ggaaacagtc cccggctcga  4440
tgtggcgcta gatgagagtg gtgacttctc cctggtggag gatgacggtc cccccatgag  4500
agagatcata ctcaaggtgg tcctgatgac catctgtggc atgaacccaa tagccatacc  4560
```

```
ctttgcagct ggagcgtggt acgtatacgt gaagactgga aaaaggagtg gtgctctatg  4620
ggatgtgcct gctcccaagg aagtaaaaaa gggggagacc acagatggag tgtacagagt  4680
aatgactcgt agactgctag gttcaacaca agttggagtg ggagttatgc aagaggggt   4740
cttttcacact atgtggcacg tcacaaaagg atccgcgctg agaagcggtg aagggagact  4800
tgatccatac tggggagatg tcaagcagga tctggtgtca tactgtggtc catggaagct  4860
agatgccgcc tgggacgggc acagcgaggt gcagctcttg gccgtgcccc cggagagag   4920
agcgaggaac atccagactc tgcccggaat atttaagaca aaggatgggg acattggagc  4980
ggttgcgctg gattacccag caggaacttc aggatctcca atcctagaca agtgtgggag  5040
agtgatagga ctttatggca atggggtcgt gataaaaaat gggagtttatg ttagtgccat  5100
cacccaaggg aggagggagg aagagactcc tgttgagtgc ttcgagcctt cgatgctgaa  5160
gaagaagcag ctaactgtct tagacttgca tcctggagct gggaaaacca ggagagttct  5220
tcctgaaata gtccgtgaag ccataaaaac aagactccgt actgtgatct tagctccaac  5280
cagggttgtc gctgctgaaa tggaggaagc ccttagaggg cttccagtgc gttatatgac  5340
aacagcagtc aatgtcaccc actctggaac agaaatcgtc gacttaatgt gccatgccac  5400
cttcacttca cgtctactac agccaatcag agtcccccaac tataatctgt atattatgga  5460
tgaggcccac ttcacagatc cctcaagcat agcagcaaga ggatacattt caacaagggt  5520
tgagatgggc gaggcggctg ccatcttcat gaccgccacg ccaccaggaa cccgtgacgc  5580
atttccggac tccaactcac caattatgga caccgaagtg gaagtcccag agagagcctg  5640
gagctcaggc tttgattggg tgacggatca ttctggaaaa acagtttggt ttgttccaag  5700
cgtgaggaac ggcaatgaga tcgcagcttg tctgacaaag gctggaaaac gggtcataca  5760
gctcagcaga aagactttg agacagagtt ccagaaaaca aaacatcaag agtgggactt  5820
tgtcgtgaca actgacattt cagagatggg cgccaacttt aaagctgacc ggtcataga  5880
ttccaggaga tgcctaaagc cggtcatact tgatggcgag agagtcattc tggctggacc  5940
catgcctgtc acacatgcca gcgctgccca gaggaggggg cgcataggca ggaatcccaa  6000
caaacctgga gatgagtacc tgtatggagg tgggtgcgca gagactgacg aagaccatgc  6060
acactggctt gaagcaagaa tgctccttga caatatttac ctccaagatg gcctcatagc  6120
ctcgctctat cgacctgagg ccgacaaagt agcagccatt gagggagagt tcaagcttag  6180
gacggagcaa aggaagacct ttgtggaact catgaaaaga ggagatcttc ctgtttggct  6240
ggcctatcag gttgcatctg ccggaataac ctacacagat agaagatggt gctttgatgg  6300
cacgaccaac aacaccataa tggaagacag tgtccggcaa gggtgtgga ccagacacgg  6360
agagaaaaga gtgctcaaac cgaggtggat ggacgccaga gtttgttcag atcatgcggc  6420
cctgaagtca ttcaaggagt ttgccgctgg gaaaagagga cggcttttg gagtgatgga  6480
agccctggga acactgccag gacacatgac agagagattc caggaagcca ttgacaacct  6540
cgctgtgctc atgcgggcag agactggaag caggccttac aaagccgcgg cggcccaatt  6600
gccggagacc ctagagacca ttatgctttt ggggttgctg gaacagtct cgctgggaat  6660
cttttttcgtc ttgatgagga acaagggcat agggaagatg ggctttggaa tggtgactct  6720
tggggccagc catggctca tgtggctctc ggaaattgag ccagcagaa ttgcatgtgt  6780
cctcattgtt gtgttcctat tgctggtggt gctcatacct gagccagaaa agcaaagatc  6840
tccccaggac aaccaaatgg caatcatcat catggtagca gtaggtcttc tgggcttgat  6900
taccgccaat gaactcggat ggttggagag aacaaagagt gacctaagcc atctaatggg  6960
aaggagagag gaggggcaa ccataggatt ctcaatggac attgacctgc ggccagcctc  7020
agcttgggcc atctatgctg ccttgacaac tttcattacc ccagccgtcc aacatgcagt  7080
gaccacttca tacaacaact actccttaat ggcgatggcc acgcaagctg gagtgttgtt  7140
tggtatgggc aaagggatgc cattctacgc atgggacttt ggagtcccgc tgctaatgat  7200
aggttgctac tcacaattaa caccctgac cctaatagtg gccatcattt tgctcgtggc  7260
gcactacatg tacttgatcc cagggctgca ggcagcagct gcgcgtgctg cccagaagag  7320
aacggcagct ggcatcatga agaaccctgt tgtggatgga atagtggtga ctgacattga  7380
cacaatgaca attgaccccc aagtggagaa aaagatggga caggtgctac tcatagcagt  7440
agccgtctcc agcgccatac tgtcgcggac cgcctggggg tggggaggg ctgggccct   7500
gatcacagcc gcaacttcca ctttgtggga aggctctccg aacaagtact ggaactcctc  7560
tacagccact tcactgtgta acatttttag gggaagttac ttggctgaga cttctctaat  7620
ctacacagta acaagaaacg ctggcttggt caagagacgt ggggtgaa caggagagac  7680
cctgggagag aaatgaagg cccgcttgaa ccagatgtcg gccctggagt ctactcta    7740
caaaaagtca ggcatcaccg aggtgtgcag agaagaggcc cgccgcgccc tcaaggacgg  7800
tgtggcaacg ggaggccatg ctgtgtcccg aggaagtgca aagctggtgg ttggtggga   7860
gcggggatac ctgcagccct atggaaaggt cattgatctt ggatgtggca gagggggctg  7920
gagttactac gccgccacca tccgcaaagt tcaagaagtg aaaggataca caaaaggagg  7980
ccctggtcat gaagaacccg tgttggtgca agctatgggg tggaacatag tccgtcttaa  8040
gagtggggtg gacgtctttc atatggcggc tgagccgtgt gacacgttgc tgtgtgacat  8100
aggtgagtca tcatctagtc ctgaagtgga agaagcacgg acgctcagag tcctctccat  8160
ggtggggat tggcttgaaa aaagaccagg agccttttgc ataaaagtgt tgtgcccata  8220
caccagcact atgatggaaa ccctggagcg actgcagcgt aggtatgggg gaggactggt  8280
cagagtgcca ctctcccgca actctacaca tgagatgtac tgggtctctg gagcgaaaag  8340
caaccatata aaaagtgtgt ccaccacgag ccagtcctc ttggggcgca tggacagcc   8400
taggaggcca gtgaaatatg aggaggatgt gaatctcggc tctggcacgc gggctgtggt  8460
aagctgcgct gaagctccca acatgaagat cattggtaac cgcattgaaa ggatccgcag  8520
tgagcacgcg gaaacgtggt tctttgacga aaaccaccca tataggacat gggcttacca  8580
tggaagctat gtggcccca cacagggtc agcgtcctct ctaataaacg gggttgtcag  8640
gctcctgtca aaacccgg atgtggtgac tggagtcaca gcgaatagca gtgaccgacac  8700
cacaccgtat ggtcagcaaa gagttttcaa ggaaaagtg gacactaggg tgccagaccc  8760
ccaagaaggc actcgtcagg ttatgagcat ggtctcttcc tggttgtgga aagagctagg  8820
caaacacaaa cgaccacgag tctgtaccaa agaagagttc atcaacaagg ttcgtagcaa  8880
tgcagcatta ggggcaatat ttgaagagga aaagagtgg aagactgcag tggaagctgt  8940
gaacgatcca aggttctggg ctctagtgga caaggaagag gcaccacctg tgagaggaa   9000
gtgccagagt tgtgtgtaca acatgatggg aaaaagagaa aagaaacaag gggaattggt  9060
aaaggccaag ggcagccgcg ccatctggta tatgtggcta ggggctagat ttctagagtt  9120
cgaagccctt ggattcttga acgaggatca ctggatgggg agagaaact caggaggtgg  9180
tgttgaaggg ctgggattac aaagactcgg atatgtccta gaagagatga gtcgcatacc  9240
aggaggaagg atgtatgcag atgacactgc tggctgggac acccgcatca gcaggtttga  9300
```

```
tctggagaat gaagctctaa tcaccaacca aatggagaaa gggcacaggg ccttggcatt   9360
ggccataatc aagtacacat accaaaacaa agtggtaaag gtccttagac cagctgaaaa   9420
agggaaaaca gttatggaca ttatttcgag acaagaccaa aggggagcg gacaagttgt    9480
cacttacgct cttaacacat ttaccaacct agtggtgcaa ctcattcgga atatggaggc   9540
tgaggaagtt ctagagatgc aagacttgtg gctgctgcgg aggtcagaga aagtgaccaa   9600
ctggttgcag agcaacggat gggataggc caaacgaatg gcagtcagtg gagatgattg    9660
cgttgtgaag ccaattgatg ataggtttgc acatgccctc aggttcttga atgatatggg   9720
aaaagttagg aaggacacac aagagtggaa accctcaact ggatgggaca actgggaaga   9780
agttccgttt tgctcccacc acttcaacaa gctccatctc aaggacggga ggtccattgt   9840
ggttccctgc cgccaccaag atgaactgat tggccgggcc cgcgtctctc caggggcggg   9900
atggagcatc cgggagactg cttgcctagc aaaatcatat gcgcaaatgt ggcagctcct   9960
ttatttccac agaagggacc tccgactgat ggccaatgcc atttgttcat ctgtgccagt  10020
tgactgggtt ccaactggga gaactacctg gtcaatccat ggaaagggag aatggatgac  10080
cactgaagac atgcttgtgg tgtggaacag agtgtgattt gaggagaacg accacatgga  10140
agacaagacc ccagttacga aatggacaga cattccctat ttgggaaaaa gggaagactt  10200
gtggtgtgga tctctcatag ggcacagacc gcgcaccacc tggctgaga acattaaaaa   10260
tacagtcaac atggtgcgca ggatcatagg tgatgaagaa aagtcatgg actacctatc   10320
caccaagtt cgctacttgg gtgaagaagg gtctacacct ggagtgctgt gagcaccaat   10380
cttaatgttg tcaggcctgc tagtcagcca cagcttgggg aaagctgtgc agcctgtgac  10440
ccctccagga gaagctgggt aaccaagcct atagtcaggc cgagaacgcc atggcacgga  10500
agaagccatg ctgcctgtga gcccctcaga ggacactgag tcaaaaaacc ccacgcgctt  10560
ggaggcgcag gatgggaaaa gaaggtggcg accttcccca cccttcaatc tgggggcctga  10620
actgagatc agctgtggat ctccagaaga gggactagtg gttagaggag acccccccgga   10680
aaacgcaaaa cagcatattg acgctgggaa agaccagaga ctccatgagt ttccaccacg  10740
ctggccgcca ggcacagatc gccgaatagc ggcggccgt gtggggaaat cca            10793

SEQ ID NO: 4           moltype = DNA   length = 10675
FEATURE                Location/Qualifiers
source                 1..10675
                       mol_type = genomic DNA
                       organism = Zika virus
SEQUENCE: 4
gttgttgatc tgtgtgaatc agactgcgac agttcgagtt tgaagcgaaa gctagcaaca     60
gtatcaacag gttttatttt ggatttgaa acgagagttt ctggtcatga aaaacccaaa    120
aaagaaatcc ggaggattcc ggattgtcaa tatgctaaaa cgcggagtag cccgtgtgag    180
ccccttggg ggcttgaaga ggctgccagc cggacttctg ctgggtcatg ggcccatcag    240
gatggtcttg gcgattctag cctttttgag attcacggca atcaagccat cactgggtct   300
catcaataga tgggggttcag tggggaaaaa agaggctatg gaaacaataa agaagttcaa   360
gaaagatctg gctgccatgc tgagaataat caatgctaag aaggagaaga gagacgaagg   420
cgcagatact agtgtcggaa ttgttggcct cctgctgacc acagctatgg cagcggaggt   480
cactagacgt gggagtgcat actatatgta cttggacaga acgatgctg gggaggccat   540
atcttttcca accacattgg ggatgaataa gtgttatata cagatcatgg atcttggaca   600
catgtgtgat gccaccatga gctatgaatg ccctatgctg gatgagggg tggaaccaga   660
tgacgtcgat tgttggtgca acacgacgtc aacttgggtt gtgtacggaa cctgccatca   720
caaaaaggt gaagcacgga gatctagaag agctgtgacg ctccctctcc attccaccag   780
gaagctgcaa acgcggtcgc aaacctggtt ggaatcaaga gaatacacaa agcacttgat   840
tagagtcgaa aattggatat tcaggaaccc tggcttcgcg ttagcagcag ctgccatgca   900
ttggctttg ggaagctcaa cgagccaaaa agtcatatac ttggtcatga tactgctgat   960
tgccccggca tacagcatca ggtgcatagg agtcagcaat agggactttg tggaaggtat  1020
gtcaggtggg acttggggttg atgttgtctt ggaacatgga ggttgtgtca ccgtaatggc  1080
acaggacaaa ccgactgtcg acatagagct ggttacaaca acagtcagca catggcggga  1140
ggtaagatcc tactgctatg aggcatcaat atcagacatg gcttctgaca gccgctgccc  1200
aacacaaggt gaagcctacc ttgacaagca atcagacact caatatgtct gcaaaagaac  1260
gttagtggac agaggctggg gaaatggatg tggactttt ggcaaaggga gcctggtgac  1320
atgcgctaag tttgcatgct ccaagaaaat gaccgggaag agcatccagc cagagaatct  1380
ggagtaccgg ataatgctgt cagttcatgg ctcccagcac agtgggatga tcgttaatga  1440
cacaggacat gaaactgatg agaatagagc gaaagttgag ataacgccca ttcaccgag   1500
agccgaagcc accctgggg gttttggaag cctaggactt gattgtgaac cgaggacagg  1560
ccttgacttt tcagatttgt attacttgac tatgaataac aagcactggt tggttcaaa   1620
ggagtggttc cacgacattc cattaccttg gcacgctggg gcagacaccg gaactccaca  1680
ctggaacaac aaagaagcac tggtagagtt caaggacgca catgccaaaa ggcaaactgt  1740
cgtggttcta gggagtcaag aaggagcagt tcacacggcc cttgctggag ctctggaggc  1800
tgagatggat ggtgcaaagg aaggctgtc ctctggccac ttgaaatgtc gcctgaaaat  1860
ggataaactt agattgaagg gcgtgtcata ctccttgtgt actgcagctt tcacattcac  1920
caagatcccg gctgaaacac tgcacggac agtcacagtg gaggtacagt acgcagggac  1980
agatggacct tgcaaggttc agctcagat ggcggtggac atgcaaactc tgaccccagt  2040
tgggaggttg ataaccgcta accccgtaat cactgaaagc actgagaact ctaagatgat  2100
gctgaactt gatccaccat ttgggactc ttacattgtc ataggagtcg gggagaagaa  2160
gatcacccac cactggcaca ggagtggcag caccattgga aaagcattg aagccactgt  2220
gagaggtgcc aagagaatgg cagtcttggg agacacagcc tgggacttg atcagttgg   2280
aggcgctctc aactcattgg gcaagggcat ccatcaaatt tttggagcag cttttcaaatc  2340
attgtttgga ggaatgtcct ggttctcaca aattctcatt ggaacgttgc tgatgtggtt  2400
gggtctgaac acaaagaatg gatctatttc ccttatgtgc ttggcttag gggagtgtt   2460
gatctttcta tccacagcg tctctgctga tgtggggtgc tcggtggact tctcaaagaa  2520
gggagacgaga tgcggtacag gggtgttcgt ctataacgac gttgaagcct ggagggacag  2580
gtacaagtac catcctgact ccccccgtag attggcagca gcagtcaagc aagcctggga  2640
agatggtatc tgcgggatct cctctgtttc aagaatgaa aacatcatgt ggagatcagt  2700
agaagggag ctcaacgcaa tcctggaaga gaatggagtt caactgacgg tcgttgtggg  2760
atctgtaaaa aaccccatgt ggagaggtcc acagagattg cccgtgcctg tgaacgagct  2820
```

```
gccccacggc tggaaggctt gggggaaatc gtatttcgtc agagcagcaa agacaaataa   2880
cagctttgtc gtggatggtg acacactgaa ggaatgccca ctcaaacata gagcatggaa   2940
cagctttctt gtggaggatc atgggttcgg ggtatttcac actagtgtct ggctcaaggt   3000
tagagaagat tattcattag agtgtgatcc agccgttatt ggaacagctg ttaagggaaa   3060
ggaggctgta cacagtgatc taggctactg gattgagagt gagaagaatg acacatggag   3120
gctgaagagg gcccatctga tcgagatgaa aacatgtgaa tggccaaagt cccacacatt   3180
gtggacagat ggaatagaag agagtgatct gatcataccc aagtctttag ctgggccact   3240
cagccatcac aataccagag agggctacag gacccaaatg aaagggccat ggcacagtga   3300
agagcttgaa attcggtttg aggaatgccc aggcactaag gtccacgtgg aggaaacatg   3360
tggaacaaga ggaccatctc tgagatcaac cactgcaagc ggaagggtga tcgaggaatg   3420
gtgctgcagg gagtgcacaa tgcccccact gtcgttccgg gctaaagatg gctgttggta   3480
tggaatggaa ataaggccca ggaaagaacc agaaagcaac ttagtaaggt caatggtgac   3540
tgcaggatca actgatcaca tggaccactt ctcccttgga gtgcttgtga tcctgctcat   3600
ggtgcaggaa gggctgaaga agagaatgac cacaaagatc atcataagca catcaatggc   3660
agtgctggta gctatgatcc tgggaggatt ttcaatgagt gacctggcta agcttgcaat   3720
tttgatgggt gccaccttcg cggaaatgaa cactggagga gatgtagctc atctggcgct   3780
gatagcggca ttcaaagtca gaccagcgtt gctggtatct ttcatcttca gagctaattg   3840
gacaccccgt gaaagcatgc tgctggcctt ggcctcgtgt cttttgcaaa ctgcgatctc   3900
cgccttggaa ggcgacctga tggttctcat caatggtttt gctttggcct ggttggcaat   3960
acgagcgatg gttgttccac gcactgataa catcaccttg gcaatcctgg ctgctctgac   4020
accactggcc cggggcacac tgcttgtggc gtggagagca ggccttgcta cttgcggggg   4080
gtttatgctc ctctctctga agggaaaagg cagtgtgaag aagaacttac catttgtcat   4140
ggccctggga ctaaccgctg tgaggctggt cgaccccatc aacgtggtgg gactgctgtt   4200
gctcacaagg agtgggaagc ggagctggcc ccctagcgaa gtactcacag ctgttggcct   4260
gatatgcgca ttggctggag ggttcgccaa ggcagatata gagatggctg ggcccatggc   4320
cgcggtcggt ctgctaattg tcagttacgt ggtctcagaa aagagtggtg acatgtacat   4380
tgaaagagca ggtgacatca catgggaaaa agatgcggaa gtcactggaa acagtccccg   4440
gctcgatgtg gcgctagatg agagtggtga tttctccctg gtggaggatg acggtccccg   4500
catgagagag atcatactca aggtggtcct gatgaccatc tgtggcatga acccaatagc   4560
catacccttt gcagctggag cgtggtacgt atacgtgaag actggaaaaa ggagtggtga   4620
tctatgggat gtgcctgctc ccaaggaagt aaaaaagggg gagaccacag atggagtgta   4680
cagagtaatg actcgtagac tgctaggttc aacacaagtt ggagtgggag ttatgcaaga   4740
gggggtcttt cacactatgt ggcacgtcac aaaaggatcc gcgctgagaa gcggtgaagg   4800
gagacttgat ccatactggg gagatgtcaa gcaggatctg gtgtcatact gtggtccatg   4860
gaagctagat gccgcctggg atgggcacag cgaggtgcag ctcttggccg tgcccccgg   4920
agagagagcg aggaacatcc agactctgcc cggaatatt aagacaaagg atggggacat   4980
tggagccggt tcgctggatt acccagcagg aacttcagga tctccaatcc tagacaagtg   5040
tgggagagtg ataggacttt atggcaatgg ggtcgtgatc aaaaacggga gttatgttag   5100
tgccatcacc caagggagga gggaggaaga gactcctgtt gagtgcttcg agccctcgat   5160
gctgaagaag aagcagctaa ctgtcttaga cttgcatcct ggagctggga aaaccaggag   5220
agttcttcct gaaatagtcc gtgaagcat aaaaacaaga ctccgtactg tgatcttagc   5280
tccaaccagg gttgtcgctg ctgaaatgga ggaggccctt agagggcttc cagtgcgtta   5340
tatgacaaca gcagtcaatg tcacccactc tggaacagaa atcgtcgact taatgtgcca   5400
tgccacccttc acttcacgtc tactacagcc aatcagagtc cccaactata atctgtatat   5460
tatggatgag gcccacttca cagatccctc aagtatagca gcaagaggat acatttcaac   5520
aagggttgag atgggcgagg cggctgccat cttcatgacc gccacgccac caggaacccg   5580
tgacgcattt ccggactcca actcaccaat tatggacacc gaagtggaag tcccagagag   5640
agcctggagc tcaggctttg attgggtgac ggatcattct ggaaaaacag tttggtttgt   5700
tccaagcgtg aggaacggca atgagatcgc agcttgtctg acaaaggctg aaaacgggt   5760
catacagctc agcagaaaga cttttgagac agagttccag aaaacaaaac atcaagagtg   5820
ggacttttgtc gtgacaactg acatttcaga gatgggcgac aactttaaag ctgaccgtgt   5880
catagattcc aggagatgcc taaagccggt catacttgat ggcgagagag tcattctggc   5940
tggacccatg cctgtcacac atgccagcgc tgcccagagg aggggcgca taggcaggaa   6000
tcccaacaaa cctggagatg agtatctgta tggaggtggg tgcgcagaga ctgacgaaga   6060
ccatgcacac tggcttgaag caagaatgct ccttgacaat atttacctcc aagatggcct   6120
catagcctcg ctctatcgac ctgaggcgaa caagtagcaa gccattgagg gagagttcaa   6180
gcttaggacg gagcaaagga gacctttgt ggaactcatg aaaagaggag atcttcctgt   6240
ttggctggcc tatcaggttg catctgccgg aataacctac acagatagaa gatggtgctt   6300
tgatggcacg accaacaaca ccataatgga agacagtgtg ccggcagagg tgtggaccag   6360
acacgagag aaaagagtgc tcaaaccgag gtggatggac gccagagttt gttcagatca   6420
tgcggccctg aagtcattca aggagtttgc cgctgggaaa agaggagcgg cttttggagt   6480
gatggaagcc ctgggaacac tgccaggaca catgacagag agattccagg aagccattga   6540
caacctcgct gtgctcatgc gggcagagac tggaagcagg ccttacaaag ccgcggcggc   6600
ccaattgccg gagaccctag agaccataat gcttttgggg ttgctggaa cagtctccgt   6660
gggaatcttc ttcgtcttga tgaggaacaa gggcataggg aagatgggct ttggaatggt   6720
gactcttggg gccagcgcat ggctcatgtg gctctcggaa attgagccag ccagaattgc   6780
atgtgtcctc attgttgtgt tcctattgct ggtggtgctc taccctgagc cagaaaagca   6840
aagatctccc caggacaacc aaatggcaat catcatcatg gtagcagtag gtcttctggg   6900
cttgattacc gccaatgaac tcggatggtt ggagagaaca aagagtgacc taagccatct   6960
aatgggaagg agagaggagg gggcaaccat aggattctca atggacattg acctgcggcc   7020
agcctcagct tgggccatct atgctgcctt gacaactttc attaccccag ccgtccaaca   7080
tgcagtgacc acctcataca acaactactc cttaatggcg atgccacgc aagctggagt   7140
gttgtttggc atgggcaaag gatgccatt ctacgcatgg gactttggag tccgctgct   7200
aatgataggt tgctactcac aattaacacc cctgaccctc tcattttgct   7260
cgtggcgcac tacatgtact tgatcccagg gctgcaggca gcagctgcgc gtgctgccca   7320
gaagagaacg gcagctggca tcatgaagaa ccctgttgtg gatggaatag tggtgactga   7380
cattgacaca atgacaattg accccaagt ggagaaaaag atgggacagg tgctactcat   7440
agcagtagcc gtcccagcg ccatactgtc gcggaccgcc tggggtggg gggaggctgg   7500
ggctctgatc acagccgcaa cttccacttt gtgggaaggc tctccgaaca agtactggaa   7560
```

```
ctcctctaca gccacttcac tgtgtaacat ttttagggga agttacttgg ctggagcttc   7620
tctaatctac acagtaacaa gaaacgctgg cttggtcaag agacgtgggg gtggaacagg   7680
agagaccctg ggagagaaat ggaaggcccg cttgaaccag atgtcggccc tggagttcta   7740
ctcctacaaa aagtcaggca tcaccgaggt gtgcagagaa gaggcccgcc gcgccctcaa   7800
ggacggtgtg gcaacgggag gccatgctgt gtcccgacga agtgcaaagc tgagatggtt   7860
ggtggagcgg ggatacctgc agccctatgg aaaggtcatt gatcttggat gtggcagagg   7920
gggctggagt tactacgtcg ccaccatccg caaagttcaa gaagtgaaag gatacacaaa   7980
aggaggccct ggtcatgaag aacccgtgtt ggtgcaaagc tatgggtgga acatagtccg   8040
tcttaagagt ggggtggacg tcttttcatat ggcggctgag ccgtgtgaca cgttgctgtg   8100
tgacataggt gagtcatcat ctagtcctga agtggaagaa gcacggacgc tcagagtcct   8160
ctccatggtg ggggattggc ttgaaaaaag accaggagcc ttttgtataa aagtgttgtg   8220
cccatacacc agcactatga tggaaaccct ggagcgactg cagcgtaggt atgggggagg   8280
actggtcaga gtgccactct cccgcaactc tacacatgag atgtactggg tctctggagc   8340
gaaaagcaac accataaaaa gtgtgtccac cacgagccag ctcctcttgg ggcgcatgga   8400
cgggcctagg aggccagtga aatatgagga ggatgtgaat ctcggctctg gcacgcgggc   8460
tgtggtaagc tgccgctgaag ctcccaacat gaagatcatt ggtaaccgca ttgaaaggat   8520
ccgcagtgag cacgcggaaa cgtggttctt tgacgagaac cacccatata ggacatgggc   8580
ttaccatgga agctatgagg ccccccacaca agggtcagcg tcctctctaa taaacggggt   8640
tgtcaggctc ctgtcaaaac cctgggatgt ggtgactgga gtcacaggaa tagccatgac   8700
cgacaccaca ccgtatggtc agcaaagagt tttcaaggaa aaagtggaca ctagggtgcc   8760
agaccccaa gaaggcactc gtcaggttat gagcatggtc tcttcctggt tgtgaaaga    8820
gctaggcaaa cacaaacggc cacgagtctg caccaaagaa gagttcatca acaaggttcg   8880
tagcaatgca gcattagggg caatatttga agaggaaaaa gagtggaaga ctgcagtgga   8940
agctgtgaac gatccaaggt tctgggctct agtggacaag gaaagagagc accacctgag   9000
aggagagtgc cagagctgtg tgtacaacat gatgggaaaa agagaaaaga aacaagggga   9060
atttggaaag gccaagggca gccgcgccat ctggtatatg tggctagggg ctagatttct   9120
agagttcgaa gcccttggat tcttgaacga ggatcactgg atggggagag agaactcagg   9180
aggtggtgtt gaagggctgg gattacaaag actcggatat gtcctagaag agatgagtcg   9240
tataccagga ggaaggatgt atgcagatga cactgctggc tgggacaccc gcattagcag   9300
gtttgatctg gagaatgaag ctctaatcac caaccaaatg gagaaaggcc acagggcctt   9360
ggcattggcc ataatcaagt acacatacca aaacaaagtg gtaaaggtcc ttagaccagc   9420
tgaaaaaggg aaaacagtta tggacattat ttcgagacaa gaccaaaggg ggagcggaca   9480
agttgtcact tacgctctta acacatttac caacctagtg gtgcaactca ttcggaatat   9540
ggaggctgag gaagttctag agatgcaaga cttgtggctc ctgcggaggt cagagaaagt   9600
gaccaactgg ttgcagagca acggatggga taggctcaaa cgaatggcag tcagtggaga   9660
tgattgcgtt gtgaagccaa ttgatgatag gtttgcacat gccctcaggt tcttgaatga   9720
tatgggaaaa gttaggaagg acacacaaga gtggaaaccc tcaactggat gggacaactg   9780
ggaagaagtt ccgttttgct cccaccactt caacaagctc catctcaagg acgggaggtc   9840
cattgtggtt ccctgccgcc accaagatga actgattggc cgggcccgcg tctctccagg   9900
ggcgggatgg agcatccggg agactgcttg cctagcaaaa tcatatgcgc aaatgtggca   9960
gctcctttat ttccacagaa gggacctccg actgatggcc aatgccattt gttcatctgt  10020
gccagttgac tgggttccaa ctgggagaac tacctggtca atccatggaa agggagaatg  10080
gatgaccact gaagacatgc ttgtggtgtg gaacagagtg tggattgagg agaacgacca  10140
catgaagac aagaccccag ttacgaaatg gacagacatt ccctatttgg gaaaaaggga  10200
agacttgtgg tgtggatctc tcataggggca cagaccgcgc accacctggg ctgagaacat  10260
taaaaacaca gtcaacatgg tgcgcaggat cataggtgat gaagaaaagt acatggacta  10320
cctatccacc caagttcgct acttgggtga agaagggtct acggtgtaagc              10380
accaatctta atgttgtcag gcctgctagt cagccacagc ttggggaaag ctgtgcagcc  10440
tgtgacccc ccaggagaag ctgggaaacc aagcctatag tcaggccgag aacgccatgg   10500
cacggaagaa gccatgctgc ctgtgagccc tcagaggac actgagtcaa aaaccccac   10560
gcgcttggag gcgcaggatg ggaaaagaag gtggcgacct tccccaccct tcaatctggg  10620
gcctgaactg gagatcagct gtggatctcc agaagaggga ctagtggtta gagga       10675
```

SEQ ID NO: 5        moltype = DNA   length = 10676
FEATURE               Location/Qualifiers
source                1..10676
                       mol_type = genomic DNA
                       organism = Zika virus
SEQUENCE: 5

```
gttgttactg ttgctgactc agactgcgac agttcgagtt tgaagcgaaa gctagcaaca     60
gtatcaacag gttttatttg gatttggaaa cgagagtttc tggtcatgaa aaacccaaaa    120
aagaaatccg gaggattccg gattgtcaat atgctaaaac gcggagtagc ccgtgtgagc    180
cccttggg gcttgaagag gctgccagcc ggacttctgc tgggtcatgg gcccatcagg      240
atggtcttgg caattctagc ctttttgaga ttcacgacaa tcaagccatc actgggtctc    300
atcaatagat ggggttcagt ggggaaaaaa gaggctatgg aaataataaa gaagttcaag    360
aaagatctgg ctgccatgct gagaataatc aatgctagga aggagaagaa gagacgaggc    420
gcagatacta gtgtcggaat tgttggcctc tgctgaccca gctatggc agcggaggtc      480
actagacgtg ggagtgcata ctatatgtac ttggacagaa acgatgctgg ggaggccaca    540
tcttttccaa ccacattggg gatgaataag tgttatataac agatcatgaa tcttggacac    600
atgtgtgatg ccaccatgag ctatgaatgc cctatgctgg atgaggggt ggaaccagat     660
gacgtcgatt gttggtgcaa cacgacgtca acttgggttg tgtacggaac ctgccatcac    720
aaaaagggtt aagcacggag atctagaaga gctgtgacgc tcccctccca ttccactagg    780
aagctgcaaa cgcggtcgca aacctggttg gaatcaagag aatacacaaa gcacttgatt    840
agagtcgaaa attggatatt caggaaccct ggcttcgcgt tagcagcgac tgccatcgct    900
tggcttttgg gaagctcaac gagccaaaaa gtcatatact tggtcatgat actgctgatt    960
gccccggcat acagcatcag gtgcatagga gtcagcaata gggactttgt ggaaggtatg   1020
tcaggtggga cttgggttga tgttgtcttg gaacatggag gttgtgtcac cgtaatggca   1080
caggacaaac cgactgtcga catagagctg gttacaacaa cagtcagcaa catggcggag   1140
gtaagatcct actgctatga ggcatcaata tcagacatgg cttcggacag ccgctgccca   1200
```

```
acacaaggtg aagcctacct tgacaagcaa tcagacactc aatatgtctg caaaagaacg 1260
ttagtggaca gaggctgggg aaatggatgt ggacttttg gcaaagggag tctggtgaca 1320
tgcgctaagt ttgcatgctc caagaaaatg accgggaaga gcatccagcc agagaatctg 1380
gagtaccgga taatgctgtc agttcatggc tcccagcaca gtgggatgat cgttaatgac 1440
acaggacatg aaactgatga gaatagagcg aaggttgaga taacgcccaa ttcaccaaga 1500
gccgaagcca ccctgggggg ttttggaagc ctaggacttg attgtgaacc gaggacaggc 1560
cttgactttt cagatttgta ttacttgact atgaataaca agcactggtt ggttcacaag 1620
gagtggttcc acgacattcc attaccttgg cacgctgggg cagacaccgg aactccacac 1680
tggaacaaca aagaagcact ggtagagttc aaggacgcac atgccaaaag gcaaactgtc 1740
gtggttctag ggagtcaaga aggagcagtt cacacggccc ttgctggagc tctggaggct 1800
gagatggatg gtgcaaaggg aaggctgtcc tctggccact tgaaatgtcg cctgaaaatg 1860
gataaactta gattgaaggg cgtgtcatac tccttgtgta ccgcagcgtt cacattcacc 1920
aagatcccgg ctgaaacact gcacgggaca gtcacagtgg aggtacagta cgcagggaca 1980
gatggacctt gcaaggttcc agctcagatg gcggtggaca tgcaaactct gaccccagtt 2040
gggaggttga taaccgctaa ccccgtaatc actgaaagca ctgagaactc taagatgatg 2100
ctggaacttg atccaccatt tggggactct tacattgtca taggagtcgg ggagaagaag 2160
atcacccacc actggcacag gagtggcagc accattggaa aagcatttga agccactgtg 2220
agaggtgcca agagaatggc agtcttggga gacacagcct gggactttgg atcagttgga 2280
ggcgctctca actcattggg caagggcatc catcaaattt ttggagcagc tttcaaatca 2340
ttgtttggag gaatgtcctg gttctcacaa attctcattg gaacgttgct gatgtggttg 2400
ggtctgaaca caaagaatgg atctatttcc cttatgtgct tggccttagg gggagtgttg 2460
atcttcttat ccacagccgt ctctgctgat gtgggggtgc ggttggactt ctcaaagaag 2520
gagacgagat gcggtacagg ggtgttcgtc tataacgacg ttgaagcctg gagggacagg 2580
tacaagtacc atcctgactc cccccgtaga ttggcagcag cagtcaagca agcctgggaa 2640
gatggtatct gcgggatctc ctctgtttca agaatgcgaaa acatcatgtg gagatcagta 2700
gaaggggagc tcaacgcaat cctggaagag aatggagttc aactgaccgt cgttgtggga 2760
tctgtaaaaa accccatgtg gagaggtcca cagagattgc ccgtgcctgt gaacgagctg 2820
ccccacggct ggaaggcttg ggggaaatcg cacttcgtca gagcagcaaa gacaaataac 2880
agctttgtcg tggatggtga cactgaag gaatgcccac tcaaacatag gcatggaac 2940
agctttcttg tggaggatca tgggttcggg gtatttcaca ctagtctgtcg gctcaaggtt 3000
agagaagatt attcattaga gtgtgatcca gccgttattg gaacagctgt taagggaaag 3060
gaggctgtac acagtgatct aggctactgg attgagagtg agaagaatga cacatggagg 3120
ctgaagaggg cccatctgat cgagatgaaa acatgtgaat ggccaaagtc ccacacattg 3180
tggacagatg gaatagaaga gagtgatctg atcatcccca agtcttttagc tgggccactc 3240
agccatcaca ataccagaga gggctacagg acccaaatga aaggccatg gcacagtgaa 3300
gagcttgaaa ttcggtttga ggaatgccca ggcactaagg tccacgtgga ggaaacatgt 3360
ggaacaagag gaccatctct gagatcaacc actgcaagcg gaagggtgat cgaggaatgc 3420
tgctgcaggg agtgcacaat gccccactg tcgttccggg ctaagatgg ctgttggtat 3480
ggaatggaga taaggcccag gaaagaacca gaaagcaact tagtaaggtc aatggtgact 3540
gcaggatcaa ctgatcacat ggatcacttc tcccttggag tgcttgtgat tctgctcatg 3600
gtgcaggaag ggctgaagaa gagaatgacc acaaagatca tcataagcac atcaatggca 3660
gtgctggtag ctatgatcct gggaggattt tcaatgagtg acctggctaa gcttgcaatt 3720
ttgatggtg ccaccttcgc ggaaatgaac actggaggag atgtagctca tctggcgctg 3780
atagcggcat tcaaagtcag accagcgttg ctggtatctt tcatcttcag agctaattgg 3840
acaccccgtg aaagcatgct gctggccttg gcctcgtgtc ttttgcaaac tgcgatctcc 3900
gccttggaag gcgacctgat ggttctcatc aatggttttg ctttgcctg gttggcaata 3960
cgagcgatgg ttgttccacg cactgataac atcacccttg caatcctgc tgctctgaca 4020
ccactggccc ggggcacact gcttgtggcg tggagagcag gccttgctac ttgcgggggg 4080
tttatgctcc tctctctgaa gggaaaaggc agtgtgaaga gaacttacc atttgtcatg 4140
gccctgggac taaccgctgt gaggctggtc gaccccatca acgtggtggg gctgctgttg 4200
ctcacaagga gtgggaagcg gagctggccc cctagcgaag tactcacagc tgttggcgta 4260
atatgcgcat tggctggagg gttcgccaag gcagatatag agatggctgg gcccatggcc 4320
gcggtcggtc tgctaattgt cagttacgtg gtctcaggaa agagtgtgga catgtacatt 4380
gaaagagcag gtgacatcac atgggaaaaa gatgcggaag tcactggaaa cagtcccgg 4440
ctcgatgtgg cgctagatga gagtggtgat ttctcctgt ggaggatga cggtcccccc 4500
atgagagaga tcatactcaa ggtggtcctg atgaccatct gtggcatgaa cccaatagcc 4560
ataccctttg cagctggagc gtggtacgta tacgtgaaga ctggaaaaag gagtggtgct 4620
ctatgggatg tgcctgctcc caaggaagta aaaaggggg agaccacaga tggagtgtac 4680
agagtaatga ctcgtagact gctaggttca acacaagttg gagtgggagt tatgcaagag 4740
ggggtctttc acactatgtg gcacgtcaca aaaggatccg cgctgagaag cggtgaaggg 4800
agacttgatc catactgggg agatgtcaag caggatctgg tgtcatactg tggtccatgg 4860
aagctagatg ccgcctggga cgggcacagc gaggtcagc tcttggccgt gccccccgga 4920
gagagagcga ggaacatcca gactctgccc ggaatattta agacaaagga tggggacatt 4980
ggagcggttg cgctggatta cccagcagga acttcaggat ctccaatcct agacaagtgt 5040
gggagagtga taggacttta tggcaatggg gtcgtgatca aaaatgggag ttatgttagt 5100
gccatcaccc aagggaggag ggaggaagag actcctgttg agtgcttcga gccttcgatg 5160
ctgaagaaga agcagctaac tgtcttagac ttgcatcctg agctgggaa aaccaggaga 5220
gttcttcctg aaaatagtcg tgaagccata aaaaacaagac tccgtactgt gatcttagct 5280
ccaaccaggg ttgtcgctgc tgaaatggag gaagcccta gagggcttcc agtgcgttat 5340
atgacaacag cagtcaatgt cacccactct ggaacagaaa tcgtcgactt aatgtgccat 5400
gccaccttca cttcacgtct actacagcca atcagagtcc caactataa tctgtatatt 5460
atggatgagg cccacttcac agatcccctca agtatagcag caagaggata catttcaaca 5520
agggttgaga tgggcgaggc ggctgccatc ttcatgaccg ccacgccacc aggaaccccgt 5580
gacgcatttc cggactccaa ctcaccaatt atggacaccg aagtgaagt cccagagaga 5640
gcctggagct caggctttga ttgggtgacg gattattctg gaaaaacagt ttggtttgtt 5700
ccaagcgtga ggaacggcaa tgagatcgca gcttgtctga caaaggctgg aaaacgggtc 5760
atacagctca gcaaaagac ttttgagaca gagttccaga aaacaaaaca tcaagagtgg 5820
gactttgtcg tgacaactga catttcagag atgggcgcca actttaaagc tgaccgtgtc 5880
atagattcca ggagatgcct aaagccggtc atacttgatg gcgagagagt cattctggct 5940
```

```
ggacccatgc ctgtcacaca tgccagcgct gcccagagga gggggcgcat aggcaggaat    6000
cccaacaaac ctggagatga gtatctgtat ggaggtgggt gcgcagagac tgacgaagac    6060
catgcacact ggcttgaagc aagaatgctc cttgacaata tttacctcca agatggcctc    6120
atagcctcgc tctatcgacc tgaggccgac aaagtagcag ccattgaggg agagttcaag    6180
cttaggacgg agcaaaggaa gacctttgtg gaactcattga aaagaggaga tcttcctgtt    6240
tggctggcct atcaggttgc atctgccgga ataacctaca cagatagaag atggtgcttt    6300
gatggcacga ccaacaacac cataatggaa gacagtgtgc cggcagaggt gtggaccaga    6360
cacggagaga aaagagtgct caaaccgagg tggatggacg ccagagtttg ttcagatcat    6420
gcggccctga agtcattcaa ggagtttgcc gctgggaaaa gaggagcggc ttttggagtg    6480
atggaagccc tgggaacact gccaggacac atgacagaga gattccagga agccattgac    6540
aacctcgctg tgctcatgcg ggcagagact ggaagcaggc cttacaaagc cgcggcggcc    6600
caattgccgg agaccctaga gaccattatg cttttgggt tgctgggaac agtctcgctg    6660
ggaatctttt tcgtcttgat gaggaacaag ggcatagga agatgggctt tggaatggtg    6720
actcttgggg ccagcgcatg gctcatgtgg ctctcggaaa ttgagccagc cagaattgca    6780
tgtgtcctca ttgttgtgtt cctattgctg gtggtgctca tacctgagcc agaaaagcaa    6840
agatctcccc aggacaacca aatgcaatc atcatcatgg tagcagtagg tcttctgggc    6900
ttgattaccg ccaatgaact cggatggttg agagaacaa agagtgacct aagccatcta    6960
atgggaagga gagggaggg ggcaaccatg ggattctcaa ttgacattga cctgcggcca    7020
gcctcagctt gggccatcta tgctgccttg acaactttca ttaccccagc cgtccaacat    7080
gcagtcagcc acttcatacaa caactactc ttaatggcga tggccacgca agctggagtg    7140
ttgtttggta tgggcaaagg gatgccatte tacgcatggg actttggagt cccgctgcta    7200
atgatagttt gctactcaca attaacgccc ctgacctaa tagtgccat cattttgctc    7260
gtggcgcact acatgtactt gatcccaggg ctgcaggcag cagctgcgcg tgctgcccag    7320
aagagaacgg cagctggcat catgaagaac cctgttgtgg atggaatagt ggtgactgac    7380
attgacacaa tgacaattga ccccccaagtg agaaaaaga tgggacaggt gctactcatg    7440
gcagtagccg tctccagcgc catactgtcg cggaccgcct gggggtgggg ggaggctggg    7500
gccctgatca cagccgcaac ttccacttg tgggaaggct ctccgaacaa gtactggaac    7560
tcctctacag ccacttcact gtgtaacatt tttaggggaa gttacttggc tggagcttct    7620
ctaatctaca cagtaacaag aaacgctggc ttggtcaaga gacgtggggg tggaacagga    7680
gagacctgg gagagaaatg gaaggcccgc ttgaaccaga tgtcggccct ggagttctac    7740
tcctacaaaa agtcaggcat caccgaggtg tgcagagaa aggcccgccg cgccctcaag    7800
gacggtgtgg caacgggagg ccatgctgtg tcccgaggaa gtgcaaagct gagatggttg    7860
gtggagcggg gatacctgca gcctatgga aaggtcattg atcttggatg tggcagaggg    7920
ggctggagtt actacgccgc caccatccgc aaagttcaag aagtgaaagg atacacaaaa    7980
ggaggccctg gtcatgaaga accgtgttg gtgcaaagct atgggtggaa catagtccgt    8040
cttaagagtg gggtggacgt cttttcatatg gcgctgagc cgtgtgacac gttgctgtgt    8100
gacatagtg agtcatcatc tagtcctgaa gtggaagaag cacggacgct cagagtcctc    8160
tccatggtgg gggattggct tgaaaaaaga ccaggagcct tttgtataaa agtgttgtgc    8220
ccatacacca gcactatgat ggaaaccctg agcgactgc agcgtaggta tgggggagga    8280
ctggtcagag tgccactctc ccgcaactct acacatgaca tgtactgggt ctctggagcg    8340
aaaagcaaca ccataaaag tgtgtccacc acgagccagc tcctcttggg gcgcatggac    8400
gggcctagga ggccagtgaa atatgaggag atgtgtaatc tcggctctgg cacgcgggct    8460
gtggtaagct gcgctgaagc tcccaacatg aagatcattg gtaaccgcat tgaaaggtc    8520
cgcagtgagc acgcggaaac gtggttcttt gacgagaacc acccatatag gacatgggct    8580
taccatggaa gctatgaggc cccacacaca gggtcagcgt cctctctaat aaacggggtt    8640
gtcaggctcc tgtcaaaacc ctgggatgtg gtgactgag tcacaggaat agccatgacc    8700
gacaccacac cgtatggtca gcaaagagtt ttcaaggaaa aagtggacac tagggtgcca    8760
gacccccaag aaggcactcg tcaggttatg gcatggtct cttcctggtt gtggaaagag    8820
ctaggcaaac acaaacggcc acgagtctgt accaaagaag agttcatcaa caaggttcgt    8880
agcaatgcag cattagggc aatatttgaa gaggaaaaag agtggaagac tgcagtgaa    8940
gctgtgaacg atccaagtt ctgggctcta gtggacaaag aagagagca ccacctgaca    9000
ggagagtgcc agagttgtgt gtacaacatg atgggaaaa gagaaaagaa acaaggggaa    9060
tttgaaaagg ccaagggcag ccgcgccatc tggtatatgt ggctaggggc tagatttcta    9120
gagttcgaag cccttggatt cttgaacgag atcactggga tggggagaga gaactcagga    9180
ggtggtttg aagggctggg attacaaaga ctcggatatg tcctagaaga gatgagtcgc    9240
ataccaggag gaaggatgta tgcagatgac actgctggct gggacaccg catcagcagg    9300
tttgatctgg agaatgaagc tctaatcacc aaccaaatgg agaaagggca cagggccttg    9360
gcattggcca taatcaagta cacataccaa aacaaagtgg taaaggtcct tagaccagct    9420
gaaaaaggga agacagttat ggacattatt cgagacaag accaaagggg gagcggacaa    9480
gttgtcactt acgctcttaa cacatttacc aacctagtgg tgcaactcat tcggaatatg    9540
gaggctgagg aagttctaga gatgcaagac ttgtggctgc tgcggaggtc agagaaagtg    9600
accaactggt tgcagagcaa cggatggat aggctcaaac gaatggcagt cagtggagat    9660
gattgcgttg tgaagccaat tgatgatagg tttgcacatg ccctcaggtt cttgaatgat    9720
atggggaaag ttaggaagga cacacaagag tggaaaccct ggcttggtgg gcaggaatgg    9780
gaagaagttc cgttttgctc ccaccactt aacaagctcc atctcaagga cgggaggtcc    9840
attgtggttc cctgccgcca ccaagatgaa ctgattggcc gggcccgcgt ctctccaggg    9900
gcgggatgga gcatccggga gactgcttgc ctagcaaaat catatgcgca aatgtggcag    9960
ctcctttatt tccacagaag ggacctccga ctgatgccca atgccatttg ttcatctgtg   10020
ccagttgact gggttccaac tgggagaact acctggtcaa tccatggaaa gggagaatgt   10080
atgaccactg aagacatgct tgtggtgtgg aacagagtgt ggattgagga gaacgaccac   10140
atggaagaca gaccccagt tacgaaatgg acagacattc cctatttggg aaaaagggaa   10200
gacttgtggt gtgatctct catagggcac agaccgcgca ccacctgggc tgagaacatt   10260
aaaaacacag tcaacatggt gcgcaggatc ataggtgatg aagaaagta catggactac   10320
ctatccacc aagttcgcta cttgggtgaa gagggtctca catggtgaaca   10380
ccaatcttaa tgttgtcagg cctgctagtc agccacagct tggggaaagc tgtgcagcct   10440
gtgaccccc caggagaagc tgggaaacca agcctatagt caggccgaga acgccatggc   10500
acggaagaag ccatgctgcc tgtgagcccc tcagaggaca ctgagtcaaa aaccccacg   10560
cgcttggagg cgcaggatgg gaaaagaagg tggcgacctt ccccacccct caatctgggg   10620
cctgaactgg agatcagctg tggatctcca gaagagggac tagtggttag aggaga       10676
```

-continued

```
SEQ ID NO: 6            moltype = DNA  length = 10808
FEATURE                 Location/Qualifiers
source                  1..10808
                        mol_type = genomic DNA
                        organism = Zika virus
SEQUENCE: 6
agttgttgat ctgtgtgaat cagactgcga cagttcgagt ttgaagcgaa agctagcaac  60
agtatcaaca ggttttattt tggatttgga aacgagagtt tctggtcatg aaaaacccaa  120
aaaagaaatc cggaggattc cggattgtca atatgctaaa acgcggagta gcccgtgtga  180
gcccctttgg gggcttgaag aggctgccag ccggacttct gctgggtcat gggcccatca  240
ggatggtctt ggcaattcta gcctttttga gattcacggc aatcaagcca tcactgggtc  300
tcatcaatag atggggttca gtggggaaaa aagaggctat ggaaataata aagaagttca  360
agaaagatct ggctgccatg ctgagaataa tcaatgctag gaaggagaag aagagacgag  420
gcgcagatac tagtgtcgga attgttggcc tcctgctgac cacagctatg gcagcggagg  480
tcactagacg tgggagtgca tactatatgt acttggacag aaacgatgct ggggaggcca  540
tatcttttcc aaccacattg gggatgaata agtgttatat acagatcatg gatcttggac  600
acatgtgtga tgccaccatg agctatgaat gccctatgct ggatgagggg gtggaaccag  660
atgacgtcga ttgttggtgc aacacgacgt caacttgggt tgtgtacgga acctgccatc  720
acaaaaaagg tgaagcacgg agatctagaa gagctgtgac gctcccctcc cattccacta  780
ggaagctgca aacgcggtcg caaacctggt tggaatcaag agaatacaca aagcacttga  840
ttagagtcga aaattggata ttcaggaacc ctggcttcgc gttagcagca gctgccatcg  900
cttggctttt gggaagctca acgagccaaa aagtcatata cttggtcatg atactgctga  960
ttgccccggc atacagcatc aggtgcatag gagtcagcaa tagggacttt gtggaaggta  1020
tgtcaggtgg gacttgggtt gatgttgtct tggaacatgg aggttgtgtc accgtaatgg  1080
cacaggacaa accgactgtc gacatagagc tggttacaac aacagtcagc aacatggcgg  1140
aggtaagatc ctactgctat gaggcatcaa tatcagacat ggcttcggac agccgctgcc  1200
caacacaagg tgaagcctac cttgacaagc aatcagacac tcaatatgtc tgcaaaagaa  1260
cgttagtgga cagaggctgg ggaaatggat gtggactttt tggcaaaggg agcctggtga  1320
catgcgctaa gtttgcatgc tccaagaaaa tgaccgggaa gagcatccag ccagagaatc  1380
tggagtaccg gataatgctg tcagttcatg gctcccagca cagtgggatg atcgttaatg  1440
acacaggaca tgaaactgat gagaatagag cgaaggttga gataacgccc aattcaccaa  1500
gagccgaagc caccctgggg ggttttggaa gcctaggact tgattgtgaa ccgaggacag  1560
gccttgactt ttcagatttg tattacttga ctatgaataa caagcactgg ttggtccaca  1620
aggagtggtt ccacgacatt ccattacctt ggcacgctgg ggcagacacc ggaactccac  1680
actggaacaa caaagaagca ctggtagagt tcaaggacgc acatgccaaa aggcaaactg  1740
tcgtggttct agggagtcaa gaaggagcag ttcacacggc ccttgctgga gctctggagg  1800
ctgagatgga tggtgcaaag ggaaggctgt cctctggcca cttgaaatgt cgcctgaaaa  1860
tggataaact tagattgaag ggcgtgtcat actccttgtg taccgcagcg ttcacattca  1920
ccaagatccc ggctgaaaca ctgcacggga cagtcacagt ggaggtacag tacgcaggga  1980
cagatggacc ttgcaaggtt ccagctcaga tggcggtgga catgcaaact ctgaccccag  2040
ttgggaggtt gataaccgct aaccccgtaa tcactgaaag cactgagaac tctaagatga  2100
tgctggaact tgatccacca tttggggact cttacattgt cataggagtc ggggagaaga  2160
agatcaccca ccactggcac aggagtggca gcaccattgg aaaagcattt gaagccactg  2220
tgagaggtgc caagagaatg gcagtcttgg gagacacagc ctgggacttt ggatcagttg  2280
gaggcgctct caactcattg ggcaagggca tccatcaaat ttttggagca gctttcaaat  2340
cattgtttgg aggaatgtcc tggttctcac aaatcctcat tggaacgttg ctgatgtggt  2400
tgggtctgaa cacaaagaat ggatctattt cccttatgtg cttggcctta ggggggagtgt  2460
tgatcttctt atccacagcc gtctctgctg atgtggggtg ctcggtggac ttctcaaaga  2520
aggagacgag atgcggtaca ggggtgttcg tctataacga cgttgaagcc tggagggaca  2580
ggtacaagta ccatcctgac tccccccgta gattggcagc agcagtcaag caagcctggg  2640
aagatggtat ctgcgggatc tcctctgttt caagaatgga gaacatcatg tggagatcag  2700
tagaaggggga gctcaacgca atcttggaag agaatggagt tcaactgacg gtcgttgtgg  2760
gatctgtaaa aaaccccatg tggagaggtc cacagagatt gcccgtgcct gtgaacgagc  2820
tgccccacgg ctggaaggct tgggggaaat cgtacttcgt cagagcagca aagacaaata  2880
acagctttgt cgtggatggt gacacactga aggaatgccc actcgaacat agagcatgga  2940
acagctttct tgtggaggat catgggttcg ggtatttcca cactagtgtc tggctcaagg  3000
ttagagaaga ttattcatta gagtgtgatc cagccgttat tggaacagct gttaagggga  3060
aggaggctgt acacagtgat ctaggctact ggattgagag tgagaagaat gacacatgga  3120
ggctgaagag ggcccatcta atcgagatga aaacatgtga atggccaaag tcccacacat  3180
tgtgggcaga tggaatagaa gagagtgatc tgatcattcc caagtcttta gctgggccac  3240
tcagccatca caataccaga gagggctaca ggacccaaat gaaagggcca tggcacagtg  3300
aagagcttga aattcggttt gaggaatgcc cgggcactaa ggtccacgtg gaggaaacat  3360
gtggaacaag aggaccatct ctgagatcaa ccactgcaag cggaagggtg atcgaggaat  3420
ggtgctgcag ggagtgcaca atgcccccac tgtcgttccg ggctaaagat ggctgttggt  3480
atggaatgga gataaggccc aggaaagaac cagaaagcaa cttagtaagg tcagtggtga  3540
ctgcaggatc aactgatcac atggatcact tctcccttgg agtgcttgtg attctgctca  3600
tggtgcagga agggctgaag aagagaatga ccacaaagat catcataagc acatcaatgg  3660
cagtgctggt agctatgatc ctgggaggat tttcaatgag tgacctggct aagcttgcaa  3720
ttttgatggg cgccaccttc gcggaaatga acactggagg agatgtagct catctggcgc  3780
tgatagcggc attcaaagtc agaccagcgt tgctggtatc tttcatcttc agagctaatt  3840
ggacaccccg tgaaagcatg ctgctggcct tggcctcgtg tcttttgcaa actgcgatct  3900
ccgccttgga aggcgacctg atggttctca tcaatggttt tgctttggcc tggttggcaa  3960
tacgagcgat ggttgttcca cgcactgata acatcacctt ggcaatcctg gctgctctga  4020
caccactggc ccggggcaca ctgcttgtgg cgtggagagc aggccttgct acttgcgggg  4080
ggtttatgct cctctctctg aagggaaaag gcagtgtgaa gaagaactta ccatttgtca  4140
tggccctggg actaaccgct gtgaggctgg tcgaccccat caacgtggtg ggactgctgt  4200
tgctcacaag gagtgggaag cggagctggc cccctagcga agtactcaca gctgttggcc  4260
tgatatgcgc attggctgga gggttcgcca aggcagatat agagatggct gggcccatgg  4320
```

```
ccgcggtcgg tctgctaatt gtcagttacg tggtctcagg aaagagtgtg gacatgtaca 4380
ttgaaagagc aggtgacatc acatgggaaa aagatgcgga agtcactgga aacagtcccc 4440
ggctcgatgt ggcgctagat gagagtggtg atttctccct ggtggaggat gacggtcccc 4500
ccatgagaga gatcatactc aaggtggtcc tgatgaccat ctgtggcatg aacccaatag 4560
ccataccctt tgcagctgga gcgtggtacg tatacgtgga gactggaaaa aggagtggtg 4620
ctctatggga tgtgcctgct cccaaggaag taaaaaaggg ggagaccaca gatggagtgt 4680
acagagtaat gactcgtaga ctgctaggtt caacacaagt tggagtggga gttatgcaag 4740
aggggggtctt tcacactatg tggcacgtca caaaaggatc cgcgctgaga agcggtgaag 4800
ggagacttga tccatactgg ggagatgtca agcaggatct ggtgtcatac tgtggtccat 4860
ggaagctaga tgccgcctgg gacgggcaca gcgaggtgca gctcttggcc gtgcccccg 4920
gagagagagc gaggaacatc cagactctgc ccggaatatt taagacaaag gatgggggaca 4980
ttggagcggt tgcgctggat tacccagcag gaacttcagg atctccaatc ctagacaagt 5040
gtgggagagt gataggactt tatggcaatg gggtcgtgat caaaaatggg agttatgtta 5100
gtgccatcac ccaagggagg agggaggaag agactcctgg gttgcttc gagccttcga 5160
tgctgaagaa gaagcagcta actgtcttag acttgcatcc tggagctggg aaaaccagga 5220
gagttcttcc tgaaatagtc cgtgaagcca taaaaacaag actccgtact gtgatcttag 5280
ctccaaccag ggttgtcgct gctgaaatgg aggaagccct tagagggctt ccagtgcgtt 5340
atatgacaac agcagtcaat gtcacccact ctggaacaga aatcgtcgac ttaatgtgcc 5400
atgccacctt cacttcacgt ctactacagc caatcagagt ccccaactat aatctgtata 5460
ttatggatga ggcccacttc acagatccct caagtatagc agcaagagga tacatttcaa 5520
caagggttga tgggcgag gcggctgcca tcttcatgac cgccacgcca ccaggaaccc 5580
gtgacgcatt tccggactcc aactcaccaa ttatggacaa cgaagtggaa gtcccagaga 5640
gagcctggag ctcaggcttt tgattgggtga cggatcattc tggaaaaaca gtttggttg 5700
ttccaagcgt gaggaacggc aatgagatcg cagcttgtct gacaaaggct ggaaaacggg 5760
tcatacagct cagcagaaag acttttgaga cagagttcca gaaaacaaaa catcaagagt 5820
gggactttgt cgtgacaact gacatttcag agatgggtgc caacttttaaa gctgaccgtg 5880
tcatagattc caggagatgc ctaaagccgg tcatacttga tggcgagaga gtcattttgg 5940
ctggacccat gcctgtcaca catgccagcg ctgcccagag gaggggggcgc ataggcagga 6000
atcccaacaa acctggagat gagtatctgt atggaggtgg gtgcgcagag actgacgaag 6060
accatgcaca ctggcttgaa gcaagaatgc tccttgacaa tatttaacctc caagatgcgt 6120
tcatagcctc gctctatcga cctgaggccg acaaagtagc agccattgag ggagagttca 6180
agcttaggac ggagcaaagg aagaccttttg tggaactcat gaaaagagga gatcttcctg 6240
tttggctggc ctatcaggtt gcatctgccg gaataaccta cacagataga agatggtgct 6300
ttgatggcac gaccaacaac accataatgg aagacagtgt gccggcagag gtgtggacca 6360
gacacggaga gaaagagtg ctcaaaccga ggtggatgga cgccagagtt tgttcagatc 6420
atgcggccct gaagtcattc aaggagtttg ccgctgggaa aagaggagcg gcttttggag 6480
tgatggaagc cctgggaaca ctgccaggac acatgacaga gagattccag gaagccattg 6540
acaacctcgc tgtgctcatg cgggcagaga ctggaagcag gccttacaaa gccgcggcgg 6600
cccaattgcc ggagaccta gagaccatta tgcttttggg gttgctggga acagtctcgc 6660
tgggaatctt tttcgtcttg atgaggaaca agggcatagg gaagatgggc tttggaatgg 6720
tgactcttgg ggcagcgca tggctcatgt ggctctcgga aattgagcca gccagaattg 6780
catgtgtcct cattgttgtg ttcctattgc tggtggtgct catacctgag ccagaaaagc 6840
aaagatctcc ccaggacaac caaatggcaa tcatcatcat ggtagcagta ggtcttctgg 6900
gcttgattac cgccaatgaa ctcggatggt tggagagaac aaaaagtgac ctaagccatc 6960
taatgggaag gagagaggag ggagcaacca taggattctc aatggacatt gacctgcggc 7020
cagcctcagc ttgggccatc tatgctgcct tgacaacttt cattaccca gccgtccaac 7080
atgcagtgac cacttcatac aacaactact ccttaatggc gatgccacg caagctggag 7140
tgttgtttgg tatgggcaaa gggatgccat tctacgcatg gacttttgga gtcccgctgc 7200
taatgatagg ttgctactca caattaacac ccctgacct aatagtgccc atcattttgc 7260
tcgtggcgca ctacatgtac ttgatcccag gctgcaggc agcagctgcg cgtgctgccc 7320
agaagagaac ggcagctggc atcatgaaga accctgttgt ggatgaata gtggtgactg 7380
acattgacac aatgacaatt gacccccaag tggagaaaaa gatgggacag gtgctactca 7440
tagcagtagc agtctccagc gccatactgt cgcggaccgc ctgggggtgg ggggaggctg 7500
gggcctgat cacagccgca acttccactt tgtgggaagg ctctccgaac aagtactgga 7560
actcctctac agccacttca ctgtgtaaca ttttagggg aagttacttg gctggagctt 7620
ctctaatcta catagtaaca agaaacgctg gcttggtcaa agacgtgagg ggtggaacag 7680
gagagaccct gggagagaaa tggaaggccc gcttgaacca gatgtcggcc ctggagttct 7740
actcctacaa aaagtcaggc atcaccgagg tgtgcagaga gaggccgcc cgcgccctca 7800
aggatggtgt ggcaacggga gccatgctg tgtcccgagg aagtcaaagg ctgagatggt 7860
tggtggagcg gggatacctg cagcccatg gaaaggtcat tgatcttgga tgtgcagag 7920
ggggctggag ttactacgcc gccaccatcc gcaaagttca agaagtgaaa ggatacacaa 7980
aaggaggccc tggtcatgaa gaacccgtgt tggtgcaaag ctatgggtgg aacatagtcc 8040
gtcttaagag tggggtggac gtctttcata tggcggctga gccgtgtgac acgttgctgt 8100
gtgacatagg tgagtcatca tctagtcctg aagtggaaga agcacggacg ctcagagtcc 8160
tctccatgt gggggattgg cttgaaaaaa gaccaggagc cttttgtata aaagtttgt 8220
gcccatacac cagcactatg atggaaaccc tggagcgact gcagcgtagg tatgggggag 8280
gactggtcag agtgccactc tcccgcaact ctacacatga gatgtactgg gtctctctgag 8340
cgaaaagcaa caccataaaa agtgtgtcca ccacgagcca gctcctcttg gggcgcatgg 8400
acgggccag gaggccagtg aaatatgagg aggatgtgaa tctcggctct ggcacgcttg 8460
ctgtggtaag ctgcgctgaa gctcccaaca tgaagatcat tggtaaccgc attgaaagga 8520
tccgcagtga gcacgcggaa acgtggttct ttgacgagaa ccaccatat aggacatggg 8580
cttaccatga aagctatgag gcccccacac aagggtcagc gtcctctcta ataaacgggg 8640
ttgtcaggct cctgtcaaaa ccctgggatg tggtgactgg agtcacagga atagccatga 8700
ccgacaccac accgtatggt cagcaaaggg ttttcaagga aaaagtggac actaggggtc 8760
cagacccca agaaggcact cgtcaggtta tgagcatggt ctcttcctgg ttgtggaaag 8820
agctaggcaa acacaaacgg ccacgagtct gtaccaaaga agttcatc aacaaggttc 8880
gtagcaatgc agcattaggg gcaatatttg aagaggaaaa agagtggaag actgcagtgg 8940
aagctgtgaa cgatccaagg ttctgggctc tagtggcaca ggaagagag caccacctga 9000
gaggagagtg ccagagttgt gtgtacaaca tgatgggaaa aagagaaaag aaacaagggg 9060
```

```
aatttggaaa ggccaagggc agccgcgcca tctggtatat gtggctaggg gctagatttc  9120
tagagttcga agcccttgga ttcttgaacg aggatcactg gatgggagaa gagaactcag   9180
gaggtggtgt tgaagggctg ggattacaaa gactcggata tgtcctagaa gagatgagtc   9240
gcataccagg aggaaggatg tatgcagatg acactgctgg ctgggacacc cgcatcagca   9300
ggttcgatct ggagaatgaa gctctaatca ccaaccaaat ggagaaaggg catagggcct   9360
tggcattggc cataatcaag tacacatacc aaaacaaagt ggtaaaggtc cttagaccag   9420
ctgaaaaagg gaaacagtt atggacatta tttcgagaca agaccaaagg gggagcggac   9480
aagttgtcac ttacgctctt aacacattta ccaacctagt ggtgcaactc attcggaata   9540
tggaggctga ggaagttcta gagatgcaag acttgtggct gctgcggagg tcagagaaag   9600
tgaccaactg gttgcagagc aacgatgggt ataggctcaa acgaatggca gtcagtggag   9660
atgattgcgt tgtgaagcca attgatgata ggtttgcaca tgccctcagg ttcttgaatg   9720
atatgggaaa agttaggaag gacacacaag agtggaaacc ctcaactgga tgggacaact   9780
gggaagaagt tccgttttgc tcccaccact tcaacaagcc ccatctcaag gacgggaggt   9840
ccattgtggt tccctgccgc caccaagatg aactgattgg ccgggccgc gtctctccag    9900
gggcgggatg gagcatccgg gagactgctt gcctagcaaa atcatatgcg caaatgtggc   9960
agctccttta tttccacaga agggacctcc gactgatggc caatgccatt tgttcatctg  10020
tgccagttga ctgggttcca actgggagaa ctacctggtc aatccatgga aagggagaat  10080
ggatgaccac tgaagacatg cttgtggtgt ggaacagagt gtggattgga gaacgacc    10140
acatggaaga caagaccccca gttacgaaat ggacagacat tccctatttg ggaaaaaggg  10200
aagacttgtg gtgtggatct ctcatagggc acagaccgcg caccacctgg gctgagaaca  10260
ttaaaaacac agtcaacatg gtgcgcagga tcataggtga tgaagaaaag tacatggact  10320
acctatccac ccaagttcgc tacttgggtg aagaaggtct tacacctgga gtgctgtaag  10380
caccaatctt aatgttgtca ggcctgctag tcagccacac cttggggaaa gctgtgcagc  10440
ctgtgacccc cccaggagaa gctgggaaac caagcctata gtcaggccga gaacgccatg  10500
gcacggaaga agccatgctg cctgtgagcc cctcagagga cactgagtca aaaaaccca    10560
tgcgcttgga ggcgcaggat gggaaaagaa ggtggcaacc ttcccccacc ttcaatctgg  10620
ggcctgaact ggagatcagc tgtggatctc cagaagaggg actagtggtt agaggagacc  10680
ccccggaaaa cgcaaaacag catattgacg ctgggaagaa ccagagactc catgagtttc  10740
caccacgctg gccgccaggc acagatcgcc gaatagcggc ggccggtgtg gggaaatcca  10800
tgggtctt                                                            10808

SEQ ID NO: 7          moltype = DNA  length = 10807
FEATURE               Location/Qualifiers
source                1..10807
                      mol_type = genomic DNA
                      organism = Zika virus
SEQUENCE: 7
agttgttgat ctgtgtgaat cagactgcga cagttcgagt ttgaagcgaa agctagcaac    60
agtatcaaca ggttttattt tggatttgga aacgagagtt tctggtcatg aaaaacccaa   120
aaaagaaatc cggaggattc cggattgtca atatgctaaa acgcggagta gcccgtgtga   180
gcccctttgg gggcttgaag aggctgccag ccggacttct gctgggtcat gggcccatca   240
ggatggtctt ggcgattcta gccttttga gattcacggc aatcaagcca tcactgggtc   300
tcatcaatag atgggttca gtgggaaaaa aagaggctat ggaaataata aagaagttca    360
agaaagatct ggctgccatg ctgagaataa tcaatgctag gaaggagaag aagagacgag   420
gcacagatac tagtgtcgga attgttggcc tcctgctgac cacagctatg gcagcggagg   480
tcactagacg tgggagtgca tactatatgt acttggacag aagcgatgct ggggaggcca   540
tatcttttcc aaccacactg gggatgaata gtgttataac agatgtcttg gac          600
acatgtgtga tgccaccatg agctatgaat gccctatgct ggatgagggg gtagaaccag   660
atgacgtcga ttgttggtgc aacacgacgt caacttgggt tgtgtacgga acctgccatc   720
acaaaaaagg tgaagcacgg agatccagaa gagctgtgac gctcccctcc cattccacta   780
ggaagctgca aacgcggtcg cagacctggt tggaatcaag agaatacaca aagcacttga   840
ttagagtcga aaattggata ttcaggaacc ctgcttcgc gttagcagca gctgccatcg   900
cttggctttt gggaagctca acgagccaaa agtcatata cttggtcatg atactgctga   960
ttgccccggc atacagcatc aggtgcatag gagtcagtaa tagggacttt gtggaaggta  1020
tgtcaggtgg gacttgggtt gatgttgtct tggaacatgg aggttgtgtc accgtaatgg  1080
cacaggacaa accgactgtc gacatagagc tggttacaaa caagtcagc aacatgcgg   1140
aggtaagatc ctactgctat gaggcatcaa tatcggacat ggcttcggac agccgctgcc  1200
caacacaagg tgaagcctac cttgacaagc aatcagacac tcaatatgtc tgcaaaagaa  1260
cgttagtgga cagaggctgg ggaaatggat gtggactttt tggcaaaggg agcctggtga  1320
catgcgctaa gtttgcatgc tccaagaaaa tgacccggaa gagcatccag ccagagaatc  1380
tggagtaccg gataatgctg tcagttcatg gctcccagca cagtgggatg atcgttaatg  1440
acacaggaca tgaaactgat gagaatagag cgaaggttga gataacgccc aattcaccaa  1500
gagccgaagc cacccctggg ggttttgaa gcctaggact tgattgtgaa ccgaggacag   1560
gccttgactt ttcagatttg tattacttga ctatgaacaa caagcactgg ttggttcaca   1620
aggagtggtt ccacgacatt ccattacctt ggcacactgg ggcagacacc ggaactccac  1680
actgaacaa caaagaagca ctggtagagt tcaaggacgc acatgccaaa aggcaaactg   1740
tcgtggttct agggagtcaa gaaggagcag ttcacacggc ccttgctgga gctctggagg  1800
ctgagatgga tggtgcaaag ggaaggctgt cctctgccca cttgaaatgt cgcctgcaaa  1860
tggataaact tagattgaag ggcgtgtcat actctcttgt taccgcagcg ttccattca    1920
ccaagatccc ggctgaaaca ctgcacggga cagtccacgt ggaggtacag tacgcaggga  1980
cagatgggcc ttgcaaggtt ccagctcaga tggcggtgga catgcaaact ctgacccag    2040
ttgggaggtt gataaccgct aaccccgtaa tcactgaagg cactgagaac ctaagatga   2100
tgctggaact tgatccacca tttggggact cttacattgt cataggagtc ggggagaaga  2160
agatcaccca ccactggcac aaggagtgga gcaccatttg aaaagcattt gaagccactg   2220
tgagaggtgc caagagaatg gcagtcttgg gagacacagc tgggacttt ggatcagttg    2280
gaggcgttct taactcattg ggcaagggca tccatcaaat ttttggagca gctttcaaat  2340
cattgtttgg aggaatgtcc tggttctcac aaattctcat tggaacgttg ctgatgtggt  2400
tgggtctgaa tacaaagaat ggatctatttt ccctatgtg cttggcctta gggggagtgt  2460
tgatcttctt atccacagcc gtctccgctg atgtggggtg ctcggtggac ttctcaaaga  2520
```

-continued

```
aggaaacgag atgcggtaca ggggtgttcg tctataacga cgttgaagcc tggagggaca  2580
ggtacaagta ccatcctgac tcccctcgta gattggcagc agtagtcaag caagcctggg  2640
aagatggtat ctgtgggatc tcctctgttt caagaatgga aaacatcatg tggagatcag  2700
tagaagggga gctcaacgca atcctggaag agaatggagt tcaactgacg gtcgttgtgg  2760
gatctgtaaa aaacccatg tggagaggtc cacagagatt gcccgtgcct gtgaacgagc  2820
tgccccacgg ctggaaggct tgggggaaat cgtacttcgt cagagcagca aagacaaata  2880
acagctttgt cgtggatggt gacacactga aggaatgccc actcaaacat agagcatgga  2940
acagctttct tgtggaggat catgggttcg gggtatttca cactagtgtc tggctcaagg  3000
ttagaagaaga ttattcacta gagtgtgatc cagccgtcat tggaacagct gttaagggaa  3060
aggaggctgt acacagtgat ctaggctact ggattgagag tgagaagaac gacacatgga  3120
ggctgaggag ggcccacctg atcgagatga aacatgtga atggccaaag tcccacacat  3180
tgtgacagga tggaatagaa gagagtgatc tgatcatacc caagtcttta gctgggccac  3240
tcagccatca caacaccaga gagggctaca ggacccaaat gaaagggcca tggcacagtg  3300
aagagcttga aattcggttt gaggaatgcc caggcactaa ggtccacgtg gaggaaacat  3360
gtggaacaag aggaccatct ctgagatcaa ccactgcaag cggaagggtg atcgaggaat  3420
ggtgctgcag ggagtgcaca atgccccccac tgtcgttccg ggctaaagat ggctgttggt  3480
atggaatgga gataaggccc aggaaagaac cagaaagtaa cttagtaagg tcaatggtga  3540
ctgcaggatc aactgatcac atggatcact ttttcccttgg agtgcttgtg attctgctca  3600
tggtgcagga agggctgaag aagagaatga ccacaaagat catcataagc acatcaatgg  3660
cagtgctggt agctatgatc ctgggaggat tttcaatgag tgatctggct aagcttgcaa  3720
ttttgatggg tgccaccttt gcggaaatga acactgggag gatgtagct catctggcgc  3780
tggtagcgcc attcaaagtc agaccagcgt tgctggtatc tttcatcttc agagctaatt  3840
ggacaccccg tgaaagcatg ctgctggcct tggcctcgtg tcttttgcaa actgcgatct  3900
ccgccttgga aggcgacctg atggttctca tcaatggttt tgctttgcc tggttggcaa  3960
tacgagcgat ggttgttcca cgcactgaca atatccacctt ggcaatcctg gctgctctga  4020
caccactggc ccgggcaca ctgcttgtgg cgtggagagc aggccttgct acttgcgggg  4080
ggttcatgct cctctctctg aaggggaaag gcagtgtgaa gaagaactta ccatttgtca  4140
tggccctggg actaaccgct gtgaggctgg tcgaccccat caacgtgtg ggactgctgt  4200
tgctcacaag gagtgggaag cggagctggc ccccatagcga agtactcaca gctgttggcc  4260
tgatatgcgc attggctgga gggttcgcca aggcagatat agagatggct gggcccatgg  4320
ccgcggtcgg tctgctaatt gtcagttacg tggtctcagg aaaagagtgtg gacatgtaca  4380
ttgaaagagc aggtgacatc acatgggaaa aagatgcgga agttactgga aacagtcccc  4440
ggctcgatgt ggcactagat gagagtgtg atttctccct ggtggaggat gacggtcccc  4500
ccatgagaga gatcatactc aaagtggtcc tgatgaccat ctgtggcatg aacccaatag  4560
ccatacccct tgcagctgga gcgtggtacg tatacgtgaa aactggaaaa aggagtggtg  4620
ctctatggga tgtgcctgct cccaaggaag taaaaagg ggagaccaca gatgagtgt  4680
acagagtaat gactcgtaga ctgctaggtt caacacaagt tggagtggga gttatgcaag  4740
agggggtctt tcacactatg tggcatgtca caaaaggatc cgcgctgaga agcggtgaag  4800
ggagacttga tccatactgg agagatgtca agcaggatct ggtgtcatac tgtggtccat  4860
ggaagctaga tgccgcctgg acgggcaca gcgaggtgca gctcttggcc gtgccccccg  4920
gagagagagc gaggaacatc cagactctgc ccggaatatt taagacaaag gatggggaca  4980
ttggagcggt tgcgctggac tatccagcag gaacttcagg atctccaatc ctagacaagt  5040
gtgggagagt gataggactc tatgcaatg gggtcgtgat caagaatggg agtttatgtca  5100
gtgccatcac ccaagggagg agggaggaag agactcctgt tgagtgcttc gagccttcga  5160
tgctgaagaa gaagcagcta actgtcttag acttgcatcc tggagctggg aaaaccagga  5220
gagttcttcc tgaaatagtc cgtgaagcca taaaaacgag actccgtact gtgatcttag  5280
ctccaaccag ggttgtcgct gctgaaatgg aggaagccct tagagggcct tagcagtcgtt  5340
atatgacaac agcagtcaat gtcacccatt ctgggacaga aatcgttgac ttaatgtgcc  5400
atgccaccct cacttcacgt ctactacagc caatcagagt ccccaactat aatctgtata  5460
ttatggatga ggcccacttc acagatccct caagtatagc agcaagagga tacatttcaa  5520
caagggttga gatgggcgag gcagctgcca tcttcatgac cgccacgccca ccaggaaccc  5580
gtgacgcatt cccggactcc aactcaccaa ttatgacac cgaagtggaa gtcccagaga  5640
gagcctggag ctcaggcttt gattgggtga cggatcattc tggaaaaaca gtttggtttg  5700
tcccaagcgt gaggaacggc aatgagatcg cagcttgtct gacaaaggct ggaaaacggg  5760
tcatacagct cagcagaaag acttttgaga cagagttcca gaaaacaaaa catcaagagt  5820
gggacttcgt cgtgacaact gacatttcag agatgggcgc caactttaaa gctgaccgtg  5880
tcatagattc caggagatgc ctaaagccgg tcatacttga tggcgagaga gtcattctgg  5940
ctggacccat gcctgtcaca catgccagcg ctgcccagag gaggggcgc ataggcagga  6000
atcccaacaa acctggagat gagtatctgt atggaggtgg gtgcgcagag actgatgaag  6060
accatgcaca ctggcttgaa gcaagaatgc tccttgacaa tatttacctc caagatggcc  6120
tcatagcctc gctctatcga cctgaggcca acaaagtagc agccattgag ggagagttca  6180
agcttaggac ggagcaaagg aagacctttg tggaactcat gaaaagagga gatcttcctg  6240
tttggctggc ctatcaggtt gcatctgccg gaataaccta cacagataga agatggtgct  6300
ttgatggcat gaccaacaac accataatgg aagacagtgt gccggcagg gtgtggacca  6360
gacacgagaa gaaagagtgt ctcaaaccga ggtggatgga cgccagagtt tgttcagatc  6420
atgcggccct gaagtcattc aaggagtttg ccgctgggaa aagaggagcg gcttttggag  6480
tgatggaagc cctgggaaca ctgccaggac acatgacgga gagattccag gaagccattg  6540
acaacctcgc tgtgctcatg cgggcagaga ctggaagcag gcccttacaa gccgcggcgg  6600
cccaattgcc ggagaccctg agaccatta tgctttttgg gttgctggga acagtctcga  6660
tgggaatctt tttcgtcttg atgcggaaca agggcatagg gaagatgggc tttgaaatgg  6720
tgactcttgg ggccagcgca tggctcatgt ggctctcgga aattgagcca gccagaattg  6780
catgcgtcct cattgttgtg ttcctattgc tggtggtgct cataccctgag ccagaaaagc  6840
aaagatcccc ccaggacaac caaatggcaa tcatcatcat ggtagcagta ggtcttctgg  6900
gcttgattac cgccaatgaa ctcggatggt tggagagaac aaagagtgac ctaagccatc  6960
taatgggaag gagagaggag ggggcaacca taggattctc aatggacatt gacctgcggc  7020
cagcctcggc ctgggccatc tatgctgccc tgcaacttt cattacccca gccgtccaac  7080
atgcagtgac cacttcatac aacaactact cccttaatgg cgatggccacg caagctgag  7140
tgttgtttgg tatgggcaaa gggatgccat tctacgcatg gacttttgga gtcccgctgc  7200
taatgatagg ttgctactca caattaacac ccctgaccct aatagtggct atcattttgc  7260
```

```
tcgtggcgca ctacatgtac ttgatcccag ggctgcaggc agcagctgcg cgtgctgccc  7320
agaagagaac ggcagctggc atcatgaaga accctgttgt ggatggaata gtggtgactg  7380
acattgacac aatgactatt gacccccaag tggagaaaaa gatgggacag gtgctactca  7440
tagcagtagc cgtctccagc gccatactgt cgcggaccgc ctgggggtgg ggggaagctg  7500
gggccctgat cacagctgca acttccactt tgtgggaagg ctctccgaac aagtactgga  7560
actcctctac agccacttca ctgtgcaaca tttttagggg aagttacttg gctggagctt  7620
ctctaatcta cacagtaaca agaaacgctg gcttggtcaa gagacgtggg ggtggaacag  7680
gagagaccct gggagagaaa tggaaggccc gcttgaacca gatgtcggcc ctggagttct  7740
actcctacaa aaagtcaggc atcaccgagg tgtgcagaga agaggcccgc cgcgccctca  7800
aggacggtgt ggcaacggga ggccatgctg tgtcccgagg aagtgcaaag ctgagatggt  7860
tggtggagcg gggatacctg cagccctatg gaaaggtcat tgatcttgga tgtggcagag  7920
ggggctggag ttactacgcc gccaccatcc gcaaagttca agaagtgaaa ggatacacaa  7980
aaggaggccc tggtcatgaa gaacccatgt tggtgcaaag ctatgggtgg aacatagtcc  8040
gtcttaagag tggggtggac gtctttcata tggcggctga gccgtgtgac acgttgctgt  8100
gtgacatagg tgagtcatca tctagtcctg aagtggaaga agcacggacg ctcagagtcc  8160
tctccatggt gggggattgg cttgaaaaaa gaccaggagc cttttgtgta aaagtgttgt  8220
gcccatacac cagcactatg atggaaaccc tggagcgact gcagcgtagg tatgggggag  8280
gactggtcag agtgccactc tcccgcaact ctacacatga gatgtactgg gtctctggag  8340
cgaaaagcaa caccataaaa agtgtgtcca ccacgagcca gctcctcttg ggcgcatgg  8400
acgggcccag gaggccagtg aaatatgagg aggatgtgaa tctcggctct ggcacgcggg  8460
ctgtggtaag ctgcgctgaa gctcccaaca tgaagatcat tggtaaccgc attgaaagga  8520
tccgcagtga gcacgcggaa acgtggttct ttgacgagaa ccacccatat aggacatggg  8580
cttaccatgg aagctatgag gcccctacac aagggtcagc gtcctctcta ataaacgggg  8640
ttgtcaggct cctgtcaaaa ccctgggatg tggtgactgg agtcacagga atagccatga  8700
ccgacaccac accgtatggt cagcaaagag ttttcaagga aaaagtggac accagggtgc  8760
cagaccccca agaaggcact cgtcaggtta tgagcatggt ctcttcctgg ttgtggaaag  8820
agctaggcaa acacaaacgg ccacgagtct gtaccaaaga agagttcatc aacaaggttc  8880
gtagcaatgc agcattaggg gcaatatttg aagaggaaaa agagtggaag accgcagtgg  8940
aagctgtgaa cgatccaagg ttctgggctc tagtggacaa ggaaagagag caccacctga  9000
gaggagagtg ccagagctgt gtgtacaaca tgatgggaaa aagagaaaag aaacaagggg  9060
aatttggaaa ggccaagggc agccgcgcca tctggtatat gtggctaggg gctagatttc  9120
tagagttcga agcccttgga ttcttaaatg aggatcactg gatggggaga gagaactcag  9180
gaggtggtgt tgaagggctg ggattacaaa gactcggata tgtcctagaa gagatgagtc  9240
gcataccagg aggaaggatg tatgcagatg acactgctgg ctgggacacc cgcatcagca  9300
ggtttgatct ggagaatgaa gctttaatca ccaaccaaat ggagaaaggg cacagggcct  9360
tagcattggc cataatcaag tacacatacc aaaacaaagt ggtaaaggtc cttagaccag  9420
ctgaaaaagg gaagacagtt atggacatta tttcaagaca agaccaaagg gggagcggac  9480
aagttgtcac ttacgctctt aacacattta ccaacctagt ggtgcaactc attcggaata  9540
tggaggctga ggaagttcta gagatgcaag acttgtggct gctgcggagg tcagagaaag  9600
tgaccaactg gttgcagagc aacggatggg ataggctcaa acgaatggca gtcagtggag  9660
atgattgcgt tgtgaagcca attgatgata ggtttgcaca tgccctcagg ttcttgaatg  9720
atatgggaaa agttaggaag gacacacaag agtggaaacc ctcaactgga tgggacaact  9780
gggaagaagt tccgttttgt tcccaccact tcaacaagct ccatctcaag gacgggaggt  9840
ccattgtggt tccctgccgc caccaagatg aactgattgg ccgggcccgt gtctctccag  9900
gggcgggatg gagcatccgg gagactgctt gcctagcaaa gtcatatgcg caaatgtggc  9960
agctccttta tttccacaga agggacctcc gactgatggc caatgccatc tgttcatctg  10020
tgccagttga ctgggttcca actgggagaa ctacctggtc aatccatgga aagggagaat  10080
ggatgaccac tgaagacatg cttgtggtgt ggaacagagt gtggattgag gagaacgacc  10140
acatggaaga caagacccca gttacgaaat ggacagacat tccctatctg ggaaaaaggg  10200
aagacttgtg gtgtggatct ctcatagggc acagaccgcg caccacctgg gctgagaaca  10260
ttaaaaacac agtcaacatg gtgcgcagga tcataggtga tgaagaaaag tacatggact  10320
acctatccac ccaagttcgc tacttgggtg aagaagggtc tacacctgga gtgctataag  10380
caccaatctt agtgttgtca ggcctgctag tcagccacag cttggggaaa gctgtgcagc  10440
ctgtgacccc cccaggagag gctgggaaac caagcccata gtcaggccga gaacgccatg  10500
gcacggaaga agccatgctg cctgtgagcc cctcagagga cactgagtca aaaaacccca  10560
cgcgcttgga ggcgcaggat gggaaaagaa ggtggcgacc ttccccaccc ttcaatctgg  10620
ggcctgaact ggagatcagc tgtggatctc cagaagaggg actagtggtt agaggagacc  10680
ccccggaaaa cgcaaaacag catattgacg ctgggaaaga ccagagactc catgagtttc  10740
caccacgctg gccgccaggc acagatcgcc gaatagcggc ggccggtgtg gggaaatcca  10800
tgggtct                                                            10807
```

```
SEQ ID NO: 8            moltype = DNA  length = 10807
FEATURE                 Location/Qualifiers
source                  1..10807
                        mol_type = genomic DNA
                        organism = Zika virus
SEQUENCE: 8
agttgttgat ctgtgtgaat cagactgcga cagttcgagt ttgaagcgaa agctagcaac  60
agtatcaaca ggttttattt tggatttgga aacgagagtt tctggtcatg aaaaacccaa  120
aaaagaaatc cggaggattc cggattgtca atatgctaaa acgcggagta gcccgtgtga  180
gcccctttgg gggcttgaag aggctgccag ccggacttct gctgggccat gggcccatca  240
ggatggtctt ggcgatacta gcctttttga gattcacggc aatcaagcca tcactgggtc  300
tcatcaatag atggggttca gtggggaaaa aagaggctat ggaaataata aagaagttca  360
agaaagatct ggctgccatg ctgagaataa tcaatgctag gaaggagaag aagagacgag  420
gcgcagatac tagcgtcgga attgttggcc tcctcctgac cacagccatg gcagtagagg  480
tcactagacg tgggagtgca tactatatgt acttggacag aagcgatgct ggggaggcca  540
tatcttttcc aaccacactg ggatgaata agtgttacat acaaatcatg gatcttggac  600
acatgtgtga tgccaccatg agctatgaat gccctatgtt ggatgagggg gtagaaccag  660
atgacgtcga ttgctggtgc aacacgacat caacttgggt tgtgtatgga acctgccacc  720
```

```
acaaaaaagg tgaagcacgg agatctagaa gagctgtgac gctcccctcc cattccacta   780
ggaagctgca aacgcggtcg cagacctggt tggaatcaag agaatacaca aagcacctga   840
ttagagttga aaattggata ttcaggaacc ctggcttcgc gttagcagca gctgtcatcg   900
cttggctttt gggaagttca acgagccaaa aagtcatata tctggtcatg atactgctga   960
ttgccccggc atacagcatc aggtgcatag gagtcagcaa tagggacttt gtggaaggta  1020
tgtcaggtgg gacttgggtt gatgttgtct tggaacatgg aggttgtgtt accgtaatga  1080
cacaggacaa accgactgtc gacatagagc tggttacaac aacagtcagc aacatggcgg  1140
aggtaagatc ctactgctat gaggcatcaa tatcggatat ggcttcggac agccgctgcc  1200
caacacaagg tgaggcctac cttgacaagc agtcagacac tcaatatgtc tgcaaaagaa  1260
cgttagtgga cagaggctgg ggaaatggat gtggactttt tggcaaaggg agcctggtga  1320
catgcgctaa gtttgcatgc tccaagaaaa tgaccgggaa gagcatccag ccagagaatc  1380
tggagtaccg gataatgctg tcagttcatg gctcccagca cagtgggatg atcgttaatg  1440
acacaggaca tgaaactgat gagaatagag cgaaggttga gataacgccc aattcaccaa  1500
gagccgaagc cacccctggg ggttttggga gcctaggact tgattgtgaa ccgaggacag  1560
gccttgactt ttcagatttg tattacctga ctatgaataa caagcactgg ttggttcaca  1620
aggagtggtt ccacgacatt ccattacctt ggcatgctgg ggcagacact ggaactccac  1680
attggaacaa caaagaagca ctggtagagt tcaaggacgc acatgcaaaa aggcaaactg  1740
tcgtggttct agggagtcaa gaaggagcag ttcacacggc ccttgctgga gctctggagg  1800
ctgagatgga tggagccaag ggaaggctgt cctctggcca cttgaaatgt cgcctgaaaa  1860
tggataaact tagattgaag ggcgtgtcat actccttgtg cactgcagcg ttcacattca  1920
ccaagatccc ggctgaaaca ctgcacggga cagtcacagt ggaggtacag tacgcaggga  1980
cagatgacc ttgcaaggtt ccagctcaga tggcggtgga tatgcaaact ctgacccca  2040
ttgggaggtt gataaccgct aaccctgtaa tcactgaaag caccgagaac tctaagatga  2100
tgctggaact tgatccacca tttggggact cttacattgt cataggagtc ggggagaaga  2160
agatcaccca tcactggcac aggagtggca gcaccattgg aaaagcattt gaagccactg  2220
tgagaggtgc caagagaatg gcagtcttgg gagacacagc ctgggacttt ggatcagttg  2280
ggggtgctct caactcattg ggcaaggcac tccatcaaat ttttggagca gctttcaaat  2340
cattgttcgg aggaatgtcc tggttctcac aaattctcat tggaacgttg ctggtgtggt  2400
tgggtctgaa tacaaagaat ggatctattt cccttacgtg cttggcctta gggggagtgt  2460
tgatcttctt atccacagcc gtttctgctg atgtgggtga ctcggtggac ttctcaaaga  2520
aggaaacgag atgcggtaca ggggtgttcg tctataacga cgttgaagcc tggaggaca  2580
ggtacaagta ccatcctgac tcccctcgta gattggcagc agcagtcaag caagcctggg  2640
aagatgggat ctgtgggatc tcctctgtct caagaatgga aaacatcatg tggagatcag  2700
tagaagggga gctcaacgca atcctggaag agaatggagt tcaactgacg gtcgttgtgg  2760
gatctgtaaa aaaccccatg tggagaggtc cacagagatt gcccgtgcct gtgaacgagc  2820
tgccccacgg ctggaaggct tggggaaat cgtacttcgt cagagcagca aagacaaata  2880
acagctttgt cgtggatggt gacacactga aggaatgccc actcaaacat agagcatgga  2940
acagcttttct tgtggaggat catgggtttg gggtatttca cactagtgtc tggctcaagg  3000
ttagagaaga ttattcatta gagtgtgatc cagccgtcat tggaacagct gctaagggaa  3060
aggaggctgt gcacagcgat ctaggctact ggattgagag tgagaagaac gacacatgga  3120
ggctgaagag ggcccacctg atcgagatga aacatgtga atggcaaag tcccacacat  3180
tgtgacaga tggagtagaa gaaagtgatc tgatcatacc caagtcttta gctgggccac  3240
tcagccatca caaccagaa gggctaca ggactcaaga gaaagggcca tggcacagtg  3300
aagagcttga aattcggttt gaggaatgcc caggcactaa ggtccacgtg gaggaaacat  3360
gtgggacaag aggaccatcc ctgagatcaa ccactgcaag cggaagggtg atcgaggaat  3420
ggtgctgcag ggaatgcaca atgcccccac tgtcgttccg agctaaagat ggctgttggt  3480
atggaatgga gataaggccc aggaaagaac cagaaagtaa cttagtaagg tcaatggtga  3540
ctgcaggatc aactgatcac atggatcact tctctcttgg agtgcttgtg atttgctca  3600
tggtgcagga agggctgaag aagagaatga ccacaaagat catcataagc acatcaatgg  3660
cagtgctggt agccatgatc ctgggaggat tttcaatgag tgacctggct aagcttgcaa  3720
ttttgatggg tgccaccttc gcggaaatga acactggagg agatgtagct catttggcgc  3780
tgatagcggc attcaaagtc agacctgcgt tgctggtatc tttcatcttc agagctaatt  3840
ggacacccg tgagagcatg ctgctggcct tggcctcgtg tcttctgcaa actgcgatct  3900
ccgccttgga aggcgacctg atggttctca tcaatggttt tgctttggcc tggttggcaa  3960
tacgagcgat ggttgttcca cgcactgaca acatcaccct tgcaatcctg gctgctctga  4020
caccactggc ccgggcaca ctgcttgtgg cgtggagagc aggccttgct acttgcgggg  4080
ggttcatgct cctctctctg aaggggaaag gcagtgtgaa gaagaaccta ccatttgtca  4140
tggcctgg actaactgct gtgaggctgg tcgaccccat caacgtggtg ggactgctgt  4200
tgctcacaag gagtgggaag cggagctggc cccctagtga agtactcaca gctgttgcc  4260
tgatatgcgc attggctgga gggttcgcca aggcggatat agagatggct gggcccatgg  4320
ccgcggtcgg tctgctaatt gtcagttacg tggtctcagg aaagagtgtg gacatgtaca  4380
ttgaaagagc aggtgacatc acatgggaaa agatgcggaa atcactggaa acagtcccc  4440
ggctcgatgt ggcactagat gagagtggtg atttctccct agtggaggat gatggtccac  4500
ccatgagaga gatcatactc aaagtgtcc tgatgaccat ctgcggcatg aacccaatag  4560
ccatacccct tgcagctgga gcgtggtacg tgtatgtgag gactggaaaa aggagtggtg  4620
ctctatggga tgtgcctgct cccaaggaag taaaaagggg ggagaccaca gatgagtgt  4680
acagagtaat gactcgtaga ctgcttggtt caacacaagt tggagtggga gtcatgcaag  4740
aggggggtct tcacactatg tggcacgtca caaaggatc cgcgctgaga agcggtgaag  4800
ggagactgga tccatactgg ggagatgtca agcaggatct ggtgtcatac tgtggtccgt  4860
ggaagctaga cgccgcctgg gacgggcaca gcgaggtgca gctcttggcc gtgcccccg  4920
gagagagagc gaggaacatc cagactctgc ccggaacatt taagacaaag gatgggaca  4980
ttggagcagt tgcgctggac tacccagcag gaacttcagg atctccaatc ctagacaagt  5040
gtgggagagt gataggactc tatggtaatg gggtcgtgat aaaaaatggg agttatgtta  5100
gtgccatcac ccaagggag agggaagag agctcctgt tgagcttcg  5160
tgctgaagaa gaagcagcta actgtcttag acctgcatcc tggagccggg aaaaccagga  5220
gagttcttcc tgaaatagtc cgtgaagcca taaaaacaag actccgtact gtgatcttag  5280
ctccaaccag ggtcgtcgct gctgaaatgg aggaagccct tagggcttc ccagttcgtt  5340
atatgacaac agcagtcaat gtcacccatt ctgggacaga aatcgttgac ttaatgtgcc  5400
atgctacctt cacttcacgc ctactacaac caatcagagt cccaactat aatttgtata  5460
```

```
ttatggatga ggcccacttc acagatccct caagtatagc agcaagagga tacatttcaa 5520
caagggttga gatgggcgag gcggctgcca tcttcatgac cgccacgcca ccaggaaccc 5580
gtgacgcatt cccggactcc aactcaccaa ttatggacac cgaggtggaa gtcccagaga 5640
gagcctggag cacaggcttt gattgggtga cggatcattc tgggaaaaca gtctggtttg 5700
ttccaagcgt gaggaacggc aatgacatcg cagcttgtct gacaaaggct ggaaaacggg 5760
tcatacagct cagcagaaag acttttgaga cagagttcca gaaaacgaaa aatcaagagt 5820
gggacttcgt cgtgacaacc gacatttcag agatgggcgc caactttaaa gctgaccgtg 5880
tcatagattc caggagatgc ttaaagccgg tcatacttga tggcgagaga gtcattttgg 5940
ctggacccat gcctgtcaca catgccagcg ctgctcagag gaggggcgc ataggcagga 6000
atcccaacaa acctggagat gagtatctgt atggaggtgg gtgcgcagag actgatgaag 6060
atcacgcaca ctggcttgaa gcaagaatgc ttcttgacaa catttacctc caagatggcc 6120
tcatagcttc gctctatcga cctgaggccg acaaagtagc agctattgag ggagagttca 6180
agcttaggac ggagcaaagg aagacctttg tggaactcat gaaaagagga gatcttccgg 6240
tttggttggc ctatcaggtt gcatctgccg gaataaccta cacagataga agatggtgct 6300
ttgatggcat gaccaacaac accataatgg aagacagtgt gccggcagag gtgtggacca 6360
gatacggaga gaaaagagtg ctcaaaccga ggtggatggt cgccagagtt tgttcagatc 6420
atgcggccct gaagtcattc aaagagtttg ccgctgggaa aagaggagcg gccttttggag 6480
tgatagaagc cctgggaaca ctgccaggac acatgacaga ggagattccag gaagccattg 6540
acaacctcgc tgtgctcatg cgggcagaga ctggaagcag gccttacaaa gccgcggcgg 6600
cccaattgcc ggagacccta gagaccatta tgcttttggg gttgctggaa acagtctcgc 6660
tgggaatctt tttcgtcttg atgcggaaca agggcatggg gaagatgggc tttgaatgg 6720
tgactcttgg ggccagcgca tggctttatgt ggctctcaga aattgagcca gccagaattg 6780
catgtgtcct cattgtcgtg ttcctattgc tggtggtgct cataccctgag ccagaaaagc 6840
aaagatctcc tcaggacaac caaatggcaa tcatcatcat ggtagcagtg ggtcttctgg 6900
gcttgattac cgccaatgaa ctcggatggt tggagagaac aaaaagtgac ctaagccatc 6960
taatggggaa g gagagagag ggggcaacca caggattctc aatggacatt gacctgcgtc 7020
cagcctcagc ttgggctatc tatgctgctc tgacaacttt catcaccca gccgtccaac 7080
atgcggtgac cacttcatac aacaactact ccttaatggc gatggccacg caagctgggg 7140
tgttgtttgg tatgggcaaa gggatgccat tctacgcatg gacttttgga gtcccgctgc 7200
taatgatggg ttgctactca caattaacac ctctgaccct aatagtggcc atcatttgc 7260
tcgtggcgca ctacatgtac ttgatccag gctgcaggc agcagctgcg cgggctgccc 7320
agaagagaac ggcagctggc atcatgaaga accctgttgt ggatggaata gtggtgactg 7380
acattgacac aatgacaatt gaccccaag tggaaaaaaa gatggggcag gtgctactca 7440
tagcagtagc cgtctccagc gccatactgt cgcgggaccgc ctgggggtgg ggggaggctg 7500
gggccctgat cacagctgca acttccacct tgtgggaagg ctctccgaac aagtactgga 7560
actcctccac agccacttca ctgtgtaaca ttttttagggg aagttacttg gctgagcttt 7620
ctctaatcta cacagtaaca agaaacgctg gcttggtcaa gagacgtggg ggtggaacgg 7680
gagagaccct gggagagaaa tggaaggccc gcctgaacca gatgtcggcc ctggagttct 7740
actcctacaa aaagtcaggc atcaccgagg tgtgcagaga agagggcccgc cgtgccctca 7800
aggacggtgt ggcaacagga ggccatgctg tgtcccgagg aagtgcaaag cttagatggc 7860
tggtggagag aggatacctg cagccctatg gaaaggtcat tgatcttgga tgtggcagag 7920
ggggctggag ttactatgcc gccaccatcc gcaaagttca ggaagtgaaa ggatacacaa 7980
aaggaggccc tggtcatgaa gaaccatgt tggtgcaaga ctatggggtgg aacatatgtcc 8040
gtcttaagag tgggggtggac gtctttcaca tggcggctga gccgtgtgac actttgctgt 8100
gtgatatagg tgagtcatca tctagtcctg aagtcggaaga agcacggacg ctcagagtcc 8160
tctccatggt gggggattgg cttgaaaaaa gaccaggagc cttttgtata aagtgttgt 8220
gcccatacac cagcactatg atggaaaccc tggagcgact gcagcgtagg tatgggggag 8280
gactggtcag ggtgccactc tcccgcaact ctacacatga gatgtactgg gtctctggag 8340
cgaaaagcaa caccataaaa agtgtgtcca ccacgagcca gctcctcttg gggcgcatgg 8400
acgggcccag gaggccagtg aaatatgagg aggatgtgaa tctcggctct ggcacgcggg 8460
ctgtgtaag ctgcgctgaa gctcccaaca tgaagatcat tggtaaccgc attgagagga 8520
tccgcagtga gcacgcggaa acgtggttct ttgacgagaa ccacccatat aggacatggg 8580
cttaccatgg aagctatgag gcccctacac aagggtcagc gtcctctcta ataaacgggg 8640
ttgtcaggct cctgtcaaaa ccctgggatg tggtgactgg agtcacagga atagccatga 8700
ctgacaccac accgtatggt cagcaaaagg ttttcaagga aaaagtggac ctaggggtgc 8760
cagaccccca agaaggcact cgtcaggtta tgagcatgat ctcttcctgg ttatggaagg 8820
agctaggcaa acacaaacgg ccacgagtct gtaccaaaga agagttcatc aacaaggttc 8880
gtagcaatgc agcattaggg gcaatatttg aagaggaaaa agagtggaag actgcagtgg 8940
aagctgtgaa tgatccaagg ttctgggctc tagtggaaa ggaaagagag catcacctga 9000
gaggagagtg tcagagctgt gtgtacaaca tgatggaaa aagagaaaag aaacaaggsg 9060
aatttggaaa ggccaaggc agccgcgcca tctggtatat gtggctaggg ctagattcc 9120
tagagttcga agcccttgga ttcttgaatg aggatcattg gatggggaga gagaattcag 9180
gaggtggtgt tgaaggactg ggattacaaa gactcggata tgtcctagaa gagatgagtc 9240
gcataccagg aggaaggatg tatgcagatg atactgctgg ccgtgaacc cgcatcagca 9300
ggtttgatct ggagaatgaa gctctaatca ccaaccaaat ggagaaaggg cacagggcct 9360
tggcattggc cataatcaag tacacatacc aaaacaaagt ggtaaaggtc cttaggaccag 9420
ctgaaaaagg gaagacagtt atggacatta tttcaagaca agaccaaagg gggagcggac 9480
aagttgtcac ttacgctctt aatacattca caaccctggt ggtgcagctc attcggaata 9540
tggaggctgg gaaagttcta gagatgcaag acttgtggct gctgcggagg ccagagaaag 9600
tgaccaactg gttgcaaagc aacggatggg ataggctcaa aagaatggca gtcagtggag 9660
atgattcgct tgtgaaacca attgatgata ggtttgcaca tgccctcagg ttcttgaatg 9720
atatgggaaa agtaggaag acacacaag agtgaaacc ctcaactgga tgggacaact 9780
gggaagaagt tccgttttgc tcccaccact tcaacaaact ccatcttaag gacggaggt 9840
ccattgtggt ccctgccgc caccaagatg aactgattgg ccgagcccgc gtatcaccag 9900
gggcgggatg gagcatccgg gagactgctt gcctagcaaa atcatatgcg caaatgtggc 9960
agctcctta tttccacaga agggacctcc gactgatggc caatgccatt tgttcatctg 10020
tgccagttga ttgggttcca actggagaa ctacctggtc aatccatgga aagggagaat 10080
ggatgaccac tgaagacatg cttgtggtat ggaacagagt gtggattgag gaaaacgacc 10140
acatggaaga caagacccca gttacaaaat ggacagacat tccctatttg ggaaaaagag 10200
```

```
aagacttgtg gtgtggatct ctcatagggc acagaccgcg tactacctgg gctgagaaca   10260
tcaaaaatac agtcaacatg atgcgcagga tcataggtga tgaagaaaag tacatggact   10320
acctatccac ccaggttcgc tacttgggtg aagaagggtc cacacctgga gtgctgtaag   10380
caccaatctt agtgttgtca ggcctgctag tcagccacag cttggggaaa gctgtgcagc   10440
ctgtgacccc cccaggagaa gctgggaaac caagcctata gtcaggccga gaacgccatg   10500
gcacggaaga agccatgctg cctgtgagcc cctcagagga cactgagtca aaaaacccca   10560
cgcgcttgga ggcgcaggat gggaaaagaa ggtggcgacc ttccccaccc ttcaatctgg   10620
ggcctgaact ggagatcagc tgtggatctc cagaagaggg actagtggtt agaggagacc   10680
cccggaaaa cgcaaaacag catattgacg ctggaaaaga ccagagactc catgagtttc   10740
caccacgctg gccgccaggc acagatcgcc gaatagcggc ggccggtgtg gggaaatcca   10800
tgggtct                                                            10807

SEQ ID NO: 9        moltype = DNA  length = 10648
FEATURE             Location/Qualifiers
source              1..10648
                    mol_type = genomic DNA
                    organism = Zika virus
SEQUENCE: 9
gacagttcga gtttgaagcg aaagctagca acagtatcaa caggttttat ttggatttgg     60
aaacgagagt ttctggtcat gaaaaaccca aaaaagaaat ccggaggatt ccggattgtc    120
aatatgctaa aacgcggagt agcccgtgtg agccccttg ggggcttgaa gaggctgcca     180
gccggacttc tgctgggtca tgggcccatc aggatgtct tggcgattct agccttttg      240
agattcacgg caatcaagcc atcactgggg ctcatcaata gatggggttc agtggggaaa    300
aaagaggcta tggaaataat aaagaagttc aagaaagatc tggctgccat gctgagaata    360
atcaatgcta ggaaggagaa gaagagacga ggcgcagata ctagtgtcgg aattgttggc    420
ctcctgctga ccacagctat ggcagcggag gtcactagac gtgggagtgc atactatatg    480
tacttggaca gaaacgatgc tgggggaggcc atatctttc caaccacatt ggggatgaat    540
aagtgttata tacagatcat ggatcttgga cacatgtgtg atgccaccat gagctatgaa    600
tgccctatgc tggatgaggg ggtggaacca gatgacgtcg attgttggtg caacacgacg    660
tcaacttgtg ttgtgtacgg aacctgccat caaaaaaag gtgaagcacg gagatctaga    720
agagctgtga cgctcccctc ccattccact aggaagctgc aaacgcggtc gcaaacctga    780
ttggaatcaa gagaatacac aaagcacttg attagagtcg aaaattggat attcaggaac    840
cctggcttcg cgttagcagc agctgccatc gcttggcttt tgggaagctc aacgagccaa    900
aaagtcatat acttggtcat gatactgctg attgccccgg catacagcat caggtgcata    960
ggagtcagca ataggggactt tgtggaaggt atgtcaggtg ggacctgggt tgatgttgtc   1020
ttggaacatg gaggttgtgt caccgtaatg gcacaggaca aaccgactgt cgacatagag   1080
ctggttacaa caacagtcag caacatggcg gaggtaagat cctactgcta tgaggcatca   1140
atatcagaca tggcttcgga cagccgctgc ccaacacaag gtgaagccta ccttgacaag   1200
caatcagaca ctcaatatgt ctgcaaaaga acgttagtgg acagaggctg gggaaatgga   1260
tgtggacttt ttggcaaagg gagcctggtg acatgcgcta agtttgcatg ctccaagaaa   1320
atgaccggga agagcatcca gccagagaat ctggagtacc ggataatgct gtcagttcat   1380
ggctcccagc acagtgggat gattgttaat gacacaggac atgaaactga tgaaataga    1440
gcgaaagttg agataacgcc caattcacca agagccgaag ccaccctggg gggttttga    1500
agcctaggac ttgattgtga accgaggaca ggccttgact tttcagattt gtattacttg   1560
actatgaata caagcactg gttggttcac aaggagtggt tccacgacat tccattacct    1620
tggcacgctg ggcagacac cggaactcca cactggaaca caaagaagc actggtagag    1680
ttcaaggacg cacatgccaa aagcaaact gtcgtggttc taggagtca agaaggagca    1740
gttcacacgg cccttgctgg agctctggag gctgagatgg atggtgcaaa gggaaggctg    1800
tcctctggcc acttgaaatg tcgcctgaaa atggataaac ttagattgaa gggcgtgtca    1860
tactccttgt gtactgcagc gttcacattc accaagatcc cggctgaaac actgcacggg    1920
acagtacag tggaggtaca gtacgcaggg acagatgac cttgcaaggt tccagctcag    1980
atggcggtgg acatgcaaac tctgacccca gttgggaggt tgataaccgc taaccccgta   2040
atcactgaaa gcactgagaa ctcaagatg atgctgaac ttgatccacc atttggggac    2100
tcttacattg tcataggagt cggggagaag aagatcaccc accactggca caggagtggc    2160
agcaccattg gaaaagcatt tgaagccact gtgagagtg ccaagagaat ggcagtcttg    2220
ggagacacag cctgggactt tggatcagtt ggaggcgctc tcaactcatt gggcaagggc    2280
atccatcaaa ttttttggagc agctttcaaa tcattgtttg gaggaatgtc ctggttctca    2340
caaattctca ttggaacgtt gctgatgtgg ttgggtctga acacaaagaa tggatctatt    2400
tcccttatgt gcttggcctt aggggagtg ttgatcttct tatccacagc cgtctctgct    2460
gatgtggggt gctcggtgga cttctcaaag aaggagacga gatgcggtac agggtgttc    2520
gtctataacg acgttgaagc ctggagggac aggtacaagt accatcctga ctccccccgt    2580
agattggcag cagcagtcaa gcaagcctgg aagatggta tctgcgggat ctcctctgtt    2640
tcaagaatgg aaaacatcat gtggagatca gtagaagggg agctcaacgc aatcctggaa    2700
gagaatggag ttcaactgac ggtcgttgtg ggatctgtaa aaaaccccat gtggagaggt    2760
ccacagagat tgcccgtgcc tgtgaacgag ctgccccacg gctggaaggc ttggggaaa    2820
tcgtacttcg tcagagcagc aaagacaaat aacagctttg tcgtggatgg tgacacactg    2880
aaggaatgcc cactcaaaca tagagcatgg aacagctttc ttgtggagga tcatgggttc    2940
ggggtatttc acacctagtgt ctggctcaag gttagagaag attattcatt agagtgtgat    3000
ccagccgtta ttggaacagc tgttaaggga aggaggctgg tacacagtta tctaggctac    3060
tggattgaga gtgagaagaa tgacacatgg aggctgaaga gggccatctt gatcgagatg    3120
aaaacatgtg aatggccaaa gtcccacaca ttgtggacag atgaatagaa agagagtgat    3180
ctgatcatac ccagtctttt agctgggcca ctcagccatc acaataccag agagggctac    3240
aggacccaaa tgaagggcc atggcacagt gaagagcttg aaattcggtt tgaggaatgc    3300
ccaggcacta aggtccacgt ggaggaaaca tgtggaaaca gaggaccctc tctgagatca    3360
accactgcaa gcgggaaggg tgatcgagga tggtgctgca gggagtgcac aatgcccca    3420
ctgtcgttcc gggctaaaga tggctgttgg tatggaatgg agataaggcc caggaaagaa    3480
ccagaaagca acttagtaag gtcaatggtg actgcaggat caactgatca catggaccac    3540
ttctcccttg gagtgcttgt gattctgctc atggtgcagg aagggctgaa gaagagatg    3600
accacaaaga tcatcataag cacatcaatg gcagtgctgt tagctatgat cctgggagga    3660
```

```
ttttcaatga gtgacctggc taagcttgca attttgatgg gtgccacctt cgcggaaatg  3720
aacactggag gagatgtagc tcatctggcg ctgatagcgg cattcaaagt cagaccagcg  3780
ttgctggtat ctttcatctt cagagctaat tggacacccc gtgaaagcat gctgctggcc  3840
ttggcctcgt gtcttttgca aactgcgatc tccgccttgg aaggcgacct gatggttctc  3900
atcaatggtt ttgctttggc ctggttggca atacgagcga tggttgttcc acgcactgat  3960
aacatcacct tggcaatcct ggctgctctg acaccactgg cccggggcac actgcttgtg  4020
gcgtggagag caggccttgc tacttgcggg gggtttatgc tcctctctct gaagggaaaa  4080
ggcagtgtga agaagaactt accatttgtc atggccctgg gactaaccgc tgtgaggctg  4140
gtcgacccca tcaacgtggt gggactgctg ttgctcacaa ggagtgggaa gcggagctgg  4200
ccccctagcg aagtactcac agctgttggc ctgatatgcg cattggctgg agggttcgcc  4260
aaggcagata tagagatggc tgggcccatg gccgcggtcg gtctgctaat tgtcagttac  4320
gtggtctcag gaaagagtgt ggacatgtac attgaaagag caggtgacat cacatgggaa  4380
aaagatgcgg aagtcactgg aaacagtccc cggctcgatg tggcgctaga tgagagtggt  4440
gatttctccc tggtggagga tgacggtccc cccatgagag agatcatact caaggtggtc  4500
ctgatgacca tctgtggcat gaacccaata gccatacccc ttgcagctgg agcgtggtac  4560
gtatacgtga agactggaaa aaggagtggt gctctatggg atgtgcctgc tcccaaggaa  4620
gtaaaaaagg gggagaccac agatgagtg tacagagtaa tgactcgtag actgctaggt  4680
tcaacacaag ttggagtggg agttatgcaa gagggggtct ttcacactat gtggcacgtc  4740
acaaaaggat ccgcgctgag aagcggtgaa gggagacttg atccatactg gggagatgtc  4800
aagcaggatc tggtgtcata ctgtggtcca tggaagctag atgccgcctg ggacgggcac  4860
agcgaggtgc agctcttggc cgtgccccc ggagagagag cgaggaacat ccagactctg  4920
cccggaatat ttaagacaaa ggatgggac attggagcgg ttgcgctgga ttacccagca  4980
ggaacttcag gatctccaat cctagacaag tgtgggagag tgataggact ttatggcaat  5040
ggggtcgtga tcaaaaatgg gagttatgtt agtgccatca cccaagggag gagggaggaa  5100
gagactcctg ttgagtgctt cgagcctcg atgctgaaga agaagcagct aactgtctta  5160
gacttgcatc ctggagctgg gaaaaccagg agagttcttc ctgaaatagt ccgtgaagcc  5220
ataaaaacaa gactccgtac tgtgatctta gctccaacca gggttgtcgc tgctgaaatg  5280
gaggaggccc ttagagggct tccagtgcgt tatatgacaa cagcagtcaa tgtcacccac  5340
tctgaacag aaatcgtcga cttaatgtgc catgccacct tcacttcacg tctactacag  5400
ccaatcagag tccccaacta taatctgtat attatggatg aggcccactt cacagatccc  5460
tcaagtatag cagcaagagg atacatttca acaagggttg agatgggcga ggcggctgcc  5520
atcttcatga ccgccacgcc accaggaacc cgtgacgcat ttccggactc caactcacca  5580
attatgcaca ccgaagtgga agtcccagag agagcctgga gctcaggctt tgattgggtg  5640
acggatcatt ctgaaaaac agttggtttt gttccaagcg tgaggaacgg caatgagatc  5700
gcagcttgtc tgacaaaggc tggaaaacgg gtcatacagc tcagcagaaa gactttgag  5760
acagagttcc agaaaacaaa acatcaagag tgggactttg tcgtgacaac tgacatttca  5820
gagatgggcg ccaactttaa agctgaccgt gtcatagatt ccaggagatg cctaaagccg  5880
gtcatacttg atggcgagag agtcattctg gctgggccca tgcctgtcac acatgccagc  5940
gctgcccaga ggagggggcg cataggcagg aatcccaaca acctggaga tgagtatctg  6000
tatgagggtg ggtgcgcaga gactgacgaa gaccatgcac actggcttga agcaagaatg  6060
ctccttgaca atatttacct ccaagatggc ctcatagcct cgtctatcg acctgaggcc  6120
gacaaagtag cagccattga gggagagttc aagcttagga cggagcaaag gaagaccttt  6180
gtggaactca tgaaaagagg agatcttcct gtttggctgg cctatcaggt tgcatctgcc  6240
ggaataacct acacagatag aagatggtgc tttgatggca cgaccaacaa caccataatg  6300
gaagacagtg tgccggcaga ggtgtggacc agacacggag agaaaagagt gctcaaaccg  6360
aggtggatgg acgccagagt ttgttcagat catgcggccc tgaagtcatt caaggagttt  6420
gccgctggga aaagaggagc ggcttttgga gtgatggaag ccctgggaac actgccagga  6480
cacatgacag agagattcca ggaagccatt gacaacctcg ctgtgctcat gcgggcagag  6540
actgaagcag gccttacaa agccgcggcg gcccaattgc cggagaccct agaccattt   6600
atgcttttgg ggttgctggg aacagtctcg ctggaatct tcttcgtctt gatgaggaac  6660
aagggcatag ggaagatggg cttttggaatg gtgactcttg gggccagcgc atggctcatg  6720
tggctctcgg aaattgagcc agcagaatt gcatgtgtcc tcattgttgt gtttctattg  6780
ctggtggtgc tcataccctga gccagaaaag caaagatctc cccaggacaa ccaaatggca  6840
atcatcatca tggtagcagt aggtcttctg ggcttgatta ccgccaatga actcggatgg  6900
ttgagagaa caaagagtga cctaagccat taatgagaga ggagagaggg gggcaacc   6960
ataggattct caatggacat tgacctgcgg ccagcctcag cttgggccat ctatgctgcc  7020
ttgacaactt tcattacccc agccgtccaa catgcagtga ccacttcata caacaactac  7080
tccttaatgg cgatggccac gcaagctgga gtgttgtttg gtatgggcaa agggatgcca  7140
ttctacgcat gggactttgg agtcccgctg ctaatgatag gttgctactc acaattaaca  7200
cccctgaccc taatagtggc catcatttg ctcgtggcgc actacatgta cttgatccca  7260
gggctgcagg cagcagctgc gcgtgctgcc cagaagagaa cggcagctgg catcatgaag  7320
aaccctgttg tggatggaat agtggtgact gacattgaca caatgacaat tgaccccaa   7380
gtggagaaaa agatgggaca ggtgctactc atagcagtag ccgtctccag cgccatactg  7440
tcgcgaaccg cctgggggtg gggggaggct ggggccctga tcacagccgc aacttccact  7500
ttgtgggaag gctctccgaa caagtactgg aactcctcta cagccacttc actgtgtaac  7560
atttttaggg gaagttactt ggctggagct tctctaatct acacagtaac aagaaacgct  7620
ggcttggtca gagacgtggg ggtggaaca ggagagaccc tggagagaa atggaaggcc  7680
cgcttgaacc agatgtcggc cctggagttc tactcctaca aaaagtcagg catcaccgag  7740
gtgtgcagag aagaggcccg ccgcgccctc aaggacggtg tggcaacggg aggccatgct  7800
gtgtcccgag gaagtgcaaa gctgcgatgg ttggtggagc ggggatacct gcagcccta t  7860
ggaaaggtca ttgatcttgg atgtggcaga ggggctgga gttactacgc cgccaccatc  7920
cgcaaagttc aagaagtgaa aggatacaca aaggaggcc ctggtcatga gaacccgtg   7980
ttggtgcaaa gctatgggtg gaacatagtc cgtcttaaga gtgggtggga cgtctttcat  8040
atggcgctg accgtgtga cacgttgctg tgtgacatag gtgagtcatc atctagtcct  8100
gaagtgggaag aagcacggac gctcagagtc ctccatggt gggggattgg gcttgaaaaa  8160
agaccaggag cctttgtgtat aaaggtgttg tgcccataca ccagcactat gatggaaacc  8220
ctggagcgac tgcagcgtag gtatggggga ggactggtca gagtgccact ctcccgcaac  8280
tctacacatg agatgtattg ggtctctgga gcgaaagca acaccataaa agtgtgtcc   8340
accacgagcc agctcctctt ggggcgcatg gacgggccta ggaggccagt gaaatatgag  8400
```

-continued

```
gaggatgtga atctcggctc tggcacgcgg gctgtggtaa gctgcgctga agctcccaac   8460
atgaagatca ttggtaaccg cattgaaagg atccgcagtg agcacgcgga aacgtggttc   8520
tttgacgaga accacccata taggacatgg gcttaccatg gaagctatga ggcccccaca   8580
caagggtcag cgtcctctct aataaacggg gttgtcaggc tcctgtcaaa accctgggat   8640
gtggtgactg gagtcacagg aatagccatg accgacacca caccgtatgg tcagcaaaga   8700
gttttcaagg aaaaagtgga cactagggtg ccagacccc aagaaggcac tcgtcaggtt    8760
atgagcatgg tctcttcctg gttgtggaaa gagctaggca acacaaacg gccacgagtc    8820
tgtaccaaaa aagagttcat caacaaggtt cgtagcaatg cagcattagg ggcaatattt   8880
gaagaggaaa aagagtggaa gactgcagtg gaagctgtga acgatccaag gttctgggct   8940
ctagtggata aggaaagaga gcaccacctg agaggagagt gccagagttg tgtgtacaac   9000
atgatggaaa aaagagaaaa gaaacaaggg gaatttggaa aggccaaggg cagccgcgcc   9060
atctggtata tgtggctagg ggctagattt ctagagttcg aagcccttgg attcttgaac   9120
gaggatcact ggatggggag agagaactca ggaggtggtg ttgaagggct gggattacaa   9180
agactcggat atgtcctaga agagatgagt cgtataccag gaggaagat gtatgcagat   9240
gacactgctg gctgggacac ccgcatcagc aggtttgatc tggagaatga agctctaatc   9300
accaaccaaa tggaaaaagg gcacagggcc ttggcattgg ccataatcaa gtacacatac   9360
caaaacaaag tggtaaaggt ccttagacca gctgaaaaag gaaaacagt tatggacatt   9420
atttcgagac aagaccaaag ggggacggga caagttgtca cttacgctct taacacattt   9480
accaacctag tggtgcaact cattcggaat atggaggctg aggaagttct agagatgcaa   9540
gacttgtggc tgctgcggag gtcagagaaa gtgaccaact ggttgcagag caacggatgg   9600
gataggctca aacgaatggc agtcagtgga gatgattgcg ttgtgaagcc aattgatgat   9660
aggttttgcac atgccctcag gttcttgaat gatatgggaa aagttaggaa ggacacacaa   9720
gagtggaaac cctcaactgg atgggacaac tgggaagaag ttcgtttttg ctcccaccac   9780
ttcaacaagc tccatctcaa ggacgggagg tccattgtgg ttccctgccg ccaccaagat   9840
gaactgattg gccgggcccg cgtctctcca ggggcgggat ggagcatccg ggagactgct   9900
tgcctagcaa aatcatatgc gcaaatgtgg cagctccttt atttccacag aagggacctc   9960
cgactgatgg ccaatgccat ttgttcatct gtgccagttg actgggttcc aactgggaga  10020
actacctggt caatccatgg aaagggagaa tggatgacca ctgaagacat gcttgtggtg  10080
tggaacagag tgtggattga ggagaacgac cacatggaag acaagacccc agttacgaaa  10140
tggacagaca tccccattt ggggaaaagg gaagacttgt ggtgtggatc tctcatcggg   10200
cacagaccgc gcaccacctg ggctgagaac attaaaaaca cagtcaacat ggtgcgcagg  10260
atcataggtg atgaagaaaa gtacatggac tacctatcca cccaagttcg ctacttgggt  10320
gaagaagggg ctacacctgg agtgctgtaa gcaccagtct taatgttgtc aggcctgcta  10380
gtcagccaca gcttggggaa agctgtgcag cctgtgaccc ccccaggaga agctgggaaa  10440
ccaagcctat agtcaggccg agaacgccat ggcacggaag aagccatgct gcctgtgagc  10500
ccctcagagg acactgagtc aaaaaacccc acgcgcttgg aggcgcagga tgggaaaaga  10560
aggtggcgac cttccccacc cttcaatctg gggcctgaac tggagatcag ctgtggatct  10620
ccagaagagg gactagtggt tagaggag                                      10648
```

```
SEQ ID NO: 10          moltype = DNA   length = 10676
FEATURE                Location/Qualifiers
source                 1..10676
                       mol_type = genomic DNA
                       organism = Zika virus
SEQUENCE: 10
gttgttactg ttgctgactc agactgcgac agttcgagtt tgaagcgaaa gctagcaaca     60
gtatcaacag gttttatttg gatttggaaa cgagagtttc tggtcatgaa aaacccaaaa    120
aagaaatccg gaggattccg gattgtcaat atgctaaaac gcggagtagc ccgtgtgagc    180
ccctttgggg gcttgaagag gctgccagcc ggacttctgc tgggtcatgg gcccatcagg    240
atggtcttga caattctagc cttttgaga ttcacggcaa tcaagccatc actgggtctc     300
atcaatagat ggggttcagt ggggaaaaaa gatgctatgt aaataataaa gaagttcaag    360
aaagatctgg ctgccatgct gagaataatc aatgctagga aggagaagaa gagacgaggc    420
gcagatacta gtgtcggaat tgttggcctc ctgctgacca cagctatggc agcggaggtc    480
actagacgtg gagtgcata ctatatgtac ttggacagaa acgatgctgg ggaggccata     540
tcttttccaa ccacattggg gatgaataag tgttatatac agatcatgga tcttggacac    600
atgtgtgatg ccaccatgag ctatgaatgc cctatgctgg atgaggggt ggaaccagat     660
gacgtcgatt gttggtgcaa cacgacgtca acttgggttg tgtacggaac ctgccatcac    720
aaaaaaggtg aagcacggag atctagaaga gctgtgacgc tccttcccca ttccactagg    780
aagctgcaaa cgccggtcgca aacctggttg gaatcaagag aatacacaaa gcacttgatt    840
agagtcgaaa attggatatt caggaaccct ggcttcgcgt tagcagcagc tgccatcgct    900
tggcttttgg gaagctcaac gagccaaaaa gtcatatact tggtcatgat actgctgatt    960
gccccggcat acagcatcag gtgcatagga gtcagcaata gggactttgt ggaaggtatg   1020
tcaggtggga cttgggttga tgttgtcttg gaacatggag gttgtgtcac cgcaatggca   1080
caggacaaac cgactgtcga catagagctg gttacaacaa cagtcagcaa catgcgggaa   1140
gtaagatcct actgctatga ggcatcaata tcagacatgg cttcggacag ccgctgccca   1200
acacaaggtg aagcctacct tgacaagcaa tcagacactc aatatgtttg caaaagaacg   1260
ttagtggaca gaggctgggg aaatggatgt ggacttttg gcaaagggag tctggtgaca   1320
tgcgctaagt ttgcatgctc caagaaaatg accgggaaga gcatccagcc agagaatctg   1380
gagtaccgga taatgctgtc agttcatggc tcccagcaca gtgggatgct cgttaatgac   1440
acaggacatg aaactgatga gaatagagcg aaggttgaga taacgcccaa ttcaccaaga   1500
gccgaagcca cctgggggg ttttggaagc ctaggacttg attgtgaacc gaggacaggc   1560
cttgactttt cagatttgta ttacttgact atgaataaca gcactggtt ggctcacaag   1620
gagtggttcc acgacattcc attccttgg cacgctgggg cagccaccgg aactccacac   1680
tggaacaaca agaagcact ggtagagttc aaggacgcac acgccaactgt   1740
gtggttctag ggagtcaaga aggagcagtt cacacggccc ttgctggagc tctgaggct   1800
gagatggatg gtgcaaaggg aaggctgtcc tctggccact tgaaatgtcg cctgaaaatg   1860
gataaactta gattgaaggg cgtgtcatac tccttgtgta ccgcagcgtt cacattcacc   1920
aagatcccg ctgaaacagt ggacgggaca gtcacagtgg agggacagta cggagggaca   1980
gatgaccttt gcaaggttcc agctcagatg gcggtggaca tgcagactct gacccagtt   2040
```

```
gggaggttga taaccgctaa ccccgtaatc actgaaagca ctgagaactc taagatgatg   2100
ctggaacttg atccaccatt tggggactct tacattgtca taggagtcgg ggagaagaag   2160
atcacccacc actggcacag gagtggcagc accattggaa aagcatttga agccactgtg   2220
agaggtgcca agagaatggc agtcttggga gacacagcct gggactttgg atcagttgga   2280
ggcgctctca actcattggg caagggcatc catcaaatta ttggagcagc tttcaaatca   2340
ttgtttggag gaatgtcctg gttctcacaa attctcattg ggacgttgct gatgtggttg   2400
ggtctgaaca caaagaatgg atctatttcc cttatgtgct tggccttagg gggagtgttg   2460
atcttcttat ccacagccgt ctcaggtggt gtggggtgct cggtggactt ctcaaagaag   2520
gagacgagat gcggtacagg ggtgttcgtc tataacgatg ttgaagcctg gagggacagg   2580
tacaagtacc atcctgactc ccccgtaga ttggcagcag cagtcaagca agcctgggaa   2640
gatggtatct gcgggatctc ctctgtttca agaatggaaa acatcatgtg gagatcagta   2700
gaaggggagc tcaacgcaat cctggaagag aatggagttc aactgacggt cgttgtggga   2760
tctgtaaaaa acccatgtg gagaggtcca cagagattgc ccgtgcctgt gaacgagctg   2820
ccccacggct ggaaggcttg ggggaaatcg tacttcgtca gagcagcaaa gacaaataac   2880
agctttgtcg tggatggtga cactgaag aatgcccac tcaaacatag agcatggaac      2940
agctttcttg tggaggatca tgggttcggg gtatttcaca ctagtgtctg gctcaaggtt   3000
agagaagact attggttaga gtgtgatcca gccgttattg aacagctgt taagggaaag    3060
gaggctgtac acagtgatct aggctactgg attgagagtg agaagaatga cacatggttg   3120
ctgaagaggg cccatctgat cgagatgaaa acatgtgaat ggccaaagtc ccacacattg   3180
tggacagatg aatagaaga gagtgatctg atcatacccca gtctttagc tgggccactc    3240
agccatcaca atgccagaga gggctacagg acccaaatga aagggccatg gcacagtgaa   3300
gagcttgaaa ttcggtttga ggaatgccca ggcactaagg tccacgtggg ggaaacatgt   3360
ggaacaagag gaccatctct gagatcaacc actgcaagcg gaagggtgat cgaggaatgc   3420
tgctccaggg agtgcacaat gccccactg tccttccagg ctaaagatgg ctgttggtat   3480
ggaatggaga taaggcccag gaaagaacca gaaagcaact tagtaaggtc aatggtgact   3540
gcaggatcaa ctgatcacat ggatcacttc tcccttgtga tgcttgtgat tctgctcatg   3600
gtgcaggaag ggctgaagaa gagaatgacc acaaagatca tcataagcac atcaatggca   3660
gtgctggtag ctatgatcct gggaggattt tcaatgagtg acctggctaa gcttgcaatt   3720
ttgatggtgt ccaccttcgc ggaaatgaac actggaggag atgtagctca tctggcgctg   3780
atagcggcat tcaaagtcag accagcgttg ctggtatctt tcatcttcag agctaattgg   3840
acacccccgtg aaagcatgct gctggccttg gcctcgtgtc ttttgcaaac tgcgatctcc   3900
gccttggaag gcgacctgat ggttctcatc aatggttttg ctttggcctg gttggcaata   3960
cgagcgatgg ttgttccacg cactgataac atcacccttag caatcctggc tgctctgaca   4020
ccactggccc ggggcacact gcttgtggcg tggagagcag gccttgctac ttgcggggg    4080
tttatgctcc tctctctgaa gggaaaaggc agtgtgaaga agaacttacc atttgtcatg   4140
gccctgggac taaccgctgt gaggctggtc gaccccatca acgtggtggg actgctgttg   4200
ctcacaagga gtgggaagcg gagctggccc cctagcgaag tactcacagc tgttggcctg   4260
atatgcgcat tggctggagg gttcgccaag gcagatatag agatggctgg gcccatggcc   4320
gcggtcggtc tgctaattgt cagttacgtg gtctcaggaa agagtgtgaa catgtacatt   4380
gaaagagcag gtgacatcac atgggaaaaa gatgcggaag tcactggaaa cagtccccgg   4440
ctcgatgtgg cgctagatga gagtggtgat ttctccctgg tggaggatga cggtccccc    4500
atgagagaga tcatactcaa ggtggtcctg atgaccatct gtggcatgaa cccaatagcc   4560
ataccctttg cagctggagc gtggtacgta tacgtgaaga gtggaaaaag gagtggtgct   4620
ctatgggatg tgcctgctcc caaggaagta aaaaagggg agaccacaga tggagtgtac   4680
agagtaatga ctcgcagact gctaggttca acacaagttg gagtgggagt tatgcaagag   4740
ggggtctttc acactatgtg gcacgtcaca aaaggatccg cgctgagaag cggtgaaggg   4800
agacttgatc catactgggg agatgtcaag caggatctgg tgtcatactg tggtccatgg   4860
aagctagatc ccgcctggga cgggcacagc gaggtgcagc tcttggccgt gcccccccgga   4920
gagagagcga ggaacatcca gactctgccc ggaatattta agacaaagga tgggacatt    4980
ggagcggttg cactggatta cccagcagga acttcaggat ctccaatcct agacaagtgt   5040
gggagagtga taggactttta tggcaatggg gtcgtgatca aaatgggga ttatgttagt   5100
gccatcaccc aagggaggag ggaggaagag actcctgttg agtgcttcga gccttcgatg   5160
ctgaagaaga agcagctaac tgtcttagac ttgcatccctg gagctgggaa accaggaga    5220
gttcttcctg aaatagtccg tgaagccata aaaacaagac tccgtactgt gatcttggct   5280
ccaaccaggg ttgtcgctgc tgaaatggca gaggcccta gggcttcc agtgcgttat        5340
atgacaacag cagtcaatgt cacccactct ggaacagaaa tcgtcgactt aatgtgccat   5400
gccaccttca cttcacgtct actacagcca attagagtcc ccaactataa tctgtatatt   5460
atggatgagg cccacttcac agatcccta agtatagcag caagaggata catttcaaca   5520
agggttgaga tgggcgaggc ggctgccatc ttcatgaccg ccacgccacc aggaacccgt   5580
gacgcatttc cggactccaa ctcaccaatt atggacaccg aagtggaagt cccagagta    5640
gcctggagct caggctttga ttgggtgacg gagtattctg gaaaaacagt ttggtttgtt   5700
ccacgcgtga ggaacggcaa tgagatcgca gcttgtctga caaaggctgg aaaacgggtc   5760
atacagctca gcagaaagac ttttgagaca gagttccaga aaacaaaaca tcaagagtgg   5820
gactttgtcg tgacaactga catttcagag atgggcgcca actttaaggc tgacatggtc   5880
atagattcca ggagatgcct aaagccggtc atacttggtg gcgagagagt cattctggct   5940
ggacccatgc ctgtcacaca tgccagcgct gcccagagga gggggcgcat aggcaggaat   6000
cccaacaaac ctgagatga tatctgtat ggaggtgggt gcgcagagac tgacgaagac    6060
catgcacact ggcttgaagc aagaatgctc cttgacaata tttacctcca agatggcctc   6120
atagcctcgc tctatcgacc tgaggccgac aaagtacag ccattgaggg agatgttcaag    6180
cttaggacgg agcaaaggaa gacctttgtg gaactcatga aaagaggaga tcttcctgtt   6240
tggctggcct atcaggttgc atctgccgga ataacctaca agatagaag atggtgcttt   6300
gatggcacga ccaacaacac cataatgaa acagtgtgc cggcagaggt gtggaccaga    6360
cacgagaga aagagtgct caaaccgagg tggatgacg ccagagtttg ttcagatcat     6420
gccgccctga gtcattcaa ggagtttgcc gctgggaaa ggagcggc ttttggagtg        6480
atggaagccc tgggaacact gccaggacac atgacagaga gattccagga agccattgac   6540
aacctcgctg tgctcatgcg ggcagagact ggaagcaggc cttacaaagc cgcggcggcc   6600
caattgccgg agaccctaga gaccattatg ctttggggt tgctgggaac agtcgctg      6660
ggaatctttt tcgtcttgat gaggaacaag ggcataggga gatgggcctt ggaatggtg    6720
actcttgggg ccagcgcatg gctcatgtgg ctctcggaaa ttgagccagc cagaattgca   6780
```

```
tgtgtcctca ttgttgtgtt cctattgctg gtggtgctca tacctgagcc agaaaagcaa  6840
agatctcccc aggacaacca aatggccatc atcatcatgg tagcagtagg tcttctgggc  6900
ttgattaccg ccaatgaact cggatggttg gagagaacaa agagtgacct aagccatcta  6960
atgggaagga gagaggaggg ggcaaccatg ggattctcaa tggacattga cctgcggcca  7020
gcctcagctt gggccatcta tcctgccttg acatctttca ttaccccagc cgtccaacat  7080
gcagtgacca cttcatacaa caactactcc ttaatggcga tggccacgca agctggagtg  7140
ttgtttggta tgggcaaagg gatgccattc tacgcatggg actttggagt cccgctgcta  7200
atgataggtt gctactcaca attaacgccc ctgaccctaa tagtggccat cattttgctc  7260
gtggcgcact acatgtactt gatcccaggg ctgcaggcag cagctgcgcg tgctgcccag  7320
aagagaacgg cagctggcat catgaagaac cctgttgtgg agggaatagt ggtgactgac  7380
attgacacaa tgacaattga cccccaagtg gagaaaaaga tgggacaggt gctactcatg  7440
gcagtagccg tctccagcgc catactgtcg aggaccgcct gggggtgggg ggaggctggg  7500
gccctgatca cagccgcaac ttccactttg tgggaaggct ctccgaacaa gtactggaac  7560
tcctctacag ccacctcact gtgtaacatt tttaggggaa gttacttggc tggagcttct  7620
ctaatctaca cagtaacaag aaacgctggc ttggtcaaga gacgtggggg tggaacagga  7680
gagaccctgg gagagaaatg gaaggcccgc ttgaaccaga tgtcggccct ggagttctac  7740
tcctacaaaa agtcaggcat caccgaggtg tgcagagaag aggcccgccg cgccctcaag  7800
gacggtgtgg caacgggagg ccatgctgtg tcccgaggaa gtgcaaagct gagatggttg  7860
gtggagcggg gatacctgca gccctatgga aaggtcattg atcttggatg tggcagaggg  7920
ggctggagtt actacgccgc caccatccgc aaagttcaag aagtgaaagg atacacaaaa  7980
ggaggccctg gtcatgaaga acccgtgttg gtgcaaagct atgggtggaa catagtccgt  8040
cttaagagtg gggtggacgt ctttcatatg gcggctgagc cgtgtgacac gttgctgtgt  8100
gacataggtg agtcatcatc tagtcctgaa gtggaagaag cacggacgct cagagtcctc  8160
tccatggtgg gggattggct tgaaaaaaga ccaggagcct tttgtataaa agtgttgtgc  8220
ccatacacca gcactatgat ggaaaccctg gagcgactgc agcgtaggta tgggggagga  8280
ctggtcagag tgccactctc ccgcaactct acacatgaga tgtactgggt ctctggagcg  8340
aaaagcaaca ccataaaaag tgtgtccacc acgagccagc tcctcttggg gcgcatggac  8400
gggcctagga ggccagtgaa atatgaggag gatgtgaatc tcggctctgg cacgcgggct  8460
gtggtaagct gcgctgaagc tcccaacatg aagatcattg gtaaccgcat tgaaaggatc  8520
cgcgctgaga aagcggaaac gtggttcttt gacgagaacc acccatatag gacatgggct  8580
taccatggaa gctatgatgc cgccacacaa gggtcagcgt cctctctaat aaacggggtt  8640
gtcaggctcc tgtcaaaacc ctgggatgtg gtgactggag tcacaggaat agccatgacc  8700
gacaccacac cgtatggtca gcaaagagtt ttcaaggaaa aagtggacac tagggtgcca  8760
gacccccaag aaggcactcg tcaggttatg agcatggtct cttcctggtt gtggaaagag  8820
ctaggcaaac acaaacggcc acgagtctgt accaaagaag agttcatcaa caaggttcgt  8880
agcaatgcag cattaggggc aatatttgaa gaggaaaaag agtggaagac tgcagtggaa  8940
gctgtgaacg atccaaggtt ctgggctcta gtggacaagg aaagagagca ccacctgaga  9000
ggagagtgcc agagttgtgt gtacatcaca atggaaaaaa gagaaaagaa acaaggggaa  9060
tttggaaagg ccaagggcag ccgcgccatc tggtatatgt ggctaggggc tagatttcta  9120
gagttcgaag cccttggatt cttgaacgag gatcactgga tggggagaga gaactcagga  9180
ggtggtgttg aagggctggg attacaaaga ctcggatatg tcctagaaga gatgagtcgc  9240
ataccaggag gaaggatgta tgcagatgac actgctggct gggacacccg catcagcagg  9300
tttgatctgg agaatgaagc tctaatcacc aaccaaatgg agaaagggca cagggccttg  9360
gcattggcca taatcaagta cacataccaa aacaaagtgg taaaggtcct tagaccagct  9420
gaaaaaggga agacagttat ggacattatt tcgagacaag accaaagggg gagcggacaa  9480
gttgtcactt acgctctcaa cacatttacc aacctagtgg tgcaactcat tcggaatatg  9540
gaggctgagg aagttctaga gatgcaagac ttgtggctgc tgcggaggtc agagaaagtg  9600
accaactggt tgcagagcaa cggatgggat aggctcaaac gaatggcggt cagtggagat  9660
gattgcgttg tgaaaccaat tgatgatagg tttgcacatg ccctcaggtt cttgaatgat  9720
atgggaaaag ttaggaagga cacacaagag tggaaaccct caactggatg ggacaactgg  9780
gaagaagttc ccttctgctc ccaccacttc aacaagctcc atctcaagga cgggaggtcc  9840
attgtggttc cctgccgcca ccaagatgaa ctgattggcc gggcccgcgt ctctccaggg  9900
gcgggatgga gcatccggga gactgcttgc ctagcaaaat catatgcgca aatgtggcag  9960
ctcctttatt tccacagaag ggacctccga ctgatggcca atgccatttg ttcatctgtg  10020
ccagttgact gggttccaac tgggagaact acctggtcaa tccatggaaa gggagaatgg  10080
atgaccactg aagacatgct tgtggcgtgg aacagagtgt ggattgagga gaacgaccac  10140
atggaagaca agaccccagt cacgaaatgg acagacattc cctatttggg aaaaagggaa  10200
gacttgtggt gtggatctct catagggcac agaccgcgca ccacctgggc tgagaacatt  10260
aaaaacacag tcaacatggt gcgcaggatc ataggtgatg aagaaaagta catggactac  10320
ctatccaccc aagttcgcta cttgggtgaa gaagggtcta cacctggagt gctgtaagca  10380
ccaatcttaa tgttgtcagg cctgctagtc agccacagct tggggaaagc tgtgcagcct  10440
gtgacccccc caggagaagc tgggaaacca agcctatagt caggccgaga acgccatggc  10500
acggaagaag ccatgctgcc tgtgagcccc tcagaggaca ctgagtcaaa aaaccccacg  10560
cgcttggagg cgcaggatgg gaaaagaagg tggcgacctt ccccaccctt caatctgggg  10620
cctgaactgg agatcagctg tggatctcca gaagagggac tagtggttag aggaga      10676

SEQ ID NO: 11          moltype = DNA  length = 10807
FEATURE                Location/Qualifiers
source                 1..10807
                       mol_type = genomic DNA
                       organism = Zika virus
SEQUENCE: 11
agttgttgat ctgtgtgagt cagactgcga cagttcgagt ctgaagcgag agctaacaac  60
agtatcaaca ggtttaattt ggatttggaa acgagagttt ctggtcatga aaaacccaaa  120
gaagaaatcc ggaggattcc ggattgtcaa tatgctaaaa cgcggagtag cccgtgtaaa  180
ccccttggga ggtttgaaga ggttgccagc cggacttctg ctgggtcatg gacccatcag  240
aatggttttg gcgatactag ccttttttgag atttacagca atcaagccat cactgggcct  300
tatcaacaga tggggttccg tggggaaaaa agaggctatg gaaataataa agaagttcaa  360
gaaagatctt gctgccatgt tgagaataat caatgctagg aaagagagga agagacgtgg  420
```

-continued

```
cgcagacacc agcatcggaa tcattggcct cctgctgact acagccatgg cagcagagat   480
cactagacgc gggagtgcat actacatgta cttggatagg agcgatgccg ggaaggccat   540
ttcgtttgct accacattgg gagtgaacaa gtgccacgta cagatcatgg acctcgggca   600
catgtgtgac gccaccatga gttatgagtg ccctatgctg gatgagggag tggaaccaga   660
tgatgtcgat tgctggtgca acacgacatc aacttggctt gtgtacggaa cctgtcatca   720
caaaaaaggt gaggcacggc gatctagaag agccgtgacg ctcccttctc actctacaag   780
gaagttgcaa acgcggtcgc agacctggtt agaatcaaga gaatacacga agcacttgat   840
caaggttgaa aactggatat tcaggaaccc cgggtttgcg ctagtggccg ttgccattgc   900
ctggcttttg ggaagctcga cgagccaaaa agtcatatac ttggtcatga tactgctagt   960
tgccccggca tacagtatca ggtgcattgg agtcagcaat agagacttcg tggagggcat  1020
gtcaggtggg acctgggttg atgttgtctt ggaacatgga ggctgcgtta ccgtgatggc  1080
acaggacaag ccaacagttg acatagagtt ggtcacgacg acggttagta acatggccga  1140
ggtaagatcc tattgctacg aggcatcgat atcggacatg gcttcggaca gtcgttgccc  1200
aacacaaggt gaagcctacc ttgacaagca atcagcacat caaaagaac gcaaaagaac  1260
attagtggac agaggttggg gaaacggttg tggacttttt ggcaaaggga gcttggtgac  1320
atgtgccaag tttacgtgtt ctaagaagat gaccgggaag agcattcaac cggaaaatct  1380
ggagtatcgg ataatgctat cagtgcatgg ctcccagcat agcgggatga ctgtcaatga  1440
tataggatat gaaactgacg aaaatagagc gaaagtcgag gttacgccta attcaccaag  1500
agcggaagca accttgggag gctttggaag cttaggactt gactgtgaac caaggacagg  1560
ccttgacttt tcagatctgt attacctgac catgaacaat aagcattggt tggtgcacaa  1620
agagtggttt catgacatcc cattgccttg gcatgctggg gcagacactg gaactccaca  1680
ctggaacaac aaaagaggcat tggtagaatt caaggatgcc cacgccaaga ggcaaaccgt  1740
cgtcgttctg gggagccagg aaggagccgt tcacacggct ctcgctgagc tctagaggc  1800
tgagatggat ggtgcaaagg gaaagctgtt ctctggccat tgaaatgcc gcctaaaaat  1860
ggacaagctt agattgaagg gcgtgtcata ttccttgtgc actgcggcat tcacattcac  1920
caaggtccca gctgaaacac tgcatggaac agtcacagtg gaggtgcagt atgcagggac  1980
agatggaccc tgcaagatcc cagtccagat ggcggtggac atgcagaccc tgaccccagt  2040
tggaaggctg ataaccgcca accccgtgat tactgaaagc actgagaact caaagatgat  2100
gttggagctt gacccaccat tggggattc ttacattgtc ataggagttg gggacaagaa  2160
aatcacccac cactggcata ggagtggtag ccatcatgga aaggcatttg aggccactgt  2220
gagaggcgcc aagagaatgg cagtcctggg ggatacagcc tggacttcg gatcagtcgg  2280
gggtgtgttc aactcactgg gtaagggcat tcaccagatt tttggagcag ccttcaaatc  2340
actgtttgga ggaatgtcct ggttctcaca gatcctcata ggcacgctgc tagtgtggtt  2400
aggttttgaac acaaagaatg gatctatctc cctcacatgc cttgccctgg ggggagtgat  2460
gatcttcctc tccacggctg ttctgctga cgtcgggtgc tcagtggact tctcaaaaaa  2520
ggaaacgaga tgtggcacgg gggtattcat ctataatgat gttgaagcct ggagggaccg  2580
gtacaagtac catcctgact cccccgcag attggcagca gcagtcaagc aggcctggga  2640
agaggggatc tgtgggatct catccgtttc aagaatggaa aacatcatgt ggaaatcagt  2700
agaaggggag ctcaatgcta tcctagagga gaatgagatt caactgacag ttgttgtggg  2760
atctgtaaaa aaccccatgt ggagaggtcc acaaagattg ccagtgcctg tgaatgagct  2820
gccccatggc tggaaagcct gggggaaatc gtatttttgtt agggcggcaa agaccaacaa  2880
cagttttgtt gtcgacggtg acacactgaa ggaatgtccg cttgagcaca gagcatgaa  2940
tagtttttctt gtggaggatc accgggtttgg agtcttccaa ccagtgtct ggcttaaggt  3000
cagagaagat tactcattag aatgtgaccc agccgtcata ggaacagctg ttaagggaag  3060
ggaggccgcg cacagtgatc tgggctattg gattgaaagt gaaaagaatg acacatggag  3120
gctgaagagg gcccacctga ttgagatgaa acatgtgaa tggccaaagt ctcacacatt  3180
gtggacagat ggagtagaag aaaagtgatct tatcataccc aagtcttag ctggtccact  3240
cagccaccac aacaccagag agggttacag aacccaagtg aaaggggcat ggcacagtga  3300
agagcttgaa atccggttgt aggaatgtcc aggcaccaag gttacgtgg aggagacatg  3360
cggaactaga ggaccatctc tgagatcaac tactgcaagt ggaagggtca ttgaggaatg  3420
gtgctgtagg gaatgcacaa tgccccact atcgtttgga gcaaaagacg gctgctgta  3480
tggaatggag ataagcccca ggaaaagaacc agagagcaac ttagtgaggt caatggtgac  3540
agcgggtgtca accgatcata tggaccactt ctctcttgga gtgcttgtga ttctactcat  3600
ggtgcaggag gggttgaaga agagaatgac acacaagatc atcatgagca catcaatggc  3660
agtgctggta gtcatgatct tggggaggatt ttcaatgagt gacctggcca agcttgtgat  3720
cctgatgggt gctactttcg cagaaatgaa cactggagga gatgtagctc acttggcatt  3780
ggtagcggca tttaaagtca gaccagcctt gctggtctcc ttcattttca gagccaattg  3840
gacacccgt gagagcatgc tgctagccct ggcttcgtgt cttctgcaaa ctgcgatctc  3900
tgctcttgaa ggtgacttga tggtcctcat taatggattt gctttggcct ggttggcaat  3960
tcgagcaatg gccgtgccac gcactgacaa catcgctcta ccaatcttgg ctgctctaac  4020
accactagct cgaggcacac tgctcgtggc atggagagcg ggcctggcta cttgtggagg  4080
gatcatgctc ctctccctga agggaaagg tagtgtgaag aagaacctgc atttgtcat  4140
ggccctggga ttgacagctg tgagggtagt agacccatt aatgtggtag gactactgtt  4200
actcacaagg agtgggaagc ggagctggcc ccctagtgaa gttctcacag ccgttgcct   4260
gatatgtgca ctggccggag ggtttgcaa gcagacatt gagatggctg gacccatggc  4320
tgcagtaggc ttgctaattg tcagctatgt ggtctcggga aagagtgtgg acatgtacat  4380
tgaaagagca ggtgacatca catggggaaaa ggacgcggaa gtcactggaa acagtcctcg  4440
gcttgacgtg gcactggatg agagtggtga ttttcctcttg gtagaggaag atggtccacc  4500
catgagagag atcatactta aggtgtcct gatggccctc tgtggcatga acccaatagc  4560
tatacctttt gctgcaggag cgtggtatgt gtatgtgaag actgggaaaa ggagtggcgc  4620
cctctggac gtgcctgctc ccaaagaagt gaagaaagga gagccacag atggagtgta  4680
cagagtgatg actcgcagac tgctaggttc aacacaggtt ggagtgggag tcatgcaaga  4740
gggagtcttc cacaccatgt ggcacgttac aaaaggagcc gcactgagga gcggtgaggg  4800
aagactgact ccatactggg gggatgtcaa gcaggacttc gtgtcacctg gtggccttg   4860
gaagttggat gcagcttggg atggactcag cgaggtacag cttttggccg tacctccccgg  4920
agagagggcc agaaacattc agaccctgcc tggaatattc aagacaaagg acgggggacat  4980
cggagcagtt gctctggact accctgcagg gacctcagga tctccgatcc tagacaaatg  5040
tggaagagtg ataggactct atggcaatgg ggttgtgatc aagaatggaa gctatgttag  5100
tgctataacc caggaaaga gggaggagga gactccggtt gaatgtttcg aaccctcgat  5160
```

```
gctgaagaag aagcagctaa ctgtcttgga tctgcatcca ggagccggaa aaaccaggag   5220
agttcttcct gaaatagtcc gtgaagccat aaaaaagaga ctccggacag tgatcttggc   5280
accaactagg gttgtcgctg ctgagatgga ggaggccttg agaggacttc cggtgcgtta   5340
catgacaaca gcagtcaacg tcacccattc tgggacagaa atcgttgatt tgatgtgcca   5400
tgccactttc acttcacgct tactacaacc catcagagtc cctaattaca atctctacat   5460
catggatgaa gcccacttca cagaccectc aagtatagct gcaagaggat atatatcaac   5520
aagggttgaa atgggcgagg cggctgccat ttttatgact gccacaccac caggaacccg   5580
tgatgcgttt cctgactcta actcaccaat catggacaca gaagtggaag tcccagagag   5640
agcctggagc tcaggctttg attgggtgac agaccattct gggaaaacag tttggttcgt   5700
tccaagcgtg agaaacggaa atgaaatcgc agcctgtctg acaaaggctg gaaagcgggt   5760
catacagctc agcaggaaga cttttgagac agaatttcag aaaacaaaaa atcaagagtg   5820
ggactttgtc ataacaactg acatctcaga gatgggcgcc aacttcaagg ctgaccgggt   5880
catagactct aggagatgcc taaaaccagt catacttgat ggtgagagag tcatcttggc   5940
tgggcccatg cctgtcacgc atgctagtgc tgctcagagg agaggacgta taggcaggaa   6000
ccctaacaaa cctggagatg agtacatgta tggaggtggg tgtgcagaga ctgatgaagg   6060
ccatgcacac tggcttgaag caagaatgct tcttgacaac atctacctcc aggatggcct   6120
catagcctcg ctctatcggc ctgaggccga taaggtagcc gccattgagg gagagtttaa   6180
gctgaggaca gagcaaagga agaccttcgt ggaactcatg aagagaggaa accttccegt   6240
ctggctagcc tatcaggttg catctgccgg aataacttac acagacagaa gatggtgctt   6300
tgatggcaca accaacaaca ccataatgga agacagcgta ccagcagagg tgtgacaaaa   6360
gtatggagag aagagagtgc tcaaaccgag atggatggat gctagggtct gttcagacca   6420
tgcggccctg aagtcgttca aagaattcgc cgctggaaaa agaggagcgg ctttgggagt   6480
aatggaggcc ctgggaacac tgccaggaca catgacagag aggtttcagg aagccattga   6540
caacctcgcc gtgctcatgc gagcagagac tggaagcagg ccttataagg cagcggcagc   6600
ccaactgccg gagaccctag agaccattat gctcttaggt ttgctgggaa cagtttcact   6660
ggggatcttc ttcgtcttga tgcggaataa gggcatcggg aagatggcct ttgaatggt   6720
aacccttggg gccagtgcat ggctcatgtg gcttcggaa attgaaccag ccagaattgc   6780
atgtgtcctc attgttgtgt ttttattact ggtggtgctc ataccegage cagagaagca   6840
aagatctccc caagataacc agatggcaat tatcatcatg gtggcagtgg gccttctagg   6900
tttgataact gcaaacgaac ttggatggct ggaaagaaca aaaaatgaca tagctcatct   6960
aatgggaagg agaagaagaag gagcaaccat gggattctca atggacattg atctgcggcc   7020
agcctccgcc tgggcatatcg atgccgcatt gacaactctc atcaccccag ctgtccaaca   7080
tgcggtaacc acttcataca acaactactc cttaatggcg atgccacac aagctggagt   7140
gctgtttggc atgggcaaag ggatgccatt ttatgcatgg gacctttggag tcccgctgct   7200
aatgatgggt tgctattcac aattaacacc cctgactctg atagtacctta tcattctgct   7260
tgtggcgcac tacatgtact tgatcccagg cctacaagcg gcagcagcgc gtgctgccca   7320
gaaaaggaca gcagctggca tcatgaagaa tcccgttgtg gatggaatag tggtaactga   7380
cattgacaca atgacaatag ccccccaggt ggagaagaag atgggacaag tgttactcat   7440
agcagtagcc atctccagtg ctgtgctgct gcggaccgcc tggggatggg ggaggctgg   7500
agctctgatc acagcagcga cctccacctt gtgggaaggc tctccaaaca atactggaa   7560
ctcctctaca gccacctcac tgtgcaacat cttcagagga agctatctgg caggagcttc   7620
ccttatctat acagtgacga gaaacgctgg cctggttaag agacgtggag gtgggacggg   7680
agagactctg ggagagaagt ggaaagctcg tctgaatcag atgtcggecc tggagttcta   7740
ctcttataaa aagtcaggta tcactgaagt gtgtagagag gaggctcgcc gtgccctcaa   7800
ggatgagagtg gccacaggag gacatgccgt atcccgggga agtgcaaagc tcagatggtt   7860
ggtggagaga ggatatctgc agcccatgg gaaggttgtt gacctcggat gtggcagagg   7920
gggctggagc tattatgcceg ccaccatccg caaagtgcag gaggtgagag gatacacaaa   7980
gggaggtccc ggtcatgaag aacccatgct ggtgcaaagc tatgggtgga acatagttcg   8040
tctcaagagt ggagtggacg tcttccacat ggcggctgag ccgtgtgaca ctctgctgtg   8100
tgacataggt gagtcatcat ctagtcctga agtggaagag acacgaacac tcagagtgct   8160
ctctatgttg ggggactggc ttgaaaaaag accaggggcc ttctgtataa aggtgctgtg   8220
cccatacacc agcactatga tggaaaccat ggagcgactg caacgtaggc atggggagg   8280
attagtcaga gtgccattgt ctcgcaactc cacacatgag atgtactggg tctctgggc   8340
aaagagcaac atcataaaaa gtgtgtccac cacaagtcag ctcctcctgg gacgcatgga   8400
tggcccagg aggccagtga aatatgagga ggatgtgaac ctcggctggg gtacacgagc   8460
tgtggcaagc tgtgctgagg ctcctaacat gaaaatcatc ggcaggcgca ttgagagaat   8520
ccgcaatgaa catgcagaaa catggttttc tgatgaaaac caccatatca ggacatgggc   8580
ctaccatggg agctacgaag cccccacgca aggatcagcg tcttccctcg tgaacggggt   8640
tgttagactc ctgtcaaagc cttgggacgt ggtgactgga gttacaggaa tagcatgac   8700
tgacaccaca ccatacgcc aacaaagagt cttcaaagaa aaagttggaca ccagggtgcc   8760
agatccccaa gaaggcactc gccaggtaat gaacatagtc tcttcctggc tgtggaagga   8820
gctgggaaaa cgcaagcggc cacgcgtctg caccaaagaa gagtttatca acaaggtcgg   8880
cagcaatgca gcactgggag caatatttga gaggaaaaa gaatggaaga cggctgtga   8940
agctgtgaat gatccaaggt tttgggccct agtggataag gagagagaac accacctgag   9000
aggagagtgt cacagctgtg tgtacaacat gatggggaaa agagaaaga agccaaggaa   9060
gttcggaaaa gcaaaggta gccgcgccat ctggtacatg tggttgggag ccagattctt   9120
ggagtttgaa gcccttggat tcttgaacga ggaccattgg atgggaagag aaaactcagg   9180
aggtggagtc gaagggttag gattgcaaag acttggatac attctagaag aaatgaatcg   9240
gcaccaggga ggaaagatgt acgcagatga cactgctggc tgggacaccc gcattagtaa   9300
gtttgatctg gagaatgaag ctctgattac caaccaaatg gaggaaggc acagaactct   9360
ggcgttggcc gtgattaaat acacatacca aaacaaagtg gtgaaggttc tcagaccagc   9420
tgaaggagga aaacagttaa tggacatcat ttcaagacaa gaccagagag ggagtggaca   9480
agttgtcact tatgctctca acacattcac caactttggt gtgcagctta ccggaacat   9540
ggaagctgag gaagtgttag agatgcaaga cttatggtgct ttgaggggaa cagagaagt   9600
gaccagatgg ttgcagagca atggatggga tagactcaaa cgaatggcgg tcagtggaga   9660
tgactgcgtt gtgaagccaa tcgatgatag gtttgcacat gccctcaggt tcttgaatga   9720
catgggaaaa gttaggaaag acacacagga gtggaaccc tcgactggat ggagcaattg   9780
ggaagaagtc cgttctgct cccaccactt caacaagctg tacctcaagg atgggagatc   9840
cattgtggtc ccttgccgcc accaagatga actgattggc cgagctcgcg tctcaccagg   9900
```

```
ggcaggatgg agcatccggg agactgcctg tcttgcaaaa tcatatgcgc agatgtggca   9960
gctcctttat ttccacagaa gagaccttcg actgatggct aatgccattt gctcggctgt  10020
gccagttgac tgggtaccaa ctgggagaac cacctggtca atccatgaa agggagaatg   10080
gatgaccact gaggacatgc tcatggtgtg aatagagtg tggattgagg agaacgacca   10140
tatggaggac aagactcctg taacaaaatg dacagacatt ccctatctag gaaaaaggga   10200
ggacttatgg tgtggatccc ttataggca cagaccccgc accacttggg ctgaaaacat   10260
caaagacaca gtcaacatgg tgcgcaggat cataggtgat gaagaaaagt acatggacta  10320
tctatccacc caagtccgct acttgggtga ggaagggtcc acacccggag tgttgtaagc  10380
accaattttta gtgttgtcag gcctgctagt cagccacagt ttggggaaag ctgtgcagcc  10440
tgtaaccccc ccaggagaag ctgggaaacc aagctcatag tcaggccgag aacgccatgg  10500
cacgaagaa gccatgctgc ctgtgagccc ctcagaggac actgagtcaa aaaccccac   10560
gcgcttggaa gcgcaggatg ggaaaagaag gtggcgacct tccccaccct tcaatctggg  10620
gcctgaactg gagactagct gtgaatctcc agcagggga ctagtggtta gaggagaccc  10680
cccggaaaac gcaaaacagc atattgacgc tgggaaagac cagagactcc atgagtttcc  10740
accacgctgg ccgccaggca cagatcgccg aacagcggcg gccggtgtgg ggaaatccat  10800
ggttttct                                                            10807

SEQ ID NO: 12            moltype = DNA  length = 10794
FEATURE                  Location/Qualifiers
source                   1..10794
                         mol_type = genomic DNA
                         organism = Zika virus
SEQUENCE: 12
agttgttgat ctgtgtgagt cagactgcga cagttcgagt ctgaagcgag agctaacaac     60
agtatcaaca ggtttaattt ggatttggaa acgagagttt ctggtcatga aaaaccccaa    120
agaagaaatc cggaggatcc ggattgtcaa tatgctaaca cgcggagtag cccgtgtaaa    180
ccccttggga ggtttgaaga ggttgccagc cggacttctg ctgggtcatg gacccatcag    240
aatggttttg gcgatactag cctttttgag atttacagca atcaagccat cactgggcct    300
tatcaacaga tgggggttccg tgggaaaaa agaggctatg gaaataataa agaagttcaa    360
gaaagatctt gctgccatgt tgagaataat caatgacaga aaagagagga gagacgtgg    420
cgcagacacc agcatcggaa tcattggcct cctgctgact acagccatgg cagcagagat    480
cactagacgc gggagtgcat actacatgta cttggatagg agcatgccg ggaaggccat    540
ttcgtttgct accacattgg gagtgaacaa gtgccacgta cagatcatgg acctcgggca    600
catgtgtgac gccaccatga gttatgagtg ccctatgctg gatgagggag tggaaccaga    660
tgatgtcgat tgctggtgca acacgacatc aacttgggt gtgtacggaa cctgtcatca    720
caaaaaggt gaggcacggc gatctagaag agccgtgacg ctcccttctc actctacaag    780
gaagttgcaa acgcggtcgc agaccctggt agaatcaaga gaatacacga agcacttgat    840
caaggttgaa aactggatat tcaggaaccc cgggttgcg ctagtggccg ttgccattgc    900
ctggcttttg ggaagctcga cgagccaaaa agtcatatac ttggtcatga tactgctgat    960
tgccccggca tacagtatca ggtgcattgg agtcagcaat agagacttcg tggagggcat   1020
gtcaggtggg acctgggttg atgtttgtctt ggaacatgga ggctgcgtta ccgtgatggc   1080
acaggacaag ccaacagtcg acatagagtt ggtcacgacg acgttagta acatggccga    1140
ggtaagatcc tattgctacg aggcatcgat atccggacta gcttcggaca gtcgttgccc   1200
aacacaaggt gaagcctacc ttgacaagca atcagacact caatatgtct gcaaaagaac   1260
attagtggac agaggttggg aaacggttg tggactttt ggcaaaggga gcttggtgac    1320
atgtgccaag tttacgtgtt ctaagaagat gaccggggaag agcattcaac ggaaaatct    1380
ggagtatcgg ataatgctat cagtgcatgg ctcccagcat agcgggatga ttggatatga    1440
aactgacgaa gatagagcga agtcgaggt tacgcctaat tcaccaagag cggaagcaac    1500
cttgggaggc tttggaagct taggacttga ctgtgaaccca ggacaggcc ttgacttttc    1560
agatctgtat tacctgacca tgaacaataa gcattggttg gtgcacaaag agtggttca    1620
tgcatcccca ttgccttggc atgctggggc agacaccgga actccacact ggaacaacaa   1680
agaggcattg gtagaattca aggatgccca cgccaagagg caaacgtcg tcgttctggg   1740
gagccaggaa ggagccgttc acggtctct cgctggagct ctagaggctg agatggatgg   1800
tgcaaaggga aggctgttct ctggcatt gaaatgccgc ctaaaatgg acaagcttag    1860
attggaggc gtgtcatatt cctgtgcac tgcggcattc acattcacca agttcccagc    1920
tgaaacactg catggaacag tcagtggga ggtgcagtat gcagggacag atggaccctg    1980
caagatccca gtccagatgg cggtggacat gcagaccctg accccagttg aaggctgat    2040
aaccgccaac cccgtgatta ctgaaagcac tgagaactca aagatgatgt ggagctga    2100
cccaccatttt gggattctt acattgtcat aggagttggg gacaagaaa tcacccacca   2160
ctggcatagg agtggtagca ccatcgaaa gcatttgag gccactgtga gaggcgccaa    2220
gagaatggca gtcctgggg atacagcctg ggacttccga tcagtcgggg gtgtgttcaa    2280
ctcactgggg aagggcattc accagatttt tggagcagcc ttcaaatcac tgtttggagg   2340
aatgtcctgt ttctcacaga tcctcatagg cacgctgcta gtgtgttag gtttgaacac   2400
aaagaatgga tctatctccc tcacatgctt ggccctgggt ggagtgatga tcttcctctc   2460
cacggctgtt tctgctgacg tggggtgctc agtggacttc tcaaaaaagg aaacgagatg   2520
tggcacgggg gtattcatct ataatgatgt tgaagcctgg agggaccggt acaagtacca   2580
tcctgactcc ccccgcagat tggcagcagc agtcaagcag gctgggaag aggggatctg   2640
tgggatctca tccgtttcaa gaatgaaaa catcatgtgg aaatcagtag aaggggagct   2700
caatgctatc ctagaggaga tggagttca actgagcagt gttgtaaaaa a             2760
ccccatgtgg agaggtccac aaagattgcc agtgcctgtg aatgagctgc cccatggctg   2820
gaaagcctgg gggaaatcgt attttgttag gcgcaaag accaacaaca gttttgttgt    2880
cgacggtgac acactgaagg aatgtccgct tgagcacaga gcatgaata gttttcttgt    2940
ggaggatcac gggtttggag tcttccacac cagtgtctgc cttaaggtca gagaagatta   3000
ctcattagaa tgtgaccagg ccgtcatagg aacagctgta aagggaagag cgccgca      3060
cagtgatctg ggctattgga ttgaaagtga aaagaatgac acatggaggc tgaagagggc   3120
ccacctgatt gagatgaaaa catgtgaatg ccaaagtct cacacattgt ggacagatgc    3180
agtagaagaa agtgatctta tcatacccaa gtctttagct ggtccactca gccaccacaa    3240
caccagagag ggttacagaa cccaagtgaa agggccatgg cacagtgaag gcttgaaat    3300
ccggtttgag gaatgtccag gcaccaaggt ttacgtggag gagacatgcg gaactagagg   3360
```

```
accatctctg agatcaacta ctgcaagtgg aagggtcatt gaggaatggt gctgtaggga   3420
atgcacaatg cccccactat cgtttcgagc aaaagacggc tgctggtatg aatggagat   3480
aaggcccagg aaagaaccag agagcaactt agtgaggtca atggtgacag cggggtcaac   3540
cgatcatatg gaccacttct ctcttggagt gcttgtgatt ctactcatgg tgcaggaggg   3600
gttgaagaag agaatgacca caaagatcat catgagcaca tcaatggcag tgctggtagt   3660
catgatcttg ggaggatttt caatgagtga cctggccaag cttgtgatcc tgatgggtgc   3720
tactttcgca gaaatgaaca ctggaggaga tgtagctcac ttggcattgg tagcggcatt   3780
taaagtcaga ccagccttgc tggtctcctt cattttcaga gccaattgga caccccgtga   3840
gagcatgctg ctagccctgg cttcgtgtct tctgcaaact gcgatctctg ctcttgaagg   3900
tgacttgatg gtcctcatta atggatttgc tttggcctgg ttggcaattc gagcaatgac   3960
cgtgccacgc actgacaaca tcgctctacc aatcttggct gctctaacac cactagctcg   4020
aggcacactg ctcgtggcat ggagagcggg cctggctact tgtggaggga tcatgctcct   4080
ctccctgaaa gggaaaggta gtgtgaagaa gaacctgcca tttgtcatgg ccctgggatt   4140
gacagctgtg agggtagtag accctattaa tgtggtagga ctactgttac tcacaaggag   4200
tgggaagcgg agctgcccc ctagtgaagt tctcacagcc gttggcctga tatgtgcact   4260
ggccggaggg tttgccaagg cagacattga gatggctgga cccatggctg cagtaggctt   4320
gctaattgtc agctatgtgg tctcgggaaa gagtgtggac atgtacattg aaagagcagg   4380
tgacatcaca tgggaaaagg acgcggaagt cactggaagt agtcctcggc ttgacgtggc   4440
actggatgag agtggtgact tctccttggt agaggaagat ggtccaccca tgagagagat   4500
catactcaag gtggtcctga tggccatctg tggcatgaac ccaatagcta tacctttgc   4560
tgcaggagcc tggtatgtgt atgtgaagac tgggaaaagg agtggcgccc tctgggacgt   4620
gcctgctccc aaagaagtga agaaaggaga gaccacagat gagtgtgaga gagtgatgac   4680
tcgcagactg ctaggttcaa cacaggttgg agtgggagtc atgcaagagg gagtcttcca   4740
caccatgtgg cacgttacaa aaggagccgc actgaggagc ggtgagggaa gacttgatcc   4800
atactggggg gatgtcaagc aggacttggt gtcatactgt gggccttgga gttggatgc   4860
agcttgggat ggactcagcg aggtacagct ttttggcttg cctcccggag agagggccag   4920
aaacattcag accctgcctg gaatattcaa gacaaaggac ggggacatcg gagcagttgc   4980
tctggactac cctgcaggga cctcaggatc tccgatccta gacaaatgtg gaagagtgat   5040
aggactctat ggcaatgggg ttgtgatcaa gaatggaagc tatgttagtg ctataaccca   5100
gggaaagagg gaggaggaga ctccggttga atgtttcgaa ccctcgatgc tgaagaagaa   5160
gcagctaact gtcttggatc tgcatccagg agccgaaaa accaggagag ttcttcctga   5220
aatagtccgt gaagccataa aaagagact ccggacagtg atcttggcac caactagggt   5280
tgtcgctgct gagatggagg aggccttgag aggacttccg gtgcgttaca tgacaacagc   5340
agtcaacgtc acccattctg ggacagaaat cgttgatttg atgtgccatg ccactttcac   5400
ttcacgctta ctacaaccca tcagagtccc taattacaat ctcaacatca tggatgaagc   5460
ccacttcaca gacccctcaa gtatagctgc aagaggatac atatcaacaa gggttgaaat   5520
gggcgaggcg gctgccattt ttatgactgc cacaccacca ggaaccccgt gatgcgtttcc   5580
tgactctaac tcaccaatca tggacacaga agtggaagtc ccagagagag cctggagctc   5640
aggcttttgat tgggtgacag accattctgg gaaaacagtt tggttcgttc caagcgtgag   5700
aaacggaaat gaaatcgcag cctgtctgac aaaggctgga aagcgggtca tacagctcag   5760
caggaagact tttgagacag aatttcagaa aacaaaaaat caagagtggg actttgtcat   5820
aacaactgac atctcagaga tgggcgccaa cttcaaggct gaccgggtca tagactctag   5880
gagatgccta aaaccagtca tacttgatgg tgagagagtc atcttggctg ggcccatgcc   5940
tgtcacgcat gctagtgctg ctcagaggag aggacgtata ggcaggaacc ctaacaaacc   6000
tggagatgag tacatgtatg gaggtgggtg tgcagagact gatgaaggcc atgcacactg   6060
gcttgaagca agaatgcttc ttgacaacat ctacctccag gatggcctca tagcctcgct   6120
ctatcggcct gaggccgata aggtagccgc cattgaggga gagtttaagc tgaggacaga   6180
gcaaaggaag accttcgtgg aactcatgaa gagaggagac cttcccgtct ggctagccta   6240
tcaggttgca tctgccggaa taacttacac agacagaaga tggtgctttg atggcacaac   6300
caacaacacc ataatggaag acagtgtacc agcagaggtt tggacaaagt atggagaaa   6360
gagagtgctc aaaccgagat ggatggatgc tagggtctgt tcagaccatg cggccctgaa   6420
gtcgttcaaa gaattcgccg ctggaaaaag aggagcggct ttgggagtaa tggaggccct   6480
gggaacactg ccaggacaca tgacagagag gtttcaggaa gccattgaca acctcgccgt   6540
gctcatgcga gcagagactg gaagcaggcc ttataaggca gcggcagccc aactgccgga   6600
gaccctagag accattatgc tcttaggttt gctgggaaca gtttcactgg ggatccttct   6660
cgtcttgatg cggaataagg gcatcggaaa gatgggcttt ggaatggtaa cccttgggc   6720
cagtgcatgg ctcatgtggc tttcggaaat tgaaccagcc agaattgcat gtgtcctcat   6780
tgttgtgttt ttattactgg tggtgctcat acccgagcca gagaagcaaa gatctcccca   6840
agataaccag atggcaatta tcatcatggt ggcagtgggc cttctaggtt tgataactgc   6900
aaacgaactt ggatggctgg aaagaacaaa aaatgacata gctcatctaa tgggaaggag   6960
agaagaagga gcaaccatgg gattctcaat ggacattgat ctgcggccag cctccgcctg   7020
ggctatctat gccgcattga caactctcat caccccagct gtccaacatg cggtaaccac   7080
ttcatacaac aactactcct taatggcgat ggccacacaa gctggagtgc tgtttggcat   7140
gggcaaaggg atgccatttta tgcatgggga ccttggagtc ccgtgctaa tgtgggttg   7200
ctattcacaa ttaacacccc tgactctgat agtagctatc attctgcttg tggcgcacta   7260
catgtacttg atcccaggcc tacaagcggc agcagcgcgt gctgcccaga aaggacagc   7320
agctggcatc atgaagaatc cgttgtggga tggaatagtg gtaactgaca ttgacacaat   7380
gacaatagac ccccaggtgg agaagaagat gggacaagtg ttactcatag cagtagccat   7440
ctccagtgct gtgctgctgc ggaccgcctg gggatgggga gaggctggac ctctgatcag   7500
agcagcgacc tccaccttgt gggaaggctc tccaaacaaa tactggaact cctctacagc   7560
cacctcactg tgcaacatct tcagaggaag ctatctggca ggagcttccc ttatctatac   7620
agtgacgaga aacgctggcc tggttaagag acgtggaggt gggacgggag agactctggg   7680
agagaagtgg aaagctcgtc tgaatcagat gtcggccctg gagttctact cttataaaaa   7740
gtcaggtatc actgaagtgt gtagagaggca ggctgccgt gcctcaaggg atggagtggc   7800
cacaggagga catgccgtat cccgggaag tgcaaagatc atggtggg aggagagagg   7860
atatctgcag ccctatggga aggttgttga cctcggatgt ggcagagggg gctgagcta   7920
ttatgccgcc accatccgca aagtgcagga ggtgagagga tacacaaagg aggtcccgg   7980
tcatgaagaa cccatgctgg tgcaaagcta tgggtgaaac atagttcgtc tcaagagtgg   8040
agtggacgtc ttccacatgg cggctgagcc gtgtgacact ctgctgtgtg acataggtga   8100
```

-continued

```
gtcatcatct agtcctgaag tggaagagac acgaacactc agagtgctct ctatggtggg    8160
ggactggctt gaaaaaagac caggggcctt ctgtataaag gtgctgtgcc catacaccag    8220
cactatgatg gaaaccatgg agcgactgca acgtaggcat gggggaggat tagtcagagt    8280
gccattgtgt cgcaactcca cacatgagat gtactgggtc tctggggcaa agagcaacat    8340
cataaaaagt gtgtccacca caagtcagtc cctcctgggg cgcatggatg gccccaggag    8400
gccagtgaaa tatgaggagg atgtgaacct cggctcgggt acacgagctg tgcaagctg    8460
tgctgaggct cctaacatga aaatcatcgg caggcgcatt gagagaatcc gcaatgaaca    8520
tgcagaaaca tggtttcttg atgaaaacca cccatacagg acatgggcct accatggagt    8580
ctacgaagcc cccacgcaag gatcagcgtc ttccctcgtg aacgggggttg ttagactcct    8640
gtcaaagcct tgggacgtgg tgactggagt tacaggaata gccatgactg acaccacacc    8700
atacggccaa caaagagtct tcaaagaaaa agtggacacc agggtgccag atcccccaaga    8760
aggcactcgc caggtaatga acatagtctc ttcctggctg tggaaggagc tggggaaacg    8820
caagcggcca cgcgtctgca ccaaagaaga gtttatcaac aaggtgcgca gcaatgcagc    8880
actgggagca atatttgaag aggaaaaaga atggaagacg gctgtgaaga ctgtgaattga    8940
tccaaggttt tgggcccctag tggataggga gagagaacac cacctgagag gagagtgtca    9000
cagctgtgtg tacaacatga tgggaaaaag agaaaagaag caaggagagt tcgggaaagc    9060
aaaaggtagc cgcgccatct ggtacatgtg gttgggagcc agattcttgg agtttgaagc    9120
ccttgattc ttgaacgagg accattggat gggaagagaa aactcaggag gtggagtcga    9180
agggttagga ttgcaaagac ttggatacat tctagaagaa atgaatcggg caccaggagg    9240
aaagatgtac gcagatgaca ctgctggctg ggacacccgc attagtaagt ttgatctgga    9300
gaatgaagct ctgattacca accaaatgga ggaagggcac agaactctgg cgttggccgt    9360
gattaaatac acataccaaa acaaagtggt gaaggttctc agtccagctg aaggaggaaa    9420
aacagttatg gacatcattt caagacaaga ccagagaggg agtggacaag ttgtcactta    9480
tgctctcaac acattcacca acttggtggt gcagcttatc cggaacatgg aagctgagga    9540
agtgttagag atgcaagact tatggttgtt gaggaagcca gagaaagtga ccagatggtt    9600
gcagagcaat ggatgggata gactcaaacg aatggcgtc agtggagatg actgcgttgt    9660
gaagccaatc gatgataggt ttgcacatgc cctcaggttc ttgaatgaca tgggaaaagt    9720
taggaaaagac acacaggagt ggaaaccctc gactggatgg agcaattggg aagaagtccc    9780
gttctgctcc caccacttca acaagctgta cctcaaggat gggagatcca ttgtggtccc    9840
ttgccgccac caagatgaac tgattggccg agctcgcgtc tcaccaggag caggatggga    9900
catccgggag actgcctgtc ttgcaaaatc atatgcgcag atgtggcagc tcctttattt    9960
ccacagaaga gaccttcgac tgatggctaa tgccatttgc tcggctgtgc cagttgactg    10020
ggtaccaact gggagaacca cctggtcaat ccatggaaag ggagaatgga tgaccactga    10080
ggacatgctc atggtgtgga ataagtgtg gattgaggag aacgaccata tggaggacaa    10140
gactcctgta acaaaatgga cagacattcc ctatctagga aaaagggagg acttatggtg    10200
tggatcccctt ataggggaca gaccccgcac cacttgggct gaaaacatca agacacagt    10260
caacatggtc gcaggatca taggtgatga agaaaagtac atggactatc tatccacccaa    10320
agtccgctac ttggggtgagg aagggtccac acccggagtg ttgtaagcac caatttttagt    10380
gttgtcaggc ctgctagtca gccacagttt ggggaaagct gtgcagcctg taaccccccc    10440
aggagaagct gggaaaccaa gctcatagtc aggccgagaa cgccatggca cggaagaagc    10500
catgctgcct gtgagccct cagaggacac tgagtcaaaa accccacgc gcttggaagc    10560
gcaggatggg aaaagaaggt ggcgaccttc cccaccctttc aatctgggc ctgaactgga    10620
gactgctgt gaatctccag cagggggact aggttaga ggagaccccc cggaaaacgc    10680
aaaacagcat attgacgtgg gaaagaccag agactccatg agtttccacc acgctggccg    10740
ccaggcacag atcgccgaac ttcggcggcc ggtgtgggga aatccatggt ttct        10794
```

| | | |
|---|---|---|
| SEQ ID NO: 13 | moltype = DNA   length = 10617 | |
| FEATURE | Location/Qualifiers | |
| source | 1..10617 | |
| | mol_type = genomic DNA | |
| | organism = Zika virus | |

SEQUENCE: 13

```
agtatcaaca ggttttattt tggatttgga aacgagagtt tctggtcatg aaaaacccaa      60
aaaagaaatc cggaggattc cggattgtca atatgctaaa acgcggagta gcccgtgtga     120
gccccttgg gggcttgaag aggctgccag ccggacttct gctgggtcat gggcccatca     180
ggatggtctt ggcgattcta gccttttga gattcacggc aatcaagcca tcactgggtc     240
tcatcaatag atgggttca gtggggaaaa aagaggctat ggaataata aagaagttca     300
agaaagatct ggctgccatg ctgagaataa tcaatgctag gaaggagaag aagagacgag     360
gcgcagatac tagtgtcgga attgttggcc tcctgctgac cacagctatg gcagcggagg     420
tcactagacg tgggagtgca tactatatgt acttggacag aaacgacgct ggggaggcca     480
tatctttttcc aaccacattg gggatgaata agtgttatat acagatcatg gatcttggac     540
acatgtgtga tgccaccatg agctatgaat gccctatgct ggatgagggg gtggaaccag     600
atgacgtcga ttgttggtgc aacacgacgt caacttgggt tgtgtacgga acctgccatc     660
acaaaaaagg tgaagcacgg agatctagaa gagctgtgac gctccccta cattccacta     720
ggaagctgca aacgcggtcg caaacctggt tggaatcaag agaatacaca aagcacttga     780
ttagagtcga aaattggata ttcaggaacc ctggcttcgc gttagcagca gctgccatcg     840
cttggctttt gggaagctca acgagccaaa aagtcatata cttggtcatg atactgctga     900
ttgccccggc atacagcatc aggtgcatag gagtcagcaa tagggacttt gtggaggtca     960
tgtcaggtgg gacttgggtt gatgttgtct tggaacatgg aggttgtgtc accgtaatgg    1020
cacaggacaa accgactgtc gacatagagc tggttacaac aacagtcagc aaccatgcgg    1080
aggtaagatc ctactgctat gaggcatcaa tatcggacat ggcttcggac agccgctgcc    1140
caacacaagg tgaagcctac cttgacaagc aatcagacac tcaatatgtc tgcaaaaga    1200
cgttagtgga cagaggctgg ggaaatggat gtggacttt tggcaaggg agcctggtg    1260
catgcgctaa gtttgcatgc tccaagaaaa tgaccgggaa gagcatccag ccagagaatc    1320
tggagtaccg gataatgctg tcagttcatg gctcccagca cagtgggatg atcgttaatg    1380
acacaggaca tgaaactgat gagaatagag caaggttga gataacgccc aattcaccaa    1440
gagccgaagc caccctgggg ggttttgaa gcctaggact tgattgtgaa ccgaggacag    1500
gcctgacttt tcagatttg tattacttga ctatgaataa caagcactgg ttggttcaca    1560
aggagtggtt ccacgacatt ccattacctt ggcacgctgg gcagacacc ggaactccac    1620
```

```
actggaacaa caaagaagca ctggtagagt tcaaggacgc acatgccaaa aggcaaactg  1680
tcgtggttct agggagtcaa gaaggagcag ttcacacggc ccttgctgga gctctggagg  1740
ctgagatgga tggtgcaaag ggaaggctgt cctctggcca cttgaaatgt cgcctgaaaa  1800
tggataaact tagattgaag ggcgtgtcat actccttgtg taccgcagcg ttcacattca  1860
ccaagatccc ggctgaaaca ctgcacggga cagtcacagt ggaggtacag tacgcaggga  1920
cagatggacc ttgcaaggtt ccagctcaga tggcggtgga catgcaaact ctgaccccga  1980
ttgggaggtt gataaccgct aaccccgtaa tcactgaaag cactgagaac tctaagatga  2040
tgctggaact tgatccacca tttggggact cttacattgt cataggagtc ggggagaaga  2100
agatcaccca ccactggcac aggagtggca gcaccattgg aaaagcattt gaagccactg  2160
tgagaggtgc caagagaatg gcagtcttgg gagacacagc ctgggacttt ggatcagttg  2220
gaggcgctct caactcattg gcaagggca tccatcaaat ttttggagca gctttcaaat  2280
cattgtttgg aggaatgtcc tggttctcac aaattctcat tggaacgttg ctgatgtggt  2340
tgggtctgaa cacaaagaat ggatctattt cccttatgtg cttggcctta gggggagtgt  2400
tgatcttctt atccacagct gtctctgctg atgtgggtgg ctcggtggac ttctcaaaga  2460
aggagacgag atgcggtaca ggggtgttcg tctataacga cgttgaagcc tggagggaca  2520
ggtacaagta ccatcctgac tcccccgta gattggcagc agcagtcaag caagcctggg  2580
aagatggtat ctgtgggatc tcctctgttt caagaatgga aaacatcatg tggagatcag  2640
tagaagggga gctcaacgca atcctggaag agaatggaat tcaactgacg gtcgttgtgg  2700
gatctgtaaa aaaccccatg tggagaggtc cacagagatt gcccgtgcct gtgaacgagc  2760
tgccccacgg ctggaaggct tggggaaat cgtacttcgt cagagcagca aagacaaata  2820
acagctttgt cgtggatggt gacacactga aggaatgccc actcaaacat agagcatgga  2880
acagctttct tgtggaggat catgggttcg gggtatttca cactagtgtc tggctcaagg  2940
ttagagaaga ttattcatta gagtgtgatc cagccgttat tggaacagct gttaagggaa  3000
aggaggctgt acacagtgat ctaggctact ggattgagag tgagaagaat gacacatgga  3060
ggctgaagag ggcccatctg atcgagatga aaacatgtga atggccaaag tcccacacat  3120
tgtggacaga tggaatagaa gagagtgatc tgatcatacc caagtctta gctgggcac  3180
tcagccatca caataccaga gagggctaca ggacccaaat gaaagggcca tggcacagtg  3240
aagagcttga aattcggttt gaggaatgcc caggcactaa ggtccacgtg gaggaaacat  3300
gtggaacaag gaggaccatct ctgagatcaa ccactgcaag cggaagggtg atcgaggaat  3360
ggtgctgcag ggagtgcaca atgcccccac tgtcgttccg ggctaaagat ggctgttggt  3420
atggaatgga gataaggccc aggaaagaac cagaaagtaa cttagtaagg tcaatggtga  3480
ctgcaggatc aactgatcac atggatcact ctcccttgg agtgcttgtg attctgctca  3540
tggtgcagga agggctgaag aagagaatga ccacaaagat catcataagc acatcgatgg  3600
cagtgctggt agctatgatc ctgggaggat tttcaatgag tgacctggct aagcttgcaa  3660
ttttgatggg tgccaccttc gcggaaatga acactggaag agatgtaagt catctggcgc  3720
tgatagcggc attcaaagtc agaccagcgt tgctggtatc tttcatcttc agagctaatt  3780
ggacaccccg tgaaagcatg ctgctggcct tggcctcgtg tcttttgcaa actgcgatct  3840
ccgccttgga aggcgacctg atggttctca tcaatggttt tgctttggcc tggttggcaa  3900
tacgagcgat ggttgttcca cgcactgata acatcacctt gctgtctctga  3960
caccactggc ccggggcaca ctgcttgtgg cgtggagagc aggccttgct acttgcgggg  4020
ggtttatgct cctctctctg aagggaaaag gcagtgtgaa gaagaactta ccatttgtca  4080
tggccctggg actaaccgct gtgaggctgg tcgaccccat caacgtggtg ggactgctgt  4140
tgctcacaag gagtgggaag cggagcctgg ccctagcga agtactcaca gctgttggcc  4200
tgatatgcgc attggctgga gggttcgcca aggcagatat agagatggct gggcccatgg  4260
ccgcggtcgg tctgctaatt gtcagttacg tggtctcagg aaaagagtgtg gacatgtaca  4320
ttgaaagagc aggtgacatc acatgggaaa agatgcggaa agtcactgga aacagtcccc  4380
ggctcgatgt ggcgctagat gagagtggtg atttctccct ggtggaggat gacggtcccc  4440
ccatgagaga gatcatactc aaggtggtcc tgatgaccat ctgtggcatg aacccaatag  4500
ccataccctt tgcagctgga gcgtggtacg tatacgtgaa gactgaaaaa aggagtggtg  4560
ctctatggga tgtgcctgct cccaaggaag taaaaaggg ggagaccaca gatggagtgt  4620
acagagtaat gactcgtaga ctgctaggtt caacacaagt tggagtggga gttatgcaag  4680
aggggggtct ttcacactatg tggcacgtca caaaaggatc cgcgctgaga agcggtgaag  4740
ggagacttga tccatactgg ggagatgtca agcaggatct ggtgtcatac tgtggtccat  4800
ggaagctaga tgccgcctgg gacgggcaca gcgaggtgca gctcttggcc gtgccccccg  4860
gagagagagc gaggaacatc cagactctgc ccggaatatt taagacaaag gatgggaca  4920
ttggagcggt tgcgctggat taccccagcag gaacttcagg atctccaatc ctagacaagt  4980
gtgggagagt gataggactt tatggcaatg gggtcgtgat caaaaatggg agttatgtta  5040
gtgccatcac ccaagggagg agggaggaag agactcctgt tgagtgcttc gagccttcga  5100
tgctgaagaa gaagcagcta actgtcttag acttgcatcc tggagctggg aaaaccagga  5160
gagttcttcc tgaaatagtc cgtgaagcca taaaaacaag actccgtact gtgatcttag  5220
ctccaaccag ggttgtcgct gctgaaatgg aggaagccct tagagggctt ccagtgcgtt  5280
atatgacaac agcagtcaat gtcacccact ctggaacaga aatcgtcgac ttaatgtgcc  5340
atgccacctt cacttcacgt ctactacagc caatcagagt ccccaactat aatctgtata  5400
ttatgatga ggcccacttc acagatcctt caagtatcgc agcaagagga tacatttcaa  5460
caagggttga gatgggcgag gcggctgcca tcttcatgac cgccacgcca ccaggaaccc  5520
gtgacgcatt tccggactcc aactcaccaa ttatggacac cgaagtggaa gtcccagaga  5580
gagcctggag ctcaggcttt gattgggtga cggatcattc tggaaaaaca gtttggtttg  5640
ttccaagcgt gaggaacggc aatgagatcg cagcttgtct gacaaaggct ggaaaacggg  5700
tcatacagct cagcagaaag actttgaga cagagttcca gaaaacaaaa catcaagagt  5760
gggactttgt cgtgacaact gacatttcag agatgggcgc caactttaaa gctgaccgtg  5820
tcatagattc caggagatgc ctaaagccgg tcatacttga tggcgagaga gtcattctgg  5880
ctggacccat gcctgtcaca catgccagcg ctgcccagag gagggggcgc ataggcagga  5940
atcccaacaa acctggagat gagtatctgt atggaggtgg gtgcgcagag actgacgaag  6000
accatgcaca ctggcttgaa gcaagaatgc tccttgacaa tatttacctc caagatgcct  6060
tcatagcctc gctctatcga cctgaggccg acaaagtagc agccattgag ggagagttca  6120
agcttaggac ggagcaaagg aagactttg tggaactcat gaaaagagga gatcttcctg  6180
tttggctggc ctatcaggtt gcatctgccg gaataaccta cacagataga agatggtgct  6240
ttgatggcac gaccaacaac accataatgg aagacagtgt gccggcagag gtgtggacca  6300
gacacggaga gaaaagagtg ctcaaaccga ggtggatgga cgccagagtt tgttcagatc  6360
```

```
atgcggccct gaagtcattc aaggagtttg ccgctgggaa aagaggagcg gcttttggag   6420
tgatggaagc cctggaaca  ctgccaggac acatgacaga gagattccag gaagccattg   6480
acaacctcgc tgtgctcatg cgggcagaga ctggaagcag gccttacaaa gccgcggcgg   6540
cccaattgcc ggagaccota gagaccatta tgcttttggg gttgctggga acagtctcgc   6600
tgggaatctt tttcgtcttg atgaggaaca agggcatagg gaagatgggc tttggaatgg   6660
tgactcttgg ggccagcgca tggctcatgt ggctctcgga aattgagcca gccagaattg   6720
catgtgtcct cattgttgtg ttcctattgc tggtggtgct cataccgag ccagaaaagc    6780
aaagatctcc ccaggacaac caaatggcaa tcatcatcat ggtagcagta ggtcttctgg   6840
gcttgattac cgccaatgaa ctcggatggt tggagagaac aaagagtgac ctaagccatc   6900
taatgggaag gagagaggag ggggcaacca taggattctc aatggacatt gacctgcgc    6960
cagcctcagc ttgggccatc tatgctgcct tgacaacttt cattaccca  gccgtccaac   7020
atgcagtgac cacttcatac aacaactact ccttaatggc gatggccacg caagctggag   7080
tgttgtttgg tatgggcaaa gggatgccat tctacgcatg ggactttgga gtcccgctgc   7140
taatgatagg ttgctactca caattaacac ccctgaccag atcattttgc                7200
tcgtggcgca ctacatgtac ttgatcccag ggctgcaggc agcagctgcg cgtgctgccc   7260
agaagagaac ggcagctggc atcatgaaga accctgttgt ggatgaaata gtggtgactg   7320
acattgacac aatgacaatt gaccccccaag tggagaaaaa gatgggacag tgctactca    7380
tagcagtagc cgtctccagc gccatactgt cgccgaccgc atagtggctg gggaggctg    7440
gggccctgat cacagcggca acttccactt tgtgggaagg ctctccgaac aagtactgga   7500
actcctctac agccacttca ctgtgtaaca ttttaggg   aagttacttg gctggagctt     7560
ctctaatcta cacagtaaca agaaacgctg gcttggtcaa gagacgtggg ggtggaacag   7620
gagagaccct gggagagaaa tggaaggccc gcttgaacca gatgtcggcc ctggagttct   7680
actcctacaa aaagtcaggc atcaccgagg tgtgcagaga agaggccgc  cgcgccctca    7740
aggacggtgt ggcaacggga ggccatgctg tgtcccgagg aagtgcaaag ctgagatggt   7800
tggtggagcg gggatacctg cagccctatg aaaggtcat  tgatcttgga tgtggcagag   7860
ggggctggag ttactacgcc gccaccatcc gcaaagttca agaagtgaaa ggatacacaa   7920
aaggaggccc tggtcatgaa gaacccatgt tggtgcaaag ctatgggtgg aacatagtcc   7980
gtcttaagag tggggtggac gtctttcata tggcggctga gccgtgtgac acgttgctgt   8040
gtgacatagg tgagtcatca tctagtcctg aagtggaaga agcacggacg ctcagagtcc   8100
tctccatggt ggggattgg cttgaaaaaa gaccaggagc cttttgtata aaagtgttgt    8160
gcccatacac cagcactatg atggaaaccc tggagcgact gcagcgtagg tatgggggag   8220
gactggtcag agtgccactc tcccgcaact ctacacatga gatgtactgg gtctctggag   8280
cgaaagcaa  caccataaaa agtgtgtcca ccacgagcca gctcctcttg gggcgcatgg    8340
acgggcccag gaggccagtg aaatatgagg aggatgtgaa tctcggctct ggcacgcggg   8400
ctgtgttaag ctgcgctgaa gctcccaaca tgaagtcat  tggtaaccgc attgaaagga    8460
tccgcagtga gcacgcggaa acgtggttct ttgacgagaa ccacccatat aggacatggg   8520
cttaccatga aagctatgag gcccccacac aagggtcagc gtcctctcta ataaacgggg   8580
ttgtcaggct cctgtcaaaa ccctgggatg tggtgactgg agtcacagga atagccatga   8640
ccgacaccac accgtatggt cagcaaagag ttttcaagga aaaagtggac actagggtgc   8700
cagaccccca agaaggcact cgtcaggtta tgagcatggt ctcttcctgg ttgtggaaag   8760
agctaggcaa acacaaacgg ccacgagtct gtaccaaaga agatttcatc aacaaggttc   8820
gtagcaatgc agcattaggg gcaatatttg aagaggaaaa agagtggaag actgcagtgg   8880
aagctgtgaa cgatccaagg ttctgggctc tagtgcaaga ggaaagagg   caccacctga    8940
gaggagagtg ccagacctgt gtgtacaaca atgatggaaa aagagaaaag aaacaagggg    9000
aatttggaaa ggcaagggc  agccgcgcca tctggtatat gtggctaggg gctagatttc     9060
tagagttcga agcccttgga ttcttgaacg aggatcactg gatggggaga gagaactcag   9120
gaggtggtgt tgaagggctg ggattacaaa gactcggata tgtcctagaa gagatgagtc   9180
gcataccagg aggaaggatg tatgcagatg acactgctgg ctgggacacc cgcatcagca   9240
ggtttgatct ggagaatgaa gctctaatca ccaaccaaat ggagaaaggg cacgggcct    9300
tggcattggc cataatcaag tacacatacc aaaacaaagt ggtaaggtc  cttagaccag    9360
ctgaaaaagg gaagacagtt atggacatta tttcgagaca agaccaaagg gagcgcggac   9420
aagttgtcac ttacgctctt aacacattta ccaacctagt ggtgcaactc attcggaata   9480
tggaggctga ggaagttcta gagatgcaag acttgtggct gctgcggagg tcagagaaag   9540
tgaccaactg gttgcagagc aacggatggg ataggctcaa cgaatggca  gtcagtggag    9600
atgattcgt  tgtgaagcca attgatgata ggttgcaca  tgccctcagg ttcttgaatg     9660
atatgggaaa agttaggaag gacacacaag agtggaaacc ctcaactgga tgggacaact   9720
gggaagaagt tccgttttgc tcccaccact tcaacaagct ccatctcaag gacggggaggt  9780
ccattgtggt tccctgccgc caccaagatg aactgattgg ccgggcccgc gtctctccag   9840
gggcgggatg gagcatccgg gagactgctt gcctagcaaa atcatatgcg caaatgtggc   9900
agctccttta tttccacaga agggaccctc gactgatggc caatgccatt tgttcatctg  9960
tgccagttga ctgggttcca actgggagaa ctacctggtc aatccatgga aagggagaat  10020
ggatgaccac tgaagacatg cttgtggtgt ggaacagagt gtggattgag agaacgacc   10080
acatggaaga caagacccca gttacgaaat ggacagacat tccctatttg ggaaaaaggg  10140
aagacttgtg gtgtggatct ctcatagggc acagaccgc  caccacctgg gctgaaaaca    10200
ttaaaaacac agtcaacatg gtgcgcagga tcataggtga tgaagaaag  tacatggact    10260
acctatccac ccaagttcgc tacttgggtg aagaagggtc tacacctgga gtgctgtaag   10320
caccaatctt agtgttgtca ggcctgctag tcagccacag cttggggaaa gctgtgcagc   10380
ctgtgacccc cccaggagaa gctgggaaac caagcctata gtcaggccga gaacgccatg   10440
gcacggaaga agccatgctg cctgtgagcc cctcagagga cactgagtca aaaaacccca   10500
cgcgcttgga ggcgcaggat gggaaaagaa ggtggcgacc ttccccaccc ttcaatctgg   10560
ggcctgaact ggagatcagc tgtggatctc cagaagaggg actagtggtt agaggag      10617
SEQ ID NO: 14         moltype = AA  length = 498
FEATURE               Location/Qualifiers
source                1..498
                      mol_type = protein
                      organism = Zika virus
SEQUENCE: 14
IRCIGVSNRD FVEGMSGGTW VDVVLEHGGC VTVMAQDKPT VDIELVTTTV SNMAEVRSYC   60
```

```
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MIVNDENRAK VEVTPNSPRA EATLGGFGSL  180
GLDCEPRTGL DFSDLYYLTM NNKHWLVHKE WFHDIPLPWH AGADTGTPHW NNKEALVEFK  240
DAHAKRQTVV VLGSQEGAVH TALAGALEAE MDGAKGRLFS GHLKCRLKMD KLRLKGVSYS  300
LCTAAFTFTK VPAETLHGTV TVEVQYAGTD GPCKVPAQMA VDMQTLTPVG RLITANPVIT  360
ESTENSKMML ELDPPFGDSY IVIGVGDKKI THHWHRSGST IGKAFEATVR GAKRMAVLGD  420
TAWDFGSVGG VFNSLGKGIH QIFGAAFKSL FGGMSWFSQI LIGTLLVWLG LNTKNGSISL  480
TCLALGGVMI FLSTAVSA                                                498

SEQ ID NO: 15          moltype = AA  length = 498
FEATURE                Location/Qualifiers
source                 1..498
                       mol_type = protein
                       organism = Zika virus
SEQUENCE: 15
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MIVNDENRAK VEVTPNSPRA EATLGGFGSL  180
GLDCEPRTGL DFSDLYYLTM NNKHWLVHKE WFHDIPLPWH SGADTETPHW NNKEALVEFK  240
DAHAKRQTVV VLGSQEGAVH TALAGALEAE MDGAKGRLSS GHLKCRLKMD KLRLKGVSYS  300
LCTAAFTFTK VPAETLHGTV TVEVQYAGRD GPCKVPAQMA VDMQTLTPVG RLITANPVIT  360
ESTENSKMML ELDPPFGDSY IVIGVGDKKI THHWHRSGSI IGKAFEATVR GAKRMAVLGD  420
TAWDFGSVGG VFNSLGKGIH QIFGAAFKSL FGGMSWFSQI LIGTLLVWLG LNTKNGSISL  480
TCLALGGVMI FLSTAVSA                                                498

SEQ ID NO: 16          moltype = AA  length = 504
FEATURE                Location/Qualifiers
REGION                 156..162
                       note = misc_feature - X=any amino acid
source                 1..504
                       mol_type = protein
                       organism = Zika virus
SEQUENCE: 16
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MIVNDXXXXX XXNRAEVEVT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLFSGHLK CRLKMDKLRL  300
KGVSYSLCTA AFTFTKVPAE TLHGTVTVEV QYAGTDGPCK VPAQMAVDMQ TLTPVGRLIT  360
ANPVITESTE NSKMMLELDP PFGDSYIVIG VGDKKITHHW HRSGSTIGKA FEATVRGAKR  420
MAVLGDTAWD FGSVGGVFNS LGKGIHQIFG AAFKSLFGGM SWFSQILIGT LLVWLGLNTK  480
NGSISLTCLA LGGVMIFLST AVSA                                         504

SEQ ID NO: 17          moltype = AA  length = 504
FEATURE                Location/Qualifiers
REGION                 152..156
                       note = misc_feature - X=any amino acid
source                 1..504
                       mol_type = protein
                       organism = Zika virus
SEQUENCE: 17
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MXXXXXGHET DENRAKVEVT PNSPRAEATL  180
GGFGSLGLDC EPRTGLDFSD LYYLTMNNKH RLVRKEWFHD IPLPWHAGAD TGTPHWNNKE  240
ALVEFKDAHA KRQTVVVLGS QEGAVHTALA GALEAEMDGA KGRLFSGHLK CRLKMDKLRL  300
KGVSYSLCTA AFTFTKVPAE TLHGTVTVEV QYAGTDGPCK VPAQMAVDMQ TLTPVGRLIT  360
ANPVITESTE NSKMMLELDP PFGDSYIVIG VGDKKITHHW LKKGSSIGKA FEATVRGAKR  420
MAVLGDTAWD FGSVGGVFNS LGKGVHQIFG AAFKSLFGGM SWFSQILIGT LLVWLGLNTK  480
NGSISLTCLA LGGVMIFLST AVSA                                         504

SEQ ID NO: 18          moltype = AA  length = 504
FEATURE                Location/Qualifiers
source                 1..504
                       mol_type = protein
                       organism = Zika virus
SEQUENCE: 18
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MIVNDIGHET DENRAKVEVT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLFSGHLK CRLKMDKLRL  300
KGVSYSLCTA AFTFTKVPAE TLHGTVTVEV QYAGTDGPCK VPAQMAVDMQ TLTPVGRLIT  360
ANPVITESTE NSKMMLELDP PFGDSYIVIG VGDKKITHHW HRSGSTIGKA FEATVRGAKR  420
MAVLGDTAWD FGSVGGVFNS LGKGIHQIFG AAFKSLFGGM SWFSQILIGT LLVWLGLNTK  480
NGSISLTCLA LGGVMIFLST AVSA                                         504

SEQ ID NO: 19          moltype = AA  length = 504
FEATURE                Location/Qualifiers
```

```
source                      1..504
                            mol_type = protein
                            organism = Zika virus
SEQUENCE: 19
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIVNDIGHET DENRAKVEVT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLFSGHLK CRLKMDKLRL   300
KGVSYSLCTA AFTFTKVPAE TLHGTVTVEV QYAGTDGPCK VPAQMAVDMQ TLTPVGRLIT   360
ANPVITESTE NSKMMLELDP PFGDSYIVIG VGDKKITHHW HRSGSTIGKA FEATVRGAKR   420
MAVLGDTAWD FGSVGGVFNS LGKGIHQIFG AAFKSLFGGM SWFSQILIGT LLVWLGLNTK   480
NGSISLTCLA LGGVMIFLST AVSA                                         504

SEQ ID NO: 20               moltype = AA   length = 504
FEATURE                     Location/Qualifiers
source                      1..504
                            mol_type = protein
                            organism = Zika virus
SEQUENCE: 20
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIVNDIGHET DENRAKVEVT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLFSGHLK CRLKMDKLRL   300
KGVSYSLCTA AFTFTKVPAE TLHGTVTVEV QYAGTDGPCK VPAQMAVDMQ TLTPVGRLIT   360
ANPVITESTE NSKMMLELDP PFGDSYIVIG VGDKKITHHW HRSGSTIGKA FEATVRGAKR   420
MAVLGDTAWD FGSVGGVFNS LGKGVHQIFG AAFKSLFGGM SWFSQILIGT LLVWLGLNTK   480
NGSISLTCLA LGGVMIFLST AVSA                                         504

SEQ ID NO: 21               moltype = AA   length = 504
FEATURE                     Location/Qualifiers
source                      1..504
                            mol_type = protein
                            organism = Zika virus
SEQUENCE: 21
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIVNDIGHET DENRAKVEVT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLFSGHLK CRLKMDKLRL   300
KGVSYSLCTA AFTFTKVPAE TLHGTVTVEV QYAGTDGPCK VPAQMAVDMQ TLTPVGRLIT   360
ANPVITESTE NSKMMLELDP PFGDSYIVIG VGDKKITHHW HRSGSTIGKA FEATVRGAKR   420
MAVLGDTAWD FGSVGGVFNS LGKGVHQIFG AAFKSLFGGM SWFSQILIGT LLVWLGLNTK   480
NGSISLTCLA LGGVMIFLST AVSA                                         504

SEQ ID NO: 22               moltype = AA   length = 504
FEATURE                     Location/Qualifiers
source                      1..504
                            mol_type = protein
                            organism = Zika virus
SEQUENCE: 22
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIVNDTGHET DENRAKVEVT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLFSGHLK CRLKMDKLRL   300
KGVSYSLCTA AFTFTKVPAE TLHGTVTVEV QYAGTDGPCK VPAQMAVDMQ TLTPVGRLIT   360
ANPVITESTE NSKMMLELDP PFGDSYIVIG VGDKKITHHW HRSGSTIGKA FEATVRGAKR   420
MAVLGDTAWD FGSVGGVFNS LGKGIHQIFG AAFKSLFGGM SWFSQILIGT LLVWLGLNTK   480
NGSISLTCLA LGGVMIFLST AVSA                                         504

SEQ ID NO: 23               moltype = AA   length = 504
FEATURE                     Location/Qualifiers
source                      1..504
                            mol_type = protein
                            organism = Zika virus
SEQUENCE: 23
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MTVNDIGYET DENRAKVEVT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGKLFSGHLK CRLKMDKLRL   300
KGVSYSLCTA AFTFTKVPAE TLHGTVTVEV QYAGTDGPCK IPVQMAVDMQ TLTPVGRLIT   360
ANPVITESTE NSKMMLELDP PFGDSYIVIG VGDKKITHHW HRSGSTIGKA FEATVRGAKR   420
MAVLGDTAWD FGSVGGVFNS LGKGIHQIFG AAFKSLFGGM SWFSQILIGT LLVWLGLNTK   480
NGSISLTCLA LGGVMIFLST AVSA                                         504

SEQ ID NO: 24               moltype = AA   length = 504
```

```
FEATURE                 Location/Qualifiers
source                  1..504
                        mol_type = protein
                        organism = Zika virus
SEQUENCE: 24
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MTVNDIGYET DENRAKVEVT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGKLFSGHLK CRLKMDKLRL  300
KGVSYSLCTA AFTFTKVPAE TLHGTVTVEV QYAGTDGPCK IPVQMAVDMQ TLTPVGRLIT  360
ANPVITESTE NSKMMLELDP PFGDSYIVIG VGDKKITHHW HRSGSTIGKA FEATVRGAKR  420
MAVLGDTAWD FGSVGGVFNS LGKGIHQIFG AAFKSLFGGM SWFSQILIGT LLVWLGLNTK  480
NGSISLTCLA LGGVMIFLST AVSA                                        504

SEQ ID NO: 25           moltype = AA  length = 504
FEATURE                 Location/Qualifiers
source                  1..504
                        mol_type = protein
                        organism = Zika virus
SEQUENCE: 25
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MIVNDTGYET DENRAKVEVT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGKLFSGHLK CRLKMDKLRL  300
KGVSYSLCTA AFTFTKVPAE TLHGTVTVEV QYAGTDGPCK IPVQMAVDMQ TLTPVGRLIT  360
ANPVITESTE NSKMMLELDP PFGDSYIVIG VGDKKITHHW HRSGSTIGKA FEATVRGAKR  420
MAVLGDTAWD FGSVGGVFNS LGKGIHQIFG AAFKSLFGGM SWFSQILIGT LLVWLGLNTK  480
NGSISLTCLA LGGVMIFLST AVSA                                        504

SEQ ID NO: 26           moltype = AA  length = 504
FEATURE                 Location/Qualifiers
source                  1..504
                        mol_type = protein
                        organism = Zika virus
SEQUENCE: 26
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MIVNDIGHET DENRAKVEVT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLFSGHLK CRLKMDKLRL  300
KGVSYSLCTA VCTAAKVPAE TLHGTVTVEV QYAGTDGPCK VPAQMAVDMQ TLTPVGRLIT  360
ANPVITESTE NSKMMLELDP PFGDSYIVIG VGDKKITHHW HRSGSTIGKA FEATVRGAKR  420
MAVLGDTAWD FGSVGGVFNS LGKGIHQIFG AAFKSLFGGM SWFSQILIGT LLVWLGLNTK  480
NGSISLTCLA LGGVMIFLST AVSA                                        504

SEQ ID NO: 27           moltype = AA  length = 500
FEATURE                 Location/Qualifiers
source                  1..500
                        mol_type = protein
                        organism = Zika virus
SEQUENCE: 27
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MIGYETDEDR AKVEVTPNSP RAEATLGGFG  180
SLGLDCEPRT GLDFSDLYYL TMNNKHWLVH KEWFHDIPLP WHAGADTGTP HWNNKEALVE  240
FKDAHAKRQT VVVLGSQEGA VHTALAGALE AEMDGAKGRL FSGHLKCRLK MDKLRLKGVS  300
YSLCTAAFTF TKVPAETLHG TVTVEVQYAG TDGPCKIPVQ MAVDMQTLTP VGRLITANPV  360
ITESTENSKM MLELDPPFGD SYIVIGVGDK KITHHWHRSG STIGKAFEAT VRGAKRMAVL  420
GDTAWDFGSV GGVFNSLGKG IHQIFGAAFK SLFGGMSWFS QILIGTLLVW LGLNTKNGSI  480
SLTCLALGGV MIFLSTAVSA                                             500

SEQ ID NO: 28           moltype = AA  length = 500
FEATURE                 Location/Qualifiers
source                  1..500
                        mol_type = protein
                        organism = Zika virus
SEQUENCE: 28
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MIGYETDEDR AKVEVTPNSP RAEATLGGFG  180
SLGLDCEPRT GLDFSDLYYL TMNNKHWLVH KEWFHDIPLP WHAGADTGTP HWNNKEALVE  240
FKDAHAKRQT VVVLGSQEGA VHTALAGALE AEMDGAKGRL FSGHLKCRLK MDKLRLKGVS  300
YSLCTAAFTF TKVPAETLHG TVTVEVQYAG TDGPCKIPVQ MAVDMQTLTP VGRLITANPV  360
ITESTENSKM MLELDPPFGD SYIVIGVGDK KITHHWHRSG STIGKAFEAT VRGAKRMAVL  420
GDTAWDFGSV GGVFNSLGKG IHQIFGAAFK SLFGGMSWFS QILIGTLLVW LGLNTKNGSI  480
SLTCLALGGV MIFLSTAVSA                                             500
```

```
SEQ ID NO: 29              moltype = AA  length = 500
FEATURE                    Location/Qualifiers
source                     1..500
                           mol_type = protein
                           organism = Zika virus
SEQUENCE: 29
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIGYETDEDR AKVEVTPNSP RAEATLGSFG   180
SLGLDCEPRT GLDFSDLYYL TMNNKHWLVH KEWFHDIPLP WHAGADTGTP HWNNKEALVE   240
FKDAHAKRQT VVVLGSQEGA VHTALAGALE AEMDGAKGRL FSGHLKCRLK MDKLRLKGVS   300
YSLCTAAFTF TKVPAETLHG TVTVEVQYAG TDGPCKIPVQ MAVDMQTLTP VGRLITANPV   360
ITESTENSKM MLELDPPFGD SYIVIGVGDK KITHHWHRSG STIGKAFEAT VRGAKRMAVL   420
GDTAWDFGSV GGVFNSLGKG IHQIFGAAFK SLFGGMSWFS QILIGTLLVW LGLNTKNGSI   480
SLTCLALGGV MIFLSTAVSA                                               500

SEQ ID NO: 30              moltype = AA  length = 504
FEATURE                    Location/Qualifiers
source                     1..504
                           mol_type = protein
                           organism = Zika virus
SEQUENCE: 30
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHTGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITEGTE NSKMMLELDP PFGDSYIVIG VGEKKITHHW HRSGSTIGKA FEATVRGAKR   420
MAVLGDTAWD FGSVGGVLNS LGKGIHQIFG AAFKSLFGGM SWFSQILIGT LLMWLGLNTK   480
NGSISLMCLA LGGVLIFLST AVSA                                          504

SEQ ID NO: 31              moltype = AA  length = 504
FEATURE                    Location/Qualifiers
source                     1..504
                           mol_type = protein
                           organism = Zika virus
SEQUENCE: 31
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHTGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITEGTE NSKMMLELDP PFGDSYIVIG VGEKKITHHW HRSGSTIGKA FEATVRGAKR   420
MAVLGDTAWD FGSVGGVLNS LGKGIHQIFG AAFKSLFGGM SWFSQILIGT LLMWLGLNTK   480
NGSISLMCLA LGGVLIFLST AVSA                                          504

SEQ ID NO: 32              moltype = AA  length = 504
FEATURE                    Location/Qualifiers
source                     1..504
                           mol_type = protein
                           organism = Zika virus
SEQUENCE: 32
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                          504

SEQ ID NO: 33              moltype = AA  length = 504
FEATURE                    Location/Qualifiers
source                     1..504
                           mol_type = protein
                           organism = Zika virus
SEQUENCE: 33
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                          504
```

```
SEQ ID NO: 34              moltype = AA  length = 504
FEATURE                    Location/Qualifiers
source                     1..504
                           mol_type = protein
                           organism = Zika virus
SEQUENCE: 34
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 35              moltype = AA  length = 504
FEATURE                    Location/Qualifiers
source                     1..504
                           mol_type = protein
                           organism = Zika virus
SEQUENCE: 35
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 36              moltype = AA  length = 504
FEATURE                    Location/Qualifiers
source                     1..504
                           mol_type = protein
                           organism = Zika virus
SEQUENCE: 36
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 37              moltype = AA  length = 504
FEATURE                    Location/Qualifiers
source                     1..504
                           mol_type = protein
                           organism = Zika virus
SEQUENCE: 37
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 38              moltype = AA  length = 504
FEATURE                    Location/Qualifiers
source                     1..504
                           mol_type = protein
                           organism = Zika virus
SEQUENCE: 38
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
```

```
NGSISLMCLA LGGVLIFLST AVSA                                              504

SEQ ID NO: 39           moltype = AA  length = 504
FEATURE                 Location/Qualifiers
source                  1..504
                        mol_type = protein
                        organism = Zika virus
SEQUENCE: 39
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                         504

SEQ ID NO: 40           moltype = AA  length = 504
FEATURE                 Location/Qualifiers
source                  1..504
                        mol_type = protein
                        organism = Zika virus
SEQUENCE: 40
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                         504

SEQ ID NO: 41           moltype = AA  length = 504
FEATURE                 Location/Qualifiers
source                  1..504
                        mol_type = protein
                        organism = Zika virus
SEQUENCE: 41
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                         504

SEQ ID NO: 42           moltype = AA  length = 504
FEATURE                 Location/Qualifiers
source                  1..504
                        mol_type = protein
                        organism = Zika virus
SEQUENCE: 42
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                         504

SEQ ID NO: 43           moltype = AA  length = 504
FEATURE                 Location/Qualifiers
source                  1..504
                        mol_type = protein
                        organism = Zika virus
SEQUENCE: 43
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
```

```
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 44           moltype = AA  length = 504
FEATURE                 Location/Qualifiers
source                  1..504
                        mol_type = protein
                        organism = Zika virus
SEQUENCE: 44
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 45           moltype = AA  length = 504
FEATURE                 Location/Qualifiers
source                  1..504
                        mol_type = protein
                        organism = Zika virus
SEQUENCE: 45
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 46           moltype = AA  length = 504
FEATURE                 Location/Qualifiers
source                  1..504
                        mol_type = protein
                        organism = Zika virus
SEQUENCE: 46
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 47           moltype = AA  length = 504
FEATURE                 Location/Qualifiers
source                  1..504
                        mol_type = protein
                        organism = Zika virus
SEQUENCE: 47
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 48           moltype = AA  length = 504
FEATURE                 Location/Qualifiers
source                  1..504
                        mol_type = protein
                        organism = Zika virus
SEQUENCE: 48
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
```

```
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 49           moltype = AA  length = 504
FEATURE                 Location/Qualifiers
source                  1..504
                        mol_type = protein
                        organism = Zika virus
SEQUENCE: 49
IRCIGVSNRD FVEGMSGGTW VDIVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 50           moltype = AA  length = 504
FEATURE                 Location/Qualifiers
source                  1..504
                        mol_type = protein
                        organism = Zika virus
SEQUENCE: 50
IRCIGVSNRD FVEGMSGGTW VDIVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 51           moltype = AA  length = 504
FEATURE                 Location/Qualifiers
source                  1..504
                        mol_type = protein
                        organism = Zika virus
SEQUENCE: 51
IRCIGVSNRD FVEGMSGGTW VDVVLEHGGC VTVMAQDKPT VDIELVTTTV SNMAEIRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 52           moltype = AA  length = 504
FEATURE                 Location/Qualifiers
source                  1..504
                        mol_type = protein
                        organism = Zika virus
SEQUENCE: 52
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGT QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 53           moltype = AA  length = 504
FEATURE                 Location/Qualifiers
source                  1..504
                        mol_type = protein
                        organism = Zika virus
SEQUENCE: 53
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGT QEGAVHTALA GALEAEMDGA KGRLSSGHLK CRLKMDKLRL    300
```

```
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 54           moltype = AA  length = 504
FEATURE                 Location/Qualifiers
source                  1..504
                        mol_type = protein
                        organism = Zika virus
SEQUENCE: 54
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGARR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 55           moltype = AA  length = 504
FEATURE                 Location/Qualifiers
source                  1..504
                        mol_type = protein
                        organism = Zika virus
SEQUENCE: 55
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLVWLGLNTK    480
NGSISLMCLA LGGVLIFLST AVSA                                          504

SEQ ID NO: 56           moltype = AA  length = 504
FEATURE                 Location/Qualifiers
source                  1..504
                        mol_type = protein
                        organism = Zika virus
SEQUENCE: 56
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNAK    480
NGSISLMCLA LGGVLIFLST AVSA                                          504

SEQ ID NO: 57           moltype = AA  length = 504
FEATURE                 Location/Qualifiers
source                  1..504
                        mol_type = protein
                        organism = Zika virus
SEQUENCE: 57
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNAK    480
NGSISLMCLA LGGVLIFLST AVSA                                          504

SEQ ID NO: 58           moltype = AA  length = 504
FEATURE                 Location/Qualifiers
source                  1..504
                        mol_type = protein
                        organism = Zika virus
SEQUENCE: 58
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
```

```
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDTQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 59            moltype = AA  length = 504
FEATURE                  Location/Qualifiers
source                   1..504
                         mol_type = protein
                         organism = Zika virus
SEQUENCE: 59
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNGTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 60            moltype = AA  length = 504
FEATURE                  Location/Qualifiers
source                   1..504
                         mol_type = protein
                         organism = Zika virus
SEQUENCE: 60
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLAQMAVDMQ   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 61            moltype = AA  length = 504
FEATURE                  Location/Qualifiers
source                   1..504
                         mol_type = protein
                         organism = Zika virus
SEQUENCE: 61
IRCIGVSNRD FVEGMSGGTW VDVVLEHGGC VTVMAQDKPA VDIELVTTTV SNMAEVRSYC   60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLVWLGLNTK   480
NGSISLTCLA LGGVLIFLST AVSA                                         504

SEQ ID NO: 62            moltype = AA  length = 504
FEATURE                  Location/Qualifiers
source                   1..504
                         mol_type = protein
                         organism = Zika virus
SEQUENCE: 62
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLVWLGLNTK   480
NGSISLTCLA LGGVLIFLST AVSA                                         504

SEQ ID NO: 63            moltype = AA  length = 504
FEATURE                  Location/Qualifiers
source                   1..504
                         mol_type = protein
                         organism = Zika virus
SEQUENCE: 63
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
```

```
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLVWLGLNTK    480
NGSISLTCLA LGGVLIFLST AVSA                                          504

SEQ ID NO: 64           moltype = AA  length = 504
FEATURE                 Location/Qualifiers
source                  1..504
                        mol_type = protein
                        organism = Zika virus
SEQUENCE: 64
IRCIGVSNRD FVEGMSGGTW VDVVLEHGGC VTVMAQDKPT VDIELVSTTV SNMAEVRSYC     60
YEATISDIAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTAVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 65           moltype = AA  length = 504
FEATURE                 Location/Qualifiers
REGION                  1..504
                        note = misc_feature - X=any amino acid
source                  1..504
                        mol_type = protein
                        organism = Zika virus
SEQUENCE: 65
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDXGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGDKKITHHW XRSGSTIGKA FEATVRGAKR    420
MAVLGDTAWD FGSVGGALNS LGKGIHQIFG AAFKSLFGGM SWFSQILIGT LLVWLGLNTK    480
NGSISLTCLA LGGVLIFLST AVSA                                          504

SEQ ID NO: 66           moltype = AA  length = 504
FEATURE                 Location/Qualifiers
source                  1..504
                        mol_type = protein
                        organism = Zika virus
SEQUENCE: 66
IRCIGVSNRD FVEGMSGGTW VDVVLEHGGC VTAMAQDKPT VDIELVTTTV SNMAEVRSYC     60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MLVNDTGHET DENRAKVEIT PNSPRAEATL    180
GGFGSLGLDC EPRTGLDFSD LYYLTMNNKH WLAHKEWFHD IPLPWHAGAA TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TVDGTVTVEG QYGGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIIG AAFKSLFGGM SWFSQILIGT LLVWLGLNTK    480
NGSISLMCLA LGGVLIFLST AVSG                                          504

SEQ ID NO: 67           moltype = AA  length = 504
FEATURE                 Location/Qualifiers
source                  1..504
                        mol_type = protein
                        organism = Zika virus
SEQUENCE: 67
IRCIGVSNRD FVEGMSGGTW VDVVLEHGGC VTAMAQDKPT VDIELVTTTV SNMAEVRSYC     60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLAHKEWFHD IPLPWHAGAA TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TVDGTVTVEG QYGGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIIG AAFKSLFGGM SWFSQILIGT LLVWLGLNTK    480
NGSISLMCLA LGGVLIFLST AVSG                                          504

SEQ ID NO: 68           moltype = AA  length = 504
FEATURE                 Location/Qualifiers
source                  1..504
                        mol_type = protein
                        organism = Zika virus
SEQUENCE: 68
```

```
ISCIGVSNRD LVEGMSGGTW VDVVLEHGGC VTEMAQDKPT VDIELVTMTV SNMAEVRSYC    60
YEASLSDMAS ASRCPTQGEP SLDKQSDTQS VCKRTLGDRG WGNGCGIFGK GSLVTCSKFT   120
CCKKMPGKSI QPENLEYRIM LPVHGSQHSG MIVNDIGHET DENRAKVEVT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLFSGHLK CRLKMDKLRL   300
KGVSYSLCTA AFTFTKVPAE TLHGTVTVEV QSAGTDGPCK VPAQMAVDMQ TLTPVGRLIT   360
ANPVITESTE NSKMMLELDP PFGDSYIVIG VGDKKITHHW HRSGSTIGKA FEATVRGAKR   420
MAVLGDTAWD FGSVGGVFNS LGKGIHQIFG AAFKSLFGGM SWFSQILIGT LLVWLGLNTK   480
NGSISLTCLA LGGVMIFLST AVSA                                         504

SEQ ID NO: 69            moltype = AA  length = 498
FEATURE                  Location/Qualifiers
source                   1..498
                         mol_type = protein
                         organism = Zika virus
SEQUENCE: 69
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIVNDENRAK VEVTPNSPRA EATLGGFGSL   180
GLDCEPRTGL DFSDLYYLTM NNKHWLVHKE WFHDIPLPWH AGADTGTPHW NNKEALVEFK   240
DAHAKRQTVV VLGSQEGAVH TALAGALEAE MDGAKGRLFS GHLKCRLKMD KLRLKGVSYS   300
LCTAAFTFTK VPAETLHGTV TVEVQYAGTD GPCKVPAQMA VDMQTLTPVG RLITANPVIT   360
ESTENSKMML ELDPPFGDSY IVIGVGDKKI THHWHRSGST IGKAFEATVR GAKRMAVLGD   420
TAWDFGSVGG VFNSLGKGIH QIFGAAFKSL FGGMSWFSQI LIGTLLVWLG LNTKNGSISL   480
TCLALGGVMI FLSTAVSA                                                498

SEQ ID NO: 70            moltype = DNA  length = 26
FEATURE                  Location/Qualifiers
misc_feature             1..26
                         note = synthetic polynucleotide
misc_feature             1..26
                         note = n=inosine
source                   1..26
                         mol_type = other DNA
                         organism = synthetic construct
SEQUENCE: 70
ncncncncnc ncncncncnc ncncnc                                        26

SEQ ID NO: 71            moltype = AA  length = 11
FEATURE                  Location/Qualifiers
REGION                   1..11
                         note = synthetic peptide
source                   1..11
                         mol_type = protein
                         organism = synthetic construct
SEQUENCE: 71
KLKLLLLLKL K                                                        11

SEQ ID NO: 72            moltype = DNA  length = 10773
FEATURE                  Location/Qualifiers
source                   1..10773
                         mol_type = genomic DNA
                         organism = Zika virus
SEQUENCE: 72
cagactgcga cagttcgagt ttgaagcgaa agctagcaac agtatcaaca ggttttattt    60
tggatttgga aacgagagtt tctggtcatg aaaaacccaa aaaagaaatc cggaggattc   120
cggattgtca atatgctaaa acgcggagta gcccgtgtga gcccctttgg gggcttgaag   180
aggctgccag ccggacttct gctgggtcat gggcccatca ggatggtctt ggcgattcta   240
gcctttttga gattcacggc aatcaagcca tcactgggtc tcatcaatag atgggggtca   300
gtggggaaaa aagaggctat ggaaataata aagaagttca gaaagatct ggctgccatg   360
ctgagaataa tcaatgctag gaaggagaag aagagacgag gcgcagatac tagtgtcgga   420
attgttggcc tcctgctgac cacagcatg gcagcggagg tcactagacg tgggagtgca   480
tactatatgt acttggacag aaacgacgct ggggaggcca tatctttcc aaccacattg   540
gggatgaata agtgttatat acagatcatg gatcttgac acatgtgga tgccaccatg   600
agctatgaat gccctatgct ggatgagggg gtgaaccag atgacgtcga ttgttggtgc   660
aacacgacgt caacttgggt tgtgtacgga acctgccatc acaaaaaagg tgaagcacgg   720
agatctagaa gagctgtgac gctcccctcc cattccacta ggaagctgca aacgcggtcg   780
caaacctggt tggaatcaag agaatacaca aagcacttga ttagagtga aaattggata   840
ttcaggaacc ctggcttcgc gttagcagca gctgccatcg cttgctttt gggaagctca   900
acgagccaaa aagtcatata cttggtcatg atactgctga ttgccccggc atacagcatc   960
aggtgcatag gagtcagcaa tagggacttt gtggaaggta tgtcaggtgg gacttgggtt  1020
gatgttgtct ggaacatgg aggttgtgtc accgtaatgg cacaggacaa accgactgtc  1080
gacatagagc tggttacaac aacagtcagc aacatgcgg aggtaagatc ctactgctat  1140
gaggcatcaa tatcggacat ggcttcggac agccgctgc aatccacaag gtcaagctac  1200
cttgacaagc aatcagacac tcaatatgtc tgcaaaagaa cgttagtgga cagaggctgg  1260
ggaaatggat gtggatttt tggcaaaggg agcctggtga catgcgctaa gtttgcatgc  1320
tccaagaaaa tgaccgggaa gagcatccag ccagagaatc tggagtaccg gataatgctg  1380
tcagttcatg gctcccagca cagtgggatg atcgttaatg acaggacaga tgaaactgat  1440
gagaatagag cgaaggttga gataacgccc aattcaccaa gagccgaagc caccctgggg  1500
```

```
ggttttggaa gcctaggact tgattgtgaa ccgaggacag gccttgactt ttcagatttg   1560
tattacttga ctatgaataa caagcactgg ttggttcaca aggagtggtt ccacgcatt    1620
ccattacctt ggcacgctgg ggcagacacc ggaactccac actggaacaa caaagaagca   1680
ctggtagagt tcaaggacgc acatgccaaa aggcaaactg tcgtggttct agggagtcaa   1740
gaaggagcag ttcacacggc ccttgctgga gctctggaga ctgagatgga tggtgcaaag   1800
ggaaggctgt cctctggcca cttgaaatgt cgcctgaaaa tggataaact tagattgaag   1860
ggcgtgtcat actccttgtg taccgcagcg ttcacattca ccaagatccc ggctgaaaca   1920
ctgcacggga cagtcacagt ggaggtacag tacgcaggga cagatggacc ttgcaaggtt   1980
ccagctcaga tggcggtgga catgcaaact ctgaccccac ttgggaggtt gataaccgat   2040
aaccccgtaa tcactgaaag cactgagaac tctaagatga tgctggaact tgatccacca   2100
tttggggact cttacattgt cataggagtc gggggagaaga agatcaccca ccactgcac   2160
aggagtggca gcaccattgg aaaagcattt gaagccactg tgagaggtgc caagagaatg   2220
gcagtcttgg gagacacagc ctgggacttt ggatcagttg gaggcgctct caactcattg   2280
ggcaagggca tccatcaaat ttttggagca gctttcaaat cattgtttgg aggaatgtcc   2340
tggttctcac aaattctcat tggaacgttg ctgatgtggt tgggtctgaa cacaaagaat   2400
ggatctattt cccttatgtg cttggcctta gggggagtgt tgatcttctt atccacagct   2460
gtctctgctg atgtggggtg ctcggtggac ttctcaaaga aggagacgag atgcggtaca   2520
ggggtgttcg tctataacga cgttgaagcc tggagggaca ggtacaagta ccatcctgac   2580
tccccccgta gattggcagc agcagtcaag caagcctggg aagtaggtat ctgtgggatc   2640
tcctctgttt caagaatgga aaacatcatg tggagatcag tagaagggga gctcaacgca   2700
atcctggaag agaatggagt tcaactgacg gtcgttgtgg gatctgtaaa aaaccccatg   2760
tggagaggtc cacagagatt gcccgtgcct gtgaacgagc tgccccacgg ctggaaggct   2820
tgggggaaat cgtacttcgt cagagcagca aagacaaata acagctttgt cgtggatggt   2880
gacacactga aggaatgccc actcaaacat agagcatgga acagctttct tgtggaggat   2940
catgggttcg gggtatttca cactagtgtc tggctcaagg ttagaagaa ttattcatta   3000
gagtgtgatc cagccgttat tggaacagct gttaaggaa aggaggctgt acacagtgat   3060
ctaggctact ggattgagag tgagaagaat gacacatgga ggctgaagag ggcccatctg   3120
atcgagatga aaacatgtga atggccaaag tcccacacat tgtggacaga tggaatagaa   3180
gagagtgatc tgatcatacc caagtctta gctgggccac tcagccatca caataccaga   3240
gagggctaca ggacccaaat gaaagggcca tggcacagtg aagagcttga aattcggttg   3300
gaggaatgcc caggcactaa ggtccacgtg gaggaaacat gtggaacaag gaccatct    3360
ctgagatcaa ccactgcaag cggaaggtgtg atcgaggaat ggtgctgcag ggagtgcaca   3420
atgccccac tgtcgttccg ggctaaagat ggctgttggt atggaatgga gataaggcc    3480
aggaaagaac cagaaagtaa cttagtaagg tcaatggtga ctgcaggatc aactgatcac   3540
atggatcact tctcccttgg agtgcttgtg attctgctca tggtcaggat ctggtcagga agggctgaag   3600
aagagaatga ccacaaagat catcataagc acatcgatgg cagtgctggt agctatgatc   3660
ctgggaggat tttcaatgag tgacctgct aagcttgcaa ttttgatggg tgccaccttc   3720
gcggaaatga acactggagg agatgtagct catctggcgc tgatagcggc attcaaagtc   3780
agaccagcgt tgctggtatc ttcatcttc agagctaatt ggacaccccg tgaaagcatg   3840
ctgctggcct tggcctcgtg tctttttcaa actgcgatct ccgccttgga aggcgacctg   3900
atggttctca tcaatggttt tgcctttggc tggttggcaa tacgagcgat ggttgttcca   3960
cgcactgata acatcacctt ggcaatcctg gctgctctga caccactggc ccggggcaca   4020
ctgcttgtgg cgtgggaagc aggccttgct acttgcggg ggtttatgct cctctcttg    4080
aagggaaaag gcagtgtgaa gaagaactta ccatttgtca tggcctgggg actaaccgct   4140
gtgaggctgg tcgaccccat caacgtggtg ggactgctgt tgctcacaag gagtgggaag   4200
cggagctggc ccctagcga agtactcaca gctgttggcc tgatatgcgc attggctgga   4260
gggttcgcca aggcagatat agatggct gggcccatgg ccgcggtcgg tctgctaatt   4320
gtcagttacg tggtctcagg aaagagtgtg gacatgtaca ttgaaagagc aggtgacatc   4380
acatgggaaa aagatgcgga agtcactgga aacagtcccc ggctcgatgt ggcgctagat   4440
gagagtggtc atttctccct ggtggaggat gacggtcccc ccatgagaga gatcatactc   4500
aaggtggtcc tgatgaccat ctgtggcatg aacccaatag ccataccctt tgcagctgga   4560
gcgtggtacg tatacgtgaa gactggaaaa aggagtggtg ctctatggga tgtgcctgct   4620
cccaaggaag taaaaagggg ggagaccaca gatggagtgt acagagtaat gactcgtaga   4680
ctgctaggtt caacacaagt tggagtggga gttatgcaag gggggtctt tcacactatg   4740
tggcacgtca caaaaggatc cgcgctgaga agcggtgaag gagactga tccatactgg   4800
ggagatgtca agcaggatct ggtgtcatac tgtggtccat ggaagctaga tgccgcctgg   4860
gacgggcaca gcgaggtgca gctcttggcc gtgcccccg gagagagagc gaggaacatc   4920
cagactctgc ccggaatatt taagacaaag gatgggaca ttggagcggt tgcgctggat   4980
tacccagcag gaacttcagg atctccaatc ctagacaagt gtggaagt gataggactt   5040
tatggcaatg gggtcgtgat caaaaatggg agttatgtta tgccatcac ccaagggagg   5100
agggaggaag agactcctgt tgagtgcttc gagccttcga tgctgaagaa gaagcagcta   5160
actgtcttag acttgcatcc tggagctggg aaaaccagga gagttcttcc tgaaatagtc   5220
cgtgaagcca taaaaacaag actccgtact gtgatcttag ctccaaccag ggttgtcgct   5280
gctgaaatgg aggaagccct tagagggctt ccagtgcgtt atatgacaac agcagtcaat   5340
gtcacccact ctggaacaga aatcgtcgac ttaatgtgcc atgccacctt cacttcacgt   5400
ctactacagc caatcagagt ccccaactat aatctgtata ttatggatga ggcccacttc   5460
acagatccct caagtatagc agcaagagga tacatttcaa caagggttga gatgggcgag   5520
gcggctgcca tcttcatgac cgccacgcca ccaggaaccc gtgacgcatt tccggactcc   5580
aactcaccaa ttatggacac cgaagtggaa gtcccagaga gagcctggag ctcaggcttt   5640
gattgggtga cggatcattc tggaaaaaca gtttggtttg ttccaagcgt gaggaacggc   5700
aatgagatcg cagcttgtct gacaaaggct ggaaaacggg tcatacagct cagcagaaag   5760
acttttgaga cagagttcca gaaaacaaaa catcaagagt gggactttgt cgtgacaact   5820
gacatttcag agatgggcgc caactttaaa gctgaccgtg tcatagattc caggagatgc   5880
ctaaagccgg tcatacttga tggcgagaga gtcattctga gtggacccat gcctgtcaca   5940
catgccagcg ctgcccagag gaggggcgc ataggcagga tcccaacaa acctggagat   6000
gagtatctgt atggaggtgg gtgcgcagag actgacgaag accatgcaca ctggcttgaa   6060
gcaagaatgc tccttgacaa tatttacctc caagatggcc tcatagcctc gctctatcga   6120
cctgaggccg acaaagtagc agccattgag ggagagttca gcttaggac ggagcaaagg   6180
aagacctttg tggaactcat gaaaagagga gatcttcctg tttggctggc ctatcaggtt   6240
```

```
gcatctgccg gaataaccta cacagatgga agatggtgct ttgatggcac gaccaacaac  6300
accataatgg aagacagtgt gccggcagag gtgtggacca gacacggaga gaaaagagtg  6360
ctcaaaccga ggtggatgga cgccagagtt tgttcagatc atgcggccct gaagtcattc  6420
aaggagtttg ccgctgggaa aagaggagcg gcttttggag tgatggaagc cctgggaaca  6480
ctgccaggac acatgacaga gagattccag gaagccattg acaacctggc tgtgctcatg  6540
cgggcagaga ctggaagcag gcctttacaaa gccgcggcgg cccaattgcc ggagacccta  6600
gagaccatta tgcttttggg gttgctggga acagtctcgc tgggaatctt tttcgtcttg  6660
atgaggaaca agggcatagg gaagatgggc tttggaatgg tgactcttgg ggccagcgca  6720
tggctcatgt ggctctcgga aattgagcca gccagaattg catgtgtcct cattgttgtg  6780
ttcctattgc tggtggtgct catacctgag ccagaaaagc aaagatctcc ccaggacaac  6840
caaatggcaa tcatcatcat ggtagcagta ggtcttctgg gcttgattac cgccaatgaa  6900
ctcggatggt tggagagaac aaagagtgac ctaagccatc taatgggaag agagaggag   6960
ggggcaacca taggattctc aatggacatt gacctgcggc cagcctcagc ttgggccatc  7020
tatgctgcct tgacaacttt cattaccca gccgtcaac atgcagtgac cacttcatac   7080
aacaactact ccttaatggc gatggccacg caagctggag tgttgtttgg tatgggcaaa  7140
gggatgccat tctacgcatg ggactttgga gtcccgctgc taatgatagg ttgctactca  7200
caattaacac ccctgacccct aatagtggcc atcattttgc tcgtggcgca ctacatgtac  7260
ttgatcccag ggctgcaggc agcagctgcg cgtgctgccc agaagagaac ggcagctggc  7320
atcatgaaga accctgttgt ggatggaata gtggtgactg acattgacac aatgacaatt  7380
gacccccaag tggagaaaaa gatgggacag gtgctactca tagcagtagc cgtctccagc  7440
gccatactgt cgcggaccgc ctgggggtgg ggggaggctg ggccctgat cacagcggca   7500
acttccactt tgtgggaagg ctctccgaac aagtactgga actcctctac agccacttca  7560
ctgtgtaaca ttttttaggggg aagttacttg gctggagctt ctctaatcta cacagtaaca  7620
agaaacgctg gcttggtcaa gagacgtggg ggtggaacag gagagaccct gggagagaaa  7680
tggaaggccc gcttgaacca gatgtcggcc ctggagttct actcctacaa aaagtcaggc  7740
atcaccaggg tgtgcagaga agaggccgcc cgcgccctca acgacggtgt ggcaacggga  7800
ggccatgctg tgtcccgagg aagtgcaaag ctgagatggt tggtggagcg gggatacctg  7860
cagcccctatg aaaggtcat tgatcttgga tgtggcagag ggggctggag ttactacgcc  7920
gccaccatcc gcaaagttca agaagtgaaa ggatacacaa aaggaggccc tggtcatgaa  7980
gaaccatgt tggtgcaaag ctatgggtgg aacatagtcc gtcttaagag tgggtggag   8040
gtctttcata tggcggctga gccgtgtgac acgttgctgt gtgacatagg tgagtcatca  8100
tctagtcctg aagtggaaga agcacggacg ctcagagtcc tctccatggt ggggattgg   8160
cttgaaaaaa gaccaggagc cttttgtata aaagtgttgt gcccatacac cagcactatg  8220
atggaaaccc tggagcgact gcagctagg tatggggag gactggtcag agtgccactc  8280
tcccgcaact ctacacatga gatgtactgg gtctctgagg cgaaaagcaa caccataaaa  8340
agtgtgtcca ccacgagcca gctcctcttg gggcgcatgg acgggcccag gaggccagtg  8400
aaatatgagg aggatgtgaa tctcggctct ggcacgcggg ctgtggtaag ctgcgctgaa  8460
gctcccaaca tgaagatcat tggtaaccgc attgaaagga tccgcagtga gcacgcggaa  8520
acgtggttct ttgacgagaa ccaccatat aggacatgg cttaccatgg aagctatgag   8580
gcccccacac aagggtcagc gtcctctcta ataaacgggg ttgtcaggct cctgtcaaaa  8640
ccctgggatg tggtgactgg agtcacagga atagccatga ccgacaccac accgtatggt  8700
cagcaaagag ttttcaagga aaaagtggac actagggtgc cagaccccca agaaggcact  8760
cgtcaggtta tgagcatggt ctcttcctgg ttgtggaaag gataggcaa acacaaacgg  8820
ccacgagtct gtaccaaaga agagttcatc aacaaggttc gtagcaatgc agcattaggg  8880
gcaatatttg aagaggaaaa agagtggaag actgcagtgg aagctgtgaa cgatccaagg  8940
ttctgggctc tagtggacaa ggaaagagag caccacctga gggagagtg ccagagttgt   9000
gtgtacaaca tgatgggaaa aagagaaaag aaacaagggg aatttggaaa ggccaagggc  9060
agccgcgcca tctggtatat gtggctaggg gctagatttc tagagttcga agcccttgga  9120
ttcttgaacg aggatcactg gatggggaga gagaactcag gaggtgtgt tgaagggctg   9180
ggattacaaa gactcggata tgtcctagaa gagatgagtc gcataccagg aggaaggatg  9240
tatgcagatg acactgctgg ctgggacacc cgcatcagca ggtttgatct ggagaatgaa  9300
gctctaatca ccaaccaat ggagaaaggg cacagggcct tggcattggc cataatcaag   9360
tacacatacc aaaacaaagt ggtaaaggtc cttagaccag ctgaaaaagg gaagacagtt  9420
atggacatta tttcgagaca agaccaaagg gggagcggac aagttgtcac ttacgctctt  9480
aacacattta ccaacctagt ggtcaactc attcggaata tggaggctga ggaagttcta  9540
gagatgcaag acttgtggct gctgcggagg tcagagaaag tgaccaactg gttgcagagc  9600
aacgatggg ataggctcaa acgaatggca gtcagtggag atgattgcgt tgtgaagcca  9660
attgatgata ggtttgcaca tgccctcagg ttcttgaatg atatgggaaa agttaggaag  9720
gacacacaag agtggaaacc ctcaactgga tgggacaagt gggacaagt tccgtttttgc  9780
tcccaccact tcaacaagct ccatctcaag gacgggaggt ccattgtggt tccctgccgc  9840
caccaagatg aactgattgg ccgggcccgc gtctctccag gggcgggatg gagcatccgg  9900
gagactgctt gcctagcaaa atcatatgcg caaatgtggc agctccttta tttccacaga  9960
agggacctcc gactgatggc caatgccatt tgttcatctg tgccagttga ctgggttcca  10020
actgggagaa ctacctggtc aatccatgga aagggagaat aggaccac tgaagacatg  10080
cttgtggtgt ggaacagagt gtggattgag gagaacgacc acatggaaga caagcccca   10140
gttacgaaat ggacagacat tccctatttg ggaaaaaggg aagacttgtg tgtggatctc  10200
ctcatagggc acagaccgcg caccacctgg gctgagaaca ttaaaaacac agtcaacatg  10260
gtgcgcagga tcataggtga tgaagaaaag tacatggact acctatccac ccaagttcgc  10320
tacttgggtg aagaaggttc tacacctgga gtgctgtaa caccaatctt agtgttgtca   10380
ggcctgctag tcagccacag cttgggaaaa gctgtgcagc ctgtgacccc cccaggagaa  10440
gctgggaaac caagcctata gtcaggccga gaacgccatg gcacgaaga agccatgctg  10500
cctgtgagcc cctcagagga cactgagtca aaaaccccca cgcgcttgga ggcgcaggat  10560
gggaaaagaa ggtggcgacc ttccccaccc ttcaatctgg ggcctgaact ggagatcagc  10620
tgtggacttc cagaagagacc actagtggtt agaggaaacag cacaaaacag  10680
catattgacg ctgggaaaga ccagagactc catgagtttc caccacctg gccgccaggc  10740
acagatcgcc gaatagcggc ggccggtgtg ggg                              10773

SEQ ID NO: 73       moltype = AA   length = 3423
FEATURE             Location/Qualifiers
```

| source | 1..3423 |
| --- | --- |
| | mol_type = protein |
| | organism = Zika virus |

SEQUENCE: 73

```
MKNPKKKSGG FRIVNMLKRG VARVSPFGGL KRLPAGLLLG HGPIRMVLAI LAFLRFTAIK    60
PSLGLINRWG SVGKKEAMEI IKKFKKDLAA MLRIINARKE KKRRGADTSV GIVGLLLTTA   120
MAAEVTRRGS AYYMYLDRND AGEAISFPTT LGMNKCYIQI MDLGHMCDAT MSYECPMLDE   180
GVEPDDVDCW CNTTSTWVVY GTCHHKKGEA RRSRRAVTLP SHSTRKLQTR SQTWLESREY   240
TKHLIRVENW IFRNPGFALA AAAIAWLLGS STSQKVIYLV MILLIAPAYS IRCIGVSNRD   300
FVEGMSGGTW VDVVLEHGGC VTVMAQDKPT VDIELVTTTV SNMAEVRSYC YEASISDMAS   360
DSRCPTQGEA YLDKQSDTQY VCKRTLVDRG WGNGCGLFGK GSLVTCAKFA CSKKMTGKSI   420
QPENLEYRIM LSVHGSQHSG MIVNDTGHET DENRAKVEIT PNSPRAEATL GGFGSLGLDC   480
EPRTGLDFSD LYYLTMNNKH WLVHKEWFHD IPLPWHAGAD TGTPHWNNKE ALVEFKDAHA   540
KRQTVVVLGS QEGAVHTALA GALEAEMDGA KGRLSSGHLK CRLKMDKLRL KGVSYSLCTA   600
APFTFTKIPAE TLHGTVTVEV QYAGTDGPCK VPAQMAVDMQ TLTPVGRLIT ANPVITESTE   660
NSKMMLELDP PFGDSYIVIG VGEKKITHHW HRSGSTIGKA FEATVRGAKR MAVLGDTAWD   720
FGSVGGALNS LGKGIHQIFG AAFKSLFGGM SWFSQILIGT LLMWLGLNTK NGSISLMCLA   780
LGGVLIFLST AVSADVGCSV DFSKKETRCG TGVFVYNDVE AWRDRYKYHP DSPRRLAAAV   840
KQAWEDGICG ISSVSRMENI MWRSVEGELN AILEENGVQL TVVVGSVKNP MWRGPQRLPV   900
PVNELPHGWK AWGKSYFVRA AKTNNSFVVD GDTLKECPLK HRAWNSFLVE DHGFGVFHTS   960
VWLKVREDYS LECDPAVIGT AVKGKEAVHS DLGYWIESEK NDTWRLKRAH LIEMKTCEWP  1020
KSHTLWTDGI EESDLIIPKS LAGPLSHHNT REGYRTQMKG PWHSEELEIR FEECPGTKVH  1080
VEETCGTRGP SLRSTTASGR VIEEWCCREC TMPPLSFRAK DGCWYGMEIR PRKEPESNLV  1140
RSMVTAGSTD HMDHFSLGVL VILLMVQEGL KKRMTTKIII STSMAVLVAM ILGGFSMSDL  1200
AKLAILMGAT FAEMNTGGDV AHLALIAAFK VRPALLVSFI FRANWTPRES MLLALASCLL  1260
QTAISALEGD LMVLINGFAL AWLAIRAMVV PRTDNITLAL LAALTPLARG TLLVAWRAGL  1320
ATCGGFMLLS LKGKGSVKKN LPFVMALGLT AVRLVDPINV VGLLLLLTRSG KRSWPPSEVL  1380
TAVGLICALA GGFAKADIEM AGPMAAVGLL IVSYVVSGKS VDMYIERAGD ITWEKDAEVT  1440
GNSPRLDVAL DESGDFSLVE DDGPPMREII LKVVLMTICG MNPIAIPFAA GAWYVYVKTG  1500
KRSGALWDVP APKEVKKGET TDGVYRVMTR RLLGSTQVGV GVMQEGVFHT MWHVTKGSAL  1560
RSGEGRLDPY WGDVKQDLVS YCGPWKLDAA WDGHSEVQLL AVPPGERARN IQTLPGIFKT  1620
KDGDIGAVAL DYPAGTSGSP ILDKCGRVIG LYGNGVVIKN GSYVSAITQG RREEETPVEC  1680
FEPSMLKKKQ LTVLDLHPGA GKTRRVLPEI VREAIKTRLR TVILAPTRVV AAEMEEALRG  1740
LPVRYMTTAV NVTHSGTEIV DLMCHATFTS RLLQPIRVPN YNLYIMDEAH FTDPSSIAAR  1800
GYISTRVEMG EAAAIFMTAT PPGTRDAFPD SNSPIMDTEV EVPERAWSSG FDWVTDHSGK  1860
TVWFVPSVRN GNEIAACLTK AGKRVIQLSR KTFETEFQKT KHQEWDFVVT TDISEMGANF  1920
KADRVIDSRR CLKPVILDGE RVILAGPMPV THASAAQRRG RIGRNPNKPG DEYLYGGGCA  1980
ETDEDHAHWL EARMLLDNIY LQDGLIASLY RPEADKVAAI EGEFKLRTEQ RKTFVELMKR  2040
GDLPVWLAYQ VASAGITYTD RRWCFDGTTN NTIMEDSVPA EVWTRHGEKR VLKPRWMDAR  2100
VCSDHAALKS FKEFAAGKRG AAFGVMEALG TLPGHMTERF QEAIDNLAVL MRAETGSRPY  2160
KAAAAQLPET LETIMLLGLL GTVSLGIFFV LMRNKGIGKM GFGMVTLGAS AWLMWLSEIE  2220
PARIACVLIV VFLLLVVLIP EPEKQRSPQD NQMAIIIMVA VGLLGLITAN ELGWLERTKS  2280
DLSHLMGRRE EGATIGFSMD IDLRPASAWA IYAALTTFIT PAVQHAVTTS YNNYSLMAMA  2340
TQAGVLFGMG KGMPFYAWDF GVPLLMIGCY SQLTPLTLIV AIILLVAHYM YLIPGLQAAA  2400
ARAAQKRTAA GIMKNPVVDG IVVTDIDTMT IDPQVEKKMG QVLLIAVAVS SAILSRTAWG  2460
WGEAGALITA ATSTLWEGSP NKYWNSSTAT SLCNIFRGSY LAGASLIYTV TRNAGLVKRR  2520
GGGTGETLGE KWKARLNQMS ALEFYSYKKS GITEVCREEA RRALKDGVAT GGHAVSRGSA  2580
KLRWLVERGY LQPYGKVIDL GCGRGGWSYY AATIRKVQEV KGYTKGGPGH EEPMLVQSYG  2640
WNIVRLKSGV DVFHMAAEPC DTLLCDIGES SSSPEVEEAR TLRVLSMVGD WLEKRPGAFC  2700
IKVLCPYTST MMETLERLQR RYGGGLVRVP LSRNSTHEMY WVSGAKSNTI KSVSTTSQLL  2760
LGRMDGPRRP VKYEEDVNLG SGTRAVVSCA EAPNMKIIGN RIERIRSEHA ETWFFDENHP  2820
YRTWAYHGSY EAPTQGSASS LINGVVRLLS KPWDVVTGVT GIAMTDTTPY GQQRVFKEKV  2880
DTRVPDPQEG TRQVMSMVSS WLWKELGKHK RPRVCTKEEF INKVRSNAAL GAIFEEEKEW  2940
KTAVEAVNDP RFWALVDKER EHHLRGECQS CVYNMMGKRE KKQGEFGKAK GSRAIWYMWL  3000
GARFLEFEAL GFLNEDHWMG RENSGGGVEG LGLQRLGYVL EEMSRIPGGR MYADDTAGWD  3060
TRISRFDLEN EALITNQMEK GHRALALAII KYTYQNKVVK VLRPAEKGKT VMDIISRQDQ  3120
RGSGQVVTYA LNTFTNLVVQ LIRNMEAEEV LEMQDLWLLR RSEKVTNWLQ SNGWDRLKRM  3180
AVSGDDCVVK PIDDRFAHAL RFLNDMGKVR KDTQEWKPST GWDNWEEVPF CSHHFNKLHL  3240
KDGRSIVVPC RHQDELIGRA RVSPGAGWSI RETACLAKSY AQMWQLLYFH RRDLRLMANA  3300
ICSSVPDWV PTGRTTWSIH GKGEWMTTED MLVVWNRVWI EENDHMEDKT PVTKWTDIPY  3360
LGKREDLWCG SLIGHRPRTT WAENIKNTVN MVRRIIGDEE KYMDYLSTQV RYLGEEGSTP  3420
GVL                                                                3423
```

| SEQ ID NO: 74 | moltype = DNA length = 28 |
| --- | --- |
| FEATURE | Location/Qualifiers |
| misc_feature | 1..28 |
| | note = primer |
| source | 1..28 |
| | mol_type = other DNA |
| | organism = synthetic construct |

SEQUENCE: 74 ttaggatccg ttgttgatct gtgtgaat                                          28

| SEQ ID NO: 75 | moltype = DNA length = 26 |
| --- | --- |
| FEATURE | Location/Qualifiers |
| misc_feature | 1..26 |
| | note = primer |
| source | 1..26 |
| | mol_type = other DNA |

```
                              organism = synthetic construct
SEQUENCE: 75
taactcgagc gtacacaacc caagtt                                              26

SEQ ID NO: 76          moltype = DNA  length = 27
FEATURE                Location/Qualifiers
misc_feature           1..27
                       note = primer
source                 1..27
                       mol_type = other DNA
                       organism = synthetic construct
SEQUENCE: 76
ttaggatcct cactagacgt gggagtg                                             27

SEQ ID NO: 77          moltype = DNA  length = 29
FEATURE                Location/Qualifiers
misc_feature           1..29
                       note = primer
source                 1..29
                       mol_type = other DNA
                       organism = synthetic construct
SEQUENCE: 77
taactcgaga agccatgtcy gatattgat                                           29

SEQ ID NO: 78          moltype = DNA  length = 26
FEATURE                Location/Qualifiers
misc_feature           1..26
                       note = primer
source                 1..26
                       mol_type = other DNA
                       organism = synthetic construct
SEQUENCE: 78
ttaggatccg catacagcat caggtg                                              26

SEQ ID NO: 79          moltype = DNA  length = 27
FEATURE                Location/Qualifiers
misc_feature           1..27
                       note = primer
source                 1..27
                       mol_type = other DNA
                       organism = synthetic construct
SEQUENCE: 79
taactcgagt gtggagttcc ggtgtct                                             27

SEQ ID NO: 80          moltype = DNA  length = 31
FEATURE                Location/Qualifiers
misc_feature           1..31
                       note = primer
source                 1..31
                       mol_type = other DNA
                       organism = synthetic construct
SEQUENCE: 80
ttaggatccg aatagagcga argttgagat a                                        31

SEQ ID NO: 81          moltype = DNA  length = 28
FEATURE                Location/Qualifiers
misc_feature           1..28
                       note = primer
source                 1..28
                       mol_type = other DNA
                       organism = synthetic construct
SEQUENCE: 81
taactcgagt ggtgggtgat cttcttct                                            28

SEQ ID NO: 82          moltype = DNA  length = 31
FEATURE                Location/Qualifiers
misc_feature           1..31
                       note = primer
source                 1..31
                       mol_type = other DNA
                       organism = synthetic construct
SEQUENCE: 82
ttaggatcca gtcacagtgg aggtacagta c                                        31

SEQ ID NO: 83          moltype = DNA  length = 27
FEATURE                Location/Qualifiers
misc_feature           1..27
                       note = primer
source                 1..27
```

```
                              mol_type = other DNA
                              organism = synthetic construct
SEQUENCE: 83
taactcgagc rcagatacca tcttccc                                           27

SEQ ID NO: 84                 moltype = DNA   length = 28
FEATURE                       Location/Qualifiers
misc_feature                  1..28
                              note = primer
source                        1..28
                              mol_type = other DNA
                              organism = synthetic construct
SEQUENCE: 84
ttaggatccc ttatgtgctt ggccttag                                          28

SEQ ID NO: 85                 moltype = DNA   length = 26
FEATURE                       Location/Qualifiers
misc_feature                  1..26
                              note = primer
source                        1..26
                              mol_type = other DNA
                              organism = synthetic construct
SEQUENCE: 85
taactcgagt cttcagcctc catgtg                                            26

SEQ ID NO: 86                 moltype = DNA   length = 29
FEATURE                       Location/Qualifiers
misc_feature                  1..29
                              note = primer
source                        1..29
                              mol_type = other DNA
                              organism = synthetic construct
SEQUENCE: 86
ttaggatcca atgcccactc aaacataga                                         29

SEQ ID NO: 87                 moltype = DNA   length = 30
FEATURE                       Location/Qualifiers
misc_feature                  1..30
                              note = primer
source                        1..30
                              mol_type = other DNA
                              organism = synthetic construct
SEQUENCE: 87
taactcgagt cattctcttc ttcagccctt                                        30

SEQ ID NO: 88                 moltype = DNA   length = 26
FEATURE                       Location/Qualifiers
misc_feature                  1..26
                              note = primer
source                        1..26
                              mol_type = other DNA
                              organism = synthetic construct
SEQUENCE: 88
ttaggatcca agggtgatcg aggaat                                            26

SEQ ID NO: 89                 moltype = DNA   length = 29
FEATURE                       Location/Qualifiers
misc_feature                  1..29
                              note = primer
source                        1..29
                              mol_type = other DNA
                              organism = synthetic construct
SEQUENCE: 89
taactcgagt tcccttcaga gagaggagc                                         29

SEQ ID NO: 90                 moltype = DNA   length = 28
FEATURE                       Location/Qualifiers
misc_feature                  1..28
                              note = primer
source                        1..28
                              mol_type = other DNA
                              organism = synthetic construct
SEQUENCE: 90
ttaggatcct cttttgcaaa ctgcgatc                                          28

SEQ ID NO: 91                 moltype = DNA   length = 27
FEATURE                       Location/Qualifiers
misc_feature                  1..27
                              note = primer
```

```
source                  1..27
                        mol_type = other DNA
                        organism = synthetic construct
SEQUENCE: 91
taactcgagt ccagctgcaa agggtat                                        27

SEQ ID NO: 92           moltype = DNA  length = 28
FEATURE                 Location/Qualifiers
misc_feature            1..28
                        note = primer
source                  1..28
                        mol_type = other DNA
                        organism = synthetic construct
SEQUENCE: 92
ttaggatccg tgtggacatg tacattga                                       28

SEQ ID NO: 93           moltype = DNA  length = 26
FEATURE                 Location/Qualifiers
misc_feature            1..26
                        note = primer
source                  1..26
                        mol_type = other DNA
                        organism = synthetic construct
SEQUENCE: 93
taactcgagc ccattgccat aaagtc                                         26

SEQ ID NO: 94           moltype = DNA  length = 28
FEATURE                 Location/Qualifiers
misc_feature            1..28
                        note = primer
source                  1..28
                        mol_type = other DNA
                        organism = synthetic construct
SEQUENCE: 94
ttaggatcct catactgtgg tccatgga                                       28

SEQ ID NO: 95           moltype = DNA  length = 26
FEATURE                 Location/Qualifiers
misc_feature            1..26
                        note = primer
source                  1..26
                        mol_type = other DNA
                        organism = synthetic construct
SEQUENCE: 95
taactcgagg cccatctcaa cccttg                                         26

SEQ ID NO: 96           moltype = DNA  length = 26
FEATURE                 Location/Qualifiers
misc_feature            1..26
                        note = primer
source                  1..26
                        mol_type = other DNA
                        organism = synthetic construct
SEQUENCE: 96
ttaggatcct agagggcttc cagtgc                                         26

SEQ ID NO: 97           moltype = DNA  length = 31
FEATURE                 Location/Qualifiers
misc_feature            1..31
                        note = primer
source                  1..31
                        mol_type = other DNA
                        organism = synthetic construct
SEQUENCE: 97
taactcgaga tactcatctc caggtttgtt g                                   31

SEQ ID NO: 98           moltype = DNA  length = 30
FEATURE                 Location/Qualifiers
misc_feature            1..30
                        note = primer
source                  1..30
                        mol_type = other DNA
                        organism = synthetic construct
SEQUENCE: 98
ttaggatccg aaaacaaaac atcaagagtg                                     30

SEQ ID NO: 99           moltype = DNA  length = 31
FEATURE                 Location/Qualifiers
misc_feature            1..31
```

```
                              note = primer
source                        1..31
                              mol_type = other DNA
                              organism = synthetic construct
SEQUENCE: 99
taactcgagg aatctctctg tcatgtgtcc t                              31

SEQ ID NO: 100                moltype = DNA  length = 26
FEATURE                       Location/Qualifiers
misc_feature                  1..26
                              note = primer
source                        1..26
                              mol_type = other DNA
                              organism = synthetic construct
SEQUENCE: 100
ttaggatcct tgatggcacg accaac                                    26

SEQ ID NO: 101                moltype = DNA  length = 28
FEATURE                       Location/Qualifiers
misc_feature                  1..28
                              note = primer
source                        1..28
                              mol_type = other DNA
                              organism = synthetic construct
SEQUENCE: 101
ttaggatccg ttgttgatct gtgtgaat                                  28

SEQ ID NO: 102                moltype = DNA  length = 26
FEATURE                       Location/Qualifiers
misc_feature                  1..26
                              note = primer
source                        1..26
                              mol_type = other DNA
                              organism = synthetic construct
SEQUENCE: 102
taactcgagc aggtcaatgt ccattg                                    26

SEQ ID NO: 103                moltype = DNA  length = 30
FEATURE                       Location/Qualifiers
misc_feature                  1..30
                              note = primer
source                        1..30
                              mol_type = other DNA
                              organism = synthetic construct
SEQUENCE: 103
ttaggatcct gttgtgttcc tattgctggt                                30

SEQ ID NO: 104                moltype = DNA  length = 25
FEATURE                       Location/Qualifiers
misc_feature                  1..25
                              note = primer
source                        1..25
                              mol_type = other DNA
                              organism = synthetic construct
SEQUENCE: 104
taactcgagt gatcagrgcc ccagc                                     25

SEQ ID NO: 105                moltype = DNA  length = 26
FEATURE                       Location/Qualifiers
misc_feature                  1..26
                              note = primer
source                        1..26
                              mol_type = other DNA
                              organism = synthetic construct
SEQUENCE: 105
ttaggatcct gctgcccaga agagaa                                    26

SEQ ID NO: 106                moltype = DNA  length = 26
FEATURE                       Location/Qualifiers
misc_feature                  1..26
                              note = primer
source                        1..26
                              mol_type = other DNA
                              organism = synthetic construct
SEQUENCE: 106
taactcgagc accaacaygg gttctt                                    26

SEQ ID NO: 107                moltype = DNA  length = 25
FEATURE                       Location/Qualifiers
```

```
                              misc_feature        1..25
                                                  note = primer
                              source              1..25
                                                  mol_type = other DNA
                                                  organism = synthetic construct
                              SEQUENCE: 107
                              ttaggatcct caaggacggt gtggc                                      25

SEQ ID NO: 108      moltype = DNA   length = 28
                              FEATURE             Location/Qualifiers
                              misc_feature        1..28
                                                  note = primer
                              source              1..28
                                                  mol_type = other DNA
                                                  organism = synthetic construct
                              SEQUENCE: 108
                              taactcgagc aatgatcttc atgttggg                                   28

SEQ ID NO: 109      moltype = DNA   length = 26
                              FEATURE             Location/Qualifiers
                              misc_feature        1..26
                                                  note = primer
                              source              1..26
                                                  mol_type = other DNA
                                                  organism = synthetic construct
                              SEQUENCE: 109
                              ttaggatcct atgggggagg actggt                                     26

SEQ ID NO: 110      moltype = DNA   length = 25
                              FEATURE             Location/Qualifiers
                              misc_feature        1..25
                                                  note = primer
                              source              1..25
                                                  mol_type = other DNA
                                                  organism = synthetic construct
                              SEQUENCE: 110
                              taactcgagc ccagaacctt ggatc                                      25

SEQ ID NO: 111      moltype = DNA   length = 25
                              FEATURE             Location/Qualifiers
                              misc_feature        1..25
                                                  note = primer
                              source              1..25
                                                  mol_type = other DNA
                                                  organism = synthetic construct
                              SEQUENCE: 111
                              ttaggatcca gaccccccaag aaggc                                     25

SEQ ID NO: 112      moltype = DNA   length = 26
                              FEATURE             Location/Qualifiers
                              misc_feature        1..26
                                                  note = primer
                              source              1..26
                                                  mol_type = other DNA
                                                  organism = synthetic construct
                              SEQUENCE: 112
                              taactcgagc ccctttggtc ttgtct                                     26

SEQ ID NO: 113      moltype = DNA   length = 29
                              FEATURE             Location/Qualifiers
                              misc_feature        1..29
                                                  note = primer
                              source              1..29
                                                  mol_type = other DNA
                                                  organism = synthetic construct
                              SEQUENCE: 113
                              ttaggatcca ggaaggatgt atgcagatg                                  29

SEQ ID NO: 114      moltype = DNA   length = 30
                              FEATURE             Location/Qualifiers
                              misc_feature        1..30
                                                  note = primer
                              source              1..30
                                                  mol_type = other DNA
                                                  organism = synthetic construct
                              SEQUENCE: 114
                              taactcgaga catttgcgca tatgattttg                                 30

SEQ ID NO: 115      moltype = DNA   length = 28
```

```
FEATURE            Location/Qualifiers
misc_feature       1..28
                   note = primer
source             1..28
                   mol_type = other DNA
                   organism = synthetic construct
SEQUENCE: 115
ttaggatcca ggaaggacac acaagagt                                              28

SEQ ID NO: 116     moltype = DNA  length = 26
FEATURE            Location/Qualifiers
misc_feature       1..26
                   note = primer
source             1..26
                   mol_type = other DNA
                   organism = synthetic construct
SEQUENCE: 116
taactcgaga caggctgcac agcttt                                                26

SEQ ID NO: 117     moltype = DNA  length = 28
FEATURE            Location/Qualifiers
misc_feature       1..28
                   note = primer
source             1..28
                   mol_type = other DNA
                   organism = synthetic construct
SEQUENCE: 117
ttaggatcct ctctcatagg gcacagac                                              28
```